(12) United States Patent
Kuntz et al.

(10) Patent No.: US 8,093,239 B2
(45) Date of Patent: Jan. 10, 2012

(54) IMIDAZOPYRIDINE KINASE INHIBITORS

(75) Inventors: Kevin Kuntz, Durham, NC (US); David Edward Uehling, Durham, NC (US); Alex Gregory Waterson, Durham, NC (US); Kyle Allen Emmitte, Durham, NC (US); Kirk Stevens, Durham, NC (US); John Brad Shotwell, Durham, NC (US); Stephon Cornell Smith, Durham, NC (US); Kristen E. Nailor, Durham, NC (US); James M. Salovich, Durham, NC (US); Brian John Wilson, Durham, NC (US); Mui Cheung, King of Prussia, PA (US); Robert Anthony Mook, Durham, NC (US); Erich W. Baum, Durham, NC (US); Ganesh Moorthy, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 852 days.

(21) Appl. No.: 12/128,099

(22) Filed: May 28, 2008

(65) Prior Publication Data

US 2008/0300242 A1    Dec. 4, 2008

Related U.S. Application Data

(60) Provisional application No. 60/941,423, filed on Jun. 1, 2007, provisional application No. 61/024,294, filed on Jan. 29, 2008, provisional application No. 61/035,135, filed on Mar. 10, 2008.

(51) Int. Cl.
| | |
|---|---|
| A61K 31/55 | (2006.01) |
| A61K 31/505 | (2006.01) |
| A61K 31/497 | (2006.01) |
| A61K 31/535 | (2006.01) |
| C07D 243/08 | (2006.01) |
| C07D 413/14 | (2006.01) |
| C07D 403/14 | (2006.01) |
| C07D 239/02 | (2006.01) |

(52) U.S. Cl. ............... 514/218; 514/233.2; 514/252.18; 514/275; 540/575; 544/122; 544/295; 544/297

(58) Field of Classification Search .................. 514/218, 514/275, 252.18, 233.2; 540/575; 544/122, 544/295, 297
See application file for complete search history.

(56) References Cited

U.S. PATENT DOCUMENTS

2010/0216779 A1 *   8/2010   Baum et al. .................... 514/218

FOREIGN PATENT DOCUMENTS

| WO | 0114375 A | 3/2001 |
|---|---|---|
| WO | 03000682 A | 1/2003 |
| WO | 2004080390 A | 9/2004 |
| WO | 2005060571 A | 7/2005 |

* cited by examiner

*Primary Examiner* — James O Wilson
*Assistant Examiner* — Ebenezer O Sackey
(74) *Attorney, Agent, or Firm* — J. Scott Young

(57) ABSTRACT

The present invention provides imidazopyridine compounds, compositions containing the same, as well as processes for the preparation and methods for their use as pharmaceutical agents.

37 Claims, No Drawings

IMIDAZOPYRIDINE KINASE INHIBITORS

RELATED APPLICATIONS

This application claims priority to U.S. Provisional Patent Application Ser. Nos. 60/941,423, filed 1 Jun. 2007; 61/024,294, filed 29 Jan. 2008; and 61/035,135, filed 10 Mar. 2008.

FIELD OF THE INVENTION

The present invention relates to imidazopyridine compounds, compositions containing the same, as well as processes for the preparation and methods of using such compounds and compositions.

BACKGROUND OF THE INVENTION

Receptor tyrosine kinases (RTKs) have been implicated in cellular signaling pathways that control various cellular functions, including cell division, growth, metabolism, differentiation and survival, through reversible phosphorylation of the hydroxyl groups of tyrosine residues in proteins. Extracellular signals are transduced via activation of the cell surface receptors, with amplification and propagation using a complex choreography of cascades of protein phosphorylation and protein dephosphorylation events to avoid uncontrolled signaling. These signaling pathways are highly regulated, often by complex and intermeshed kinase pathways where each kinase may itself be regulated by one or more other kinases and protein phosphatases. The biological importance of these finely tuned systems is such that a variety of cell proliferative disorders have been linked to defects in one or more of the various cell signaling pathways mediated by tyrosine or serine/threonine kinases.

Receptor tyrosine kinases (RTKs) catalyze phosphorylation of certain tyrosyl amino acid residues in various proteins, including themselves, which govern cell growth, proliferation and differentiation. Insulin-like growth factor-1 receptor (IGF-1R) is a transmembrane tyrosine kinase ubiquitous among fetal and post-natal cell types.

The IGF signaling axis is made up of multiple ligands (IGF-1, IGF-2 and Insulin), at least six high affinity ligand binding proteins and proteases, multiple receptors (IGF-1R & IGF-2R, IR and IRR), and many other down stream signaling proteins (Pollak, M N et al., Nature Reviews Cancer (2004) 4(7):505-518). The structure and function of the IGF-1R has been reviewed by Adams et al., Cell. Mol. Life Sci. (2000) 57:1050-1093 and Benito, M et al., Int J Biochem Cell Biol (1996) 28(5):499-510. The receptor is activated by the ligands IGF-1 and IGF-2, which are mitogenic proteins that signal through the IGF-1R and IR in an endocrine, paracrine or autocrine manner. Activation of the IGF-1 receptor tyrosine kinase elicits cellular responses which include cellular proliferation and protection of cells from apoptosis. (Id.) Over expression of IGF-1R leads to malignant transformation of cultured cells, while down regulation can reverse the transformed phenotype of tumor cells and potentially render them susceptible to apoptosis. (Id.)

There are two splice variants of the IR gene, the IR-β isoform which regulates glucose uptake and is expressed in liver, muscle and adipose tissue, and the exon 11 variant human insulin receptor isoform A (IR-A) binds IGF-2 with high affinity and promotes proliferation and protection from apoptosis (Sciacca L. Oncogene (2002) 21(54):8240-8250). IR-A is predominantly expressed in fetal tissue and malignancies and at this receptor, IGF-2 is more potent than insulin in stimulating cancer cell migration. (Sciacca, Oncogene (2002) supra). Insulin receptor-related receptor tyrosine kinase (IRR) has 79% homology with the kinase domain of IR and is expressed only in a few limited cell types (Dandekar, A A et al., Endocrinology (1998) 139(8):3578-3584).

IGF-1R is a hetero-tetrameric, transmembrane, cell surface receptor tyrosine kinase. (Benito, Int J Biochem Cell Biol (1996)) An IGF-1 binding domain is part of the extracellular alpha-chain of IGF-1R, whereas the intracellular beta-chain contains the tyrosine kinase domain. Three tyrosine residues represent autophosphorylation sites, specifically $Tyr^{1131}$, $Tyr^{1135}$, and $Tyr^{1136}$, within the activation loop of the IGF-1R beta catalytic domain (Li, W et al., J. Biol. Chem. (2006) 281(33):23785-23791). Phosphorylation of all three is required for full receptor activation, and precedes phosphorylation of juxtamembrane tyrosines and carboxy terminus serines. The insulin receptor has three similar autophosphorylation sites on the activation loop and juxtamembrane region. Activation and autophosphorylation results in the recruitment of multiple docking proteins and the generation of intracellular signaling (Benito, Int J Biochem Cell Biol (1996)). Once activated, IGF-1R and IR can phosphorylate or interact directly with a number of intracellular protein substrates, including IRS-1, IRS-2, Grb2, Grb10, Grb14, Shc, SOC, 14.3.3, FAK, or indirectly with other proteins like PI3K and MAPK (Benito, M et al. Int J Biochem Cell Biol (1996) 28(5):499-510) (Brown, G C et al., Biochem. J (1992) 284: 1-13; Bruning, J C et al., Mol. Cell (1998) 2(5):559-569). Focal adhesion kinase (FAK) is of particular interest because of its role as a regulator of cell survival, proliferation, migration and invasion. FAK is activated by growth factor receptors such as IGF-1R, by binding through its N-terminal domain and autophosphorylation at $Tyr^{397}$. Activated or over expressed FAK is common in a wide variety of cancers, and may play a role in human carcinogenesis (van Nimwegen, M J et al., Biochem. Pharmacol. (2007) 73(5):597-609).

In addition to its role in cancers, the IGF receptor plays important and diverse roles in growth and development (Benito, M et al. Int J Biochem Cell Biol (1996) 28(5):499-510). IGF-1R has been implicated in several metabolic, and immunological diseases (Walenkamp, M J et al., Horm. Res. (2006) 66(5):221-230; Kurmasheva, R. T et al., Biochim. Biophys. Acta—Rev on Cancer (2006) 1766(1):1-22; Bateman, J M et al., Cell. Mol. Life Sci. (2006) 63(15):1701-1705, LeRoith, D, et al., Can. Lett. (2003) 195:127-137 and Samani A, et al., Endocrine Reviews 28(1):20-47.)

The role of the IGF/IGF-1R signaling system in cancer has been thoroughly examined over the last 15 years. In particular, the implication of IGF-1R in human cancer stems from its roles in stimulating mitogenesis, mobility and metastasis and in protecting against apoptosis. (Kurmasheva, Biochim. Biophys. Acta (2006).) Interest has grown with the understanding that in addition to its antiapoptotic and mitogenic roles, IGF/IGF-1R signaling seems to be necessary for the establishment and continuation of a transformed phenotype. It has been well established that constitutive activation or over expression, often results in non-adherent cell growth, even under serum depleted conditions in vitro, and is associated with the formation of tumors in nude mice. (Kaleko M et al, Mol Cell Biol. (1990) 10(2): 464-473). Perhaps even more importantly, it has been firmly established that cells, in which the gene encoding for IGF-1R has been deactivated, are totally resistant to transformation by agents which are normally capable of immortalizing normal cells, such as over expression of PDGFR or EGFR, the T antigen of the SV40 virus, the E5 protein of bovine papilloma virus, and activated ras. (DeAngelis T et al., Cell. Physiol. (1995) 164( ):214-221; Coppola D et al., Mol. Cell. Biol. (1994) 14(7):4588-4595; Morrione A J, Virol. 1995 695300-5303; Sell C et al., Mol. Cell. Biol. (1994) 14(6):3604-3612; Sell C et al., Proc. Natl. Acad. Sci. USA (1993) 90(23):11217-11221). Thus, IGF-1R has been identified as the major survival factor that protects from oncogene induced cell death (Harrington et al., EMBO J. (1994) 13():3286-3295). IGF-1R is expressed in a large number and variety of tumors and the IGFs amplify the tumor growth through their interaction with the receptor. Evidence supporting the role of IGF-1R in carcinogenesis can be found in studies using monoclonal antibodies directed towards the receptor which inhibit the proliferation of numerous cell lines in culture and in vivo (Arteaga C et al., Cancer Res. (1989) 49(22):6237-6241; Li et al., Biochem. Biophys. Res. Com. (1993) 196(1):92-98; Scotlandi K et al., Cancer Res. (1998) 58(18):4127-4131). Dominant negative IGF-1R is capable of inhibiting tumor proliferation (Jiang et al., Oncogene (1999) 18(44):6071-6077). The IGF signaling axis is implicated in various tumor types including:

breast cancer (Surmacz, J. Mammary Gland Bio. Neoplasia (2000) 5(1):95-105, LeRoith, Can. Lett. (2003) and Artega, Cancer Res. (1989)), sarcoma including soft-tissue sarcoma (e.g., cartilage sarcoma, connective tissue (chondrosarcoma) and fibrous matrix (fibrosarcoma)) and hard bony sarcomas (e.g., Ewing's sarcoma, osteosarcoma and giant cell tumor of bone) (Scotlandi, Cancer Res. (1998)

lung cancer, including non-small cell and small cell lung carcinomas and mesotheliomas (Jiang, Y et al., Oncogene (1999) 18:6071-6077 and LeRoith, Can. Lett. (2003), prostate cancer (Djavan et al., World J Urol. (2001) 19(4): 225-233; O'Brien et al., Urology (2001) 58(1):1-7 and LeRoith, Can. Lett. (2003)), colorectal cancer (Guo et al., Gastroenterology, 1992, 102, 1101-1108; Durai, R et al., Int. J Colorectal Dis. (2005) 20(3):203-220 and LeRoith, Can. Lett. (2003)), renal cancer (Kellerer M. et al., Int. J. Cancer (1995) 62(5): 501-507), pancreatic cancer (Bergmann, U et al., Cancer Res. (1995) 55(10):2007-2011), hematologic cancers, including lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma, megakaryoblastic leukemia, acute megakaryocytic leukemia, promyelocytic leukemia, erythroleukemia, malignant lymphoma, Hodgkins lymphoma, non-Hodgkins lymphoma, lymphoblastic T cell lymphoma, Burkitt's lymphoma, follicular lymphoma, myelodysplastic syndromes, (Zumkeller W et al., Leuk. Lymph (2002) 43(3):487-491; and Qi, Ann Hematol. (2006) 85:95-101), neuroblastomas (Zumkeller, W et al., Horm. Metab. Res. 1999, 31, 138-141), primary CNS tumors including: astrocytomas (also known as "gliomas") including glioblastoma multiforme; meningiomas and medulloblastomas (Zumkeller, W et al., Mol. Pathol. (2001) 54(4):227-229, Del Valle L, et al., Clin. Cancer Res. (2002) 8:1822-1830 and Trojan et al., Proc. Natl. Acad. Sci. USA (1992) 89:4874-4878), secondary CNS tumors, i.e., metastases in the central nervous system (e.g., the brain), of a tumor originating outside of the central nervous system (Burfeind P, et al, PNAS (1996) 93:7263-7268), head and neck cancer (Wu X., et al, Clin. Cancer Res. (2004) 10:3988-95), thyroid cancer (Vella V et al., J. Clin. Endocrinol. Metab. (2002) 87:245-254; Vella V et al., Mol. Pathol. (2001) 54(3):121-124), hepatocarcinoma (Alexia, C et al., Biochem. Pharmacol. (2004) 68:1003-1015), ovarian cancer, vulval cancer, cervical cancer, endometrial cancer, testicular cancer (Neuvians T P, et al, Neoplasia (2005) 7:446-56), bladder cancer (Zhao H., et al, J. Urology (2003) 169:714-717), esophageal cancer (Sohda M, et al, Anticancer Research. (2004) 24:3029-3034), gastric cancer (Jiang, Y, et al, Clinical & Experimental Metastasis (2004) 21:755-64), buccal cancer, cancer of the mouth, (Brady G et al., Int. J. of Oral & Maxillofacial Surg. (2007) 36:259-62).

GIST (gastrointestinal stromal tumor) (Trent J C, et al, Cancer. (2006) 107:1898-908), and skin cancer including melanoma (Yeh A H, et al, Oncogene. (2006) 25:6574-81).

Thus, in virtually all types of human cancers there is a strong association between dysregulation of IGF signaling and carcinogenesis (Bohula E A et al., Anticancer Drugs (2003) 14(9):669-682). Inhibition of IGF-1R and/or IR expression or function has been shown to block tumor growth and metastasis and also enhance sensitivity to other antineoplastic therapies, including cytotoxic drugs and radiation. (Bohula, Anticancer Drugs (2003).

Other receptor tyrosine kinases, the ErbB family tyrosine kinases, includes EGFR, ErbB2, ErbB3 and ErbB4. Aberrant activity in the ErbB family kinases has been implicated in a range of hyperproliferative disorders including psoriasis, rheumatoid arthritis, bronchitis and several cancers. The biological role of ErbB family RTKs and their implication in different disease states has been widely discussed (Ullrich, A., et al., *Cell* (Apr. 20, 1990) 61: 203-212; Aaronson, S., *Science* (1991) 254:1146-1153; Salomon, D., et al., *Crit. Rev. Oncol./Hematol.* (1995) 19:183-232; Woodburn, J. R., *Pharmacol. Ther.* (1999) 82: 2-3, 241-250; Normanno, N., et al., *Curr. Drug Targets* (2005) 6:243-257; and Hynes, N. et al., *Nat. Rev. Cancer* (2005) 5:341-345). In particular, elevated EGFR activity has been implicated in non-small cell lung, squamous cell lung, breast, bladder, head and neck squamous cell, esophageal, gastric, colorectal, pancreatic, thyroid, glial, cervical and ovarian cancers (Salomon (1995) supra; Woodburn (1999) supra; Normanno (2005) supra; Hynes (2005) supra). Furthermore, overexpression and/or mutation of ErbB2 has been implicated in non-small cell lung, breast, ovarian, esophageal, gastric, colorectal, glial, pancreatic and cervical cancers (Salomon (1995) supra; Normanno (2005) supra; Hynes (2005) supra). A timeline of events pertaining to the role of the ErbB family kinases in cancer may be found in Gschwind, A., et al., *Nat. Rev. Cancer* (2004) 4:361-370. By virtue of the role played by the ErbB family kinases in these cancers and the relative success of inhibitors of these kinases in the clinic, it is widely acknowledged that inhibitors of one or more ErbB family kinases will be useful for the treatment of such cancers.

PCT Publication No. WO03/031446, published 17 Apr. 2003 to GlaxoSmithKline, recites antiviral compounds of the formula:

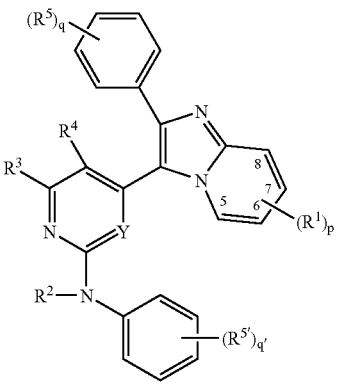

I wherein:
p is 0, 1 or 2;
each $R^1$ is the same or different and is independently selected from the group consisting of halo, alkyl, alkenyl, alkynyl, cycloalkyl, cycloalkenyl, Ay, Het, —$OR^7$, —OHet, —C(O)$R^9$, —C(O)Het, —$CO_2R^9$, —C(O)$NR^7R^8$, —C(NH)$NR^7R^8$, —S(O)$_nR^9$, —S(O)$_2NR^7R^8$, —$NR^7R^8$, —$NR^7$Ay, —NHHet, —$R^{10}$cycloalkyl, —$R^{10}$Het, —$R^{10}OR^9$, —$R^{10}SO_2NHCOR^9$, —$R^{10}NR^7R^8$, cyano, nitro and azido; or
two adjacent $R^1$ groups together with the atoms to which they are bonded form a $C_{5-6}$ cycloalkyl or 5- or 6-membered heterocyclic group including 1 or 2 heteroatoms;
each $R^7$ and $R^3$ are the same or different and are independently selected from the group consisting of H, alkyl, alkenyl, cycloalkyl, cycloalkenyl, —C(O)$R^9$, —$CO_2R^9$, —C(O)$NR^9R^{11}$, —C(NH)$NR^9R^{11}$, —$SO_2R^{10}$, —$SO_2NR^9R^{11}$, —$R^{10}$cycloalkyl, —$R^{10}OR^9$ and —$R^{10}NR^9R^{11}$;
each $R^9$ and $R^{11}$ are the same or different and are independently selected from the group consisting of H, alkyl, cycloalkyl, —$R^{10}$cycloalkyl, —$R^{10}$OH, —$R^{10}(OR^{10})_w$ where w is 1-10 and —$R^{10}NR^{10}R^{10}$;
each $R^{10}$ is the same or different and is independently selected from the group consisting of alkyl, cycloalkyl, alkenyl, cycloalkenyl and alkynyl;
Ay is aryl;
Het is a 5- or 6-membered heterocyclic or heteroaryl group;
$R^2$ is selected from the group consisting of H, alkyl and cycloalkyl;
n is 0, 1 or 2;
Y is N or CH;
$R^3$ and $R^4$ are the same or different and are each independently selected from the group consisting of H, halo, alkyl, alkenyl, cycloalkyl, Ay, Het, —$OR^7$, —C(O)$R^7$, —$CO_2R^7$, —$SO_2NHR^9$, —$NR^7R^8$, —NHHet and —$NHR^{10}$Het;
q and q' are the same or different and are each independently selected from the group consisting of 0, 1, 2 and 3; and
each $R^5$ and $R^{5'}$ are the same or different and are independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —C(O)$R^9$, —C(O)Ay, —C(O)Het, —$CO_2R^9$, —C(O)$NR^7R^8$, —C(O) $NR^7$Ay, —C(O)$NHR^{10}$Het, —C(S)$NR^9R^{11}$, —C(NH) $NR^7R^8$, —C(NH)$NR^7$Ay, —S(O)$_nR^9$, —S(O)$_2NR^7R^8$,
—S(O)$_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Het, —$R^{10}OR^9$, —$R^{10}$C(O)$R^9$, —$R^{10}CO_2R^9$, —$R^{10}$C(O) $NR^9R^{11}$, —$R^{10}$C(O)$NR^7$Ay, —$R^{10}$C(O)$NHR^{10}$Het, —$R^{10}$C(S)$NR^9R^{11}$, —$R^{10}$C(NH)$NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido; or
two adjacent $R^5$ or $R^{5'}$ groups together with the atoms to which they are bonded form a $C_{5-6}$ cycloalkyl or aryl.

PCT Publication No. WO2003/000689, published 3 Jan. 2003 to GlaxoSmithKline recites antiviral compounds of the formula:

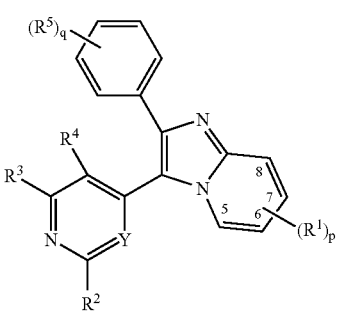

I wherein:
p is 0, 1, 2, 3 or 4;
each $R^1$ is the same or different and is independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —C(O)$R^9$, —C(O)Ay, —C(O)Het, —$CO_2R^9$, —C(O)$NR^7R^8$, —C(O)$NR^7$Ay, —C(O)$NHR^{10}$Ay, —C(O)$NHR^{10}$Het, —C(S)$NR^9R^{11}$, —C(NH)$NR^7R^8$, —C(NH)$NR^7$Ay, —S(O)$_nR^9$, —S(O)$_n$Ay, —S(O)$_n$Het, —S(O)$_2NR^7R^8$, —S(O)$_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Ay, —$R^{10}$Het, —$R^{10}$O—C(O)$R^9$, —$R^{10}$O—C(O)Ay, —$R^{10}$O—C(O) Het, —$R^{10}$O—S(O)$_nR^9$, —$R^{10}OR^9$, —$R^{10}$C(O)$R^9$, —$R^{10}CO_2R^9$, —$R^{10}$C(O)$NR^9R^{11}$, —$R^{10}$C(O)$NR^7$Ay, —$R^{10}$C(O)$NHR^{10}$Het, —$R^{10}$C(S)$NR^9R^{11}$, —$R^{10}$C(NH) $NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido; or
two adjacent $R^1$ groups together with the atoms to which they are bonded form a $C_{5-6}$cycloalkyl or a 5 or 6-membered heterocyclic ring containing 1 or 2 heteroatoms;
each $R^7$ and $R^8$ are the same or different and are independently selected from the group consisting of H, alkyl, cycloalkyl, alkenyl, cycloalkenyl, —$OR^9$, —C(O)$R^9$, —$CO_2R^9$, —C(O)$NR^9R^{11}$, —C(S)$NR^9R^{11}$, —C(NH) $NR^9R^{11}$, —$SO_2R^{10}$, —$SO_2NR^9R^{11}$, —$R^{10}$cycloalkyl, —$R^{10}OR^9$, —$R^{10}$C(O)$R^9$, —$R^{10}CO_2R^9$, —$R^{10}$C(O) $NR^9R^{11}$, —$R^{10}$C(S)$NR^9R^{11}$, —$R^{10}$C(NH)$NR^9R^{11}$, —$R^{10}SO_2R^{10}$, —$R^{10}SO_2NR^9R^{11}$, —$R^{10}SO_2NHCOR^9$, —$R^{10}NR^9R^{11}$, —$R^{10}NHCOR^9$, —$R^{10}NHSO_2R^9$ and —$R^{10}NHC(NH)NR^9R^{11}$;
each $R^9$ and $R^{11}$ are the same or different and are independently selected from the group consisting of H, alkyl, cycloalkyl, —$R^{10}$cycloalkyl, —$R^{10}$OH, —$R^{10}(OR^{10})_w$ where w is 1-10 and —$R^{10}NR^{10}R^{10}$;
each $R^{10}$ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

$R^2$ is selected from the group consisting of halo, alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_n NR^7R^8$, —$S(O)_n$Het, —$NR^7R^8$, —NHHet, —$NHR^{10}$Ay, —$NHR^{10}$Het, —$R^{10}NR^7R^8$ and —$R^{10}NR^7$Ay;

n is 0, 1 or 2;

Y is N or CH;

$R^3$ and $R^4$ are the same or different and are each independently selected from the group consisting of H, halo, alkyl, alkenyl, cycloalkyl, Ay, Het, —$OR^7$, —OAy, —$C(O)R^7$, —C(O)Ay, —$CO_2R^7$, —$CO_2$Ay, —$SO_2NHR^9$, —$NR^7R^8$, —$NR^7$Ay, —NHHet, —$NHR^{10}$Het, —$R^{10}$cycloalkyl, —$R^{10}OR^7$, —$R^{10}$OAy, —$R^{10}NR^7R^8$ and —$R^{10}NR^7$Ay;

q is 0, 1, 2, 3, 4 or 5; and each $R^5$ is the same or different and is independently selected from the group consisting of halo, alkyl, alkenyl, alkynyl, cycloalkyl, cycloalkenyl, Ay, Het, —$OR^7$, —OAy, —OHet, —$OR^{10}$Ay, —$OR^{10}$Het, —$C(O)R^9$, —C(O)Ay, —C(O)Het, —$CO_2R^9$, —$C(O)NR^7R^8$, —$C(O)NR^7$Ay, —$C(O)NHR^{10}$Het, —$C(S)NR^9R^{11}$, —$C(NH)NR^7R^8$, —$C(NH)NR^7$Ay, —$S(O)_nR^9$, —$S(O)_2NR^7R^8$, —$S(O)_2 NR^7$Ay, —$NR^7R^8$, —$NR^7$Ay, —NHHet, —$NHR^{10}$Ay, —$NHR^{10}$Het, —$R^{10}$cycloalkyl, —$R^{10}$Het, —$R^{10}OR^9$, —$R^{10}C(O)R^9$, —$R^{10}CO_2R^9$, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido; or two adjacent $R^5$ groups together with the atoms to which they are bonded form a $C_{5-6}$ cycloalkyl or aryl;

wherein when Y is CH, $R^3$ is not —$NR^7$Ay.

PCT Publication No. WO 91/00092 to SmithKline Beecham Corp. refers to imidazo[1,2-a]pyridine compounds of formula (I)

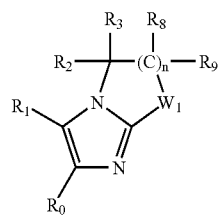

wherein:

$W_1$ is —$(CR_4R_5)$—$(CR_6R_7)$—, —$CR_5$=$CR_7$—, —N=$CR_7$—, —$S(O)_m$— or —O—; one of $R_1$ and $R_0$ is 4-pyridyl or $C_{1-4}$alkyl-4-pyridyl, provided that when $R_1$ is $C_{1-4}$alkyl-4-pyridyl the alkyl substituent is located at the 2-position of the pyridine ring, and the other of $R_1$ and $R_0$ is (a) phenyl or monosubstituted phenyl wherein said substituent is $C_{1-3}$alkylthio, $C_{1-3}$alkylsulfinyl, $C_{2-5}$1-alkenyl-1-thio, $C_{2-5}$1-alkenyl-1-sulfinyl, $C_{3-5}$2-alkenyl-1-thio, $C_{3-5}$2alkenyl-1-sulfinyl, 1-acyloxy-1-alkylthio, $C_{1-2}$alkoxy, halo, $C_{1-4}$alkyl or Z wherein Z is —S—S— $Z_1$ and $Z_1$ is phenyl or $C_{1-9}$alkyl; or (b) disubstituted phenyl wherein said substituents are independently $C_{1-3}$alkylthio, $C_{1-2}$alkoxy, halo or $C_{1-4}$alkyl; or (c) disubstituted phenyl wherein one of said substituents is $C_{1-3}$alkylsulfinyl, $C_{2-5}$1-alkenyl-1-thio, $C_{2-5}$1-alkenyl-1-sulfinyl, $C_{3-5}$2-alkenyl-1-thio, $C_{3-5}$2alkenyl-1-sulfinyl, or 1-acyloxy-1-alkylthio and the other is $C_{1-2}$alkoxy, halo or $C_{1-4}$alkyl; or (d) disubstituted phenyl wherein the substituents are the same and are $C_{1-3}$alkylsulfinyl, $C_{2-5}$1-alkenyl-1-thio, $C_{2-5}$1-alkenyl-1-sulfinyl, $C_{3-5}$2-alkenyl-1-thio, $C_{3-5}$2alkenyl-1-sulfinyl, or 1-acyloxy-1-alkylthio or wherein the substituents together form a methylene dioxy group; or (e) monosubstituted phenyl wherein said substituent is

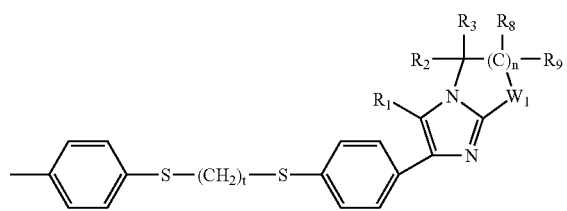

t is 0 or 1; $W_1$, $R_1$, $R_2$, $R_3$, $R_4$, $R_5$, $R_6$, $R_7$, $R_8$ and $R_9$ are as defined herein;

provided that:

1) when $W_1$ is —$(CR_4R_5)$—$(CR_6R_7)$— then n is 0 or 1;

and $R_2$, $R_3$, $R_4$, $R_5$, $R_6$, $R_7$, $R_8$ and $R_9$ are independently —H or $C_{1-2}$alkyl; and when $R_1$ or $R_0$ is 4-pyridyl, the other of $R_1$ and $R_0$ is other than mono-$C_{1-2}$alkoxy-substituted phenyl or mono-halo-substituted phenyl; or when n is 0, $R_4$ and $R_5$ together are oxo; $R_4$ and $R_5$ are both fluoro, or one of $R_4$ and $R_5$ is H and the other is OH;

2) when $W_1$ is —$CR_5$=$CR_7$— or —N=$CR_7$— then n is 1;

$R_3$, $R_5$, $R_7$ and $R_9$ are independently —H or $C_{1-2}$alkyl; and $R_2$ and $R_8$ together represent a double bond in the B ring such that the B ring is an aromatic pyridine or pyrimidine ring;

3) when $W_1$ is —$S(O)_m$— then m is 0, 1 or 2;

n is 1 or 2;

$R_3$ and $R_9$ are independently —H or $C_{1-2}$alkyl;

$R_2$ and $R_8$ are independently —H or $C_{1-2}$alkyl or $R_2$ and $R_8$ together represent a double bond in the B ring such that the B ring is an aromatic thiazole ring; further provided that:

(a) when $R_2$ and $R_8$ are independently —H or $C_{1-2}$alkyl and $R_1$ or $R_0$ is 4-pyridyl, then the other of $R_1$ and $R_0$ is other than mono-$C_{1-2}$alkoxy-substituted phenyl or mono-halo-substituted phenyl; and (b) when $R_2$ and $R_8$ together represent a double bond in the B ring such that the B ring is an aromatic thiazole ring, the m is 0 and n is 1; and 4) when $W_1$ is —O— then n is 1;

$R_3$ and $R_9$ are independently —H or $C_{1-2}$alkyl; and $R_2$ and $R_8$ together represent a double bond in the B ring such that the B ring is an aromatic oxazole ring;

or a pharmaceutically acceptable salt thereof for use in the inhibition of interleukin-1 and tumor necrosis factor production by monocytes and/or macrophages.

PCT Publication No. WO 01/14375 to AstraZeneca AB relates to imidazo[1,2-a]pyridine and pyrazolo[2,3-a]pyridine derivatives of formula (I)

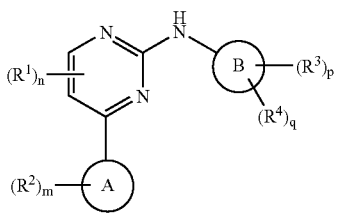

wherein Ring A is a imidazo[1,2-a]pyridine or pyrazolo[2,3-a]pyrid-3-yl; R² is as defined therein, m is 0-5; wherein the values of R² may be the same or different; R¹ is as defined therein; n is 0 to 2, wherein the values of R¹ may be the same or different; Ring B is phenyl or phenyl fused to a $C_{5-7}$cycloalkyl ring; R³ is as defined therein; p is 0-4; wherein the values of R³ may be the same or different; R⁴ is as defined therein; q is 0-2; wherein the values of R⁴ may be the same or different; and wherein p+q≦5; or a pharmaceutically acceptable salt or an in vivo hydrolysable ester thereof. The use of the compounds of formula (I) in the inhibition of cell cycle kinases CDK2, CDK4 and CDK6 are also described.

SUMMARY OF THE INVENTION

In a first aspect of the present invention, there is provided a compound of formula (I):

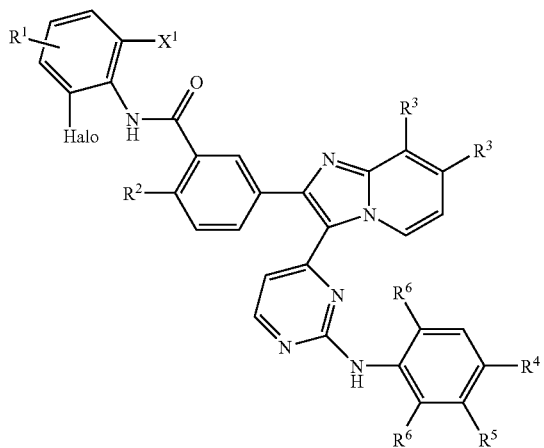

wherein:
X¹ is H or halo;
R¹ is H, halo or haloalkyl;
R² is H or O-alkyl;
each R³ is the same or different and is independently selected from H, halo, alkyl, haloalkyl and O-alkyl;
one of R⁴ and R⁵ is selected from H, halo, alkyl and O-alkyl, and the other is a moiety selected from:

—O—(CHR⁷)$_a$—R⁸ (i)

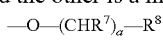

—(CHR⁹)$_b$—(A)—(R¹⁰)$_n$ and (ii)

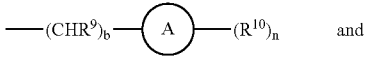

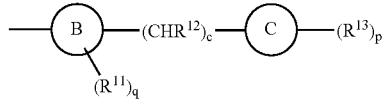

—(B)—(CHR¹²)$_c$—(C)—(R¹³)$_p$ (iii)
    |
  (R¹¹)$_q$ wherein:
(i) each R⁷ is the same or different and is independently selected from H, alkyl and OH;
a is 0, 1, 2 or 3;
R⁸ is selected from NH₂, N(H)alkyl, N(alkyl)₂ and a group of formula (iv):

—(D)—R¹⁴ (iv)

wherein:
Ring D is a 5-6 membered N-heterocycle optionally including 1 or 2 additional heteroatoms selected from N, O and S and
R¹⁴ is selected from H, halo, alkyl, OH, O-alkyl, oxo, SO₂alkyl, alkylene-O-alkyl and alkylene-SO₂alkyl;
(ii) b is 0, 1, 2 or 3;
each R⁹ is the same or different and is independently selected from H, alkyl and OH;
Ring A is selected from 5-10 membered heterocycles including 1, 2 or 3 heteroatoms selected from N, O and S and 5-6 membered heteroaryls including 1, 2 or 3 heteroatoms selected from N, O and S;
n is 0, 1 or 2;
each R¹⁰ is the same or different and is independently selected from halo, alkyl, haloalkyl, OH, O-alkyl, oxo, NH₂, N(H)alkyl, N(alkyl)₂, N(alkylene-O-alkyl)₂, C(O)alkyl, SO₂alkyl, alkylene-O-alkyl, alkylene-NH₂, alkylene-N(H)alkyl, alkylene-N(alkyl)₂, alkylene-C(O)alkyl, and alkylene-SO₂alkyl;
(iii) c is 0, 1 or 2;
each R¹² is the same or different and is independently H or alkyl;
Ring B is selected from cyclohexylene, 5-6 membered heterocycles including 1, 2 or 3 heteroatoms selected from N, O and S and 5-6 membered heteroaryls including 1, 2 or 3 heteroatoms selected from N, O and S;
q is 0 or 1;
R¹¹ is halo, alkyl or haloalkyl;
Ring C is a 5-10 membered heterocycle including 1, 2 or 3 heteroatoms selected from N, O and S;
p is 0, 1 or 2;
each R¹³ is the same or different and is independently selected from halo, alkyl, haloalkyl, OH, O-alkyl, oxo, NH₂, N(H)alkyl, N(alkyl)₂, N(alkylene-O-alkyl)₂, C(O)alkyl, SO₂alkyl, alkylene-O-alkyl, alkylene-NH₂, alkylene-N(H)alkyl, alkylene-N(alkyl)₂, alkylene-C(O)alkyl, and alkylene-SO₂alkyl; and
each R⁶ is the same or different and is independently selected from H, halo, alkyl, haloalkyl, O-alkyl and O-haloalkyl;
or a pharmaceutically acceptable salt thereof.
Selected compounds of the formula (I) include:
3-[3-(2-{[4-(1,4'-bipiperidin-1'-yl)-2-(methyloxy)phenyl]amino}-4-pyrimidinyl)imidazo[1,2-a]pyridin-2-yl]-N-(2,6-difluorophenyl)benzamide;

N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide;

N-(2,6-difluorophenyl)-3-(3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide;

N-(2,6-difluorophenyl)-3-(3-{2-[(5-methyl-2-(methyloxy)-4-{4-[2-(methylsulfonyl)ethyl]-piperazinyl}phenyl)amino]-4-pyrimidinyl}imidazo[1,2-a]pyridin-2-yl)benzamide;

N-(2,6-difluorophenyl)-2-(ethyloxy)-5-(3-{2-[(5-methyl-2-(methyloxy)-4-{4-[2-(methylsulfonyl)ethyl]-1-piperazinyl}phenyl)amino]-4-pyrimidinyl}imidazo[1,2-a]pyridin-2-yl)benzamide;

N-(2,6-difluorophenyl)-2-(ethyloxy)-5-(3-{2-[(5-methyl-2-(methyloxy)-4-{1-[2-(methylsulfonyl)ethyl]-4-piperidinyl}phenyl)amino]-4-pyrimidinyl}imidazo[1,2-a]pyridin-2-yl)benzamide;

N-(2,6-difluorophenyl)-5-(7-fluoro-3-{2-[(2-(methyloxy)-4{-4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide;

N-(2,6-difluorophenyl)-5-(3-{2-[(2-(ethyloxy)-5-methyl-4-{4-[2-(methylsulfonyl)ethyl]-1-piperidinyl}phenyl)amino]-4-pyrimidinyl}imidazo[1,2-a]pyridin-2-yl)-2-(methyloxy)benzamide; and N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide;

and pharmaceutically acceptable salts thereof.

In a second aspect, the present invention provides N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide and pharmaceutically acceptable salts thereof.

In a third aspect, the present invention provides N-(2,6-difluorophenyl)-3-(3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide and pharmaceutically acceptable salts thereof.

In a fourth aspect, the present invention provides 3-[3-(2-{[4-(1,4'-bipiperidin-1'-yl)-2-(methyloxy)phenyl]amino}-4-pyrimidinyl)imidazo[1,2-a]pyridin-2-yl]-N-(2,6-difluorophenyl)benzamide and pharmaceutically acceptable salts thereof.

In a fifth aspect, the present invention provides N-(2,6-difluorophenyl)-5-(3-{2-[(2-(ethyloxy)-5-methyl-4-{4-[2-(methylsulfonyl)ethyl]-1-piperidinyl}phenyl)amino]-4-pyrimidinyl}imidazo[1,2-a]pyridin-2-yl)-2-(methyloxy)benzamide and pharmaceutically acceptable salts thereof.

In a sixth aspect, the present invention provides N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide and pharmaceutically acceptable salts thereof. In a particular embodiment, the compound is as the monocitric acid (citrate) salt. In another particular embodiment, the compound is the free base.

In a seventh aspect of the present invention, there is provided a pharmaceutical composition comprising a compound of formula (I) or a pharmaceutically acceptable salt thereof. In one embodiment, the pharmaceutical composition further comprises one or more of pharmaceutically acceptable carriers, diluents and excipients.

In an eighth aspect of the present invention, there is provided a method of treating a susceptible neoplasm in a mammal in need thereof, comprising administering to the mammal a therapeutically effective amount of a compound of formula (I) or a pharmaceutically acceptable salt thereof.

In a ninth aspect of the present invention, there is provided a method of treating breast cancer in a mammal in need thereof, comprising administering to the mammal a therapeutically effective amount of a compound of formula (I) or a pharmaceutically acceptable salt thereof.

In another aspect of the present invention, there is provided a method for treating sarcoma in a mammal in need thereof which comprises administering to the mammal a therapeutically effective amount of a compound of formula (I) or a pharmaceutically acceptable salt thereof.

In another aspect of the present invention, there is provided a method of treating lung cancer in a mammal in need thereof which comprises administering to the mammal a therapeutically effective amount of a compound of formula (I) or a pharmaceutically acceptable salt thereof.

In another aspect of the present invention, there is provided a method of treating non-small cell lung carcinoma in a mammal in need thereof which comprises administering to the mammal a therapeutically effective amount of a compound of formula (I) or a pharmaceutically acceptable salt thereof.

In another aspect of the present invention, there is provided a method for treating prostate cancer in a mammal in need thereof which comprises administering to the mammal a therapeutically effective amount of a compound of formula (I) or a pharmaceutically acceptable salt thereof.

In another aspect of the present invention, there is provided a method for treating colorectal cancer in a mammal in need thereof which comprises administering to the mammal a therapeutically effective amount of a compound of formula (I) or a pharmaceutically acceptable salt thereof.

In another aspect of the present invention, there is provided a method for treating pancreatic cancer in a mammal in need thereof which comprises administering to the mammal a therapeutically effective amount of a compound of formula (I) or a pharmaceutically acceptable salt thereof.

In another aspect of the present invention, there is provided a method for treating a hematologic cancer in a mammal in need thereof which comprises administering to the mammal a therapeutically effective amount of a compound of formula (I) or a pharmaceutically acceptable salt thereof.

In another aspect of the present invention, there is provided a method for treating multiple myeloma in a mammal in need thereof which comprises administering to the mammal a therapeutically effective amount of a compound of formula (I) or a pharmaceutically acceptable salt thereof.

In another aspect of the present invention, there is provided a method for treating head and neck cancer in a mammal in need thereof which comprises administering to the mammal a therapeutically effective amount of a compound of formula (I) or a pharmaceutically acceptable salt thereof.

In another aspect of the present invention, there is provided a method for treating ovarian cancer in a mammal in need thereof which comprises administering to the mammal a therapeutically effective amount of a compound of formula (I) or a pharmaceutically acceptable salt thereof.

In a further aspect of the present invention, there is provided a process for preparing a compound of formula (I). The process comprises reacting a compound of formula (V):

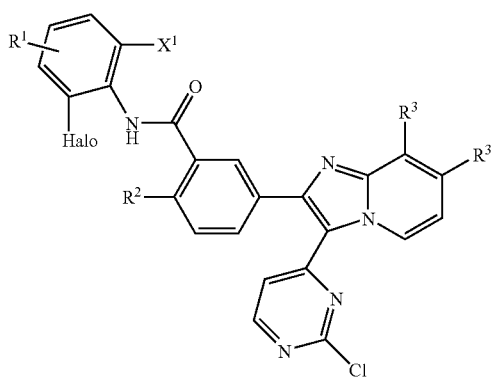

with an aniline of formula (VI):

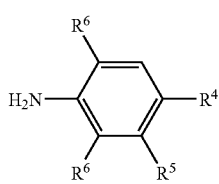

wherein all variables are as defined above.

In another aspect of the present invention, there is provided a process for preparing a compound of formula (I). The process comprises reacting a compound of formula (XV):

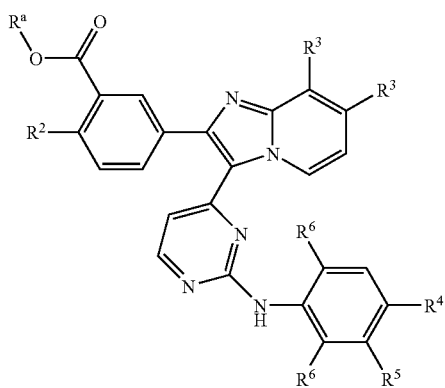

wherein $R^a$ is alkyl or cycloalkyl, and all other variables are as defined above; with an aniline of formula (IX):

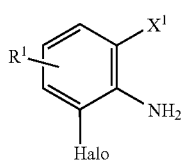

wherein all variables are as defined above.

In another aspect of the present invention, there is provided a compound of formula (I), or a pharmaceutically acceptable salt thereof for use in therapy.

In another aspect of the present invention, there is provided a compound of formula (I), or a pharmaceutically acceptable salt thereof for use in the treatment of a susceptible neoplasm (e.g., breast cancer, sarcomas, lung cancer (including non-small cell lung carcinoma), prostate cancer, colorectal cancer, renal cancer, pancreatic cancer, hematologic cancers (including multiple myeloma), neuroblastomas, primary CNS tumors, secondary CNS tumors, head and neck cancer, thyroid cancer, hepatocarcinoma, ovarian cancer, vulval cancer, cervical cancer, endometrial cancer, testicular cancer, bladder cancer, esophageal cancer, gastric cancer, buccal cancer, cancer of the mouth, GIST (gastrointestinal stromal tumor) or skin cancer (including melanoma), in a mammal (e.g., human) in need thereof.

In another aspect, there is provided a compound of formula (I), or a pharmaceutically acceptable salt thereof for use in the treatment of breast cancer, sarcomas, lung cancer, non-small cell lung carcinoma, prostate cancer, colorectal cancer, pancreatic cancer, hematologic cancers, multiple myeloma, head and neck cancer or ovarian cancer, in a mammal (e.g., human) in need thereof.

In another aspect of the present invention, there is provided the use of a compound of formula (I), or a pharmaceutically acceptable salt thereof for the preparation of a medicament for use in the treatment of a susceptible neoplasm (e.g., breast cancer, sarcomas, lung cancer (including non-small cell lung carcinoma), prostate cancer, colorectal cancer, renal cancer, pancreatic cancer, hematologic cancers (including multiple myeloma), neuroblastomas, primary CNS tumors, secondary CNS tumors, head and neck cancer, thyroid cancer, hepatocarcinoma, ovarian cancer, vulval cancer, cervical cancer, endometrial cancer, testicular cancer, bladder cancer, esophageal cancer, gastric cancer, buccal cancer, cancer of the mouth, GIST (gastrointestinal stromal tumor) or skin cancer (including melanoma), in a mammal (e.g., human) in need thereof.

In another aspect of the present invention, there is provided the use of a compound of formula (I), or a pharmaceutically acceptable salt thereof for the preparation of a medicament for use in the treatment of breast cancer, sarcoma, lung cancer, non-small cell lung carcinoma, prostate cancer, colorectal cancer, pancreatic cancer, hematologic cancers, multiple myeloma, head and neck cancer or ovarian cancer, in a mammal (e.g., human) in need thereof.

In another aspect of the present invention, there is provided a pharmaceutical composition comprising a compound of formula (I), or a pharmaceutically acceptable salt thereof for use in the treatment of a susceptible neoplasm (e.g., breast cancer, sarcomas, lung cancer (including non-small cell lung carcinoma), prostate cancer, colorectal cancer, renal cancer, pancreatic cancer, hematologic cancers (including multiple myeloma), neuroblastomas, primary CNS tumors, secondary CNS tumors, head and neck cancer, thyroid cancer, hepatocarcinoma, ovarian cancer, vulval cancer, cervical cancer, endometrial cancer, testicular cancer, bladder cancer, esophageal cancer, gastric cancer, buccal cancer, cancer of the mouth, GIST (gastrointestinal stromal tumor) or skin cancer (including melanoma), in a mammal (e.g., human) in need thereof.

These and other aspects of the invention are described in further detail in the description and examples which follow.

DETAILED DESCRIPTION OF THE INVENTION

As used herein the term "IGF-1R family tyrosine kinase" refers to IGF-1R tyrosine kinase (herein "IGF-1R"), insulin receptor tyrosine kinase (herein "IR") and Insulin receptor-related receptor tyrosine kinase (herein "IRR").

As used herein the term "ErbB family kinase" refers to ErbB kinases and their dimerization partners including EGFR (also known as ErbB1), ErbB2, ErbB3 and ErbB4.

As used herein, "compound(s) of formula (I)" means any compound having the structural formula (I) as defined by the variable definitions provided, solvate, hydrate, and amorphous and crystalline forms, including one or more polymorphic forms, and mixtures thereof. In the case of compounds of formula (I) which possess one or more chiral centers, the compounds may be in the form of a racemic mixture, or one or more isomerically enriched or pure stereoisomers, including enantiomers and diastereomers thereof. In such embodiments, "compound(s) of formula (I)" includes the racemic form as well as the enriched or pure enantiomers and diasteriomers. Enantiomerically enriched or pure compounds will be designated using conventional nomenclature, including the designations +, −, R, S, d, l, D and L, according to the predominant isomer present. Where a compound of the invention contains an alkenyl or alkenylene group, cis (E) and trans (Z) isomerism may also occur. In such embodiments, "compound(s) of formula (I)" includes the individual stereoisomers of the compound, which will be indicated using conventional, cis/trans nomenclature. It should also be understood that compounds of formula (I) may exist in tautomeric forms other than that shown in the formula and alternative tautomeric forms are also included within "compound(s) of formula (I)."

As used herein, "compound(s) of the invention" means a compound of formula (I) (as defined above) in any version, i.e., as the free base or as a pharmaceutically acceptable salt thereof. The compound as any version may be in any form, including solvates, hydrates, amorphous or crystalline forms, including specific polymorphic forms, or mixture of forms.

Intermediates may also be present as salts. In reference to intermediates, the phrase "compound(s) of formula (number)" means a compound having that structural formula or a pharmaceutically acceptable salt thereof.

The term "alkyl" as used herein refers to linear or branched hydrocarbon chains having from 1 to 8 carbon atoms (i.e., $C_{1-8}$alkyl), unless a different number of atoms is specified. Examples of "alkyl" as used herein include, but are not limited to, methyl, ethyl, n-propyl, n-butyl, n-pentyl, isobutyl, isopropyl and tert-butyl. Similarly, the term "alkylene" refers to linear or branched divalent hydrocarbon chains containing from 1 to 8 carbon atoms, unless a different number of atoms is specified. Examples of "alkylene" as used herein include, but are not limited to, methylene, ethylene, propylene, butylene and isobutylene.

As used herein, the term "cycloalkyl" refers to a saturated monocyclic carbocyclic ring having from 3 to 8 carbon atoms, unless a different number of atoms is specified. "Cycloalkyl" includes by way of example cyclopropyl, cyclobutyl, cyclopentyl, cyclohexyl, cycloheptyl and cyclooctyl.

The terms "Halo", "halo" or "halogen" are synonymous and refer to fluoro, chloro, bromo and iodo. "Halo" is specifically used to identify a particular substituent of formula (I) designated as such.

As used herein, "haloalkyl" refers to an alkyl, as defined above, substituted by one or more halogen atoms, fluoro, chloro, bromo or iodo. Where the haloalkyl group has fewer than 8 carbon atoms, the number of carbon atoms in the group is indicated as, for example, halo$C_{1-3}$alkyl. Examples of haloalkyl as used herein include, but are not limited to fluoromethyl, difluoromethyl, trifluoromethyl, fluoroethyl, trifluoroethyl and the like.

The term "oxo" as used herein refers to the group =O attached directly to a carbon atom of a hydrocarbon ring (e.g., cyclohexyl), or a C, N or S of a heterocyclic or heteroaryl ring to result in oxides, —N-oxides, sulfones and sulfoxides.

As used herein, the terms "heterocycle" and "heterocyclic" are synonymous and refer to monocyclic saturated or unsaturated non-aromatic groups, fused or bridged bicyclic saturated or unsaturated non-aromatic groups and spiro systems, each having from 5 to 10 members (unless a different number of members is specified) including 1, 2, 3 or 4 heteroatoms selected from N, O and S, unless a different number of heteroatoms is specified. In all embodiments wherein the heterocycle includes 2 or more heteroatoms, the heteroatoms may be the same or different and are independently selected from N, O and S. In all embodiments wherein the compound of formula (I) includes two or more heterocyclic groups, the heterocyclic groups may be the same or different and are independently selected. Examples of particular heterocyclic groups include but are not limited to tetrahydrofuran, dihydropyran, tetrahydropyran, pyran, thietane, 1,4-dioxane, 1,3-dioxane, 1,3-dioxalane, piperidine, piperazine, pyrrolidine, morpholine, thiomorpholine, thiazolidine, oxazolidine, tetrahydrothiopyran, tetrahydrothiophene and the like.

As used herein, the term "N-heterocycle" refers to monocyclic saturated or unsaturated non-aromatic groups, fused or bridged bicyclic saturated or unsaturated non-aromatic groups and spiro systems, each having from 5 to 10 members (unless a different number of members is specified) including at least one N and optionally 1, 2 or 3 additional heteroatoms selected from N, O and S, unless a different number of additional heteroatoms is specified. By "additional heteroatoms" is meant 1, 2 or 3 heteroatoms in addition to the N already specified in the N-heterocycle ring. In all embodiments wherein the heterocycle includes 1 or more additional heteroatoms, the heteroatoms may be the same or different and are independently selected from N, O and S. In all embodiments wherein the compound of formula (I) includes two or more N-heterocyclic groups, the N-heterocyclic groups may be the same or different and are independently selected. N-heterocycles may be bound through the N of the N-heterocyclic ring. Examples of N-heterocycles include piperidine, piperazine, pyrrolidine, morpholine and thiomorpholine.

As used herein, the term "heteroaryl" refers to aromatic, monocyclic groups, aromatic fused bicyclic groups and fused bicyclic groups which have both aromatic and non-aromatic rings, each having from 5 to 10 members (unless a different number of members is specified) including 1, 2, 3, or 4 heteroatoms selected from N, O and S, unless a different number of heteroatoms is specified. In all embodiments wherein the heteroaryl includes 2 or more heteroatoms, the heteroatoms may be the same or different and are independently selected from N, O and S. In all embodiments wherein the compound of formula (I) includes two or more heteroaryl groups, the heteroaryl groups may be the same or different and are independently selected. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, tetrahydropyrimidine, triazine, quinoline, tetrahydroquinoline, isoquinoline, tetrahydroisoquinoline, benzofuran, benzothiophene, indole, indoline, indazole, benzodioxane, benzodioxin, benzodithiane, benzoxazine, benzopiperidine and benzopiperzine.

As used herein, the term "N-heteroaryl" refers to aromatic, monocyclic groups, aromatic fused bicyclic groups and fused bicyclic groups which have both aromatic and non-aromatic rings, each having from 5 to 10 members (unless a different number of members is specified) including at least one N and optionally 1, 2 or 3 additional heteroatoms selected from N, O and S, unless a different number of heteroatoms is specified. By "additional heteroatoms" is meant 1, 2 or 3 heteroatoms in addition to the N already present in the N-heteroaryl. In all embodiments wherein the heteroaryl includes 1 or more additional heteroatoms, the heteroatoms may be the same or different and are independently selected from N, O and S. In all embodiments wherein the compound of formula (I) includes two or more N-heteroaryl groups, the N-heteroaryl groups may be the same or different and are independently selected. Examples of N-heteroaryls include pyrrole, imidazole, pyrazole, thiazole, isoxazole, pyridine, pyridazine, pyrazine, pyrimidine, triazine, quinoline, isoquinoline, indole, indoline, benzopiperidine and benzopiperzine.

As used herein, the term "members" (and variants thereof e.g., "membered") in the context of heterocyclic and heteroaryl groups refers to the total number of ring atoms, including carbon and heteroatoms N, O and/or S. Thus, an example of a 6-membered heterocyclic ring is piperidine and an example of a 6-membered heteroaryl ring is pyridine.

As used herein, the term "optionally" means that the invention includes both embodiments wherein the described condition is and is not met. Thus, an N-heterocycle optionally including 1, 2 or 3 additional heteroatoms describes N-heterocycles including no additional heteroatoms as well as N-heterocycles including 1, 2 or 3 additional heteroatoms.

The present invention provides compounds of formula (I):

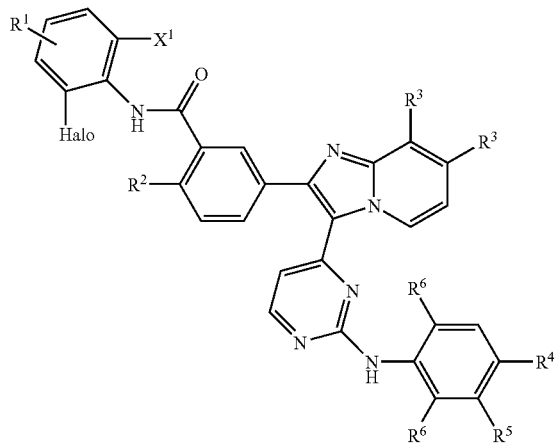

(I)

wherein:
$X^1$ is H or halo;
$R^1$ is H, halo or haloalkyl;
$R^2$ is H or O-alkyl;
each $R^3$ is the same or different and is independently selected from H, halo, alkyl, haloalkyl and O-alkyl;
one of $R^4$ and $R^5$ is selected from H, halo, alkyl and O-alkyl, and the other is a moiety selected from:

 (i)

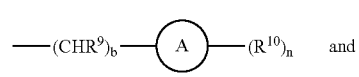 and (ii)

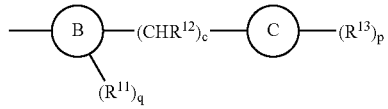 (iii)

wherein:
(i) each $R^7$ is the same or different and is independently selected from H, alkyl and OH;
a is 0, 1, 2 or 3;
$R^8$ is selected from $NH_2$, N(H)alkyl, N(alkyl)$_2$ and a group of formula (iv):

 (iv)

wherein:
Ring D is a 5-6 membered N-heterocycle optionally including 1 or 2 additional heteroatoms selected from N, O and S and
$R^{14}$ is selected from H, halo, alkyl, OH, O-alkyl, oxo, $SO_2$alkyl, alkylene-O-alkyl and alkylene-$SO_2$alkyl;
(ii) b is 0, 1, 2 or 3;
each $R^9$ is the same or different and is independently selected from H, alkyl and OH;
Ring A is selected from 5-10 membered heterocycles including 1, 2 or 3 heteroatoms selected from N, O and S and 5-6 membered heteroaryls including 1, 2 or 3 heteroatoms selected from N, O and S;
n is 0, 1 or 2;
each $R^{10}$ is the same or different and is independently selected from halo, alkyl, haloalkyl, OH, O-alkyl, oxo, $NH_2$, N(H)alkyl, N(alkyl)$_2$, N(alkylene-O-alkyl)$_2$, C(O)alkyl, $SO_2$alkyl, alkylene-O-alkyl, alkylene-$NH_2$, alkylene-N(H)alkyl, alkylene-N(alkyl)$_2$, alkylene-C(O)alkyl, and alkylene-$SO_2$alkyl;
(iii) c is 0, 1 or 2;
each $R^{12}$ is the same or different and is independently H or alkyl;
Ring B is selected from cyclohexylene, 5-6 membered heterocycles including 1, 2 or 3 heteroatoms selected from N, O and S and 5-6 membered heteroaryls including 1, 2 or 3 heteroatoms selected from N, O and S;
q is 0 or 1;
$R^{11}$ is halo, alkyl or haloalkyl;
Ring C is a 5-10 membered heterocycle including 1, 2 or 3 heteroatoms selected from N, O and S;
p is 0, 1 or 2;
each $R^{13}$ is the same or different and is independently selected from halo, alkyl, haloalkyl, OH, O-alkyl, oxo, $NH_2$, N(H)alkyl, N(alkyl)$_2$, N(alkylene-O-alkyl)$_2$, C(O)alkyl, $SO_2$alkyl, alkylene-O-alkyl, alkylene-$NH_2$, alkylene-N(H)alkyl, alkylene-N(alkyl)$_2$, alkylene-C(O)alkyl, and alkylene-$SO_2$alkyl; and
each $R^6$ is the same or different and is independently selected from H, halo, alkyl, haloalkyl, O-alkyl and O-haloalkyl;
and pharmaceutically acceptable salts thereof.

The compounds of formula (I) and the compounds of the invention are described in the conventional manner employing variables to represent a number of possible substituents or groups. The original, particular and preferred definitions of variables described herein apply equally to compounds of formula (I) and compounds of the invention. For brevity, the following description will refer to "compounds of the invention" rather than to both compounds of formula (I) as compounds of the invention encompasses all compounds of formula (I). It should be understood that the definition of variables utilized to describe the compounds of the invention will be selected in light of the knowledge possessed by the ordinarily skilled organic chemist such that embodiments which such chemist would consider to be obviously inoperative or unstable are avoided. For example, the organic chemist of ordinary skill in the art would appreciate that moieties such as —N(H)CH$_2$F, —N(H)CH$_2$NH$_2$, —OCH$_2$NH$_2$ and the like, result in unstable acetyls, aminals or iminium ions. As such, the present invention should be understood such that the variables are defined in a manner which avoids such embodiments.

In one embodiment, the compounds of the invention are defined wherein $X^1$ is halo. In one particular embodiment, Halo and $X^1$ are both F.

$R^1$ may be bound at any one of the 3-, 4- or 5-position of the phenyl ring as numbered below.

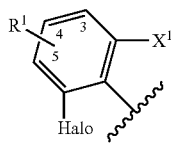

wherein all variables are as defined above.

In one preferred embodiment, $R^1$ is bound at the 4-position of the phenyl ring.

In one embodiment, $R^1$ is H or halo. In one particular embodiment, $R^1$ is H. In another embodiment, $X^1$ is halo and $R^1$ is H.

A particular embodiment of the compounds of the invention is defined wherein $R^1$ is bound at the 4-position of the phenyl ring and Halo, $X^1$ and $R^1$ are all F. One preferred embodiment of the compounds of the invention is defined wherein Halo and $X^1$ are both F and $R^1$ is H. This embodiment is depicted by the formula (I-a):

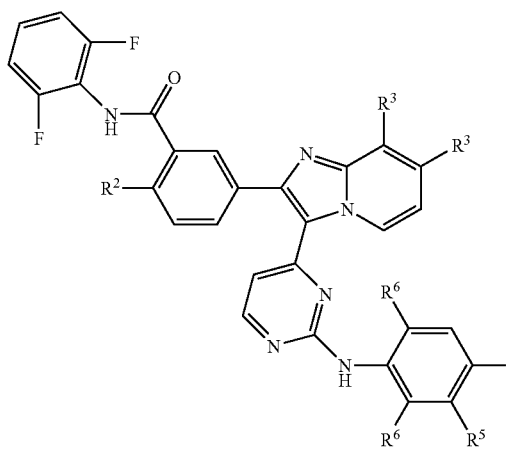

(I-a)

wherein all variables are as defined above.

In one embodiment, the compounds of the invention are defined wherein $R^2$ is H or O—C$_{1-3}$alkyl (e.g., particularly O-methyl, O-ethyl, O-isopropyl and O-n-propyl). In one particular embodiment, $R^2$ is H. In another particular embodiment, $R^2$ is O-methyl. In another particular embodiment, $R^2$ is O-ethyl.

In one embodiment, the compounds of the invention are defined wherein each $R^3$ is the same or different and is independently selected from H, halo, C$_{1-3}$alkyl, haloC$_{1-3}$alkyl and O—C$_{1-3}$alkyl, or any subset thereof. In one particular embodiment, at least 1 $R^3$ is H and the other is selected from H, halo, C$_{1-3}$alkyl, haloC$_{1-3}$alkyl and O—C$_{1-3}$alkyl, or any subset thereof. In one particular embodiment, at least 1 $R^3$ is H and the other is selected from H, F, Cl, methyl, CF$_3$ and O-methyl, or any subset thereof. In one particular embodiment, both $R^3$ are H. In one particular embodiment, 1 $R^3$ is H and the other is F.

The present invention is defined such that one of $R^4$ and $R^5$ is selected from H, halo, alkyl and O-alkyl and the other of $R^4$ and $R^5$ is a moiety selected from:

—O—(CHR$^7$)$_a$—R$^8$ (i)

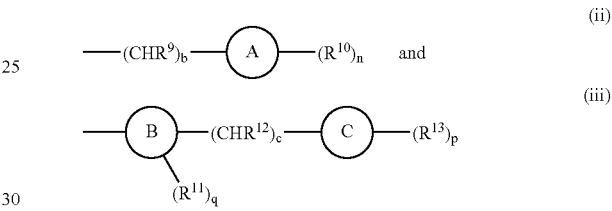

wherein all variables are as defined above.

According to one embodiment of the invention, one of $R^4$ and $R^5$ is selected from H, halo, alkyl and O-alkyl, and the other is a moiety (i).

In one embodiment, $R^4$ is selected from H, halo, alkyl and O-alkyl, and $R^5$ is a moiety of formula (I). In one embodiment, $R^4$ is H and $R^5$ is a moiety (i). A particular embodiment of the compounds of the invention is depicted in formula (I-a(i)):

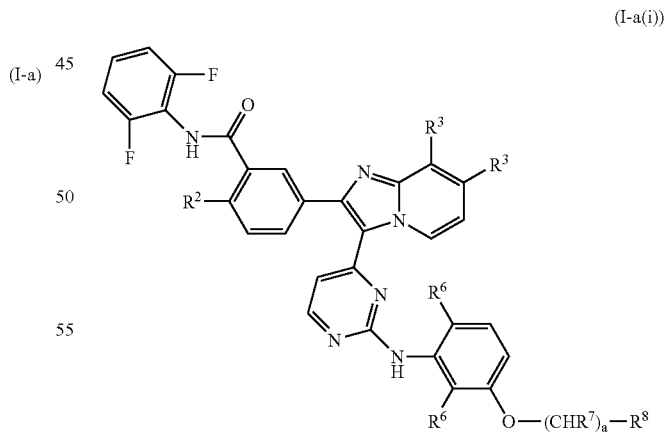

(I-a(i))

wherein all variables are as defined above.

In one embodiment, the moiety (i) is defined wherein a is 2 or 3. In one particular embodiment, a is 2.

In one embodiment, the moiety (i) is defined wherein each $R^7$ is the same or different and is independently H or OH. In one particular embodiment, each $R^7$ is H. A particular embodiment the moiety (i) is defined wherein a is 2 or 3 and each $R^7$ the same or different and is independently H or OH. A preferred embodiment of the invention is defined wherein $R^5$ is a moiety (i), a is 2 and each $R^7$ is H.

In one embodiment, the moiety (i) is defined wherein $R^8$ is selected from $N(alkyl)_2$ and a group of formula (Iv):

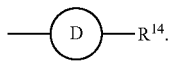
(iv)

is referred to herein as "Ring D." Ring D may be bound to the alkylene or substituted alkylene group through any available carbon or heteroatom of the ring. The group of formula (Iv) is defined wherein Ring D is selected from 5-6 membered monocyclic N-heterocycles optionally including 1 or 2 additional heteroatoms selected from N, O and S and $R^{14}$ is selected from H, halo, alkyl, OH, O-alkyl, oxo, $SO_2$alkyl, alkylene-O-alkyl and alkylene-$SO_2$alkyl. Ring D may be bound to the alkylene or substituted alkylene group through any available carbon or heteroatom of the ring. In one particular embodiment, the moiety (i) is defined wherein $R^8$ is selected from $N(C_{1-3}alkyl)_2$ and a group of formula (Iv). In one preferred embodiment, $R^8$ is $N(CH_3)_2$. In another preferred embodiment, $R^8$ is a group of formula (Iv) wherein Ring D is selected from pyrrolidinyl, piperidinyl, piperazinyl, morpholine and thiomorpholine, or any subset thereof. In one embodiment, Ring D is selected from pyrrolidinyl, piperidinyl and piperazinyl, or any subset thereof.

$R^{14}$ may be bound to Ring D through any suitable carbon or heteroatom of the ring (to provide, for example, N-methyl or N-oxides). In one embodiment, $R^{14}$ is H, oxo (including N-oxide) or alkyl (including N-alkyl), or any subset thereof. In one particular embodiment, $R^{14}$ is H, oxo (including N-oxide) or methyl (including N-methyl). In another embodiment, the compounds of the invention are defined wherein one of $R^4$ and $R^5$ is selected from H, halo, alkyl and O-alkyl, and the other is a moiety of formula (ii):

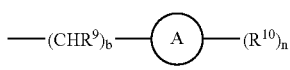
(ii)

wherein:
b is 0, 1, 2 or 3;
each $R^9$ is the same or different and is independently selected from H, alkyl and OH;

is referred to herein as "Ring A"
Ring A is selected from 5-10 membered heterocycles including 1, 2 or 3 heteroatoms selected from N, O and S and 5-6 membered heteroaryls including 1, 2 or 3 heteroatoms selected from N, O and S;
n is 0, 1 or 2; and each $R^{10}$ is the same or different and is independently selected from halo, alkyl, haloalkyl, OH, O-alkyl, oxo, $NH_2$, N(H)alkyl, $N(alkyl)_2$, $N(alkylene-O-alkyl)_2$, C(O)alkyl, $SO_2$alkyl, alkylene-O-alkyl, alkylene-$NH_2$, alkylene-N(H)alkyl, alkylene-$N(alkyl)_2$, alkylene-C(O)alkyl, and alkylene-$SO_2$alkyl.

In particular embodiment, $R^5$ is H and $R^4$ is a moiety of formula (II). A particular embodiment of the compounds of the invention is depicted in formula (I-a(ii)):

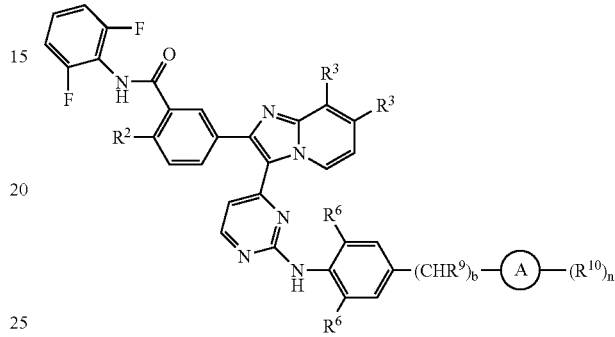
(I-a(ii))

wherein all variables are as defined above.

In one embodiment of the moiety (ii), b is 0, 1 or 2 and each $R^9$ is H. In one preferred embodiment, the moiety of formula (II) is defined wherein b is 0. This embodiment is depicted as the moiety (ii-a):

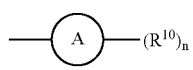
(ii-a)

wherein Ring A, n and $R^{10}$ are as defined above.

In the moiety of formula (II) (which includes the moiety (ii-a)), Ring A is bound to the phenyl ring (when b is 0) or to the optional group $(CHR^9)_b$ through any available C or heteroatom of the ring (N or S). In one embodiment, the moiety (ii) is defined wherein Ring A is selected from 5-6 membered monocyclic heterocycles and heteroaryls including 1, 2 or 3 heteroatoms selected from N, O and S. In one particular embodiment, the moiety (ii) is defined wherein Ring A is selected from 5-6 membered monocyclic N-heterocycles and N-heteroaryls optionally including 1 or 2 additional heteroatoms selected from N, O and S. In one particular embodiment, the moiety (ii) is defined wherein Ring A is selected from 5-6 membered monocyclic N-heterocycles optionally including 1 additional heteroatom selected from N, O and S. In a preferred embodiment, Ring A is selected from piperidinyl, piperazinyl, morpholinyl, thiomorpholinyl, pyrrolidinyl, pyrazolyl, oxazolyl and oxadiazolyl, or any subset thereof. In one preferred embodiment, Ring A is piperidinyl or piperazinyl, or any subset thereof.

Each $R^{10}$ may be bound to Ring A through any suitable carbon or heteroatom (to provide, for example, N-methyl or N-oxides). In one embodiment, the moiety (ii) is defined wherein n is 0 or 1. In one embodiment, n is 0.

In one embodiment wherein n is 1, $R^{10}$ is selected from halo, alkyl, haloalkyl, O-alkyl, oxo, $NH_2$, N(H)alkyl, $N(alkyl)_2$, $SO_2$alkyl, alkylene-$N(alkyl)_2$ and alkylene-$SO_2$alkyl, or any subset thereof. In one particular embodiment wherein n is 1, $R^{10}$ is selected from alkyl, haloalkyl, N(alkyl)$_2$, SO$_2$alkyl and alkylene-SO$_2$alkyl, or any subset thereof. In one embodiment, R$^{10}$ is SO$_2$alkyl. In one embodiment, R$^{10}$ is alkylene-SO$_2$alkyl. Specific, but non-limiting, examples of groups defining R$^{10}$ include methyl, CF$_3$, ethyl, CH$_2$CH$_2$F, isopropyl, n-propyl, OH, O-methyl, N(CH$_3$)$_2$, CH$_2$—N(CH$_3$)$_2$ and CH$_2$CH$_2$—SO$_2$CH$_3$, or any subset thereof.

lene-N(H)alkyl, alkylene-N(alkyl)$_2$, alkylene-C(O) alkyl and alkylene-SO$_2$alkyl.

In a particular embodiment, R$^5$ is H, F, Cl, methyl or ethyl, or any subset thereof, and R$^4$ is a moiety (iii). A particular embodiment of the compounds of the invention is depicted as formula (I-a(iii)):

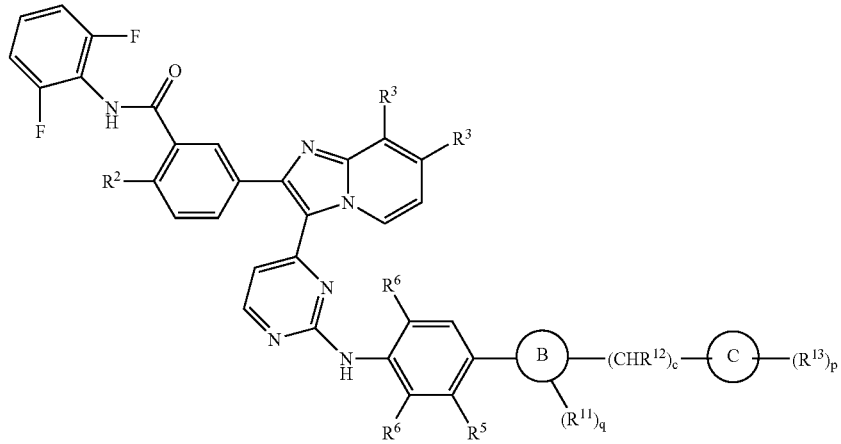

(I-a(iii))

In another embodiment, the compounds of the invention are defined wherein one of R$^4$ and R$^5$ is selected from H, halo, alkyl and O-alkyl, and the other is a moiety (iii):

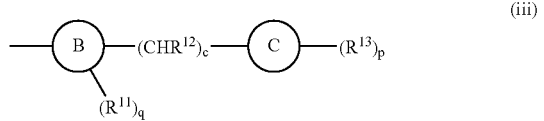

(iii)

wherein:
c is 0, 1 or 2;
each R$^{12}$ is the same or different and is independently H or alkyl;

is referred to herein as "Ring B;"
Ring B is selected from cyclohexylene, 5-6 membered heterocycles including 1, 2 or 3 heteroatoms selected from N, O and S and 5-6 membered heteroaryls including 1, 2 or 3 heteroatoms selected from N, O and S;
q is 0 or 1;
R$^{11}$ is halo, alkyl or haloalkyl;

is referred to herein as "Ring C;"
Ring C is a 5-10 membered heterocycle including 1, 2 or 3 heteroatoms selected from N, O and S;
p is 0, 1 or 2; and
each R$^{13}$ is the same or different and is independently selected from halo, alkyl, haloalkyl, OH, O-alkyl, oxo, NH$_2$, N(H)alkyl, N(alkyl)$_2$, N(alkylene-O-alkyl)$_2$, C(O) alkyl, SO$_2$alkyl, alkylene-O-alkyl, alkylene-NH$_2$, alkywherein all variables are as defined above.

In one particular embodiment, q is 0. When q is 0, R$^{11}$ is either not present (e.g., the valences of the ring atoms are all filled), or it is H (where the valences of the ring atoms are unfilled).

In those embodiments, wherein q is 1, R$^{11}$ may be bound to Ring B through any suitable carbon or heteroatom (to provide, for example, N-methyl). In one embodiment, the moiety (iii) is defined wherein R$^{11}$ is halo, methyl or CF$_3$, or any subset thereof.

In one embodiment, the moiety (iii) is defined wherein c is 1 or 2 and each R$_{12}$ is H. In one embodiment, the moiety (iii) is defined wherein c is 0 or 1. In one preferred embodiment, q is 0, c is 1 and R$_{12}$ is H. Thus, in one particular embodiment, the moiety (iii) is a moiety (iii-a):

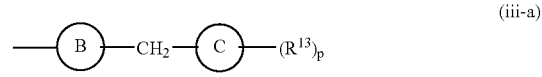

(iii-a)

wherein all variables are as defined above.

In one preferred embodiment, the compounds of the invention are defined wherein R$^5$ is H, F, Cl or methyl, or any subset thereof, and R$^4$ is a moiety (iii-a).

In one preferred embodiment, the moiety (iii) is defined wherein c is 0. In one particular embodiment, q is 0 and c is 0. Thus, in one particular embodiment, the moiety (iii) is a moiety (iii-b):

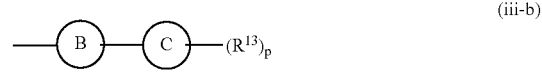

(iii-b)

wherein all variables are as defined above.

In one preferred embodiment, the compounds of the invention are defined wherein R$^5$ is H and R$^4$ is a moiety (iii-b). A particular embodiment of the compounds of the invention is depicted as formula (I-a(iii)b)):

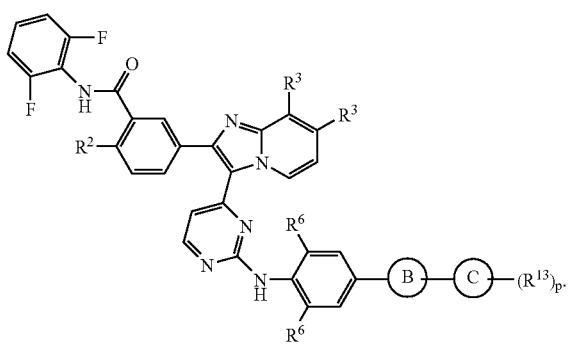

(I-a(iii)b)

wherein all variables are as defined above.

In the moiety of formula (iii) (which includes the moieties (iii-a) and (iii-b)), Ring B is bound to the phenyl ring and to the optional group $(CHR^{12})_c$ or to Ring C (when c is 0) through any available C or heteroatom (N or S). In one embodiment, the moiety (iii) is defined wherein Ring B is selected from 5-6 membered monocyclic heterocycles including 1, 2 or 3 heteroatoms selected from N, O and S and 5-6 membered monocyclic heteroaryls including 1, 2 or 3 heteroatoms selected from N, O and S. In one particular embodiment, Ring B is selected from 5-6 membered monocyclic N-heterocycles and N-heteroaryls optionally including 1 or 2 additional heteroatoms selected from N, O and S. Specific examples of groups defining Ring B include piperidinyl, piperazinyl and oxadiazolyl, or any subset thereof. In one embodiment wherein Ring B is a N-heterocycle, Ring B is bound to the phenyl or optional group $(CHR^{12})_c$ or to Ring C (when c is 0), through the N of the N-heterocycle.

In the moiety of formula (iii), Ring C is bound to the optional group $(CHR^{12})_c$ or to Ring B (when c is 0) through any available C or heteroatom (N or S). In one embodiment, the moiety (iii) is defined wherein Ring C is selected from 5-6 membered monocyclic and 9-10 membered fused bicyclic and spiro N-heterocycles optionally including 1 or 2 additional heteroatoms selected from N, O and S. In one particular embodiment, Ring C is a 5-6 membered monocyclic N-heterocycle optionally including 1 or 2 additional heteroatoms selected from N, O and S. Specific examples of groups defining Ring C include:

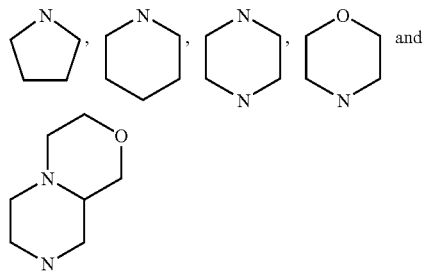

(the point of binding to Ring B and optional substituent $R^{13}$ not shown).

In one embodiment wherein Ring C is a N-heterocycle, Ring C is bound to the optional group $(CHR^{12})_c$ or to Ring B, through the N of the N-heterocycle.

In one embodiment, the moiety of formula (Iii) is defined wherein p is 0 or 1. In one particular embodiment, the moiety of formula (iii) is defined wherein p is 0. In another particular embodiment, the moiety of formula (iii) is defined wherein p is 1.

In those embodiments wherein p is 1 or 2, $R^{13}$ may be bound to Ring C through any suitable carbon or heteroatom (to provide, for example, N-methyl or N-oxides). In one embodiment, each $R^{13}$ is the same or different and is independently selected from alkyl, haloalkyl, OH, O-alkyl, oxo, $NH_2$, $N(H)$alkyl, $N(alkyl)_2$, $SO_2$alkyl, alkylene-$NH_2$, alkylene-$N(H)$alkyl, alkylene-$N(alkyl)_2$ and alkylene-$SO_2$alkyl, or any subset thereof. In one particular embodiment, p is 1 and $R^{13}$ is selected from alkyl, haloalkyl, OH, O-alkyl, $N(alkyl)_2$, $SO_2$alkyl and alkylene-$SO_2$alkyl, or any subset thereof. In one particular embodiment, p is 1 and $R^{13}$ is haloalkyl. In one particular embodiment, p is 1 and $R^{13}$ is $SO_2$alkyl. In one particular embodiment, p is 1 and $R^{13}$ is alkylene-$SO_2$alkyl. Specific examples of groups defining $R^{13}$ include F, methyl, $CF_3$, $CH_2CH_2F$, OH, $N(CH_3)_2$, $SO_2$—$CH_3$, and $CH_2CH_2SO_2CH_3$.

In one embodiment, the compounds of the invention are defined wherein at least one $R^6$ is H. In one particular embodiment, one $R^6$ is H and the other $R^6$ is selected from H, $C_{1-4}$alkyl and O—$C_{1-3}$alkyl. In one preferred embodiment, one $R^6$ is H and the other $R^6$ is O-methyl. In another preferred embodiment, one $R^6$ is H and the other $R^6$ is O-ethyl. In another preferred embodiment, both $R^6$ are H.

It is to be understood that the present invention includes all combinations and subsets of the particular groups defined hereinabove in the compounds of the invention and the compounds of formula (I).

Specific examples of compounds of formula (I) include those recited in the Examples which follow and pharmaceutically acceptable salts thereof.

Preferred compounds of the formula (I) include but are not limited to:

3-[3-(2-{[4-(1,4'-bipiperidin-1'-yl)-2-(methyloxy)phenyl]amino}-4-pyrimidinyl)imidazo[1,2-a]pyridin-2-yl]-N-(2,6-difluorophenyl)benzamide;

N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide;

N-(2,6-difluorophenyl)-3-(3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide;

N-(2,6-difluorophenyl)-3-(3-{2-[(5-methyl-2-(methyloxy)-4-{4-[2-(methylsulfonyl)ethyl]-1-piperazinyl}phenyl)amino]-4-pyrimidinyl}imidazo[1,2-a]pyridin-2-yl)benzamide;

N-(2,6-difluorophenyl)-2-(ethyloxy)-5-(3-{2-[(5-methyl-2-(methyloxy)-4-{4-[2-(methylsulfonyl)ethyl]-1-piperazinyl}phenyl)amino]-4-pyrimidinyl}imidazo[1,2-a]pyridin-2-yl)benzamide;

N-(2,6-difluorophenyl)-2-(ethyloxy)-5-(3-{2-[(5-methyl-2-(methyloxy)-4-{1-[2-(methylsulfonyl)ethyl]-4-piperidinyl}phenyl)amino]-4-pyrimidinyl}imidazo[1,2-a]pyridin-2-yl)benzamide;

N-(2,6-difluorophenyl)-5-(7-fluoro-3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide;

N-(2,6-difluorophenyl)-5-(3-{2-[(2-(ethyloxy)-5-methyl-4-{4-[2-(methylsulfonyl)ethyl]-1-piperidinyl}phenyl)amino]-4-pyrimidinyl}imidazo[1,2-a]pyridin-2-yl)-2-(methyloxy)benzamide; and N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide;

and pharmaceutically acceptable salts thereof.

A particular preferred compound of formula (I) is N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide

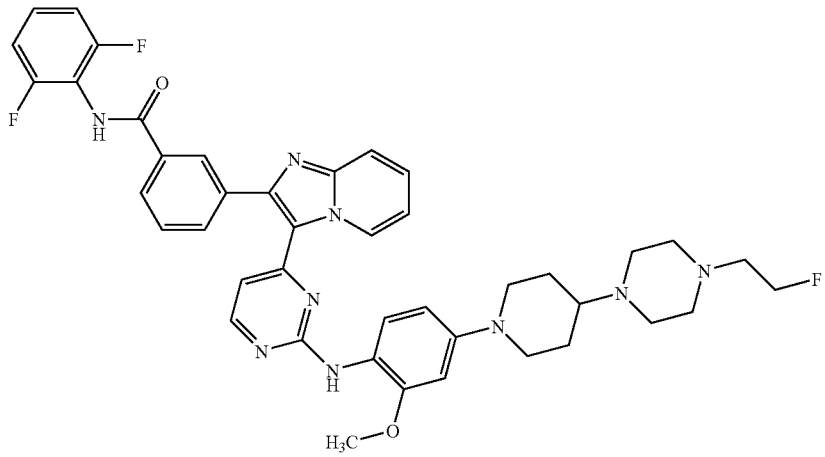

and pharmaceutically acceptable salts thereof.

Another particular preferred compound of formula (I) is N-(2,6-difluorophenyl)-3-(3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide

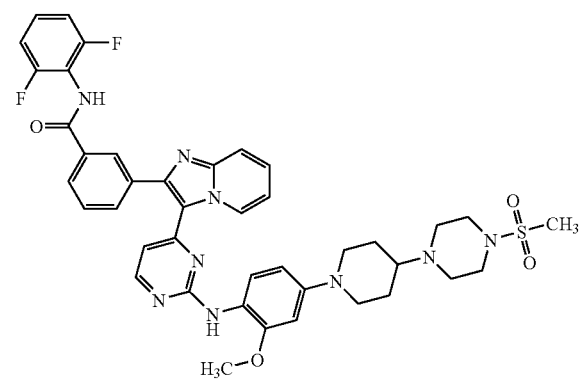

and pharmaceutically acceptable salts thereof.

Another particular preferred compound of formula (I) is 3-[3-(2-{[4-(1,4'-bipiperidin-1'-yl)-2-(methyloxy)phenyl]amino}-4-pyrimidinyl)imidazo[1,2-a]pyridin-2-yl]-N-(2,6-difluorophenyl)benzamide

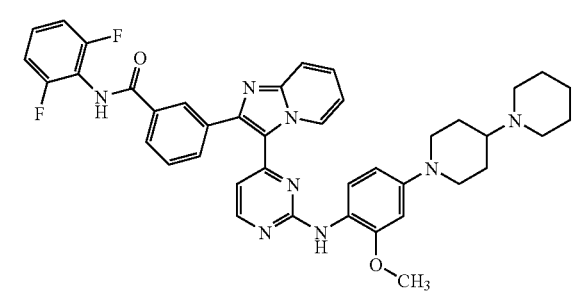

and pharmaceutically acceptable salts thereof.

Another particular preferred compound of formula (I) is N-(2,6-difluorophenyl)-5-(3-{2-[(2-(ethyloxy)-5-methyl-4-{4-[2-(methylsulfonyl)ethyl]-1-piperidinyl}phenyl)amino]-4-pyrimidinyl}imidazo[1,2-a]pyridin-2-yl)-2-(methyloxy)benzamide

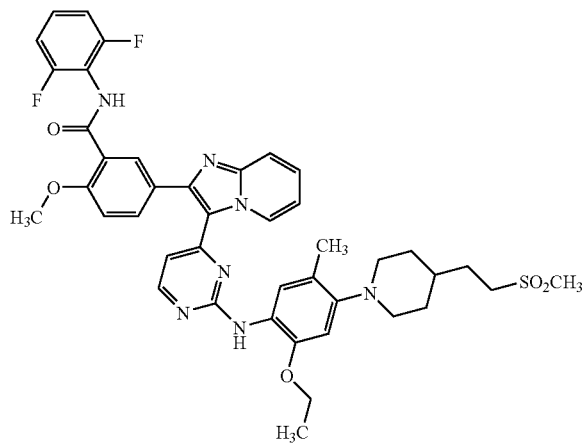

and pharmaceutically acceptable salts thereof. In a particular embodiment, the compound is as the free base. In another particular embodiment, the compound is as the mono methanesulfonic acid salt Another particular preferred compound of formula (I) is N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide

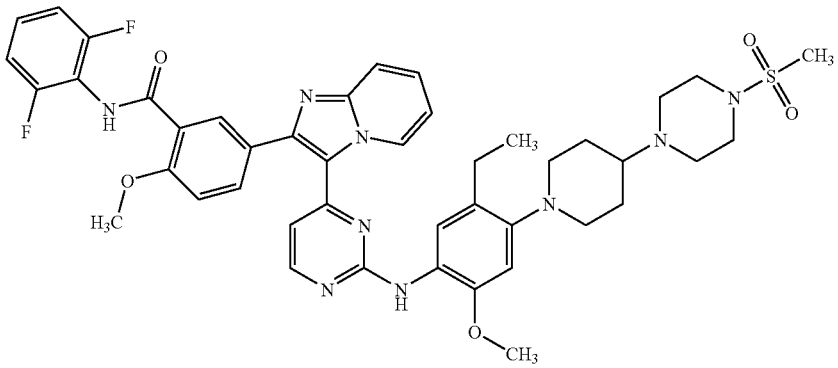

and pharmaceutically acceptable salts thereof. In a particular embodiment, the compound is as the free base. In another particular embodiment, the compound is as the monocitric acid (citrate) salt.

It will be appreciated by those skilled in the art that the compounds of formula (I) may also be utilized in the form of a pharmaceutically acceptable salt thereof. The pharmaceutically acceptable salts of the compounds of formula (I) include conventional salts formed from pharmaceutically acceptable (i.e., non-toxic) inorganic or organic acids or bases as well as quaternary ammonium salts. Representative salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate (methanesulfonic acid), methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, such as oxalic and trifluoroacetic, which are not themselves pharmaceutically acceptable, may be useful in the preparation of salts useful as intermediates in obtaining compounds of this invention and these form a further aspect of the invention. In one embodiment, the compound of formula (I) is in the form of the hydrochloride salt. In one embodiment, the compound of formula (I) is in the form of the methane sulfonic acid salt.

Processes for preparing pharmaceutically acceptable salts of compounds such as the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts of the compound. Processes for preparing pharmaceutically acceptable salts of intermediates are known in the art and are analogous to the processes for preparing pharmaceutically acceptable salts of other compounds such as the compounds of formula (I).

Compounds of the invention are believed to inhibit one or more kinases and in particular one or more IGF-1R family tyrosine kinases. Compounds of the invention may also inhibit one or more other kinases, and particularly other tyrosine kinases. Certain compounds of the invention inhibit IGF-1R ("IGF-1R inhibitor") or inhibit IR ("IR inhibitor"), or inhibit both. For brevity herein, there term "IGF-1R/IR inhibitor" refers to inhibitors of either IGF-1R or IR or both. Certain compounds of the invention may inhibit both IGF-1R and IR and also one or more ErbB family kinases ("ErbB inhibitor"). It is well documented that IGF-1R inhibitors, IR inhibitors and ErbB inhibitors (e.g., EGFR and ErbB2 inhibitors) are believed to be useful as anticancer and antitumor agents. The anticancer and antitumor effects of these kinase inhibitors is currently believed to result from inhibition of IGF-1R and IR and/or ErbB family kinases, and the effect of such inhibition on cell lines whose growth and/or viability is dependent on the kinase activity of IGF-1R or IR and/or ErbB family kinases.

Compounds of the invention may be IGF-1R inhibitors, and/or IR inhibitors, and optionally also ErbB family kinases inhibitors. Certain compounds of the invention may inhibit both IGF-1R, IR and also one or more ErbB family kinases. In particular, certain compounds of the invention may inhibit one or both of IGF-1R and IR and one or both of EGFR and ErbB2.

Some compounds of the invention may be selective inhibitors of IGF-1R family tyrosine kinases, and particularly IGF-1R and IR, ("selective IGF-1R inhibitor"), meaning that preferential inhibition of IGF-1R family tyrosine kinases is significantly greater than that of any number of other kinases, for example by a factor of 5-fold or more. Certain compounds of the invention may be selective inhibitors of ErbB family kinases ("selective ErbB inhibitor"), meaning that preferential inhibition of one or more ErbB family kinases is significantly greater than that of any number of other kinases, for example by a factor of 5-fold or more. Still other compounds of the invention may selectively inhibit IGF-1R family tyrosine kinases and one or more ErbB family kinases over other kinases ("selective dual IGF-1R/ErbB inhibitor"), meaning that inhibition of IGF-1R family tyrosine kinases and one or more ErbB family kinases is significantly greater than that of any number of other kinases, for example by a factor of 5-fold or more.

However, the present invention is not limited to compounds which are selective inhibitors of IGF-1R family tyrosine kinases or both IGF-1R family tyrosine kinases and ErbB family kinases. The present invention expressly contemplates that certain compounds of the invention may possess activity against multiple kinases, including kinases other than IGF-1R family tyrosine kinases and ErbB family kinases. For example, particular compounds of the invention may possess activity against multiple other kinases, including but not limited to Src, VEGFR, PDGFR, Met, c-Kit, Lyn, Lck, Aurora A and B, Syk, p38, BTK and BRK, as well. Particular compounds of the invention may be deemed to be unselective, meaning that they are not considered by one skilled in the art to be selective for any particular kinase over others.

As used herein, an IGF-1R/IR inhibitor is a compound that exhibits a $pIC_{50}$ of greater than about 6 against one or both of IGF-1R and IR in the IGF-1R enzyme inhibition (TR-FRET) assay described below and/or an $IC_{50}$ of at least about 1 μM potency against IGF-1R cellular autophosphorylation and/or in cell proliferation of a cell line that is dependent upon IGF signaling (e.g., Colo205, NCl—H929) in at least one of the assays described below. In a particular embodiment, an IGF-1R/IR inhibitor refers to a compound of the invention that exhibits a $pIC_{50}$ of greater than about 7 against one or both of IGF-1R and IR in the IGF-1R enzyme inhibition assay described below and/or an $IC_{50}$ of at least about 500 nM potency against IGF-1R cellular autophosphorylation and/or in the cell proliferation of a cell line that is dependent upon IGF signaling (e.g., Colo205, NCl—H929) in at least one of the assays described below.

An ErbB inhibitor is a compound which exhibits a $pIC_{50}$ of greater than about 6 against at least one ErbB family kinase in the ErbB inhibition enzyme assay described below and/or an $IC_{50}$ of at least about 1 μM potency against at least one cell line (e.g., BT474 or HN5) that over expresses at least one ErbB family kinase in the cellular proliferation assay described below. In one particular embodiment, a ErbB inhibitor refers to a compound of the invention which exhibits a $pIC_{50}$ of greater than about 7 against at least one ErbB family kinase in the ErbB inhibition enzyme assay described below and/or an $IC_{50}$ of at least about 500 nM potency against at least one cell line that over expresses at least one ErbB family kinase in the cellular proliferation assay described below.

The present invention provides compounds for use in medical therapy in a mammal in need thereof. In particular, the present invention provides methods for the treatment of several conditions in a mammal in need thereof, all of which comprise the step of administering a therapeutically effective amount of a compound of the invention. All methods described herein are applicable to mammals, and particularly to humans. As used herein, the term "treatment" or "treating" in the context of therapeutic methods, refers to alleviating the specified condition, eliminating or reducing the symptoms of the condition, slowing or eliminating the progression invasion or metastatic spread of the condition and preventing or delaying the reoccurrence of the condition in a previously afflicted subject. The present invention further provides use of a compounds of the invention for preparation of a medicament for the treatment of several conditions in a mammal (e.g., human) in need thereof.

More particularly, the present invention provides compounds for use in the treatment of, a condition mediated by one or more IGF-1R family tyrosine kinases (e.g., IGF-1R and IR) in a mammal in need thereof. The present invention further provides methods for the treatment of a condition mediated by one or more IGF-1R family tyrosine kinases (e.g., IGF-IR and IR) in a mammal in need thereof, which method comprises administering to the mammal a therapeutically effective amount of the compound of the invention.

In another embodiment, the present invention provides compounds for use in regulating, modulating, binding, or inhibiting IGF-1R or IR in a mammal. The invention also provides methods for regulating, modulating, binding, or inhibiting IGF-1R or IR in a mammal in need thereof, comprising administering to the mammal a therapeutically effective amount of a compound of the invention. "Regulating, modulating, binding or inhibiting IGF-1R or IR" refers to regulating, modulating, binding or inhibiting the activity of IGF-1R or IR, as well as regulating, modulating, binding or inhibiting any overexpression of an upstream regulator of IGF-1R or IR in order to inhibit the cellular potency of its signaling ability.

As a particular aspect, the invention provides compounds for use in the treatment of a condition mediated by inappropriate activity of one or more IGF-1R family tyrosine kinases (particularly IGF-1R or IR), in a mammal in need thereof. The present invention further provides methods for the treatment of condition mediated by inappropriate activity of one or more IGF-1R family tyrosine kinases (particularly IGF-1R or IR), in a mammal in need thereof, comprising administering to the mammal, a therapeutically effective amount of a compound of the invention. In an additional aspect, the present invention provides the use of a compound of the invention for the preparation of a medicament for the treatment of a condition mediated by inappropriate activity of one or more IGF-1R family tyrosine kinases (particularly IGF-1R or IR), in a mammal. One example of a condition mediated by inappropriate activity of one or more IGF-1R family tyrosine kinases includes neoplasms.

By "inappropriate activity" is meant kinase activity that deviates from the expected activity for that kinase (e.g., IGF-1R) or for an upstream regulator of that kinase (e.g., IGF-1R), in a particular mammal. The inappropriate activity of an IGF-1R family tyrosine kinase may arise from one or more of IGF-1R, IR and IRR (particularly IGF-1R or IR), or an upstream regulator of an IGF-1R family tyrosine kinase (particularly IGF-1R or IR). Inappropriate IGF-1R family tyrosine kinase activity may take the form of, for instance, an abnormal increase in activity, or an aberration in the timing and/or control of IGF-1R family tyrosine kinases. Such inappropriate activity may result, for example, from overexpression or mutation of the protein kinase, upstream regulator, receptor or ligand and/or change in the expression patterns of IGF binding proteins leading to inappropriate or uncontrolled activation of the corresponding kinase or receptor.

Thus, in one embodiment, the present invention provides compounds for use in the treatment of a condition which directly or indirectly results from altered signaling of one or more IGF-1R family tyrosine kinases (particularly IGF-1R and IR) in a mammal in need thereof. The present invention provides methods for the treatment of a condition which directly or indirectly results from altered signaling of one or more IGF-1R family tyrosine kinases (particularly IGF-1R and IR) in a mammal in need thereof, comprising administering to the mammal, a therapeutically effective amount of a compound of the invention. In an additional aspect, the present invention provides the use of a compound of the invention for the preparation of a medicament for the treatment of a condition which directly or indirectly results from altered signaling of one or more IGF-1R family tyrosine kinases (particularly IGF-1R and IR) in a mammal. One example of a condition which directly or indirectly results from altered signaling of IGF-1R family tyrosine kinases includes neoplasms.

Furthermore, it is also contemplated that unwanted IGF-1R family tyrosine kinase may reside in an abnormal source, such as a malignancy. Thus, the level of IGF-1R family tyrosine kinase activity does not need to be abnormal to be considered inappropriate in the case where the activity derives from an abnormal source including, but not limited to, upstream activators or malignancy. In one embodiment is provided compounds for use in the treatment of a condition which directly or indirectly results from mutation or overexpression of the receptor or the ligands or a change in the expression patterns of IGF binding proteins of IGF-1R or IR in a mammal in need thereof. The present invention provides methods for the treatment of a condition which directly or indirectly results from mutation or overexpression of the receptor or the ligands or a change in the expression patterns of IGF binding proteins of IGF-1R or IR in a mammal in need thereof, comprising administering to the mammal, a therapeutically effective amount of a compound of the invention. In an additional aspect, the present invention provides the use of a compound of the invention for the preparation of a medicament for the treatment of a condition which directly or indirectly results from mutation or overexpression of the receptor or the ligands or a change in the expression patterns of IGF binding proteins of IGF-1R or IR in a mammal. One example of a condition which directly or indirectly results from mutation or overexpression of the receptor or the ligands or a change in the expression patterns of IGF binding proteins of IGF-1R or IR includes neoplasms.

Compounds of the invention may be used in the treatment of conditions attenuated by inhibition of an IGF-1R family tyrosine kinase (particularly, IGF-1R or IR). Further provided are methods for treating a condition attenuated by inhibition of an IGF-1R family tyrosine kinase (particularly, IGF-1R or IR) in a mammal in need thereof, comprising administering to the mammal, a therapeutically effective amount of a compound of the invention. Also provided is a compound of the invention for the preparation of a medicament for the treatment of a condition attenuated by inhibition of an IGF-1R family tyrosine kinase (particularly, IGF-1R or IR) in a mammal. Conditions attenuated by inhibition of IGF-1R family tyrosine kinases, and particularly IGF-1R and IR, include but are not limited to neoplasms.

In addition to the foregoing methods and because certain compounds of the invention may also inhibit one or more ErbB family kinases as well, the present invention also provides compounds for use in the treatment of a condition mediated by an IGF-1R family tyrosine kinases (e.g., IGF-1R and IR) and at least one ErbB family kinase (e.g., EGFR and ErbB2) in a mammal in need thereof. The present invention further provides methods for the treatment of a condition mediated by an IGF-1R family tyrosine kinase (e.g., IGF-IR and IR) and at least one ErbB family kinase (e.g., EGFR and ErbB2) in a mammal in need thereof, which method comprises administering to the mammal a therapeutically effective amount of the compound of the invention.

In another embodiment, the present invention provides compounds for use in regulating, modulating, binding, or inhibiting IGF-1R or IR and at least one ErbB family kinase (e.g., EGFR and ErbB2) in a mammal. The invention also provides methods for regulating, modulating, binding, or inhibiting IGF-1R or IR and at least one ErbB family kinase (e.g., EGFR and ErbB2) in a mammal in need thereof, comprising administering to the mammal a therapeutically effective amount of a compound of the invention. "Regulating, modulating, binding or inhibiting" in the context of IGF-1R family kinases is defined above. "Regulating, modulating, binding or inhibiting at least one ErbB family kinase" refers to regulating, modulating, binding or inhibiting the activity of at least one ErbB family kinase, as well as regulating, modulating, binding or inhibiting any overexpression of at least one ErbB family kinase to inhibit the cellular potency of its signaling ability.

As a particular aspect, the invention provides compounds for use in the treatment of a condition mediated by inappropriate activity of one or more IGF-1R family tyrosine kinases (particularly IGF-1R or IR) and at least one ErbB family kinase (particularly EGFR and ErbB2), in a mammal in need thereof. The present invention further provides methods for the treatment of a condition mediated by inappropriate activity of one or more IGF-1R family tyrosine kinases (particularly IGF-1R or IR) and at least one ErbB family kinase (particularly EGFR and ErbB2), in a mammal in need thereof, comprising administering to the mammal, a therapeutically effective amount of a compound of the invention. In an additional aspect, the present invention provides the use of a compound of the invention for the preparation of a medicament for the treatment of a condition mediated by inappropriate activity of at least one IGF-1R family tyrosine kinase and at least one ErbB family kinase (particularly EGFR and ErbB2), in a mammal. One example of a condition mediated by inappropriate activity of one or more IGF-1R family tyrosine kinases and at least one ErbB family kinase (particularly EGFR and ErbB2) includes neoplasms.

"Inappropriate activity" is defined above, as is a description of inappropriate activity of IGF-1R family tyrosine kinases. The inappropriate activity of an ErbB family kinase may arise from one or more of EGFR, ErbB2 or ErbB4 (more particularly EGFR or ErbB2). Inappropriate ErbB family kinase activity may take the form of, for instance, an abnormal increase in activity, or an aberration in the timing and/or control of ErbB family kinase activity or an upstream activator of ErbB family kinases. Such inappropriate activity may result, for example, from overexpression or mutation of the protein kinase, upstream activator, receptor or ligand and/or change in the expression patterns of IGF binding proteins leading to inappropriate or uncontrolled activation of the corresponding kinase or receptor.

In one embodiment, the present invention provides compounds for use in the treatment of a condition which directly or indirectly results from altered signaling of one or more IGF-1R family tyrosine kinases (particularly IGF-1R and IR) and overexpression of at least one ErbB family kinase (particularly EGFR and/or ErbB2) in a mammal in need thereof. The present invention provides methods for the treatment of a condition which directly or indirectly results from altered signaling of one or more IGF-1R family tyrosine kinases (particularly IGF-1R and IR) and overexpression of at least one ErbB family kinase (particularly EGFR and/or ErbB2) in a mammal in need thereof, comprising administering to the mammal, a therapeutically effective amount of a compound of the invention. In an additional aspect, the present invention provides the use of a compound of the invention for the preparation of a medicament for the treatment of a condition which directly or indirectly results from altered signaling of one or more IGF-1R family tyrosine kinases (particularly IGF-1R and IR) and overexpression of at least one ErbB family kinase (particularly EGFR and/or ErbB2) in a mammal. One example of a condition which directly or indirectly results from altered signaling of an IGF-1R family tyrosine kinase and overexpression of at least one ErbB family kinase includes neoplasms.

As in the case of IGF-1R family tyrosine kinases, it is contemplated that the unwanted ErbB family kinase activity may reside in an abnormal source, such as a malignancy. Thus, the level of ErbB family kinase activity does not need to be abnormal to be considered inappropriate in the case where the activity derives from an abnormal source including, but not limited to, upstream activators or malignancy. In one embodiment is provided compounds for use in the treatment of a condition which directly or indirectly results from mutation or overexpression of the receptor or the ligands or a change in the expression patterns of IGF binding proteins of IGF-1R or IR and overexpression of at least one ErbB family kinase (particularly EGFR or ErbB2) in a mammal in need thereof. The present invention provides methods for the treatment of a condition which directly or indirectly results from mutation or overexpression of the receptor or the ligands or a change in the expression patterns of IGF binding proteins of IGF-1R or IR and overexpression of at least one ErbB family kinase (particularly EGFR or ErbB2) in a mammal in need thereof, comprising administering to the mammal, a therapeutically effective amount of a compound of the invention. In an additional aspect, the present invention provides the use of a compound of the invention for the preparation of a medicament for the treatment of a condition which directly or indirectly results from mutation or overexpression of the receptor or the ligands or a change in the expression patterns of IGF binding proteins of IGF-1R or IR and overexpression of at least one ErbB family kinase (particularly EGFR or ErbB2) in a mammal. One example of a condition which directly or indirectly results from mutation or overexpression of the receptor or the ligands or a change in the expression patterns of IGF binding proteins of IGF-1R or IR and overexpression of at least one ErbB family kinase (particularly EGFR or ErbB2) includes neoplasms.

Compounds of the invention may be used in the treatment of conditions attenuated by inhibition of one or more IGF-1R family tyrosine kinases (particularly, IGF-1R or IR) and at least one ErbB family kinase (particularly EGFR or ErbB2). Further provided are methods for treating a condition attenuated by inhibition of one or more IGF-1R family tyrosine kinase (particularly, IGF-1R or IR) and at least one ErbB family kinase (particularly EGFR or ErbB2) in a mammal in need thereof, comprising administering to the mammal, a therapeutically effective amount of a compound of the invention. Also provided is a compound of the invention for the preparation of a medicament for the treatment of a condition attenuated by inhibition of one or more IGF-1R family tyrosine kinase (particularly, IGF-1R or IR) and at least one ErbB family kinase (particularly EGFR or ErbB2) in a mammal. Conditions attenuated by inhibition of IGF-1R family tyrosine kinases, and particularly IGF-1R and IR, and at least one ErbB family kinase (particularly EGFR or ErbB2) include but are not limited to neoplasms.

Compounds of the invention may be used in the treatment of a neoplasm and particularly a susceptible neoplasm in a mammal (e.g., human) in need thereof. The present invention further provides the use of a compound of the invention for the preparation of a medicament for the treatment of a neoplasm, and particularly a susceptible neoplasm, in a mammal (e.g., human) in need thereof. The present invention also provides a method for treating a susceptible neoplasm (cancer or tumor) in a mammal in need thereof, which method comprises administering to the mammal a therapeutically effective amount of the compound of the invention. "Susceptible neoplasm" as used herein refers to neoplasms which are susceptible to treatment by a kinase inhibitor and particularly neoplasms that are susceptible to treatment by an IGF-1R/IR inhibitor and neoplasms that are susceptible to treatment by an IGF-1R/IR inhibitor and an ErbB family kinase inhibitor. Susceptible neoplasms include neoplasms which exhibit indicators of inappropriate activity of IGF-1R family tyrosine kinases and optionally also indicators of inappropriate activity of ErbB family kinases. For example, neoplasms which exhibit altered signaling or uncontrolled activation of IGF-1R or IR are "susceptible neoplasms" as that term is used herein. Similarly neoplasms which exhibit overexpression of one or more ErbB family kinases (particularly EGFR and/or ErbB2) are "susceptible neoplasms" as that term is used herein. Neoplasms which exhibit indicators of inappropriate activity of IGF-1R family tyrosine kinases and are therefore susceptible to treatment with an IGF-1R inhibitor are known in the art, and include both primary and metastatic tumors and cancers. Neoplasms which exhibit indicators of inappropriate activity of one or more ErbB family kinases and are therefore susceptible to treatment with an ErbB inhibitor are known in the art, and include both primary and metastatic tumors and cancers.

Specific examples of susceptible neoplasms within the scope of the present invention include, but are not limited to:
breast cancer,
sarcoma including soft-tissue sarcoma (e.g., cartilage sarcoma, connective tissue (chondrosarcoma) and fibrous matrix (fibrosarcoma)) and hard bony sarcomas,
lung cancer, including non-small cell and small cell lung carcinomas and mesotheliomas,
prostate cancer,
colorectal cancer,
renal cancer,
pancreatic cancer,
hematologic cancers, including lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma, megakaryoblastic leukemia, acute megakaryocytic leukemia, promyelocytic leukemia, erythroleukemia, malignant lymphoma, Hodgkins lymphoma, non-Hodgkins lymphoma, lymphoblastic T cell lymphoma, Burkitt's lymphoma, follicular lymphoma, myelodysplastic syndromes,
neuroblastomas,
primary CNS tumors including: astrocytomas (also known as "gliomas") including glioblastoma multiforme; meningiomas and medulloblastomas,
secondary CNS tumors, i.e., metastases in the central nervous system (e.g., the brain), of a tumor originating outside of the central nervous system,
head and neck cancer,
thyroid cancer,
hepatocarcinoma,
ovarian cancer, vulval cancer, cervical cancer, endometrial cancer,
testicular cancer,
bladder cancer,
esophageal cancer,
gastric cancer,
buccal cancer, cancer of the mouth,
GIST (gastrointestinal stromal tumor) and
skin cancer including melanoma.

In one particular embodiment, the susceptible neoplasm is breast cancer and the present invention provides a method for treating breast cancer in a mammal in need thereof which comprises administering to the mammal, a therapeutically effective amount of a compound of the invention. In another embodiment, the susceptible neoplasm is sarcoma and the invention provides a method for treating sarcoma in a mammal in need thereof which comprises administering to the mammal, a therapeutically effective amount of a compound of the invention. In another embodiment, the susceptible neoplasm is lung cancer (including non-small cell lung carcinomas (NSCLC) small cell lung carcinomas and mesotheliomas, and particularly NSCLC) and the present invention provides a method of treating lung cancer (e.g., NSCLC) in a mammal in need thereof which comprises administering to the mammal, a therapeutically effective amount of a compound of the invention. In another embodiment, the susceptible neoplasm is prostate cancer and the invention provides a method for treating prostate cancer in a mammal in need thereof which comprises administering to the mammal, a therapeutically effective amount of a compound of the invention. In another embodiment, the susceptible neoplasm is colorectal cancer and the present invention provides a method for treating colorectal cancer in a mammal in need thereof which comprises administering to the mammal, a therapeutically effective amount of a compound of the invention. In another embodiment, the susceptible neoplasm is pancreatic cancer and the invention provides a method for treating pancreatic cancer in a mammal in need thereof which comprises administering to the mammal, a therapeutically effective amount of a compound of the invention. In another embodiment, the susceptible neoplasm is a hematologic cancer and the invention provides a method for treating a hematologic cancer in a mammal in need thereof which comprises administering to the mammal, a therapeutically effective amount of a compound of the invention. In one particular embodiment, the hematologic cancer is multiple myeloma. In another embodiment, the susceptible neoplasm is head and neck cancer and the invention provides a method for treating head and neck cancer in a mammal in need thereof which comprises administering to the mammal, a therapeutically effective amount of a compound of the invention. In another embodiment, the susceptible neoplasm is ovarian cancer and the invention provides a method for treating ovarian cancer in a mammal in need thereof which comprises administering to the mammal, a therapeutically effective amount of a compound of the invention.

The compounds of the invention can be used alone in the treatment of each of the foregoing conditions or can be used to provide additive or potentially synergistic effects with certain existing chemotherapies, biological or immunotherapeutics (including monoclonal antibodies) and vaccines, and/or be used to restore effectiveness of certain existing chemotherapies and radiation. It is documented that IGF-1R family tyrosine kinase inhibitors may increase the sensitivity to other chemotherapies.

As used herein, the term "therapeutically effective amount" means an amount of a compound of formula (I) which is sufficient, in the subject to which it is administered, to elicit the biological or medical response of a cell culture, tissue, system, mammal (including human) that is being sought, for instance, by a researcher or clinician. The term also includes within its scope, amounts effective to enhance normal physiological function. For example, a therapeutically effective amount of a compound of the invention for the treatment of a condition mediated by IGF-1R family tyrosine kinase (e.g., a condition attenuated by inhibition of e.g., IGF-1R or IR) is an amount sufficient to treat the condition in the particular subject. Similarly, a therapeutically effective amount of a compound of the invention for the treatment of a susceptible neoplasm is an amount sufficient to treat the particular susceptible neoplasm in the subject. In one embodiment of the present invention, a therapeutically effective amount of a compound of the invention is an amount sufficient to regulate, modulate, bind or inhibit at least one IGF-1R family tyrosine kinase. In one particular embodiment, a therapeutically effective amount of a compound of the invention is an amount sufficient to regulate, modulate, bind or inhibit at least one IGF-1R family tyrosine kinase and at least one ErbB family kinase. In one specific example of the foregoing embodiment, the therapeutically effective amount of a compound of the invention is an amount sufficient to regulate, modulate, bind or inhibit IGF-1R, IR and one or both of EGFR and ErbB2 kinases.

The precise therapeutically effective amount of the compounds of the invention will depend on a number of factors including, but not limited to, the species, age and weight of the subject being treated, the precise condition requiring treatment and its severity, the bioavailability and other properties of the specific compound being administered, the nature of the formulation, and the route of administration, and will ultimately be at the discretion of the attendant physician or veterinarian. Based on efficacy data from animal (mouse) model described below, an estimated Human Equivalent Dosing (HED) range for humans may be calculated using the following formula.

$$\text{HED (mg/kg)} = \text{Dose in animal (mg/kg)} * (\text{Wt animal}/\text{Wt humans})^{0.33}$$

Using this calculation, an estimated dose of a compound of the invention for treatment may be in the range of 0.2 to 136 mg/kg body weight of recipient (mammal) per day and more usually in the range of 1 to 100 mg/kg body weight per day. Acceptable daily dosages may be from about 0.1 to about 10000 mg/day, and preferably from about 0.1 to about 1000 mg/day. Thus, for a 70 kg adult human being treated for a condition mediated by IGF-1R, the actual amount per day may be from about 70 to about 7000 mg, more usually from about 70 to about 1000 mg, and particularly from about 70 to about 500 mg; and this amount may be given in a single dose per day or more usually in a number (such as two, three, four, five or six) of sub-doses per day such that the total daily dose is the approximately the same. A therapeutically effective amount of a pharmaceutically acceptable salt of a compound of formula (I) may be determined as a proportion of the therapeutically effective amount of the compound of formula (I) per se. It is envisaged that similar dosing would be appropriate for treatment of the susceptible neoplasms described above.

While it is possible that, for use in therapy, a therapeutically effective amount of a compound of the invention may be administered as the raw chemical, it is typically presented as the active ingredient of a pharmaceutical composition or formulation. Accordingly, the invention further provides a pharmaceutical composition comprising a compound of the invention. The pharmaceutical composition may further comprise one or more pharmaceutically acceptable carriers, diluents, and/or excipients. The carrier(s), diluent(s) and/or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the invention with one or more pharmaceutically acceptable carriers, diluents and/or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the invention (as a free-base, solvate (including hydrate) or salt, and in any form), depending on the condition being treated, the route of administration, the bioavailability of the specific compound, the species being treated, and the age, weight and condition of the patient. Preferred unit dosage formulations are those containing a daily dose, weekly dose, monthly dose, a sub-dose, or an appropriate fraction thereof, of an active ingredient. Such pharmaceutical formulations may be prepared by any of the methods well known in the pharmacy art.

Pharmaceutical formulations may be adapted for administration by any appropriate route, for example by the oral (including capsules, tablets, liquid-filled capsules, disintegrating tablets, immediate, delayed and controlled release tablets, oral strips, solutions, syrups, buccal and sublingual), nasal, inhalation, topical (including transdermal), rectal, vaginal or parenteral (including subcutaneous, intramuscular, intravenous or intradermal) route. Such formulations may be prepared by any method known in the art of pharmacy, for example by bringing into association the active ingredient with the carrier(s), excipient(s) or diluent. Generally, the carrier, excipient or diluent employed in the pharmaceutical formulation is "non-toxic," meaning that it/they is/are deemed safe for consumption in the amount delivered in the pharmaceutical composition, and "inert" meaning that it/they does/do not appreciably react with or result in an undesired effect on the therapeutic activity of the active ingredient. Pharmaceutical formulations adapted for oral administration may be presented as discrete units such as liquid-filled or solid capsules; immediate, delayed or controlled release tablets; powders or granules; solutions or suspensions in aqueous or non-aqueous liquids; edible foams or whips; oil-in-water liquid emulsions, water-in-oil liquid emulsions or oral strips, such as impregnated gel strips.

For instance, for oral administration in the form of a tablet or capsule, the active ingredient can be combined with an oral pharmaceutically acceptable carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a pharmaceutically acceptable alcoholic vehicle. Suspensions can be formulated by dispersing the compound in a pharmaceutically acceptable vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the invention may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* (1986) 3(6):318.

Pharmaceutical formulations adapted for topical administration may be formulated as ointments, creams, suspensions, lotions, powders, solutions, pastes, gels, sprays, aerosols or oils. For treatments of external tissues, such as skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical formulations adapted for topical administrations to the eye include eye drops wherein the active ingredient is dissolved or suspended in a suitable carrier, especially an aqueous solvent. Pharmaceutical formulations adapted for topical administration in the mouth include lozenges, pastilles and mouth washes.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient. Pharmaceutical formulations adapted for administration by inhalation include fine particle dusts or mists, which may be generated by means of various types of metered dose pressurized aerosols, metered dose inhalers, dry powder inhalers, nebulizers or insufflators.

Pharmaceutical formulations adapted for parenteral administration include aqueous and non-aqueous sterile injection solutions which may contain anti-oxidants, buffers, bacteriostats and solutes which render the formulation of pharmaceutically acceptable tonicity with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavoring agents.

In the above-described methods of treatment and uses, a compound of the invention may be employed alone, in combination with one or more other compounds of the invention or in combination with other therapeutic methods or agents. In particular, in methods of treating a condition attenuated or otherwise improved by inhibition of IGF-1R or IR and in methods of treating susceptible neoplasms, combination with other chemotherapeutic, biologic, hormonal, antibody and supportive care agents is envisaged as well as combination with surgical therapy and radiotherapy. Supportive care agents include analgesics and anti-emetics. Anti-emetics include but are not limited to $5HT_3$ antagonists such as ondansetron, granisetron, dolasetron, palonosetron and the like; proclorperazine, metaclopromide, diphenhydramine, promethazine; dexamethasone, lorazepam; haloperidol, dronabinol, olanzapine; and neurokinin-1 antagonists such as aprepitant, fosaprepitant and casopitant administered alone or in various combinations.

The term "chemotherapeutic" as used herein refers to any chemical agent having a therapeutic effect on the subject to which it is administered. "Chemotherapeutic" agents include but are not limited to anti-neoplastic agents. As used herein, "anti-neoplastic agents" include both cytotoxic and cytostatic agents including biological, immunological and vaccine therapies. Combination therapies according to the present invention thus comprise the administration of at least one compound of formula (I) and the use of at least one other treatment method. In one embodiment, combination therapies according to the present invention comprise the administration of at least one compound of the invention and surgical therapy. In one embodiment, combination therapies according to the present invention comprise the administration of at least one compound of the invention and radiotherapy. In one embodiment, combination therapies according to the present invention comprise the administration of at least one compound of the invention and at least one supportive care agent (e.g., at least one anti-emetic agent). In one embodiment, combination therapies according to the present invention comprise the administration of at least one compound of the invention and at least one other chemotherapeutic agent. In one particular embodiment, the present invention comprises the administration of at least one compound of the invention and at least one anti-neoplastic agent.

As an additional aspect, the present invention provides the methods of treatment and uses as described above, which comprise administering a compound of the invention together with at least one chemotherapeutic agent. In one particular embodiment, the chemotherapeutic agent is an anti-neoplastic agent. In another embodiment, the present invention provides a pharmaceutical composition as described above further comprising at least one other chemotherapeutic agent, more particularly, the chemotherapeutic agent is an anti-neoplastic agent. The present invention also provides methods of treatment and uses as described above, which comprise administering a compound of the invention together with at least one supportive care agent (e.g., anti-emetic agent).

The compounds of the invention and at least one additional anti-neoplastic or supportive care therapy may be employed in combination concomitantly or sequentially in any therapeutically appropriate combination. The administration of a compound of the invention with one or more other anti-neoplastic agents may be in combination in accordance with the invention by administration concomitantly in (1) a unitary pharmaceutical composition including both or all compounds or (2) separate pharmaceutical compositions each including one or more of the compounds. The components of the combination may be administered separately in a sequential manner wherein one anti-neoplastic agent is administered first and the other(s) second or vice versa. Such sequential administration may be close in time or remote in time.

When a compound of the invention is used in combination with an anti-neoplastic and/or supportive care agent, the dose of each compound may differ from that when the compound is used alone. Appropriate doses will be readily appreciated by those skilled in the art. The appropriate dose of the compound(s) of the invention and the other therapeutically active agent(s) and the relative timings of administration will be selected in order to achieve the desired combined therapeutic effect, and are within the expertise and discretion of the attendant clinician.

Typically, any chemotherapeutic agent that has activity against a susceptible neoplasm being treated with a compound of the invention may be utilized in combination with the compounds the invention, provided that the particular agent is clinically compatible with therapy employing a compound of the invention. Typical anti-neoplastic agents useful in the present invention include, but are not limited to: alkylating agents, anti-metabolites, antitumor antibiotics, antimitotic agents, topoisomerase I and II inhibitors, hormones and hormonal analogues; signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents. Alkylating agents are non-phase specific anti-neoplastic agents and strong electrophiles. Typically, alkylating agents form covalent linkages, by alkylation, to DNA through nucleophilic moieties of the DNA molecule such as phosphate, amino, and hydroxyl groups. Such alkylation disrupts nucleic acid function leading to cell death. Alkylating agents may be employed in combination with the compounds of the invention in the compositions and methods described above. Examples of alkylating agents include but are not limited to: nitrogen mustards such as cyclophosphamides, temozolomide, melphalan, and chlorambucil; oxazaphosphorines; alkyl sulfonates such as busulfan; nitrosoureas such as carmustine; triazenes such as dacarbazine; and platinum coordination complexes such as cisplatin, oxaliplatin and carboplatin.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. The end result of discontinuing S phase is cell death. Antimetabolite neoplastic agents may be employed in combination with the compounds of the invention in the compositions and methods described above. Examples of antimetabolite anti-neoplastic agents include purine and pyrimidine analogues and anti-folate compounds, and more specifically, hydroxyurea, cytosine, arabinoside, ralitrexed, tegafur, fluorouracil (e.g., 5 FU), methotrexate, cytarabine, mercaptopurine and thioguanine.

Antitumor antibiotic agents are non-phase specific agents, which bind to or intercalate with DNA. Typically, such action disrupts ordinary function of the nucleic acids, leading to cell death. Antitumor antibiotics may be employed in combination with the compounds of the invention in the compositions and methods described above. Examples of antitumor antibiotic agents include, but are not limited to, actinomycins such as dactinomycin; anthracyclines such as daunorubicin, doxorubicin, idarubicin, epirubicin and mitoxantrone; mitomycin C and bleomycins.

Antimicrotubule or antimitotic agents are phase specific agents active against the microtubules of tumor cells during M or the mitosis phase of the cell cycle. Antimitotic agents may be employed in combination with the compounds of the invention in the compositions and methods described above. Examples of antimitotic agents include, but are not limited to, diterpenoids, vinca alkaloids, polo-like kinase (PLK) inhibitors and CenpE inhibitors. Examples of diterpenoids include, but are not limited to, paclitaxel and its analog docetaxel. Examples of vinca alkaloids include, but are not limited to, vinblastine, vincristine, vindesine and vinorelbine. PLK inhibitors are discussed further below.

Topoisomerase inhibitors include inhibitors of Topoisomerase II and inhibitors of Topoisomerase I. Topoisomerase II inhibitors, such as epipodophyllotoxins are antineoplastic agents derived from the mandrake plant, that typically affect cells in the S and $G_2$ phases of the cell cycle by forming a ternary complex with topoisomerase II and DNA, causing DNA strand breaks. The strand breaks accumulate and cell death follows. Examples of epipodophyllotoxins include, but are not limited to, etoposide and teniposide. Camptothecins, including camptothecin and camptothecin derivatives are available or under development as Topoisomerase I inhibitors. Examples of camptothecins include, but are not limited to amsacrine, irinotecan, topotecan, and the various optical forms of 7-(4-methylpiperazino-methylene)-10,11-ethylenedioxy-20-camptothecin. Topoisomerase inhibitors may be employed in combination with the compounds of the invention in the compositions and methods described above.

Hormones and hormonal analogues are useful compounds for treating cancers in which there is a relationship between the hormone(s) and growth and/or lack of growth of the cancer. Antitumor hormones and hormonal analogues may be employed in combination with the compounds of the invention in the compositions and methods described above.

Examples of hormones and hormonal analogues believed to be useful in the treatment of neoplasms include, but are not limited to antiestrogens, such as tamoxifen, toremifene, raloxifene, fulvestrant, iodoxyfene and droloxifene; anti-androgens; such as flutamide, nilutamide, bicalutamide and cyproterone acetate; adrenocorticosteroids such as prednisone and prednisolone; aminoglutethimide and other aromatase inhibitors such as anastrozole, letrazole, vorazole, and exemestane; progestrins such as megestrol acetate; 5α-reductase inhibitors such as finasteride and dutasteride; and gonadotropin-releasing hormones (GnRH) and analogues thereof, such as Leutinizing Hormone-releasing Hormone (LHRH) agonists and antagonists such as goserelin luprolide, leuprorelin and buserelin.

Signal transduction pathway inhibitors are those inhibitors which block or inhibit a chemical process which evokes an intracellular change. As used herein this change is cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myo-inositol signaling, and Ras oncogenes. Signal transduction pathway inhibitors may be employed in combination with the compounds of the invention in the compositions and methods described above.

Several protein tyrosine kinases catalyze the phosphorylation of specific tyrosine residues in various proteins involved in the regulation of cell growth. Such protein tyrosine kinases can be broadly classified as receptor or non-receptor kinases.

Receptor tyrosine kinase inhibitors which may be combined with the compounds of the invention include those involved in the regulation of cell growth, which receptor tyrosine kinases are sometimes referred to as "growth factor receptors." Examples of growth factor receptor inhibitors, in addition to IGF-1R family tyrosine kinase inhibitors, include but are not limited to inhibitors of: epidermal growth factor family receptors (EGFR, ErbB2, and ErbB4); platelet derived growth factor receptors (PDGFRs), vascular endothelial growth factor receptors (VEGFRs), tyrosine kinase with immunoglobulin-like and epidermal growth factor homology domains (TIE-2), macrophage colony stimulating factor (c-fms), c-kit, c-met, fibroblast growth factor receptors (FG-FRs), hepatocyte growth factor receptors (HGFRs), Trk receptors (TrkA, TrkB, and TrkC), ephrin (Eph) receptors, the RET protooncogene, and Akt kinases.

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin®) is an example of an anti-erbB2 antibody inhibitor of growth factor function. One example of an anti-erbB1 antibody inhibitor of growth factor function is cetuximab (Erbitux™, C225). Bevacizumab (Avastin®) is an example of a monoclonal antibody directed against VEGFR. Examples of small molecule inhibitors of epidermal growth factor receptors include but are not limited to lapatinib (Tykerb™) and erlotinib (TARCEVA®). Imatinib (GLEEVEC®) is one example of a PDGFR inhibitor. Examples of VEGFR inhibitors include pazopanib, ZD6474, AZD2171, PTK787, sunitinib and sorafenib.

In one embodiment, the present invention provides methods of treatment of any of the various conditions enumerated above comprising administering a compound of the invention in combination with an EGFR or ErbB2 inhibitor. In one particular embodiment, the methods of the present invention comprise administering a compound of the invention in combination with lapatinib. In one particular embodiment, the methods of the present invention comprise administering a compound of the invention in combination with trastuzumab. In one particular embodiment, the methods of the present invention comprise administering a compound of the invention in combination with erlotinib. In one particular embodiment, the methods of the present invention comprise administering a compound of the invention in combination with gefitinib.

In another embodiment, the present invention provides methods of treatment of any of the various conditions enumerated above comprising administering a compound of the invention in combination with a VEGFR inhibitor. In one particular embodiment, the methods of the present invention comprise administering a compound of the invention in combination with pazopanib.

Tyrosine kinases that are not transmembrane growth factor receptor kinases are termed non-receptor, or intracellular tyrosine kinases. Inhibitors of non-receptor tyrosine kinases are sometimes referred to as "anti-metastatic agents" and are useful in the present invention. Targets or potential targets of anti-metastatic agents, include, but are not limited to, c-Src, Lck, Fyn, Yes, Jak, abl kinase (c-Abl and Bcr-Abl), FAK (focal adhesion kinase) and Bruton's tyrosine kinase (BTK). Non-receptor kinases and agents, which inhibit non-receptor tyrosine kinase function, are described in Sinha, S, and Corey, S. J., (1999) *J. Hematother. Stem Cell Res.* 8:465-80; and Bolen, J. B. and Brugge, J. S., (1997) *Annu. Rev. of Immunol.* 15:371-404.

SH2/SH3 domain blockers are agents that disrupt SH2 or SH3 domain binding in a variety of enzymes or adaptor proteins including, but not limited to, PI3-K p85 subunit, Src family kinases, adaptor molecules (Shc, Crk, Nck, Grb2) and Ras-GAP. Examples of Src inhibitors include but are not limited to dasatinib and BMS-354825 (J. Med. Chem (2004) 47:6658-6661).

Inhibitors of serine/threonine kinases may also be used in combination with the compounds of the invention in any of the compositions and methods described above. Examples of serine/threonine kinase inhibitors that may also be used in combination with a compound of the present invention include, but are not limited to polo-like kinase inhibitors (Plk family e.g., Plk1, Plk2, and Plk3), which play critical roles in regulating processes in the cell cycle including the entry into and the exit from mitosis; MAP kinase cascade blockers, which include Ras/Raf kinase inhibitors, mitogen or extracellular regulated kinases (MEKs), and extracellular regulated kinases (ERKs); Aurora kinase inhibitors (including inhibitors of Aurora A and Aurora B); protein kinase C(PKC) family member blockers, including inhibitors of PKC subtypes (alpha, beta, gamma, epsilon, mu, lambda, iota, zeta); inhibitors of kappa-B (IkB) kinase family (IKK-alpha, IKK-beta); PKB/Akt kinase family inhibitors; and inhibitors of TGF-beta receptor kinases. Examples of Plk inhibitors are described in PCT Publication No. WO04/014899 to GlaxoSmithKline. Other examples of serine/threonine kinase inhibitors are known in the art. In another embodiment, the present invention provides methods of treatment of any of the various conditions enumerated above comprising administering a compound of the invention in combination with a Plk inhibitor. In one particular embodiment, the methods of the present invention comprise administering a compound of the invention in combination with 5-{6-[(4-Methyl piperazin-1-yl)methyl]-1H-benzimidazol-1-yl}-3-{(1R)-1-[2-(trifluoromethyl)phenyl]ethoxy}thiophene-2-carboxamide.

Urokinase, also referred to as urokinase-type Plasminogen Activator (uPA), is a serine protease. Activation of the serine protease plasmin triggers a proteolysis cascade which is involved in thrombolysis or extracellular matrix degradation. Elevated expression of urokinase and several other components of the plasminogen activation system have been correlated with tumor malignancy including several aspects of cancer biology such as cell adhesion, migration and cellular mitotic pathways as well. Inhibitors of urokinase expression may be used in combination with the compounds of the invention in the compositions and methods described above.

Inhibitors of Ras oncogene may also be useful in combination with the compounds of the invention. Such inhibitors include inhibitors of farnesyltransferase, geranyl-geranyl transferase, and CAAX proteases as well as anti-sense oligonucleotides, ribozymes and immunotherapy. Such inhibitors have been shown to block Ras activation in cells containing mutant Ras, thereby acting as antiproliferative agents.

Other inhibitors of kinases involved in the IGF-1R signaling axis may also be useful in combination with the compounds of the invention. Such inhibitors include but are not limited to inhibitors of JNK1/2/3, PI3K, AKT and MEK, and 14.3.3 signaling inhibitors. Examples of AKT inhibitors are described in PCT Publication No. WO 2007/058850, published 24 May 2007 which corresponds to PCT Application No. PCT/US2006/043513, filed 9 Nov. 2006, to GlaxoSmithKline. One particular AKT inhibitor disclosed therein is 4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol.

Cell cycle signaling inhibitors, including inhibitors of cyclin dependent kinases (CDKs) are also useful in combination with the compounds of the invention in the compositions and methods described above. Examples of cyclin dependent kinases, including CDK2, CDK4, and CDK6 and inhibitors for the same are described in, for instance, Rosania G. R., et al., *Exp. Opin. Ther. Patents* (2000) 10:215-230.

Receptor kinase angiogenesis inhibitors may also find use in the present invention. Inhibitors of angiogenesis related to VEGFR and TIE-2 are discussed above in regard to signal transduction inhibitors (both are receptor tyrosine kinases). Other inhibitors may be used in combination with the compounds of the invention. For example, anti-VEGF antibodies, which do not recognize VEGFR (the receptor tyrosine kinase), but bind to the ligand; small molecule inhibitors of integrin (alpha$_v$ beta$_3$) that inhibit angiogenesis; endostatin and angiostatin (non-RTK) may also prove useful in combination with the compounds of the invention. One example of a anti-VEGF antibody is bevacizumab (AVASTIN®).

Inhibitors of phosphatidyl inositol-3-OH kinase family members including blockers of PI3-kinase, ATM, DNA-PK, and Ku may also be useful in combination with the present invention.

Also of potential use in combination with the compounds of the invention are myo-inositol signaling inhibitors such as phospholipase C blockers and myoinositol analogues.

Antisense therapies may also be used in combination with the compounds of the invention. Examples of such antisense therapies include those directed towards the targets described above such as ISIS 2503 and gene therapy approaches such as those using thymidine kinase or cytosine deaminase.

Agents used in immunotherapeutic regimens may also be useful in combination with the compounds of the invention. Immunotherapeutic regimens include ex-vivo and in-vivo approaches to increasing immunogenicity of patient tumor cells such as transfection with cytokines (IL-2, IL-4, GMCFS and MCFS), approaches to increase T-cell activity, approaches with transfected immune cells and approaches with anti-idiotypic antibodies. Another potentially useful immunotherapeutic regimen is monoclonal antibodies with wild-type Fc receptors that may illicit an immune response in the host (e.g., IGF-1R monoclonal antibodies).

Agents used in proapoptotic regimens (e.g., Bcl-2 antisense oligonucleotides) may also be used in combination with the compounds of the invention. Members of the Bcl-2 family of proteins block apoptosis. Upregulation of Bcl-2 has therefore been linked to chemoresistance. Studies have shown that the epidermal growth factor (EGF) stimulates anti-apoptotic members of the Bcl-2 family (i.e., mcl-1). Therefore, strategies designed to downregulate the expression of Bcl-2 in tumors have demonstrated clinical benefit and are now in Phase II/III trials, namely Genta's G3139 bcl-2 antisense oligonucleotide. Such proapoptotic strategies using the antisense oligonucleotide strategy for Bcl-2 are discussed in Water, J. S., et al., *J. Clin. Oncol.* (2000) 18:1812-1823; and Kitada, S., et al., *Antisense Res. Dev.* (1994) 4:71-79.

Compounds of the invention may be prepared using the processes described below. In all of the schemes described below, it is understood that protecting groups may be employed where necessary in accordance with general principles known to those of skill in the art, for example, see Green, T. W. and Wuts, P. G. M. (1991) *Protecting Groups in Organic Synthesis*, John Wiley & Sons. The selection of a particular protecting group and processes for installation and removal of protecting groups is within the skill of those in the art. The selection of processes for installation and removal of protecting groups as well as the reaction conditions and order of their execution shall be consistent with the preparation of compounds of formula (I).

Compounds of the invention may be prepared by a process outlined in Scheme 1 below.

Scheme 1

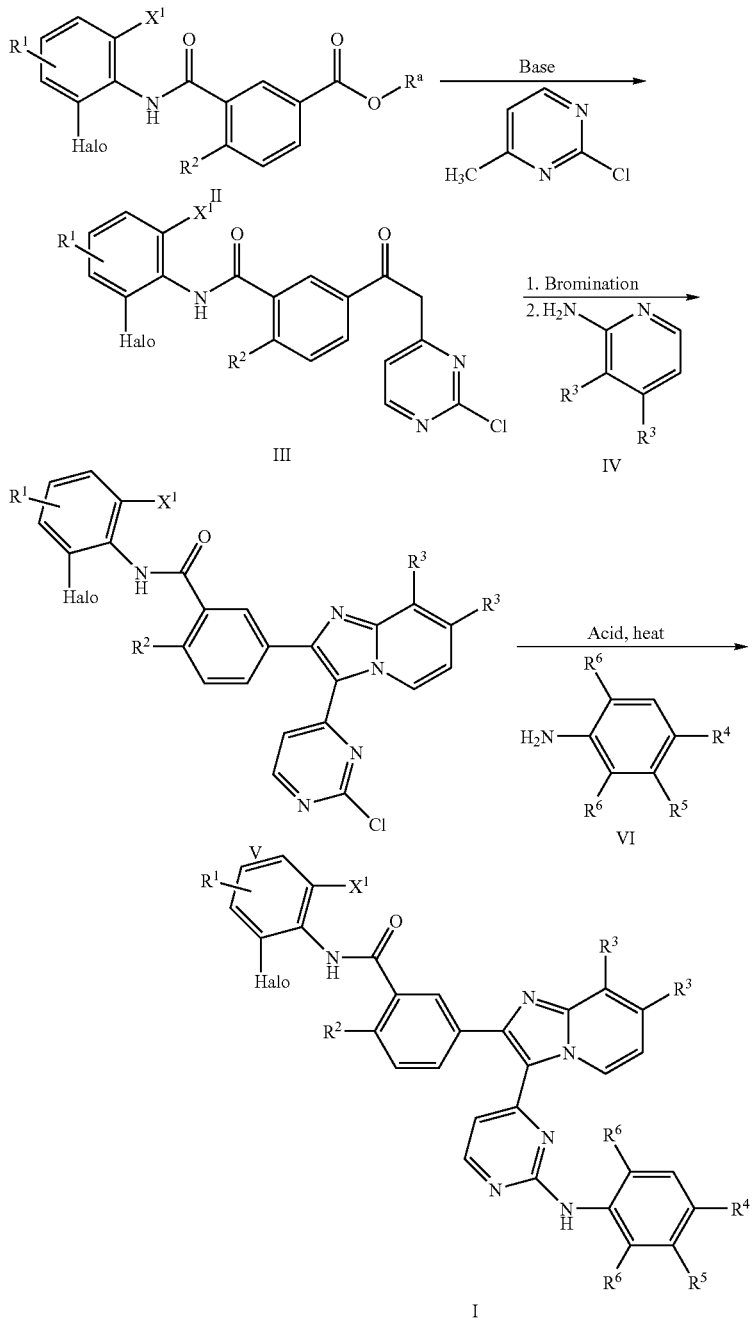

wherein:

R$^a$ is alkyl or cycloalkyl; and all other variables are as defined above.

Generally, the process for preparing the compounds of formula (I) (all formulas and all other variables having been defined above) comprises the steps of:

a) reacting 2-chloro-4-methylpyrimidine with a suitable base and an aryl amide of formula (II) to prepare a compound of formula (III);
b) reacting the compound of formula (III) with a brominating reagent followed by cyclization with an aminopyridine of formula (IV) to prepare a compound of formula (V);
c) reacting a compound of formula (V) with an aniline of formula (VI) under acidic conditions with heating to prepare the compound of formula (I).

The process may further comprise the optional steps of:

d) converting the compound of formula (I) to a pharmaceutically acceptable salt thereof; and/or
e) converting the compound of formula (I) or pharmaceutically acceptable salt thereof to a different compound of formula (I) or pharmaceutically acceptable salt thereof.

More specifically, compounds of formula (I) may be prepared by reacting a compound of formula (V) with an aniline of formula (VI) under acidic conditions with heating.

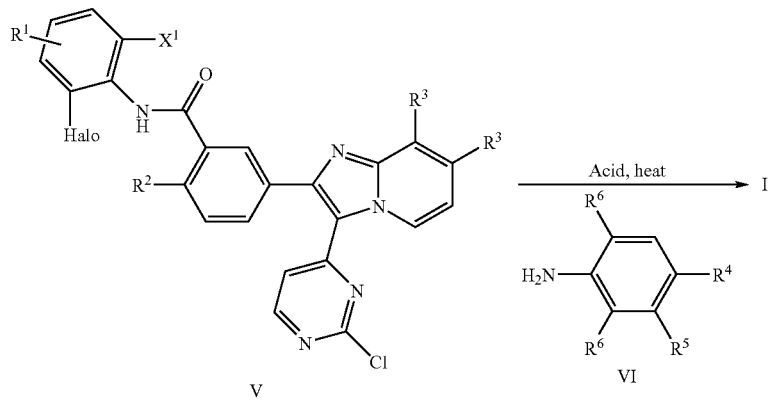

wherein all variables are as defined above.

The reaction is typically carried out by mixing the compound of formula (V) with an aniline of formula (VI) in a suitable solvent in the presence of a suitable acid with heating. Typical solvents include but are not limited to isopropyl alcohol, trifluoroethanol, dioxane, and N,N-dimethylformamide. Suitable acids include but are not limited to hydrochloric acid, p-toluenesulfonic acid, and pyridinium p-toluenesulfonate. The reaction is typically carried out at temperatures ranging from about 50° C. to about 120° C. The reaction may optionally be performed under microwave conditions at temperatures typically ranging from about 120° C. to about 200° C. Anilines of formula (yl) are either commercially available or can be prepared according to methods known to those skilled in the art.

Compounds of formula (V) may be prepared by reacting a compound of formula (III) with a brominating reagent followed by cyclization with an aminopyridine of formula (IV).

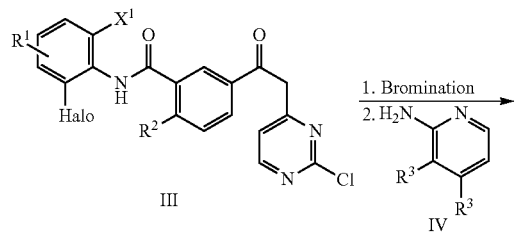

wherein all variables are as defined above.

Suitable brominating reagents include but are not limited to N-bromosuccinimide (NBS), bromine, and tetrabutylammonium tribromide. Suitable solvents for the bromination step include but are not limited to dichloromethane, chloroform, dioxane, tetrahydrofuran, and dichloroethane. The bromination step is typically carried out at ambient temperature. Suitable solvents for cyclization with the aminopyridine of formula (IV) include but are not limited to dioxane, tetrahydrofuran, and N—N-dimethylformamide. The cyclization step with aminopyridines of formula (IV) is typically carried out with a two to four fold excess of the aminopyridine, at temperatures ranging from 40° C. to 100° C. Aminopyridines of formula (IV) are commercially available or can be prepared according to methods known to those skilled in the art.

Compounds of formula (III) may be prepared by reacting 2-chloro-4-methylpyrimidine with a suitable base and an aryl amide of formula (II).

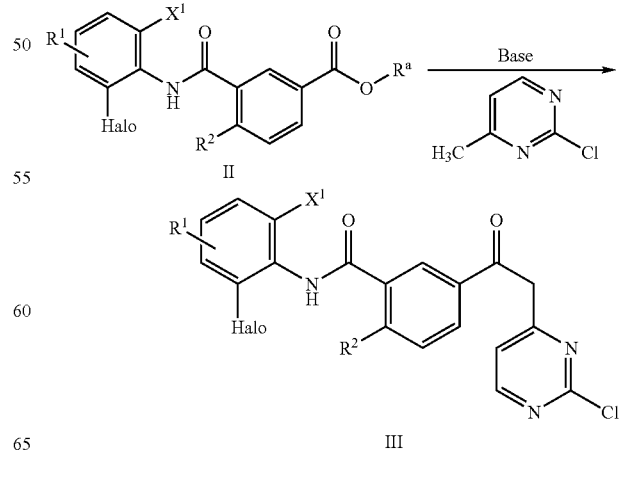

wherein all variables are as defined above.

The reaction can be carried out by reacting an aryl amide of formula (II) and 2-chloro-4-methylpyrimidine with a suitable base at temperatures typically ranging from about −78° C. to ambient temperature. Suitable solvents include but are not limited to tetrahydrofuran, dioxane, and 1,2-dimethoxyethane. Suitable bases include but are not limited to lithium bis(trimethylsilyl)amide, lithium diisopropylamide, and sodium bis(trimethylsilyl)amide.

The aryl amides of formula (II), may be conveniently prepared according to the following Scheme.

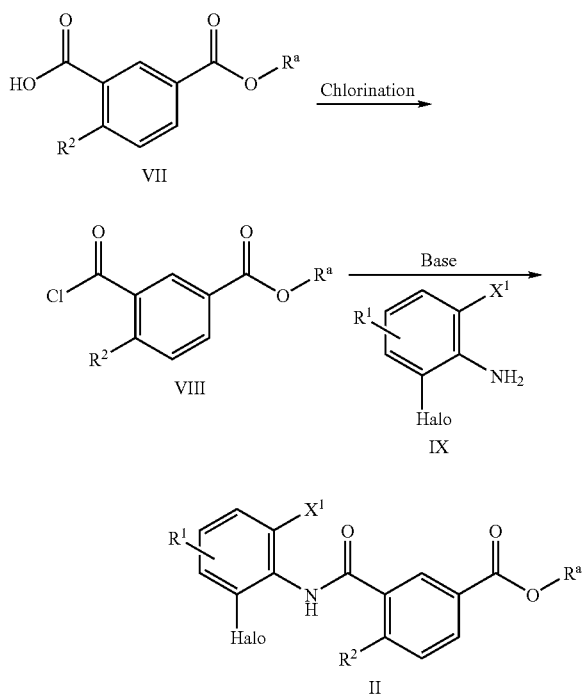

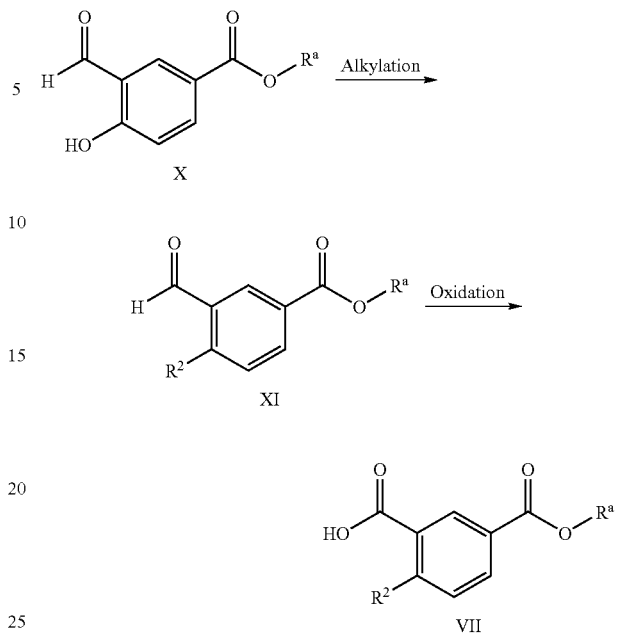

wherein all variables are as defined above.

More specifically, the aryl amides of formula (II) may be prepared by an reacting acid chloride of formula (VIII) with an aniline of formula (IX) in the presence of a suitable base. Suitable bases include but are not limited to trialkylamines and pyridines. Suitable solvents for this reaction include but are not limited to dichloromethane, chloroform, dichloroethane, diethyl ether and tetrahydrofuran. The reaction is typically carried out at ambient temperature. Anilines of formula (IX) are either commercially available or may be prepared according to methods known to those skilled in the art.

The acid chloride of formula (VIII) may be prepared by reacting a carboxylic acid of formula (VII) with a chlorinating reagent. Suitable chlorinating reagents include but are not limited to oxalyl chloride with N,N-dimethylformamide, thionyl chloride and N-chlorosuccinimide. Typical solvents for this reaction include but are not limited to dichloromethane, chloroform, benzene and toluene. The reaction is typically carried out at temperatures ranging from about 0° C. to about 110° C.

Carboxylic acids of formula (VII) wherein $R^2$ is H are commercially available or can be readily prepared by one skilled in the art. Carboxylic acids of formula (VII) wherein $R^2$ is O-alkyl may be conveniently prepared according to the following Scheme.

wherein $R^2$ is O-alkyl and all other variables are as defined above.

The carboxylic acids of formula (VII) wherein $R^2$ is O-alkyl, may be prepared by reacting an aryl ether of formula (XI) with a suitable oxidizing agent under appropriate conditions. Suitable oxidizing agents and conditions include but are not limited to sodium chlorite and sulfamic acid in dioxane and water at ambient temperature and chromium (VI) oxide and sulfuric acid in acetone at ambient temperature.

The aryl ethers of formula (XI) may be prepared by reacting a phenol of formula (X) with a suitable alkylating agent in the presence of base. Suitable alkylating agents include but are not limited to alkyl halides, alkyl methanesulfonates, alkyl trifluoromethyl-sulfonates and alkyl benzenesulfonates. Typical solvents include but are not limited to N,N-dimethylformamide, dimethylsulfoxide, acetone and 2-butanone. The reaction is typically run at temperatures ranging from ambient temperature to about 120° C. Phenols of formula (X) can be prepared using methods described in the literature (e.g., Hofslokken, N. U.; Skattebol, L. *Acta Chemica Scandinavica* 1999, 53, 258-262).

Compounds of formula (I) wherein $R^2$ is H may also be prepared according to the process outlined in Scheme 2 below.

Scheme 2

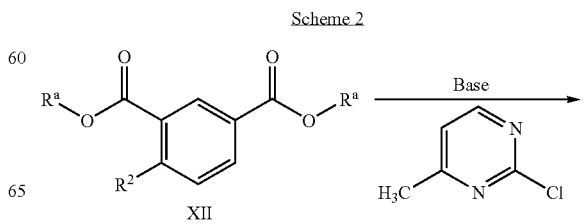

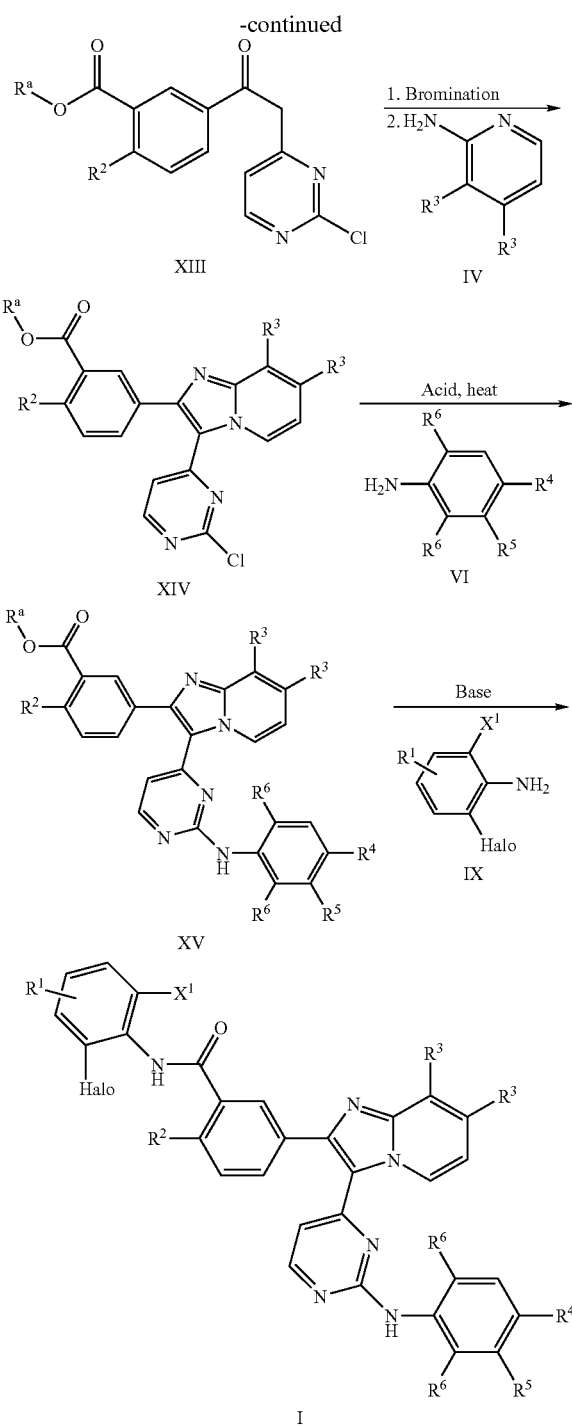

b) reacting the aryl ester of formula (XIII) with a brominating reagent followed by cyclization with an aminopyridine of formula (IV) to prepare a compound of formula (XIV);

c) reacting the compound of formula (XIV) with an aniline of formula (VI) under acidic conditions with heating to prepare a compound of formula (XV);

d) reacting the compound of formula (XV) with a suitable base and an aniline of formula (IX) to prepare the compound of formula (I).

The process may further comprise the optional steps of:

e) converting the compound of formula (I) to a pharmaceutically acceptable salt thereof; and/or f) converting the compound of formula (I) or pharmaceutically acceptable salt thereof to a different compound of formula (I) or pharmaceutically acceptable salt thereof.

More specifically, compounds of formula (I) may be prepared by reacting a compound of formula (XV) with a suitable base and an aniline of formula (IX)

wherein all variables are as defined above.

The reaction may be carried out in a suitable solvent. Suitable solvents include but are not limited to tetrahydrofuran, dioxane and 1,2-dimethoxyethane. Suitable bases include but are not limited to lithium bis(trimethylsilyl)amide, lithium diisopropylamide and sodium bis(trimethylsilyl)amide. Typical conditions involve the use of an excess of base (3 to 5 equivalents) and an excess of the aniline of formula (IX) (3 to 5 equivalents). The reaction is typically run between 0° C. and ambient temperature. Anilines of formula (IX) are either commercially available or can be prepared according to methods known to one skilled in the art.

Compounds of formula (XV) may be prepared by reacting compound of formula (XIV) with an aniline of formula (VI) under acidic conditions with heating.

wherein:

$R^2$ is H;

$R^a$ is alkyl or cycloalkyl, and all other variables are as defined above.

Generally, the process for preparing the compounds of formula (I) wherein $R^2$ is H according to this process, comprises the steps of:

a) reacting 2-chloro-4-methylpyrimidine with a suitable base and a diester of formula (XII) to prepare an aryl ester of formula (XIII);

-continued

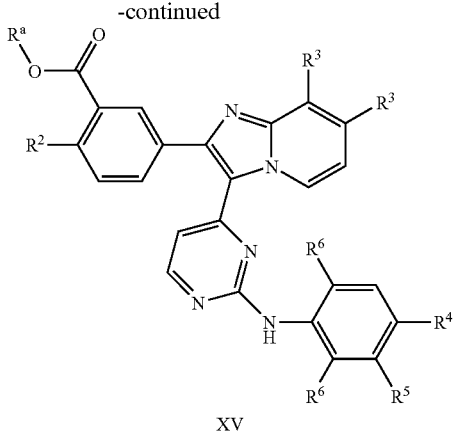

XV wherein all variables are as defined above.

The reaction may be carried out by mixing a compound of formula (XIV) with an aniline of formula (VI) in a suitable solvent in the presence of a suitable acid with heating. Typical solvents include but are not limited to isopropyl alcohol, trifluoroethanol, dioxane and N,N-dimethylformamide. Suitable acids include but are not limited to hydrochloric acid, p-toluenesulfonic acid and pyridinium p-toluenesulfonate. The reaction is typically carried out at temperatures ranging from about 50° C. to about 120° C. The reaction may optionally be performed under microwave conditions at temperatures typically ranging from about 120° C. to about 200° C. Anilines of formula (VI) are either commercially available or can be prepared according to methods known to those skilled in the art.

Compounds of formula (XIV) may be prepared by reacting an ester of formula (XIII) with a brominating reagent followed by treatment with an aminopyridine of formula (IV).

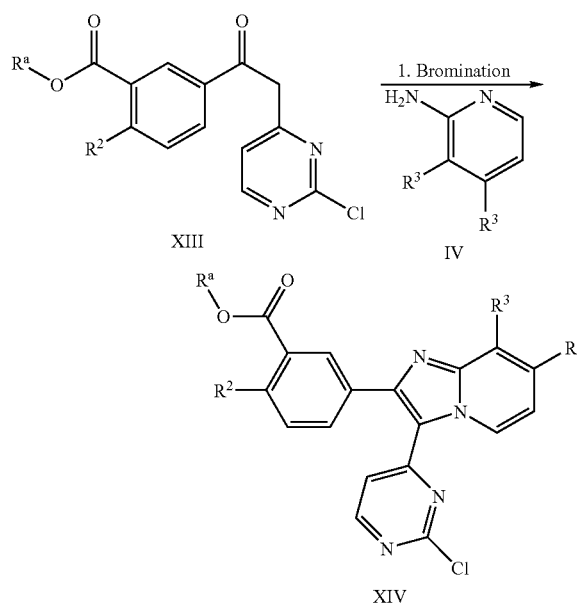

wherein all variables are as defined above in connection with Scheme 4.

This reaction may be carried out using the methods described above for the preparation of a compound of formula (V).

Esters of formula (XIII) may be prepared by reacting 2-chloro-4-methylpyrimidine with a suitable base and a diester of formula (XII), using the methods described above for the preparation of a compound of formula (III).

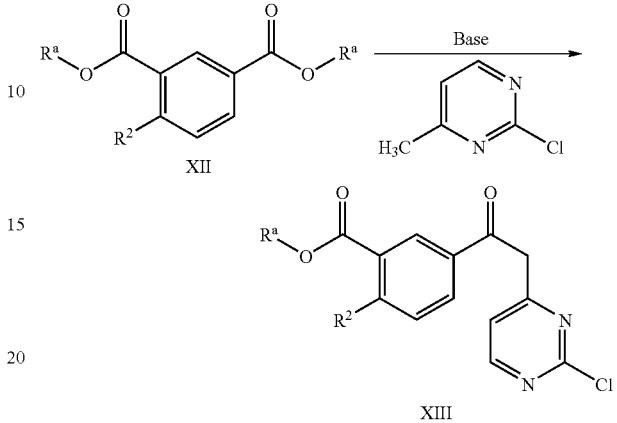

wherein all variables are as defined above.

Diesters of formula (XII) are either commercially available or can be prepared according to methods known to those skilled in the art.

The order of the steps of the foregoing reaction schemes is not critical to the practice of the present invention and the compounds of the invention may be prepared using any suitable order of steps according to the ordinarily skilled organic chemist. For example, compounds of the invention may also be prepared according to the process outlined in Scheme 3 below.

Scheme 3

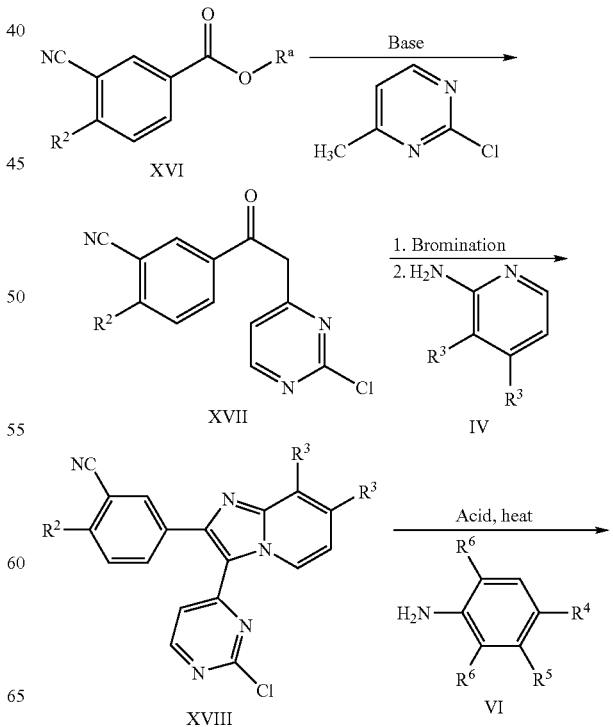

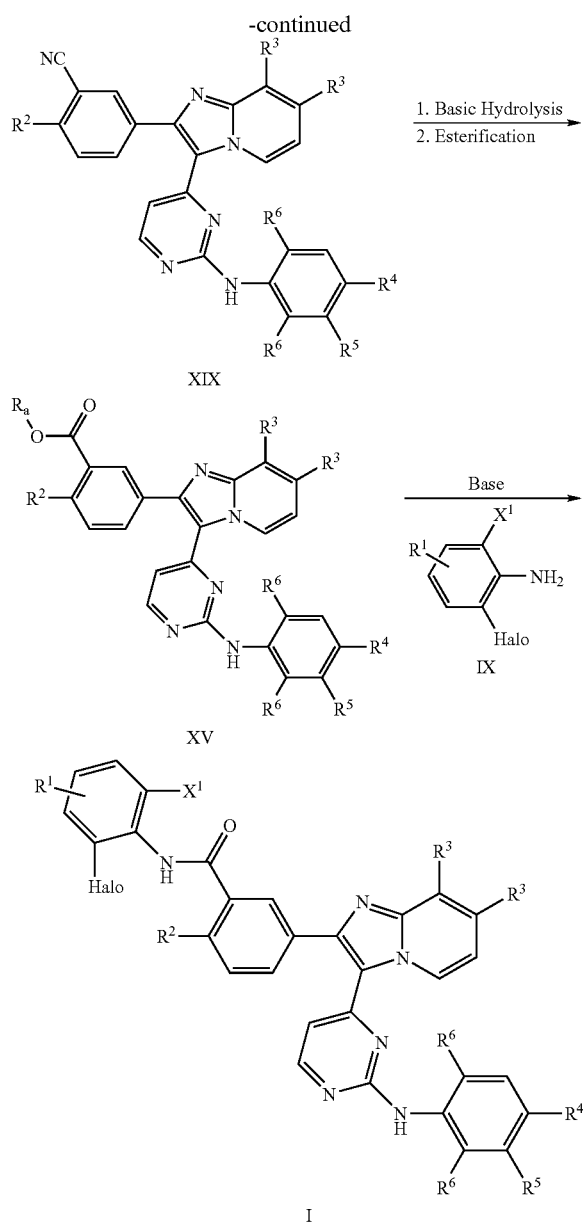

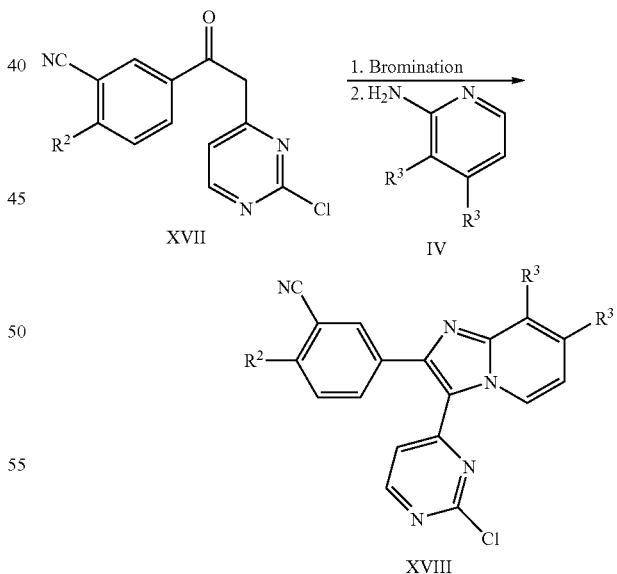

wherein:
R$^a$ is alkyl or cycloalkyl; and
all other variables are as defined above.

Generally, the process for preparing the compounds of formula (I) according to Scheme 3 comprises the steps of:
a) reacting 2-chloro-4-methylpyrimidine with a suitable base and an ester of formula (XVI) to prepare compound of formula (XVII);
b) reacting the compound of formula (XVII) with a brominating reagent followed by cyclization with an aminopyridine of formula (IV) to prepare a compound of formula (XVIII);
c) reacting the compound of formula (XVIII) with an aniline of formula (VI) under acidic conditions with heating to prepare a compound of formula (XIX);
d) hydrolyzing the compound of formula (XIX) followed by esterification to afford a compound of formula (XV);
e) reacting the compound of formula (XV) with a suitable base and an aniline of formula (IX) to prepare the compound of formula (I).

The process may further comprise the optional steps of:
f) converting the compound of formula (I) to a pharmaceutically acceptable salt thereof; and/or
g) converting the compound of formula (I) or pharmaceutically acceptable salt thereof to a different compound of formula (I) or pharmaceutically acceptable salt thereof.

Methods for the reaction of a compound of formula (XV) with an aniline of formula (IX) are described above.

According to this process, compounds of formula (XV) may be prepared by hydrolyzing a compound of formula (XIX) with aqueous acid followed by esterification. The basic hydrolysis reaction may be carried out in a mixture of a suitable solvent and water. Suitable solvents include but are not limited to tetrahydrofuran, dioxane, methanol and ethanol. Suitable bases include but are not limited to sodium hydroxide and potassium hydroxide. The reaction is typically run between 25 and 100° C. The esterification step may be carried out in a suitable solvent in the presence of acid. Suitable solvents include but are not limited to methanol and ethanol. Suitable acids include but are not limited to hydrochloric acid, p-toluenesulfonic acid and sulfuric acid.

Compounds of formula (XIX) may be prepared by reacting a compound of formula (XVIII) with an aniline of formula (VI) under acidic conditions with heating in the same manner as described above for the reaction of a compound of formula (XIV) with the aniline of formula (VI) to prepare a compound of formula (XV).

Compounds of formula (XVIII) may be prepared by reacting the compound of formula (XVII) with a brominating reagent followed by cyclization with an aminopyridine of formula (IV) in the same manner as described above for the reaction of a compound of formula (III) with the aminopyridine of formula (IV) to prepare a compound of formula (V).

wherein all variables are as defined above.

Compounds of formula (XVII) may be prepared by reacting 2-chloro-4-methylpyrimidine with a suitable base and an ester of formula (XVI) in the same manner as described above for the reaction of an aryl amide of formula (II) with 2-chloro-4-methylpyrimidine.

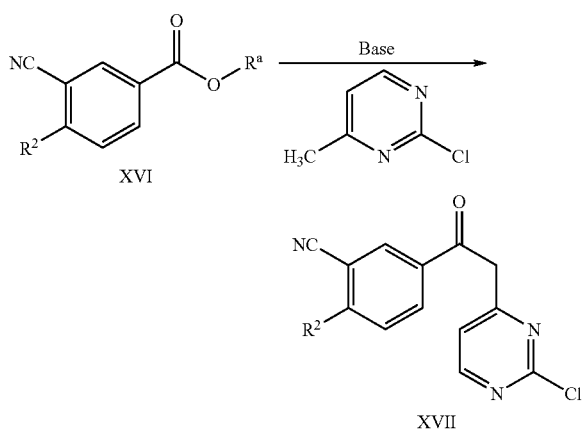

wherein all variables are as defined above.

Compounds of formula (XVI) are either commercially available or can be prepared according to methods known to one skilled in the art. As will be appreciated by those skilled in the art, this process may if desired be carried out wherein the ester of formula (XVI) (i.e., —CO$_2$R$^a$) is replaced by a Weinreb's amide (i.e., a compound of formula (XVI-a):

XVI-a

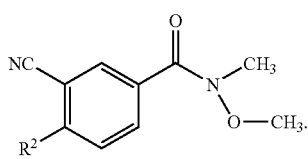

The reaction conditions for this step are analogous to those described for the compounds of formula (XVI).

It will be appreciated by those skilled in the art that choice of the reaction sequence employed to prepare a particular compound of formula (I) may depend upon the specific compound of formula (I) that is desired as well as the preference and availability of starting materials.

As will be apparent to those skilled in the art, a compound of formula (I) may be converted to another compound of formula (I) using techniques well known in the art. For example, a compound of formula (I-B) may be converted to a compound of formula (I-C) by reacting with acetic anhydride in the presence of a base.

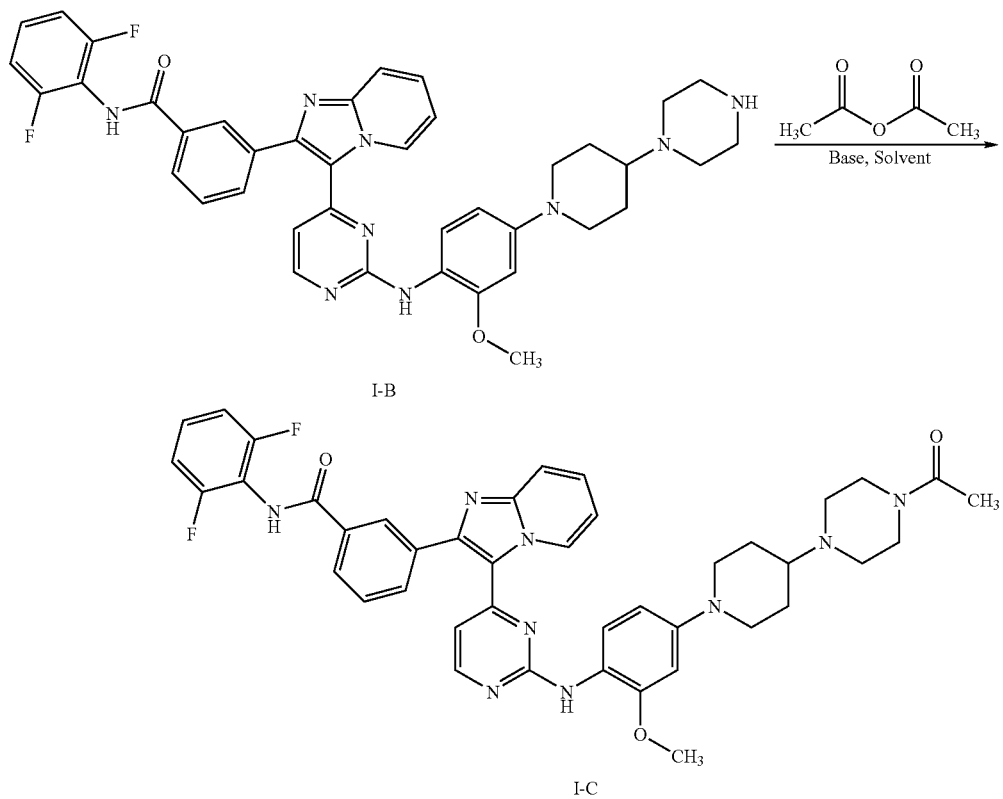

Suitable solvents for this reaction include but are not limited to dichloromethane, chloroform, tetrahydrofuran and toluene. Suitable bases for this reaction include but are not limited to trialkylamines an pyridines.

As another example, a compound of formula I-D may be converted to a compound of formula I-E by reductive alkylation using techniques described herein below as well as those know in the art.

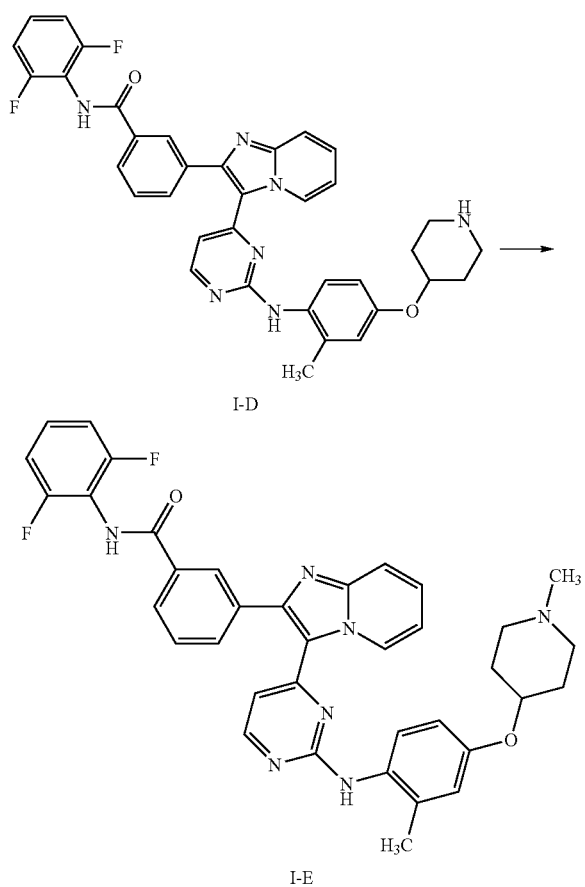

I-D

I-E

Based upon this disclosure and the examples contained herein one skilled in the art can readily convert a compound of formula (I) or a pharmaceutically acceptable salt or solvate thereof into a different compound of formula (I), or a pharmaceutically acceptable salt or solvate thereof.

The present invention also provides radiolabeled analogs of compounds of formula (I) (i.e., a compound of formula (I) having a radiolabel bound thereto) and biotinylated analogs compounds of formula (I) (i.e., a compound of formula (I) having biotin bound thereto) and solid-support-bound versions thereof, i.e. a compound of formula (I) having a radiolabel or biotin bound thereto. Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I). In one embodiment, the compounds of formula (I) are tritiated.

The radiolabeled compounds of formula (I) and biotinylated compounds of formula (I) are useful in assays for the identification of compounds which inhibit at least one IGF-1R family tyrosine kinase (particularly IGF-1R and/or IR) and/or at least one ErbB family kinase, for the identification of compounds for the treatment of a condition capable of being treated with an IGF-1R inhibitor, IR inhibitor or an ErbB inhibitor, e.g., for the treatment of neoplasms susceptible to treatment with an IGF-1R inhibitor, IR inhibitor or an ErbB inhibitor. The present invention also provides an assay method for identifying such compounds, which method comprises the step of specifically binding a radiolabeled compound of the invention or a biotinylated compound of the invention to the target protein or cellular homogenate. More specifically, suitable assay methods will include competition binding assays. The radiolabeled compounds of the invention and biotinylated compounds of the invention and solid-support-bound versions thereof, can also be employed in assays according to the methods conventional in the art.

The following examples are intended for illustration only and are not intended to limit the scope of the invention in any way. The invention is defined by the claims which follow.

EXAMPLES

As used herein, the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Reference to an example or a step in a example with respect to a particular compound indicates that the compound may be made using the procedure described in the referenced example or step. Such reference is not an indication that the compound is from the same batch of material produced in the referenced example or step. While steps in a particular example maybe described sequentially, this is not an indication that the steps were performed one right after another. The following abbreviations may be used in the examples and throughout the specification:

atm (atmosphere);
g (grams);
mg (milligrams);
h (hour(s));
min (minutes);
L (liters);
mL (milliliters);
μL (microliters);
M (molar);
mM (millimolar);
nm (nanomolar);
μm (micromolar);
mol (moles);
mmol (millimoles);
mp (melting point);
psi (pounds per square inch);
rt (room temperature);
TLC (thin layer chromatography);
RP (reverse phase;
$H_2$ (hydrogen);
$N_2$ (nitrogen)
$Ac_2O$ (acetic anhydride);
APC (Allophycocyanin)
ATP (adenosine triphosphate);
BOC (tert-butyloxycarbonyl);
BOC-On (2-tert-butoxycarbony-loxyimino)-2-phenylacetonitrile);
BSA (bovine serum albumin)
CHAPS (3-[3-Cholamidopropyl)-Dimethylammonio]-1-Propanesulfonate);
$CHCl_3$ (chloroform);
$Cs_2CO_3$ (cesium carbonate);
DCE (dichloroethane);
DCM ($CH_2Cl_2$; dichloromethane);
DABCO (1,4-diazabicyclo[2.2.2]octane)

DMF (N,N-dimethylformamide);
DMSO (dimethylsulfoxide); LCMS (liquid chromatography mass
DTT (Dithiothreitol); spectrometry);
EDTA (ethylenediaminetetraacetic acid);
EtOH (ethanol); LiOH (lithium hydroxide);
EtOAc (ethyl acetate);
Eu (Europium);
GST (Glutathione S-transferase);
HCl (hydrochloric acid)
HEPES (4-(2-hydroxyethyl)-1-piperazine ethane sulfonic acid);
hIGF1R or IGF-1R (human Insulin-like growth factor 1 receptor kinase);
hIR (human insulin receptor kinase);
HOAc (acetic acid);
$HNO_3$ (nitric acid);
HPLC (high pressure liquid chromatography);
HRP (horseradish peroxidase);
iPrOH (isopropanol);
$K_2CO_3$ (potassium carbonate);
$KHSO_4$ (potassium hydrogensulfate);
KOH (potassium hydroxide);
LAH (lithium aluminum hydride)
LCMS (liquid chromatography mass spectrometry);
LiHMDS (lithium hexamethyldisilazide);
LiOH (lithium hydroxide);
Me (methyl; —$CH_3$)
MeOH (methanol);
$MgCl_2$ (magnesium chloride);
$MgCO_3$ (magnesium carbonate);
$MgSO_4$ (magnesium sulfate);
$NaBH_4$ (Sodium borohydride);
NCBI (National Center for Biotechnology Information);
NaCl (sodium chloride);
$Na_2CO_3$ (sodium carbonate);
$NaHCO_3$ (sodium bicarbonate);
NaH (sodium hydride);
NaHMDS (sodium hexamethyldisilazide);
$Na_2SO_4$ (sodium sulfate);
NBS (N-bromosuccinimide);
NCS (N-chlorosuccinimide)
$NH_4Cl$ (ammonium chloride):
$NH_4OH$ (ammonium hydroxide);
$Pd_2(dba)_3$ (Tris(dibenzylideneacetone)-dipalladium (0)
$Pd(PPh_3)_4$ (Tetrakis(triphenylphosphine)-palladium(0)
$PdCl_2(dppf)$*DCM (Dichloro[1,1'-bis-(diphenylphosphino)ferrocene]palladium (II) dichloromethane adduct);
PhMe (toluene);
TEA (triethylamine);
TFA (trifluoroacetic acid);
THF (tetrahydrofuran) and
Tris-HCl (Tris(hydroxymethyl)amino-methane hydrochloride).

Intermediate Example 1

3-[3-(2-chloro-4-pyrimidinyl)imidazo[1,2-a]pyridin-2-yl]-N-(2,6-difluorophenyl)-benzamide

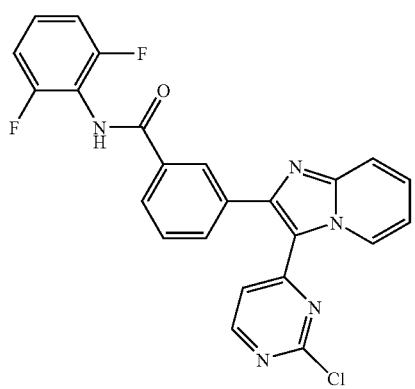

Step A: methyl 3-{[(2,6-difluorophenyl)amino]carbonyl}benzoate

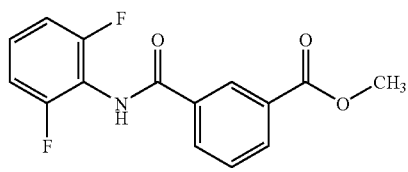

3-[(Methyloxy)carbonyl]benzoic acid (11.0 g, 61.1 mmol) was dissolved in 600 mL of dichloromethane with stirring. Oxalyl chloride (16.3 mL, 183.2 mmol) was added dropwise by addition funnel as a solution in 100 mL of DCM. DMF (3.0 mL) was added via syringe. The reaction was stirred overnight at rt and then concentrated in vacuo.

The resultant solid was further dried under high vacuum pressure. The solid was dissolved in 600 mL of DCM with stirring. Pyridine (24.5 mL, 305.3 mmol), (4-dimethylamino)-pyridine (3.7 g, 30.5 mmol), and 2,6-difluoroaniline (19.7 mL, 183.2 mmol) were added to the solution. The reaction was stirred overnight and poured into 1N HCl. The layers were separated, and the aqueous layer was washed twice with DCM. The combined organic layers were dried over $MgSO_4$, filtered, and concentrated in vacuo. The crude product was purified by flash chromatography. The clean fractions (by TLC) were concentrated in vacuo to afford 14.87 g (84%) of the desired product. $^1$H NMR (400 MHz, Step B: 3-[(2-chloro-4-pyrimidinyl)acetyl]-N-(2,6-fluorophenyl)benzamide and 3-[(E)-2-(2-chloro-4-pyrimidinyl)-1-hydroxyethenyl]-N-(2,6-difluorophenyl)benzamide

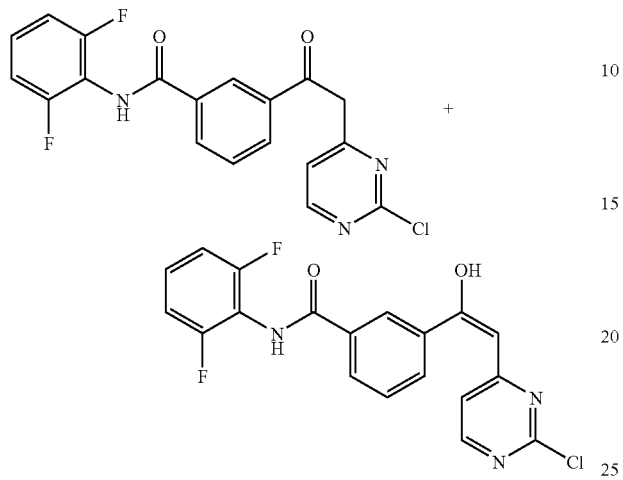

Methyl 3-{[(2,6-difluorophenyl)amino]carbonyl}benzoate (5.24 g, 18.0 mmol) was dissolved in 50 mL of THF with stirring and cooled to 0° C. Lithium bis(trimethylsilyl)amide (54 mL, 1.0M in THF, 54 mmol) was added slowly via syringe. 2-Chloro-4-methylpyrimidine (2.55 g, 19.8 mmol) was dissolved in 20 mL of THF and added dropwise via addition funnel. The addition funnel was rinsed with 10 mL of THF. The reaction was stirred at 0° C. for 1 hour and then allowed to warm to rt. The reaction was quenched with 10% aqueous ammonium chloride solution. The mixture was poured into water and EtOAc, and the layers were separated. The organic layer was washed with brine, and the combined aqueous layers were extracted with EtOAc. The combined organic layers were dried over MgSO₄, filtered, and concentrated in vacuo. The resultant solid was triturated with 50% EtOAc/hexanes and filtered. The solid was washed with 50% diethyl ether/hexanes. The solid was air dried and collected to afford 3.60 g (52%) of the desired product. The filtrate was concentrated and purified by flash chromatography. The clean fractions (by TLC) were concentrated in vacuo to afford an additional 2.13 g (31%) of the desired product. $^1$H NMR (400 MHz, DMSO-$d_6$) δ [Ketone] 10.37 (s, 1H), 8.24 (d, J=7.9 Hz, 2H), 7.73 (t, J=7.9 Hz, 1H), 4.76 (s, 2H); [Enol] 13.56 (s, 1H), 10.31 (s, 1H), 8.46 (s, 1H), 8.10 (d, J=7.9 Hz, 2H), 7.67 (t, J=7.9 Hz, 1H), 6.64 (s, 1H); [Peaks not assigned to either ketone or enol form] 8.74 (d, J=5.1 Hz), 8.65-8.56 (m), 7.60 (d, J=4.9 Hz), 7.47-7.43 (m), 7.21 (t, J=8.2 Hz).

Step C: 3-[3-(2-chloro-4-pyrimidinyl)imidazo[1,2-a]pyridin-2-yl]-N-(2,6-difluorophenyl)-benzamide A tautomeric mixture of 3-[(2-chloro-4-pyrimidinyl)acetyl]-N-(2,6-fluorophenyl)benzamide and 3-[(E)-2-(2-chloro-4-pyrimidinyl)-1-hydroxyethenyl]-N-(2,6-difluorophenyl)benzamide (5.73 g, 14.8 mmol) was dissolved in 150 mL of DCM with stirring. NBS (2.63 g, 14.8 mmol) was added in a single portion, and the reaction was stirred for 15 minutes. The reaction was concentrated in vacuo. Dioxane (100 mL) was added to dissolve the residue with stirring. 2-Aminopyridine (4.18 g, 44.4 mmol) was added, and the reaction was heated to 60° C. for 16 hours. The reaction was cooled to rt and poured into half-saturated NaHCO₃ solution and EtOAc. The layers were separated, and the organic layer was washed with brine. The combined aqueous layers were extracted with EtOAc. The combined organic layers were dried over MgSO₄, filtered, and concentrated in vacuo. The mixture was purified by flash chromatography to afford 5.26 g (77%) of the desired product. $^1$H NMR (400 MHz, DMSO-$d_6$): δ 10.20 (s, 1H), 9.40 (d, J=7.0 Hz, 1H), 8.56 (d, J=5.3 Hz, 1H), 8.33 (s, 1H), 8.08 (d, J=7.9 Hz, 1H), 7.85 (d, J=7.9 Hz, 1H), 7.81 (d, J=9.0 Hz, 1H), 7.66-7.54 (m, 2H), 7.89 (m, 1H), 7.27-7.15 (m, 4H).

Intermediate Example 2

5-[3-(2-chloro-4-pyrimidinyl)imidazo[1,2-a]pyridin-2-yl]-N-(2,6-difluorophenyl)-2-(methyloxy)benzamide

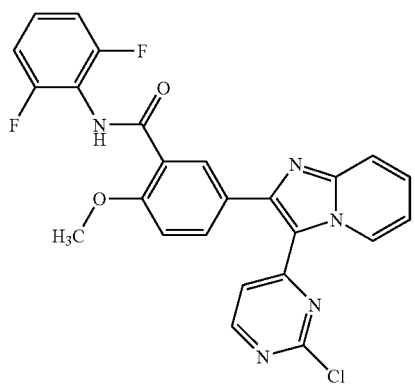

Step A: Methyl 3-formyl-4-hydroxybenzoate

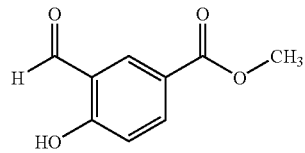

Methyl 4-hydroxybenzoate (3.00 g, 19.7 mmol) and magnesium chloride (2.81 g, 29.5 mmol) were stirred in 100 mL of acetonitrile. TEA (10.3 mL, 73.9 mmol) was added via syringe. Paraformaldehyde (12.0 g, 133 mmol) was added in a single portion and the reaction was heated to reflux. The reaction was stirred at reflux for 24 hours and cooled to rt. The reaction was quenched by the addition of approximately 100 mL of 1N HCl and poured into EtOAc. The layers were separated, and the organic layer was washed with brine. The combined aqueous layers were extracted with EtOAc. The combined organic layers were dried over MgSO₄, filtered, and concentrated in vacuo. The crude product was purified by flash chromatography. The clean fractions (by TLC) were concentrated in vacuo to afford 2.06 g (58%) of the desired product. $^1$H NMR (400 MHz, DMSO-$d_6$): δ 11.54 (s, 1H), 10.27 (s, 1H), 8.21 (d, J=2.4 Hz, 1H), 8.03 (dd, J=8.8, 2.4 Hz, 1H), 7.07 (d, J=8.8 Hz, 1H), 3.79 (s, 3H).

Step B: methyl 3-formyl-4-(methyloxy)benzoate

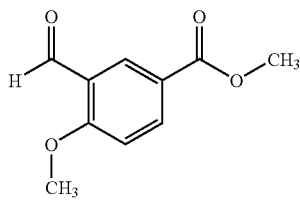

Methyl 3-formyl-4-hydroxybenzoate (2.06 g, 11.4 mmol) and K$_2$CO$_3$ (2.36 g, 17.1 mmol) were stirred in 50 mL of DMF. Methyl iodide (1.42 mL, 22.8 mmol) was added via syringe, and the reaction was stirred for 6 hours at rt. The reaction was poured into H$_2$O and diethyl ether, and the layers were separated. The organic layer was washed with brine, and the combined aqueous layers were extracted with diethyl ether. The combined organic layers were dried over MgSO$_4$, filtered, and concentrated in vacuo to afford 2.24 g of crude desired product. $^1$H NMR (400 MHz, DMSO-d$_6$): δ 10.33 (s, 1H), 8.23 (d, J=2.2 Hz, 1H), 8.20 (dd, J=8.8, 2.2 Hz, 1H), 7.36 (d, J=8.8 Hz, 1H), 3.99 (s, 3H), 3.83 (s, 3H).

Step C: 2-(methyloxy)-5-[(methyloxy)carbonyl]benzoic acid

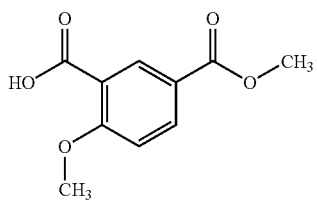

Crude methyl 3-formyl-4-(methyloxy)benzoate from the previous step was dissolved in 40 mL of dioxane with stirring. Sulfamic acid (5.87 g, 60.5 mmol) in 20 mL of H$_2$O was added to the stirring solution. Sodium chlorite (1.68 g, 80% by weight, 18.6 mmol) in 20 mL of H$_2$O was added dropwise via addition funnel. The reaction was stirred for 40 min and poured into EtOAc and H$_2$O. The layers were separated, and the organic layer was washed with brine. The combined aqueous layers were extracted with EtOAc, and the combined organic layers were dried over MgSO$_4$, filtered, and concentrated in vacuo. The solid was transferred to an Erlenmeyer flask with the aid of 30-40 mL of DCM. Approximately 50 mL of hexanes was added. Air was blown over the solution to allow most of the DCM to evaporate. Diethyl ether was added (20-30 mL), and the suspension was filtered. The solid was washed with hexanes, collected, and dried to afford 1.96 g (82% over 2 steps) of the desired compound. $^1$H NMR (400 MHz, DMSO-d$_6$): δ 12.92 (br s, 1H), 8.22 (d, J=2.2 Hz, 1H), 8.07 (dd, J=8.8, 2.2 Hz, 1H), 7.24 (d, J=8.8 Hz, 1H), 3.88 (s, 3H), 3.82 (s, 3H).

Step D: methyl 3-{[(2,6-difluorophenyl)amino]carbonyl}-4-(methyloxy)benzoate

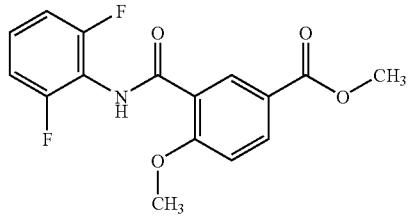

2-(Methyloxy)-5-[(methyloxy)carbonyl]benzoic acid (1.96 g, 9.33 mmol) was suspended in 60 mL of DCM with stirring. DMF (0.036 mL, 0.46 mmol) was added via syringe. Oxalyl chloride (7.0 mL, 2.0M in dichloromethane, 14 mmol) was added dropwise via addition funnel. The addition funnel was rinsed with 10 mL of DCM. The reaction was stirred for 2 hours and concentrated in vacuo. The resultant solid was further dried under high vacuum pressure. The solid was dissolved in 60 mL of DCM with stirring. Pyridine (3.8 mL, 47 mmol), (4-dimethylamino)pyridine (0.0570 g, 0.467 mmol), and 2,6-difluoroaniline (3.0 mL, 28 mmol) were added to the solution. The reaction was stirred for 18 hours and poured into 1N HCl. The layers were separated, and the aqueous layer was washed once with DCM and once with diethyl ether. The combined organic layers were dried over MgSO$_4$, filtered, and concentrated in vacuo. The crude product was purified by flash chromatography. The clean fractions (by TLC) were concentrated in vacuo to afford 1.56 g (52%) of the desired product. $^1$H NMR (400 MHz, DMSO-d$_6$): δ 9.81 (s, 1H), 8.31 (d, J=2.0 Hz, 1H), 8.10 (dd, J=8.8, 2.0 Hz, 1H), 7.38 (m, 1H), 7.31 (d, J=88 Hz, 1H), 7.22-7.13 (m, 2H), 3.97 (s, 3H), 3.82 (s, 3H).

Step E: 5-[(2-Chloro-4-pyrimidinyl)acetyl]-N-(2,6-difluorophenyl)-2-(methyloxy)benzamide and 5-[(E)-2-(2-chloro-4-pyrimidinyl)-1-hydroxyethenyl]-N-(2,6-difluorophenyl)-2-(methyloxy)benzamide

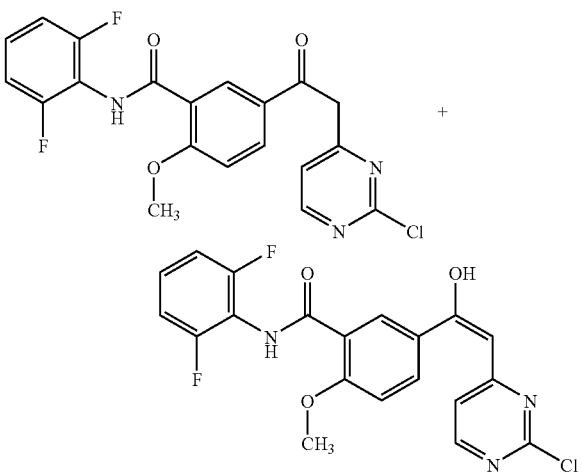

Methyl 3-{[(2,6-difluorophenyl)amino]carbonyl}-4-(methyloxy)benzoate (1.56 g, 4.86 mmol) was dissolved in 50 mL of THF with stirring and cooled to 0° C. Lithium bis(trimethylsilyl)amide (14.6 mL, 1.0M in THF, 14.6 mmol) was added slowly via syringe. 2-Chloro-4-methylpyrimidine (0.750 g, 5.83 mmol) was dissolved in 10 mL of THF and added dropwise via addition funnel. The addition funnel was rinsed with 10 mL of THF. The reaction was stirred at 0° C. for 1 hour and quenched with saturated ammonium chloride solution. The mixture was poured into H$_2$O and EtOAc, and the layers were separated. The organic layer was washed with brine, and the combined aqueous layers were extracted with EtOAc. The combined organic layers were dried over MgSO$_4$, filtered, and concentrated in vacuo. The crude product was purified by flash chromatography. The clean fractions (by TLC) were concentrated in vacuo to afford 1.26 g (62%) of the desired product. The proton NMR is a mixture of the keto and enol tautomers (~2:1). $^1$H NMR (400 MHz, DMSO-d$_6$): δ 13.58 (s, 1H, enol), 9.83 (s, 1H, keto), 9.82 (s, 1H, enol), 8.72 (m, 1H, keto), 8.54 (m, 1H, enol), 8.34 (s, 1H, keto), 8.22 (m, 1H, both), 8.06 (m, 1H, enol), 7.56 (m, 1H, keto), 7.42-7.31 (m, 2H, both+1H, enol), 7.22-7.14 (m, 2H, both), 6.55 (s, 1H, enol), 4.66 (s, 2H, keto), 4.00 (s, 3H, keto), 3.97 (s, 3H, enol).

Step F: 5-[3-(2-chloro-4-pyrimidinyl)imidazo[1,2-a]pyridin-2-yl]-N-(2,6-difluorophenyl)-2-(methyloxy)benzamide A tautomeric mixture of 5-[(2-Chloro-4-pyrimidinyl)acetyl]-N-(2,6-difluorophenyl)-2-(methyloxy)benzamide and 5-[(E)-2-(2-chloro-4-pyrimidinyl)-1-hydroxyethenyl]-N-(2,6-difluorophenyl)-2-(methyloxy)benzamide (1.26 g, 3.02 mmol) was dissolved in 60 mL of DCM with stirring. NBS (0.538 g, 3.02 mmol) was added in a single portion. The reaction was stirred for 20 minutes and concentrated in vacuo. The residue was dissolved in 60 mL of dioxane with stirring, and 2-aminopyridine (0.853 g, 9.06 mmol) was added in a single portion. The reaction was heated at 60° C. with an oil bath for 24 hours and cooled to rt. The reaction was stirred at rt for an additional 40 hours. The reaction was poured into half-saturated NaHCO$_3$ solution and EtOAc, and the layers were separated. The organic layer was washed with brine, and the combined aqueous layers were extracted twice with EtOAc. The combined organic layers were dried over MgSO$_4$, filtered, and concentrated in vacuo. The crude product was purified by flash chromatography. Impure fractions were concentrated and further purified by flash chromatography. The combined clean fractions (by TLC) from both runs were combined and concentrated in vacuo to afford 1.07 g (72%) of the desired product. $^1$H NMR (400 MHz, DMSO-d$_6$): δ 9.80 (s, 1H), 9.40 (d, J=7.0 Hz, 1H), 8.57 (d, J=5.1 Hz, 1H), 8.10 (d, J=1.5 Hz, 1H), 7.84-7.77 (m, 2H), 7.57 (m, 1H), 7.39 (m, 1H), 7.33-7.26 (m, 2H), 7.24-7.14 (m, 3H), 3.99 (s, 3H).

Intermediate Example 3 methyl 3-[3-(2-chloro-4-pyrimidinyl)imidazo[1,2-a]pyridin-2-yl]benzoate

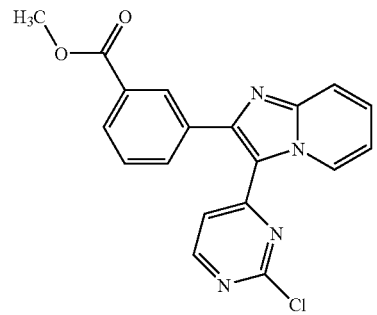

Step A: methyl 3-[(2-chloro-4-pyrimidinyl)acetyl]benzoate and methyl 3-[(E)-2-(2-chloro-4-pyrimidinyl)-1-hydroxyethenyl]benzoate To a solution of dimethyl 1,3-benzenedicarboxylate (14.6 g, 75.2 mmol) in dry THF (75 mL) at 0° C., LiHMDS (1M in THF, 120 mL, 120 mmol) was added and the solution was allowed to stir for 10 min at 0° C. A solution of 2-chloro-4-methylpyrimidine (3.1 g, 24.1 mmol) in 10 mL of THF was then added dropwise to the reaction mixture at 0° C. over 10 min. The reaction mixture turns black. The solution was allowed to stir 30 minutes at 0° C. The reaction mixture was then quenched at 0° C. with MeOH and the solvent was removed in vacuo. The residue was diluted with EtOAc and washed with H$_2$O. The H$_2$O layer was extracted twice with EtOAc, dried with MgSO$_4$ and evaporated onto silica gel. Purification by flash chromatography provided 6.1 g (87%) of the title product as a light yellow solid. MS (ESI): 291 [M+H]$^+$.

Step B: methyl 3-[3-(2-chloro-4-pyrimidinyl)imidazo[1,2-a]pyridin-2-yl]benzoate

A tautomeric mixture of methyl 3-[(2-chloro-4-pyrimidinyl)acetyl]benzoate and methyl 3-[(E)-2-(2-chloro-4-pyrimidinyl)-1-hydroxyethenyl]benzoate (2.49 g, 8.58 mmol) was dissolved in anhydrous DCM (40.0 mL). NBS (1.53 g, 8.59 mmol) was added and the reaction was stirred at rt. Twenty minutes later LCMS showed complete conversion of methyl 3-[(2-chloro-4-pyrimidinyl)acetyl]benzoate, and the solvent was removed via rotary evaporation to give the intermediate as a yellow solid. This was used directly in the next step without further purification. The crude material was dissolved in dioxane (100 mL) and 2-aminopyridine (2.42 g, 25.7 mmol) was added. The reaction mixture was stirred at 60° C. overnight. The solvent was removed and the residue was adsorbed onto silica gel. The crude material was purified via silica gel chromatography to give 2.30 g (73% yield over 2 steps) of the title compound as a yellow solid. MS (ESI+) m/z 365 [M+H].

Intermediate Example 4

5-[3-(2-chloro-4-pyrimidinyl)imidazo[1,2-a]pyridin-2-yl]-2-(methyloxy)benzonitrile

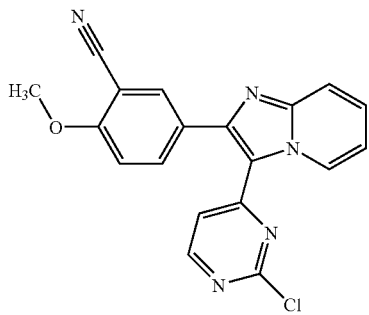

Step A: 5-[(2-chloro-4-pyrimidinyl)acetyl]-2-(methyloxy)benzonitrile and 5-[(Z)-2-(2-chloro-4-pyrimidinyl)-1-hydroxyethenyl]-2-(methyloxy)benzonitrile

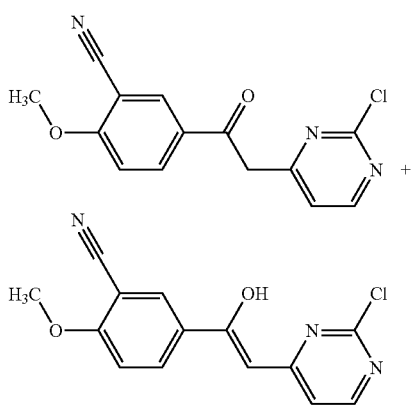

To methyl-3-cyano-4-methoxybenzoate (10.6 g, 55.6 mmol) in THF (600 mL) cooled to 0° C. was added lithium bis(trimethylsilyl)amide (110 mL, 1M in THF, 110 mmol) followed by 2-chloro-4-methylpyrimidine (4.84 g, 37.7 mmol) in THF (100 mL) via addition funnel. Upon completion by TLC, the reaction was quenched with saturated ammonium chloride, extracted with DCM and EtOAC, dried (MgSO4) and concentrated. Purification by flash chromatography followed by trituration with diethyl ether provided the title compound (9.99 g, 34.2 mmol, 92%) as a mixture of tautomers. Ketone tautomer: ¹H NMR (400 MHz, DMSO-d6) δ ppm 4.00 (s, 3H), 4.64 (s, 2H), 7.38 (t, J=9.4 Hz, 1H), 7.54 (d, J=5.1 Hz, 1H), 8.26 (dd, J=8.9, 2.1 Hz, 1H), 8.42 (d, J=2.0 Hz, 1H), 8.71 (d, J=4.9 Hz, 1H). Enol tautomer: ¹H NMR (400 MHz, DMSO-d6) δ ppm 3.97 (s, 3H), 6.58 (br. s., 1H), 7.26 (d, J=5.1 Hz, 1H), 8.11-8.16 (m, 1H), 8.20-8.25 (m, 2H), 8.56 (d, J=5.3 Hz, 1H), 13.52 (br. s., 1H).

Step B: 5-[3-(2-chloro-4-pyrimidinyl)imidazo[1,2-a]pyridin-2-yl]-2-(methyloxy)-benzonitrile To a tautomeric mixture of 5-[(2-chloro-4-pyrimidinyl)acetyl]-2-(methyloxy)benzonitrile and 5-[(Z)-2-(2-chloro-4-pyrimidinyl)-1-hydroxyethenyl]-2-(methyloxy)benzonitrile (2.87 g, 10.0 mmol) in DCM (250 mL) was added NBS (1.78 g, 10.0 mmol) in one portion. Upon completion by TLC, the reaction was concentrated. The residue was taken up in dioxane (100 mL) and 2-aminopyridine (2.89 g, 30.7 mmol) was added. The reaction was stirred at 65° C. overnight. The reaction was poured into half saturated NaHCO3, extracted with DCM and EtOAc, dried (MgSO4), concentrated and triturated with diethyl ether to provide the title compound (2.36 g, 6.50 mmol, 65%). ¹H NMR (400 MHz, DMSO-d6) δ ppm 3.96 (s, 3H), 7.18-7.25 (m, 2H), 7.33 (d, J=9.0 Hz, 1H), 7.52-7.58 (m, 1H), 7.77 (d, J=9.0 Hz, 1H), 7.92 (dd, J=8.8, 2.4 Hz, 1H), 8.00 (d, J=2.2 Hz, 1H), 8.56 (d, J=5.5 Hz, 1H), 9.34-9.39 (m, 1H).

Intermediate Example 5

3-[3-(2-chloro-4-pyrimidinyl)imidazo[1,2-a]pyridin-2-yl]benzonitrile

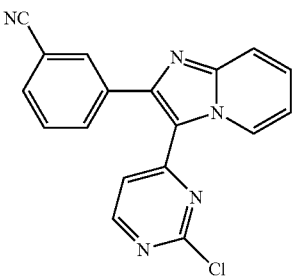

Step A: 3-[(2-chloro-4-pyrimidinyl)acetyl]benzonitrile and 3-[(E)-2-(2-chloro-4-pyrimidinyl)-1-hydroxyethenyl]benzonitrile

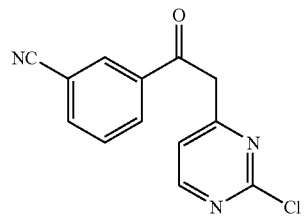

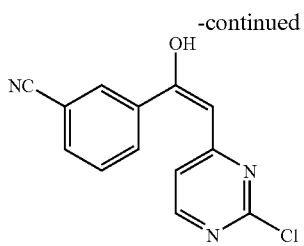

Lithium bis(trimethylsilyl)amide (1M in THF, 36.0 mL, 36.0 mmol) was added to 100 mL of THF and cooled to −78° C. 2-Chloro-4-methylpyrimidine (3.07 g, 23.9 mmol) in 20 mL of THF was added dropwise over 10 minutes. The addition funnel was rinsed with 10 mL of THF. The reaction was stirred 20 minutes, and 3-cyano-N-methyl-N-(methyloxy) benzamide (see *Organic Lett.* 2006, 8, 4843-4846) (5.00 g, 26.3 mmol) in 25 mL of THF was added dropwise over 10 minutes. The addition funnel was rinsed with 10 mL of THF. The reaction was stirred for one hour and allowed to warm to 0° C. The reaction was quenched with saturated ammonium chloride solution and poured into H$_2$O and EtOAc. The layers were separated, and the organic layer was washed with brine. The combined aqueous layers were extracted with EtOAc. The combined organic layers were dried over MgSO$_4$, filtered, and concentrated in vacuo. The residue was purified by flash chromatography to afford the product contaminated with 3-cyano-N-methyl-N-(methyloxy)benzamide. The mixture was triturated with 30% EtOAc in hexanes, filtered, and the solid washed with 30% EtOAc in hexanes followed by hexanes. The yellow solid was collected to provide 1.56 g (25%) of the title compound as an approximately 1:1 mixture of ketone and enol tautomers. $^1$H NMR (400 MHz, DMSO-d$_6$) δ [Enol tautomer] 13.45 (s, 1H), 6.70 (s, 1H); [Ketone tautomer]-4.72 (s, 2H); [Aromatic protons] 8.72 (d, J=5.1 Hz, 1H), 8.62 (d, J=5.3 Hz, 1H), 8.47 (s, 1H), 8.30 (s, 1H), 8.26 (d, J=7.9 Hz, 1H), 8.16 (d, J=8.1 Hz, 1H), 8.13 (d, J=7.9 Hz, 1H), 7.96 (d, J=7.9 Hz, 1H), 7.76 (t, J=7.9 Hz, 1H), 7.70 (t, J=7.9 Hz, 1H), 7.56 (d, J=5.1 Hz, 1H), 7.33 (d, J=5.3 Hz, 1H).

Step B: 3-[3-(2-chloro-4-pyrimidinyl)imidazo[1,2-a]pyridin-2-yl]benzonitrile

A mixture of tautomers, 3-[(2-chloro-4-pyrimidinyl)acetyl]benzonitrile and 3-[(E)-2-(2-chloro-4-pyrimidinyl)-1-hydroxyethenyl]benzonitrile, (1.56 g, 6.05 mmol) was dissolved in 100 mL of DCM with stirring and cooled to 0° C. NBS (1.08 g, 6.07 mmol) was added and the reaction was allowed to warm to rt. The reaction was stirred for one hour and concentrated in vacuo. The residue was dissolved in dioxane with stirring. 2-Aminopyridine (1.71 g, 18.2 mmol) was added, and the reaction was heated to 60° C. The reaction was stirred overnight and cooled to rt. The reaction was poured into H$_2$O and EtOAc. The layers were separated, and the organic layer was washed with brine. The combined aqueous layers were extracted with DCM (2×) and EtOAc. The combined organic layers were dried over MgSO$_4$, filtered, and concentrated in vacuo. The residue was purified by flash chromatography, and fractions containing product were concentrated in vacuo. The residue was triturated with diethyl ether and hexanes (~1:1), filtered, and the solid was washed with diethyl ether and hexanes (~1:1). The solid was collected to provide 1.50 g (75%) of the title compound. $^1$H NMR (400 MHz, DMSO-d$_6$) δ 9.35 (d, J=7.0 Hz, 1H), 8.60 (d, J=5.3 Hz, 1H), 8.14 (s, 1H), 7.98 (d, J=7.9 Hz, 1H), 7.93 (d, J=7.9 Hz, 1H), 7.81 (d, J=8.8 Hz, 1H), 7.67 (t, J=7.9 Hz, 1H), 7.59 (dd, J=6.8, 1.1 Hz, 1H), 7.31-7.17 (m, 2H).

Intermediate Example 6

5-[3-(2-chloro-4-pyrimidinyl)imidazo[1,2-a]pyridin-2-yl]-N-(2,6-difluorophenyl)-2-(ethyloxy)benzamide

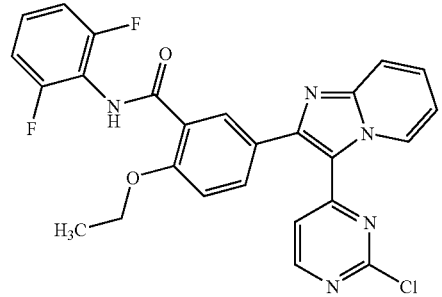

The title compound was prepared in an analogous manner to that described for 5-[3-(2-chloro-4-pyrimidinyl)imidazo[1,2-a]pyridin-2-yl]-N-(2,6-difluorophenyl)-2-(methyloxy)benzamide (Intermediate Example 2) with the following notable exception: ethyl iodide was used instead of methyl iodide in the procedure outlined in step B. MS (M+H, ES+) 506.

Intermediate Example 7

5-[3-(2-chloro-4-pyrimidinyl)imidazo[1,2-a]pyridin-2-yl]-N-(2,6-difluorophenyl)-2-[(1-methylethyl)oxy]benzamide

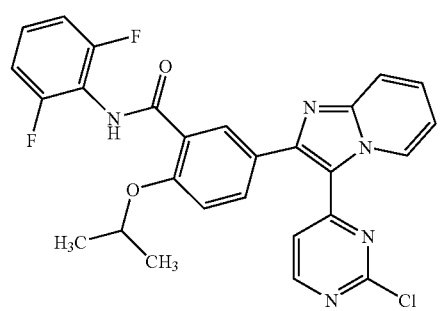

The title compound was prepared in an analogous to that described for 5-[3-(2-chloro-4-pyrimidinyl)imidazo[1,2-a]pyridin-2-yl]-N-(2,6-difluorophenyl)-2-(methyloxy)benzamide (Intermediate Example 2) with the following notable exception: isopropyl iodide was used instead of methyl iodide in the procedure outlined in step B. MS (M+H, ES+) 520.

Example 1

N-(2,6-difluorophenyl)-5-(3-{2-[(3-{[2-(dimethylamino)ethyl]oxy}phenyl)-amino]-4-pyrimidinyl}imidazo[1,2-a]pyridin-2-yl)-2-(methyloxy)benzamide

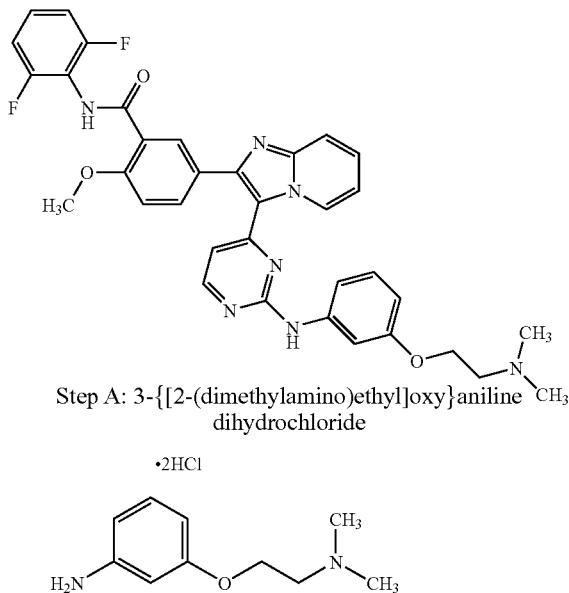

Step A: 3-{[2-(dimethylamino)ethyl]oxy}aniline dihydrochloride

To 3-aminophenol (10.9 g, 100 mmol) in DMF (100 mL) cooled with an ice/H₂O bath was added NaH (8.90 g, 222 mmol) in 4 portions. 2-(Dimethylamino)ethylchloride hydrochloride (15.8 g, 110 mmol) was then added in 3 portions and the reaction was stirred at rt overnight. The reaction was poured into H₂O (600 mL) and extracted with EtOAc. The combined organic layer was washed with brine, dried (MgSO₄) and concentrated. Purification by flash column chromatography (flash chromatography), treatment with HCl (50.0 mL, 4M in dioxane, 200 mmol) and concentration provided the title compound (14.0 g, 56.0 mmol, 56%). $^1$H NMR (400 MHz, DMSO-$d_6$) δ ppm 2.80 (s, 6H), 3.46 (t, J=4.8 Hz, 2H), 4.30 (t, J=4.9 Hz, 2H), 6.58-6.66 (m, 3H), 7.18 (t, J=8.2 Hz, 1H), 8.55 (br.s., 2H), 10.70 (br.s., 1H).

Step B: 5-(3-{2-[(3-{[2-(dimethylamino)ethyl]oxy}phenyl)amino]-4-pyrimidinyl}imidazo-[1,2-a]pyridin-2-yl)-2-(methyloxy)benzonitrile

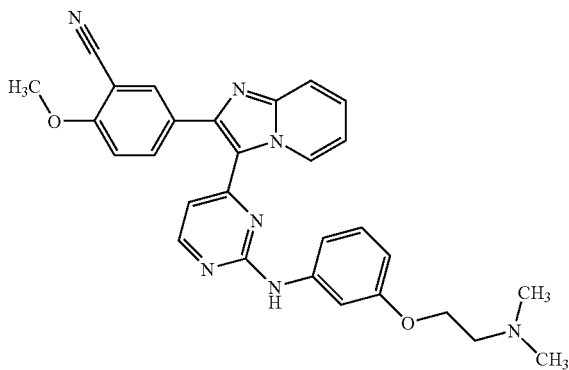

To 5-[3-(2-chloro-4-pyrimidinyl)imidazo[1,2-a]pyridin-2-yl]-2-(methyloxy)benzonitrile (Intermediate Example 4) (2.02 g, 5.57 mmol) and 3-{[2-(dimethylamino)ethyl]oxy}aniline dihydrochloride (1.67 g, 6.58 mmol) in trifluoroethanol (20 mL) was added HCl (0.700 mL, 4M in dioxane, 2.8 mmol). The reaction was stirred at 84° C. for 2 days. The reaction was poured into half saturated NaHCO₃, extracted with DCM and EtOAc, dried (MgSO₄), concentrated and triturated with diethyl ether to provide the title compound (2.63 g, 5.18 mmol, 93%). $^1$H NMR (400 MHz, DMSO-$d_6$) δ ppm 2.17 (s, 6H), 2.57 (t, J=5.7 Hz, 2H), 3.96 (s, 5H), 6.55 (d, J=8.4 Hz, 1H), 6.63 (d, J=5.1 Hz, 1H), 7.07 (t, J=7.0 Hz, 1H), 7.16 (t, J=8.1 Hz, 1H), 7.26 (d, J=8.4 Hz, 1H), 7.33 (d, J=9.2 Hz, 1H), 7.45-7.53 (m, 2H), 7.74 (d, J=9.2 Hz, 1H), 7.92 (dd, J=9.0, 2.0 Hz, 1H), 7.99 (d, J=1.8 Hz, 1H), 8.39 (d, J=5.1 Hz, 1H), 9.49 (d, J=6.2 Hz, 1H), 9.77 (s, 1H).

Step C: methyl 5-(3-{2-[(3-{[2-(dimethylamino)ethyl]oxy}phenyl)amino]-4-pyrimidinyl}-imidazo[1,2-a]pyridin-2-yl)-2-(methyloxy)benzoate

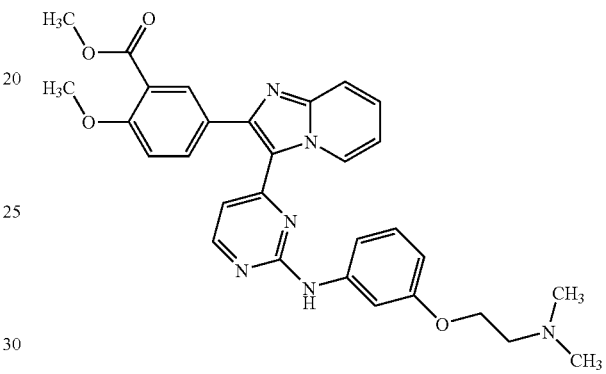

5-(3-{2-[(3-{[2-(dimethylamino)ethyl]oxy}phenyl)amino]-4-pyrimidinyl}imidazo[1,2-a]pyridin-2-yl)-2-(methyloxy)benzonitrile (2.63 g, 5.2 mmol) in EtOH and 6N NaOH (15 mL) was stirred at 80° C. Upon completion by MS, the reaction was poured into a H₂o/diethyl ether mixture and the organic layer was washed with 1N NaOH. The combined aqueous layer was acidified with HCl (37% in water) and subsequently concentrated. The residue was taken up in MeOH and treated with para-toluenesulfonic acid (1.07 g, 6.21 mmol) at 65° C. until complete by MS. The mixture was poured into half saturated NaHCO₃, extracted with DCM and EtOAc, dried (MgSO₄) and concentrated. Purification by flash chromatography provided the title compound (2.35 g, 4.36 mmol, 84%). $^1$H NMR (400 MHz, DMSO-$d_6$) δ ppm 2.16 (s, 6H), 2.56 (t, J=5.9 Hz, 2H), 3.77 (s, 3H), 3.86 (s, 3H), 3.96 (t, J=5.7 Hz, 2H), 6.55 (dd, J=8.1, 2.2 Hz, 1H), 6.67 (d, J=5.5 Hz, 1H), 7.06 (t, J=7.0 Hz, 1H), 7.14-7.23 (m, 2H), 7.26 (s, 1H), 7.45-7.52 (m, 2H), 7.73 (d, J=9.2 Hz, 1H), 7.78 (dd, J=8.6, 2.4 Hz, 1H), 8.01 (d, J=2.2 Hz, 1H), 8.39 (d, J=5.5 Hz, 1H), 9.48 (s, 1H), 9.77 (s, 1H).

Step D: N-(2,6-difluorophenyl)-5-(3-{2-[(3-{[2-(dimethylamino)ethyl]oxy}phenyl)amino]-4-pyrimidinyl}imidazo[1,2-a]pyridin-2-yl)-2-(methyloxy)benzamide To methyl 5-(3-{2-[(3-{[2-(dimethylamino)ethyl]oxy}phenyl)amino]-4-pyrimidinyl}imidazo[1,2-a]pyridin-2-yl)-2-(methyloxy)benzoate (2.35 g, 4.36 mmol) and 2,6-difluoroaniline (2.35 mL, 21.8 mmol) in THF (30 mL) was added sodium bis(trimethylsilyl)amide (26.0 mL, 1M in THF, 26.0 mmol) in one portion. Upon completion by MS, the reaction was poured into half saturated NaHCO₃, extracted with DCM and EtOAc, dried (MgSO₄) and concentrated. Purification by flash chromatography and trituration with diethyl ether provided the title compound (2.05 g, 3.23 mmol, 74%). ¹H NMR (400 MHz, DMSO-d$_6$) δ ppm 2.16 (s, 6H), 2.56 (br. s., 2H), 3.98 (br. s., 5H), 6.55 (d, J=7.7 Hz, 1H), 6.69 (d, J=4.4 Hz, 1H), 7.01-7.11 (m, 1H), 7.17 (d, J=7.3 Hz, 3H), 7.27 (s, 2H), 7.32-7.42 (m, 1H), 7.42-7.54 (m, 2H), 7.74 (d, J=8.8 Hz, 1H), 7.81 (d, J=8.1 Hz, 1H), 8.15 (s, 1H), 8.37 (d, J=4.4 Hz, 1H), 9.49 (br. s., 1H), 9.78 (d, J=12.5 Hz, 2H). MS (M+H, ES+) 636.

Example 2

N-(2,6-difluorophenyl)-5-(3-{2-[(3-{[2-(dimethylamino)ethyl]oxy}phenyl)amino]-4-pyrimidinyl}-7-methylimidazo[1,2-a]pyridin-2-yl)-2-(methyloxy)benzamide

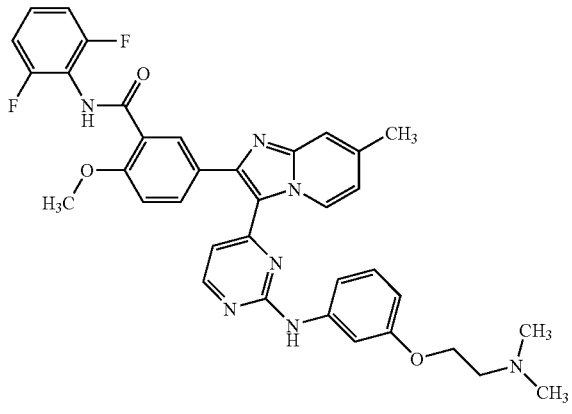

The title compound (0.17 g, 0.25 mmol, 72% in final step) was prepared in an analogous manner to that of N-(2,6-difluorophenyl)-5-(3-{2-[(3-{[2-(dimethylamino)ethyl]oxy}phenyl)amino]-4-pyrimidinyl}-imidazo[1,2-a]pyridin-2-yl)-2-(methyloxy)benzamide (Example 1) with the following notable exception: 4-methyl-2-pyridinamine was used instead of 2-aminopyridine in the step outlined in Intermediate Example 4, step B. ¹H NMR (400 MHz, DMSO-d$_6$) δ ppm 2.16 (s, 6H), 2.41 (s, 3H), 2.58 (t, J=5.6 Hz, 2H), 3.97 (s, 5H), 6.54 (d, J=6.2 Hz, 1H), 6.64 (d, J=5.1 Hz, 1H), 6.89 (d, J=7.1 Hz, 1H), 7.12-7.21 (m, 3H), 7.21-7.30 (m, 2H), 7.31-7.42 (m, 1H), 7.50 (s, 2H), 7.77 (d, J=7.9 Hz, 1H), 8.11 (s, 1H), 8.31 (d, J=5.5 Hz, 1H), 9.40 (d, J=6.8 Hz, 1H), 9.71 (s, 1H), 9.77 (s, 1H). MS (M+H, APCI+) 650.

Example 3

N-(2,6-difluorophenyl)-5-[3-{2-[(3-{[2-(dimethylamino)ethyl]oxy}phenyl)amino]-4-pyrimidinyl}-7-(methyloxy)imidazo[1,2-a]pyridin-2-yl]-2-(methyloxy)benzamide

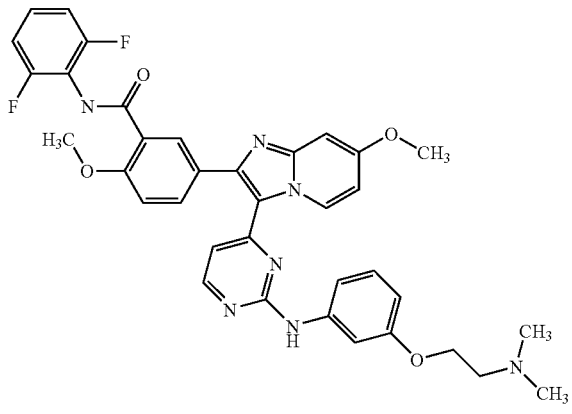

The title compound (0.022 g, 0.033 mmol, 35% in final step) was prepared in an analogous manner to that of Example 1 with the following notable exception: 4-(methyloxy)-2-pyridinamine (J. Chem. Soc., Perkin Trans 1, 2001, 2012-2021) was used instead of 2-aminopyridine in the step outlined in Intermediate Example 4, step B. ¹H NMR (400 MHz, DMSO-d$_6$) δ 9.77 (s, 1H), 9.69 (s, 1H), 9.45-9.40 (m, 1H), 8.28 (d, J=5.2 Hz, 1H), 8.14-8.09 (m, 1H), 7.80-7.73 (m, 1H), 7.49 (s, 1H), 7.40-7.32 (m, 1H), 7.31-7.22 (m, 2H), 7.21-7.12 (m, 4H), 6.76-6.70 (m, 1H), 6.65-6.61 (m, 1H), 6.55-6.50 (m, 1H), 3.99-3.93 (m, 5H), 3.88 (s, 3H), 2.56 (t, J=5.8 Hz, 2H), 2.16 (s, 6H). MS (ES+, m/z) 666 (M+1).

Example 4

5-[3-(2-{[4-(1,4'-bipiperidin-1'-yl)-2-(methyloxy)phenyl]amino}-4-pyrimidinyl)-7-methylimidazo[1,2-a]pyridin-2-yl]-N-(2,6-difluorophenyl)-2-(methyloxy)benzamide

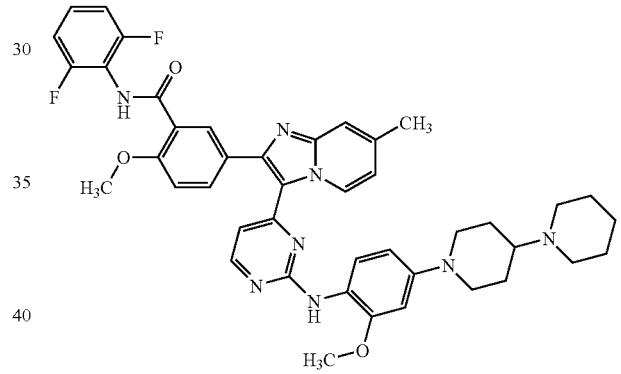

The title compound (0.08 g, 0.11 mmol, 26% in final step) was prepared in an analogous manner to that of Example 1 with the following notable exceptions:

a) 4-methyl-2-pyridinamine was used instead of 2-aminopyridine in the step outlined in Intermediate Example 4, step B;

b) 4-(1,4'-bipiperidin-1'-yl)-2-(methyloxy)aniline (Example 22, step C) was used instead of 3-{[2-(dimethylamino)ethyl]-oxy}aniline dihydrochloride in the step outlined in Example 1, step B.

¹H NMR (400 MHz, DMSO-d$_6$) δ ppm 1.35 (s, 2H), 1.45 (s, 4H), 1.50-1.60 (m, 2H), 1.77 (d, J=11.2 Hz, 2H), 2.26-2.35 (m, 1H), 2.38 (s, 4H), 2.43 (s, 3H), 2.58-2.69 (m, 2H), 3.73 (d, J=12.3 Hz, 2H), 3.77 (s, 3H), 3.96 (s, 3H), 6.44-6.49 (m, 2H), 6.65 (s, 1H), 6.77 (d, J=7.0 Hz, 1H), 7.16 (t, J=7.9 Hz, 2H), 7.25 (d, J=8.4 Hz, 1H), 7.36 (d, J=9.0 Hz, 2H), 7.45 (s, 1H), 7.74 (d, J=7.5 Hz, 1H), 8.06 (d, J=1.3 Hz, 1H), 8.14 (d, J=5.3 Hz, 1H), 8.38 (s, 1H), 9.24 (br. s., 1H), 9.76 (s, 1H). MS (M+H, ES+) 759.

Example 5

5-[3-(2-{[4-(1,4'-bipiperidin-1'-yl)-2-(methyloxy)phenyl]amino}-4-pyrimidinyl)-7-(methyloxy)imidazo[1,2-a]pyridin-2-yl]-N-(2,6-difluorophenyl)-2-(methyloxy)benzamide

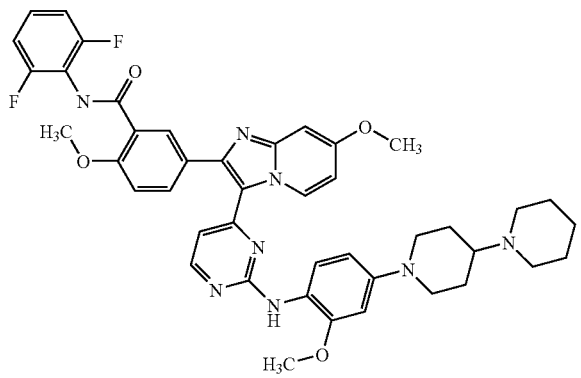

The title compound (0.13 g, 0.17 mmol, 77% in final step) was prepared in an analogous manner to that of Example 1 with the following notable exceptions:
a) 4-(methyloxy)-2-pyridinamine (*J. Chem. Soc., Perkin Trans* 1, 2001, 2012-2021) was used instead of 2-aminopyridine in the step outlined in Intermediate Example 4, step B;
b) 4-(1,4'-bipiperidin-1'-yl)-2-(methyloxy)aniline (Example 22, step C) was used instead of 3-{[2-(dimethylamino)ethyl]-oxy}aniline dihydrochloride in the step outlined in Example 1, step B.

$^1$H NMR (400 MHz, DMSO-$d_6$) δ 9.76 (s, 1H), 9.29-9.22 (m, 1H), 8.38 (s, 1H), 8.11 (d, J=5.2 Hz, 1H), 8.07-8.04 (m, 1H), 7.77-7.71 (m, 1H), 7.40-7.32 (m, 2H), 7.28-7.25 (m, 1H), 7.20-7.13 (m, 2H), 7.10-7.06 (m, 1H), 6.67-6.63 (m, 1H), 6.62-6.57 (m, 1H), 6.50-6.43 (m, 2H), 3.97 (s, 3H), 3.85 (s, 3H), 3.76 (s, 3H), 3.78-3.71 (m, 2H), 2.67-2.58 (m, 2H), 2.44-2.37 (m, 3H), 2.35-2.28 (m, 2H), 1.80-1.71 (m, 2H), 1.57-1.30 (m, 8H). MS (ES+, m/z) 775 (M+1).

Example 6

N-(2,6-difluorophenyl)-3-[3-(2-{[2-methyl-4-(4-piperidinyloxy)phenyl]amino}-4-pyrimidinyl)imidazo[1,2-a]pyridin-2-yl]benzamide

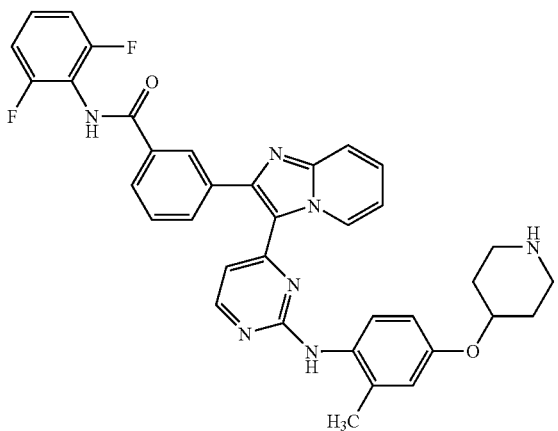

Step A: phenylmethyl 4-[(3-methyl-4-nitrophenyl)oxy]-1-piperidinecarboxylate

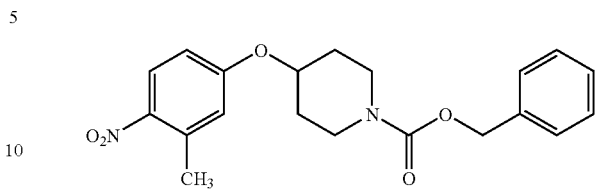

3-Methyl-4-nitrophenol (1.74 g, 11.4 mmol), triphenylphosphine (5.98 g, 22.8 mmol), and phenylmethyl 4-hydroxy-1-piperidinecarboxylate (3.99 g, 17.0 mmol) were dissolved in DCM with stirring and cooled to 0° C. Diisopropyl azodicarboxylate (3.35 mL, 17.0 mmol) was added via syringe. The reaction was stirred for 10 min and allowed to warm to rt. The reaction was stirred overnight and adsorbed onto silica gel. The crude material was purified by flash chromatography, and fractions containing product were concentrated in vacuo. The material was contaminated with 3-methyl-4-nitrophenol. The material was dissolved in diethyl ether and washed with 2N NaOH solution (3×), H$_2$O, and brine. The organic layer was dried over MgSO$_4$, filtered, and concentrated in vacuo to provide 3.67 g (87%) of the title compound. $^1$H NMR (400 MHz, DMSO-$d_6$) δ 8.02 (d, J=9.0 Hz, 1H), 7.42-7.24 (m, 5H), 7.06 (d, J=2.4 Hz, 1H), 7.01 (dd, J=9.1, 2.7 Hz, 1H), 5.07 (s, 2H), 4.76 (ddd, J=7.7, 4.2, 4.0 Hz, 1H), 3.81-3.64 (m, 2H), 3.31 (br. s., 2H), 2.52 (s, 3H), 2.01-1.88 (m, 2H), 1.63-1.49 (m, 2H).

Step B: phenylmethyl 4-[(4-amino-3-methylphenyl)oxy]-1-piperidinecarboxylate

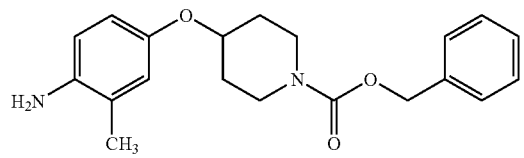

Phenylmethyl 4-[(3-methyl-4-nitrophenyl)oxy]-1-piperidinecarboxylate (0.798 g, 2.15 mmol) was dissolved in 20 mL of MeOH with stirring. Nickel(II) chloride hexahydrate (0.256 g, 1.08 mmol) was added and the mixture was cooled to 0° C. Sodium borohydride (0.163 g, 4.31 mmol) was added, and the mixture was stirred for 20 min. Additional sodium borohydride (~20 to 30 mg) was added, and the mixture was stirred for 10 min more. The reaction was quenched by the addition of approximately 15 mL of 2N sodium hydroxide solution. The mixture was poured into EtOAc and H$_2$O, and the layers were separated. The organic layer was washed with brine, and the combined aqueous layers were extracted with EtOAc. The combined organic layers were dried over MgSO$_4$, filtered, and concentrated in vacuo. The residue was purified by flash chromatography to afford 0.568 g (78%) of the title compound. $^1$H NMR (400 MHz, DMSO-$d_6$) δ 7.40-7.23 (m, 5H), 6.61-6.43 (m, 3H), 5.04 (s, 2H), 4.37 (s, 2H), 4.27-4.17 (m, 1H), 3.74-3.57 (m, 2H), 3.27-3.12 (m, 2H), 1.97 (s, 3H), 1.86-1.73 (m, 2H), 1.52-1.39 (m, 2H).

Step C: phenylmethyl 4-{[4-({4-[2-(3-cyanophenyl)
imidazo[1,2-a]pyridin-3-yl]-2-pyrimidinyl}amino)-
3-methylphenyl]oxy}-1-piperidinecarboxylate

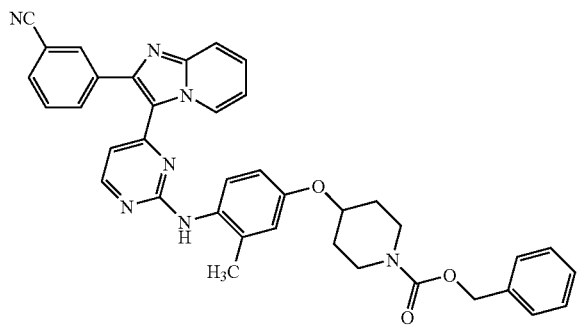

3-[3-(2-Chloro-4-pyrimidinyl)imidazo[1,2-a]pyridin-2-yl]benzonitrile (Intermediate Example 5) (0.462 g, 1.39 mmol) and phenylmethyl 4-[(4-amino-3-methylphenyl)oxy]-1-piperidinecarboxylate (0.567 g, 1.67 mmol) were dissolved in 16 mL of trifluoroethanol with stirring in a pressure vessel. HCl (4N in dioxane, 0.17 mL, 0.68 mmol) was added via syringe. The vessel was sealed and placed in an 80° C. oil bath. The reaction was stirred at 80° C. for 40 h and cooled to rt. The reaction was poured into half-saturated NaHCO$_3$ solution and DCM. The layers were separated, and the organic layer was washed with brine. The combined aqueous layers were extracted with EtOAc. The combined organic layers were dried over MgSO$_4$, filtered, and concentrated in vacuo. The residue was purified by flash chromatography to afford 0.700 g (79%) of the title compound. $^1$H NMR (400 MHz, DMSO-d$_6$) δ 9.25 (br. s., 1H), 8.90 (s, 1H), 8.20 (d, J=5.1 Hz, 1H), 8.04 (s, 1H), 7.96-7.86 (m, 2H), 7.72-7.61 (m, 2H), 7.46-7.21 (m, 7H), 6.93-6.79 (m, 3H), 6.41 (d, J=5.3 Hz, 1H), 5.06 (s, 2H), 4.59-4.50 (m, 1H), 3.77-3.65 (m, 2H), 3.36-3.21 (m, 2H), 2.18 (s, 3H), 1.97-1.86 (m, 2H), 1.61-1.49 (m, 2H).

Step D: methyl 3-[3-(2-{[2-methyl-4-(4-piperidinyloxy)phenyl]amino}-4-pyrimidinyl)imidazo[1,2-a]pyridin-2-yl]benzoate

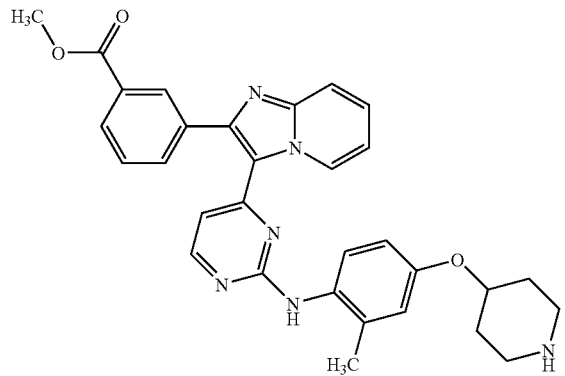

Phenylmethyl 4-{[4-({4-[2-(3-cyanophenyl)imidazo[1,2-a]pyridin-3-yl]-2-pyrimidinyl}amino)-3-methylphenyl]oxy}-1-piperidinecarboxylate (0.699 g, 1.10 mmol) was dissolved in 20 mL of EtOH with stirring. To the solution was added 20 mL of 2N NaOH solution. The reaction was placed in a 60° C. oil bath, and 20 mL of THF was added. The reaction was stirred at 60° C. overnight. Solid NaOH (1.6 g, 40 mmol) was added and the heat was increased to 80° C. Stirring was continued for 2.5 days, and the reaction was cooled to rt. The mixture was poured into H$_2$O and diethyl ether, and the layers were separated. The organic layer was washed with 1N NaOH solution. The combined aqueous layers were acidified with concentrated HCl. The aqueous layer was concentrated in vacuo. The residue was dissolved in 25 mL of MeOH with stirring. Sulfuric acid (0.29 mL, 5.4 mmol) was added, and the reaction was heated to 65° C. The reaction was stirred overnight and cooled to rt. The mixture was poured into half-saturated NaHCO$_3$ solution and DCM. The layers were separated, and the organic layer was washed with brine. The combined aqueous layers were extracted with EtOAc (2×). The combined organic layers were dried over MgSO$_4$, filtered, and concentrated in vacuo. The residue was purified by flash chromatography to afford 0.518 g (88%) of the title compound. $^1$H NMR (400 MHz, DMSO-d$_6$) δ 9.24 (br. s., 1H), 8.87 (s, 1H), 8.21 (s, 1H), 8.17 (d, J=5.1 Hz, 1H), 8.01-7.96 (m, 1H), 7.86 (d, J=7.9 Hz, 1H), 7.69 (d, J=9.0 Hz, 1H), 7.58 (t, J=7.8 Hz, 1H), 7.46-7.38 (m, 1H), 7.22 (d, J=8.6 Hz, 1H), 6.85 (s, 2H), 6.77 (dd, J=8.5, 2.7 Hz, 1H), 6.41 (d, J=5.3 Hz, 1H), 4.39-4.28 (m, 1H), 3.84 (s, 3H), 2.97-2.87 (m, 2H), 2.49-2.59 (m, 2H), 2.17 (s, 3H), 1.93-1.83 (m, 2H), 1.48-1.35 (m, 2H).

Step E: N-(2,6-difluorophenyl)-3-[3-(2-{[2-methyl-4-(4-piperidinyloxy)phenyl]-amino}-4-pyrimidinyl)imidazo[1,2-a]pyridin-2-yl]benzamide The title compound (0.227 g, 0.35 mmol, 88%) was prepared from methyl 3-[3-(2-{[2-methyl-4-(4-piperidinyloxy)phenyl]amino}-4-pyrimidinyl)imidazo[1,2-a]pyridin-2-yl]benzoate in an analogous manner to that described in Example 1, step D. $^1$H NMR (400 MHz, DMSO-d$_6$) δ ppm 0.70-0.78 (m, 1H), 0.80-0.85 (m, 1H), 1.14 (s, 2H), 1.20 (s, 2H), 1.37-1.47 (m, 1H), 1.83-1.94 (m, 2H), 2.17 (s, 2H), 2.50-2.60 (m, 1H), 2.92 (d, J=12.3 Hz, 1H), 4.30-4.38 (m, 1H), 6.43 (d, J=5.3 Hz, 1H), 6.79 (d, J=8.4 Hz, 1H), 6.85 (s, 2H), 7.15-7.26 (m, 2H), 7.34-7.46 (m, 2H), 7.60 (t, J=7.7 Hz, 1H), 7.70 (d, J=9.2 Hz, 1H), 7.81 (d, J=7.7 Hz, 1H), 8.04 (d, J=7.9 Hz, 1H), 8.16 (d, J=5.3 Hz, 1H), 8.30 (s, 1H), 8.87 (s, 1H), 9.32 (br. s., 1H), 10.22 (s, 1H).

Example 7

N-(2,6-difluorophenyl)-3-{3-[2-({2-methyl-4-[(1-methyl-4-piperidinyl)oxy]phenyl}amino)-4-pyrimidinyl]imidazo[1,2-a]pyridin-2-yl}benzamide

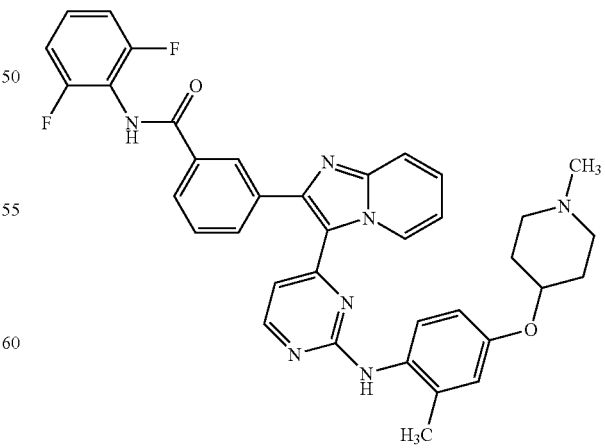

To N-(2,6-difluorophenyl)-3-[3-(2-{[2-methyl-4-(4-piperidinyloxy)phenyl]amino}-4-pyrimidinyl)imidazo[1,2-a]

pyridin-2-yl]benzamide (Example 6) (0.098 g, 0.16 mmol) in DCM (4 mL) and MeOH (2 mL) was added acetic acid (0.20 mL, 1M in DCM, 0.20 mmol) and formaldehyde (0.024 mL, 37% weight in H$_2$O, 0.32 mmol). Sodium triacetoxyborohydride (0.053 g, 0.25 mmol) in one portion and the reaction was stirred at rt until complete by MS. Purification by flash chromatography, followed by preparative HPLC chromatography (prep-HPLC) provided the title compound (0.044 g, 0.070 mmol, 43%). $^1$H NMR (400 MHz, DMSO-d$_6$) δ ppm 1.58-1.67 (m, 2H), 1.88-1.95 (m, 2H), 2.11-2.21 (m, 8H), 2.55-2.65 (m, 2H), 4.33 (s, 1H), 6.45 (d, J=5.1 Hz, 1H), 6.81 (d, J=8.1 Hz, 2H), 6.87 (s, 2H), 7.17-7.26 (m, 3H), 7.36-7.47 (m, 2H), 7.62 (t, J=7.8 Hz, 1H), 7.71 (d, J=9.1 Hz, 1H), 7.77-7.85 (m, 1H), 8.06 (d, J=9.5 Hz, 1H), 8.18 (d, J=5.3 Hz, 1H), 8.31 (s, 1H), 8.89 (s, 1H), 9.32 (br. s., 1H). MS (M+H, ES+) 646.

Example 8

N-(2,6-difluorophenyl)-3-[3-(2-{[2-methyl-4-({1-[2-(methylsulfonyl)ethyl]-4-piperidinyl}oxy)phenyl]amino}-4-pyrimidinyl)imidazo[1,2-a]pyridin-2-yl]benzamide

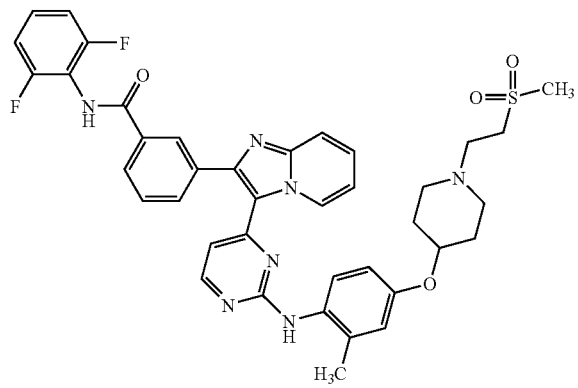

To N-(2,6-difluorophenyl)-3-[3-(2-{[2-methyl-4-(4-piperidinyloxy)phenyl]amino}-4-pyrimidinyl)imidazo[1,2-a]pyridin-2-yl]benzamide (Example 6) (0.10 g, 0.16 mmol) in THF (5 mL) was added methyl vinyl sulfone (0.028 mL, 0.32 mmol) in one portion. The reaction was stirred at rt until complete by MS. Purification by flash chromatography provided the title compound (0.048 g, 0.065 mmol, 40%). $^1$H NMR (400 MHz, DMSO-d$_6$) δ ppm 1.58-1.66 (m, 2H), 1.89-1.97 (m, 2H), 2.19 (s, 3H), 2.22-2.33 (m, 2H), 2.68-2.77 (m, 4H), 3.02 (s, 3H), 3.23-3.28 (m, 2H), 4.34-4.39 (m, 1H), 6.45 (d, J=4.9 Hz, 1H), 6.76-6.85 (m, 1H), 6.88 (s, 2H), 7.22 (dt, J=16.3, 8.2 Hz, 3H), 7.36-7.48 (m, 2H), 7.62 (t, J=7.6 Hz, 1H), 7.71 (d, J=8.8 Hz, 1H), 7.78-7.89 (m, 1H), 8.06 (d, J=7.3 Hz, 1H), 8.18 (d, J=5.1 Hz, 1H), 8.31 (s, 1H), 8.89 (s, 1H), 9.30-9.36 (m, 1H), 10.24 (s, 1H). MS (M+H, ES+) 738.

Example 9

N-(5-chloro-2-fluorophenyl)-3-(3-{2-[(3-{[2-(dimethylamino)ethyl]oxy}phenyl)amino]-4-pyrimidinyl}imidazo[1,2-a]pyridin-2-yl)benzamide

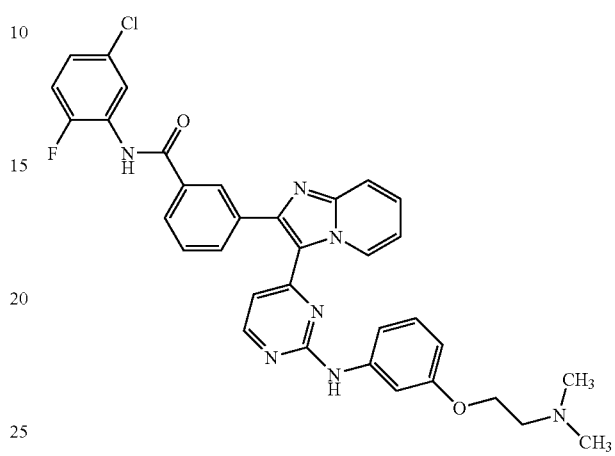

Step A: methyl 3-(3-{2-[(3-{[2-(dimethylamino)ethyl]oxy}phenyl)amino]-4-pyrimidinyl}-imidazo[1,2-a]pyridin-2-yl)benzoate A mixture of methyl 3-[3-(2-chloro-4-pyrimidinyl)imidazo[1,2-a]pyridin-2-yl]benzoate (Intermediate Example 3) (1.0 g, 2.74 mmol) and 3-{[2-(dimethylamino)ethyl]oxy}aniline dihydrochloride (Example 1, step A) (0.73 g, 2.88 mmol) in iPrOH (15 mL) was heated in the microwave at 160° C. for 20 min in the presence of catalytic concentrated HCl (aq.). The reaction mixture was concentrated onto silica gel and purified by flash chromatography to afford the title compound (1.04 g, 75%). MS (APCI+, m/z) 509 (M+1).

Step B: N-(5-chloro-2-fluorophenyl)-3-(3-{2-[(3-{[2-(dimethylamino)ethyl]oxy}phenyl)-amino]-4-pyrimidinyl}imidazo[1,2-a]pyridin-2-yl)benzamide A 1.0M solution of NaHMDS in THF (0.59 mL, 0.59 mmol) was added dropwise to a stirring solution of methyl 3-(3-{2-[(3-{[2-(dimethylamino)ethyl]oxy}phenyl)amino]-4-pyrimidinyl}imidazo[1,2-a]pyridin-2-yl)benzoate (0.100 g, 0.20 mmol) and 5-chloro-2-fluoroaniline (0.09 g, 0.59 mmol) in THF (2 mL) at rt. The reaction mixture was stirred for 0.5 h at room temperature then quenched with methanol and concentrated onto silica gel. Flash chromatography afforded the title compound (0.115 g, 94%) as a yellow solid. $^1$H NMR (400 MHz, DMSO-d$_6$) δ 10.31 (s, 1H), 9.75 (s, 1H), 9.52-9.50 (m, 1H), 8.35 (d, J=5.2 Hz, 1H), 8.31 (s, 1H), 8.01 (d, J=7.7 Hz, 1H), 7.83 (d, J=7.7 Hz, 1H), 7.77-7.72 (m, 2H), 7.61-7.57 (m, 1H), 7.51-7.47 (m, 2H), 7.36-7.24 (m, 3H), 7.17-7.06 (m, 2H), 6.60 (d, J=5.3 Hz, 1H), 6.53 (dd, J=8.2, 2.4 Hz, 1H), 3.95 (t, J=5.9 Hz, 2H), 2.55 (t, J=5.7 Hz, 2H), 2.14 (s, 6H). MS (ES+, m/z) 622 (M+1).

Example 10

3-(3-{2-[(3-{[2-(dimethylamino)ethyl]oxy}phenyl)amino]-4-pyrimidinyl}imidazo[1,2-a]pyridin-2-yl)-N-[2-fluoro-5-(trifluoromethyl)phenyl]benzamide

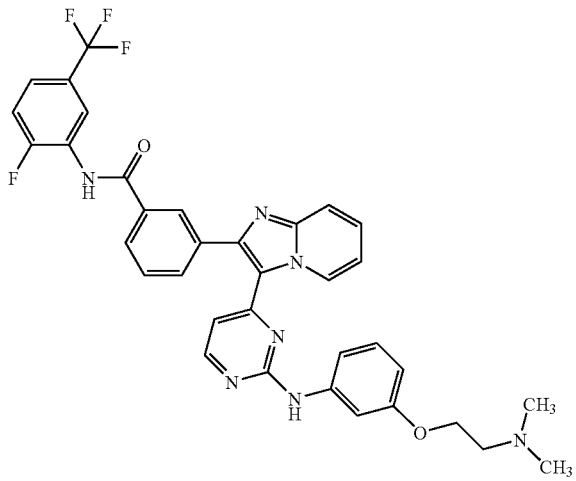

The title compound (0.074 g, 0.11 mmol, 58% in final step) was prepared in an analogous manner as that described for the synthesis of Example 9 with the following notable exception: 2-fluoro-5-(trifluoromethyl)aniline was used instead of 5-chloro-2-fluoroaniline. $^1$H NMR (400 MHz, DMSO-d$_6$) δ10.45 (bs, 1H), 9.76 (s, 1H), 9.54-9.50 (m, 1H), 8.36-8.33 (m, 2H), 8.07-8.01 (m, 2H), 7.84 (d, J=7.7 Hz, 1H), 7.76 (d, J=8.9 Hz, 1H), 7.67-7.47 (m, 5H), 7.27-7.22 (m, 1H), 7.17-7.06 (m, 2H), 6.60 (d, J=5.1 Hz, 1H), 6.55-6.52 (m, 1H), 3.94 (t, J=6.0 Hz, 2H), 2.54 (t, J=5.8 Hz, 2H), 2.14 (s, 6H). MS (APCI+, m/z) 656 (M+1).

Example 11

N-(2,6-difluorophenyl)-3-[3-(2-{[3-(1-methyl-1H-pyrazol-4-yl)phenyl]amino}-4-pyrimidinyl)imidazo[1,2-a]pyridin-2-yl]benzamide

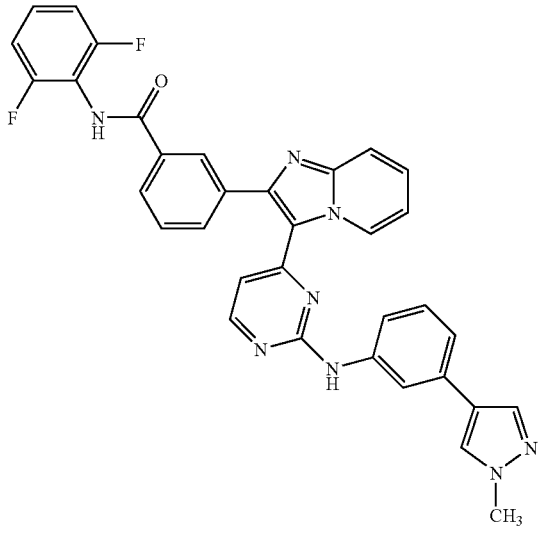

Step A: 3-(1-methyl-1H-pyrazol-4-yl)aniline

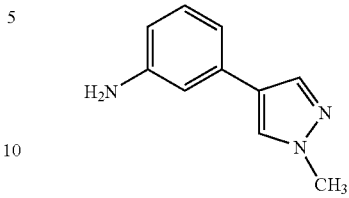

3-Bromoaniline (0.50 mL, 4.6 mmol) was dissolved in 30 mL of PhMe with stirring, and 15 mL of EtOH was added. Na$_2$CO$_3$ (3.06 g, 28.9 mmol) in 15 mL of H$_2$O was added followed by 1-Methyl-4-(4,4,5,5-tetramethyl-1,3,2-dioxaborolan-1H-pyrazole (0.955 g, 4.59 mmol). Pd(PPh$_3$)$_4$ (0.265 g, 0.229 mmol) was added, and the mixture was heated to reflux with stirring overnight. The mixture was cooled to rt and poured into EtOAc and H$_2$O. The mixture was filtered through celite, and the layers were separated. The organic layer was washed with brine. The organic layer was concentrated and purified by flash chromatography to afford 0.408 g (51%) of the desired product. $^1$H NMR (400 MHz, DMSO-d$_6$) δ 7.92 (s, 1H), 7.65 (s, 1H), 6.96 (t, J=7.7 Hz, 1H), 6.71-6.64 (m, 2H), 6.41-6.36 (m, 1H), 4.99 (br s, 2H), 3.82 (s, 3H).

Step B: N-(2,6-difluorophenyl)-3-[3-(2-{[3-(1-methyl-1H-pyrazol-4-yl)phenyl]amino}-4-pyrimidinyl)imidazo[1,2-a]pyridin-2-yl]benzamide 3-[3-(2-Chloro-4-pyrimidinyl)imidazo[1,2-a]pyridin-2-yl]-N-(2,6-difluorophenyl)-benzamide (Intermediate Example 1) (0.100 g, 0.217 mmol) and 3-(1-methyl-1H-pyrazol-4-yl)aniline (0.0563 g, 0.325 mmol) was dissolved in 4 mL of trifluoroethanol with stirring. HCl (0.11 mL, 4N in dioxane, 0.44 mmol) was added, and the vessel was sealed. The reaction was heated to 80° C. for 4.5 days and cooled to rt. The reaction was poured into half-saturated aqueous NaHCO$_3$ solution and EtOAc. The layers were separated, and the organic layer was washed with brine. The combined aqueous layers were extracted with EtOAc. The combined organic layers were dried over MgSO$_4$, filtered, and concentrated in vacuo. Purification by flash chromatography afforded a solid that was triturated with diethyl ether to yield 0.0823 g (63%) of the desired compound. $^1$H NMR (400 MHz, DMSO-d$_6$) δ 10.21 (s, 1H), 9.73 (s, 1H), 9.52 (d, J=5.1 Hz, 1H), 8.37-8.30 (m, 2H), 8.03 (d, J=7.3 Hz, 1H), 7.94 (s, 1H), 7.91 (s, 1H), 7.83 (d, J=7.3 Hz, 1H), 7.74 (d, J=8.2 Hz, 1H), 7.69 (s, 1H), 7.59 (t, J=7.7 Hz, 1H), 7.54-7.43 (m, 2H), 7.42-7.32 (m, 1H), 7.26-7.11 (m, 4H), 7.00-6.92 (m, 1H), 6.61 (d, J=5.3 Hz, 1H), 3.80 (s, 3H). MS (M+H, ES+) 599.

Example 12

3-(3-{2-[(3-{[2-(dimethylamino)ethyl]oxy}phenyl)amino]-4-pyrimidinyl}imidazo[1,2-a]pyridin-2-yl)-N-(2,4,6-trifluorophenyl)benzamide

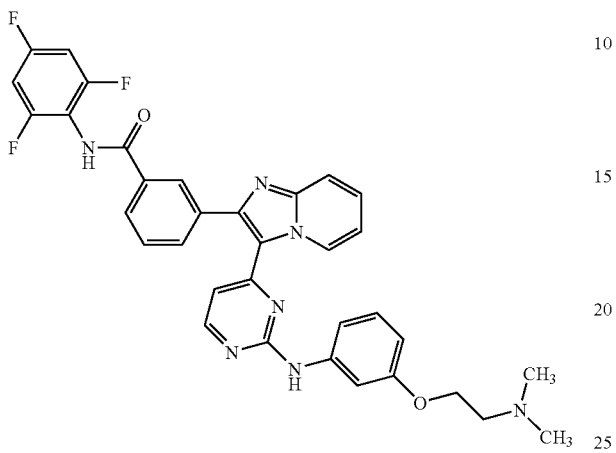

The title compound (0.040 g, 0.064 mmol, 33% in final step) was prepared in an analogous manner as that described for the synthesis of Example 9 with the following notable exception: 2,4,6-trifluoroaniline was used instead of 5-chloro-2-fluoroaniline. $^1$H NMR (400 MHz, DMSO-$d_6$) δ 10.22 (s, 1H), 9.78 (s, 1H), 9.56-9.51 (m, 1H), 8.38-8.36 (m, 2H), 8.05-8.03 (m, 1H), 7.86 (d, J=7.3 Hz, 1H), 7.77 (d, J=9.1 Hz, 1H), 7.63-7.59 (m, 1H), 7.53-7.49 (m, 2H), 7.36-7.26 (m, 3H), 7.20-7.08 (m, 2H), 6.63 (d, J=5.1 Hz, 1H), 6.58-6.53 (m, 1H), 3.96 (t, J=5.7 Hz, 2H), 2.56 (t, J=5.7 Hz, 2H), 2.16 (s, 6H). MS (APCI+, m/z) 624 (M+1).

Example 13

N-(2,4-difluorophenyl)-3-(3-{2-[(3-{[2-(dimethylamino)ethyl]oxy}phenyl)amino]-4-pyrimidinyl}imidazo[1,2-a]pyridin-2-yl)benzamide

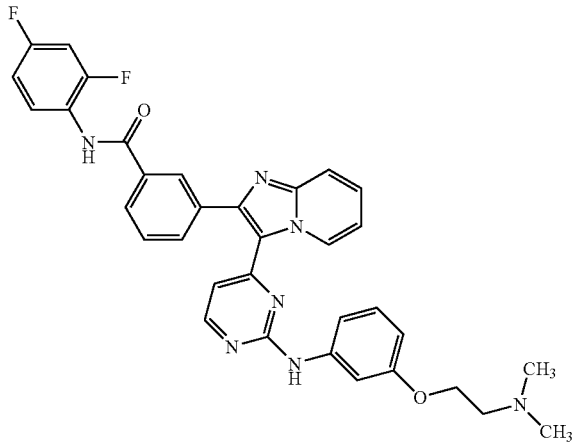

The title compound (0.0503 g, 0.0831 mmol, 76% in final step) was prepared in an analogous manner as that described for the synthesis of Example 9 with the following notable exception: 2,4-difluoroaniline was used instead of 5-chloro-2-fluoroaniline. $^1$H NMR (400 MHz, DMSO-$d_6$) δ 10.23 (s, 1H), 9.77 (s, 1H), 9.57-9.49 (m, 1H), 8.37 (d, J=5.3 Hz, 1H), 8.33 (s, 1H), 8.03 (d, J=7.7 Hz, 1H), 7.83 (dt, J=7.8, 1.3 Hz, 1H), 7.77 (d, J=9.0 Hz, 1H), 7.64-7.46 (m, 4H), 7.34 (ddd, J=10.6, 9.1, 2.9 Hz, 1H), 7.26 (d, J=9.1 Hz, 1H), 7.16 (t, J=8.1 Hz, 1H), 7.13-7.06 (m, 2H), 6.61 (d, J=5.3 Hz, 1H), 6.55 (dd, J=8.1, 1.7 Hz, 1H), 3.96 (t, J=5.8 Hz, 2H), 2.56 (t, J=5.9 Hz, 2H), 2.16 (s, 6H). MS (M+H, ES+) 606.

Example 14

N-(2,6-difluorophenyl)-3-(3-{2-[(3-{[2-(dimethylamino)ethyl]oxy}phenyl)amino]-4-pyrimidinyl}-7-methyl imidazo[1,2-a]pyridin-2-yl)benzamide

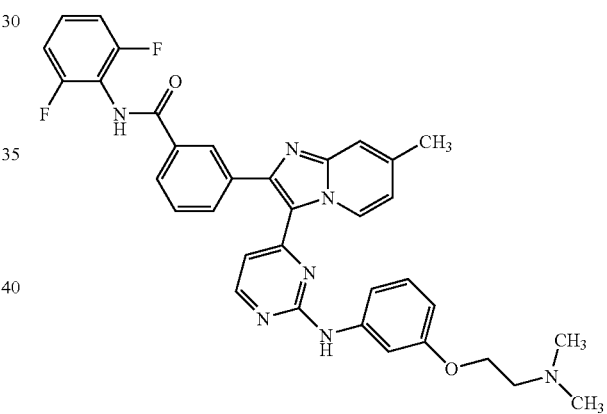

The title compound (0.060 g, 0.097 mmol, 60% in final step) was prepared in an analogous manner as that described for the synthesis of Example 9 with the following notable exceptions:

a) 4-methyl-2-pyridinamine was used instead of 2-aminopyridine in the step outlined in Intermediate Example 3, step B;

b) 2,6-difluoroaniline was used instead of 5-chloro-2-fluoroaniline in the step outlined in Example 9, step B.

$^1$H NMR (400 MHz, DMSO-$d_6$) δ 10.23 (s, 1H), 9.74 (s, 1H), 9.46-9.44 (m, 1H), 8.35-8.33 (m, 2H), 8.05-8.03 (m, 1H), 7.85-7.83 (m, 1H), 7.62-7.58 (m, 1H), 7.56-7.54 (m, 1H), 7.51-7.49 (m, 1H), 7.42-7.38 (m, 1H), 7.26-7.14 (m, 5H), 6.95-6.93 (m, 1H), 6.60 (d, J=5.2 Hz, 1H), 6.57-6.53 (m, 1H), 3.96 (t, J=5.9 Hz, 2H), 2.57 (t, J=5.8 Hz, 2H), 2.44 (s, 3H), 2.16 (s, 6H). MS (ES+, m/z) 620 (M+1).

Example 15

N-(2,3-difluorophenyl)-3-[3-{2-[(3-{[2-(dimethylamino)ethyl]oxy}phenyl)amino]-4-pyrimidinyl}-7-(methyloxy)imidazo[1,2-a]pyridin-2-yl]benzamide

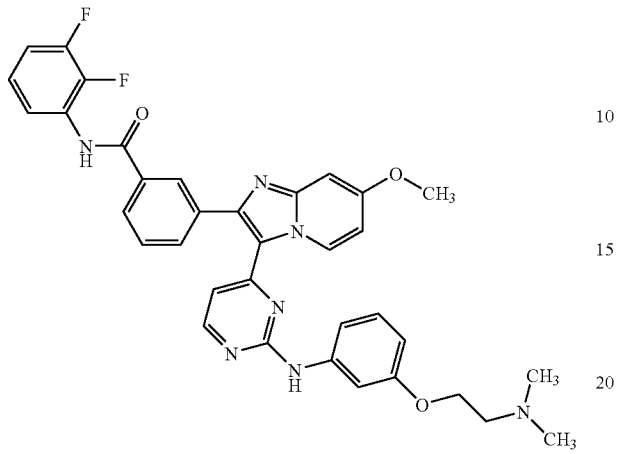

The title compound (0.11 g, 0.17 mmol, 100% in final step) was prepared in an analogous manner as that described for the synthesis of Example 9 with the following notable exceptions:
a) 4-(methyloxy)-2-pyridinamine (*J. Chem. Soc., Perkin Trans* 1, 2001, 2012-2021) was used instead of 2-aminopyridine in the step outlined in Intermediate Example 3, step B;
b) 2,3-difluoroaniline was used instead of 5-chloro-2-fluoroaniline in the step outlined in Example 9, step B.

$^1$H NMR (400 MHz, DMSO-d$_6$) δ 10.39 (s, 1H), 9.70 (s, 1H), 9.48-9.43 (m, 1H), 8.31-8.27 (m, 2H), 8.04-8.00 (m, 1H), 7.84-7.81 (m, 1H), 7.61-7.57 (m, 1H), 7.49 (s, 1H), 7.39-7.34 (m, 1H), 7.32-7.13 (m, 5H), 6.78-6.75 (m, 1H), 6.56-6.52 (m, 2H), 3.95 (t, J=6.0 Hz, 2H), 3.89 (s, 3H), 2.55 (t, J=5.7 Hz, 2H), 2.15 (s, 6H). MS (ES+, m/z) 636 (M+1).

Example 16

N-(2,4-difluorophenyl)-3-[3-{2-[(3-{[2-(dimethylamino)ethyl]oxy}phenyl)amino]-4-pyrimidinyl}-7-(methyloxy)imidazo[1,2-a]pyridin-2-yl]benzamide

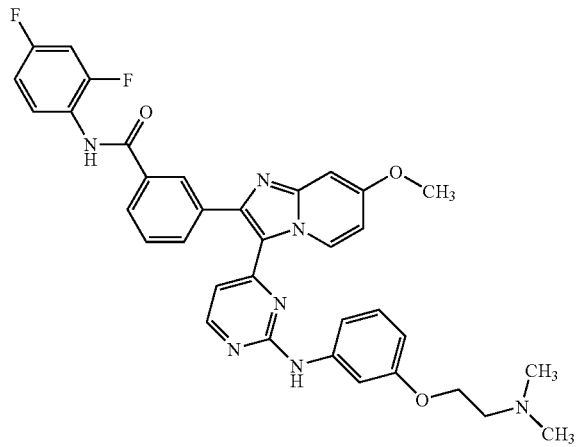

The title compound (0.088 g, 0.14 mmol, 88% in final step) was prepared in an analogous manner as that described for the synthesis of Example 9 with the following notable exceptions:
a) 4-(methyloxy)-2-pyridinamine (*J. Chem. Soc., Perkin Trans* 1, 2001, 2012-2021) was used instead of 2-aminopyridine in the step outlined in Intermediate Example 3, step B;
b) 2,4-difluoroaniline was used instead of 5-chloro-2-fluoroaniline in the step outlined in Example 9, step B.

$^1$H NMR (400 MHz, DMSO-d$_6$) δ 10.20 (s, 1H), 9.70 (s, 1H), 9.49-9.43 (m, 1H), 8.30-8.26 (m, 2H), 8.04-7.98 (m, 1H), 7.84-7.79 (m, 1H), 7.63-7.52 (m, 2H), 7.48 (s, 1H), 7.38-7.30 (m, 1H), 7.27-7.22 (m, 1H), 7.20-7.07 (m, 3H), 6.78-6.75 (m, 1H), 6.56-6.52 (m, 2H), 3.95 (t, J=5.7 Hz, 2H), 3.89 (s, 3H), 2.55 (t, J=5.7 Hz, 2H), 2.15 (s, 6H). MS (ES+, m/z) 636 (M+1).

Example 17

N-(2,6-difluorophenyl)-3-[3-{2-[(3-{[2-(dimethylamino)ethyl]oxy}phenyl)amino]-4-pyrimidinyl}-7-(methyloxy)imidazo[1,2-a]pyridin-2-yl]benzamide

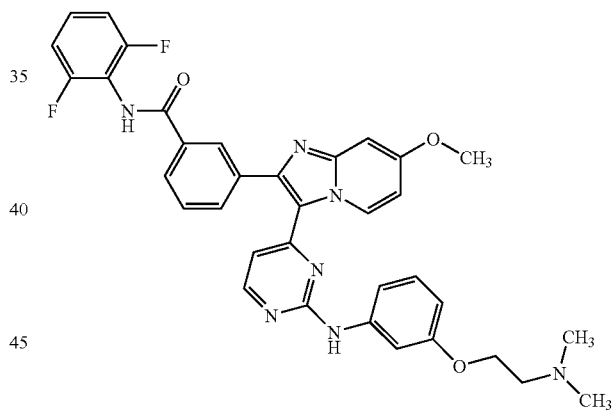

The title compound (0.042 g, 0.066 mmol, 42% in final step) was prepared in an analogous manner as that described for the synthesis of Example 9 with the following notable exceptions:
a) 4-(methyloxy)-2-pyridinamine (*J. Chem. Soc., Perkin Trans* 1, 2001, 2012-2021) was used instead of 2-aminopyridine in the step outlined in Intermediate Example 3, step B;
b) 2,6-difluoroaniline was used instead of 5-chloro-2-fluoroaniline in the step outlined in Example 9, step B.

$^1$H NMR (400 MHz, DMSO-d$_6$) δ 10.23 (s, 1H), 9.73 (s, 1H), 9.50-9.45 (m, 1H), 8.36-8.29 (m, 2H), 8.07-8.03 (m, 1H), 7.86-7.82 (m, 1H), 7.61 (at, J=7.8 Hz, 1H), 7.50 (at, J=2.2 Hz, 1H), 7.42-7.36 (m, 1H), 7.27-7.15 (m, 5H), 6.78 (dd, J=7.7, 2.6 Hz, 1H), 6.59-6.52 (m, 2H), 3.97 (t, J=5.7 Hz, 2H), 3.90 (s, 3H), 2.57 (t, J=5.8 Hz, 2H), 2.16 (s, 6H). MS (ES+, m/z) 636 (M+1).

Example 18

3-[3-(2-{[4-(1,4'-bipiperidin-1'-yl)-2-(methyloxy)phenyl]amino}-4-pyrimidinyl)-7-methylimidazo[1,2-a]pyridin-2-yl]-N-(2,6-difluorophenyl)benzamide

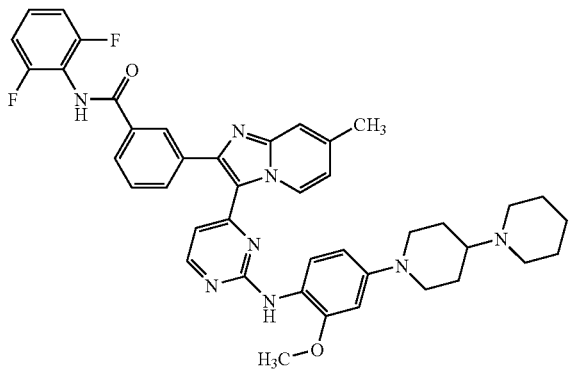

The title compound (0.10 g, 0.14 mmol, 88% in final step) was prepared in an analogous manner as that described for the synthesis of Example 9 with the following notable exceptions:

a) 4-methyl-2-pyridinamine was used instead of 2-aminopyridine in the step outlined in Intermediate Example 3, step B;

b) 4-(1,4'-bipiperidin-1'-yl)-2-(methyloxy)aniline (Example 22, step C) was used instead of 3-{[2-(dimethylamino)ethyl]-oxy}aniline dihydrochloride in the step outlined in Example 9, step A.

c) 2,6-difluoroaniline was used instead of 5-chloro-2-fluoroaniline in the step outlined in Example 9, step B.

$^1$H NMR (400 MHz, DMSO-d$_6$) δ 10.22 (s, 1H), 9.28 (bs, 1H), 8.41 (s, 1H), 8.28 (s, 1H), 8.16-8.13 (m, 1H), 8.04-8.00 (m, 1H), 7.80-7.76 (m, 1H), 7.60-7.56 (m, 1H), 7.48 (s, 1H), 7.42-7.32 (m, 2H), 7.21-7.16 (m, 2H), 6.82-6.79 (m, 1H), 6.66-6.64 (m, 1H), 6.48-6.45 (m, 1H), 6.40 (d, J=5.3 Hz, 1H), 3.77 (s, 3H), 3.76-3.70 (m, 2H), 2.67-2.59 (m, 2H), 2.45-2.27 (m, 5H), 2.39 (s, 3H), 1.80-1.72 (m, 2H), 1.58-1.31 (m, 8H). MS (ES+, m/z) 729 (M+1).

Example 19

N-(2,6-difluorophenyl)-3-(3-{2-[(3-{[2-(dimethylamino)ethyl]oxy}-2-methylphenyl)amino]-4-pyrimidinyl}imidazo[1,2-a]pyridin-2-yl)benzamide

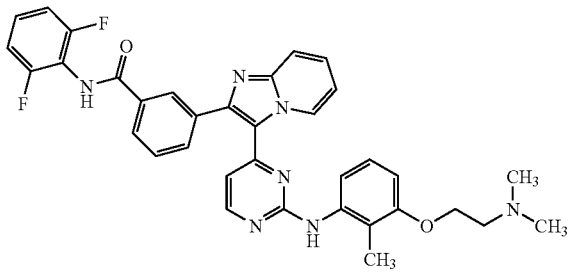

Step A: Dimethyl{2-[(2-methyl-3-nitrophenyl)oxy]ethyl}amine

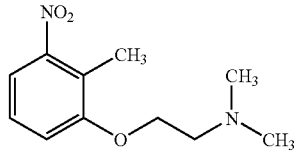

To a slurry containing 5.0 g (33 mmol) of 2-methyl-3-nitrophenol, 9.4 g (65.2 mmol) of (2-chloroethyl)dimethylamine hydrochloride, 9.0 g (65.3 mmol) of K$_2$CO$_3$, and 100 mL of H$_2$O was added 100 mL of butanol and the reaction mixture was heated at 80° C. for 13 h. The reaction mixture was extracted with EtOAc and the combined organic layers were dried over MgSO$_4$ and filtered. The solvents were removed under reduced pressure and the residue was subjected to silica gel chromatography to give 7.4 g (100%) of dimethyl{2-[(2-methyl-3-nitrophenyl)oxy]ethyl}amine as a brown oil. $^1$HNMR (400 MHz, DMSO-d$_6$) δ 7.29-7.42 (m, 3H), 4.11 (t, J=5.6 Hz, 2H), 2.66 (t, J=5.6 Hz, 2H), 2.22 (s, 3H), 2.20 (s, 6H). MS (ESI$^+$) m/z 225 [M+H].

Step B: 2-[(3-Amino-2-methylphenyl)oxy]ethyl}dimethylamine

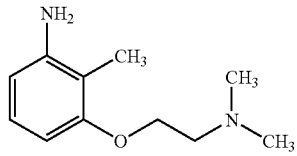

To a slurry containing 7.4 g (33 mmol) of {2-[(2-methyl-3-nitrophenyl)oxy]ethyl}amine and 60 mL of EtOH was added 700 mg of 10% Pd on carbon. The reaction mixture was subjected to a 40-50 psi atmosphere of H$_2$ for 4 h and then filtered through Celite. The solvents were removed under reduced pressure to give 6.3 g (98%) of 2-[(3-amino-2-methylphenyl)oxy]ethyl}dimethylamine as a dark oil. $^1$H NMR (400 MHz, DMSO-d$_6$) δ 6.79 (t, J=8.1 Hz, 1H), 6.25 (d, J=8.1 Hz, 1H), 6.17 (d, J=8.1 Hz, 1H), 4.76 (brs, 2H), 3.94 (t, J=5.8 Hz, 2H), 2.61 (t, J=5.8 Hz, 2H), 2.22 (s, 6H), 1.89 (s, 3H).

Step C: methyl 3-(3-{2-[(3-{[2-(dimethylamino)ethyl]oxy}-2-methylphenyl)amino]-4-pyrimidinyl]imidazo[1,2-a]pyridin-2-yl)benzoate

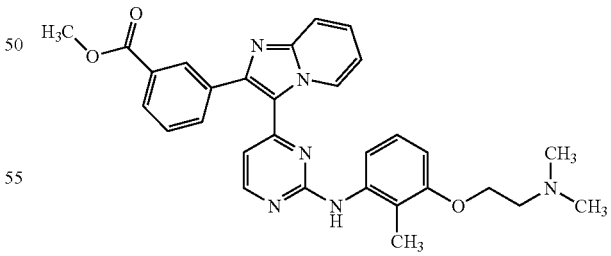

A microwave vial was charged with methyl 3-[3-(2-chloro-4-pyrimidinyl)imidazo[1,2-a]pyridin-2-yl]benzoate (Intermediate Example 3) (1.75 g, 4.79 mmol), {2-[(3-amino-2-methylphenyl)oxy]ethyl}methylamine (863 mg, 4.79 mmol), iPrOH (10 mL) and 1 drop HCl, and the reaction mixture was stirred in a microwave reactor at 140° C. for 30 min. The mixture was diluted with DCM and quenched with saturated NaHCO$_3$. The organics were separated, dried over MgSO$_4$, and the solvent was removed. The crude material was purified via silica gel chromatography to give 1.70 g (68% yield) of the title compound. MS (APCI⁺) m/z 523 [M+H].

Step D: N-(2,6-difluorophenyl)-3-(3-{2-[(3-{[2-(dimethylamino)ethyl]oxy}-2-methylphenyl)amino]-4-pyrimidinyl}imidazo[1,2-a]pyridin-2-yl)benzamide To a solution of methyl 3-(3-{2-[(3-{[2-(dimethylamino)ethyl]oxy}-2-methylphenyl)amino]-4-pyrimidinyl}imidazo[1,2-a]pyridin-2-yl)benzoate (60.0 mg, 0.115 mmol) and 2,6-difluoroaniline (0.0350 mL, 0.345 mmol) in THF (5 mL) was added sodium bis(trimethylsilyl)amide (0.46 mL, 0.460 mmol, 1.0 M solution in THF), and the reaction mixture was stirred for 5 min at rt. The mixture was quenched with saturated NaHCO₃, diluted with DCM, and the organic layer was separated. The solvent was removed and the crude material was purified via silica gel chromatography to give 70 mg (98% yield) of the title compound. ¹H NMR (400 MHz, DMSO-d₆) δ 10.24 (s, 1H), 9.36 (d, J=6.6 Hz, 1H), 9.08 (s, 1H), 8.32 (s, 1H), 8.20 (d, J=5.3 Hz, 1H), 8.06 (d, J=7.9 Hz, 1H), 7.83 (d, J=7.7 Hz, 1H), 7.72 (d, J=9.0 Hz, 1H), 7.62 (t, J=7.8 Hz, 1H), 7.42 (t, 2H), 7.12-7.28 (m, J=8.0, 8.0 Hz, 3H), 7.03 (d, J=7.5 Hz, 1H), 6.87 (d, 2H), 6.48 (d, J=5.3 Hz, 1H), 4.07 (t, J=5.8 Hz, 2H), 2.66 (t, J=5.7 Hz, 2H), 2.22 (s, 6H), 2.07 (s, 3H). MS (APCI⁺) m/z 620 [M+H].

Example 20

N-(2,6-difluorophenyl)-3-(3-{2-[(3-{[2-(dimethylamino)ethyl]oxy}phenyl)amino]-4-pyrimidinyl}imidazo[1,2-a]pyridin-2-yl)benzamide

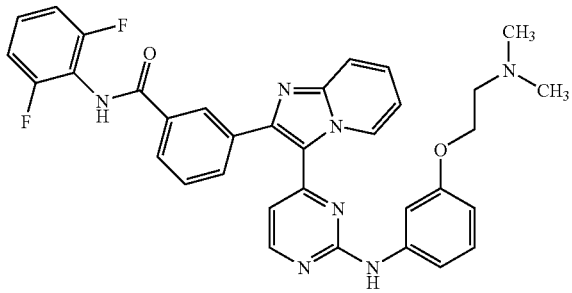

In a 5 mL microwave vial with septum cap, 3-[3-(2-chloro-4-pyrimidinyl)imidazo[1,2-a]pyridin-2-yl]-N-(2,6-difluorophenyl)-benzamide (Intermediate Example 1) (0.150 g, 0.325 mmol) and 3-{[2-(dimethylamino)ethyl]oxy}aniline hydrochloride (PCT Publication No. WO2004/087652) (0.63 g, 0.29 mmol) were taken up in iPrOH (3 mL) and concentrated HCl (5 drops) was added. The vial was sealed and heated in the microwave at 180° C. for 15 min. The crude product was adsorbed onto silica gel and flash chromatographed to give the title compound (0.047 g, 26%). ¹H NMR (400 MHz, DMSO-d₆) δ ppm 10.22 (s, 1H), 9.75 (s, 1H), 9.51 (d, J=6.6 Hz, 1H), 8.26-8.47 (m, 2H), 8.03 (d, J=7.7 Hz, 1H), 7.84 (d, J=7.7 Hz, 1H), 7.76 (d, J=9.0 Hz, 1H), 7.59 (t, J=7.8 Hz, 1H), 7.44-7.54 (m, 2H), 7.31-7.44 (m, 1H), 7.11-7.29 (m, 4H), 7.08 (t, J=6.6 Hz, 1H), 6.62 (d, J=5.3 Hz, 1H), 6.53 (dd, J=8.2, 1.6 Hz, 1H), 3.94 (t, J=5.8 Hz, 2H), 2.55 (t, J=5.7 Hz, 2H), 2.14 (s, 6H). MS (M+H, ES+) 606.

Example 21

N-(2,6-difluorophenyl)-3-(3-{2-[(5-{[2-(dimethylamino)ethyl]oxy}-2-methylphenyl)amino]-4-pyrimidinyl}imidazo[1,2-a]pyridin-2-yl)benzamide

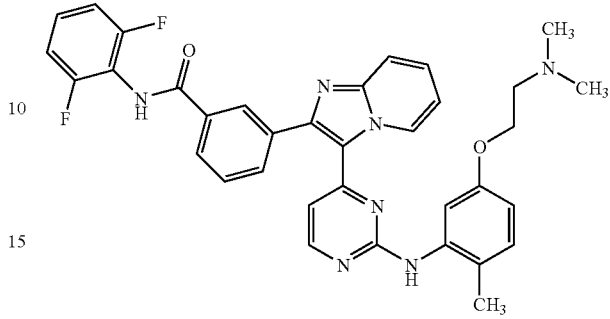

Step A: N,N-dimethyl-2-[(4-methyl-3-nitrophenyl)oxy]ethanamine

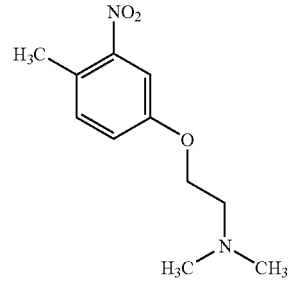

4-Methyl-3-nitrophenol (2.0 g, 13 mmol), 1-chloro-2-dimethylaminoethane hydrochloride (3.8 g, 26 mmol), and K₂CO₃ (5.4 g, 39 mmol) were added to 2-butanone (30 mL). The mixture was refluxed for 12 h after which TLC analysis revealed consumption of the starting phenol. The reaction was cooled, diluted with saturated NH₄Cl, and extracted with EtOAc. The organic layers were dried (Mg₂SO₄), filtered, concentrated, and purified via flash silica gel chromatography to afford the title compound (2.6 g, 89% yield). ¹H NMR (400 MHz, CDCl₃) δ ppm 2.34 (s, 6H), 2.53 (s, 3H), 2.74 (t, J=5.6 Hz, 2H), 4.09 (t, J=5.5 Hz, 2H), 7.10 (dd, J=8.4, 2.7 Hz, 1H), 7.22 (d, J=8.6 Hz, 1H), 7.53 (d, J=2.6 Hz, 1H).

Step B: 5-{[2-(dimethylamino)ethyl]oxy}-2-methylaniline

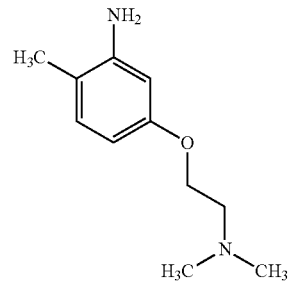

Palladium on carbon (10% by weight, 300 mg) and N,N-dimethyl-2-[(4-methyl-3-nitrophenyl)oxy]ethanamine (2.6 g, 12 mmol), dissolved in EtOH (40 mL), were transferred to a Fischer-Porter vessel. The vessel was evacuated twice and back-filled with N₂. The N₂ pressure was released and the vessel kept under a 60 psi of H₂ pressure for 12 h. The H₂ pressure was released, the reaction filtered through celite, and concentrated to provide the title compound (2.5 g, 95% yield). ¹H NMR (400 MHz, CDCl₃) δ ppm 2.09 (s, 3H), 2.32 (s, 6H), 2.69 (t, J=5.9 Hz, 2H), 3.58 (br s, 2H), 4.01 (t, J=5.9 Hz, 2H), 6.27-6.31 (m, 2H), 6.90-6.95 (m, 1H).

N-(2,6-difluorophenyl)-3-(3-{2-[(5-{[2-(dimethylamino)ethyl]oxy}-2-methylphenyl)amino]-4-pyrimidinyl}imidazo[1,2-a]pyridin-2-yl)benzamide The title compound (0.0812 g, 0.131 mmol, 45%) was prepared in an analogous manner as that described for the synthesis of Example 20 with the following notable exception: 5-{[2-(dimethylamino)ethyl]oxy}-2-methylaniline was used instead of 3-{[2-(dimethylamino)ethyl]oxy}aniline hydrochloride. ¹H NMR (400 MHz, DMSO-d₆) δ ppm 10.22 (s, 1H), 9.40 (d, J=6.8 Hz, 1H), 8.94 (s, 1H), 8.31 (s, 1H), 8.22 (d, J=5.1 Hz, 1H), 8.04 (d, J=7.9 Hz, 1H), 7.82 (d, J=7.7 Hz, 1H), 7.71 (d, J=8.8 Hz, 1H), 7.60 (t, J=7.8 Hz, 1H), 7.32-7.52 (m, 2H), 7.17 (dt, J=16.8, 8.4 Hz, 4H), 6.92 (t, J=7.0 Hz, 1H), 6.70 (dd, J=8.4, 2.2 Hz, 1H), 6.49 (d, J=5.3 Hz, 1H), 3.96 (t, J=5.7 Hz, 2H), 2.54 (t, J=5.8 Hz, 2H), 2.16 (s, 3H), 2.13 (s, 6H). MS (M+H, ES+) 620.

Example 22

3-[3-(2-{[4-(1,4'-bipiperidin-1'-yl)-2-(methyloxy)phenyl]amino}-4-pyrimidinyl)imidazo[1,2-a]pyridin-2-yl]-N-(2,6-difluorophenyl)benzamide

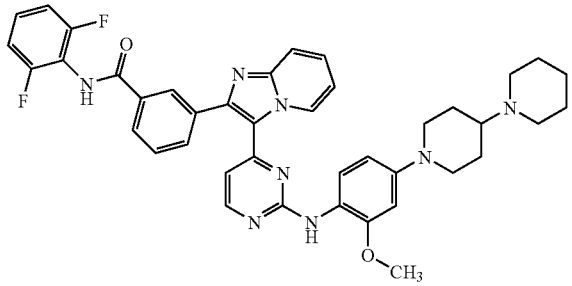

Step A: 5-fluoro-2-nitrophenyl methyl ether

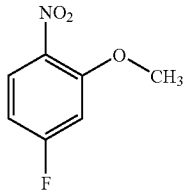

To 2-nitro-5-fluoro-phenol (56.0 g, 357 mmol) and iodomethane (24.5 mL, 393 mmol) in DMF (200 mL) was added K₂CO₃ (54.2 g, 393 mmol). Significant bubbling occurred. The mixture was stirred at rt overnight. The mixture was poured into H₂O (800 mL) and the H₂O washed with diethyl ether (3×200 mL). The ether washes were combined and washed with H₂O (2×400 mL). The ether layer was dried (MgSO₄), filtered, and rotovaped down to give the title compound (56.0 g, 327 mmol, 92%) as a yellow solid. ¹H NMR (400 MHz, CDCl₃) δ 7.96-7.90 (m, 1H), 6.79-6.67 (m, 2H), 3.93 (s, 3H).

Step B: 1'-[3-(methyloxy)-4-nitrophenyl]-1,4'-bipiperidine

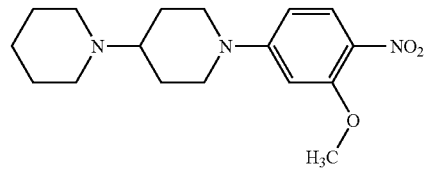

To 5-fluoro-2-nitrophenyl methyl ether (26.0 g, 152 mmol), 1,4'-bipiperidine (25.5 g, 152 mmol) and K₂CO₃ (22.9 g, 166 mmol) was added DMSO (260 mL). The mixture was stirred at room temperature for 3 days. The mixture was poured into H₂O (1000 mL) and the H₂O washed with EtOAc (2×500 mL). The EtOAc washes were combined and washed with H₂O (2×500 mL). The ether layer was dried (MgSO₄), filtered, and rotovaped down to give the title compound (47.9 g, 150 mmol, 99%) as a yellow solid. ¹H NMR (400 MHz, CDCl₃) δ 7.98 (d, J=9.5 Hz, 1H), 6.40 (dd, J=9.5 and 2.6 Hz, 1H), 6.29 (d, J=2.6 Hz, 1H), 3.99-3.93 (m, 2H), 3.93 (s, 3H), 2.98-2.89 (m, 2H), 2.58-2.48 (m, 5H), 1.99-1.90 (m, 2H), 1.70-1.55 (m, 8H), 1.48-1.40 (m, 2H).

Step C: 4-(1,4'-bipiperidin-1'-yl)-2-(methyloxy)aniline

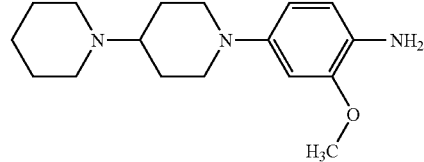

To 1'-[3-(methyloxy)-4-nitrophenyl]-1,4'-bipiperidine (47.9 g, 150 mmol) and nickel(II) chloride hexahydrate (17.8 g, 75.0 mmol) in MeOH (600 mL) and THF (300 mL) cooled to 0° C. was added NaBH₄ (~30 g, ~750 mmol) at such a rate to control the foaming which occurred. NaBH₄ was added until the yellow color disappeared from the foam (TLC confirms consumption of starting material). The mixture was rotovaped down and placed on the high vacuum overnight. EtOAc (1000 mL) was added to the solid and the slurry was stirred for 3 h. The mixture was filtered through a pad of celite, rinsing with generous amounts of EtOAc. The filtrate was washed with 0.1N NaOH (2×1000 mL), dried (MgSO₄), filtered, and rotovaped down to give the title compound (38.3 g, 133 mmol, 89%) as a pink solid. ¹H NMR (400 MHz, CDCl₃) δ 6.60 (d, J=8.4 Hz, 1H), 6.49 (d, J=2.4 Hz, 1H), 6.38 (dd, J=8.4, 2.4 Hz, 1H), 3.80 (s, 3H), 3.52-3.45 (m, 4H), 2.61-2.47 (m, 6H), 2.36-2.27 (m, 1H), 1.90-1.63 (m, 4H), 1.61-1.52 (m, 4H), 1.45-1.36 (m, 2H).

Step D: 3-[3-(2-{[4-(1,4'-bipiperidin-1'-yl)-2-(methyloxy)phenyl]amino}-4-pyrimidinyl)-imidazo[1,2-a]pyridin-2-yl]-N-(2,6-difluorophenyl)benzamide To 3-[3-(2-chloro-4-pyrimidinyl)imidazo[1,2-a]pyridin-2-yl]-N-(2,6-difluorophenyl)-benzamide (Intermediate Example 1) (14.2 g, 30.7 mmol) and 4-(1,4'-bipiperidin-1'-yl)-2-(methyloxy)aniline (8.89 g, 30.7 mmol) in 2,2,2-trifluoroethanol (142 mL) in a 350 mL glass round bottom pressure vessel was added concentrated HCl (7.7 mL, 92.1 mmol). The flask was sealed and the placed in an 85° C. oil bath for 3 days. After cooling to rt, 0.5 M sodium methoxide in MeOH (245 mL, 122.5 mmol) was added. The solvent was removed on a rotovap and the residue taken up in DCM. Silica gel (100 g) was added and the solvent removed on the rotovap. The preabsorbed solids were split into two equal portions and purified by flash chromatography. The desired fractions were combined and the solvent removed on the rotovap to give 19.0 g of a foam. The foam is dissolved in DCM (200 mL) with warming. Diethyl ether (500 mL) is added and a yellow solid precipitates. The solution was allowed to stand for 1 h. The yellow solid (17.2 g, 24.1 mmol, 78%) was collected by vacuum filtration and washed with diethyl ether. $^1$H NMR (400 MHz, DMSO-$d_6$) δ10.23 (s, 1H), 9.40 (s, 1H), 8.45 (s, 1H), 8.33 (s, 1H), 8.19 (d, J=5.2 Hz, 1H), 8.05 (d, J=8.0 Hz, 1H), 7.81 (d, J=8.0 Hz, 1H), 7.72 (d, J=9.2 Hz, 1H), 7.60 (t, J=7.7 Hz, 1H), 7.48-7.36 (m, 3H), 7.20 (t, J=8.1 Hz, 1H), 6.97 (t, J=7.2 Hz, 1H), 6.66 (d, J=2.2 Hz, 1H), 6.48-6.43 (m, 2H), 3.79 (s, 3H), 3.73 (d, J=12.5 Hz, 2H), 2.66-2.61 (m, 2H), 2.49-2.27 (m, 5H), 1.79-1.77 (m, 2H), 1.56-1.36 (m, 8H). MS (ESI) m/z=715 [M+H]$^+$.

Example 23

5-[3-(2-{[4-(1,4'-bipiperidin-1'-yl)-2-(methyloxy)phenyl]amino}-4-pyrimidinyl)imidazo[1,2-a]pyridin-2-yl]-N-(2,6-difluorophenyl)-2-(methyloxy)benzamide

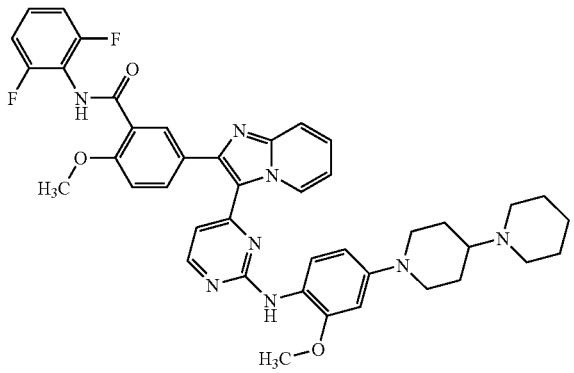

5-[3-(2-chloro-4-pyrimidinyl)imidazo[1,2-a]pyridin-2-yl]-N-(2,6-difluorophenyl)-2-(methyloxy)benzamide (Intermediate Example 2) (0.14 g, 0.28 mmol), 4-(1,4'-bipiperidin-1'-yl)-2-(methyloxy)aniline (Example 22, step C) (0.074 g, 0.25 mmol) and para-toluenesulfonic acid (0.12 g, 0.68 mmol) in iPrOH (5 mL) was heated at 180° C. for 10 min. The reaction was poured into half saturated NaHCO$_3$, extracted with DCM and EtOAc, dried (MgSO$_4$) and concentrated. Purification by flash chromatography followed by trituration with diethyl ether provided the title compound (0.099 g, 0.13 mmol, 53%). $^1$H NMR (400 MHz, DMSO-$d_6$) δ ppm 1.36 (s, 3H), 1.46 (s, 4H), 1.49-1.58 (m, 2H), 1.77 (d, J=10.4 Hz, 2H), 2.29 (s, 3H), 2.62 (t, J=12.0 Hz, 2H), 3.72 (d, J=11.9 Hz, 3H), 3.77 (s, 3H), 3.97 (s, 3H), 6.41-6.52 (m, 2H), 6.64 (s, 1H), 6.93 (t, J=7.3 Hz, 1H), 7.16 (t, J=8.1 Hz, 2H), 7.26 (d, J=8.6 Hz, 1H), 7.32-7.43 (m, 3H), 7.67 (d, J=8.6 Hz, 1H), 7.75 (d, J=8.4 Hz, 1H), 8.08 (s, 1H), 8.13-8.21 (m, 1H), 8.42 (s, 1H), 9.34 (br. s., 1H), 9.76 (s, 1H). MS (M+H, ES+) 745.

Example 24

N-(2,6-difluorophenyl)-3-(3-{2-[(5-{[2-(dimethylamino)ethyl]oxy}-2-methylphenyl)amino]-4-pyrimidinyl}imidazo[1,2-a]pyridin-2-yl)benzamide

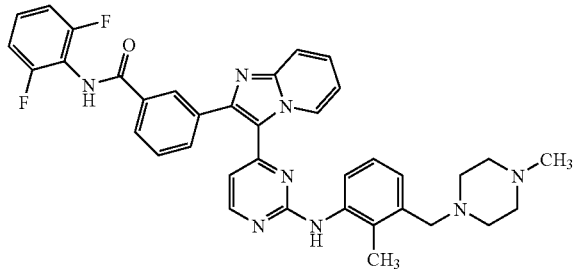

Step A: 1-methyl-4-[(2-methyl-3-nitrophenyl)methyl]piperazine

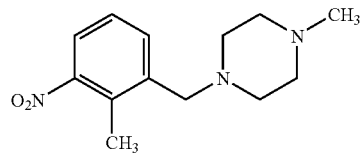

2-Methyl-3-nitrobenzaldehyde (*J. Org. Chem.* 1981, 46, 1752-1755) (1.0 g, 6.1 mmol) was dissolved in DCE and N-methylpiperazine and HOAc were added followed by sodium triacetoxyborohydride. The reaction was stirred at rt for 1 h and was then quenched with 5% K$_2$CO$_3$ solution. The reaction mixture was extracted (3×) with ethyl acetate, dried over magnesium sulfate, filtered, concentrated onto silica gel and flash chromatographed to give the title compound (1.6 g, 100%). $^1$H NMR (400 MHz, DMSO-$d_6$) δ ppm 7.69 (d, J=7.7 Hz, 1H), 7.52 (d, J=7.5 Hz, 1H), 7.34 (t, J=7.9 Hz, 1H), 3.48 (s, 2H), 2.16-2.42 (m, 1H), 2.10 (s, 3H).

Step B: 2-methyl-3-[(4-methyl-1-piperazinyl)methyl]aniline

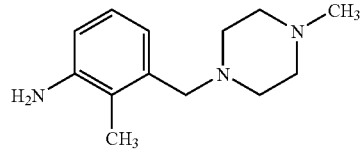

The title compound of step B was prepared from 1-methyl-4-[(2-methyl-3-nitrophenyl)methyl]-piperazine in an analogous manner as that described for the synthesis of 4-(1,4'-bipiperidin-1'-yl)-2-(methyloxy)aniline (Example 22, step C). $^1$H NMR (400 MHz, DMSO-$d_6$) δ 6.52 (d, J=6.8 Hz, 1H), 6.53 (d, J=6.8 Hz, 1H), 6.40 (d, J=7.5 Hz, 1H), 4.69 (s, 2H), 3.28 (s, 2H), 2.14-2.40 (m, 8H), 2.11 (s, 3H), 1.99 (s, 3H).

Step C: N-(2,6-difluorophenyl)-3-(3-{2-[(5-{[2-(dimethylamino)ethyl]oxy}-2-methylphenyl)amino]-4-pyrimidinyl}imidazo[1,2-a]pyridin-2-yl)benzamide In a 10 mL vial with septum cap, 3-[3-(2-chloro-4-pyrimidinyl)imidazo[1,2-a]pyridin-2-yl]-N-(2,6-difluorophenyl)-benzamide (Intermediate Example 1) (0.150 g, 0.325 mmol), 2-methyl-3-[(4-methyl-1-piperazinyl)methyl]aniline (0.107 g, 0.487 mmol) were taken up in 1,1,1-trifluoroethanol (2 mL) and 4.0M HCl in dioxane (0.162 mL, 0.650 mmol) was added. The vial was sealed and heated to 80° C. for 48 h. The reaction was cooled to rt, poured into saturated NaHCO$_3$ solution, and extracted with DCM (2×) and EtOAc (1×). Combined organic layers were dried over MgSO$_4$, filtered, and concentrated in vacuo. Purified by flash chromatography to give the title compound (0.086 g, 41%). $^1$H NMR (400 MHz, DMSO-$d_6$) δ ppm 10.22 (s, 1H), 9.28 (d, J=6.0 Hz, 1H), 9.04 (s, 1H), 8.30 (s, 1H), 8.19 (d, J=5.3 Hz, 1H), 8.04 (d, J=7.9 Hz, 1H), 7.81 (d, J=7.9 Hz, 1H), 7.69 (d, J=9.0 Hz, 1H), 7.52-7.65 (m, J=7.7, 7.7 Hz, 1H), 7.27-7.51 (m, 3H), 7.02-7.27 (m, 4H), 6.83 (t, J=6.7 Hz, 1H), 6.46 (d, J=5.1 Hz, 1H), 3.41 (s, 2H), 2.12-2.41 (m, 1H), 2.09 (s, 3H). MS (M+H, ES+) 645.

Example 25

N-(2,6-difluorophenyl)-5-{3-[2-({2-methyl-3-[(4-methyl-1-piperazinyl)methyl]phenyl}amino)-4-pyrimidinyl]imidazo[1,2-a]pyridin-2-yl}-2-(methyloxy)benzamide

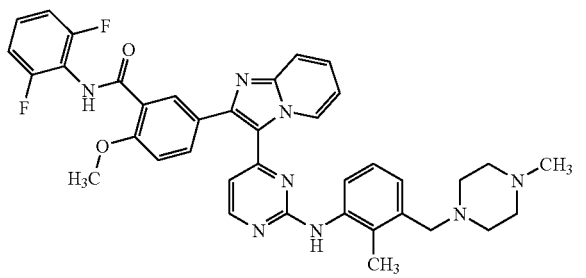

The title compound (0.0356 g, 0.052 mmol, 17%) was prepared in an analogous manner to that described for Example 24, with the following notable exception: 5-[3-(2-chloro-4-pyrimidinyl)imidazo[1,2-a]pyridin-2-yl]-N-(2,6-difluorophenyl)-2-(methyloxy)benzamide (Intermediate Example 2) was used instead of Intermediate Example 1. $^1$H NMR (400 MHz, DMSO-$d_6$) δ ppm 9.77 (s, 1H), 9.25 (d, J=6.4 Hz, 1H), 9.02 (s, 1H), 8.19 (d, J=5.1 Hz, 1H), 8.07 (br. s., 1H), 7.77 (d, J=8.4 Hz, 1H), 7.66 (d, J=8.6 Hz, 1H), 7.23-7.47 (m, 4H), 7.03-7.23 (m, 4H), 6.71-6.89 (m, 1H), 6.53 (d, J=5.1 Hz, 1H), 3.97 (s, 3H), 3.41 (s, 2H), 1.99-2.42 (m, 14H). MS (M+H, ES+) 675.

Example 26

N-(2,6-difluorophenyl)-5-[3-(2-{[4-{5-[(dimethylamino)methyl]-1,34-oxadiazol-2-yl}-2-(methyloxy)phenyl]amino}-4-pyrimidinyl)imidazo[1,2-a]pyridin-2-yl]-2-(methyloxy)benzamide

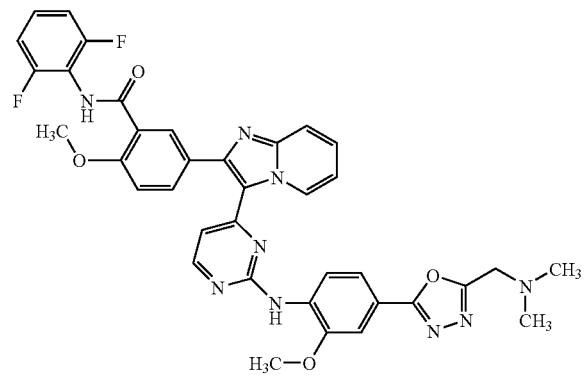

Step A: 3-(methyloxy)-4-nitrobenzohydrazide

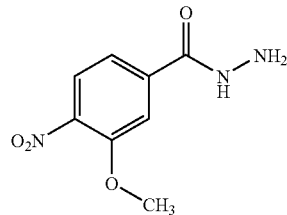

To methyl 3-methoxy-4-nitrobenzoate (5.16 g, 24.5 mmol) in EtOH (250 mL) was added hydrazine monohydrate (5.95 mL, 122 mmol) in one portion. The reaction was heated at 80° C. overnight and concentrated upon completion by TLC. The residue was taken up in EtOAc, heated and hot filtered. The filtrate was concentrated and the residue was triturated with diethyl ether to provide the title compound (3.65 g, 17.3 mmol, 71%). $^1$H NMR (400 MHz, DMSO-$d_6$) δ ppm 3.96 (s, 3H), 4.60 (br. s., 2H), 7.50 (dd, J=8.4, 1.5 Hz, 1H), 7.69 (d, J=1.8 Hz, 1H), 7.93 (d, J=8.1 Hz, 1H), 10.05 (br. s., 1H).

Step B: N'-(chloroacetyl)-3-(methyloxy)-4-nitrobenzohydrazide

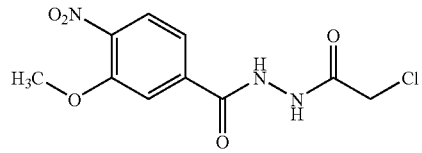

To 3-(methyloxy)-4-nitrobenzohydrazide (3.65 g, 17.3 mmol) in EtOAc (150 mL) was added chloroacetyl chloride (1.50 mL, 18.8 mmol). The reaction was stirred open to air overnight. The solid was filtered and washed with diethyl ether to provide the title compound (3.17 g, 11.0 mmol, 64%). $^1$H NMR (400 MHz, DMSO-$d_6$) δ ppm 3.98 (s, 3H), 4.21 (s, 2H), 7.56 (dd, J=8.2, 1.6 Hz, 1H), 7.74 (d, J=1.8 Hz, 1H), 7.99 (d, J=8.1 Hz, 1H), 10.48-10.54 (m, 1H), 10.82 (d, J=1.5 Hz, 1H).

Step C: 2-(chloromethyl)-5-[3-(methyloxy)-4-nitrophenyl]-1,3,4-oxadiazole

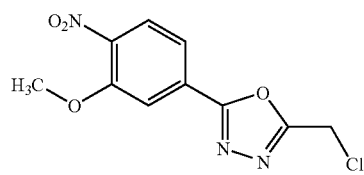

N'-(Chloroacetyl)-3-(methyloxy)-4-nitrobenzohydrazide (1.00 g, 3.48 mmol) and Burgess' reagent (0.994 g, 4.17 mmol) in THF (15 mL) was heated to 120° C. for 20 minutes in the microwave. The reaction was complete by TLC. Purification by flash chromatography provided the title compound (0.802 g, 2.93 mmol, 85%). $^1$H NMR (400 MHz, DMSO-$d_6$) δ ppm 4.04 (s, 3H), 5.16 (s, 2H), 7.72 (dd, J=8.4, 1.8 Hz, 1H), 7.84 (d, J=1.8 Hz, 1H), 8.09 (d, J=8.4 Hz, 1H).

Step D: 4-{5-[(dimethylamino)methyl]-1,3,4-oxadiazol-2-yl}-2-(methyloxy)aniline

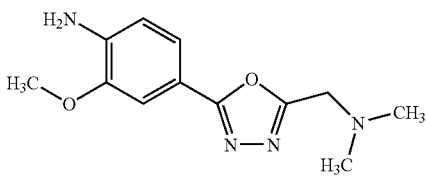

To 2-(chloromethyl)-5-[3-(methyloxy)-4-nitrophenyl]-1,3,4-oxadiazole (0.399 g, 1.48 mmol) in dioxane (10 mL) was added dimethylamine (1.87 mL, 40% weight in H$_2$O, 14.8 mmol). The reaction was heated at 60° C. overnight. The reaction was poured into half saturated NaHCO$_3$, extracted with DCM and EtOAc, dried (MgSO$_4$) and concentrated. The residue was taken up in EtOAc (20 mL) and Pd on carbon was added in one portion. The mixture was stirred at rt under H$_2$ (1 atm.) until complete by TLC. The reaction was filtered through Celite® and concentrated to provide the title compound of step D (0.326 g, 1.32 mmol, 89% over two steps). $^1$H NMR (400 MHz, DMSO-d$_6$) δ ppm 2.18-2.23 (m, 6H), 3.67-3.72 (m, 2H), 3.76-3.82 (m, 3H), 5.47-5.56 (m, 2H), 6.64-6.72 (m, 1H), 7.25 (d, J=2.0 Hz, 1H), 7.30 (dt, J=8.1, 2.1 Hz, 1H).

Step E: N-(2,6-difluorophenyl)-5-[3-(2-{[4-{5-[(dimethylamino)methyl]-1,3,4-oxadiazol-2-yl}-2-(methyloxy)phenyl]amino}-4-pyrimidinyl)imidazo[1,2-a]pyridin-2-yl]-2-(methyloxy)benzamide To 5-[3-(2-chloro-4-pyrimidinyl)imidazo[1,2-a]pyridin-2-yl]-N-(2,6-difluorophenyl)-2-(methyloxy)benzamide (Intermediate Example 2) (0.12 g, 0.25 mmol) and 4-{5-[(dimethylamino)methyl]-1,3,4-oxadiazol-2-yl}-2-(methyloxy)aniline (0.069 g, 0.28 mmol) in trifluoroethanol (5 mL) was added HCl (0.050 mL, 4 M in dioxane, 0.20 mmol). The reaction was heated at 85° C. for 48 hours. Purification by flash chromatography followed by trituration with diethyl ether provided the title compound (0.089 g, 0.12 mmol, 51%). $^1$H NMR (400 MHz, DMSO-d$_6$) δ ppm 2.23 (s, 6H), 3.76 (s, 2H), 3.96 (d, J=4.6 Hz, 6H), 6.76 (d, J=4.9 Hz, 1H), 7.03 (t, J=6.9 Hz, 1H), 7.15 (t, J=8.1 Hz, 2H), 7.26 (d, J=8.2 Hz, 1H), 7.30-7.40 (m, 1H), 7.42-7.50 (m, 1H), 7.51-7.59 (m, 2H), 7.71 (d, J=9.2 Hz, 1H), 7.78 (d, J=8.8 Hz, 1H), 8.10 (br. s., 1H), 8.35 (d, J=8.6 Hz, 1H), 8.39 (d, J=5.5 Hz, 1H), 8.69 (br. s., 1H), 9.44 (d, J=6.8 Hz, 1H), 9.74 (s, 1H). MS (M+H, ES+) 704.

Example 27

N-(2,6-difluorophenyl)-3-[3-(2-{[4-{5-[(dimethylamino)methyl]-1,34-oxadiazol-2-yl}-2-(methyloxy)phenyl]amino}-4-pyrimidinyl)imidazo[1,2-a]pyridin-2-yl]benzamide

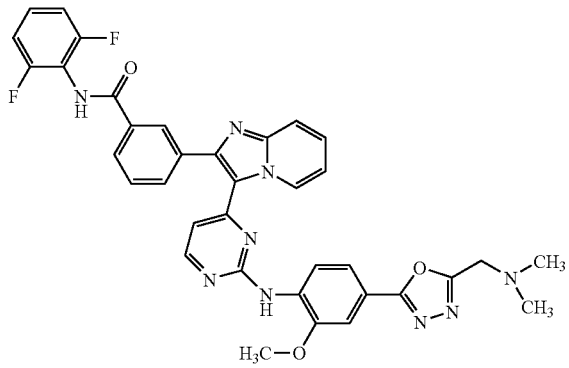

The title compound (0.10 g, 0.15 mmol, 58%) was prepared in an analogous manner to that described for the preparation Example 26, with the following notable exception: 3-[3-(2-chloro-4-pyrimidinyl)imidazo[1,2-a]pyridin-2-yl]-N-(2,6-difluorophenyl)-benzamide (Intermediate Example 1) was used instead of Intermediate Example 2. $^1$H NMR (400 MHz, DMSO-d$_6$) δ ppm 2.24 (s, 6H), 3.76 (s, 2H), 3.97 (s, 3H), 6.70 (d, J=4.8 Hz, 1H), 7.06 (t, J=6.8 Hz, 1H), 7.16 (t, J=8.0 Hz, 2H), 7.31-7.42 (m, 1H), 7.48 (d, J=15.6 Hz, 1H), 7.51-7.61 (m, 3H), 7.74 (d, J=8.8 Hz, 1H), 7.82 (d, J=7.3 Hz, 1H), 8.03 (d, J=7.7 Hz, 1H), 8.29-8.36 (m, 2H), 8.39 (d, J=5.1 Hz, 1H), 8.68 (br. s., 1H), 9.46 (d, J=1.6 Hz, 1H), 10.17 (br. s., 1H). MS (M+H, ES+) 674.

Example 28

N-(2,6-difluorophenyl)-2-(methyloxy)-5-{3-[2-({2-(methyloxy)-4-[5-(1-pyrrolidinylmethyl)-1,3,4-oxadiazol-2-yl]-phenyl}amino)-4-pyrimidinyl]imidazo[1,2-a]pyridin-2-yl}benzamide

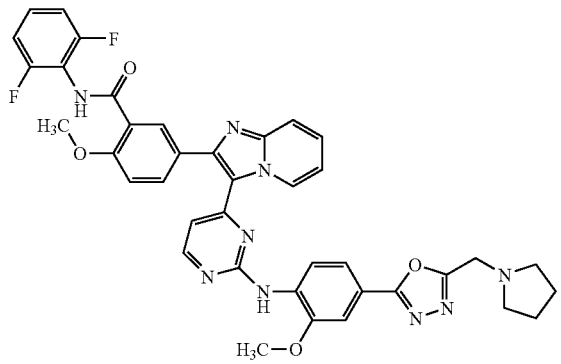

Step A: 2-[3-(methyloxy)-4-nitrophenyl]-5-(1-pyrrolidinylmethyl)-1,3,4-oxadiazole

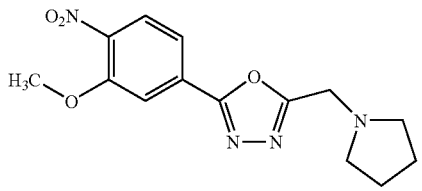

To 2-(chloromethyl)-5-[3-(methyloxy)-4-nitrophenyl]-1,3,4-oxadiazole (Example 26, step C) (1.01 g, 3.75 mmol) in dioxane (10 mL) was added pyrrolidine (0.800 mL, 9.58 mmol). The reaction was stirred at rt overnight. Upon completion by TLC, the reaction mixture was treated with BOC-anhydride (0.371 g, 1.69 mmol) and cooled to 0° C. The mixture was treated with TEA (0.279 mL, 2.00 mmol). Purification by flash chromatography provided the title compound of step A (1.13 g, 3.70 mmol, 99%). $^1$H NMR (400 MHz, DMSO-d$_6$) δ ppm 1.64-1.72 (m, 4H), 2.56 (br. s., 4H), 3.92-3.96 (m, 2H), 3.98-4.02 (m, 3H), 7.64-7.69 (m, 1H), 7.79 (br. s., 1H), 8.01-8.06 (m, 1H).

Step B: 2-(methyloxy)-4-[5-(1-pyrrolidinylmethyl)-1,3,4-oxadiazol-2-yl]aniline

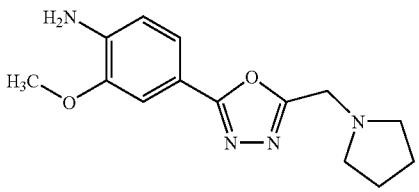

A mixture of 2-[3-(methyloxy)-4-nitrophenyl]-5-(1-pyrrolidinylmethyl)-1,3,4-oxadiazole (1.13 g, 3.70 mmol) and platinum on carbon (sulfided) in EtOAc (25 mL) was stirred under $H_2$ (1 atm.) overnight. The mixture was filtered through Celite® and concentrated. Purification by flash chromatography provided the title compound of step B (0.26 g, 0.93 mmol, 25%). $^1$H NMR (400 MHz, DMSO-$d_6$) δ ppm 1.62-1.71 (m, 4H), 2.48-2.57 (m, 4H), 3.76-3.85 (m, 5H), 5.51 (br. s., 2H), 6.64-6.71 (m, 1H), 7.25 (d, J=1.8 Hz, 1H), 7.29 (dt, J=8.1, 2.4 Hz, 1H).

Step C: N-(2,6-difluorophenyl)-2-(methyloxy)-5-{3-[2-({2-(methyloxy)-4-[5-(1-pyrrolidinylmethyl)-1,3,4-oxadiazol-2-yl]phenyl}amino)-4-pyrimidinyl]imidazo[1,2-a]pyridin-2-yl}benzamide The title compound (0.06 g, 0.08 mmol, 30%) was prepared in an analogous manner to that described for the preparation of Example 26, with the following notable exception: 2-(methyloxy)-4-[5-(1-pyrrolidinyl methyl)-1,3,4-oxadiazol-2-yl]aniline was used instead of 4-{5-[(dimethylamino)methyl]-1,3,4-oxadiazol-2-yl}-2-(methyloxy)aniline. $^1$H NMR (400 MHz, DMSO-$d_6$) δ ppm 1.68 (br. s., 4H), 2.55 (br. s., 4H), 3.90 (s, 2H), 3.96 (d, J=5.3 Hz, 6H), 6.76 (d, J=4.6 Hz, 1H), 7.03 (t, J=6.8 Hz, 1H), 7.15 (t, J=8.1 Hz, 2H), 7.26 (d, J=7.7 Hz, 1H), 7.30-7.40 (m, 1H), 7.45 (t, J=6.9 Hz, 1H), 7.50-7.57 (m, 2H), 7.71 (d, J=9.2 Hz, 1H), 7.78 (d, J=8.1 Hz, 1H), 8.10 (s, 1H), 8.34 (d, J=8.4 Hz, 1H), 8.39 (d, J=5.1 Hz, 1H), 8.70 (s, 1H), 9.45 (d, J=6.4 Hz, 1H), 9.75 (s, 1H). MS (M+H, ES+) 730.

Example 29

N-(2,6-difluorophenyl)-3-{3-[2-({2-(methyloxy)-4-[5-(1-pyrrolidinylmethyl)-1,3,4-oxadiazol-2-yl]phenyl}amino)-4-pyrimidinyl]imidazo[1,2-a]pyridin-2-yl}benzamide

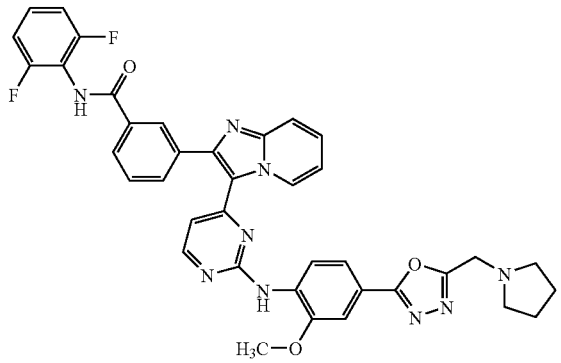

The title compound (0.04 g, 0.06 mmol, 23%) was prepared in an analogous manner to that described for the preparation Example 26, with the following notable exceptions:

a) 3-[3-(2-chloro-4-pyrimidinyl)imidazo[1,2-a]pyridin-2-yl]-N-(2,6-difluorophenyl)-benzamide (Intermediate Example 1) was used instead of Intermediate Example 2;
b) 2-(methyloxy)-4-[5-(1-pyrrolidinylmethyl)-1,3,4-oxadiazol-2-yl]aniline was used instead of 4-{5-[(dimethylamino)methyl]-1,3,4-oxadiazol-2-yl}-2-(methyloxy)aniline.

$^1$H NMR (400 MHz, DMSO-$d_6$) δ ppm 1.68 (br. s., 4H), 2.55 (br. s., 4H), 3.90 (s, 2H), 3.96 (d, J=5.3 Hz, 6H), 6.76 (d, J=4.6 Hz, 1H), 7.03 (t, J=6.8 Hz, 1H), 7.15 (t, J=8.1 Hz, 2H), 7.26 (d, J=7.7 Hz, 1H), 7.30-7.40 (m, 1H), 7.45 (t, J=6.9 Hz, 1H), 7.50-7.57 (m, 2H), 7.71 (d, J=9.2 Hz, 1H), 7.78 (d, J=8.1 Hz, 1H), 8.10 (s, 1H), 8.34 (d, J=8.4 Hz, 1H), 8.39 (d, J=5.1 Hz, 1H), 8.70 (s, 1H), 9.45 (d, J=6.4 Hz, 1H), 9.75 (s, 1H). MS (M+H, ES+) 700.

Example 30

3-[3-(2-{[5-(1,4'-bipiperidin-1'-yl)-2-(methyloxy)phenyl]amino}-4-pyrimidinyl)imidazo[1,2-a]pyridin-2-yl]-N-(2,6-difluorophenyl)benzamide

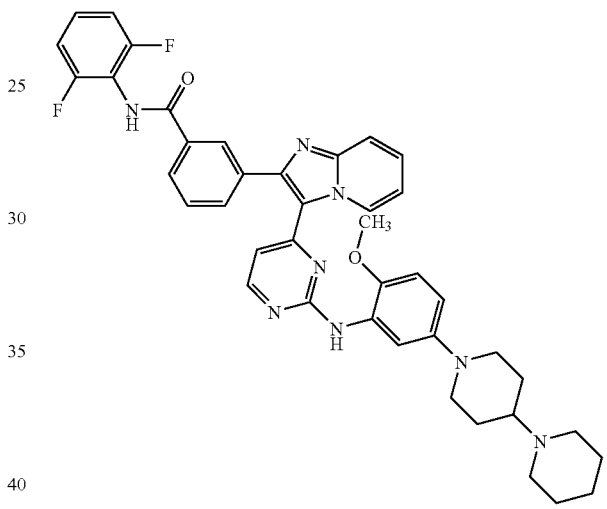

Step A: 5-(1,4'-bipiperidin-1'-yl)-2-(methyloxy)aniline

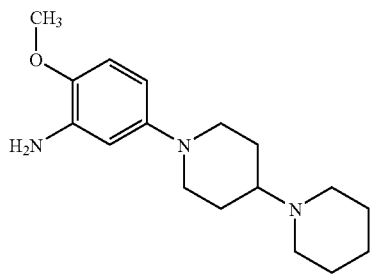

To 4-bromo-2-nitroanisole (2.02 g, 8.72 mmol) and 1,4'-bipiperidine (3.49 g, 20.7 mmol) in dioxane (80 mL) was added sequentially, cesium carbonate (6.74 g, 20.7 mmol), palladium (II) acetate (0.196 g, 0.870 mmol) and di-tert-butylphosphino-biphenyl (0.527 g, 1.77 mmol). The reaction was heated at 100° C. for 24 hours, filtered through Celite®, concentrated and purified by flash chromatography. The residue was taken up in EtOAc (100 mL) and Pd on carbon was added in one portion. The mixture was stirred at rt under $H_2$ (1 atm.) until complete by TLC. The reaction was filtered through Celite® and concentrated to provide the title compound of step A (0.667 g, 2.31 mmol, 26% over two steps). ¹H NMR (400 MHz, DMSO-d₆) δ ppm 1.32-1.40 (m, 2H), 1.43-1.54 (m, 6H), 1.73 (d, J=12.1 Hz, 2H), 2.18-2.28 (m, 1H), 2.41-2.47 (m, 6H), 3.43 (d, J=12.5 Hz, 2H), 3.65 (s, 3H), 4.52 (s, 2H), 6.06 (dd, J=8.6, 2.7 Hz, 1H), 6.28 (d, J=2.9 Hz, 1H), 6.60 (d, J=8.8 Hz, 1H).

Step B: 3-[3-(2-{[5-(1,4'-bipiperidin-1'-yl)-2-(methyloxy)phenyl]amino}-4-pyrimidinyl)-imidazo[1,2-a]pyridin-2-yl]-N-(2,6-difluorophenyl)benzamide The title compound (0.05 g, 0.06 mmol, 25%) was prepared in an analogous manner to that described for the preparation Example 26, with the following notable exceptions:
a) 3-[3-(2-chloro-4-pyrimidinyl)imidazo[1,2-a]pyridin-2-yl]-N-(2,6-difluorophenyl)-benzamide (Intermediate Example 1) was used instead of Intermediate Example 2;
b) 5-(1,4'-bipiperidin-1'-yl)-2-(methyloxy)aniline was used instead of 4-{5-[(dimethylamino)methyl]-1,3,4-oxadiazol-2-yl}-2-(methyloxy)aniline.

¹H NMR (400 MHz, DMSO-d₆) δ ppm 1.28-1.37 (m, 2H), 1.37-1.49 (m, 5H), 1.58-1.69 (m, 2H), 2.13-2.21 (m, 1H), 2.37 (s, 6H), 3.39-3.50 (m, 3H), 3.75 (s, 3H), 6.57 (d, J=5.3 Hz, 1H), 6.61 (d, J=8.6 Hz, 1H), 6.88-6.95 (m, 1H), 6.99 (t, J=6.9 Hz, 1H), 7.17 (t, J=8.3 Hz, 2H), 7.30-7.41 (m, 1H), 7.41-7.48 (m, 1H), 7.57 (t, J=7.9 Hz, 1H), 7.61 (s, 1H), 7.72 (d, J=8.8 Hz, 1H), 7.81 (d, J=7.5 Hz, 1H), 8.01 (d, J=7.0 Hz, 1H), 8.29 (d, J=4.9 Hz, 1H), 8.32 (s, 1H), 8.38 (s, 1H), 9.30-9.36 (m, 1H), 10.19 (s, 1H). MS (M+H, ES+) 715.

Example 31

5-[3-(2-{[5-(1,4'-bipiperidin-1'-yl)-2-(methyloxy)phenyl]amino}-4-pyrimidinyl)imidazo[1,2-a]pyridin-2-yl]-N-(2,6-difluorophenyl)-2-(methyloxy)benzamide

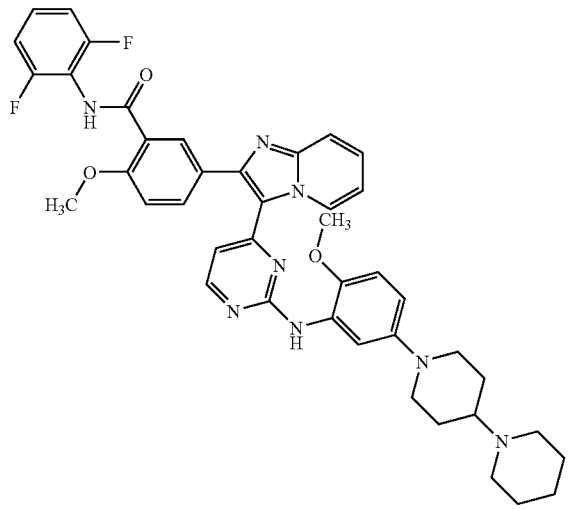

Step A: 5-[3-(2-{[5-(1,4'-bipiperidin-1'-yl)-2-(methyloxy)phenyl]amino}-4-pyrimidinyl)-imidazo[1,2-a]pyridin-2-yl]-N-(2,6-difluorophenyl)-2-(methyloxy)benzamide The title compound (0.079 g, 0.10 mmol, 43%) was prepared in an analogous manner to that described for the preparation of Example 23 with the following notable exception: 5-(1,4'-bipiperidin-1'-yl)-2-(methyloxy)aniline was used instead of 4-(1,4'-bipiperidin-1'-yl)-2-(methyloxy)aniline. ¹H NMR (400 MHz, DMSO-d₆) δ ppm 1.32 (s, 2H), 1.42 (s, 6H), 1.64 (s, 2H), 2.19 (s, 1H), 2.39 (s, 6H), 3.45 (d, J=11.5 Hz, 2H), 3.75 (s, 3H), 3.95 (s, 3H), 6.57-6.65 (m, 2H), 6.88-6.98 (m, 2H), 7.15 (t, J=8.0 Hz, 2H), 7.25 (d, J=9.7 Hz, 1H), 7.30-7.38 (m, 1H), 7.38-7.45 (m, 1H), 7.62 (s, 1H), 7.69 (d, J=9.2 Hz, 1H), 7.77 (d, J=9.0 Hz, 1H), 8.10 (br. s., 1H), 8.29 (d, J=5.3 Hz, 1H), 8.37 (s, 1H), 9.29 (d, J=7.3 Hz, 1H), 9.74 (s, 1H). MS (M+H, ES+) 745.

Example 32

3-{3-[2-({4-(1,4'-bipiperidin-1'-yl)-2-[(2-methylpropy)oxy]phenyl}amino)-4-pyrimidinyl]imidazo[1,2-a]pyridin-2-yl}-N-(2,6-difluorophenyl)benzamide

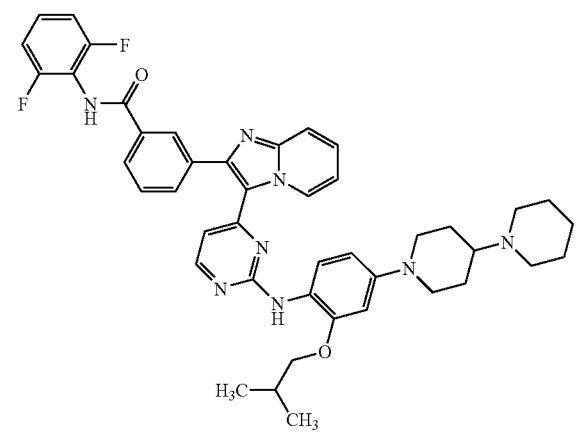

Step A: 1'-{3-[(2-methylpropyl)oxy]-4-nitrophenyl}-1,4'-bipiperidine

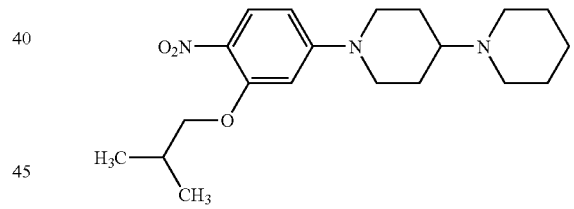

The title compound of step A (4 g, 11 mmol, 68%) was prepared in an analogous manner to that described for Example 22, steps A-B, with the following notable exception: isobutyl bromide was used instead of iodomethane in the step described in Example 22, Step A.

Step B: 4-(1,4'-bipiperidin-1'-yl)-2-[(2-methylpropyl)oxy]aniline

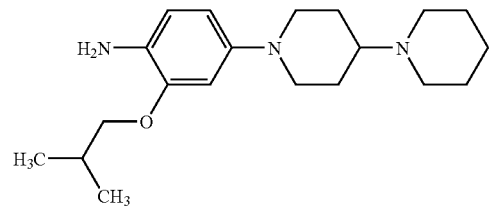

A mixture of 1'-{3-[(2-methylpropyl)oxy]-4-nitrophenyl}-1,4'-bipiperidine (4.00 g, 11.1 mmol) and Raney nickel (0.500 g) in EtOAc was stirred under $H_2$ (1 atm.) for 1 h. The mixture was filtered through a pad of Celite®, concentrated and recrystallized from EtOAc/hexanes to provide the title compound (1.40 g, 4.20 mmol, 39%). MS (M+H) 332.

Step C: Step B: 3-{3-[2-({4-(1,4'-bipiperidin-1'-yl)-2-[(2-methylpropyl)oxy]phenyl}amino)-4-pyrimidinyl]imidazo[1,2-a]pyridin-2-yl}-N-(2,6-difluorophenyl)benzamide To 3-[3-(2-chloro-4-pyrimidinyl)imidazo[1,2-a]pyridin-2-yl]-N-(2,6-difluorophenyl)-benzamide (Intermediate Example 1) (0.12 g, 0.25 mmol) and 4-(1,4'-bipiperidin-1'-yl)-2-[(2-methylpropyl)oxy]aniline (0.081 g, 0.24 mmol) in anhydrous iPrOH (3 mL) was added HCl (2 drops, 37% weight in $H_2O$). The reaction was heated at 170° C. for 33 min in the microwave. The reaction mixture was poured into half saturated $NaCO_3$, extracted with DCM and EtOAc, dried ($MgSO_4$) and concentrated. Purification by flash chromatography followed by prep-HPLC provided the title compound (0.07 g, 0.09 mmol, 36%). $^1$H NMR (400 MHz, DMSO-$d_6$) δ ppm 0.78 (d, J=6.6 Hz, 6H), 1.33-1.42 (m, 2H), 1.47 (s, 3H), 1.54 (d, J=11.7 Hz, 3H), 1.72-1.82 (m, 2H), 1.82-1.93 (m, 2H), 2.31 (s, 2H), 2.45 (s, 3H), 2.58-2.69 (m, 2H), 3.75 (d, J=6.2 Hz, 3H), 6.41-6.50 (m, 2H), 6.66 (s, 1H), 6.87-6.98 (m, 1H), 7.20 (t, J=8.2 Hz, 2H), 7.29 (d, J=10.6 Hz, 1H), 7.35-7.47 (m, 2H), 7.59 (t, J=7.9 Hz, 1H), 7.71 (d, J=9.2 Hz, 1H), 7.79 (d, J=7.7 Hz, 1H), 8.04 (d, J=8.1 Hz, 1H), 8.20 (d, J=5.1 Hz, 1H), 8.32 (s, 1H), 8.43 (s, 1H), 9.31 (d, J=9.9 Hz, 1H), 10.23 (s, 1H). MS (M+H, ES+) 757.

Example 33

3-[3-(2-{[4-(1,4'-bipiperidin-1'-yl)-2-(propyloxy)phenyl]amino}-4-pyrimidinyl)imidazo[1,2-a]pyridin-2-yl]-N-(2,6-difluorophenyl)benzamide

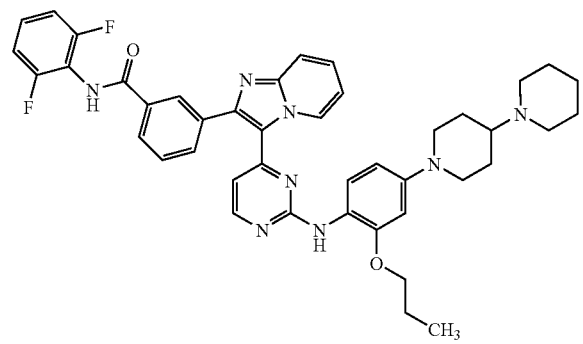

Step A: 4-(1,4'-bipiperidin-1'-yl)-2-(propyloxy)aniline

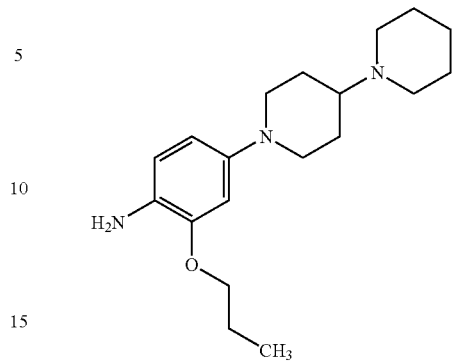

The title compound of step A (3.1 g, 9.8 mmol, 96% in final step) was prepared in a manner analogous to that described for the synthesis of Example 32, step A-B) with the following notable exception: n-propyl bromide was used instead of isobutyl bromide in Example 32, step A. MS (M+H) 318.

Step B: 3-[3-(2-{[4-(1,4'-bipiperidin-1'-yl)-2-(propyloxy)phenyl]amino}-4-pyrimidinyl)-imidazo[1,2-a]pyridin-2-yl]-N-(2,6-difluorophenyl)benzamide In a 5 mL microwave vial with septum cap, 3-[3-(2-chloro-4-pyrimidinyl)imidazo[1,2-a]pyridin-2-yl]-N-(2,6-difluorophenyl)-benzamide (Intermediate Example 1) (0.200 g, 0.433 mmol), 4-(1,4'-bipiperidin-1'-yl)-2-(propyloxy)aniline (0.137 g, 0.433 mmol) were taken up in iPrOH (3 mL) and concentrated HCl (3 drops) was added. The vial was sealed and heated in the microwave at 165° C. for 30 min. The reaction was cooled to rt, neutralized with 7N ammonia in MeOH, adsorbed onto silica gel, and flash chromatographed. Product was then triturated with diethyl ether to give the title compound (0.184 g, 58%). $^1$H NMR (400 MHz, DMSO-$d_6$) δ ppm 10.20 (s, 1H), 9.18-9.41 (m, 1H), 8.24-8.47 (m, 2H), 8.18 (d, J=4.9 Hz, 1H), 8.02 (d, J=7.5 Hz, 1H), 7.77 (d, J=7.5 Hz, 1H), 7.69 (d, J=9.0 Hz, 1H), 7.57 (t, J=7.6 Hz, 1H), 7.26-7.48 (m, 3H), 7.17 (t, J=8.1 Hz, 2H), 6.83-7.01 (m, 1H), 6.63 (br. s., 1H), 6.43 (d, J=5.1 Hz, 2H), 3.91 (t, J=6.0 Hz, 2H), 3.69 (d, J=11.4 Hz, 2H), 2.60 (t, J=11.6 Hz, 2H), 2.36-2.52 (m, 4H), 2.22-2.36 (m, 1H), 1.75 (d, J=11.0 Hz, 2H), 1.14-1.66 (m, 10H), 0.66-0.88 (m, 3H). MS (M+H) 743.

Example 34

3-[3-(2-{[4-(1,4'-bipiperidin-1'-yl)-2-(ethyloxy)phenyl]amino}-4-pyrimidinyl) imidazo[1,2-a]pyridin-2-yl]-N-(2,6-difluorophenyl)benzamide

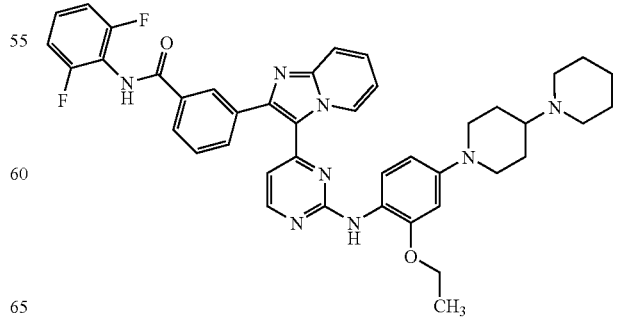

109

Step A: 4-(1,4'-bipiperidin-1'-yl)-2-(ethyloxy)aniline

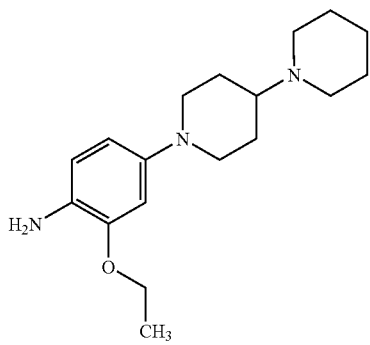

The title compound of step A (3.2 g, 10.6 mmol, 92% in final step) was prepared in a manner analogous to that described for the synthesis of 4-(1,4'-bipiperidin-1'-yl)-2-[(2-methylpropyl)oxy]aniline (Example 32, steps A-B) with the following notable exception: ethyl iodide was used instead of isobutyl bromide in Example 32, step A. MS (M+H) 304.

Step B: 3-[3-(2-{[4-(1,4'-bipiperidin-1'-yl)-2-(ethyloxy)phenyl]amino}-4-pyrimidinyl)-imidazo[1,2-a]pyridin-2-yl]-N-(2,6-difluorophenyl)benzamide The title compound (0.184 g, 0.252 mmol, 58%) was prepared in a manner analogous to that described for the synthesis of Example 33, step B) with the following notable exception: 4-(1,4'-bipiperidin-1'-yl)-2-(ethyloxy)aniline was used instead of 4-(1,4'-bipiperidin-1'-yl)-2-(propyloxy)aniline. $^1$H NMR (400 MHz, DMSO-d$_6$) δ ppm 10.24 (s, 1H), 9.29-9.47 (m, 1H), 8.35 (d, J=11.4 Hz, 2H), 8.22 (d, J=5.3 Hz, 1H), 8.04 (d, J=7.9 Hz, 1H), 7.81 (d, J=7.9 Hz, 1H), 7.72 (d, J=9.2 Hz, 1H), 7.60 (t, J=7.8 Hz, 1H), 7.33-7.53 (m, 3H), 7.13-7.30 (m, 2H), 6.96 (t, J=6.8 Hz, 1H), 6.64 (d, J=2.2 Hz, 1H), 6.35-6.55 (m, 2H), 4.05 (q, J=7.0 Hz, 2H), 3.71 (d, J=12.5 Hz, 2H), 2.62 (t, J=11.5 Hz, 2H), 2.44 (br. s., 4H), 2.21-2.37 (m, 1H), 1.69-1.85 (m, 2H), 1.30-1.64 (m, 8H), 1.23 (t, J=6.9 Hz, 3H). MS (M+H) 729.

Example 35

3-{3-[2-({4-(1,4'-bipiperidin-1'-yl)-2-[(1-methylethyl)oxy]phenyl}amino)-4-pyrimidinyl]imidazo[1,2-a]pyridin-2-yl}-N-(2,6-difluorophenyl)benzamide

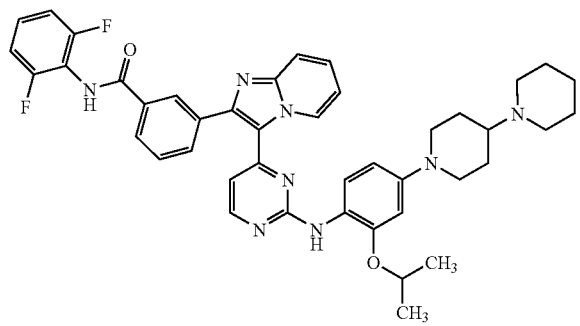

110

Step A: 4-(1,4'-bipiperidin-1'-yl)-2-[(1-methylethyl)oxy]aniline

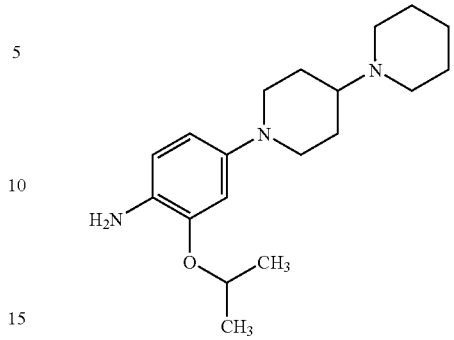

The title compound of step A (1.8 g, 5.7 mmol, 56% in final step) was prepared in a manner analogous to that described for the synthesis of Example 32, steps A-B with the following notable exception: isopropyl bromide was used instead of isobutyl bromide in Example 32, step A. MS (M+H) 318.

Step B: 3-{3-[2-({4-(1,4'-bipiperidin-1'-yl)-2-[(1-methylethyl)oxy]phenyl}amino)-4-pyrimidinyl]imidazo[1,2-a]pyridin-2-yl}-N-(2,6-difluorophenyl)benzamide The title compound (0.134 g, 0.180 mmol, 42%) was prepared in a manner analogous to that described for the synthesis of Example 33, step B with the following notable exception: 4-(1,4'-bipiperidin-1'-yl)-2-[(1-methylethyl)oxy]aniline was used instead of 4-(1,4'-bipiperidin-1'-yl)-2-(propyloxy)aniline. $^1$H NMR (400 MHz, DMSO-d$_6$) δ ppm 10.23 (s, 1H), 9.24-9.48 (m, 1H), 8.16-8.43 (m, 3H), 8.04 (d, J=7.5 Hz, 1H), 7.80 (d, J=7.5 Hz, 1H), 7.72 (d, J=9.0 Hz, 1H), 7.59 (t, J=7.7 Hz, 1H), 7.31-7.53 (m, 3H), 7.20 (t, J=8.0 Hz, 2H), 6.96 (t, J=6.4 Hz, 1H), 6.65 (br. s., 1H), 6.36-6.55 (m, 2H), 4.41-4.80 (m, 1H), 3.69 (d, J=11.9 Hz, 2H), 2.61 (t, J=11.7 Hz, 2H), 2.45 (br. s., 4H), 2.22-2.38 (m, 1H), 1.77 (d, J=11.7 Hz, 2H), 1.29-1.64 (m, 8H), 1.18 (d, J=5.9 Hz, 6H). MS (M+H) 743.

Example 36

N-(2,6-difluorophenyl)-3-{3-[2-({2-(methyloxy)-4-[4-(1-piperidinylmethyl)-1-piperidinyl]phenyl}amino)-4-pyrimidinyl]imidazo[1,2-a]pyridin-2-yl}benzamide

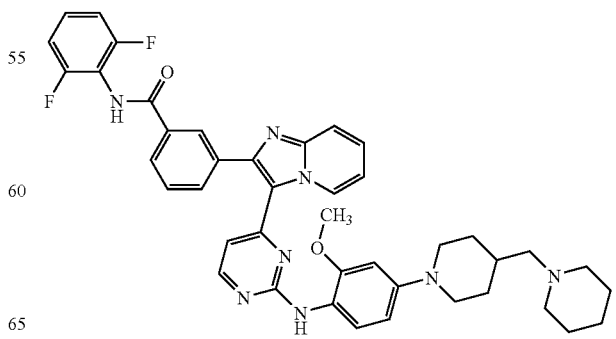

Step A: 1,1-dimethylethyl 4-formyl-1-piperidinecarboxylate

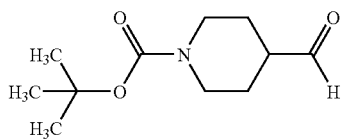

Oxalyl chloride (18.5 mL, 2M in DCM, 37.0 mmol) in DCM (230 mL) was cooled with a dry ice/acetone bath. DMSO (5.15 mL, 72.6 mmol) was added dropwise via addition funnel and the reaction was stirred for 10 min. N-Boc-4-piperidinemethanol in DCM (20 mL) was added dropwise via addition funnel and the reaction was stirred for 15 min. TEA (17.0 mL, 122 mmol) was then added dropwise via addition funnel and the reaction was warmed to rt. The reaction was diluted with diethyl ether, washed with H$_2$O and brine, dried (MgSO$_4$) and concentrated to provide the title compound (5.36 g, 25.1 mmol, 100%, approximately 96% pure, used without further purification). $^1$H NMR (400 MHz, DMSO-d$_6$) δ ppm 1.29-1.34 (m, 3H), 1.37 (s, 9H), 1.75-1.83 (m, 2H), 2.87 (s, 2H), 3.78 (d, J=13.2 Hz, 2H), 9.56 (s, 1H).

Step B: 1,1-dimethylethyl 4-(1-piperidinylmethyl)-1-piperidinecarboxylate

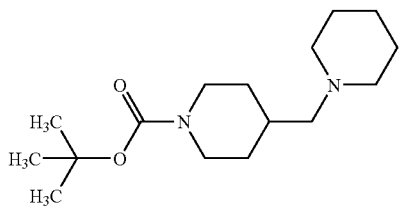

To 1,1-dimethylethyl 4-formyl-1-piperidinecarboxylate (1.02 g, 4.78 mmol) in 1,2-dichloroethane (50 mL) was added sequentially, HOAc (6.00 mL, 1M in DCM, 6.00 mmol), piperidine (1.0 mL, 10.1 mmol) and sodium triacetoxyborohydride (1.60 g, 7.55 mmol). The reaction was stirred at rt for 2 hours at which time HOAc (1.00 mL, 1M in DCM, 1.00 mmol) and sodium triacetoxyborohydride was added. When complete by TLC the reaction was quenched with saturated NaHCO$_3$ (150 mL) and extracted with DCM. The combined organic layer was washed with H$_2$O, dried (MgSO$_4$) and concentrated to provide the title compound (1.25 g, 4.43 mmol, 93%). $^1$H NMR (400 MHz, DMSO-d$_6$) δ ppm 0.80-0.91 (m, 2H), 1.29-1.35 (m, 11H), 1.38-1.46 (m, 4H), 1.59 (d, J=10.6 Hz, 3H), 2.00 (d, J=6.8 Hz, 2H), 2.21 (br. s., 4H), 2.62 (br. s., 2H), 3.85 (d, J=12.6 Hz, 2H).

Step C: 1-[3-(methyloxy)-4-nitrophenyl]-4-(1-piperidinylmethyl)piperidine

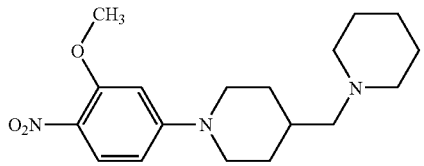

1,1-dimethylethyl 4-(1-piperidinylmethyl)-1-piperidinecarboxylate (1.25 g, 4.43 mmol) in DCM (40 mL) was cooled with an ice/H$_2$O bath. TFA (8.80 mL, 115 mmol) was added dropwise via pipette. Upon completion by TLC the reaction was quenched with 1N NaOH (115 mL) and extracted with EtOAc. The combined organic layer was washed with brine, dried (MgSO$_4$) and concentrated. The combined aqueous layer was treated with 1N NaOH, extracted with DCE/iso-propanol (4:1), dried (MgSO$_4$) and concentrated. The crude material was added to 5-fluoro-2-nitrophenyl methyl ether (Example 22, step A) (0.833 g, 4.87 mmol) and K$_2$CO$_3$ (0.992 g, 7.17 mmol) in DMSO (15 mL) and stirred at rt overnight. Upon completion by TLC, the reaction was diluted with EtOAc (250 mL), washed with H$_2$O (three times), dried (MgSO$_4$) and concentrated. Purification by flash chromatography provided the title compound (0.890 g, 2.66 mmol, 60% over two steps). $^1$H NMR (400 MHz, DMSO-d$_6$) δ ppm 1.04-1.14 (m, 2H), 1.30-1.41 (m, 2H), 1.42-1.50 (m, 4H), 1.72-1.83 (m, 3H), 2.07 (d, J=7.0 Hz, 2H), 2.27 (br. s., 4H), 2.93 (td, J=12.7, 2.2 Hz, 2H), 3.88 (s, 3H), 4.00 (d, J=13.6 Hz, 2H), 6.45 (d, J=2.6 Hz, 1H), 6.55 (dd, J=9.5, 2.6 Hz, 1H), 7.85 (d, J=9.5 Hz, 1H).

Step D: 2-(methyloxy)-4-[4-(1-piperidinylmethyl)-1-piperidinyl]aniline

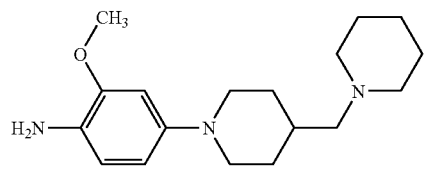

The title compound (0.806 g, 2.65 mmol, 99%) was prepared in a manner analogous to that described for Example 28, step B, with the following notable exceptions:
a) 1-[3-(methyloxy)-4-nitrophenyl]-4-(1-piperidinyl-methyl)piperidine was used instead of 2-[3-(methyloxy)-4-nitrophenyl]-5-(1-pyrrolidinyl-methyl)-1,3,4-oxadiazole;
b) Pd on carbon instead of platinum on carbon (sulfided) was used as the hydrogenation catalyst.

$^1$H NMR (400 MHz, CDCl$_3$) δ ppm 1.34-1.45 (m, 4H), 1.53-1.63 (m, 5H), 1.85 (d, J=12.8 Hz, 2H), 2.17 (d, J=7.0 Hz, 2H), 2.33 (br. s., 4H), 2.58 (td, J=12.0, 2.4 Hz, 2H), 3.39-3.48 (m, 3H), 3.50 (s, 1H), 3.83 (s, 3H), 6.43 (dd, J=8.6, 2.4 Hz, 1H), 6.54 (d, J=2.6 Hz, 1H), 6.63 (d, J=8.4 Hz, 1H).

Step E: N-(2,6-difluorophenyl)-3-{3-[2-({2-(methyloxy)-4-[4-(1-piperidinylmethyl)-1-piperidinyl]phenyl}amino)-4-pyrimidinyl]imidazo[1,2-a]pyridin-2-yl}benzamide To 3-[3-(2-chloro-4-pyrimidinyl)imidazo[1,2-a]pyridin-2-yl]-N-(2,6-difluorophenyl)-benzamide (Intermediate Example 1) (0.11 g, 0.25 mmol) and 2-(methyloxy)-4-[4-(1-piperidinylmethyl)-1-piperidinyl]aniline (0.076 g, 0.25 mmol) in trifluoroethanol (1.5 mL) was added HCl (0.13 mL, 4M in dioxane, 0.50 mmol). The reaction was heated at 170° C. for 80 min in the microwave. When complete by MS, the reaction mixture was quenched with sodium methoxide (0.5M in MeOH) and concentrated. Purification by flash chromatography, followed by prep-HPLC, and recrystallization with DCM/hexanes provided the title compound (0.082 g, 0.11 mmol, 46%). $^1$H NMR (400 MHz, DMSO-d$_6$) δ ppm 1.14-1.26 (m, 2H), 1.36 (br. s., 2H), 1.43-1.53 (m, 4H), 1.63 (br. s., 1H), 1.77 (d, J=11.7 Hz, 2H), 2.09 (d, J=7.0 Hz, 2H), 2.27 (s, 4H), 2.63 (t, J=12.1 Hz, 2H), 3.67 (d, J=11.4 Hz, 2H), 3.78 (s, 3H), 6.40-6.51 (m, 2H), 6.65 (d, J=2.2 Hz, 1H), 6.97 (t, J=7.0 Hz, 1H), 7.20 (t, J=8.1 Hz, 2H), 7.35-7.42 (m, 2H), 7.44-7.48 (m, 1H), 7.60 (t, J=7.7 Hz, 1H), 7.72 (d, J=9.2 Hz, 1H), 7.81 (d, J=7.7 Hz, 1H), 8.05 (d, J=8.1 Hz, 1H), 8.19 (d, J=5.1 Hz, 1H), 8.33 (s, 1H), 8.46 (s, 1H), 9.40 (br. s., 1H), 10.24 (s, 1H). MS (M+H, ES+) 729.

Example 37

N-(2,6-difluorophenyl)-3-(3-{2-[(2-(methyloxy)-4-{4-[(4-methyl-1-piperazinyl)methyl]-1-piperidinyl}phenyl)amino]-4-pyrimidinyl}imidazo[1,2-a]pyridin-2-yl)benzamide

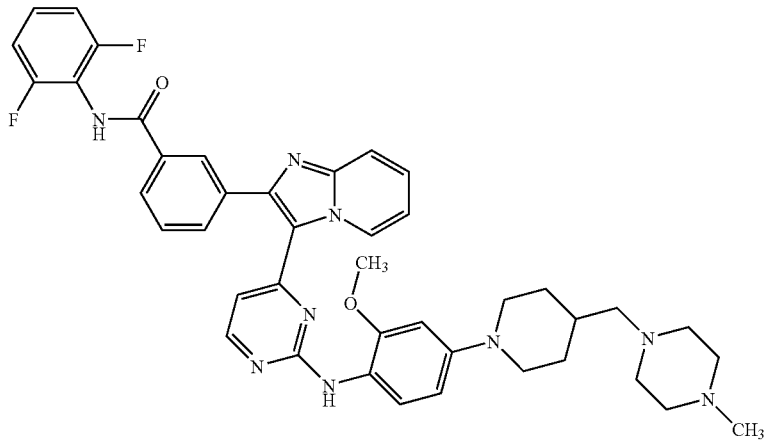

The title compound (0.045 g, 0.060 mmol, 24% in the final step) was prepared in a manner analogous to that described for Example 36 with the following notable exceptions:

a) N-methylpiperazine was used instead of piperidine in step B b) EtOH was used instead of EtOAc in step D c) 2-(methyloxy)-4-{4-[(4-methyl-1-piperazinyl)methyl]-1-piperidinyl}aniline was used instead of 2-(methyloxy)-4-[4-(1-piperidinylmethyl)-1-piperidinyl]aniline in step E.

$^1$H NMR (400 MHz, DMSO-d$_6$) δ ppm 1.16-1.27 (m, 3H), 1.63 (d, J=15.7 Hz, 2H), 1.76 (d, J=12.1 Hz, 2H), 2.10-2.18 (m, 4H), 2.27-2.39 (m, 6H), 2.63 (t, J=11.9 Hz, 3H), 3.67 (d, J=11.4 Hz, 2H), 3.79 (s, 3H), 6.42-6.52 (m, 2H), 6.65 (d, J=2.9 Hz, 1H), 6.93-7.01 (m, 1H), 7.20 (t, J=8.3 Hz, 2H), 7.36 (s, 1H), 7.45 (dd, J=15.4, 7.0 Hz, 2H), 7.61 (t, J=7.7 Hz, 1H), 7.72 (d, J=9.2 Hz, 1H), 7.81 (d, J=8.1 Hz, 1H), 8.05 (d, J=8.1 Hz, 1H), 8.20 (d, J=5.1 Hz, 1H), 8.33 (s, 1H), 8.45 (s, 1H), 9.39 (s, 1H), 10.24 (s, 1H).

Example 38

N-(2,6-difluorophenyl)-3-{3-[2-({2-(methyloxy)-4-[4-(4-morpholinyl)-1-piperidinyl]phenyl}amino)-4-pyrimidinyl]imidazo[1,2-a]pyridin-2-yl}benzamide

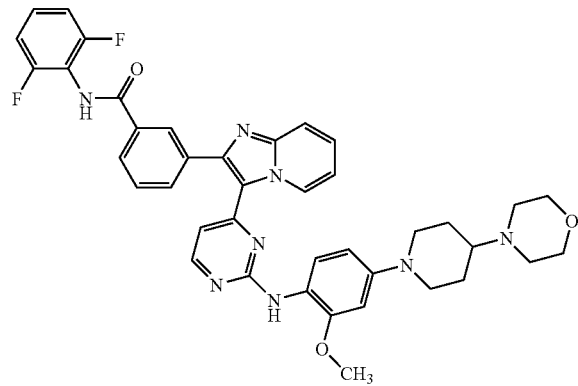

Step A: 2-(methyloxy)-4-[4-(4-morpholinyl)-1-piperidinyl]aniline

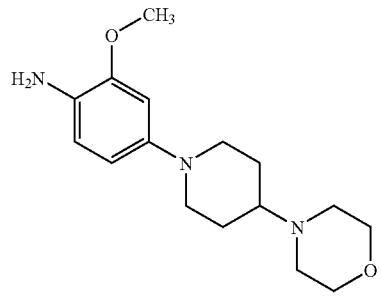

The title compound (1.74 g, 5.97 mmol, 77% in final step) was prepared in analogous manner to that described for the preparation of Example 22, steps A-C with the following notable exception: 4-(4-piperidinyl)morpholine was used instead of 1,4'-bipiperidine in Example 22, step B. $^1$H NMR (400 MHz, DMSO-d$_6$) δ 6.49-6.46 (m, 2H), 6.27 (dd, J=8.6 and 2.2 Hz, 1H), 4.19 (s, 2H), 3.71 (s, 3H), 3.57-3.54 (m, 4H), 3.41 (d, J=12.0 Hz, 1H), 2.52-2.45 (m under DMSO peak, 6H), 2.19-2.14 (m, 1H), 1.82 (d, J=12.0 Hz, 1H), 1.52-1.42 (m, 2H).

Step B: N-(2,6-difluorophenyl)-3-{3-[2-({2-(methyloxy)-4-[4-(4-morpholinyl)-1-piperidinyl]phenyl}amino)-4-pyrimidinyl]imidazo[1,2-a]pyridin-2-yl}benzamide A mixture of 3-[3-(2-chloro-4-pyrimidinyl)imidazo[1,2-a]pyridin-2-yl]-N-(2,6-difluorophenyl)-benzamide (Intermediate Example 1) (139 mg, 0.30 mmol), 2-(methyloxy)-4-[4-(4-morpholinyl)-1-piperidinyl]aniline (79 mg, 0.27 mmol) and p-toluenesulfonic acid (137 mg, 0.71 mmol) in iPrOH was heated in the microwave at 180° C. for 13.5 min. The mixture was dissolved in DCM and concentrated onto silica gel. The crude material was purified by flash column chromatography to give 129 mg (60%) of the title compound. $^1$H NMR (400 MHz, DMSO-d$_6$) δ 10.22 (s, 1H), 9.38 (br s, 1H), 8.44 (s, 1H), 8.31 (s, 1H), 8.18 (d, J=5.2 Hz, 1H), 8.03 (d, J=8.0 Hz, 1H), 7.80 (d, J=8.0 Hz, 1H), 7.71 (d, J=9.2 Hz, 1H), 7.59 (t, J=7.8 Hz, 1H), 7.46-7.35 (m, 2H), 7.19 (t, J=8.0 Hz, 1H), 6.96 (t, J=6.8 Hz, 1H), 6.65 (m, 1H), 6.48-6.43 (m, 2H), 3.77 (s, 3H), 3.71 (d, J=12.4 Hz, 2H), 3.56-3.54 (M, 4H), 2.67-2.62 (m, 2H), 2.49-2.46 (m under DMSO peak, 4H), 2.27-2.22 (m, 1H), 1.86-1.83 (m, 2H), 1.52-1.44 (m, 2H). MS (ESI) m/z=717 [M+H]$^+$.

Example 39

3-[3-(2-{[4-(1,4'-bipiperidin-1'-yl)-2-(methyloxy)phenyl]amino}-4-pyrimidinyl)-7-(methyloxy)imidazo[1,2-a]pyridin-2-yl]-N-(2,6-difluorophenyl)benzamide

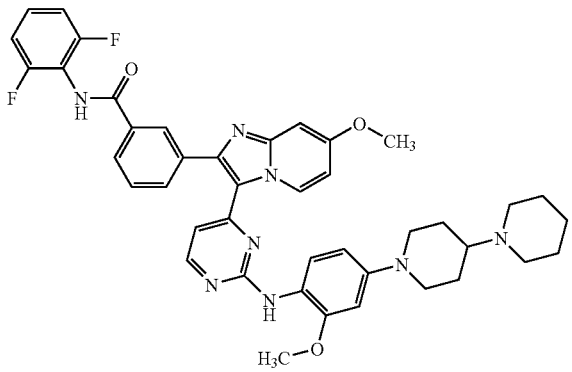

The title compound (0.57 g, 0.76 mmol, 62% in final step) was prepared in an analogous manner to that described in Example 22 with the following notable exceptions:
a) 4-(methyloxy)-2-pyridinamine (*J. Chem. Soc., Perkin Trans* 1, 2001, 2012-2021) was used instead of 2-aminopyridine in the step outlined in Intermediate Example 1, step C;
b) p-toluenesulfonic acid in iPrOH at 180° C. under microwave conditions was used instead of concentrated HCl in trifluoroethanol at 85° C. in Example 22, step D.

$^1$H NMR (400 MHz, DMSO-d$_6$) δ 10.18 (s, 1H), 9.31-9.21 (m, 1H), 8.37 (s, 1H), 8.26 (s, 1H), 8.11 (d, J=5.3 Hz, 1H), 8.02-8.00 (m, 1H), 7.78-7.76 (m, 1H), 7.57 (at, J=7.7 Hz, 1H), 7.41-7.29 (m, 2H), 7.20-7.14 (m, 2H), 7.07 (d, J=2.7 Hz, 1H), 6.65-6.59 (m, 2H), 6.45 (dd, J=8.7, 2.3 Hz, 1H), 6.36 (d, J=5.3 Hz, 1H), 3.85 (s, 3H), 3.75 (s, 3H), 3.76-3.69 (m, 2H), 2.65-2.59 (m, 2H), 2.43-2.37 (m, 3H), 2.34-2.26 (m, 2H), 1.80-1.71 (m, 2H), 1.56-1.30 (m, 8H). MS (ES+, m/z) 745 (M+1).

Example 40

3-[3-(2-{[4-(1,4'-bipiperidin-1'-yl)-2-ethylphenyl]amino}-4-pyrimidinyl)imidazo[1,2-a]pyridin-2-yl]-N-(2,6-difluorophenyl)benzamide

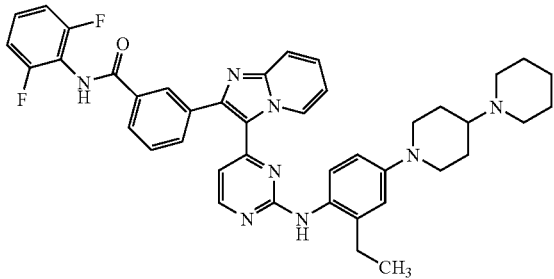

Step A: 2-bromo-4-fluoro-1-nitrobenzene

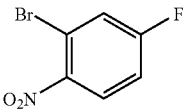

To a solution of 4-fluoroaniline (20 g, 180 mmol) in dichloromethane (100 mL) at 0° C. was added N-bromosuccinimide (34 g, 180 mmol, in 60 mL dichloromethane) dropwise. The mixture was stirred at room temperature overnight. The reaction was washed with saturated sodium sulfite, saturated sodium bicarbonate, and brine and concentrated to provide the title compound (34 g, 154.5 mmol, 100%). $^1$H NMR (400 MHz, CDCl$_3$) δ ppm 7.12-7.21 (m, 1H), 7.47 (dd, J=7.60, J=2.40, 1H), (dd, J=9.60, J=6.40, 1H).

Step B: 2-ethyl-4-fluoro-1-nitrobenzene

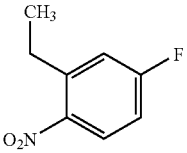

2-Bromo-4-fluoro-1-nitrobenzene (21.8 g, 100 mmol), ethyl boronic acid (7.5 g, 100 mL), K$_2$CO$_3$ (40 g, 300 mL), dichloro[1,1'-bis(diphenylphosphino)-ferrocene]palladium (II) (6 g) in dioxane (250 mL) and H$_2$O (80 mL) was flushed with N$_2$ and heated at 100° C. overnight. The reaction was diluted with EtOAc and H$_2$O and filtered through Celite®. The organic layer was separated, concentrated and purification by flash chromatography provided the title compound (4.1 g, 24.2 mmol, 24%). $^1$H NMR (400 MHz, CDCl$_3$) δ ppm 1.30 (t, J=7.78, 3H), 2.92 (q, J=7.78, 2H), 7.01-7.11 (m, 2H), 7.98 (dd, J=8.53 Hz, J=5.53 Hz, 1H).

Step C: 1'-(3-ethyl-4-nitrophenyl)-1,4'-bipiperidine

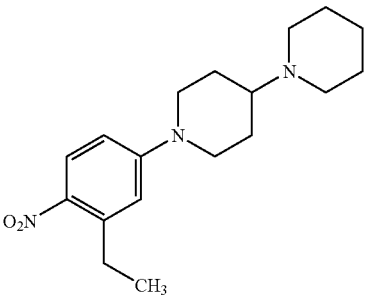

The title compound of step C (2.4 g, 7.56 mmol, 100%) was prepared in an analogous manner to that of Example 22, step B, with the following notable exceptions:
a) 2-ethyl-4-fluoro-1-nitrobenzene was used instead of 5-fluoro-2-nitrophenyl methyl ether;
b) the reaction was run at 40° C. instead of rt.

$^1$H NMR (400 MHz, CDCl$_3$) δ ppm 1.25 (t, J=7.78 Hz, 3H), 1.40-1.51, (m, 2H), 1.50-1.61 (m, 6H), 1.85-1.95 (m, 2H), 2.45-2.55 (m, 5H), 2.81-3.01 (m, 4H), 3.91-4.01 (m, 2H), 6.61-6.72 (m, 2H), 8.01 (d, J=8.01, 1H).

117

Step D: 4-(1,4'-bipiperidin-1'-yl)-2-ethylaniline

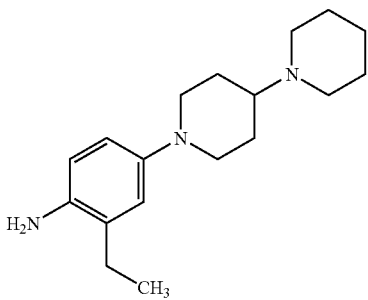

The title compound of step D (2.1 g, 7.3 mmol, 100%) was prepared from 1'-(3-ethyl-4-nitrophenyl)-1,4'-bipiperidine in an analogous manner to that described for Example 32, step B. MS (M+H) 288.

Step E: 3-[3-(2-{[4-(1,4'-bipiperidin-1'-yl)-2-ethylphenyl]amino}-4-pyrimidinyl)imidazo[1,2-a]pyridin-2-yl]-N-(2,6-difluorophenyl)benzamide The title compound (0.108 g, 0.151 mmol, 35%) was prepared in an analogous manner to that described for Example 33, step B with the following notable exception: 4-(1,4'-bipiperidin-1'-yl)-2-ethylaniline was used instead of 4-(1,4'-bipiperidin-1'-yl)-2-(propyloxy)aniline. $^1$H NMR (400 MHz, DMSO-$d_6$) δ ppm 10.21 (s, 1H), 9.16-9.43 (m, 1H), 8.79 (s, 1H), 8.28 (s, 1H), 8.12 (d, J=5.1 Hz, 1H), 8.03 (d, J=7.9 Hz, 1H), 7.79 (d, J=7.5 Hz, 1H), 7.67 (d, J=9.0 Hz, 1H), 7.59 (t, J=7.8 Hz, 1H), 7.27-7.49 (m, 2H), 7.18 (t, J=8.1 Hz, 2H), 7.10 (d, J=8.6 Hz, 1H), 6.71-6.93 (m, 3H), 6.38 (d, J=5.3 Hz, 1H), 3.71 (d, J=11.7 Hz, 2H), 3.25 (s, 2H), 2.35-2.71 (m, 7H), 1.69-1.88 (m, 2H), 1.26-1.64 (m, 8H), 1.04 (t, J=7.2 Hz, 3H). MS (M+H) 713.

Example 41

3-[3-(2-{[4-(1,4'-bipiperidin-1'-yl)-2-propylphenyl]amino}-4-pyrimidinyl)imidazo[1,2-a]pyridin-2-yl]-N-(2,6-difluorophenyl)benzamide

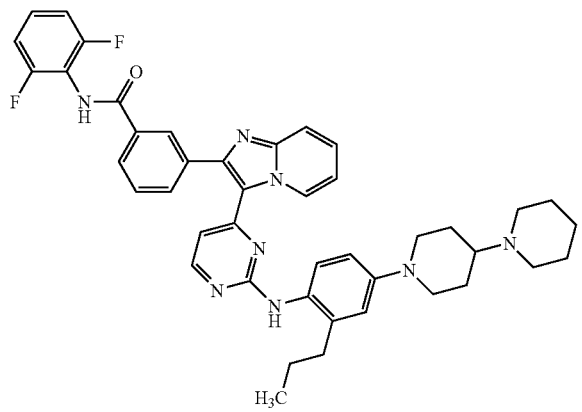

118

Step A: 4-fluoro-2-iodo-1-nitrobenzene

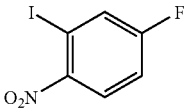

To a solution of 5-fluoro-2-nitroaniline (70.0 g, 448 mmol) in HCl (350 mL, 37% in water) at 0° C. was added sodium nitrite (32.2 g, 469 mmol, in 100 mL water) dropwise. The mixture was stirred for 1 h at which time, potassium iodide (82.0 g, 490 mmol, in 100 mL $H_2O$) was added dropwise. The mixture was stirred at rt for 2 h and then extracted with EtOAc. The organic layer was washed with brine, dried (MgSO$_4$) and purified by flash chromatography to provide the title compound (98.6 g, 368 mmol, 83%). $^1$H NMR (400 MHz, CDCl$_3$) δ ppm 7.15-7.23 (m, 1H), 7.75 (dd, J=3.50 Hz, J=7.60 Hz, 1H), 7.97 (dd, J=1.6 Hz, J=8.8 Hz, 1H).

Step B: 4-fluoro-1-nitro-2-(2-propen-1-yl)benzene

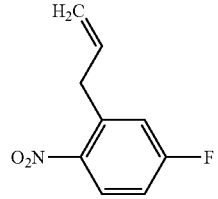

To 4-fluoro-2-iodo-1-nitrobenzene (40.0 g, 150 mmol) in THF (200 mL) at −40° C. was added phenylmagnesium chloride (80.0 mL, 2M in THF, 161 mmol) dropwise. The reaction was stirred for 30 min followed by dropwise addition of CuCN.2LiCl (26.0 g, 150 mmol) in THF. The mixture was stirred an additional 30 min at which time allyl bromide (20.0 g, 161 mmol) was added. The reaction was stirred at −40° C. for 2 h followed by rt overnight. The reaction was quenched with saturated ammonium chloride and extracted with EtOAc. The organic layer was washed with brine, dried (MgSO$_4$) and concentrated. Purification by flash chromatography provided the title compound of step B (11.0 g, 60.7 mmol, 42%). $^1$H NMR (400 MHz, CDCl$_3$) δ ppm 3.70 (d, J=6.4 Hz, 2H), 5.08-5.71 (m, 2H), 6.87-6.02 (m, 1H), 7.01-7.11 (m, 2H), 7.95-8.05 (m, 1H).

Step C: 4-fluoro-2-propylaniline

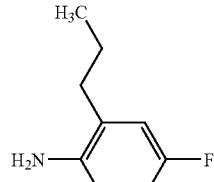

To 4-fluoro-1-nitro-2-(2-propen-1-yl)benzene (9.0 g, 50 mmol) in MeOH (100 mL) was added palladium hydroxide on carbon (2 g). The reaction mixture was stirred under $H_2$ (50 psi) at rt overnight. The solution was filtered and concentrated to provide the title compound of step C (7.4 g, 48.3 mmol, 97%). $^1$H NMR (400 MHz, CDCl$_3$) δ ppm 1.10 (t, J=7.5 Hz, 3H), 1.60-1.70 (m, 2H), 2.45 (t, J=7.2 Hz, 2H), 6.55-6.65 (m, 1H), 6.67-6.81 (m, 2H).

Step D: 4-fluoro-1-nitro-2-propylbenzene

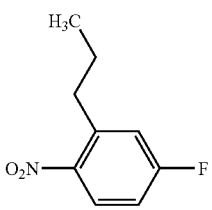

To 4-fluoro-2-propylaniline (7.4 g, 48.3 mmol) in dichloromethane (100 mL) was added meta-chloroperoxybenzoic acid (42.0 g, 240 mmol) in 3 portions at −10° C. The reaction was stirred at rt overnight. The mixture was filtered and the filtrate was washed with saturated sodium sulfite, aqueous $K_2CO_3$, brine and concentrated. Purification by flash chromatography provided the title compound of step D (4.50 g, 24.6 mmol, 56%). $^1$H NMR (400 MHz, CDCl$_3$) δ ppm 1.01 (t, J=7.53 Hz, 3H), 1.70-1.81 (m, 2H), 2.9 (t, J=7.28, 2H), 7.01-7.12 (m, 2H), 7.95 (dd, J=5.6 Hz, J=9.2 Hz, 1H).

Step E: 1'-(4-nitro-3-propylphenyl)-1,4'-bipiperidine

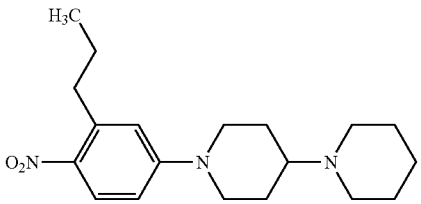

The title compound of step E (4.20 g, 12.7 mmol, 84%) was prepared in an analogous manner to that of Example 22, step B with the following notable exceptions:
a) 4-fluoro-1-nitro-2-propylbenzene was used instead of 5-fluoro-2-nitrophenyl methyl ether;
b) the reaction was run at 40° C. instead of rt.

$^1$H NMR (400 MHz, CDCl$_3$) δ ppm 1.01 (t, J=7.5 Hz, 3H), 1.41-1.52 (m, 2H), 1.51-1.71 (m, 8H), 1.90-2.01 (m, 2H), 2.40-2.61 (m, 5H), 2.81-3.00 (m, 4H), 4.00-4.10 (m, 2H), 6.6 (d, J=2.3 Hz, 1H), 6.67 (dd, J=8.9 Hz, J=2.3 Hz, 1H), 8.05 (d, J=2.3 Hz, 1H).

Step F: 4-(1,4'-bipiperidin-1'-yl)-2-propylaniline

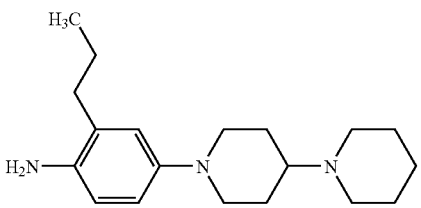

The title compound of step F (3.10 g, 10.3 mmol, 82%) was prepared from 1'-(4-nitro-3-propylphenyl)-1,4'-bipiperidine in an analogous manner to that described for Example 32, step B. MS (M+H) 302.

Step G: 3-[3-(2-{[4-(1,4'-bipiperidin-1'-yl)-2-propylphenyl]amino}-4-pyrimidinyl)imidazo-[1,2-a]pyridin-2-yl]-N-(2,6-difluorophenyl)benzamide The title compound (0.087 g, 0.12 mmol, 49%) was prepared in an analogous manner to that described for Example 36, step E with the following notable exception: 4-(1,4'-bipiperidin-1'-yl)-2-propylaniline was used instead of 2-(methyloxy)-4-[4-(1-piperidinylmethyl)-1-piperidinyl]aniline. $^1$H NMR (400 MHz, DMSO-d$_6$) δ ppm 0.79 (t, J=7.3 Hz, 3H), 1.29-1.39 (m, 2H), 1.41-1.53 (m, 8H), 1.76 (d, J=11.7 Hz, 2H), 2.26-2.36 (m, 1H), 2.39-2.44 (m, 4H), 2.47-2.51 (m, 2H), 2.61 (t, J=11.3 Hz, 2H), 3.69 (d, J=11.9 Hz, 2H), 6.38 (d, J=5.3 Hz, 1H), 6.74-6.85 (m, 3H), 7.10 (d, J=8.6 Hz, 1H), 7.17 (t, J=8.1 Hz, 2H), 7.39 (dd, J=19.7, 8.2 Hz, 2H), 7.59 (t, J=7.8 Hz, 1H), 7.67 (d, J=9.0 Hz, 1H), 7.78 (d, J=8.1 Hz, 1H), 8.02 (s, 1H), 8.12 (d, J=5.1 Hz, 1H), 8.28 (br. s., 1H), 8.77 (s, 1H), 9.27 (br. s., 1H), 10.21 (s, 1H). MS (M+H, ES+) 727.

Example 42

3-[3-(2-{[4-(1,4'-bipiperidin-1'-yl)-2-(2-methylpropyl)phenyl]amino}-4-pyrimidinyl)imidazo[1,2-a]pyridin-2-yl]-N-(2,6-difluorophenyl)benzamide

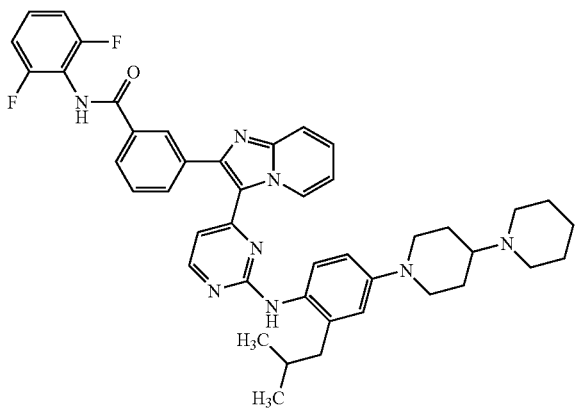

The title compound (0.092 g, 0.12 mmol, 50% in the final step) was prepared in an analogous manner to that described for Example 41 with the following notable exception: 3-bromo-2-methyl-1-propene was used instead of allyl bromide in the procedure outlined in step B. $^1$H NMR (400 MHz, DMSO-d$_6$) δ ppm 0.75 (2 s., 6H), 0.77-0.84 (m, 1H), 1.29-1.38 (m, 2H), 1.41-1.48 (m, 4H), 1.49-1.54 (m, 1H), 1.71-1.82 (m, 3H), 2.31 (t, J=12.4 Hz, 1H), 2.37-2.43 (m, 6H), 2.54-2.65 (m, 2H), 3.69 (d, J=11.9 Hz, 2H), 6.38 (d, J=5.3 Hz, 1H), 6.76 (s, 3H), 7.12 (d, J=9.5 Hz, 1H), 7.17 (t, J=8.1 Hz, 2H), 7.33-7.44 (m, 2H), 7.59 (t, J=7.8 Hz, 1H), 7.67 (d, J=9.0 Hz, 1H), 7.78 (d, J=7.7 Hz, 1H), 8.03 (d, J=7.9 Hz, 1H), 8.12 (d, J=5.3 Hz, 1H), 8.28 (s, 1H), 8.75 (s, 1H), 9.27 (br. s., 1H), 10.21 (s, 1H). MS (M+H, ES+) 742.

Example 43

3-[3-(2-{[4-(1,4'-bipiperidin-1'-yl)-2-(methyloxy)phenyl]amino}-4-pyrimidinyl)-8-methylimidazo[1,2-a]pyridin-2-yl]-N-(2,6-difluorophenyl)benzamide

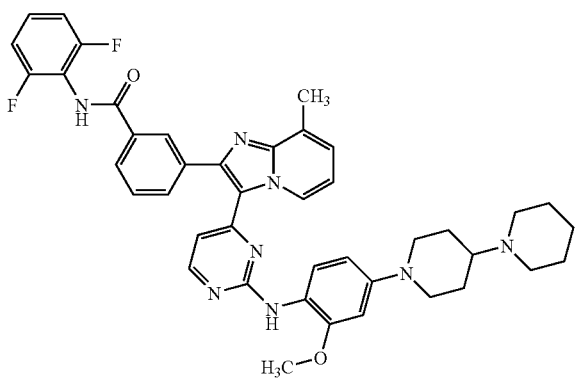

The title compound (0.11 g, 0.14 mmol, 61% in final step) was prepared in an analogous manner to that described for Example 9 with the following notable exceptions:

a) 3-methyl-2-pyridinamine was used instead of 2-aminopyridine in the step outlined in Intermediate Example 3, step B.
b) 4-(1,4'-bipiperidin-1'-yl)-2-(methyloxy)aniline (Example 22, step C) was used instead of 3-{[2-(dimethylamino)ethyl]oxy}aniline dihydrochloride in Example 9, step A;
c) 2,6-difluoroaniline was used instead of 5-chloro-2-fluoroaniline in Example 9, step B.

¹H NMR (400 MHz, DMSO-d₆) δ 10.23 (s, 1H), 9.29-9.23 (m, 1H), 8.42 (s, 1H), 8.29 (s, 1H), 8.18 (d, J=5.5 Hz, 1H), 8.07-8.04 (m, 1H), 7.82-7.78 (m, 1H), 7.61 (at, J=7.7 Hz, 1H), 7.45-7.34 (m, 2H), 7.29-7.26 (m, 1H), 7.24-7.17 (m, 2H), 6.92-6.85 (m, 1H), 6.65 (d, J=2.6 Hz, 1H), 6.46 (dd, J=8.6, 2.4 Hz, 1H), 6.42 (d, J=5.1 Hz, 1H), 3.78 (s, 3H), 3.76-3.69 (m, 2H), 2.68-2.59 (m, 2H), 2.55 (s, 3H), 2.46-2.42 (m, 3H), 2.37-2.27 (m, 2H), 1.81-1.74 (m, 2H), 1.59-1.34 (m, 8H). MS (ES+, m/z) 729 (M+1).

Example 44

3-[3-(2-{[4-(1,4'-bipiperidin-1'-yl)-2-(methyloxy)phenyl]amino}-4-pyrimidinyl)imidazo[1,2-a]pyridin-2-yl]-N-(2-chloro-4-fluorophenyl)benzamide

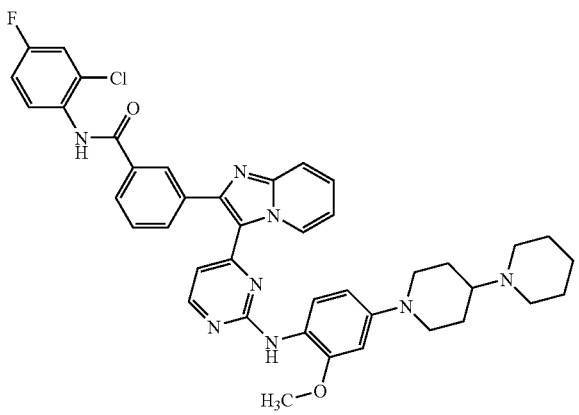

The title compound (0.082 g, 0.11 mmol, 82% in final step) was prepared in an analogous manner to that described for Example 9 with the following notable exceptions:
a) 4-(1,4'-bipiperidin-1'-yl)-2-(methyloxy)aniline (Example 22, step C) was used instead of 3-{[2-(dimethylamino)ethyl]oxy}aniline dihydrochloride in Example 9, step A;
b) 2-chloro-4-fluoroaniline was used instead of 5-chloro-2-fluoroaniline in Example 9, step B.

¹H NMR (400 MHz, DMSO-d₆) δ 10.18 (s, 1H), 9.43-9.35 (m, 1H), 8.44 (s, 1H), 8.31-8.29 (m, 1H), 8.19 (d, J=5.1 Hz, 1H), 8.05-8.00 (m, 1H), 7.84-7.79 (m, 1H), 7.75-7.70 (m, 1H), 7.63-7.51 (m, 3H), 7.49-7.43 (m, 1H), 7.42-7.33 (m, 1H), 7.30-7.23 (m, 1H), 7.01-6.95 (m, 1H), 6.66 (d, J=2.9 Hz, 1H), 6.51-6.43 (m, 2H), 3.79 (s, 3H), 3.76-3.69 (m, 2H), 2.68-2.59 (m, 2H), 2.47-2.40 (m, 3H), 2.38-2.28 (m, 2H), 1.82-1.72 (m, 2H), 1.61-1.42 (m, 5H), 1.41-1.32 (m, 2H). MS (APCI⁺, m/z) 731 (M+1).

Example 45

3-[3-(2-{[4-(1,4'-bipiperidin-1'-yl)-2-(methyloxy)phenyl]amino}-4-pyrimidinyl)imidazo[1,2-a]pyridin-2-yl]-N-(4-chloro-2-fluorophenyl)benzamide

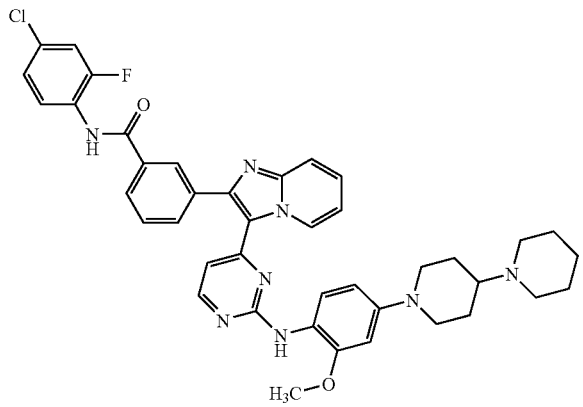

The title compound (0.081 g, 0.11 mmol, 34% in final step) was prepared in an analogous manner to that described for Example 9 with the following notable exceptions:
(a) 4-(1,4'-bipiperidin-1'-yl)-2-(methyloxy)aniline (Example 22, step C) was used instead of 3-{[2-(dimethylamino)ethyl]oxy}aniline dihydrochloride in Example 9, step A;
(b) 4-chloro-2-fluoroaniline was used instead of 5-chloro-2-fluoroaniline in Example 9, step B.

¹H NMR (400 MHz, DMSO-d₆) δ 10.29 (s, 1H), 9.43-9.34 (m, 1H), 8.45 (s, 1H), 8.30-8.27 (m, 1H), 8.21-8.17 (m, 1H), 8.05-8.00 (m, 1H), 7.81-7.77 (m, 1H), 7.74-7.70 (m, 1H), 7.68-7.41 (m, 4H), 7.40-7.28 (m, 2H), 7.01-6.94 (m, 1H), 6.65 (d, J=2.6 Hz, 1H), 6.48-6.43 (m, 2H), 3.78 (s, 3H), 3.76-3.70 (m, 2H), 2.67-2.59 (m, 2H), 2.46-2.41 (m, 3H), 2.37-2.26 (m, 2H), 1.84-1.74 (m, 2H), 1.60-1.42 (m, 5H), 1.41-1.34 (m, 2H). MS (ES+, m/z) 731 (M+1).

Example 46

N-(2,6-difluorophenyl)-3-[3-(2-{[4-(4-methyl-1,4'-bipiperidin-1'-yl)-2-(methyloxy)phenyl]amino}-4-pyrimidinyl)imidazo[1,2-a]pyridin-2-yl]benzamide

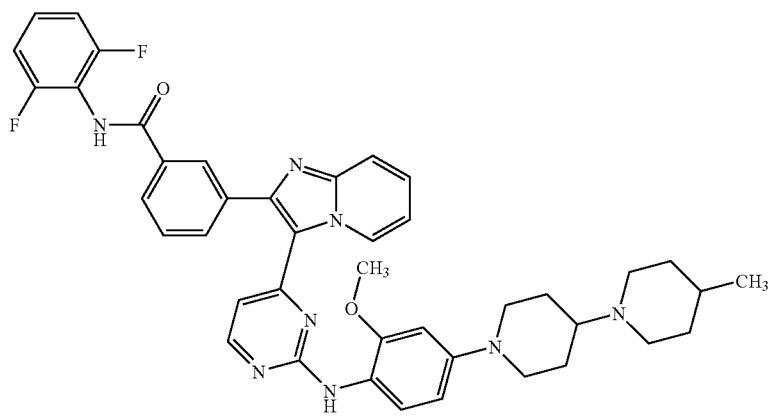

Step A: 1,1-dimethylethyl 4-methyl-1,4'-bipiperidine-1'-carboxylate

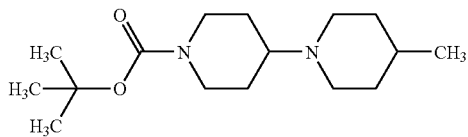

To a stirred solution, 1 h, at 0° C. of 4-methylpiperidine (15.0 g, 151 mmol), 1-boc-4-piperidone (30.1 g, 151 mmol) and HOAc (18.2 g, 303 mmol) in THF (100 mL) was added sodium triacetoxyborohydride (64.2 g, 303 mmol) in 3 portions. The mixture was stirred at rt for 18 h. The reaction was neutralized with saturated $K_2CO_3$ and the pH was adjusted to 8 with saturated $Na_2CO_3$. The mixture was diluted with DCM and separated. The organic layer was washed with $H_2O$ and concentrated to provide the title compound of step A (33.0 g, 117 mmol, 77%). $^1$H NMR (400 MHz, $CDCl_3$) δ ppm 0.71-0.90 (m, 3H), 1.11-1.20 (m, 2H), 1.31-1.50 (m, 9H), 1.50-1.65 (m, 1H), 1.70-1.90 (m, 4H), 2.01-2.30 (m, 2H), 2.71-3.10 (m, 4H), 3.60-3.91 (m, 5H).

Step B: 4-methyl-1,4'-bipiperidine dihydrochloride

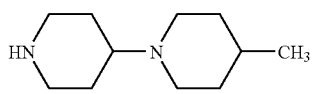

1,1-Dimethylethyl 4-methyl-1,4'-bipiperidine-1'-carboxylate (33.0 g, 117 mmol) in HCl (60.0 mL, 4M in MeOH, 240 mmol) was refluxed at 60° C. for 1 h. The reaction was concentrated and the residue was taken up in MeOH (100 mL), filtered and concentrated to provide the title compound of step B (10.8 g, 42.5 mmol, 36%). $^1$H NMR (300 MHz, $D_2O$) δ ppm 0.85 (d, J=6.22 Hz, 3H), 1.22-1.41 (m, 2H), 1.51-1.70 (m, 1H), 1.80-1.91 (m, 4H), 2.21-2.31 (m, 2H), 2.91-3.11 (m, 4H), 3.40-3.61 (m, 5H).

Step C: 4-methyl-1'-[3-(methyloxy)-4-nitrophenyl]-1,4'-bipiperidine

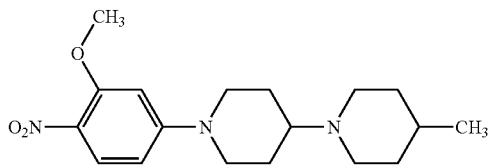

The title compound of step C (6.02 g, 18.1 mmol, 77%) was prepared in an analogous manner to that of Example 22, step B, with the following notable exceptions:
a) 4-methyl-1,4'-bipiperidine was used instead of 1,4'-bipiperidine;
b) the reaction was run at 40° C. instead of rt.
$^1$H NMR (300 MHz, $CDCl_3$) δ ppm 0.91 (d, J=9.3 Hz, 3H), 1.11-1.40 (m, 3H), 1.51-1.72 (m, 4H), 1.91-2.01 (m, 2H), 2.11-2.20 (m, 2H), 2.41-2.50 (m, 1H), 2.81-3.02 (m, 4H), 3.81-4.02 (m, 5H), 6.26 (d, J=2.4 Hz, 1H), 6.40 (dd, J=2.4 Hz, J=9.3 Hz, 1H), 8.0 (d, J=9.3 Hz, 1H).

Step D: 4-(4-methyl-1,4'-bipiperidin-1'-yl)-2-(methyloxy)aniline

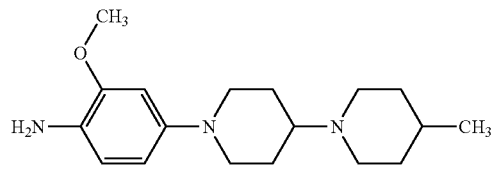

The title compound of step D (1.55 g, 5.1 mmol, 28%) was prepared from 4-methyl-1'-[3-(methyloxy)-4-nitrophenyl]-1,4'-bipiperidine in an analogous manner to that described for Example 32, step B. MS (M+H) 304.

Step E: N-(2,6-difluorophenyl)-3-[3-(2-{[4-(4-methyl-1,4'-bipiperidin-1'-yl)-2-(methyloxy)-phenyl]amino}-4-pyrimidinyl)imidazo[1,2-a]pyridin-2-yl]benzamide The title compound (0.129 g, 0.18 mmol, 70%) was prepared in an analogous manner to that described for Example 36, step E with the following notable exception: 4-(4-methyl-1,4'-bipiperidin-1'-yl)-2-(methyloxy)aniline was used instead of 2-(methyloxy)-4-[4-(1-piperidinylmethyl)-1-piperidinyl]-aniline. $^1$H NMR (400 MHz, DMSO-$d_6$) δ ppm 0.83 (d, J=6.4 Hz, 3H), 1.03 (m, 2H), 1.25 (br. s., 1H), 1.45-1.57 (m, 4H), 1.75 (d, J=11.9 Hz, 2H), 2.06 (t, J=11.9 Hz, 2H), 2.25-2.37 (m, 1H), 2.61 (t, J=11.8 Hz, 2H), 2.79 (d, J=9.9 Hz, 2H), 3.70 (d, J=12.3 Hz, 2H), 3.75 (s, 3H), 6.40-6.47 (m, 2H), 6.62 (s, 1H), 6.94 (t, J=6.8 Hz, 1H), 7.17 (t, J=8.1 Hz, 2H), 7.33-7.45 (m, 3H), 7.57 (t, J=7.8 Hz, 1H), 7.69 (d, J=9.2 Hz, 1H), 7.78 (d, J=8.2 Hz, 1H), 8.02 (d, J=7.7 Hz, 1H), 8.17 (d, J=4.9 Hz, 1H), 8.30 (s, 1H), 8.41 (s, 1H), 9.37 (br. s., 1H), 10.20 (s, 1H). MS (M+H, $APCI^+$) 729.

Example 47

N-(2,6-difluorophenyl)-3-[3-(2-{[4-{4-[(2R,6S)-2,6-dimethyl-4-morpholinyl]-1-piperidinyl}-2-(methyloxy)phenyl]amino}-4-pyrimidin)imidazo[1,2-a]pyridin-2-yl]benzamide

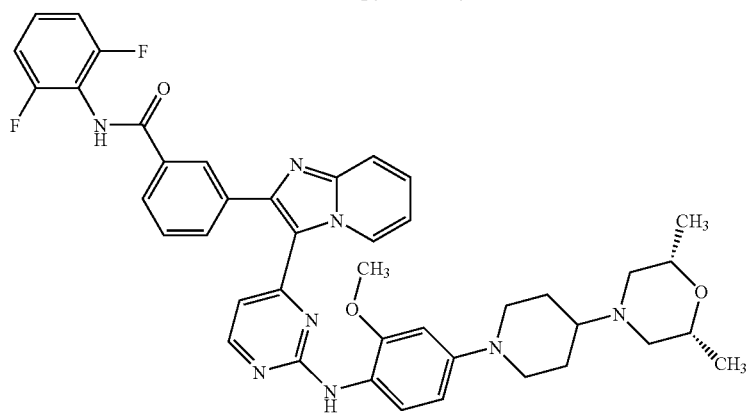

The title compound (0.11 g, 0.15 mmol, 59% in final step) was prepared in an analogous manner to that described for Example 46 with the following notable exception: cis-2,6-dimethylmorpholine was used instead of 4-methylpiperidine in the procedure outlined in step A. $^1$H NMR (400 MHz, DMSO-$d_6$) δ ppm 0.97-1.03 (2 s., 6H), 1.41-1.52 (m, 2H), 1.71-1.83 (m, 4H), 2.18-2.29 (m, 1H), 2.63 (t, J=11.5 Hz, 2H), 2.72 (d, J=11.0 Hz, 2H), 3.42-3.52 (m, 2H), 3.69 (d, J=11.7 Hz, 2H), 3.76 (s, 3H), 6.41-6.46 (m, 2H), 6.63 (d, J=2.0 Hz, 1H), 6.94 (t, J=6.8 Hz, 1H), 7.17 (t, J=8.2 Hz, 2H), 7.33-7.45 (m, 3H), 7.57 (t, J=7.8 Hz, 1H), 7.69 (d, J=8.8 Hz, 1H), 7.79 (s, 1H), 8.02 (d, J=8.2 Hz, 1H), 8.17 (d, J=5.1 Hz, 1H), 8.29 (s, 1H), 8.42 (s, 1H), 9.36 (br. s., 1H), 10.20 (s, 1H). MS (M+H, APCI$^+$) 745.

Example 48

N-(2,6-difluorophenyl)-3-[3-(2-{[4-[4-(4-methyl-hexahydro-1H-1,4-diazepin-1-yl)-1-piperidinyl]-2-(methyloxy)phenyl]amino}-4-pyrimidinyl)imidazo[1,2-a]pyridin-2-yl]benzamide

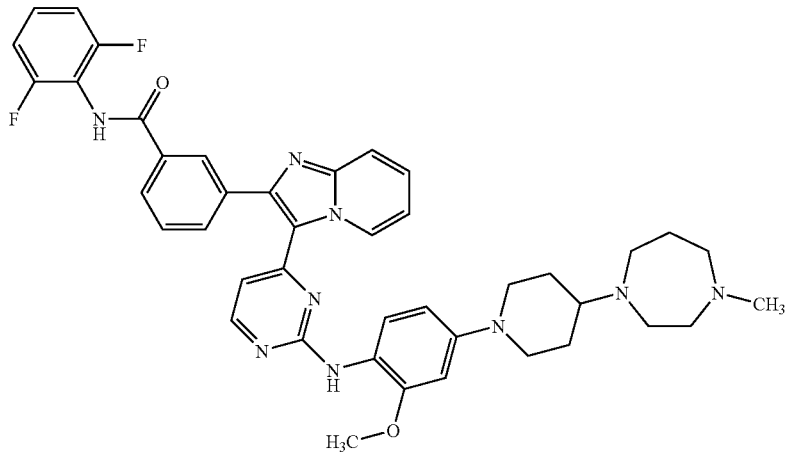

The title compound (0.088 g, 0.12 mmol, 47% in final step) was prepared in an analogous manner to that described for Example 46 with the following notable exception: 1-methyl-hexahydro-1H-1,4-diazepine was used instead of 4-methylpiperidine in the procedure outlined in step A. $^1$H NMR (400 MHz, DMSO-$d_6$) δ ppm 1.44-1.55 (m, 2H), 1.61-1.68 (m, 2H), 1.72 (d, J=12.1 Hz, 2H), 2.19 (s, 3H), 2.40-2.43 (m, 3H), 2.48-2.55 (m, 3H), 2.57-2.66 (m, 4H), 2.69 (t, J=6.1 Hz, 2H), 3.70 (d, J=14.5 Hz, 2H), 3.76 (s, 3H), 6.43 (t, J=5.8 Hz, 2H), 6.63 (s, 1H), 6.94 (t, J=6.4 Hz, 1H), 7.17 (t, J=8.1 Hz, 2H), 7.32-7.37 (m, 1H), 7.40-7.45 (m, 1H), 7.57 (t, J=7.8 Hz, 1H), 7.69 (d, J=8.8 Hz, 1H), 7.78 (d, J=8.1 Hz, 1H), 8.02 (d, J=7.7 Hz, 1H), 8.17 (d, J=5.3 Hz, 1H), 8.30 (s, 1H), 8.42 (s, 1H), 9.37 (br. s., 1H), 10.20 (s, 1H). MS (M+H, ES+) 744.

Example 49

3-[3-(2-{[4-(4-{bis[2-(methyloxy)ethyl]amino}-1-piperidinyl)-2-(methyloxy)phenyl]amino}-4-pyrimidinyl)imidazo[1,2-a]pyridin-2-yl]-N-(2,6-difluorophenyl)benzamide

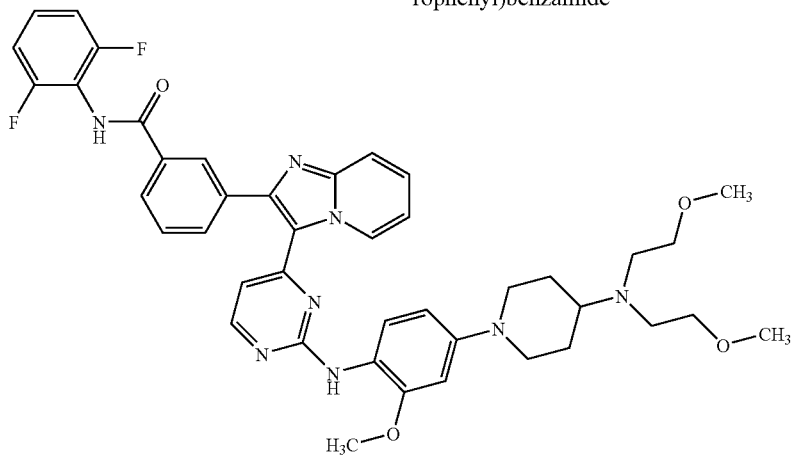

The title compound (0.11 g, 0.15 mmol, 59% in final step) was prepared in an analogous manner to that described for Example 46 with the following notable exception: bis[2-(methyloxy)ethyl]amine was used instead of 4-methylpiperidine in the procedure outlined in step A. ¹H NMR (400 MHz, DMSO-d₆) δ ppm 1.45-1.56 (m, 2H), 1.73 (d, J=13.6 Hz, 2H), 2.57-2.68 (m, 5H), 3.22 (s, 6H), 3.28-3.34 (m, 6H), 3.75 (d, J=11.4 Hz, 2H), 3.79 (s, 3H), 6.43-6.50 (m, 2H), 6.66 (d, J=2.2 Hz, 1H), 6.97 (t, J=7.2 Hz, 1H), 7.20 (t, J=8.1 Hz, 2H), 7.35-7.42 (m, 2H), 7.44-7.48 (m, 1H), 7.61 (t, J=7.9 Hz, 1H), 7.72 (d, J=8.8 Hz, 1H), 7.81 (d, J=7.7 Hz, 1H), 8.05 (d, J=8.4 Hz, 1H), 8.20 (d, J=5.1 Hz, 1H), 8.33 (s, 1H), 8.46 (s, 1H), 9.40 (br. s., 1H), 10.24 (s, 1H). MS (M+H, ES+) 764.

Example 50

N-(2,6-difluorophenyl)-3-[3-(2-{[4-[4-(hexahydro-1H-azepin-1-yl)-1-piperidinyl]-2-(methyloxy)phenyl]amino}-4-pyrimidinyl)imidazo[1,2-a]pyridin-2-yl]benzamide

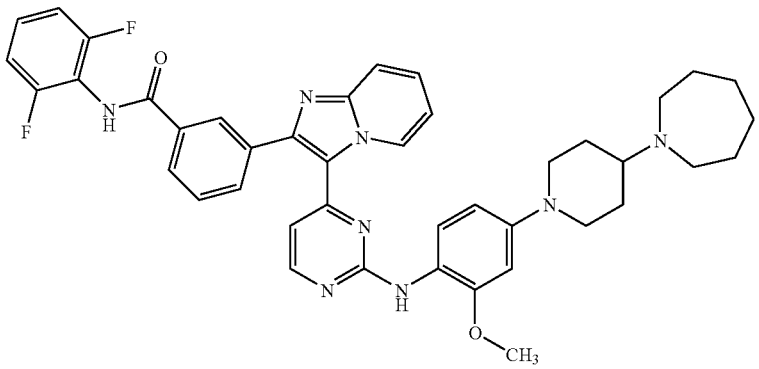

The title compound (0.203 g, 0.278 mmol, 64% in the final step) was prepared in an analogous manner to that described for Example 46 with the following notable exceptions:
a) hexahydro-1H-azepine was used instead of 4-methylpiperidine in the procedure outlined in Example 46, step A;
b) concentrated HCl and isopropanol were used instead of 4N HCl in dioxane and trifluoroethanol in Example 46, step E.
¹H NMR (400 MHz, DMSO-d₆) δ ppm 10.21 (s, 1H), 9.17-9.49 (m, 1H), 8.43 (s, 1H), 8.30 (s, 1H), 8.17 (d, J=5.1 Hz, 1H), 8.02 (d, J=7.7 Hz, 1H), 7.78 (d, J=7.7 Hz, 1H), 7.70 (d, J=9.0 Hz, 1H), 7.58 (t, J=7.8 Hz, 1H), 7.28-7.51 (m, 3H), 7.17 (t, J=8.1 Hz, 2H), 6.95 (t, J=6.7 Hz, 1H), 6.64 (br. s., 1H), 6.36-6.53 (m, 2H), 3.58-3.90 (m, 7H), 2.51-2.75 (m, 6H), 1.64-1.82 (m, 1H), 1.50 (br. s., 10H). MS (M+H) 729.

Example 51

N-(2,6-difluorophenyl)-3-[3-(2-{[4-(4-fluoro-1,4'-bipiperidin-1'-yl)-2-(methyloxy)phenyl]amino}-4-pyrimidinyl)imidazo[1,2-a]pyridin-2-yl]benzamide

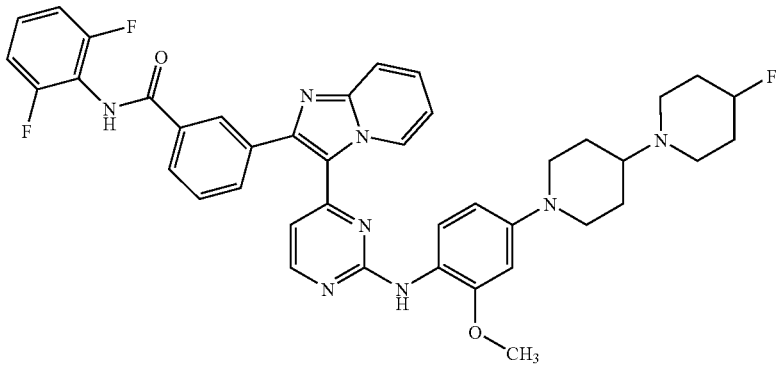

The title compound (0.200 g, 0.273 mmol, 63% in final step) was prepared in an analogous manner to that described for Example 46 with the following notable exceptions:
a) 4-fluoropiperidine was used instead of 4-methylpiperidine in the procedure outlined in Example 46, step A;
b) concentrated HCl and iPrOH were used instead of 4N HCl in dioxane and trifluoroethanol in Example 46, step E.

$^1$H NMR (400 MHz, DMSO-d$_6$) δ ppm 10.23 (s, 1H), 9.30-9.49 (m, 1H), 8.45 (s, 1H), 8.32 (s, 1H), 8.20 (d, J=5.3 Hz, 1H), 8.05 (d, J=7.9 Hz, 1H), 7.81 (d, J=7.7 Hz, 1H), 7.72 (d, J=9.0 Hz, 1H), 7.60 (t, J=7.8 Hz, 1H), 7.29-7.52 (m, 3H), 7.20 (t, J=8.1 Hz, 2H), 6.88-7.05 (m, 1H), 6.66 (d, J=2.6 Hz, 1H), 6.36-6.57 (m, 2H), 4.49-4.77 (m, 1H), 3.79 (s, 3H), 3.69-3.77 (m, 2H), 3.24-3.37 (m, 2H), 2.58-2.73 (m, 4H), 2.33-2.45 (m, 3H), 1.73-1.88 (m, 2H), 1.59-1.73 (m, 2H), 1.46-1.61 (m, 2H). MS (M+H) 733.

Example 52

N-(2,6-difluorophenyl)-3-{3-[2-({2-(methyloxy)-4-[4-(trifluoromethyl)-1,4'-bipiperidin-1'-yl]phenyl}amino)-4-pyrimidinyl]imidazo[1,2-a]pyridin-2-yl}benzamide

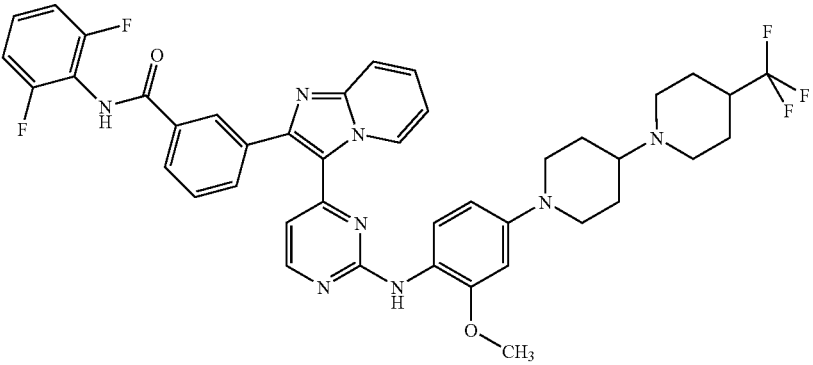

The title compound (0.240 g, 0.307 mmol, 71%) was prepared in an analogous manner to that described for Example 46 with the following notable exceptions:
a) 4-(trifluoromethyl)piperidine was used instead of 4-methylpiperidine in the procedure outlined in Example 46, step A;
b) concentrated HCl and iPrOH were used instead of 4N HCl in dioxane and trifluoroethanol in Example 46, step E.

$^1$H NMR (400 MHz, DMSO-d$_6$) δ ppm 10.21 (s, 1H), 9.37 (br. s., 1H), 8.42 (s, 1H), 8.30 (s, 1H), 8.17 (d, J=5.1 Hz, 1H), 8.02 (d, J=7.7 Hz, 1H), 7.78 (d, J=7.7 Hz, 1H), 7.69 (d, J=9.0 Hz, 1H), 7.57 (t, J=7.8 Hz, 1H), 7.29-7.49 (m, 3H), 7.17 (t, J=8.1 Hz, 2H), 6.94 (t, J=6.6 Hz, 1H), 6.63 (d, J=1.3 Hz, 1H), 6.31-6.51 (m, 2H), 3.76 (s, 3H), 3.71 (d, J=12.1 Hz, 2H), 2.91 (d, J=10.8 Hz, 2H), 2.62 (t, J=11.6 Hz, 2H), 2.31-2.42 (m, 1H), 2.02-2.25 (m, 3H), 1.74 (d, J=11.2 Hz, 4H), 1.22-1.63 (m, 4H). MS (M+H) 783.

Example 53

3-[3-(2-{[4-(1,4'-bipiperidin-1'-yl)-2-methylphenyl]amino}-4-pyrimidinyl)imidazo[1,2-a]pyridin-2-yl]-N-(2,6-difluorophenyl)benzamide

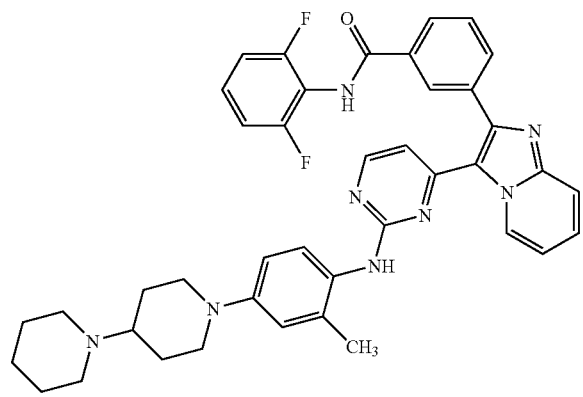

Step A: 4-(1,4'-bipiperidin-1'-yl)-2-methylaniline

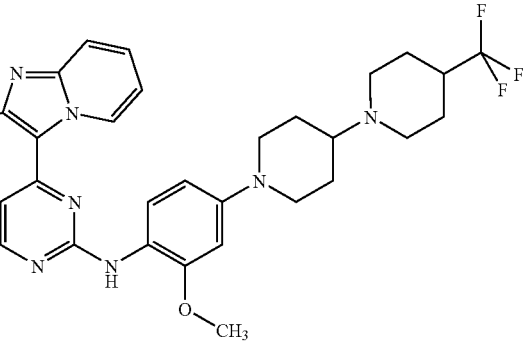

The title compound of step A (2.5 g, 9.1 mmol, 59%) was prepared in a manner analogous to that described for Example 32, steps A-B, with the following notable exception: 5-fluoro-2-nitrotoluene was used instead of 5-fluoro-2-nitrophenyl 2-methylpropyl ether in Example 32, step A. MS (M+H) 274.

Step B: 3-[3-(2-{[4-(1,4'-bipiperidin-1'-yl)-2-methylphenyl]amino}-4-pyrimidinyl)-imidazo[1,2-a]pyridin-2-yl]-N-(2,6-difluorophenyl)benzamide To 3-[3-(2-chloro-4-pyrimidinyl)imidazo[1,2-a]pyridin-2-yl]-N-(2,6-difluorophenyl)-benzamide (Intermediate Example 1) (120 mg, 0.25 mmol) and 4-(1,4'-bipiperidin-1'-yl)-2-(methyl)aniline (68 mg, 0.25 mmol) in iPrOH (2 mL) in a microwave vial was added p-toluenesulfonic acid monohydrate (110 mg, 0.60 mmol). The reaction was heated in a microwave at 175° C. for 800 seconds. After cooling to rt, the solvent was removed on a rotovap and the residue taken up in DCM. Silica gel was added and the solvent removed on the rotovap. The preabsorbed solids were purified by flash chromatography. The desired fractions were combined and the solvent removed on the rotovap to give product contaminated with an impurity. The material was dissolved in DCM, and ether was added until the solution just turned cloudy. After two days, the solids were collected by vacuum filtration and washed with diethyl ether. The yellow crystals were separated from the beige powder using tweezers. The desired product was obtained as yellow crystals (23 mg, 0.033 mmol, 13% yield). $^1$H NMR (400 MHz, DMSO-d$_6$) δ 10.24 (s, 1H), 9.35 (br s, 1H), 8.81 (s, 1H), 8.32 (s, 1H), 8.16 (d, J=5.4 Hz, 1H), 8.06 (d, J=7.9 Hz, 1H), 7.82 (d, J=7.7 Hz, 1H), 7.71 (d, J=9.0 Hz, 1H), 7.62 (dd, J=7.9, 7.7 Hz, 1H), 7.48-7.34 (m, 2H), 7.25-7.14 (m, 3H), 6.85 (br s, 1H), 6.85 (s, 1H), 6.79 (dd, J=8.6, 2.6 Hz, 1H), 6.43 (d, J=5.3 Hz, 1H), 3.72 (d, J=12.5 Hz, 2H), 2.62 (dd, J=12.1, 10.6 Hz, 2H), 2.52-2.27 (m, 5H), 2.17 (s, 3H), 1.78 (d, J=11.8 Hz, 2H), 1.60-1.34 (m, 8H). MS (ESI) m/z=699 [M+1].

Example 54

3-[3-(2-{[4-(1,4'-bipiperidin-1'-yl)-3-methyl-2-(methyloxy)phenyl]amino}-4-pyrimidinyl)imidazo[1,2-a]pyridin-2-yl]-N-(2,6-difluorophenyl)benzamide

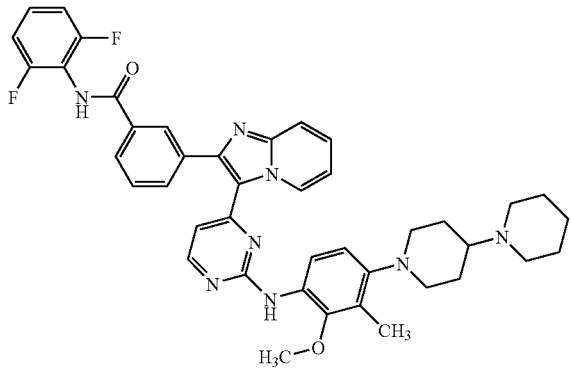

Step A: 1'-(3-chloro-2-methyl-4-nitrophenyl)-1,4'-bipiperidine

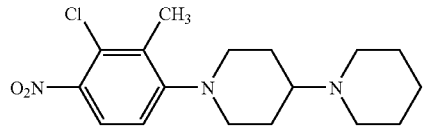

The title compound of step A (0.86 g, 5.50 mmol, 91%) was prepared in an analogous manner to that described for Example 22, step B with the following notable exceptions: a) 2-chloro-4-fluoro-3-methyl-1-nitrobenzene [Robson, M. J.; Brit. UK Pat. Appl. (1983), GB 2120655 A 19831207] was used instead of 5-fluoro-2-nitrophenyl methyl ether; b) The reaction was run between 40° C. and 50° C. rather than at rt.

$^1$H NMR (400 MHz, CDCl$_3$) δ ppm 1.41-1.51 (m, 2H), 1.55-1.65 (m, 4H), 1.71-1.80 (m, 2H), 1.91-2.01 (m, 2H), 2.31-2.40 (m, 4H), 2.51-2.60 (m, 4H), 2.65-2.75 (m, 2H), 3.21-3.30 (m, 2H), 6.9 (d, J=8.4 Hz, 1H), 7.7 (d, J=8.4 Hz, 1H).

Step B: 1'-[2-methyl-3-(methyloxy)-4-nitrophenyl]-1,4'-bipiperidine

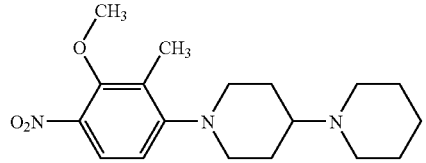

To 1'-(3-chloro-2-methyl-4-nitrophenyl)-1,4'-bipiperidine (0.50 g, 1.5 mmol) in DMF (15 mL) was added sodium methoxide (0.97 g, 1.8 mmol) at 0° C., and the mixture was stirred at rt overnight. The mixture was poured into H$_2$O, extracted with EtOAc, washed with H$_2$O, dried and concentrated to provide the title compound of step B (0.53 g, 1.6 mmol, 100% crude). $^1$H NMR (400 MHz, CDCl$_3$) δ ppm 1.41-1.50 (m, 2H), 1.61-1.71 (m, 4H), 1.70-1.81 (m, 2H), 1.91-2.01 (m, 2H), 2.25 (s, 3H), 2.35-2.45 (m, 1H), 2.51-2.60 (m, 4H), 2.65-2.75 (m, 2H), 3.21-3.30 (m, 2H), 3.9 (s, 3H), 6.75 (d, J=9.2 Hz, 1H), 7.75 (d, J=9.2 Hz, 1H).

Step C: 4-(1,4'-bipiperidin-1'-yl)-3-methyl-2-(methyloxy)aniline

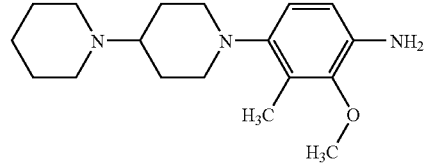

The title compound of step C (1.87 g, 6.16 mmol, 64%) was prepared from 1'-[2-methyl-3-(methyloxy)-4-nitrophenyl]-1, 4'-bipiperidine in a manner analogous to that described for Example 32, step B. MS (M+H) 304.

Step D: 3-[3-(2-{[4-(1,4'-bipiperidin-1'-yl)-3-methyl-2-(methyloxy)phenyl]amino}-4-pyrimidinyl)imidazo[1,2-a]pyridin-2-yl]-N-(2,6-difluorophenyl)benzamide The title compound (0.11 g, 0.15 mmol, 58%) was prepared in an analogous manner to that described for Example 36, step E with the following notable exception: 4-(1,4'-bipiperidin-1'-yl)-3-methyl-2-(methyloxy)-aniline was used instead of 2-(methyloxy)-4-[4-(1-piperidinylmethyl)-1-piperidinyl]-aniline. $^1$H NMR (400 MHz, DMSO-d$_6$) δ ppm 1.31-1.41 (m, 2H), 1.41-1.51 (m, 4H), 1.51-1.62 (m, 2H), 1.75 (d, J=10.4 Hz, 2H), 2.18 (s, 3H), 2.22-2.33 (m, 1H), 2.42-2.48 (m, 3H), 2.53 (t, J=11.6 Hz, 3H), 3.03 (d, J=11.4 Hz, 2H), 3.64 (s, 3H), 6.49 (d, J=5.5 Hz, 1H), 6.75 (d, J=8.8 Hz, 1H), 6.91 (t, J=7.0 Hz, 1H), 7.17 (t, J=8.1 Hz, 2H), 7.33-7.40 (m, 2H), 7.44 (d, J=7.9 Hz, 1H), 7.57 (t, J=7.8 Hz, 1H), 7.69 (d, J=9.0 Hz, 1H), 7.78 (d, J=6.8 Hz, 1H), 8.02 (d, J=7.5 Hz, 1H), 8.22 (d, J=5.3 Hz, 1H), 8.30 (s, 1H), 8.69 (s, 1H), 9.33-9.44 (m, 1H), 10.20 (s, 1H). MS (M+H, ES+) 729.

Example 55

5-[3-(2-{[4-(1,4'-bipiperidin-1'-yl)-3-methyl-2-(methyloxy)phenyl]amino}-4-pyrimidinyl)imidazo[1,2-a]pyridin-2-yl]-N-(2,6-difluorophenyl)-2-(methyloxy)benzamide

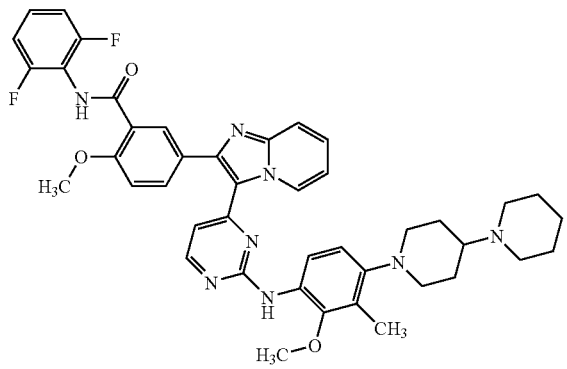

The title compound (0.106 g, 0.15 mmol, 58%) was prepared in an analogous manner to that described for Example 36, step E, with the following notable exceptions:

a) 5-[3-(2-chloro-4-pyrimidinyl)imidazo[1,2-a]pyridin-2-yl]-N-(2,6-difluorophenyl)-2-(methyloxy)benzamide (Intermediate Example 2) was used instead of 3-[3-(2-chloro-4-pyrimidinyl)imidazo[1,2-a]pyridin-2-yl]-N-(2,6-difluorophenyl)-benzamide;
b) 4-(1,4'-bipiperidin-1'-yl)-3-methyl-2-(methyloxy)-aniline was used instead of 2-(methyloxy)-4-[4-(1-piperidinylmethyl)-1-piperidinyl]-aniline.

$^1$H NMR (400 MHz, DMSO-$d_6$) δ ppm 1.30-1.40 (m, 2H), 1.41-1.50 (m, 4H), 1.51-1.62 (m, 2H), 1.76 (d, J=14.5 Hz, 2H), 2.17 (s, 3H), 2.24-2.31 (m, 1H), 2.38-2.50 (m, 3H), 2.54 (t, J=12.6 Hz, 3H), 3.03 (d, J=11.4 Hz, 2H), 3.64 (s, 3H), 3.95 (s, 3H), 6.56 (s, 1H), 6.76 (d, J=8.8 Hz, 1H), 6.88 (t, J=7.3 Hz, 1H), 7.15 (t, J=8.0 Hz, 2H), 7.25 (d, J=8.6 Hz, 1H), 7.32-7.43 (m, 3H), 7.66 (d, J=9.0 Hz, 1H), 7.74 (d, J=10.3 Hz, 1H), 8.07 (s, 1H), 8.22 (d, J=5.3 Hz, 1H), 8.67 (s, 1H), 9.32-9.41 (m, 1H), 9.75 (s, 1H). MS (M+H, ES+) 759.

Example 56

5-[3-(2-{[4-(1,4'-bipiperidin-1'-yl)-3-methyl-2-(methyloxy)phenyl]amino}-4-pyrimidinyl)imidazo[1,2-a]pyridin-2-yl]-N-(2,6-difluorophenyl)-2-(ethyloxy)benzamide

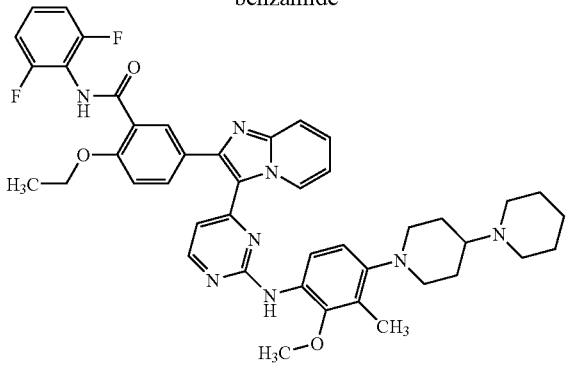

The title compound (0.041 g, 0.05 mmol, 21%) was prepared in an analogous manner to that described for Example 36, step E, with the following notable exceptions:
a) Intermediate Example 6 was used instead of 3-[3-(2-chloro-4-pyrimidinyl)imidazo[1,2-a]pyridin-2-yl]-N-(2,6-difluorophenyl)-benzamide;
b) 4-(1,4'-bipiperidin-1'-yl)-3-methyl-2-(methyloxy)-aniline was used instead of 2-(methyloxy)-4-[4-(1-piperidinylmethyl)-1-piperidinyl]-aniline.

$^1$H NMR (400 MHz, DMSO-$d_6$) δ ppm 1.38-1.48 (m, 7H), 1.51-1.63 (m, 4H), 1.70-1.82 (m, 2H), 2.19 (s, 3H), 2.24-2.36 (m, 2H), 2.50-2.60 (m, 3H), 3.00-3.10 (m, 2H), 3.65 (s, 3H), 4.24 (q, J=7.1 Hz, 2H), 6.57 (d, J=5.3 Hz, 1H), 6.76 (d, J=9.0 Hz, 1H), 6.89 (t, J=6.6 Hz, 1H), 7.17 (t, J=8.3 Hz, 2H), 7.24 (d, J=8.6 Hz, 1H), 7.31-7.40 (m, 2H), 7.42 (d, J=7.3 Hz, 2H), 7.65-7.75 (m, 2H), 8.02 (s, 1H), 8.23 (d, J=5.3 Hz, 1H), 8.68 (s, 1H), 9.36 (d, J=5.1 Hz, 1H), 9.72 (s, 1H). MS (M+H, ES+) 773.

Example 57

N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide

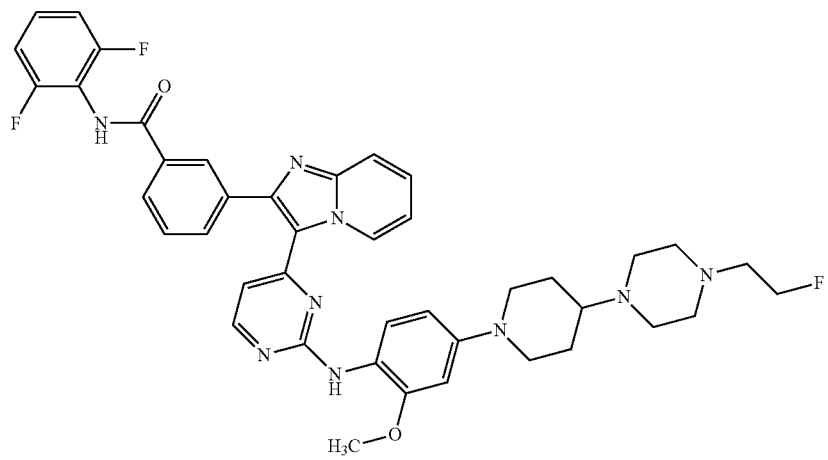

Route 1

Step A:
1-[3-(methyloxy)-4-nitrophenyl]-4-piperidinol

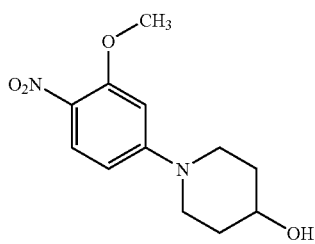

The title compound (11.0 g, 43.6 mmol, 99%) of step A was prepared in an analogous manner to that described for Example 22, step B, with the following notable exception: 4-piperidinol was used instead of 1,4'-bipiperidine. $^1$H NMR (400 MHz, d$_6$-DMSO) δ 7.84 (d, J=9.2 Hz, 1H), 6.54 (d, J=9.6 Hz, 1H), 6.46 (s, 1H), 4.73 (d, J=4.4 Hz, 1H), 3.86 (s, 3H), 3.80-3.69 (m, 3H), 3.18-3.12 (m, 2H), 1.79-1.76 (m, 2H), 1.42-1.34 (m, 2H).

Step B:
1-[3-(methyloxy)-4-nitrophenyl]-4-piperidinone

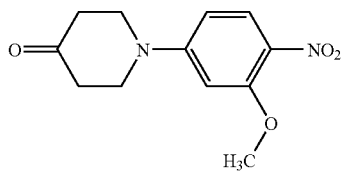

Oxalyl chloride (11.9 mL, 23.78 mmol) was dissolved in DCM (200 mL) and cooled to −78° C. DMSO (3.4 mL, 47.58 mmol) in DCM (15 mL) was added to the solution dropwise via an addition funnel. Upon completion of addition, the reaction was allowed to stir 10 min. 1-[3-(methyloxy)-4-nitrophenyl]-4-piperidinol (4.04 g, 15.86 mmol) in DMSO (6 mL) and DCM (15 mL) was added dropwise via addition funnel. Upon completion of addition, the reaction was allowed to stir 15 minutes. TEA (11.0 mL, 79.3 mmol) was then added dropwise via addition funnel. Upon completion of addition, the bath was removed and the reaction was allowed to warm to rt. The reaction was stirred until alcohol was consumed as indicated by TLC. The solvent was removed in vacuo and the residue was taken up in EtOAc. The suspension was washed twice with H$_2$O, followed by brine. The organic layer was dried with MgSO$_4$, filtered and concentrated to provide the title compound of step B (3.91 g, 15.59 mmol, 97%) as a bright yellow solid. $^1$H NMR (400 MHz, DMSO-d$_6$) δ ppm 2.47-2.51 (m, 4H), 3.82 (t, J=6.2 Hz, 4H), 3.91 (s, 3H), 6.52 (d, J=2.6 Hz, 1H), 6.61 (dd, J=9.5, 2.6 Hz, 1H), 7.91 (d, J=9.5 Hz, 1H).

Step C: 1-{1-[3-(methyloxy)-4-nitrophenyl]-4-piperidinyl}piperazine

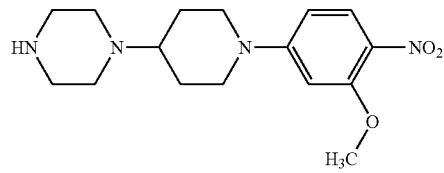

To a solution of 1-[4-amino-3-(methyloxy)phenyl]-4-piperidinone (combined batches) (17.35 g, 69.3 mmol) in toluene (600 mL) was added sequentially, TEA (25 mL, 179.4 mmol), 1-Boc-piperazine (25.36 g, 136.2 mmol), and HOAc (6.0 mL, 105.9 mmol). The solution was stirred at rt for 30 min. Sodium triacetoxyborohydride (12.2 g, 57.6 mmol) was added in one portion and stirred for 30 min. A second portion of sodium triacetoxyborohydride (12.2 g, 57.6 mmol) was added and stirring continued for 30 min. A third portion of sodium triacetoxyborohydride (12.2 g, 57.6 mmol) was added. The reaction was stirred (3 hours) until ketone was consumed as indicated by TLC. The reaction was quenched with a saturated solution of NaHCO$_3$ (600 mL) and stirred 2 days. The solution was separated and extracted with DCM (×3), dried with MgSO$_4$, filtered and concentrated. The resultant solid was dissolved in DCM (600 mL) and cooled to 0° C. TFA (110 mL) was added; the reaction was warmed to rt and stirred overnight. The reaction was cooled to 0° C. and quenched with 6N NaOH (320 mL) dropwise. The solution was separated and extracted with DCM (×3), dried with MgSO$_4$, filtered and concentrated. Purification by flash chromatography provided the title compound of step C (18.03 g, 56.10 mmol, 81%) as a yellow solid. $^1$H NMR (400 MHz, DMSO-d$_6$) δ ppm 1.41 (qd, J=12.0, 3.7 Hz, 2H), 1.77-1.84 (m, 2H), 2.38-2.47 (m, 5H), 2.67-2.73 (m, 4H), 2.88-2.98 (m, 2H), 3.32 (br. s., 1H), 3.88 (s, 3H), 4.03 (d, J=12.8 Hz, 2H), 6.48 (d, J=2.6 Hz, 1H), 6.56 (dd, J=9.5, 2.6 Hz, 1H), 7.85 (d, J=9.2 Hz, 1H).

Step D: 1-(2-fluoroethyl)-4-{1-[3-(methyloxy)-4-nitrophenyl]-4-piperidinyl}piperazine

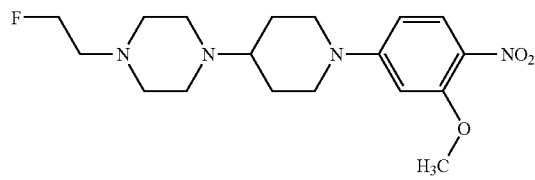

To a solution of 1-{1-[3-(methyloxy)-4-nitrophenyl]-4-piperidinyl}piperazine (18.03 g, 56.10 mmol and 2.23 g, 6.96 mmol from separate batches) in THF was added 1-iodo-2-fluoroethane (7.38 mL, 90.79 mmol). The reaction was stirred at 85° C. overnight. The solution was transferred to a sealed tube. Upon addition of 1-iodo-2-fluoroethane (7.38 mL, 90.79 mmol), the reaction was stirred at 85° C. for an additional 5 h. The solvent was removed in vacuo and the residue was taken up in H$_2$O and extracted with DCM (×3), dried with MgSO$_4$, filtered and concentrated. Purification by flash chromatography provided the title compound of step D (15.94 g, 43.50 mmol, 69%) as a yellow solid. $^1$H NMR (400 MHz, DMSO-d$_6$) δ ppm 1.38 (qd, J=11.9, 3.7 Hz, 2H), 1.79 (d, J=10.8 Hz, 2H), 2.32-2.42 (m, J=7.0, 3.7 Hz, 9H), 2.52 (dt, J$_{HF}$=28.6 Hz, J=4.9 Hz, 2H), 2.86-2.95 (m, 2H), 3.85 (s, 3H), 3.99 (d, J=13.4 Hz, 2H), 4.46 (dt, J$_{HF}$=47.8 Hz, J=4.9 Hz, 2H), 6.45 (d, J=2.4 Hz, 1H), 6.54 (dd, J=9.5, 2.6 Hz, 1H), 7.82 (d, J=9.3 Hz, 1H).

Step E: 4-{4-[4-(2-fluoroethyl)-1-piperazinyl]-1-piperidinyl}-2-(methyloxy)aniline

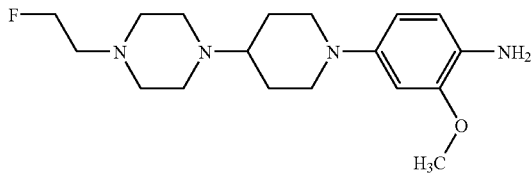

A solution of 1-(2-fluoroethyl)-4-{1-[3-(methyloxy)-4-nitrophenyl]-4-piperidinyl}piperazine (15.94 g, 43.50 mmol) in THF (200 mL) and MeOH (300 mL) was cooled to 0° C. Nickel(II) chloride hexahydrate (5.18 g, 21.80 mmol) was added in one portion. The solution was stirred for 30 min followed by portion-wise addition of NaBH$_4$ (3.29 g, 87.00 mmol). Prior to warming the reaction to rt additional nickel (II) chloride hexahydrate (5.18 g, 21.80 mmol) and NaBH$_4$ (3.29 g, 87.00 mmol) was added to the reaction. The solvent was removed in vacuo and the residue was taken up in DCM, filtered through Celite®, and washed with EtOAc. Purification by flash chromatography provided the title compound of step E (13.46 g, 40.10 mmol, 92%) as a white solid. $^1$H NMR (400 MHz, DMSO-d$_6$) δ ppm 1.46 (qd, J=11.9, 3.6 Hz, 2H), 1.76 (d, J=12.1 Hz, 2H), 2.12-2.20 (m, 1H), 2.35-2.45 (m, 10H), 2.53 (dt, J$_{HF}$=28.6 Hz, J=4.9 Hz, 2H), 3.37 (d, J=12.1 Hz, 2H), 3.68 (s, 3H), 4.14 (br. s., 2H), 4.47 (dt, J$_{HF}$=47.9 Hz, J=4.94 Hz, 2H), 6.24 (dd, J=8.2, 2.4 Hz, 1H), 6.43 (d, J=2.4 Hz, 1H), 6.45 (d, J=8.4 Hz, 1H).

Step F: N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide To 3-[3-(2-chloro-4-pyrimidinyl)imidazo[1,2-a]pyridin-2-yl]-N-(2,6-difluorophenyl)-benzamide (Intermediate Example 1) (13.5 g, 29.2 mmol) and 4-{4-[4-(2-fluoroethyl)-1-piperazinyl]-1-piperidinyl}-2-(methyloxy)aniline (9.80 g, 29.2 mmol) in 2,2,2-trifluoroethanol (140 mL) in a 350 mL glass round bottom pressure vessel was added conc. HCl (7.3 mL, 87.6 mmol). The flask was sealed and the placed in a 85° C. oil bath for 4 days. After cooling to rt, 0.5 M sodium methoxide in MeOH (234 mL, 117 mmol) was added. The solvent was removed on a rotovap and the residue taken up in DCM. Silica (100 g) was added and the solvent removed on the rotovap. The preabsorbed solids were purified by flash chromatography. The desired fractions were combined and the solvent removed on the rotovap to give 9.8 g of a yellow foam. This material was combined with four other batches prepared in similar manner. The combined impure material (53 g) was slurried in EtOH (~400 mL) and heated to 75° C. under slight vacuum on a rotary evaporator. The solid continued to dissolve until it was almost completely in solution, when yellow crystals started to come out of solution. The solution was allowed to cool to rt and was then placed in an ice bath. After an hour of sitting in an ice bath, the yellow solid was collected on a fine filter, rinsing with ice-cold EtOH (200 mL). The solid was then heated to 75° C. under high vacuum for 4 h and at rt overnight to afford the title compound (33.2 g). $^1$H NMR (400 MHz, DMSO-d$_6$) δ ppm 1.48 (qd, J=11.7, 3.5 Hz, 2H), 1.81 (d, J=12.1 Hz, 2H), 2.22-2.31 (m, 1H), 2.34-2.48 (m, 8H), 2.54 (dt, J$_{HF}$=28.8 Hz, J=4.8 Hz, 2H), 2.59-2.67 (m, 2H), 3.69 (d, J=12.45 Hz, 2H), 3.76 (s, 3H), 4.47 (dt, J$_{HF}$=48.0 Hz, J=4.8 Hz, 2H), 6.41-6.47 (m, 2H), 6.64 (d, J=2.38 Hz, 1H), 6.92-6.98 (m, 1H), 7.17 (t, J=8.06 Hz, 2H), 7.32-7.39 (m, 2H), 7.39-7.45 (m, 1H), 7.58 (t, J=7.78 Hz, 1H), 7.69 (d, J=8.97 Hz, 1H), 7.78 (d, J=7.69 Hz, 1H), 8.02 (d, J=7.51 Hz, 1H), 8.17 (d, J=5.31 Hz, 1H), 8.30 (s, 1H), 8.42 (s, 1H), 9.36 (br. s., 1H), 10.20 (s, 1H).

Example 57

Route 2: N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide

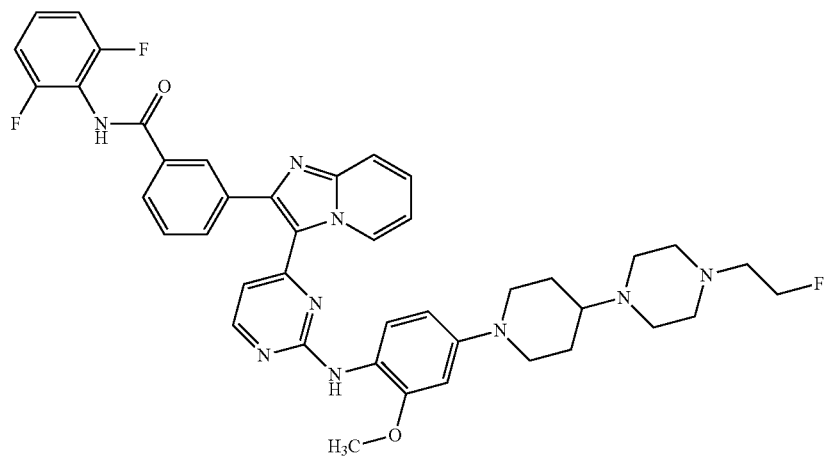

Step A: 1,1-dimethylethyl 4-(2-fluoroethyl)-1-piperazinecarboxylate

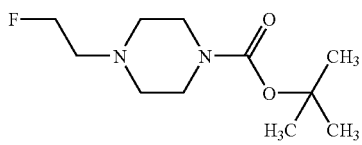

In a sealed tube, 1,1-dimethylethyl 1-piperazinecarboxylate (10.0 g, 54.0 mmol) was dissolved in 100 mL of THF. K$_2$CO$_3$ (11.2 g, 81.0 mmol) and 1-fluoro-2-iodoethane (11.3 g, 64.8 mmol) were added and the reaction was heated to 85° C. for 16 h. The reaction was cooled to rt and solids were filtered and washed with DCM. The filtrate was concentrated in vacuo being careful not to heat the H$_2$O bath past 30° C. The resulting crude product, 1,1-dimethylethyl 4-(2-fluoroethyl)-1-piperazinecarboxylate was carried on to the next step without further purification. $^1$H NMR (400 MHz, DMSO-d$_6$) δ ppm 4.48 (dt, J$_{HF}$=47.8 Hz, J=4.9 Hz, 2H), 3.24-3.28 (m, 4H), 2.57 (dt, J$_{HF}$=28.7, J=4.9 Hz, 2H), 2.31-2.36 (m, 4H), 1.34 (s, 9H).

Step B: 1-(2-fluoroethyl)piperazine dihydrochloride

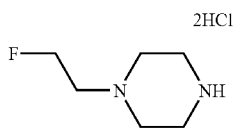

To the solution of 1,1-dimethylethyl 4-(2-fluoroethyl)-1-piperazinecarboxylate (from a different batch than previously described) (160 g, 0.68 mol) in MeOH (500 mL) was added HCl/MeOH (5M, 1000 mL), and the mixture was heated at 50° C. for 1 h before evaporating most of the solvent. The residue was filtered and washed with MeOH to give the title compound of Step B (122 g, 87% yield). $^1$H NMR (400 MHz, D$_2$O) δ ppm 3.60-3.78 (m, 10H), 4.80 (t, J=4.4 Hz, 1H), 4.92 (t, J=4.4 Hz, 1H)

Step C: 1,1-dimethylethyl 4-[4-(2-fluoroethyl)-1-piperazinyl]-1-piperidinecarboxylate

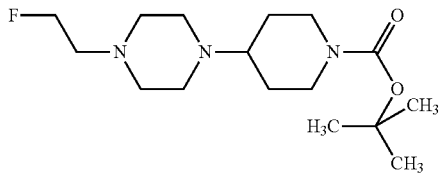

1,1-Dimethylethyl 4-oxo-1-piperidinecarboxylate (38.9 g, 195 mmol) and 1-(2-fluoroethyl)piperazine dihydrochloride (20 g, 97 mmol) were dissolved in 485 mL 1,2-DCE. TEA (81.5 mL, 585 mmol) was added and the reaction was stirred for 30 min. HOAc (8.4 mL, 146 mmol) was added and the reaction was stirred for an additional 30 min followed by the addition of sodium triacetoxyborohydride (49.6 g, 234 mmol). The reaction was stirred overnight. Saturated aqueous NaHCO$_3$ solution was added carefully until the reaction stopped bubbling. Aqueous layer was then extracted with DCM (1×) and EtOAc (3×). Combined organic layers were dried over MgSO$_4$, filtered and concentrated in vacuo. The resulting crude product was absorbed onto silica gel and purified by flash chromatography to give title compound of step C (28.95 g, 94%). $^1$H NMR (400 MHz, DMSO-d$_6$) δ ppm 4.39-4.57 (m, 2H), 3.90 (d, J=12.46 Hz, 2H), 2.61-2.73 (m, 2H), 2.47-2.61 (m, 2H), 2.36-2.47 (m, 8H), 2.24-2.35 (m, 1H), 1.69 (d, J=12.46 Hz, 2H), 1.37 (s, 9H), 1.14-1.26 (m, 2H).

Step D: 1-(2-fluoroethyl)-4-{1-[3-(methyloxy)-4-nitrophenyl]-4-piperidinyl}piperazine

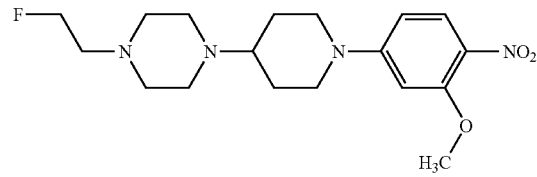

1,1-Dimethylethyl 4-[4-(2-fluoroethyl)-1-piperazinyl]-1-piperidinecarboxylate (28.95 g, 91.78 mmol) was dissolved in 76 mL of MeOH and 76 mL 37% HCl was added. Reaction was stirred for 3 h and then concentrated in vacuo and to give 1-(2-fluoroethyl)-4-(4-piperidinyl)piperazine trihydrochloride (~29 g) which was then dissolved in DMSO (200 mL). K$_2$CO$_3$ (63 g, 459 mmol) was added followed by 4-fluoro-2-(methyloxy)-1-nitrobenzene (15.7 g, 91.8 mmol) and the reaction mixture was heated to 80° C. and allowed to stir overnight. The mixture was then poured into H$_2$O and extracted with EtOAc (3×). The combined organics were dried with MgSO$_4$, filtered, and concentrated in vacuo. The resulting solids were triturated with diethyl ether to give the title compound of step E (27.13 g, 81%). MS (M+H, ES+) 367.

Step E: 4-{4-[4-(2-fluoroethyl)-1-piperazinyl]-1-piperidinyl}-2-(methyloxy)aniline

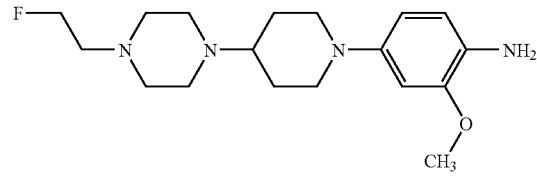

1-(2-fluoroethyl)-4-{1-[3-(methyloxy)-4-nitrophenyl]-4-piperidinyl}piperazine (27.13 g, 74.04 mmol) was taken up in EtOAc (1000 mL) and 10% Palladium on Carbon was added as a slurry in EtOAc. The reaction was placed under a balloon of hydrogen gas and was allowed to stir at rt for 3 days. The catalyst was filtered off and the filtrate was concentrated in vacuo to give the title compound of step F without further purification (24.25 g, 97%). MS (M+H, ES+) 337.

Step F: N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide This step was carried out as described above in Example 57, Route 1, Step F.

Example 58

N-(2,6-difluorophenyl)-3-(3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide

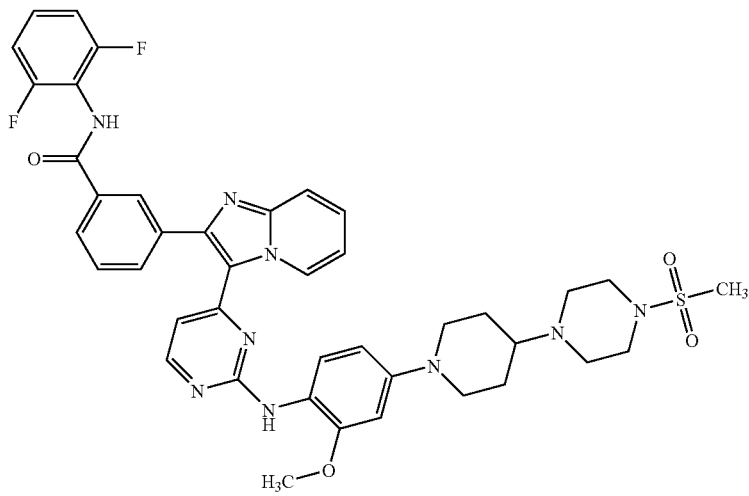

Step A: 1-{1-[3-(methyloxy)-4-nitrophenyl]-4-piperidinyl}-4-(methylsulfonyl)piperazine

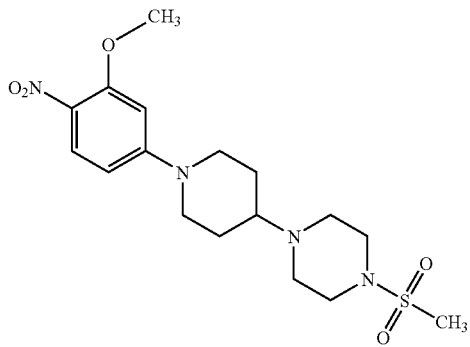

To a suspension of 1-{1-[3-(methyloxy)-4-nitrophenyl]-4-piperidinyl}piperazine (Example 57, step C) (5.0 g, 11.6 mmol), methane sulfonyl chloride (1.4 mL, 17.5 mmol) and DCM (200 mL) was added TEA (80.1 mL, 58.2 mmol). The reaction was stirred at rt and monitored by TLC. After complete consumption of the starting material the clear yellow solution was concentrated onto silica gel and purified by chromatography to afford the title compound of step A as a yellow solid (3.54 g, 76%). $^1$H NMR (400 MHz, DMSO-d$_6$) δ 7.85 (d, J=9.5 Hz, 1H), 6.57 (dd, J=9.2, 2.6 Hz, 1H), 6.48 (d, J=2.6 Hz, 1H), 4.09-4.00 (m, 2H), 3.89 (s, 3H), 3.10-3.03 (m, 4H), 2.99-2.90 (m, 2H), 2.84 (s, 3H), 2.61-2.52 (m, 5H), 1.85-1.77 (m, 2H), 1.50-1.37 (m, 2H).

Step B: 2-(methyloxy)-4-{4-[4-(methylsulfonyl)-1-piperazinyl]-1-piperidinyl}aniline

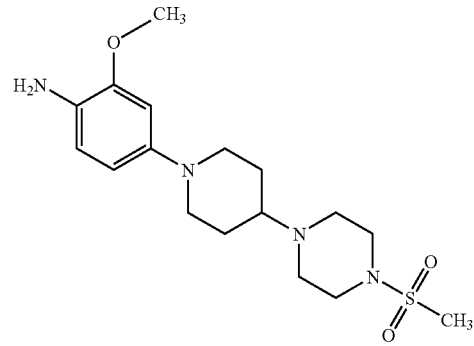

NaBH$_4$ (1.18 g, 31.1 mmol) was added carefully in portions (exothermic) to a suspension of 1-{1-[3-(methyloxy)-4-nitrophenyl]-4-piperidinyl}-4-(methylsulfonyl)-piperazine (3.54 g, 8.9 mmol), nickel(II)chloride hexahydrate (1.06 g, 4.4 mmol), MeOH (100 mL) and THF (50 mL) at 0° C. The ice bath was removed and the reaction mixture was warmed to rt. TLC analysis indicated the complete consumption of the starting material. The reaction mixture was concentrated onto silica gel and flash chromatography afforded the title compound of step B (2.93 g, 90%) as a colorless solid. $^1$H NMR (400 MHz, DMSO-d$_6$) δ 6.49-6.46 (m, 2H), 6.27 (dd, J=8.5, 2.6 Hz, 1H), 4.18 (bs, 2H), 3.71 (s, 3H), 3.44-3.38 (m, 2H), 3.11-3.04 (m, 4H), 2.84 (s, 3H), 2.61-2.54 (m, 4H), 2.35-2.26 (m, 1H), 1.80-1.77 (m, 2H), 1.56-1.46 (m, 2H).

Step C: N-(2,6-difluorophenyl)-3-(3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide A mixture of 3-[3-(2-chloro-4-pyrimidinyl)imidazo[1,2-a]pyridin-2-yl]-N-(2,6-difluorophenyl)-benzamide (Intermediate Example 1) (1.00 g, 2.2 mmol), 2-(methyloxy)-4-{4-[4-(methylsulfonyl)-1-piperazinyl]-1-piperidinyl}aniline (0.80 g, 2.2 mmol), p-toluenesulfonic acid (0.99 g, 5.2 mmol) and iPrOH (20 mL) was heated in the microwave at 175° C. for 20 min. LCMS indicated the reaction had proceeded to completion and the reaction mixture was concentrated onto silica gel. Flash chromatography afforded the title compound (1.1 μg, 65%) as a yellow solid. $^1$H NMR (400 MHz, DMSO-d$_6$) δ 10.23 (s, 1H), 9.40 (bs, 1H), 8.45 (s, 1H), 8.33-8.31 (m, 1H), 8.19 (d, J=5.2 Hz, 1H), 8.07-8.03 (m, 1H), 7.83-7.80 (m, 1H), 7.74-7.71 (m, 1H), 7.60 (at, J=7.7 Hz, 1H), 7.48-7.35 (m, 3H), 7.23-7.17 (m, 2H), 7.01-6.95 (m, 1H), 6.67 (d, J=2.5 Hz, 1H), 6.50-6.44 (m, 2H), 3.79 (s, 3H), 3.76-3.70 (m, 2H), 3.11-3.06 (m, 4H), 2.85 (s, 3H), 2.71-2.63 (m, 2H), 2.62-2.57 (m, 4H), 2.46-2.36 (m, 2H), 1.87-1.79 (m, 2H), 1.60-1.47 (m, 2H). MS (ES+, m/z) 794 (M+1).

Example 59

N-(2,6-difluorophenyl)-3-[3-(2-{[2-(methyloxy)-4-(4-{4-[2-(methylsulfonyl)ethyl]-1-piperazinyl}-1-piperidinyl)phenyl]amino}-4-pyrimidinyl)imidazo[1,2-a]pyridin-2-yl]benzamide

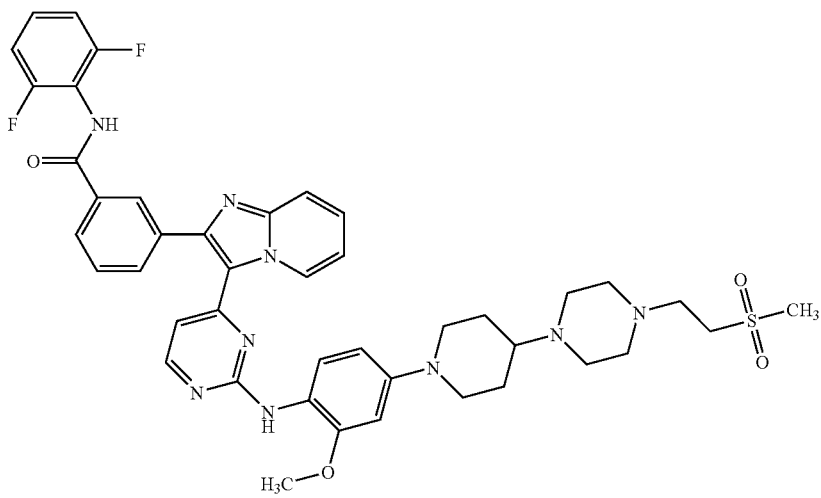

Step A: 1-{1-[3-(methyloxy)-4-nitrophenyl]-4-piperidinyl}-4-[2-(methylsulfonyl)ethyl]-piperazine

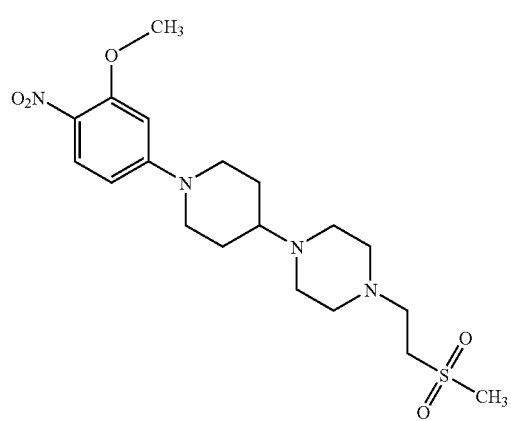

To a suspension of 1-{1-[3-(methyloxy)-4-nitrophenyl]-4-piperidinyl}piperazine (Example 57, step C) (10.0 g, 23.27 mmol) and 1,4-dioxane (400 mL) was added MeOH (~100 mL) to enhance solubility. Methyl vinyl sulfone (6.1 mL, 69.8 mmol) and Na$_2$CO$_3$ (7.4 g, 69.8 mmol) were added and the resultant mixture was heated at 80° C. overnight (~16 h). LCMS indicated that the reaction had gone to completion. The solvent was evaporated and the residue was taken up in DCM (300 mL) and filtered to remove salts. The filtrate was concentrated in vacuo to afford the title compound of step A (9.9 g, >95%) which was carried forward with no further purification. MS (ES+, m/z) 427 (M+1).

Step B: 2-(methyloxy)-4-(4-{4-[2-(methylsulfonyl)ethyl]-1-piperazinyl}-1-piperidinyl)aniline

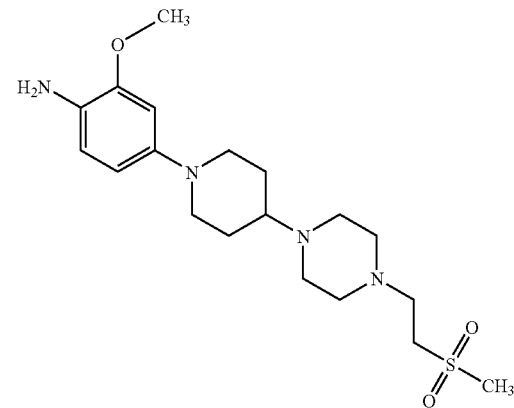

NaBH$_4$ (2.64 g, 69.8 mmol) was added carefully in portions to a suspension of 1-{1-[3-(methyloxy)-4-nitrophenyl]-4-piperidinyl}-4-[2-(methylsulfonyl)-ethyl]piperazine (9.9 g, 23.3 mmol), nickel(II)chloride hexahydrate (1.66 g, 7 mmol), MeOH (120 mL) and THF (60 mL) at 0° C. The ice bath was removed and the reaction mixture was stirred at rt overnight (~16 h). The reaction mixture was concentrated onto silica gel and flash chromatography afforded the title compound of step B (6.24 g, 68%) as a brown solid. $^1$H NMR (400 MHz, DMSO-d$_6$) δ 6.49-6.44 (m, 2H), 6.26 (dd, J=8.4, 2.6 Hz, 1H), 4.18 (bs, 2H), 3.71 (s, 3H), 3.43-3.36 (m, 2H), 3.25 (t, J=6.8 Hz, 2H), 3.00 (s, 3H), 2.65 (t, J=6.8 Hz, 2H), 2.47-2.36 (m, 4H), 2.23-2.15 (m, 1H), 1.82-1.75 (m, 2H), 1.54-1.43 (m, 2H).

Step C: N-(2,6-difluorophenyl)-3-[3-(2-{[2-(methyloxy)-4-(4-{4-[2-(methylsulfonyl)ethyl]-1-piperazinyl}-1-piperidinyl)phenyl]amino}-4-pyrimidinyl)imidazo[1,2-a]pyridin-2-yl]benzamide A mixture of 3-[3-(2-chloro-4-pyrimidinyl)imidazo[1,2-a]pyridin-2-yl]-N-(2,6-difluorophenyl)-benzamide (Intermediate Example 1) (0.70 g, 1.52 mmol), 2-(methyloxy)-4-(4-{4-[2-(methylsulfonyl)ethyl]-1-piperazinyl}-1-piperidinyl)aniline (0.60 g, 1.52 mmol), p-toluenesulfonic acid (0.69 g, 3.64 mmol) and iPrOH (15 mL) were heated in the microwave at 175° C. for 25 min. LCMS indicated the reaction had proceeded to completion and the reaction mixture was concentrated onto silica gel. Flash chromatography afforded the title compound (0.80 g, 64%) as a yellow solid. $^1$H NMR (400 MHz, DMSO-d$_6$) δ 10.23 (s, 1H), 9.40 (bs, 1H), 8.45 (s, 1H), 8.33-8.31 (m, 1H), 8.19 (d, J=5.5 Hz, 1H), 8.07-8.03 (m, 1H), 7.83-7.79 (m, 1H), 7.74-7.70 (m, 1H), 7.60 (at, J=7.9 Hz, 1H), 7.48-7.35 (m, 3H), 7.24-7.16 (m, 2H), 7.00-6.94 (m, 1H), 6.67 (d, J=2.2 Hz, 1H), 6.50-6.44 (m, 2H), 3.79 (s, 3H), 3.75-3.68 (m, 2H), 3.25 (t, J=6.6 Hz, 2H), 3.01 (s, 3H), 2.70-2.60 (m, 5H), 2.45-2.24 (m, 5H), 1.86-1.79 (m, 2H), 1.55-1.44 (m, 2H). MS (ES+, m/z) 822 (M+1).

Example 60

N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)-8-methylimidazo[1,2-a]pyridin-2-yl]benzamide

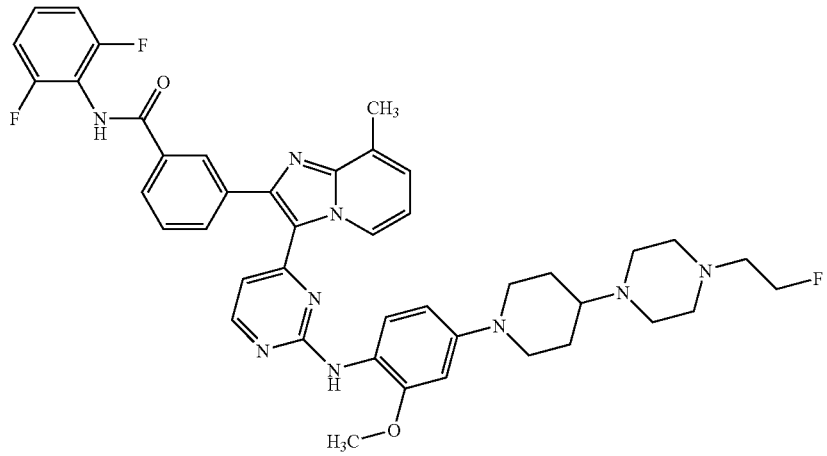

The title compound (0.10 g, 0.13 mmol, 31% in final step) was prepared in an analogous manner to that described for Example 57 with the following notable exceptions:

a) 3-methyl-2-pyridinamine was used instead of 2-aminopyridine in the procedure described in Intermediate Example 1, step C;

b) p-toluenesulfonic acid in iPrOH under microwave conditions at 180° C. were used rather than concentrated HCl in trifluoroethanol at 85° C. in the procedure described in Example 57, step F.

$^1$H NMR (400 MHz, DMSO-d$_6$) δ 10.20 (s, 1H), 9.27-9.18 (m, 1H), 8.40 (s, 1H), 8.28-8.26 (m, 1H), 8.14 (d, J=5.1 Hz, 1H), 8.04-8.01 (m, 1H), 7.78-7.75 (m, 1H), 7.58 (at, J=7.8 Hz, 1H), 7.39-7.31 (m, 2H), 7.26-7.23 (m, 1H), 7.20-7.14 (m, 2H), 6.88-6.82 (m, 1H), 6.64-6.62 (m, 1H), 6.46-6.42 (m, 1H), 6.40-6.38 (m, 1H), 4.53 (t, J=4.9 Hz, 1H), 4.41 (t, J=4.9 Hz, 1H), 3.75 (s, 3H), 3.72-3.65 (m, 2H), 2.68-2.54 (m, 4H), 2.52 (s, 3H), 2.42-2.31 (m, 3H), 2.31-2.22 (m, 1H), 1.84-1.77 (m, 2H), 1.52-1.45 (m, 2H). MS (ES+, m/z) 776 (M+1).

Example 61

N-(2,6-difluorophenyl)-5-[3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]-2-(methyloxy)benzamide

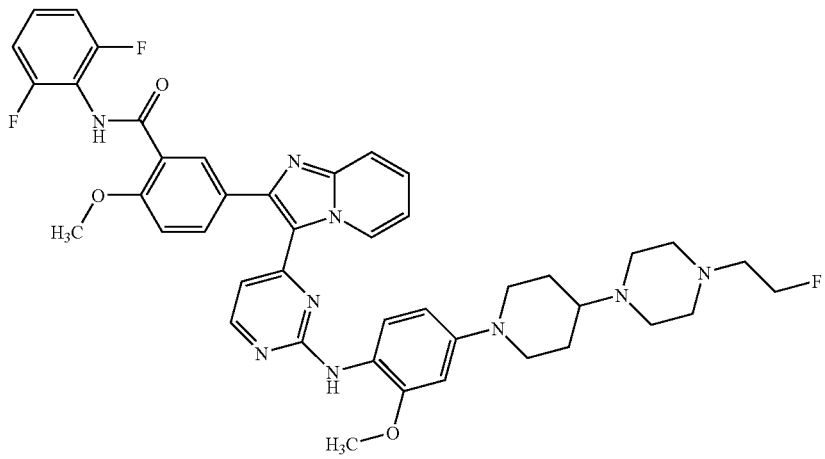

The title compound (0.73 g, 0.92 mmol, 64%) was prepared in an analogous manner to that described for N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide (Example 57, step F) with the following notable exceptions:

a) p-toluenesulfonic acid in iPrOH under microwave conditions at 175° C. were used rather than concentrated HCl in trifluoroethanol at 85° C.;

b) 5-[3-(2-chloro-4-pyrimidinyl)imidazo[1,2-a]pyridin-2-yl]-N-(2,6-difluorophenyl)-2-(methyloxy)-benzamide (Intermediate Example 2) was used instead of Intermediate Example 1.

$^1$H NMR (400 MHz, DMSO-$d_6$) δ 9.78 (s, 1H), 9.39-9.31 (m, 1H), 8.44 (s, 1H), 8.19 (d, J=5.2 Hz, 1H), 8.11-8.07 (m, 1H), 7.79-7.74 (m, 1H), 7.71-7.65 (m, 1H), 7.47-7.33 (m, 3H), 7.32-7.25 (m, 1H), 7.23-7.13 (m, 2H), 6.98-6.89 (m, 1H), 6.67 (d, J=2.6 Hz, 1H), 6.54-6.46 (m, 2H), 4.56 (t, J=5.0 Hz, 1H), 4.44 (t, J=5.0 Hz, 1H), 3.98 (s, 3H), 3.79 (s, 3H), 3.77-3.69 (m, 2H), 2.71-2.57 (m, 3H), 2.46-2.35 (m, 3H), 2.34-2.23 (m, 1H), 1.88-1.78 (m, 2H), 1.57-1.43 (m, 2H). MS (ES+, m/z) 792 (M+1).

Example 62

N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)-7-(methyloxy)imidazo[1,2-a]pyridin-2-yl]benzamide

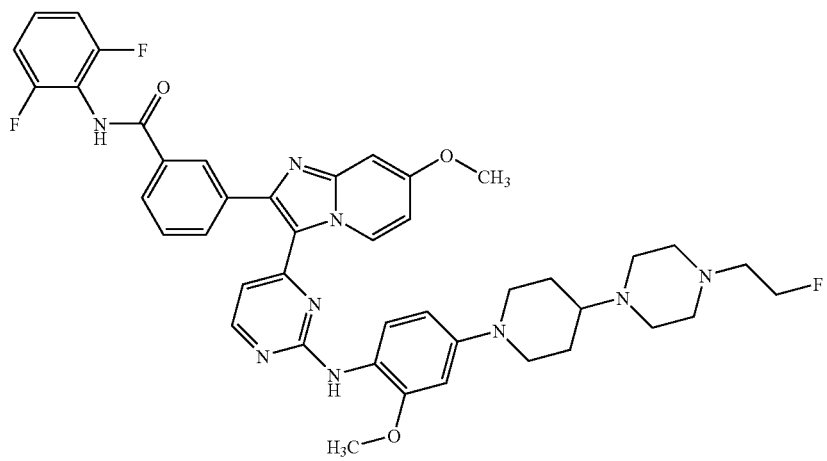

The title compound (0.028 g, 0.035 mmol, 44% in final step) was prepared in an analogous manner to that described for Example 57 with the following notable exceptions:

a) 4-(methyloxy)-2-pyridinamine (*J. Chem. Soc., Perkin Trans* 1, 2001, 2012-2021) was used instead of 2-aminopyridine in the step outlined in Intermediate Example 1, step C;

b) p-toluenesulfonic acid in iPrOH under microwave conditions at 180° C. were used rather than concentrated HCl in trifluoroethanol at 85° C. in the procedure described in Example 57, step F.

$^1$H NMR (400 MHz, DMSO-d$_6$) δ 10.22 (s, 1H), 9.33-9.24 (m, 1H), 8.42 (s, 1H), 8.29 (s, 1H), 8.13 (d, J=5.1 Hz, 1H), 8.06-8.01 (m, 1H), 7.82-7.77 (m, 1H), 7.60 (t, J=7.9 Hz, 1H), 7.45-7.33 (m, 2H), 7.23-7.17 (m, 2H), 7.10 (d, J=2.6 Hz, 1H), 6.68-6.60 (m, 2H), 6.50-6.47 (m, 1H), 6.39 (d, J=5.5 Hz, 1H), 4.56 (t, J=5.0 Hz, 1H), 4.44 (t, J=5.0 Hz, 1H), 3.88 (s, 3H), 3.78 (s, 3H), 3.77-3.71 (m, 2H), 2.72-2.57 (m, 3H), 2.46-2.35 (m, 3H), 2.34-2.25 (m, 1H), 1.87-1.78 (m, 2H), 1.55-1.45 (m, 2H). MS (ES+, m/z) 792 (M+1).

Example 63

N-(2,6-difluorophenyl)-2-(ethyloxy)-5-[3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide The title compound (0.098 g, 0.12 mmol, 49%) was prepared in an analogous manner to that described for Example 57, step F with the following notable exceptions:

a) p-toluenesulfonic acid in iPrOH under microwave conditions at 175° C. were used rather than concentrated HCl in trifluoroethanol at 85° C.;

b) Intermediate Example 6 was used instead of Intermediate Example 1.

$^1$H NMR (400 MHz, DMSO-d$_6$) δ 9.74 (s, 1H), 9.41-9.30 (m, 1H), 8.44 (s, 1H), 8.19 (d, J=5.1 Hz, 1H), 8.05-8.02 (m, 1H), 7.77-7.65 (m, 2H), 7.46-7.32 (m, 3H), 7.29-7.23 (m, 1H), 7.22-7.15 (m, 2H), 6.98-6.90 (m, 1H), 6.66 (d, J=2.2 Hz, 1H), 6.52 (d, J=5.1 Hz, 1H), 6.47 (dd, J=8.6, 2.4 Hz, 1H), 4.56 (t, J=5.0 Hz, 1H), 4.44 (t, J=5.0 Hz, 1H), 4.26 (q, J=6.8 Hz, 2H), 3.79 (s, 3H), 3.76-3.69 (m, 2H), 2.70-2.57 (m, 3H), 2.45-2.24 (m, 6H), 1.88-1.79 (m, 2H), 1.56-1.46 (m, 2H), 1.43 (t, J=6.8 Hz, 3H). MS (ES+, m/z) 806 (M+1).

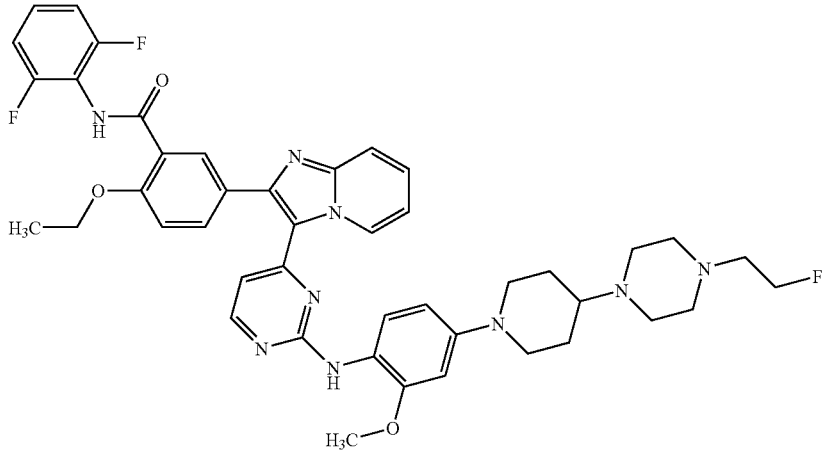

Example 64

N-(2,6-difluorophenyl)-3-[3-(2-{[4-[4-(4-ethyl-1-piperazinyl)-1-piperidinyl]-2-(methyloxy)phenyl]amino}-4-pyrimidinyl)imidazo[1,2-a]pyridin-2-yl]benzamide

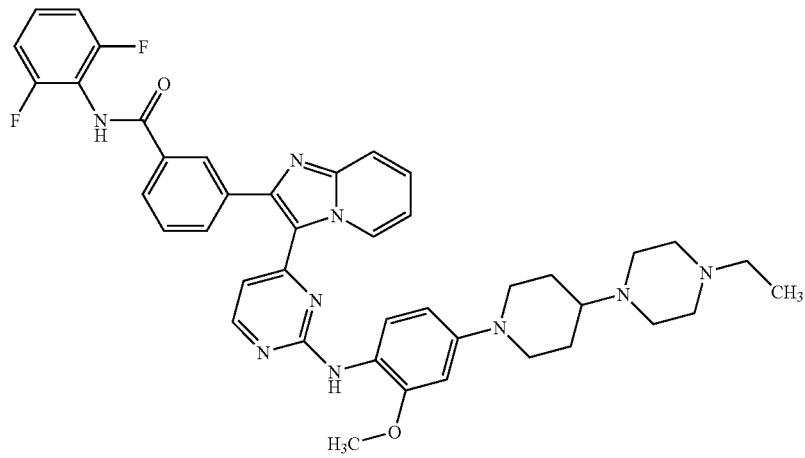

The title compound (0.17 g, 0.23 mmol, 71% in final step) was prepared in an analogous manner to that described for Example 57 with the following notable exceptions:
a) ethyl iodide was used instead of 1-iodo-2-fluoroethane in Example 57, step D;
b) p-toluenesulfonic acid in iPrOH under microwave conditions at 180° C. were used rather than concentrated HCl in trifluoroethanol at 85° C. in the procedure described in Example 57, step F.

$^1$H NMR (400 MHz, DMSO-d$_6$) δ 10.23 (s, 1H), 9.43-9.35 (m, 1H), 8.45 (s, 1H), 8.35-8.31 (m, 1H), 8.19 (d, J=5.2 Hz, 1H), 8.07-8.04 (m, 1H), 7.83-7.79 (m, 1H), 7.73-7.70 (m, 1H), 7.60 (t, J=7.9 Hz, 1H), 7.50-7.33 (m, 3H), 7.24-7.17 (m, 2H), 7.02-6.94 (m, 1H), 6.68-6.64 (m, 1H), 6.51-6.42 (m, 2H), 3.79 (s, 3H), 3.76-3.67 (m, 2H), 2.43-2.33 (m, 2H), 2.69-2.61 (m, 2H), 2.39-2.19 (m, 7H), 1.87-1.78 (m, 2H), 1.54-1.44 (m, 2H), 0.98-0.94 (m, 3H). MS (ES+, m/z) 744 (M+1).

Example 65

N-(2,6-difluorophenyl)-2-(methyloxy)-5-[3-(2-{[2-(methyloxy)-4-(4-{4-[2-(methylsulfonyl)-ethyl]-1-piperazinyl}-1-piperidinyl)phenyl]amino}-4-pyrimidinyl)imidazo-[1,2-a]pyridin-2-yl]benzamide

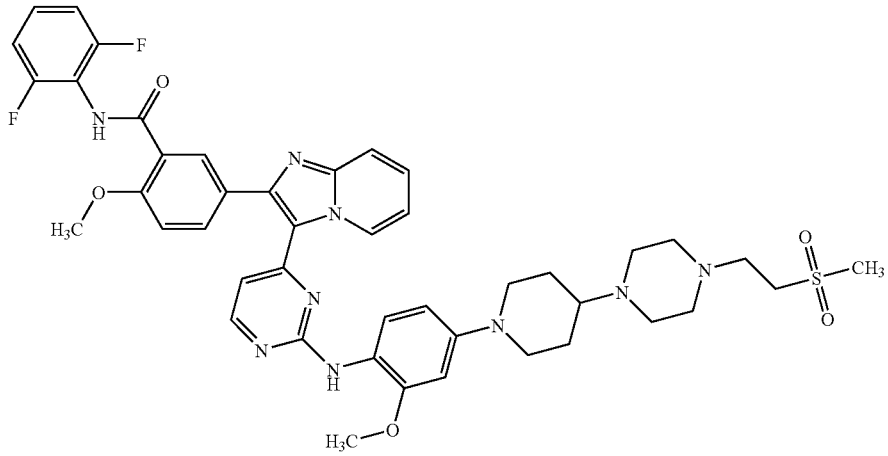

The title compound (0.098 g, 0.12 mmol, 45%) was prepared in an analogous manner to that described for Example 59, step C) with the following notable exception: Intermediate Example 2 was used instead of Intermediate Example 1.
$^1$H NMR (400 MHz, DMSO-d$_6$) δ 9.78 (s, 1H), 9.40-9.32 (m, 1H), 8.44 (s, 1H), 8.19 (d, J=5.2 Hz, 1H), 8.11-8.07 (m, 1H), 7.79-7.73 (m, 1H), 7.72-7.65 (m, 1H), 7.47-7.34 (m, 2H), 7.32-7.26 (m, 1H), 7.23-7.15 (m, 2H), 6.98-6.90 (m, 1H), 6.69-6.64 (m, 1H), 6.57-6.44 (m, 2H), 3.98 (s, 3H), 3.79 (s, 3H), 3.76-3.68 (m, 2H), 3.29-3.23 (m, 2H), 3.01 (s, 3H), 2.71-2.60 (m, 5H), 2.46-2.35 (m, 4H), 2.34-2.25 (m, 2H), 1.86-1.79 (m, 2H), 1.56-1.43 (m, 3H), 1.26-1.18 (m, 2H). MS (ES+, m/z) 852 (M+1).

Example 66

N-(2,6-difluorophenyl)-2-(ethyloxy)-5-[3-(2-{[2-(methyloxy)-4-(4-{4-[2-(methylsulfonyl)-ethyl]-1-piperazinyl}-1-piperidinyl)phenyl]amino}-4-pyrimidinyl)imidazo[1,2-a]pyridin-2-yl]benzamide

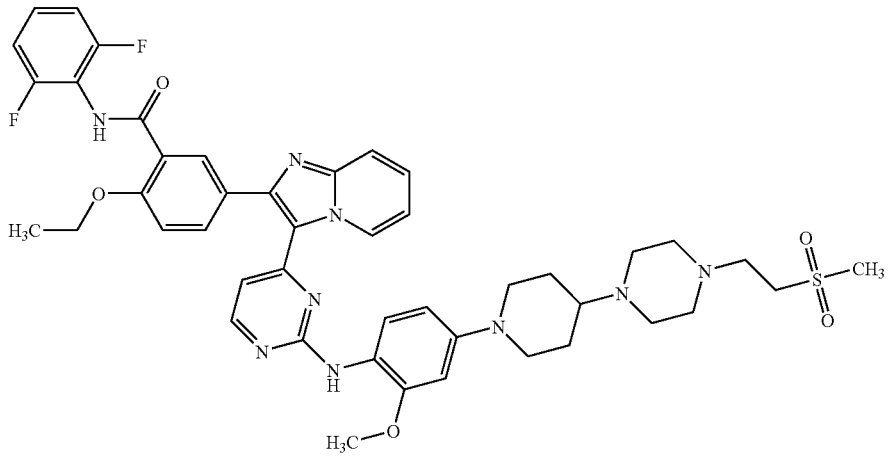

The title compound (0.14 g, 0.16 mmol, 63%) was prepared in an analogous manner to that described for Example 59, step C with the following notable exception: Intermediate Example 6 was used instead of Intermediate Example 1. $^1$H NMR (400 MHz, DMSO-d$_6$) δ 9.74 (s, 1H), 9.40-9.31 (m, 1H), 8.43 (s, 1H), 8.19 (d, J=5.1 Hz, 1H), 8.05-8.01 (m, 1H), 7.77-7.66 (m, 2H), 7.46-7.33 (m, 3H), 7.28-7.23 (m, 1H), 7.22-7.14 (m, 2H), 6.98-6.91 (m, 1H), 6.68-6.62 (m, 1H), 6.55-6.42 (m, 2H), 4.26 (q, J=6.5 Hz, 2H), 3.79 (s, 3H), 3.77-3.69 (m, 2H), 3.01 (s, 3H), 2.70-2.61 (m, 4H), 2.45-2.26 (m, 8H), 1.85-1.80 (m, 2H), 1.55-1.46 (m, 2H), 1.42 (t, J=6.8 Hz, 3H). MS (ES+, m/z) 866 (M+1).

Example 67

N-(2,6-difluorophenyl)-3-[8-methyl-3-(2-{[2-(methyloxy)-4-(4-{4-[2-(methylsulfonyl)ethyl]-1-piperazinyl}-1-piperidinyl)phenyl]amino}-4-pyrimidinyl)imidazo[1,2-a]pyridin-2-yl]benzamide

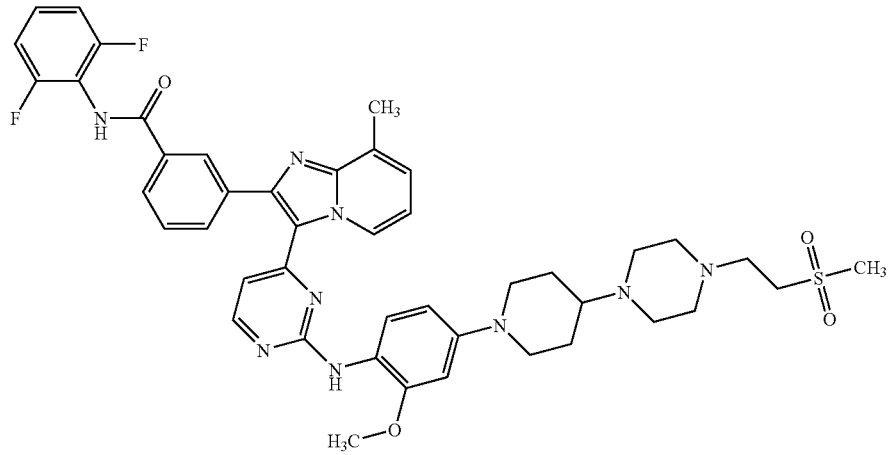

The title compound (0.14 g, 0.17 mmol, 40% in final step) was prepared in an analogous manner to that described for Example 59 with the following notable exception: 3-methyl-2-pyridinamine was used instead of 2-aminopyridine in the procedure described in Intermediate Example 1, step C. $^1$H NMR (400 MHz, DMSO-d$_6$) δ 10.23 (s, 1H), 9.33-9.20 (m, 1H), 8.44 (s, 1H), 8.31-8.28 (m, 1H), 8.17 (d, J=5.5 Hz, 1H), 8.08-8.03 (m, 1H), 7.82-7.76 (m, 1H), 7.61 (t, J=7.9 Hz, 1H), 7.47-7.33 (m, 3H), 7.31-7.26 (m, 1H), 7.24-7.18 (m, 2H), 6.92-6.85 (m, 1H), 6.65 (d, J=2.6 Hz, 1H), 6.46 (dd, J=8.8, 2.2 Hz, 1H), 6.41 (d, J=5.1 Hz, 1H), 3.78 (s, 3H), 3.75-3.68 (m, 2H), 3.29-3.23 (m, 2H), 3.01 (s, 3H), 2.70-2.60 (m, 4H), 2.55 (s, 3H), 2.45-2.24 (m, 6H), 1.86-1.79 (m, 2H), 1.55-1.44 (m, 2H). MS (ES+, m/z) 836 (M+1).

Example 68

N-(2,6-difluorophenyl)-3-(8-methyl-3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide

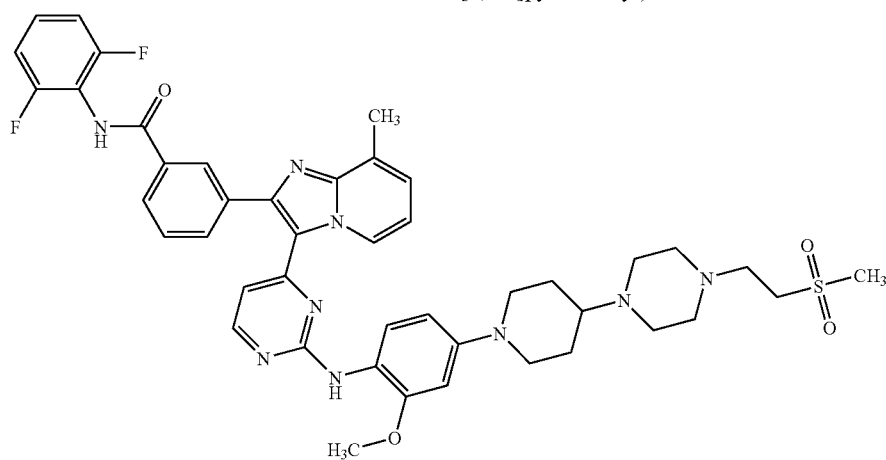

The title compound (0.25 g, 0.31 mmol, 75% in final step) was prepared in an analogous manner to that described for Example 58 with the following notable exception: 3-methyl-2-pyridinamine was used instead of 2-aminopyridine in the procedure described in Intermediate Example 1, step C. $^1$H NMR (400 MHz, DMSO-d6) δ 10.23 (s, 1H), 9.32-9.22 (m, 1H), 8.44 (s, 1H), 8.31-8.28 (m, 1H), 8.18 (d, J=5.1 Hz, 1H), 8.07-8.03 (m, 1H), 7.82-7.77 (m, 1H), 7.61 (t, J=7.9 Hz, 1H), 7.45-7.32 (m, 2H), 7.30-7.26 (m, 1H), 7.25-7.15 (m, 2H), 6.94-6.85 (m, 1H), 6.66 (d, J=2.6 Hz, 1H), 6.47 (dd, J=8.8, 2.5 Hz, 1H), 6.42 (d, J=5.5 Hz, 1H), 3.78 (s, 3H), 3.77-3.70 (m, 2H), 3.11-3.05 (m, 4H), 2.85 (s, 3H), 2.71-2.62 (m, 2H), 2.61-2.56 (m, 4H), 2.55 (s, 3H), 2.46-2.35 (m, 2H), 1.86-1.78 (m, 2H), 1.60-1.46 (m, 2H). MS (ES+, m/z) 808 (M+1).

Example 69

N-(2,6-difluorophenyl)-2-(methyloxy)-5-(3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide

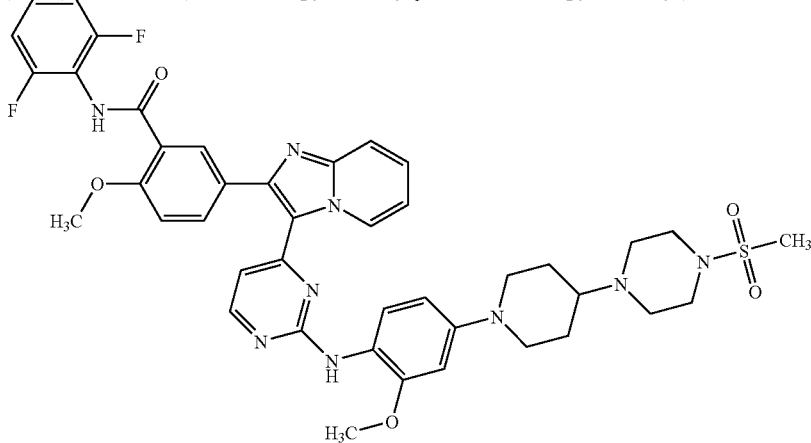

The title compound (0.26 g, 0.32 mmol, 63%) was prepared in an analogous manner to that described for Example 58, step C with the following notable exception: Intermediate Example 2 was used instead of Intermediate Example 1. $^1$H NMR (400 MHz, DMSO-d$_6$) δ 9.78 (s, 1H), 9.40-9.32 (m, 1H), 8.45 (s, 1H), 8.19 (d, J=5.5 Hz, 1H), 8.12-8.08 (m, 1H), 7.81-7.74 (m, 1H), 7.71-7.66 (m, 1H), 7.47-7.33 (m, 3H), 7.32-7.24 (m, 1H), 7.23-7.15 (m, 2H), 6.99-6.89 (m, 1H), 6.67 (d, J=2.6 Hz, 1H), 6.55-6.44 (m, 2H), 3.98 (s, 3H), 3.79 (s, 3H), 3.77-3.71 (m, 2H), 3.10-3.05 (m, 4H), 2.85 (s, 3H), 2.71-2.63 (m, 2H), 2.62-2.56 (m, 4H), 2.45-2.34 (m, 1H), 1.88-1.78 (m, 2H), 1.60-1.47 (m, 2H). MS (ES+, m/z) 412.5 [(M+2)/2].

Example 70

3-[3-(2-{[4-[4-(4-acetyl-1-piperazinyl)-1-piperidinyl]-2-(methyloxy)phenyl]amino}-4-pyrimidinyl)imidazo[1,2-a]pyridin-2-yl]-N-(2,6-difluorophenyl)benzamide

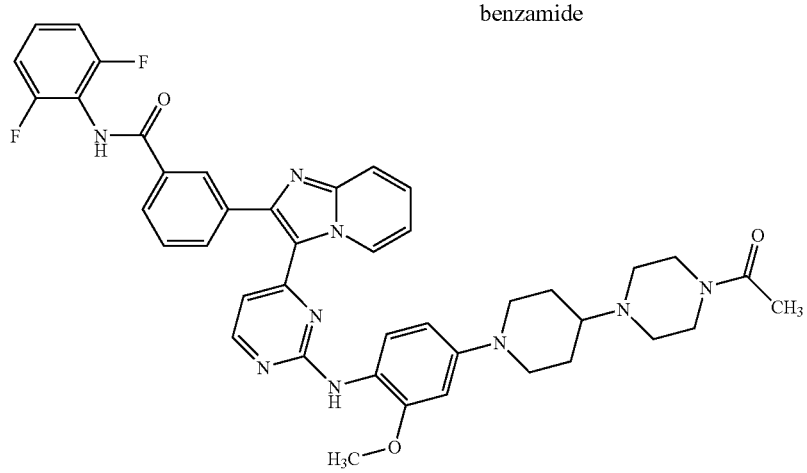

Step A: 1-acetyl-4-{1-[3-(methyloxy)-4-nitrophenyl]-4-piperidinyl}piperazine

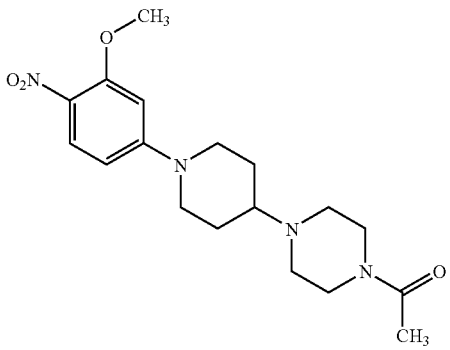

To a solution of 1-{1-[3-(methyloxy)-4-nitrophenyl]-4-piperidinyl}piperazine (Example 57, step C) (0.500 g, 1.56 mmol) in DCM (20 mL) was added Ac₂O (0.22 mL, 2.34 mmol). TEA (0.33 mL, 2.34 mmol) was then added dropwise and the resultant mixture was stirred at rt overnight. TLC indicated that the reaction had gone to completion. The reaction mixture was evaporated onto silica gel and purified by flash chromatography to afford the title compound of step A (0.52 g, 93%). ¹H NMR (400 MHz, DMSO-d₆) δ 7.85 (d, J=9.6 Hz, 1H), 6.57 (dd, J=9.5, 2.5 Hz, 1H), 6.48 (d, J=2.6 Hz, 1H), 4.07-4.00 (m, 2H), 3.88 (s, 3H), 3.41-3.34 (m, 4H), 2.99-2.89 (m, 2H), 2.43-2.36 (m, 2H), 1.95 (s, 3H), 1.85-1.78 (m, 2H), 1.48-1.38 (m, 2H).

Step B: 4-[4-(4-acetyl-1-piperazinyl)-1-piperidinyl]-2-(methyloxy)aniline

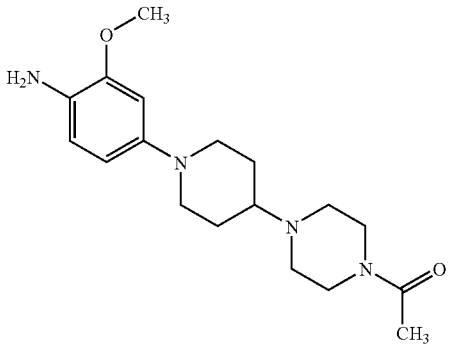

NaBH₄ (0.190 g, 5.06 mmol) was added carefully in portions (exothermic) to a suspension of 1-acetyl-4-{1-[3-(methyloxy)-4-nitrophenyl]-4-piperidinyl}piperazine (0.52 g, 1.45 mmol), nickel(II)chloride hexahydrate (0.170 g, 0.72 mmol), MeOH (8 mL) and THF (4 mL) at 0° C. The ice bath was removed and the reaction mixture was stirred at rt overnight (~16 h). The solvent was evaporated and the residue was suspended in DCM and filtered through celite. Flash chromatography afforded the title compound of step B (0.36 g, 76%). ¹H NMR (400 MHz, DMSO-d₆) δ 6.50-6.45 (m, 2H), 6.30-6.25 (m, 1H), 4.18 (bs, 2H), 3.71 (s, 3H), 3.45-3.36 (m, 6H), 2.45-2.38 (m, 3H), 2.31-2.23 (m, 1H), 1.96 (s, 3H), 1.82-1.74 (m, 2H), 1.58-1.44 (m, 2H).

Step C: 3-[3-(2-{[4-[4-(4-acetyl-1-piperazinyl)-1-piperidinyl]-2-(methyloxy)phenyl]-amino}-4-pyrimidinyl)imidazo[1,2-a]pyridin-2-yl]-N-(2,6-difluorophenyl)benzamide A mixture of Intermediate Example 1 (0.15 g, 0.32 mmol), 4-[4-(4-acetyl-1-piperazinyl)-1-piperidinyl]-2-(methyloxy) aniline (0.11 g, 0.32 mmol), p-toluenesulfonic acid (0.15 g, 0.78 mmol) and iPrOH (5 mL) was heated in the microwave at 180° C. for 15 min. LCMS indicated the reaction had proceeded to completion and the reaction mixture was concentrated onto silica gel. Flash chromatography afforded the title compound (0.11 g, 45%). ¹H NMR (400 MHz, DMSO-d₆) δ 10.23 (s, 1H), 9.45-9.34 (m, 1H), 8.45 (s, 1H), 8.34-8.30 (m, 1H), 8.19 (d, J=5.1 Hz, 1H), 8.07-8.03 (m, 1H), 7.85-7.78 (m, 1H), 7.74-7.69 (m, 1H), 7.60 (t, J=7.7 Hz, 1H), 7.50-7.34 (m, 3H), 7.23-7.17 (m, 2H), 7.00-6.95 (m, 1H), 6.66 (d, J=2.2 Hz, 1H), 6.49-6.45 (m, 2H), 3.79 (s, 3H), 3.77-3.70 (m, 2H), 3.43-3.35 (m, 4H), 2.71-2.60 (m, 2H), 2.45-2.32 (m, 4H), 1.96 (s, 3H), 1.86-1.79 (m, 2H), 1.60-1.45 (m, 2H). MS (ES+, m/z) 758 (M+1).

Example 71

N-(2,6-difluorophenyl)-3-[3-(2-{[2-(methyloxy)-4-(4-morpholinyl)phenyl]amino}-4-pyrimidinyl)imidazo[1,2-a]pyridin-2-yl]benzamide

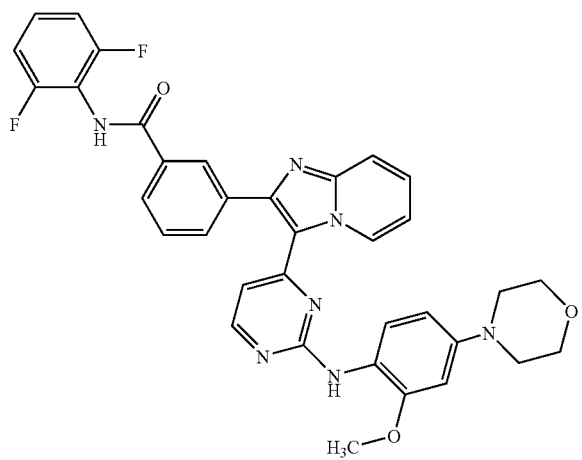

Step A: Methyl 3-[3-(2-{[2-(methyloxy)-4-(4-morpholinyl)phenyl]amino}-4-pyrimidinyl)-imidazo[1,2-a]pyridin-2-yl]benzoate

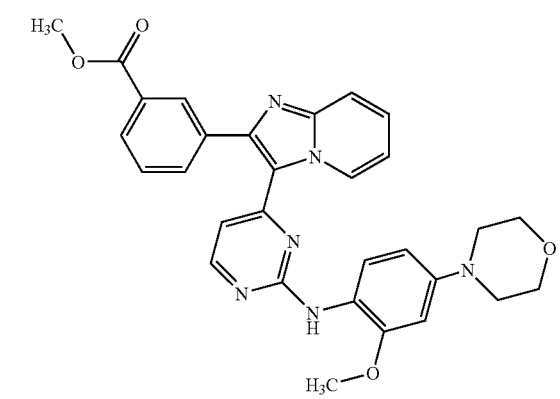

A mixture of methyl Intermediate Example 3 (150 mg, 0.41 mmol), 2-(methyloxy)-4-(4-morpholinyl)aniline (112 mg, 0.49 mmol) and 4N HCl in dioxane (0.05 mL, 0.20 mmol) in 4 mL trifluoroethanol was heated to 80° C. in a sealed tube, After 24 h, there was no conversion to desired product. The reaction was transferred to a microwave vial and heated at 180° C. for 8 min twice. The reaction was concentrated onto silica gel and purified by flash column chromatography to give 132 mg (60%) of the desired product, $^1$H NMR (400 MHz, DMSO-d$_6$) δ 9.34 (s, 1H), 8.51 (s, 1H), 8.26 (s, 1H), 8.23 (d, J=4.8 Hz, 1H), 8.02 (d, J=8.0 Hz, 1H), 7.89 (d, J=7.6 Hz, 1H), 7.73 (d, J=8.8 Hz, 1H), 7.61 (d, J=7.6 Hz, 1H), 7.49-7.43 (m, 2H), 7.00 (t, J=6.6 Hz, 1H), 6.71 (d, J=2.4 Hz, 1H), 6.50 (dd, J=8.8 and 2.4 Hz, 1H), 6.46 (d, J=4.8 Hz, 1H), 3.87 (d, 3H), 3.82 (s, 3H), 3.77-3.75 (m, 4H), 3.14-3.12 (m, 4H).

Step B: N-(2,6-difluorophenyl)-3-[3-(2-{[2-(methyloxy)-4-(4-morpholinyl)phenyl]-amino}-4-pyrimidinyl)imidazo[1,2-a]pyridin-2-yl]benzamide To a solution of methyl 3-[3-(2-{[2-(methyloxy)-4-(4-morpholinyl)phenyl]amino}-4-pyrimidinyl)imidazo[1,2-a]pyridin-2-yl]benzoate (65 mg, 0.12 mmol) in 2 mL THF was added 2,6-difluoroaniline (0.065 mL, 0.60 mmol) and a 1M solution of NaHMDS in THF (0.72 mL, 0.72 mmol). When LC/MS showed the reaction to be complete it was concentrated onto silica gel and purified by flash column chromatography to give 57 mg (75%) of the title compound. $^1$H NMR (400 MHz, DMSO-d$_6$) δ 10.20 (s, 1H), 9.38 (s, 1H), 8.45 (s, 1H), 8.27 (s, 1H), 8.18 (d, J=5.2 Hz, 1H), 8.01 (d, J=7.6 Hz, 1H), 7.78 (d, J=7.2 Hz, 1H), 7.70 (d, J=8.8 Hz, 1H), 7.60-7.52 (m, 2H), 7.47-7.40 (m, 2H), 7.35-7.30 (m, 1H), 7.11-7.07 (m, 1H), 6.98-6.94 (m, 1H), 6.67 (s, 1H), 6.48-6.43 (m, 2H), 3.78 (s, 3H), 3.73-3.72 (m, 4H), 3.10-3.09 (m, 4H). MS (ESI) m/z=634 [M+H]$^+$.

Example 72

3-[3-(2-{[4-(1,4'-bipiperidin-1'-yl)-2-(methyloxy)phenyl]amino}-4-pyrimidinyl)imidazo[1,2-a]pyridin-2-yl]-N-(2,4-difluorophenyl)benzamide

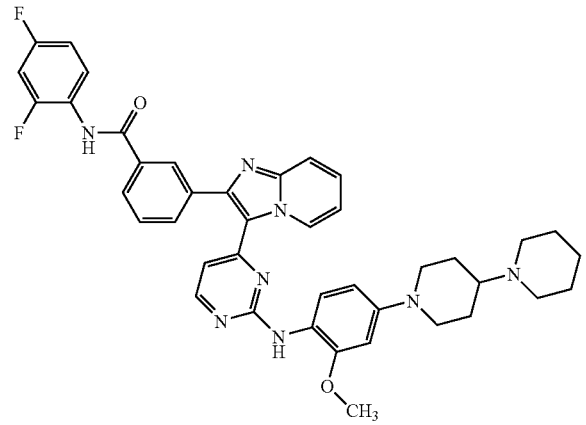

The title compound (0.036 g, 0.050 mmol, 56% in final step) was prepared in an analogous manner to that described for Example 9 with the following notable exceptions:
a) 4-(1,4'-bipiperidin-1'-yl)-2-(methyloxy)aniline (Example 22, step C) was used instead of 3-{[2-(dimethylamino)ethyl]oxy}aniline dihydrochloride in Example 9, step A;
b) 2-4-difluoroaniline was used instead of 5-chloro-2-fluoroaniline in Example 9, step B.

$^1$H NMR (400 MHz, DMSO-d$_6$) δ 10.23 (s, 1H), 9.39 (s, 1H), 8.46 (s, 1H), 8.29 (s, 1H), 8.19 (d, J=5.2 Hz, 1H), 8.03 (d, J=8.0 Hz, 1H), 7.79 (d, J=8.0 Hz, 1H), 7.72 (d, J=9.2 Hz, 1H), 7.61-7.54 (m, 2H), 7.45 (t, J=7.8 Hz, 1H), 7.38-7.32 (m, 2H), 7.13-7.09 (m, 1H), 6.97 (t, J=6.8 Hz, 1H), 6.66 (m, 1H), 6.48-6.43 (m, 2H), 3.78-3.72 (m, 5H), 2.66-2.60 (m, 2H), 2.49-2.45 (m, 6H), 2.31 (m, 1H), 1.79-1.77 (m, 2H), 1.55-1.37 (m, 6H). MS (ESI) m/z=715 [M+H]$^+$.

Example 73

N-(2,6-difluorophenyl)-3-[3-(2-{[4-(4-hydroxy-1-piperidinyl)-2-(methyloxy)phenyl]amino}-4-pyrimidinyl)imidazo[1,2-a]pyridin-2-yl]benzamide

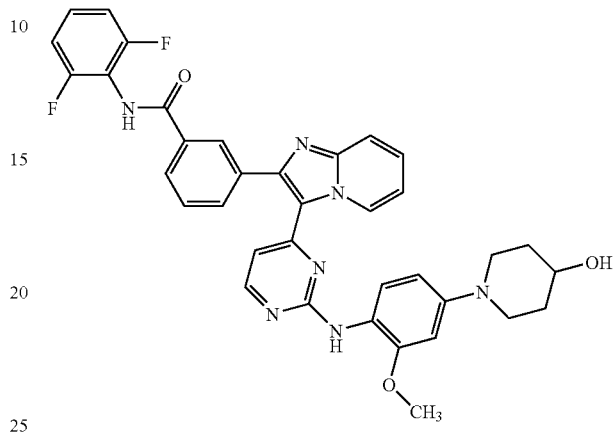

Step A
1-[4-amino-3-(methyloxy)phenyl]-4-piperidinol

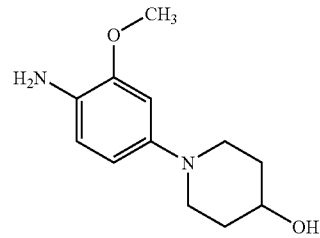

The title compound of step A (2.44 g, 11.0 mmol, 63% over 2 steps) was prepared by reduction of 1-[3-(methyloxy)-4-nitrophenyl]-4-piperidinol (Example 57, step A) in a manner analogous to that described in Example 57, step E. $^1$H NMR (400 MHz, DMSO-d$_6$) δ 6.49-6.45 (m, 2H), 6.27 (dd, J=8.4 and 2.4 Hz, 1H), 4.60 (d, J=4.0 Hz, 1H), 4.18 (s, 2H), 3.71 (s, 3H), 3.54-3.48 (m, 1H), 3.25-3.22 (m, 2H), 2.63-2.56 (M, 2H), 1.80-1.76 (m, 2H), 1.51-1.42 (m, 2H).

Step B: N-(2,6-difluorophenyl)-3-[3-(2-{[4-(4-hydroxy-1-piperidinyl)-2-(methyloxy)phenyl]amino}-4-pyrimidinyl)imidazo[1,2-a]pyridin-2-yl]benzamide A mixture of Intermediate Example 3 (730 mg, 2.0 mmol), 1-[4-amino-3-(methyloxy)phenyl]-4-piperidinol (400 mg, 1.8 mmol) and p-toluenesulfonic acid (761 mg, 4.0 mmol) in 3 mL iPrOH was heated in the microwave at 180° C. for 12 min. This was continued until there was conversion to both the methyl and isopropyl ester product. The reaction was taken up in DCM and concentrated onto silica gel. The crude material was purified by flash column chromatography to quickly get rid of the p-toluenesulfonic acid by-products. The crude material and 2,6-difluoroaniline were coupled by a method analogous to that described in Example 9, step B to give 261 mg (37% over 2 steps) of the title compound. $^1$H NMR (400 MHz, DMSO-d$_6$) δ 10.22 (s, 1H), 9.38 (br s, 1H), 8.43 (s, 1H), 8.31 (s, 1H), 8.18 (d, J=4.8 Hz, 1H), 8.03 (d, J=7.6 Hz, 1H), 7.80 (d, J=7.6 Hz, 1H), 7.70 (d, J=8.8 Hz, 1H), 7.59 (t, J=7.6 Hz, 1H), 7.46-7.35 (m, 3H), 7.19 (m, 2H), 6.96 (t, J=6.6 Hz, 1H), 6.47-6.43 (m, 2H), 4.64 (d, J=4.0 Hz, 1H), 3.77 (s, 3H), 3.61-3.50 (m, 3H), 2.84-2.78 (m, 2H), 1.82-1.79 (m, 2H), 1.51-1.44 (m, 2H). MS (ESI) m/z=648 [M+H]+.

Example 74

N-(2,6-difluorophenyl)-3-[3-(2-{[4-[4-(dimethylamino)-1-piperidinyl]-2-(methyloxy)phenyl]amino}-4-pyrimidinyl)imidazo[1,2-a]pyridin-2-yl]benzamide

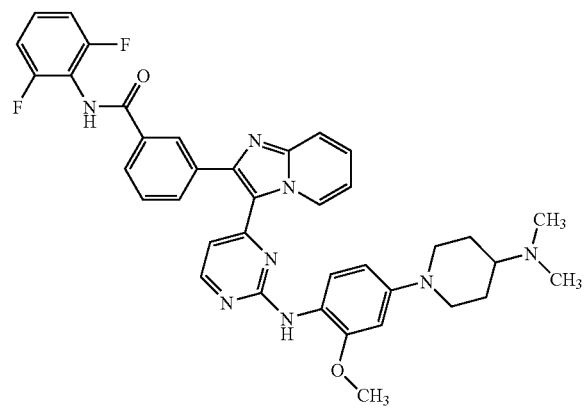

Step A: N,N-dimethyl-1-[3-(methyloxy)-4-nitrophenyl]-4-piperidinamine

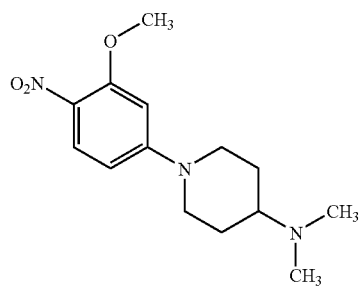

To a solution of 1-[3-(methyloxy)-4-nitrophenyl]-4-piperidinone (Example 57, step B; 1.41 g, 5.6 mmol) in 50 mL 1,2-dichloroethane was added a solution of dimethylamine (2M in THF, 5.6 mL, 11.2 mmol), HOAc (1.3 mL, 22.4 mmol) and sodium triacetoxyborohydride (1.78 g, 8.4 mmol). When TLC indicated the reaction to be complete, the solution was diluted with H₂O and extracted with DCM. The aqueous phase was brought to pH>7 with the addition of saturated NaHCO₃. This was extracted twice with DCM and EtOAc. The combined organic phases were dried over MgSO₄ and concentrated to give 1.37 g (88%) of the desired product. ¹H NMR (400 MHz, DMSO-d₆) δ 7.84 (d, J=9.6 Hz, 1H), 6.54 (dd, J=9.4 and 2.2 Hz, 1H), 6.46 (d, J=2.0 Hz, 1H), 3.99 (d, J=13.2 Hz, 1H), 3.87 (s, 3H), 2.96-2.89 (m, 2H), 2.35-2.30 (m, 1H), 2.15 (s, 6H), 1.79 (d, J=11.6 Hz, 2H), 1.42-1.32 (m, 2H).

Step B: 1-[4-amino-3-(methyloxy)phenyl]-N,N-dimethyl-4-piperidinamine

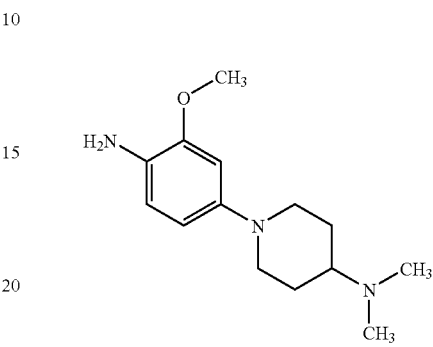

To a solution of nickel (II) chloride hexahydrate (0.58 g, 2.5 mmol) and N,N-dimethyl-1-[3-(methyloxy)-4-nitrophenyl]-4-piperidinamine (1.37 g, 4.90 mmol) in MeOH (25 mL) cooled to 0° C. was added NaBH₄ (280 mg, 7.4 mmol) slowly to avoid foaming. When TLC indicated the consumption of starting material, the solution was concentrated to a purple residue. The purple residue was taken up in EtOAc and filtered through a pad of celite. The yellow filtrate was concentrated onto silica gel and purified by flash column chromatography to give the title compound of step B (0.88 g, 74%). ¹H NMR (400 MHz, DMSO-d₆) δ 6.48-6.45 (m, 2H), 6.26 (dd, J=8.2 and 2.2 Hz, 1H), 4.17 (br s, 2H), 3.70 (s, 3H), 3.38 (d, J=12.4 Hz, 2H), 2.49-2.43 (m under DMSO peak, 2H), 2.16 (s, 6H), 2.11-2.04 (m, 1H), 1.78 (d, J=12.4 Hz, 2H), 1.50-1.40 (m, 2H).

Step C: N-(2,6-difluorophenyl)-3-[3-(2-{[4-[4-(dimethylamino)-1-piperidinyl]-2-(methyl-oxy)phenyl]amino}-4-pyrimidinyl)imidazo[1,2-a]pyridin-2-yl]benzamide 3-[3-(2-chloro-4-pyrimidinyl)imidazo[1,2-a]pyridin-2-yl]-N-(2,6-difluorophenyl)-benzamide (Intermediate Example 1) (140 mg, 0.30 mmol), 1-[4-amino-3-(methyloxy)phenyl]-N,N-dimethyl-4-piperidinamine (67 mg, 0.27 mmol) and p-toluenesulfonic acid (140 mg, 0.71 mmol) in iPrOH was heated in the microwave at 180° C. for 13.5 min. The mixture was dissolved in DCM and concentrated onto silica gel. The crude material was purified by flash column chromatography to give the title compound (142 mg, 70%). ¹H NMR (400 MHz, DMSO-d₆) δ 10.23 (s, 1H), 9.40 (s, 1H), 8.45 (s, 1H), 8.33 (s, 1H), 8.20 (d, J=5.2 Hz, 1H), 8.05 (d, J=8.0 Hz, 1H), 7.81 (d, J=7.6 Hz, 1H), 7.72 (d, J=8.8 Hz, 1H), 7.60 (t, J=7.6 Hz, 1H), 7.48-7.36 (m, 3H), 7.20 (t, J=8.2 Hz, 2H), 6.97 (t, J=6.8 Hz, 1H), 6.67 (m, 1H), 6.49-6.45 (m, 2H), 3.79 (s, 3H), 3.70 (d, J=12.4 Hz, 2H), 2.68-2.63 (m, 2H), 2.18 (s, 7H), 1.84-1.81 (m, 2H), 1.52-1.44 (m, 2H). MS (ESI) m/z=675 [M+H]+.

Example 75

3-[3-(2-{[4-(3,3-difluoro-1,4'-bipiperidin-1'-yl)-2-(methyloxy)phenyl]amino}-4-pyrimidinyl)imidazo[1,2-a]pyridin-2-yl]-N-(2,6-difluorophenyl)benzamide

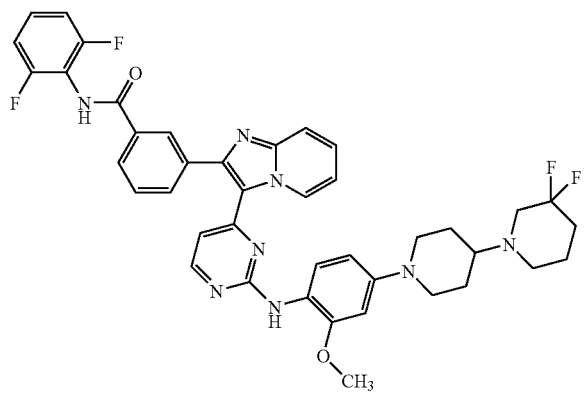

The title compound (0.106 g, 0.141 mmol, 52% in final step) was prepared in an analogous manner to that described for Example 74 with the following notable exception: 3,3-difluoropiperidine was used instead of dimethylamine in Example 74, step A. $^1$H NMR (400 MHz, DMSO-$d_6$) δ 10.21 (s, 1H), 9.38 (s, 1H), 8.43 (s, 1H), 8.31 (s, 1H), 8.18 (d, J=5.2 Hz, 1H), 8.03 (d, J=7.6 Hz, 1H), 7.80 (d, J=7.6 Hz, 1H), 7.70 (d, J=9.2 Hz, 1H), 7.59 (t, J=7.6 Hz, 1H), 7.46-7.36 (m, 3H), 7.18 (t, J=8.2 Hz, 2H), 6.97-6.94 (m, 1H), 6.65 (s, 1H), 6.47-6.43 (M, 2H), 3.78 (s, 3H), 3.74-3.71 (m, 2H), 2.75-2.61 (m, 4H), 2.47 (m under DMSO, 3H), 1.87-1.75 (m, 4H), 1.60-1.49 (m, 4H). MS (ESI) m/z=751 [M+H]$^+$.

Example 76

N-(2,6-difluorophenyl)-3-[3-(2-{[4-{4-[(3R)-3-fluoro-1-pyrrolidinyl]-1-piperidinyl}-2-(methyloxy)phenyl]amino}-4-pyrimidinyl)imidazo[1,2-a]pyridin-2-yl]benzamide

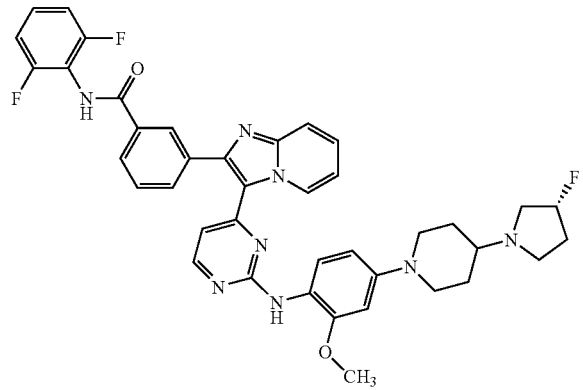

The title compound (0.123 g, 0.171 mmol, 63% in final step) was prepared in an analogous manner to that described for Example 74 with the following notable exception: (3R)-3-fluoropyrrolidine was used instead of dimethylamine in Example 74, step A. $^1$H NMR (400 MHz, DMSO-$d_6$) δ 10.22 (s, 1H), 9.38 (br s, 1H), 8.44 (s, 1H), 8.31 (s, 1H), 8.18 (d, J=5.2 Hz, 1H), 8.03 (d, J=8.0 Hz, 1H), 7.79 (d, J=8.0 Hz, 1H), 7.70 (d, J=8.8 Hz, 1H), 7.59 (t, J=7.8 Hz, 1H), 7.46-7.36 (m, 3H), 7.19 (t, J=8.2 Hz, 2H), 6.98-6.94 (m 1H), 6.66 (d, J=2.0 Hz, 1H), 6.48-6.43 (m, 2H), 5.24-5.10 (m, 1H), 3.77 (s, 3H), 3.64-3.60 (m, 2H), 2.90-2.59 (m, 5H), 2.36-2.34 (m, 1H), 2.15-2.02 (m, 2H), 1.90-1.80 (m, 3H), 1.53-1.45 (m, 2H). MS (ESI) m/z=719 [M+H]$^+$.

Example 77

N-(2,6-difluorophenyl)-3-[3-(2-{[4-{4-[(3S)-3-fluoro-1-pyrrolidinyl]-1-piperidinyl}-2-(methyloxy)phenyl]amino}-4-pyrimidinyl)imidazo[1,2-a]pyridin-2-yl]benzamide

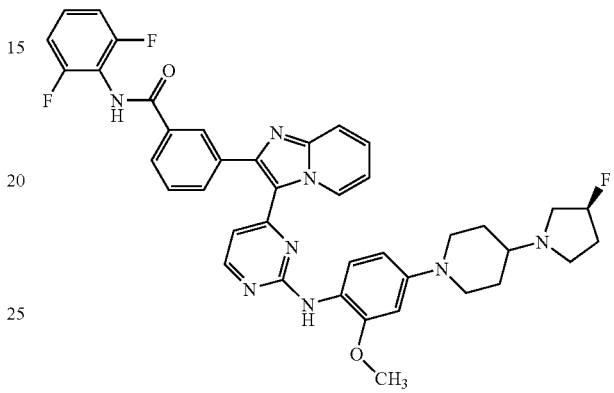

The title compound (0.109 g, 0.152 mmol, 56% in final step) was prepared in an analogous manner to that described for Example 74 with the following notable exception: (3S)-3-fluoropyrrolidine was used instead of dimethylamine in Example 74, step A. $^1$H NMR (400 MHz, DMSO-$d_6$) δ 10.22 (s, 1H), 9.38 (br s, 1H), 8.44 (s, 1H), 8.31 (s, 1H), 8.18 (d, J=5.2 Hz, 1H), 8.03 (d, J=8.0 Hz, 1H), 7.79 (d, J=8.0 Hz, 1H), 7.70 (d, J=8.8 Hz, 1H), 7.59 (t, J=7.8 Hz, 1H), 7.46-7.36 (m, 3H), 7.19 (t, J=8.2 Hz, 2H), 6.98-6.94 (m 1H), 6.66 (d, J=2.0 Hz, 1H), 6.48-6.43 (m, 2H), 5.24-5.10 (m, 1H), 3.77 (s, 3H), 3.64-3.60 (m, 2H), 2.90-2.59 (m, 5H), 2.36-2.34 (m, 1H), 2.15-2.02 (m, 2H), 1.90-1.80 (m, 3H), 1.53-1.45 (m, 2H). MS (ESI) m/z=719 [M+H]$^+$.

Example 78

N-(2,6-difluorophenyl)-3-{3-[2-({2-(methyloxy)-4-[4-(1-pyrrolidinyl)-1-piperidinyl]-phenyl}amino)-4-pyrimidinyl]imidazo[1,2-a]pyridin-2-yl}benzamide

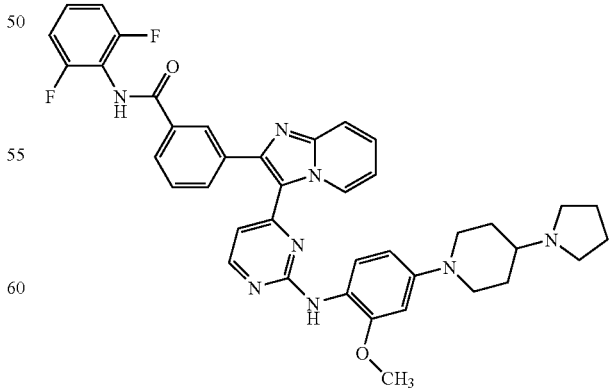

The title compound (0.128 g, 0.183 mmol, 68% in final step) was prepared in an analogous manner to that described for Example 74 with the following notable exception: pyrrolidine was used instead of dimethylamine in Example 74, step A. $^1$H NMR (400 MHz, DMSO-d$_6$) δ 10.21 (s, 1H), 9.37 (br s, 1H), 8.42 (s, 1H), 8.30 (s, 1H), 8.17 (d, J=4.8 Hz, 1H), 8.03 (d, J=8.0 Hz, 1H), 7.79 (d, J=7.6 Hz, 1H), 7.70 (d, J=9.2 Hz, 1H), 7.58 (t, J=7.6 Hz, 1H), 7.45-7.35 (m, 3H), 7.18 (t, J=8.0 Hz, 2H), 6.95 (t, J=6.6 Hz, 1H), 6.65-6.64 (m, 1H), 6.46-6.43 (m, 2H), 3.76 (s, 3H), 3.62-3.59 (m, 2H), 2.72-2.66 (m, 2H), 2.46 (m under DMSO peak, 4H), 2.07 (m, 1H), 1.90-1.87 (m, 2H), 1.64 (m, 4H), 1.53-1.44 (m, 2H). MS (ESI) m/z=701 [M+H]$^+$.

Example 79

N-(2,6-difluorophenyl)-3-{3-[2-({2-(methyloxy)-4-[4-(4-methyl-1-piperazinyl)-1-piperidinyl]phenyl}amino)-4-pyrimidinyl]imidazo[1,2-a]pyridin-2-yl}benzamide

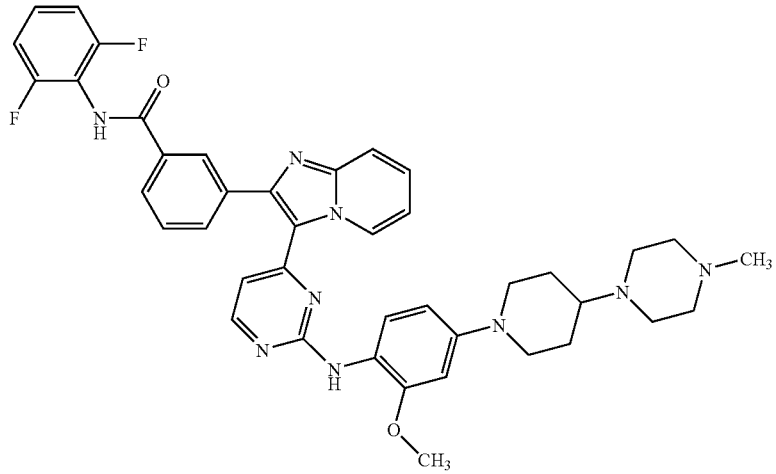

The title compound (0.144 g, 0.197 mmol, 73% in final step) was prepared in an analogous manner to that described for Example 74 with the following notable exception: N-methylpiperazine was used instead of dimethylamine in Example 74, step A. $^1$H NMR (400 MHz, DMSO-d$_6$) δ 10.22 (s, 1H), 9.38 (brs, 1H), 8.44 (s, 1H), 8.31 (s, 1H), 8.19 (dd, J=5.2 and 1.6 Hz, 1H), 8.04 (d, J=8.0 Hz, 1H), 7.80 (d, J=8.0 Hz, 1H), 7.71 (d, J=9.2 Hz, 1H), 7.59 (t, J=7.8 Hz, 1H), 7.46-7.35 (m, 3H), 7.19 (t, J=8.0 Hz, 2H), 6.96 (t, J=6.8 Hz, 1H), 6.65 (d, J=2.0 Hz, 1H), 6.47-6.44 (m, 2H), 3.78 (s, 3H), 3.72-3.69 (m, 2H), 2.67-2.61 (m, 2H), 2.49-2.47 (m under DMSO peak, 5H), 2.38-2.20 (m, 4H), 2.11 (s, 3H), 1.83-1.80 (m, 2H), 1.53-1.44 (m, 2H). MS (ESI) m/z=730 [M+H]$^+$.

Example 80

N-(2,6-difluorophenyl)-3-[3-(2-{[4-(4-hydroxy-1,4'-bipiperidin-1'-yl)-2-(methyloxy)-phenyl]amino}-4-pyrimidinyl)imidazo[1,2-a]pyridin-2-yl]benzamide

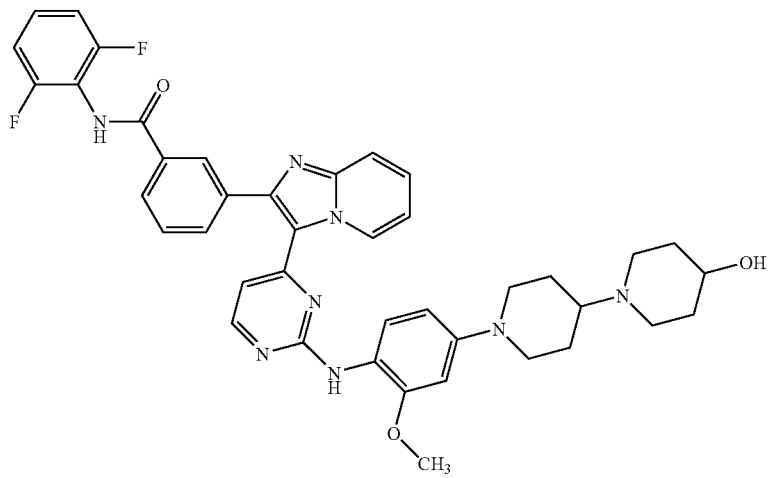

The title compound (0.142 g, 0.194 mmol, 72% in final step) was prepared in an analogous manner to that described for Example 74 with the following notable exceptions:
a) 4-piperidinol was used instead of dimethylamine in Example 74, step A;
b) H$_2$ (1 atm) and platinum on carbon in EtOAc/MeOH were used instead of nickel(II)chloride hexahydrate and NaBH$_4$ in MeOH in the nitro reduction procedure described in Example 74, step B.

$^1$H NMR (400 MHz, DMSO-d$_6$) δ 10.20 (s, 1H), 9.36 (br s, 1H), 8.41 (s, 1H), 8.30 (s, 1H), 8.17 (d, J=5.2 Hz, 1H), 8.02 (d, J=7.6 Hz, 1H), 7.78 (d, J=7.6 Hz, 1H), 7.69 (d, J=8.8 Hz, 1H), 7.57 (t, J=7.8 Hz, 1H), 7.44-7.33 (m, 3H), 7.19-7.15 (M, 2H), 6.94 (t, J=6.4 Hz, 1H), 6.63 (s, 1H), 6.45-6.42 (m, 2H), 4.46 (d, J=4.0 Hz, 1H), 3.76 (s, 3H), 3.71-3.68 (m, 2H), 3.36 (m, 1H), 2.72 (m, 2H), 2.64-2.58 (m, 2H), 2.31 (m, 1H), 2.17-2.12 (m, 2H), 1.77-1.74 (m, 2H), 1.68-1.66 (m, 2H), 1.53-1.45 (m, 2H), 1.30 (m, 1H). MS (ESI) m/z=731 [M+H]$^+$.

Example 81

N-(2,6-difluorophenyl)-5-[3-(2-{[4-(4-hydroxy-1,4'-bipiperidin-1'-yl)-2-(methyloxy)phenyl]-amino}-4-pyrimidinyl)imidazo[1,2-a]pyridin-2-yl]-2-(methyloxy)benzamide

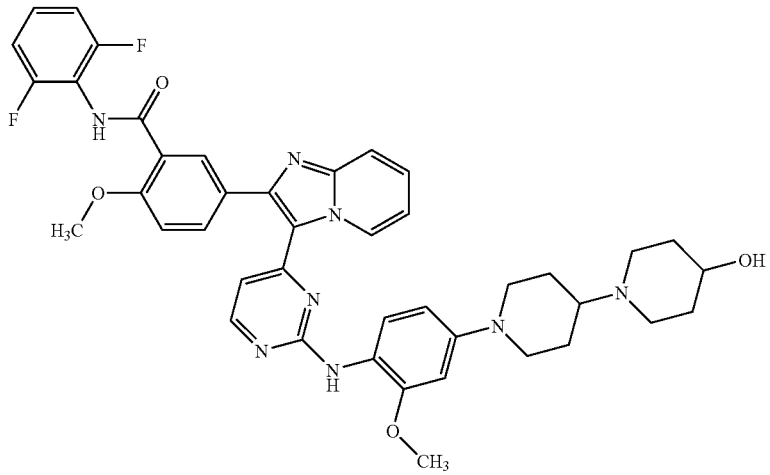

The title compound (0.144 g, 0.189 mmol, 70% in final step) was prepared in an analogous manner to that described for Example 74 with the following notable exceptions:
a) 4-piperidinol was used instead of dimethylamine in Example 74, step A;
b) H$_2$ (1 atm) and platinum on carbon in EtOAc/MeOH were used instead of nickel(II)chloride hexahydrate and NaBH$_4$ in MeOH in the nitro reduction procedure described in Example 74, step B;
c) 5-[3-(2-chloro-4-pyrimidinyl)imidazo[1,2-a]pyridin-2-yl]-N-(2,6-difluorophenyl)-2-(methyloxy)benzamide (Intermediate Example 2) was used instead of Intermediate Example 1 in Example 74, step C.

$^1$H NMR (400 MHz, DMSO-d$_6$) δ 9.75 (s, 1H), 9.32 (s, 1H), 8.40 (s, 1H), 8.17 (d, J=5.2 Hz, 1H), 8.07 (s, 1H), 7.74 (d, J=8.4 Hz, 1H), 7.66 (d, J=8.8 Hz, 1H), 7.41-7.32 (m, 3H), 7.25 (d, J=8.8 Hz, 1H), 7.15 (t, J=8.0 Hz, 2H), 6.91 (t, J=6.6 Hz, 1H), 6.62 (s, 1H), 6.50-6.43 (m, 2H), 4.46 (d, J=3.6 Hz, 1H), 3.95 (s, 3H), 3.76 (s, 3H), 3.71-3.68 (m, 2H), 3.37-3.36 (M, 2H), 2.74-2.71 (m, 2H), 2.61 (t, J=11.8 Hz, 2H), 2.31 (m, 1H), 2.17-2.12 (m, 2H), 1.77-1.74 (m, 2H), 1.68-1.66 (m, 2H), 1.53-1.45 (M, 2H), 1.34-1.27 (m, 2H). MS (ESI) m/z=761 [M+H]$^+$.

Example 82

3-[3-(2-{[4-(1,4'-bipiperidin-1'-yl)phenyl]amino}-4-pyrimidinyl)imidazo[1,2-a]pyridin-2-yl]-N-(2,6-difluorophenyl)benzamide

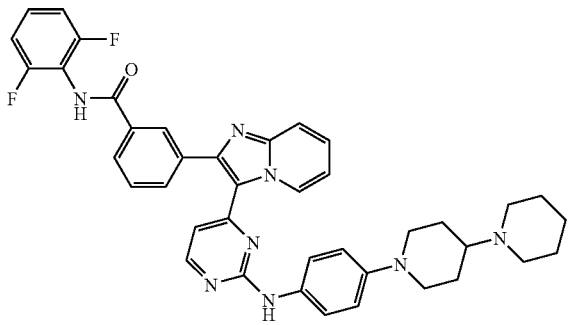

The title compound (0.119 g, 0.174 mmol, 64% in final step) was prepared in an analogous manner to that described for Example 22 with the following notable exceptions:
a) 1-fluoro-4-nitrobenzene was used instead of 5-fluoro-2-nitrophenyl methyl ether in the procedure described in Example 22, step B;
b) p-toluenesulfonic acid in iPrOH under microwave conditions at 180° C. were used rather than concentrated HCl in trifluoroethanol at 85° C. in the procedure described in Example 22, step D.

$^1$H NMR (400 MHz, DMSO-d$_6$) δ 10.22 (s, 1H), 9.46 (m, 2H), 8.35 (s, 1H), 8.27 (d, J=5.2 Hz, 1H), 8.03 (d, J=8.0 Hz, 1H), 7.82 (d, J=7.6 Hz, 1H), 7.74 (d, J=9.2 Hz, 1H), 7.59 (t, J=7.8 Hz, 1H), 7.49-7.46 (m, 3H), 7.40-7.36 (m, 1H), 7.19 (t, J=8.0 Hz, 2H), 7.04 (t, J=6.8 Hz, 1H), 6.85 (d, J=8.8 Hz, 1H), 6.53 (d, J=4.8 Hz, 1H), 3.62-3.59 (m, 2H), 2.57-2.43 (m under DMSO peak, 7H), 2.30-2.27 (m, 1H), 1.76-1.73 (m, 2H), 1.55-1.45 (m, 6H), 1.36-1.34 (m, 1H). MS (ESI) m/z=685 [M+H]$^+$.

Example 83

N-(2,6-difluorophenyl)-3-[3-(2-{[4-[(3S)-3-hydroxy-1,4'-bipiperidin-1'-yl]-2-(methyloxy)phenyl]amino}-4-pyrimidinyl)imidazo[1,2-a]pyridin-2-yl]benzamide

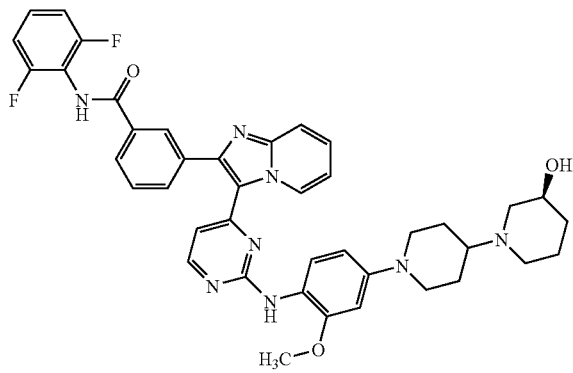

The title compound (0.046 g, 0.063 mmol, 29% in final step) was prepared in an analogous manner to that described for Example 74 with the following notable exception: (3S)-3-piperidinol was used instead of dimethylamine in Example 74, step A. $^1$H NMR (400 MHz, DMSO-$d_6$) δ 10.23 (s, 1H), 9.44-9.37 (m, 1H), 8.44 (s, 1H), 8.33-8.31 (m, 1H), 8.19 (d, J=5.1 Hz, 1H), 8.07-8.04 (m, 1H), 7.82-7.78 (m, 1H), 7.72 (d, J=8.8 Hz, 1H), 7.60 (at, J=7.9 Hz, 1H), 7.50-7.36 (m, 3H), 7.23-7.17 (m, 2H), 7.00-6.95 (m, 1H), 6.67-6.64 (m, 1H), 6.52-6.42 (m, 2H), 3.79 (s, 3H), 3.77-3.70 (m, 2H), 3.48-3.37 (bm, 1H), 2.90-2.83 (bm, 1H), 2.73-2.59 (m, 3H), 2.44-2.30 (bm, 2H), 2.10-1.96 (bm, 2H), 1.95-1.85 (bm, 1H), 1.84-1.72 (m, 2H), 1.66-1.44 (bm, 3H), 1.43-1.28 (bm, 2H). MS (APCI$^+$, m/z) 731 (M+1).

Example 84

N-(2,6-difluorophenyl)-5-[3-(2-{[4-[(3S)-3-hydroxy-1,4'-bipiperidin-1'-yl]-2-(methyloxy)-phenyl]amino}-4-pyrimidinyl)imidazo[1,2-a]pyridin-2-yl]-2-(methyloxy)benzamide

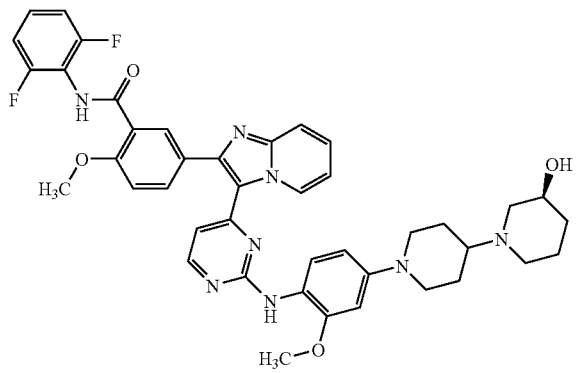

The title compound (0.030 g, 0.039 mmol, 19% in final step) was prepared in an analogous manner to that described for Example 74 with the following notable exceptions:
a) (3S)-3-piperidinol was used instead of dimethylamine in Example 74, step A.
b) 5-[3-(2-chloro-4-pyrimidinyl)imidazo[1,2-a]pyridin-2-yl]-N-(2,6-difluorophenyl)-2-(methyloxy)benzamide (Intermediate Example 2) was used instead of Intermediate Example 1 in the procedure described in Example 74, step C.

$^1$H NMR (400 MHz, DMSO-$d_6$) δ 9.78 (s, 1H), 9.40-9.32 (m, 1H), 8.45-8.41 (m, 1H), 8.22-8.18 (m, 1H), 8.12-8.07 (m, 1H), 7.79-7.73 (m, 1H), 7.71-7.66 (m, 1H), 7.46-7.35 (m, 3H), 7.32-7.25 (m, 1H), 7.23-7.14 (m, 2H), 6.97-6.92 (m, 1H), 6.72-6.65 (m, 1H), 6.54-6.45 (m, 2H), 4.55-4.52 (m, 1H), 3.98 (s, 3H), 3.81-3.70 (m, 5H), 3.50-3.35 (m, 2H), 2.89-2.82 (m, 1H), 2.74-2.57 (m, 3H), 2.43-2.31 (m, 2H), 2.14-1.97 (m, 2H), 1.90-1.85 (m, 1H), 1.83-1.71 (m, 2H), 1.64-1.45 (m, 3H), 1.41-1.30 (m, 1H). MS (APCI$^+$, m/z) 761 (M+1).

Example 85

N-(2,6-difluorophenyl)-3-{3-[2-({2-(methyloxy)-4-[4-(4-thiomorpholinyl)-1-piperidinyl]phenyl}amino)-4-pyrimidinyl]imidazo[1,2-a]pyridin-2-yl}benzamide

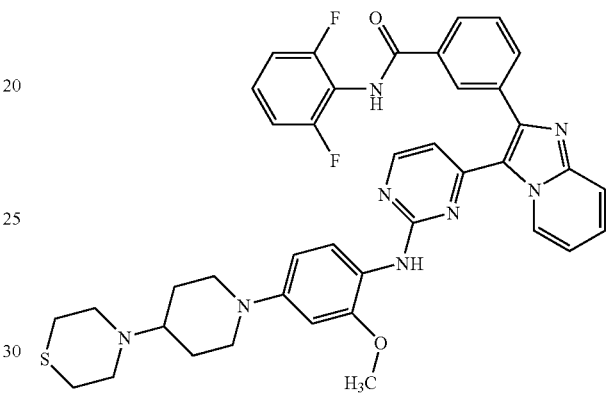

The title compound (0.150 g, 0.200 mmol, 31% in final step) was prepared in an analogous manner to that described for Example 74 with the following notable exception: thiomorpholine was used instead of dimethylamine in Example 74, step A. $^1$H NMR (400 MHz, DMSO-$d_6$) δ 10.16 (s, 1H), 9.32 (br s, 1H), 8.38 (s, 1H), 8.25 (s, 1H), 8.12 (d, J=5.3 Hz, 1H), 7.97 (d, J=7.7 Hz, 1H), 7.74 (d, J=7.7 Hz, 1H), 7.65 (d, J=9.0 Hz, 1H), 7.53 (dd, J=7.7, 7.7 Hz, 1H), 7.42-7.25 (m, 3H), 7.13 (dd, J=8.1, 8.1 Hz, 2H), 6.90 (dd, J=6.8, 6.8 Hz, 1H), 6.58 (s, 1H), 6.43-6.35 (m, 2H), 3.71 (s, 3H), 3.68 (d, J=12.1 Hz, 2H), 2.72-2.66 (m, 4H), 2.60-2.47 (m, 5H), 2.40-2.32 (m, 2H), 1.69-1.62 (m, 2H), 1.57-1.43 (m, 2H).

Example 86

N-(2,6-difluorophenyl)-3-[3-(2-{[4-{4-[(1S,4S)-5-(2-fluoroethyl)-2,5-diazabicyclo-[2.2.1]hept-2-yl]-1-piperidinyl}-2-(methyloxy)phenyl]amino}-4-pyrimidinyl)imidazo[1,2-a]pyridin-2-yl]benzamide

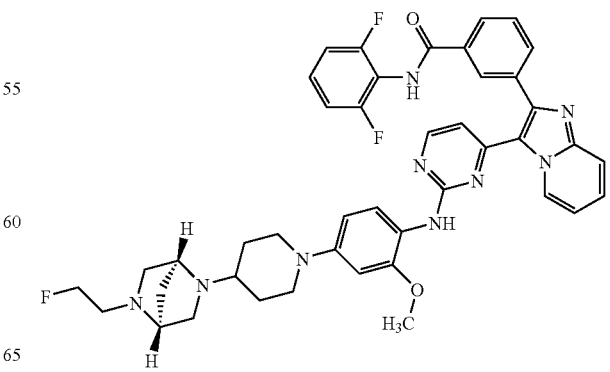

Step A: 1,1-dimethylethyl (1S,4S)-5-{1-[3-(methyloxy)-4-nitrophenyl]-4-piperidinyl}-2,5-diazabicyclo[2.2.1]heptane-2-carboxylate

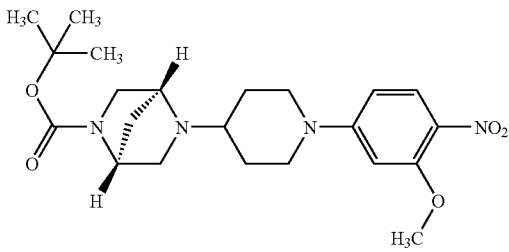

To 1-[3-(methyloxy)-4-nitrophenyl]-4-piperidinone (Example 57, step B) (0.63 g, 2.5 mmol), 1,1-dimethylethyl (1S,4S)-2,5-diazabicyclo[2.2.1]heptane-2-carboxylate (1.0 g, 5.0 mmol), HOAc (0.23 g, 3.8 mmol), TEA (0.25 g, 2.5 mmol) in DCM (20 mL) is added sodium triacetoxyborohydride (0.81 g, 3.8 mmol). The mixture was stirred for 1 h then poured into saturated NaHCO$_3$ solution (30 mL). The layers are separated and the aqueous layer washed with DCM. The organics are combined, dried (MgSO$_4$), filtered and rotovaped. DCM and silica are added and the solvent removed by rotovap. After purification by silica gel chromatography, the title compound of step A (1.0 g, 2.4 mmol, 96%) is obtained as a yellow foam. $^1$H NMR (400 MHz, CDCl$_3$) δ 7.97 (d, J=9.3 Hz, 1H), 6.39 (dd, J=9.3, 2.0 Hz, 1H), 6.28 (d, J=2.0 Hz, 1H), 4.36-4.20 (m, 1H), 3.91 (s, 3H), 3.79-3.40 (m, 4H), 3.16-3.01 (m, 4H), 2.64-2.37 (m, 2H), 1.93-1.68 (m, 4H), 1.61-1.49 (m, 2H), 1.44 (s, 9H).

Step B: (1S,4S)-2-{1-[3-(methyloxy)-4-nitrophenyl]-4-piperidinyl}-2,5-diazabicyclo-[2.2.1]heptane

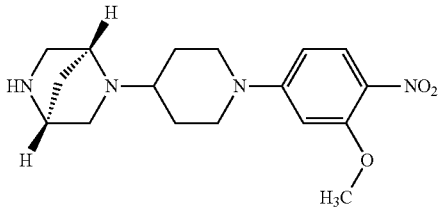

To 1,1-dimethylethyl (1S,4S)-5-{1-[3-(methyloxy)-4-nitrophenyl]-4-piperidinyl}-2,5-diazabicyclo[2.2.1]heptane-2-carboxylate (1.0 g, 2.3 mmol) in DCM (10 mL) was added TFA (10 mL). After reaction was shown to be complete by TLC, the volume is reduced on the rotovap until it weighs 4 g. The solution is diluted with DCM and poured into saturated NaHCO$_3$ solution. The layers are separated and the aqueous layer washed with DCM. The organics are combined, dried (MgSO$_4$), filtered and rotovaped to give the title compound of step B (400 mg, 1.2 mmol, 50%). $^1$H NMR (400 MHz, CDCl$_3$) δ 7.95 (d, J=9.3 Hz, 1H), 6.37 (dd, J=9.3, 2.6 Hz, 1H), 6.27 (d, J=2.6 Hz, 1H), 3.90 (s, 3H), 3.80-3.73 (m, 2H), 3.60 (br s, 2H), 3.20 (d, J=10.6 Hz, 1H), 3.12-2.95 (m, 4H), 2.87-2.81 (m, 1H), 2.64-2.55 (m, 1H), 2.36 (d, J=9.3 Hz, 1H), 1.94-1.77 (m, 3H), 1.64 (d, J=9.3 Hz, 1H), 1.59-1.46 (m, 2H). The aqueous layer is re-extracted with EtOAc and then with 85:15 DCM:iPrOH to give more of the title compound of step B (400 mg, 1.2 mmol, 50%).

Step C: (1S,4S)-2-(2-fluoroethyl)-5-{1-[3-(methyloxy)-4-nitrophenyl]-4-piperidinyl}-2,5-diazabicyclo[2.2.1]heptane

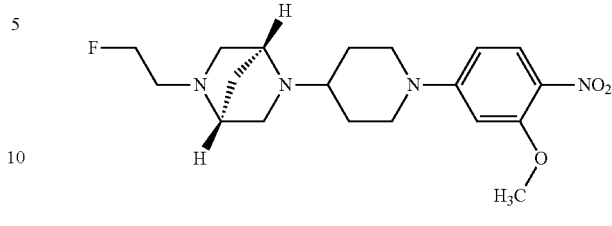

To (1S,4S)-2-{1-[3-(methyloxy)-4-nitrophenyl]-4-piperidinyl}-2,5-diazabicyclo-[2.2.1]heptane (0.40 g, 1.2 mmol) and K$_2$CO$_3$ (0.38 g, 2.8 mmol) in DMF (10 mL) was added 1-iodo-2-fluoroethane (0.26 g, 1.5 mmol), and the reaction was stirred overnight. More 1-iodo-2-fluoroethane (50 mg, 0.29 mmol) was added, and the solution stirred an additional 4 h. The solvent was removed under vacuum, and the residue was taken up in DCM. Silica was added, and the solvent removed under vacuum. Silica gel chromatography provided the title compound of step C as a yellow oil (230 mg, 0.61 mmol, 49% yield). $^1$H NMR (400 MHz, CDCl$_3$) δ 7.96 (d, J=9.3 Hz, 1H), 6.38 (dd, J=9.3, 2.4 Hz, 1H), 6.27 (d, J=2.4 Hz, 1H), 4.58-4.39 (m, 2H), 3.91 (s, 3H), 3.82-3.73 (m, 2H), 3.51 (br s, 1H), 3.34 (br s, 1H), 3.08-2.98 (m, 2H), 2.96-2.53 (m, 7H), 1.96-1.65 (m, 4H), 1.59-1.46 (m, 2H).

Step D: 4-{4-[(1S,4S)-5-(2-fluoroethyl)-2,5-diazabicyclo[2.2.1]hept-2-yl]-1-piperidinyl}-2-(methyloxy)aniline

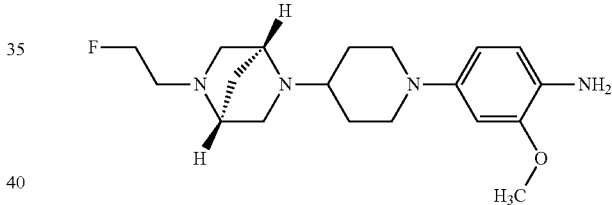

To (1S,4S)-2-(2-fluoroethyl)-5-{1-[3-(methyloxy)-4-nitrophenyl]-4-piperidinyl}-2,5-diazabicyclo[2.2.1]heptane (0.22 g, 0.58 mmol) in EtOAc (10 mL) was added Pd (10%) on carbon (50 mg). The reaction was evacuated then refilled with H$_2$ gas from a balloon. The reaction was stirred under a balloon atmosphere of H$_2$ for 4 days. The reaction was evacuated and the atmosphere replaced with N$_2$. The solution was filtered to remove Pd/C and rotovaped down to give the title compound of step D as a purple oil (200 mg, 0.57 mmol, 98% yield). $^1$H NMR (400 MHz, CDCl$_3$) δ 6.62 (d, J=8.4 Hz, 1H), 6.51 (d, J=2.6 Hz, 1H), 6.41 (dd, J=8.4, 2.6 Hz, 1H), 4.62-4.39 (m, 2H), 3.82 (s, 3H), 3.57 (br s, 1H), 3.47-3.38 (m, 2H), 3.35 (br s, 1H), 2.98-2.56 (m, 8H), 2.46-2.39 (m, 1H), 1.97-1.53 (m, 6H).

Step E: N-(2,6-difluorophenyl)-3-[3-(2-{[4-{4-[(1S,4S)-5-(2-fluoroethyl)-2,5-diazabicyclo-[2.2.1]hept-2-yl]-1-piperidinyl}-2-(methyloxy)phenyl]amino}-4-pyrimidinyl)imidazo[1,2-a]pyridin-2-yl]benzamide To 3-[3-(2-chloro-4-pyrimidinyl)imidazo[1,2-a]pyridin-2-yl]-N-(2,6-difluorophenyl)-benzamide (Intermediate Example 1) (260 mg, 0.57 mmol) and 4-{4-[(1S,4S)-5-(2-fluoroethyl)-2,5-diazabicyclo[2.2.1]hept-2-yl]-1-piperidinyl}-2-(methyloxy)aniline (200 mg, 0.57 mmol) in trifluoroethanol (2 mL) was added concentrated HCl (0.14 mL, 1.7 mmol). The reaction was heated in a sealed-tube at 85° C. for two days. After cooling to rt 0.5 N sodium methoxide in MeOH (4 mL) was added to the reaction. The solvent was removed under vacuum. DCM and silica gel were added, and the solvent removed under vacuum. The material was purified by flash chromatography. The desired fractions were combined and the solvent removed on the rotovap to give product. The material was dissolved in DCM then diethyl ether was added until the solution just turns cloudy. The solution was placed in the refrigerator. The title compound was obtained as yellow crystals which were collected by vacuum filtration, washing with ether. (120 mg, 0.15 mmol, 27% yield). $^1$H NMR (400 MHz, DMSO-d$_6$) δ10.16 (s, 1H), 9.31 (brs, 1H), 8.38 (s, 1H), 8.25 (s, 1H), 8.12 (d, J=5.1 Hz, 1H), 7.97 (d, J=7.7 Hz, 1H), 7.73 (d, J=7.5 Hz, 1H), 7.64 (d, J=9.0 Hz, 1H), 7.53 (dd, J=7.9, 7.7 Hz, 1H), 7.42-7.25 (m, 3H), 7.12 (dd, J=8.1, 8.1 Hz, 2H), 6.89 (dd, J=6.6, 6.6 Hz, 1H), 4.34 (dt, J=47.6, 4.9 Hz, 2H), 3.71 (s, 3H), 3.52 (d, J=11.7 Hz, 2H), 3.39 (s, 1H), 3.17 (s, 1H), 2.82-2.54 (m, 6H), 2.51 (d, J=9.3 Hz, 1H), 2.42-2.30 (m under DMSO peak, 2H), 1.78 (d, J=11.9 Hz, 1H), 1.69 (d, J=11.9 Hz, 1H), 1.50 (d, J=8.8 Hz, 1H), 1.42 (d, J=8.8 Hz, 1H), 1.38-1.25 (m, 2H).

Example 87

N-(2,6-difluorophenyl)-3-[3-(2-{[4-{4-[(9aS)-hexahydropyrazino[2,1-c][1,4]oxazin-8(1H)-yl]-1-piperidinyl}-2-(methyloxy)phenyl]amino}-4-pyrimidinyl)imidazo[1,2-a]pyridin-2-yl]benzamide

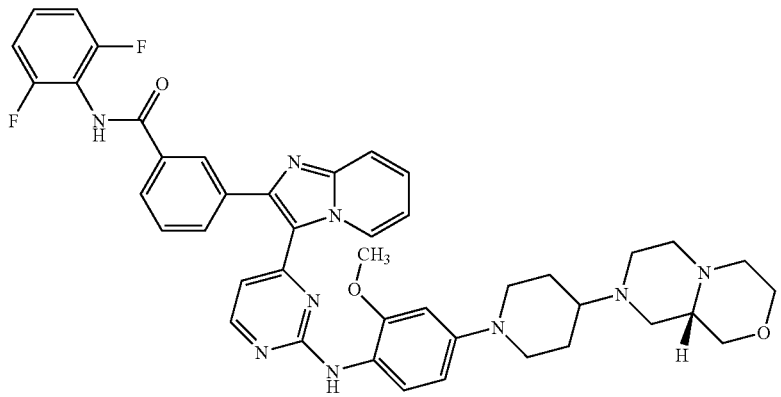

Step A: N-(phenylmethyl)-D-serine

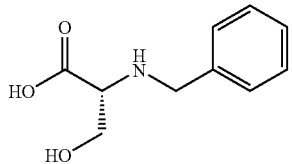

D-Serine methyl ester hydrochloride (10.0 g, 64.3 mmol) in MeOH (29 mL) was cooled in ice water bath. TEA (9.00 mL, 64.6 mmol) was added dropwise via syringe and reaction was warmed to rt. When the solution was homogenous, it was re-cooled with an ice water bath. Benzaldehyde (6.46 mL, 63.6 mmol) was added dropwise via syringe and the reaction was stirred for 30 min. NaBH$_4$ (7.84 g, 64.3 mmol) was then added in portions over 40 min and the resultant mixture was stirred for 1 h. To a separate flask, cooled in an ice bath, containing MeOH (12 mL) and H$_2$O (17 mL) was added NaOH (7.84 g, 195 mmol) in H$_2$O (16 mL). To this solution was added the NaBH$_4$ solution followed by H$_2$O (17 mL). The reaction was warmed to rt and the pH was adjusted to 9.5 using 6N HCl. The reaction mixture was washed twice with EtOAc and the pH was adjusted to 6.5 with 6N HCl. The resultant suspension was cooled in a refrigerator for 1 h. The solid was filtered, washed twice with H$_2$O (20 mL), twice with heptane (20 mL) and dried overnight at 45° C. in a vacuum oven to give the title compound of step A (4.91 g, 25.2 mmol, 39%). $^1$H NMR (400 MHz, DMSO-d$_6$) δ ppm 3.08-3.17 (m, 1H), 3.57-3.68 (m, 2H), 3.94 (q, J=13.2 Hz, 2H), 7.26-7.35 (m, 4H), 7.37-7.40 (m, 3H), 7.44-8.45 (br.s., 1H). $[α]_D^{20° C.}$=−5.3, I=100 mm, c=1.0 in 6N HCl.

Step B:
(3R)-5-oxo-4-(phenylmethyl)-3-morpholinecarboxylic acid

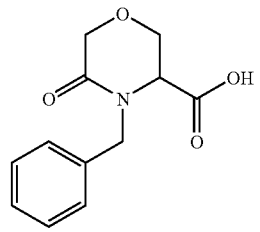

K$_2$CO$_3$ (10.6 g, 76.4 mmol) in H$_2$O (30 mL) precooled to 0° C. was added to N-(phenylmethyl)-D-serine (4.91 g, 25.2 mmol) in THF (30 mL) cooled to −10° C., internal temperature. Chloroacetyl chloride (3.30 mL, 41.4 mmol) was added dropwise, keeping the internal temperature below 5° C. After stirring for 2 h NaOH (10 mL, 50% w/w in water), precooled to 0° C. was added dropwise, keeping the internal temperature below 10° C. The reaction mixture was stirred for 2 h and subsequently warmed to rt. The reaction mixture was washed twice with heptane (20 mL) and the aqueous layer was cooled to −5° C. Concentrated HCl was added until pH <2, keeping the internal temperature below 10° C. The mixture was placed in a freezer overnight and the solid was filtered, washed twice with cold H$_2$O (20 mL) and dried at 50° C. in a vacuum oven to give the title compound of step B (3.67 g, 15.6 mmol, 62%). $^1$H NMR (400 MHz, DMSO-d$_6$) δ ppm 3.78 (d, J=15.4 Hz, 1H), 3.84-3.92 (m, 2H), 4.05-4.15 (m, 3H), 5.21 (d, J=15.2 Hz, 1H), 7.20-7.31 (m, 5H), 13.20 (br. s., 1H). $[α]_D^{20° C.}$=−108.6, I=100 mm, c=1.0 in 1N NaOH.

Step C: (3R)-5-oxo-N, 4-bis(phenylmethyl)-3-morpholinecarboxamide

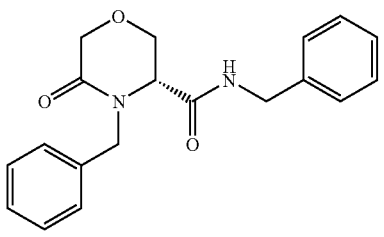

(3R)-5-oxo-4-(phenylmethyl)-3-morpholinecarboxylic acid (3.67 g, 15.6 mmol) and 1-hydroxybenzotriazole (2.53 g, 18.7 mmol) in DCM (50 mL) cooled to 0° C. N-Methylmorpholine (8.50 mL, 77.3 mmol), benzylamine (1.87 mL, 17.2 mmol) and 1-[3-(dimethylamino)propyl]-3-ethylcarbodiimide hydrochloride (3.26 g, 17.2 mmol) added sequentially. The reaction was stirred at rt overnight, washed with $H_2O$ (50 mL), 6N HCl (30 mL), $H_2O$ (50 mL) and dried over $MgSO_4$ to provide the title compound of step C (5.09 g, 15.6 mmol, 100%). $^1H$ NMR (400 MHz, DMSO-$d_6$) δ ppm 3.59 (d, J=15.2 Hz, 1H), 3.82 (t, J=2.9 Hz, 1H), 3.86-3.97 (m, 2H), 4.07-4.17 (m, 2H), 4.23-4.34 (m, 2H), 5.30 (d, J=15.4 Hz, 1H), 7.17-7.22 (m, 5H), 7.24-7.32 (m, 5H), 8.60 (t, J=5.6 Hz, 1H).

Step D: 1-phenyl-N-{[(3S)-4-(phenylmethyl)-3-morpholinyl]methyl}methanamine

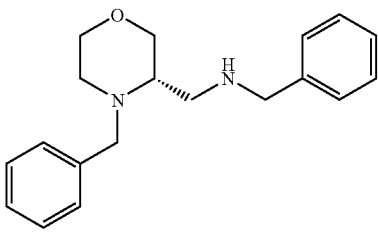

(3R)-5-oxo-N,4-bis(phenylmethyl)-3-morpholinecarboxamide (5.09 g, 15.6 mmol) in toluene (50 mL) cooled to 0° C. Red-Al® (35.0 mL, 7 mL per g carboxamide) added via addition funnel. The ice bath was removed after 2 or 3 mL Red-Al® was added. The reaction was heated at 50° C. overnight. The reaction was cooled to 0° C. and quenched slowly with 1N NaOH (50 mL) followed by diethyl ether (50 mL). The organic layer was washed with 1N NaOH (50 mL), the combined aqueous layer was back extracted with toluene (50 mL) and diethyl ether (50 mL) and dried over $MgSO_4$ to provide the title compound of step D (4.35 g, 14.7 mmol, 94%). $^1H$ NMR (400 MHz, DMSO-$d_6$) δ ppm 1.97 (br. s., 1H), 2.06 (ddd, J=12.0, 9.2, 3.4 Hz, 1H), 2.33-2.41 (m, 1H), 2.43-2.48 (m, 1H), 2.54-2.66 (m, 2H), 3.13 (d, J=13.6 Hz, 1H), 3.32-3.39 (m, 1H), 3.42 (dd, J=11.2, 8.2 Hz, 1H), 3.53 (dt, J=11.1, 3.5 Hz, 1H), 3.57-3.62 (m, 2H), 3.70 (dd, J=11.1, 3.0 Hz, 1H), 3.93 (d, J=13.6 Hz, 1H), 7.16-7.27 (m, 10H).

Step E: (9aS)-8-(phenylmethyl)hexahydropyrazino[2,1-c][1,4]oxazine-6,7-dione

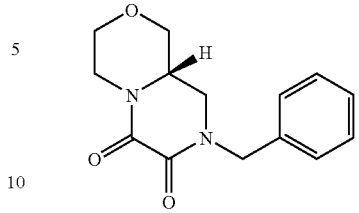

1-Phenyl-N-{[(3S)-4-(phenylmethyl)-3-morpholinyl]methyl}methanamine (4.35 g, 14.7 mmol) and diisopropylethylamine (3.30 mL, 19.1 mmol) in THF (50 mL) cooled to 0° C. Ethylchlorooxo-acetate (1.80 mL, 16.2 mmol) was added dropwise via syringe. The ice bath was removed and the reaction was stirred at rt for 2 h. The reaction mixture was concentrated, taken up in EtOAc and washed with half saturated $NaHCO_3$. The aqueous layer was back extracted with EtOAc, dried over $MgSO_4$ and azeotroped in EtOH to provide ethyl oxo((phenylmethyl){[(3S)-4-(phenylmethyl)-3-morpholinyl]methyl}amino)acetate (5.83 g, 14.7 mmol, used without further purification). Ethyl oxo((phenylmethyl){[(3S)-4-(phenylmethyl)-3-morpholinyl]methyl}amino)acetate (5.83 g, 14.7 mmol) was hydrogenated (1 atm.) with Pd on carbon (1.18 g, 20% w/w with starting morpholine) for 13 days. The reaction was filtered through Celite® and washed thoroughly with MeOH. The solution was concentrated and subsequently triturated with EtOAc providing the title compound of step E (2.06 g, 7.9 mmol, 54% over two steps). $^1H$ NMR (400 MHz, $CDCl_3$) δ ppm 3.00 (ddd, J=13.9, 12.3, 4.2 Hz, 1H), 3.14-3.23 (m, 3H), 3.49 (td, J=12.1, 2.9 Hz, 1H), 3.72-3.82 (m, J=10.0, 10.0, 6.3, 4.0 Hz, 1H), 3.87 (dd, J=11.4, 3.7 Hz, 1H), 4.02 (dd, J=11.7, 4.4 Hz, 1H), 4.28 (dd, J=13.9, 2.2 Hz, 1H), 4.61-4.67 (m, 1H), 4.70-4.75 (m, 1H), 7.26-7.38 (m, 5H). Chiral HPLC analysis (Chiralpak AS-H, 4.6×150 mm, methanol (0.1% isopropyl amine), 1.0 mL/min, UV 254 nm, 25° C.) ee=99%, retention time, S=2.99 min. $[α]_D^{20° C.}$=−9.0:I=100 mm, c=0.975 in $CHCl_3$.

Step F: (9aS)-8-(phenylmethyl)octahydropyrazino[2,1-c][1,4]oxazine

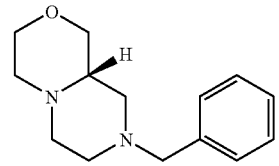

To (9aS)-8-(phenylmethyl)hexahydropyrazino[2,1-c][1,4]oxazine-6,7-dione (2.06 g, 7.90 mmol) in THF (20 mL) at 0° C. was added LAH (30.0 mL, 29.6 mmol, 1M in THF) dropwise. The solution was heated overnight at 45° C. and a subsequent 5 days at 65° C. The reaction was cooled to 0° C., quenched slowly with EtOAc (15 mL), $H_2O$ (1.2 mL), NaOH (1.20 mL, 15% w/w in $H_2O$) and $H_2O$ (3.60 mL). The resultant mixture was stirred for 1 h, diluted with EtOAc and filtered. The filter cake was taken up in 1N NaOH, extracted with diethyl ether and dried over $MgSO_4$ to afford the title compound of step F (1.80 g, 7.70 mmol, 98%). $^1H$ NMR (400 MHz, $CD_3OD$) δ ppm 1.79 (t, J=10.8 Hz, 1H), 2.27-2.39 (m, 3H), 2.66 (tt, J=10.6, 2.1 Hz, 1H), 2.74 (ddd, J=10.8, 2.6, 2.4 Hz, 1H), 2.83 (dq, J=10.8, 2.2 Hz, 1H), 3.14-3.23 (m, 1H), 3.30 (dt, J=3.3, 1.6 Hz, 2H), 3.47-3.52 (m, 1H), 3.52-3.57 (m, 1H), 3.57-3.67 (m, 2H), 3.80 (dd, J=11.5, 3.5 Hz, 1H), 7.23-7.33 (m, 5H).

Step G: (9aS)-octahydropyrazino[2,1-c][1,4]oxazine dihydrochloride

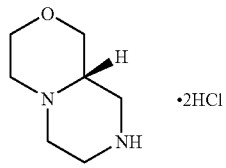

To (9aS)-8-(phenylmethyl)octahydropyrazino[2,1-c][1,4]oxazine (1.80 g, 7.70 mmol) in MeOH (30 mL) was added 6N HCl (3.00 mL, 18.0 mmol) followed by Pd on carbon (0.186 g, 10% w/w with starting oxazine). The mixture was placed under $H_2$ (1 atm) overnight. The mixture was filtered through Celite® and washed thoroughly with MeOH to provide the title compound of step G (0.851 g, 4.00 mmol, 52%). $^1$H NMR (400 MHz, CD$_3$OD) δ ppm 3.26-3.35 (m, 1H), 3.38-3.47 (m, 2H), 3.52-3.57 (m, 1H), 3.65-3.69 (m, 1H), 3.71-3.82 (m, 4H), 3.92-4.00 (m, 1H), 4.02-4.13 (m, 3H).

Step H: (9aS)-8-{1-[3-(methyloxy)-4-nitrophenyl]-4-piperidinyl}octahydropyrazino[2,1-c][1,4]oxazine

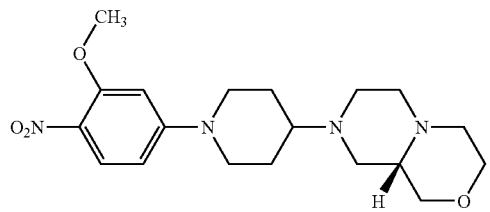

The title compound of step H (0.516 g, 1.35 mmol, 90%) was prepared in an analogous manner to that described for Example 74, step A, with the following notable exceptions:

a) (9aS)-octahydropyrazino[2,1-c][1,4]oxazine dihydrochloride was used instead of dimethylamine;

b) TEA was added to the reaction.

$^1$H NMR (400 MHz, CDCl$_3$) δ ppm 1.51 (q, J=12.0 Hz, 2H), 1.82-1.92 (m, 3H), 2.22-2.32 (m, 2H), 2.35-2.44 (m, 2H), 2.57 (d, J=10.3 Hz, 2H), 2.60 (s, 1H), 2.70 (d, J=10.8 Hz, 1H), 2.79 (d, J=10.6 Hz, 1H), 2.88 (t, J=12.2 Hz, 2H), 3.16 (t, J=10.6 Hz, 1H), 3.59 (t, J=10.8 Hz, 2H), 3.76 (d, J=9.7 Hz, 1H), 3.81-3.90 (m, 5H), 6.21 (s, 1H), 6.31 (dd, J=9.5, 2.2 Hz, 1H), 7.87 (dd, J=9.3, 1.3 Hz, 1H).

Step I: 4-{4-[(9aS)-hexahydropyrazino[2,1-c][1,4]oxazin-8(1H)-yl]-1-piperidinyl}-2-(methyloxy)aniline

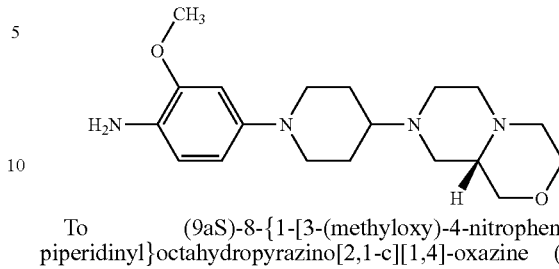

To (9aS)-8-{1-[3-(methyloxy)-4-nitrophenyl]-4-piperidinyl}octahydropyrazino[2,1-c][1,4]-oxazine (0.516 g, 1.35 mmol) in EtOAc (50 mL) was added Pd on carbon. The mixture was stirred under $H_2$ (1 atm) overnight. The mixture was filtered through Celite® to provide the title compound of step I (0.417 g, 1.20 mmol, 89%). $^1$H NMR (400 MHz, DMSO-d$_6$) δ ppm 1.44-1.56 (m, 2H), 1.77-1.88 (m, 2H), 2.10-2.22 (m, 2H), 2.42 (s, 4H), 2.48 (s, 5H), 2.58 (d, J=12.1 Hz, 1H), 2.69 (d, J=9.9 Hz, 1H), 3.04 (t, J=10.4 Hz, 1H), 3.37-3.47 (m, 3H), 3.59 (d, J=11.4 Hz, 1H), 3.66-3.73 (m, 5H), 6.25 (dd, J=8.3, 2.1 Hz, 1H), 6.43-6.51 (m, 2H).

Step J: N-(2,6-difluorophenyl)-3-[3-(2-{[4-{4-[(9aS)-hexahydropyrazino[2,1-c][1,4]oxazin-8(1H)-yl]-1-piperidinyl}-2-(methyloxy)phenyl]amino}-4-pyrimidinyl) imidazo[1,2-a]pyridin-2-yl]benzamide The title compound (0.11 g, 0.14 mmol, 56%) was prepared in an analogous manner to that described for Example 36, step E, with the following notable exception: 4-{4-[(9aS)-hexahydropyrazino[2,1-c][1,4]oxazin-8(1H)-yl]-1-piperidinyl}-2-(methyloxy)aniline was used instead of 2-(methyloxy)-4-[4-(1-piperidinylmethyl)-1-piperidinyl]-aniline. $^1$H NMR (400 MHz, DMSO-d$_6$) δ ppm 1.41-1.52 (m, 2H), 1.76 (t, J=10.5 Hz, 3H), 2.02 (t, J=9.7 Hz, 1H), 2.05-2.15 (m, 2H), 2.19-2.30 (m, 2H), 2.54 (d, J=11.9 Hz, 1H), 2.62 (t, J=11.1 Hz, 4H), 2.76 (d, J=10.1 Hz, 1H), 3.03 (t, J=10.5 Hz, 1H), 3.43 (t, J=11.3 Hz, 1H), 3.55 (dd, J=10.5, 2.3 Hz, 1H), 3.64-3.73 (m, 4H), 3.76 (s, 3H), 6.39-6.46 (m, 2H), 6.63 (d, J=2.0 Hz, 1H), 6.94 (t, J=7.1 Hz, 1H), 7.17 (t, J=8.1 Hz, 2H), 7.32-7.37 (m, 1H), 7.39-7.45 (m, 1H), 7.57 (t, J=7.7 Hz, 1H), 7.69 (d, J=9.2 Hz, 1H), 7.78 (d, J=7.7 Hz, 1H), 8.02 (d, J=7.7 Hz, 1H), 8.17 (d, J=5.3 Hz, 1H), 8.30 (s, 1H), 8.43 (s, 1H), 9.36 (br. s., 1H), 10.21 (s, 1H). MS (M+H, ES+) 772.

Example 88

N-(2,6-difluorophenyl)-5-[3-(2-{[4-{4-[(9aS)-hexahydropyrazino[2,1-c][1,4]oxazin-8(1H)-yl]-1-piperidinyl}-2-(methyloxy)phenyl]amino}-4-pyrimidinyl)imidazo[1,2-a]pyridin-2-yl]-2-(methyloxy)benzamide

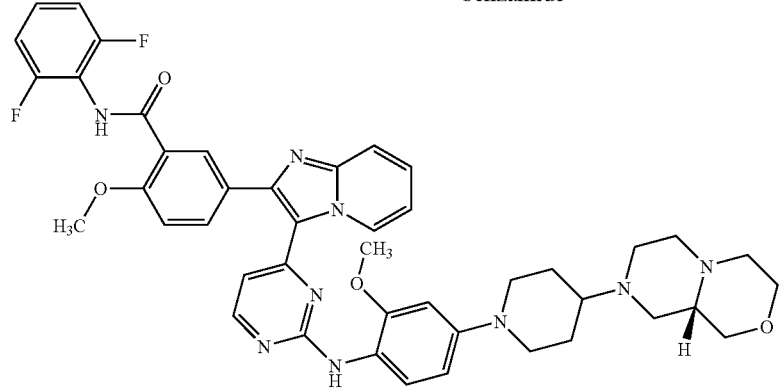

The title compound (0.11 g, 0.14 mmol, 61%) was prepared in an analogous manner to that described for Example 36, step E with the following notable exceptions:
(a) 5-[3-(2-chloro-4-pyrimidinyl)-imidazo[1,2-a]pyridin-2-yl]-N-(2,6-difluorophenyl)-2-(methyloxy)benzamide (Intermediate Example 2) was used instead of Intermediate Example 1;
(b) 4-{4-[(9aS)-hexahydropyrazino[2,1-c][1,4]oxazin-8(1H)-yl]-1-piperidinyl}-2-(methyloxy)aniline was used instead of 2-(methyloxy)-4-[4-(1-piperidinylmethyl)-1-piperidinyl]-aniline.

$^1$H NMR (400 MHz, DMSO-d$_6$) δ ppm 1.41-1.52 (m, 2H), 1.76 (t, J=10.3 Hz, 3H), 2.02 (t, J=9.9 Hz, 1H), 2.10 (t, J=11.2 Hz, 2H), 2.20-2.30 (m, 2H), 2.54 (d, J=11.7 Hz, 1H), 2.57-2.67 (m, 4H), 2.76 (d, J=10.8 Hz, 1H), 3.03 (t, J=10.5 Hz, 1H), 3.38-3.48 (m, 1H), 3.55 (dd, J=11.0, 2.2 Hz, 1H), 3.68 (t, J=11.1 Hz, 3H), 3.76 (s, 3H), 3.95 (s, 3H), 6.42-6.46 (m, 1H), 6.49 (d, J=5.1 Hz, 1H), 6.63 (d, J=2.0 Hz, 1H), 6.91 (t, J=7.1 Hz, 1H), 7.15 (t, J=8.1 Hz, 2H), 7.25 (d, J=9.0 Hz, 1H), 7.31-7.42 (m, 3H), 7.66 (d, J=9.0 Hz, 1H), 7.74 (d, J=8.2 Hz, 1H), 8.07 (s, 1H), 8.16 (d, J=5.1 Hz, 1H), 8.41 (s, 1H), 9.32 (br. s., 1H), 9.76 (s, 1H). MS (M+H, ES+) 802.

Example 89

N-(2,6-difluorophenyl)-3-[3-(2-{[2-(methyloxy)-4-(4-{1-[2-(methylsulfonyl)ethyl]-4-piperidinyl}-1-piperazinyl)phenyl]amino}-4-pyrimidinyl)imidazo[1,2-a]pyridin-2-yl]benzamide

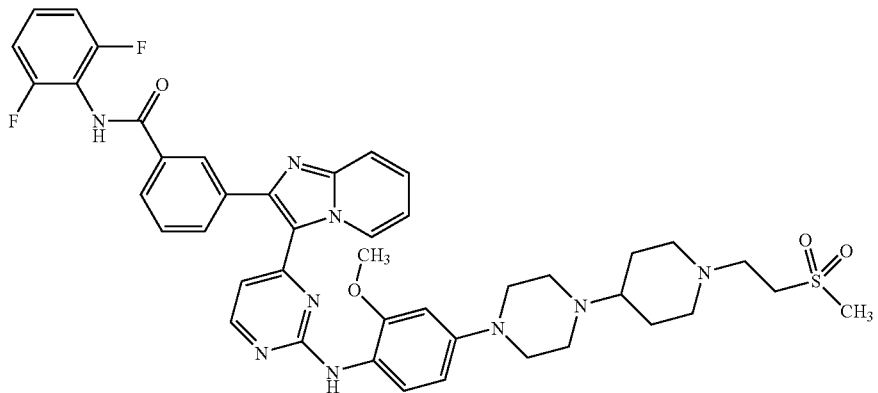

Step A: 1,1-dimethylethyl 4-[3-(methyloxy)-4-nitrophenyl]-1-piperazinecarboxylate

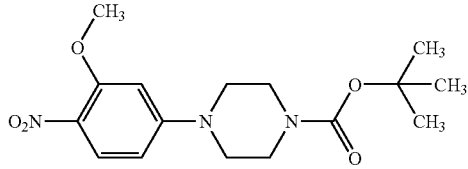

The title compound of step A (3.09 g, 9.18 mmol, 92%) was prepared in an analogous manner to that of Example 22, step B, with the following notable exception: 1,1-dimethylethyl 1-piperazinecarboxylate was used instead of 1,4'-bipiperidine. $^1$H NMR (400 MHz, DMSO-d$_6$) δ ppm 1.41 (s, 9H), 3.45 (br. s., 8H), 3.89 (s, 3H), 6.51 (s, 1H), 6.57 (s, 1H), 7.89 (s, 1H).

Step B: 1-[3-(methyloxy)-4-nitrophenyl]piperazine

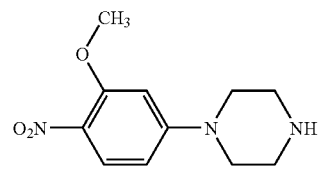

1,1-Dimethylethyl 4-[3-(methyloxy)-4-nitrophenyl]-1-piperazinecarboxylate (combined batches) (5.16 g, 15.3 mmol) in DCM was cooled with an ice/H$_2$O bath and TFA (30.0 mL, 398 mmol) was added dropwise via an addition funnel. Upon completion by TLC, the reaction was quenched slowly with 1N NaOH until the aqueous layer was basic as determined by pH paper. The mixture was extracted with DCM, dried (MgSO$_4$) and concentrated to provide the title compound of step B (3.52 g, 14.9 mmol, 97%). $^1$H NMR (400 MHz, DMSO-d$_6$) δ ppm 2.34 (br. s., 1H), 2.73-2.77 (m, 4H), 3.26-3.33 (m, 4H), 3.85 (s, 3H), 6.45 (d, J=2.4 Hz, 1H), 6.52 (dd, J=9.4, 2.5 Hz, 1H), 7.83 (d, J=9.3 Hz, 1H).

Step C: 1,1-dimethylethyl 4-{4-[3-(methyloxy)-4-nitrophenyl]-1-piperazinyl}-1-piperidine-carboxylate

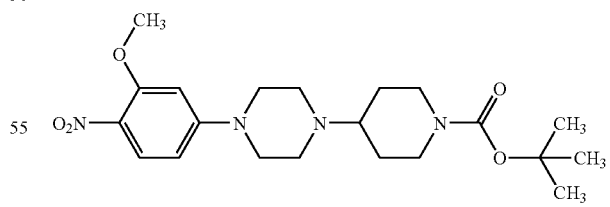

To a stirred (30 min) solution of 1-[3-(methyloxy)-4-nitrophenyl]piperazine (3.52 g, 14.9 mmol), 1-Boc-4-piperidone (5.96 g, 29.9 mmol), HOAc (24.0 mL, 1M in DCM, 24.0 mmol) and TEA (2.00 mL, 14.3 mmol) in 1,2-DCE was added in one portion sodium triacetoxyborohydride (4.82 g, 22.7 mmol). The reaction was stirred for 30 min at which time sodium triacetoxyborohydride (2.00 g, 9.40 mmol) and HOAc (10.0 mL, 1M in DCM, 10.0 mmol) was added. The reaction was stirred at rt overnight. The reaction was quenched with saturated NaHCO₃ (150 mL) and extracted with DCM. The organic layer was washed with H₂O, dried (MgSO₄) and concentrated. Purification by flash chromatography provided the title compound of step C (6.09 g, 14.5 mmol, 97%). ¹H NMR (400 MHz, DMSO-d₆) δ ppm 1.20-1.32 (m, 2H), 1.37 (s, 9H), 1.74 (d, J=10.6 Hz, 2H), 2.41 (tt, J=11.0, 3.2 Hz, 1H), 2.55-2.62 (m, 4H), 2.70 (br. s., 2H), 3.36-3.44 (m, 4H), 3.88 (s, 3H), 3.94 (d, J=13.2 Hz, 2H), 6.50 (d, J=2.6 Hz, 1H), 6.57 (dd, J=9.5, 2.6 Hz, 1H), 7.86 (d, J=9.2 Hz, 1H).

Step D: 1-[3-(methyloxy)-4-nitrophenyl]-4-(4-piperidinyl)piperazine

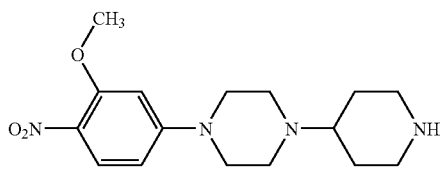

A solution of 1,1-dimethylethyl 4-{4-[3-(methyloxy)-4-nitrophenyl]-1-piperazinyl}-1-piperidinecarboxylate (5.67 g, 13.5 mmol) and DCM (110 mL) was cooled with an ice/H₂O bath. TFA (30.0 mL, 389 mmol) was added dropwise via addition funnel. Upon completion, by TLC, the reaction mixture was quenched with 1N NaOH (300 mL), extracted with DCM, dried (MgSO₄) and concentrated to provide the title compound of step D (4.01 g, 12.5 mmol, 93%). ¹H NMR (400 MHz, DMSO-d₆) δ ppm 1.20-1.31 (m, 2H), 1.68 (d, J=9.9 Hz, 2H), 2.22-2.32 (m, 2H), 2.34-2.45 (m, 2H), 2.54-2.61 (m, 4H), 2.95 (d, J=12.1 Hz, 2H), 3.36-3.43 (m, 4H), 3.88 (s, 3H), 6.50 (d, J=2.6 Hz, 1H), 6.57 (dd, J=9.4, 2.4 Hz, 1H), 7.86 (d, J=9.5 Hz, 1H).

Step E: 1-[3-(methyloxy)-4-nitrophenyl]-4-{1-[2-(methylsulfonyl)ethyl]-4-piperidinyl}-piperazine

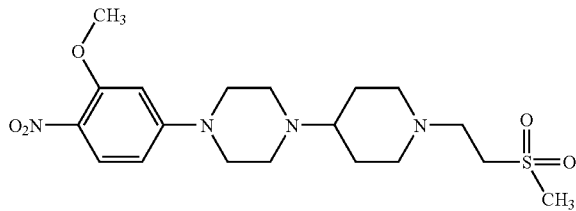

The title compound of step E (1.18 g, 2.76 mmol, 92%) was prepared from 1-[3-(methyloxy)-4-nitrophenyl]-4-(4-piperidinyl)piperazine in an analogous manner to that described for Example 8. ¹H NMR (400 MHz, DMSO-d₆) δ ppm 1.32-1.43 (m, 2H), 1.71-1.79 (m, 2H), 1.88-1.97 (m, 2H), 2.15-2.24 (m, 1H), 2.54-2.60 (m, 4H), 2.65 (t, J=6.8 Hz, 2H), 2.91 (d, J=11.0 Hz, 2H), 3.00 (s, 3H), 3.24 (t, J=6.8 Hz, 2H), 3.37-3.43 (m, 4H), 3.88 (s, 3H), 6.50 (d, J=2.6 Hz, 1H), 6.57 (dd, J=9.5, 2.6 Hz, 1H), 7.86 (d, J=9.5 Hz, 1H).

Step F: 2-(methyloxy)-4-(4-{1-[2-(methylsulfonyl)ethyl]-4-piperidinyl}-1-piperazinyl)-aniline

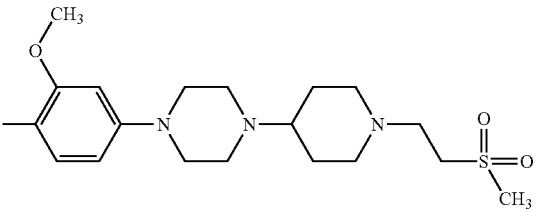

To 1-[3-(methyloxy)-4-nitrophenyl]-4-{1-[2-(methylsulfonyl)ethyl]-4-piperidinyl}piperazine (1.18 g, 2.76 mmol) in EtOAc (100 mL) and EtOH (25 mL) was added Pd on carbon in one portion. The mixture was stirred at rt under H₂ (1 atm.) until complete by TLC. The reaction was filtered through Celite® and concentrated. Purification by flash chromatography provided the title compound of step F (0.690 g, 1.75 mmol, 63%). ¹H NMR (400 MHz, DMSO-d₆) δ ppm 1.31-1.42 (m, 2H), 1.75 (d, J=11.4 Hz, 2H), 1.86-1.97 (m, 2H), 2.15 (tt, J=11.3, 3.9 Hz, 1H), 2.54-2.59 (m, 4H), 2.65 (t, J=6.8 Hz, 2H), 2.88-2.94 (m, 6H), 3.00 (s, 3H), 3.25 (t, J=6.8 Hz, 2H), 3.71 (s, 3H), 4.18 (br. s., 2H), 6.25 (dd, J=8.4, 2.6 Hz, 1H), 6.46 (d, J=2.6 Hz, 1H), 6.49 (d, J=8.4 Hz, 1H).

Step G: N-(2,6-difluorophenyl)-3-[3-(2-{[2-(methyloxy)-4-(4-{1-[2-(methylsulfonyl)ethyl]-4-piperidinyl}-1-piperazinyl)phenyl]amino}-4-pyrimidinyl)imidazo[1,2-a]pyridin-2-yl]benzamide The title compound (0.13 g, 0.16 mmol, 62%) was prepared in an analogous manner to that described for Example 36, step E, with the following notable exception: 2-(methyloxy)-4-(4-{1-[2-(methylsulfonyl)ethyl]-4-piperidinyl}-1-piperazinyl)-aniline was used instead of 2-(methyloxy)-4-[4-(1-piperidinylmethyl)-1-piperidinyl]aniline. ¹H NMR (400 MHz, DMSO-d₆) δ ppm 1.34-1.46 (m, 2H), 1.74-1.84 (m, 2H), 1.89-2.00 (m, 2H), 2.14-2.23 (m, 1H), 2.58-2.69 (m, 7H), 2.87-2.97 (m, 2H), 3.01 (s, 3H), 3.13 (s, 4H), 3.22-3.28 (m, 2H), 3.79 (s, 2H), 6.46 (d, J=5.5 Hz, 2H), 6.67 (s, 1H), 6.95-7.01 (m, 1H), 7.21 (t, J=8.1 Hz, 2H), 7.33-7.43 (m, 2H), 7.43-7.53 (m, 1H), 7.61 (t, J=7.7 Hz, 1H), 7.73 (d, J=9.5 Hz, 1H), 7.81 (d, J=8.4 Hz, 1H), 8.05 (d, J=8.4 Hz, 1H), 8.20 (d, J=5.1 Hz, 1H), 8.33 (s, 1H), 8.46 (s, 1H), 9.40 (br. s., 1H), 10.24 (s, 1H). MS (M+H, APCI⁺) 822.

Example 90

N-(2,6-difluorophenyl)-3-[3-(2-{[4-{4-[1-(2-fluoroethyl)-4-piperidinyl]-1-piperazinyl}-2-(methyloxy)phenyl]amino}-4-pyrimidinyl)imidazo[1,2-a]pyridin-2-yl]benzamide

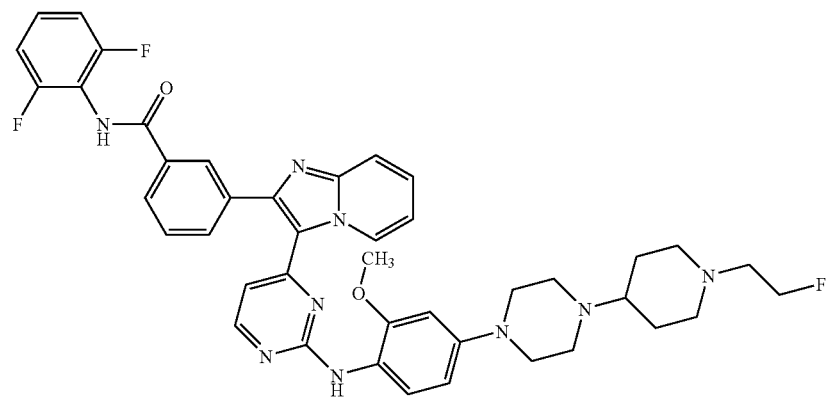

Step A: 1-[1-(2-fluoroethyl)-4-piperidinyl]-4-[3-(methyloxy)-4-nitrophenyl]piperazine

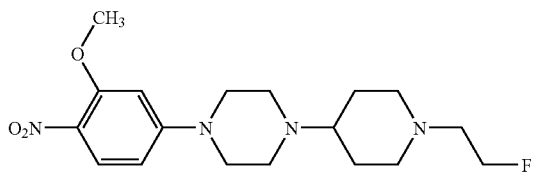

To 1-[3-(methyloxy)-4-nitrophenyl]-4-(4-piperidinyl)piperazine (Example 89, step D) (0.958 g, 2.99 mmol) and Na$_2$CO$_3$ (0.470 g, 4.43 mmol) in acetonitrile (20 mL) was added iodofluoroethane (0.500 mL, 6.15 mmol) in one portion. The resultant mixture was heated at 70° C. for 48 h. When complete by TLC, the reaction was poured into H$_2$O (150 mL), extracted with DCM and EtOAc, dried (MgSO$_4$) and concentrated. Purification by flash chromatography provided the title compound of step A (0.972 g, 2.63 mmol, 88%). $^1$H NMR (400 MHz, DMSO-d$_6$) δ ppm 1.32-1.43 (m, 2H), 1.70 (d, J=15.0 Hz, 2H), 1.94 (t, J=12.5 Hz, 2H), 2.12-2.21 (m, 1H), 2.50 (t, J=5.0 Hz, 1H), 2.52-2.58 (m, 5H), 2.88 (d, J=10.4 Hz, 2H), 3.35-3.40 (m, 4H), 3.86 (s, 3H), 4.46 (dt, J$_{HF}$=47.8 Hz, J=4.9 Hz, 2H), 6.47 (d, J=2.4 Hz, 1H), 6.54 (dd, J=9.3, 2.1 Hz, 1H), 7.83 (d, J=9.3 Hz, 1H).

Step B: 4-{4-[1-(2-fluoroethyl)-4-piperidinyl]-1-piperazinyl}-2-(methyloxy)aniline

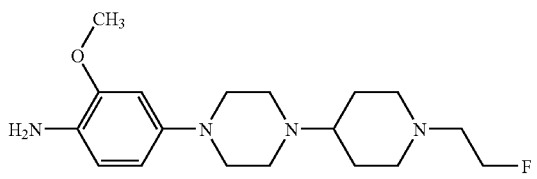

The title compound of step B (0.646 g, 1.92 mmol, 73%) was prepared from 1-[1-(2-fluoroethyl)-4-piperidinyl]-4-[3-(methyloxy)-4-nitrophenyl]piperazine in a manner analogous to that described for Example 89, step F. $^1$H NMR (400 MHz, DMSO-d$_6$) δ ppm 1.31-1.42 (m, 2H), 1.75 (d, J=11.4 Hz, 2H), 1.86-1.97 (m, 2H), 2.15 (tt, J=11.3, 3.9 Hz, 1H), 2.54-2.59 (m, 4H), 2.65 (t, J=6.8 Hz, 2H), 2.88-2.94 (m, 6H), 3.00 (s, 3H), 3.25 (t, J=6.8 Hz, 2H), 3.71 (s, 3H), 4.18 (br. s., 2H), 6.25 (dd, J=8.4, 2.6 Hz, 1H), 6.46 (d, J=2.6 Hz, 1H), 6.49 (d, J=8.4 Hz, 1H).

Step C: N-(2,6-difluorophenyl)-3-[3-(2-{[4-{4-[1-(2-fluoroethyl)-4-piperidinyl]-1-piperazinyl}-2-(methyloxy)phenyl]amino}-4-pyrimidinyl)imidazo[1,2-a]pyridin-2-yl]benzamide The title compound (0.130 g, 0.17 mmol, 67%) was prepared in an analogous manner to that described for Example 36, step E, with the following notable exception: 4-{4-[1-(2-fluoroethyl)-4-piperidinyl]-1-piperazinyl}-2-(methyloxy)aniline was used instead of 2-(methyloxy)-4-[4-(1-piperidinylmethyl)-1-piperidinyl]aniline. $^1$H NMR (400 MHz, DMSO-d$_6$) δ ppm 1.33-1.45 (m, 2H), 1.72 (d, J=10.8 Hz, 2H), 1.95 (t, J=12.0 Hz, 2H), 2.16 (t, J=10.4 Hz, 1H), 2.48-2.53 (m, 1H), 2.59 (br. s., 5H), 2.89 (d, J=10.4 Hz, 2H), 3.09 (br. s., 4H), 3.76 (s, 3H), 4.53 (dt, J$_{HF}$=47.6 Hz, J=4.7 Hz, 2H), 6.38-6.47 (m, 2H), 6.63 (s, 1H), 6.94 (t, J=6.6 Hz, 1H), 7.17 (t, J=8.1 Hz, 2H), 7.31-7.40 (m, 2H), 7.40-7.46 (m, 1H), 7.57 (t, J=7.9 Hz, 1H), 7.69 (d, J=9.2 Hz, 1H), 7.78 (d, J=7.3 Hz, 1H), 8.02 (d, J=7.3 Hz, 1H), 8.16 (d, J=5.1 Hz, 1H), 8.29 (s, 1H), 8.43 (s, 1H), 9.36 (br. s., 1H), 10.20 (s, 1H). MS (M+H, APCI+) 763.

Example 91

N-(2,6-difluorophenyl)-3-(3-{2-[(2-(ethyloxy)-4-{4-[1-(2-fluoroethyl)-4-piperidinyl]-1-piperazinyl}phenyl)amino}-4-pyrimidinyl}imidazo[1,2-a]pyridin-2-yl)benzamide

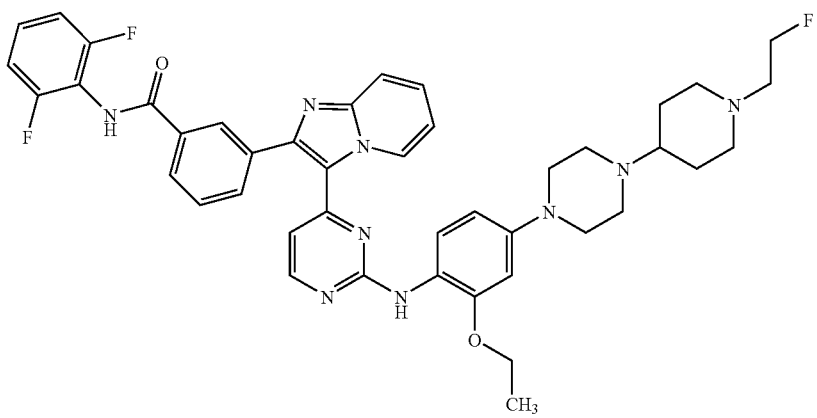

Step A: 1-[3-(ethyloxy)-4-nitrophenyl]-4-(4-piperidinyl)piperazine

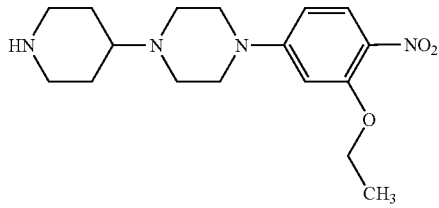

To a stirred solution of 1-[3-(ethyloxy)-4-nitrophenyl]piperazine (Example 143, step A) (0.53 g, 2.1 mmol) and 1-BOC-4-piperidone (2.1 g, 10.6 mmol) in DCE (21 mL) was added HOAc (0.25 g, 4.2 mmol) followed by addition of sodium triacetoxyborohydride (2.2 g, 10.6 mmol). The reaction was stirred under $N_2$ at rt for 3 h. The reaction was quenched with aqueous (saturated) $NaHCO_3$ and extracted with DCM (3×). The combined organic layers were dried ($MgSO_4$), filtered, and concentrated under vacuum. The residue was purified by silica gel chromatography. The desired fractions were concentrated under vacuum. The residue was dissolved and stirred in a 20% solution of TFA/DCM (50 mL) for approximately 2 h at rt. The mixture was concentrated under vacuum. The residue was dissolved in DCM and neutralized with aqueous (saturated) $NaHCO_3$. The aqueous layer was extracted with DCM (3×). The combined organic layers were dried ($MgSO_4$), filtered, and concentrated under vacuum. The residue was purified by silica gel chromatography. The desired fractions were concentrated under vacuum to give the title compound of step A (560 mg, 1.68 mmol, 79%) as a yellow solid. MS (ESI): 335 [M+H]$^+$.

Step B: 1-[3-(ethyloxy)-4-nitrophenyl]-4-[1-(2-fluoroethyl)-4-piperidinyl]piperazine

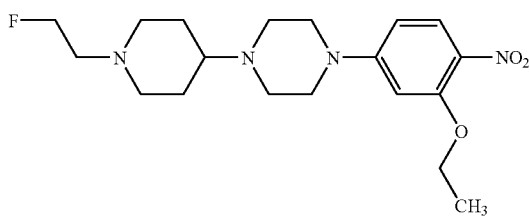

To a stirred solution of 1-[3-(ethyloxy)-4-nitrophenyl]-4-(4-piperidinyl)piperazine (0.28 g, 0.83 mmol) and 1-iodo-2-fluoroethane (0.29 g, 1.67 mmol) in acetonitrile (17 mL) was added $Na_2CO_3$ (0.106 g, 1.0 mmol). The reaction was stirred under $N_2$ and heated to reflux for 4 h. The temperature was lowered to 75° C. and the reaction was stirred overnight (approximately 16 h). The reaction was cooled to rt and then concentrated under vacuum. The residue was purified by silica gel chromatography to give the title compound of step B (206 mg, 0.54 mmol, 65%) as a yellow solid. MS (ESI): 381 [M+H]$^+$.

Step C: (2-(ethyloxy)-4-{4-[1-(2-fluoroethyl)-4-piperidinyl]-1-piperazinyl}phenyl)amine

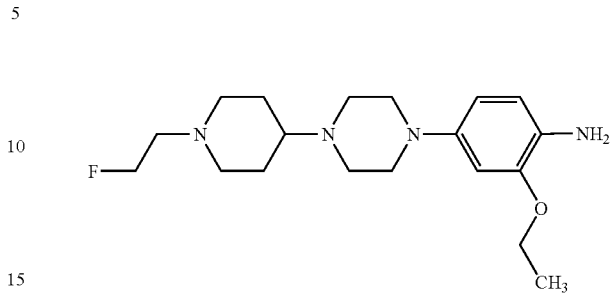

A mixture of 1-[3-(ethyloxy)-4-nitrophenyl]-4-[1-(2-fluoroethyl)-4-piperidinyl]piperazine (200 mg, 0.53 mmol) and platinum (sulfided, 5 wt. % on carbon, 50 mg, 0.013 mmol) in 20% MeOH/EtOAc (20 mL) was added to a high-pressure hydrogenation reaction flask. The reaction was purged with $N_2$ and vacuum (3×). The reaction was purged with $H_2$ and vacuum (3×). The reaction was then treated with $H_2$ at 50 psi and stirred for approximately 16 h. The reaction was degassed, then poured through a Teflon filter, washing the solid with MeOH and DCM. The filtrate was concentrated under vacuum to give the title compound of step C (136 mg, 0.38 mmol, 74%) as a brown solid. MS (ESI): 351 [M+H]$^+$.

Step D: N-(2,6-difluorophenyl)-3-(3-{2-[(2-(ethyloxy)-4-{4-[1-(2-fluoroethyl)-4-piperidinyl]-1-piperazinyl}phenyl)amino]-4-pyrimidinyl}imidazo[1,2-a]pyridin-2-yl)benzamide To 3-[3-(2-chloro-4-pyrimidinyl)imidazo[1,2-a]pyridin-2-yl]-N-(2,6-difluorophenyl)-benzamide (Intermediate Example 1) (100 mg, 0.22 mmol) and (2-(ethyloxy)-4-{4-[1-(2-fluoroethyl)-4-piperidinyl]-1-piperazinyl}phenyl)amine (68 mg, 0.20 mmol) in 2,2,2-trifluoroethanol (2 mL) was added p-toluenesulfonic acid monohydrate (140 mg, 0.74 mmol). The mixture was stirred and heated on a Biotage microwave at 150° C. for 45 min, then cooled to rt. The mixture was neutralized with 0.5M sodium methoxide in MeOH. The mixture was concentrated under vacuum and the residue purified by silica gel chromatography to give a yellow solid. The solid was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (90 mg, 0.11 mmol, 54%) as a light yellow solid. $^1$H NMR (400 MHz, DMSO-$d_6$) δ 10.24 (s, 1H), 9.37 (s, 1H), 8.36 (m, 2H), 8.22 (d, 1H, J=5.13 Hz), 8.05 (d, 1H, J=7.88 Hz), 7.81 (d, 1H, J=7.88 Hz), 7.73 (d, 1H, J=8.98 Hz), 7.61 (t, 1H, J=7.70 Hz), 7.35-7.50 (m, 3H), 7.21 (t, 2H, J=8.06 Hz), 6.97 (t, 1H, J=8.96 Hz), 6.65 (d, 1H, J=2.38 Hz), 6.44-6.50 (m, 2H), 4.56 (t, 1H, J=4.95 Hz), 4.44 (t, 1H, J=4.95 Hz), 4.06 (q, 2H, J=6.96 Hz), 3.11 (m, 4H), 2.92 (m, 2H), 2.60-2.64 (m, 4H), 2.49 (m, 1H), 2.18 (m, 1H), 1.94-2.03 (m, 2H), 1.72-1.79 (m, 2H), 1.37-1.48 (m, 2H), 1.24 (t, 3H, J=6.87 Hz), 0.82-0.87 (m, 1H). MS (ESI): 776 [M+H]$^+$.

Example 92

N-(2,6-difluorophenyl)-3-[3-(2-{[2-(ethyloxy)-4-(4-{1-[2-(methylsulfonyl)ethyl]-4-piperidinyl}-1-piperazinyl)phenyl]amino}-4-pyrimidinyl)imidazo[1,2-a]pyridin-2-yl]benzamide

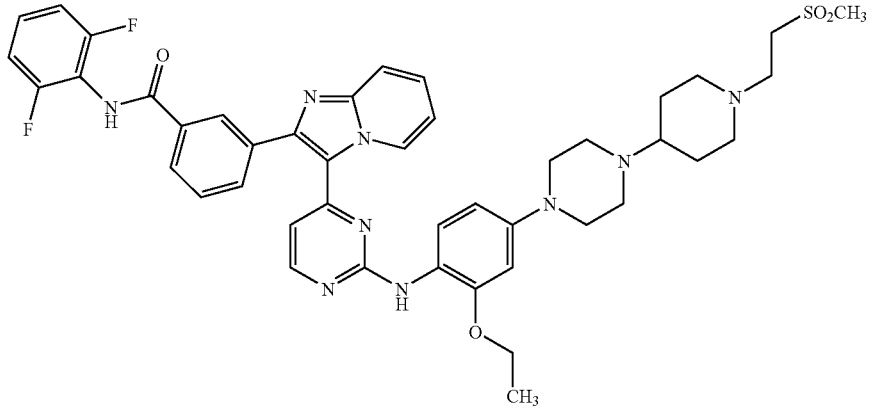

Step A: 1-[3-(ethyloxy)-4-nitrophenyl]-4-{1-[2-(methylsulfonyl)ethyl]-4-piperidinyl}-piperazine

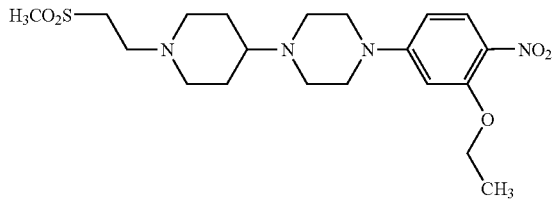

A mixture of 1-[3-(ethyloxy)-4-nitrophenyl]-4-(4-piperidinyl)piperazine (Example 91, step A) (0.30 g, 0.90 mmol) and methyl vinyl sulfone (0.29 g, 2.7 mmol) in dioxane (9.0 mL) was stirred under $N_2$. The reaction was heated to 95° C. and stirred for approximately 3 h, then cooled to rt. The reaction mixture was concentrated under vacuum. The residue was taken up in DCM and aqueous (saturated) $NaHCO_3$. The aqueous layer was extracted with DCM (3×). The combined organic layers were dried over $MgSO_4$ and concentrated under vacuum. The residue was chromatographed on silica gel to give the title compound of step A (294 mg, 0.66 mmol, 74%) as a yellow solid. $^1$H NMR (400 MHz, DMSO-$d_6$) δ 7.85 (d, 1H, J=9.35 Hz), 6.56 (dd, 1H, J=9.44 and 2.29 Hz), 6.49 (d, 1H, J=2.38 Hz), 4.17 (q, 2H, J=6.96 Hz), 3.36-3.41 (m, 4H), 3.25 (t, 2H, J=6.78 Hz), 3.01 (s, 3H), 2.92 (M, 2H), 2.66 (t, 2H, J=6.78 Hz), 2.57 (m, 4H), 2.15-2.25 (m, 1H), 1.89-1.97 (m, 2H), 1.75 (m, 2H), 1.32-1.40 (m, 5H).

Step B: [2-(ethyloxy)-4-(4-{1-[2-(methylsulfonyl)ethyl]-4-piperidinyl}-1-piperazinyl)-phenyl]amine

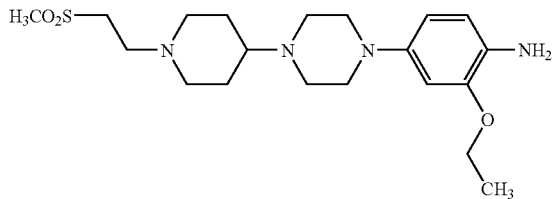

A mixture of 1-[3-(ethyloxy)-4-nitrophenyl]-4-{1-[2-(methylsulfonyl)ethyl]-4-piperidinyl}-piperazine (290 mg, 0.65 mmol) and platinum (sulfided, 5 wt. % on carbon, 50 mg, 0.013 mmol) in 20% MeOH/EtOAc (20 mL) was added to a high-pressure hydrogenation reaction flask. The reaction was purged with $N_2$ and vacuum (3×). The reaction was purged with $H_2$ and vacuum (3×). The reaction was then treated with $H_2$ at 50 psi and stirred for approximately 20 h. The reaction was degassed, then poured through a Teflon filter, washing the solid with MeOH and DCM. The filtrate was concentrated under vacuum to give the title compound of step B (256 mg, 0.62 mmol, 97%) as a brown solid. $^1$H NMR (400 MHz, DMSO-$d_6$) δ 6.50 (d, 1H, J=8.43 Hz), 6.44 (d, 1H, J=2.38 Hz), 6.26 (cd, 1H, J=2.38 and 8.43 Hz), 4.17 (br s, 2H), 3.95 (q, 2H, J=6.96 Hz), 3.25 (t, 2H, J=6.69 Hz), 3.01 (s, 3H), 2.91 (M, 6H), 2.65 (t, 2H, J=6.78 Hz), 2.57 (m, 4H), 2.10-2.20 (m, 1H), 1.89-1.97 (m, 2H), 1.76 (m, 2H), 1.28-1.32 (m, 5H).

Step C: N-(2,6-difluorophenyl)-3-[3-(2-{[2-(ethyloxy)-4-(4-{1-[2-(methylsulfonyl)ethyl]-4-piperidinyl}-1-piperazinyl)phenyl]amino}-4-pyrimidinyl)imidazo[1,2-a]pyridin-2-yl]benzamide To 3-[3-(2-chloro-4-pyrimidinyl)imidazo[1,2-a]pyridin-2-yl]-N-(2,6-difluorophenyl)-benzamide (Intermediate Example 1) (100 mg, 0.22 mmol) and 2-(ethyloxy)-4-(4-{1-[2-(methylsulfonyl)ethyl]-4-piperidinyl}-1-piperazinyl)phenyl]amine (80 mg, 0.20 mmol) in 2,2,2-trifluoroethanol (2 mL) was added p-toluenesulfonic acid monohydrate (140 mg, 0.74 mmol). The mixture was stirred and heated on a Biotage microwave at 150° C. for 45 min, then cooled to rt. The mixture was neutralized with 0.5M sodium methoxide in MeOH. The mixture was concentrated under vacuum and the residue purified by silica gel chromatography to give a yellow solid. The solid was dissolved in minimal DCM, then hexane was added until a precipitate was formed. The slurry was cooled at 0° C. for 90 min, then poured through a Teflon filter, washing the solids with cold hexanes. The solids were dried under vacuum to give the title compound (68 mg, 0.08 mmol, 42%) as a yellow solid. $^1$H NMR (400 MHz, DMSO-$d_6$) δ 10.24 (s, 1H), 9.36 (m, 1H), 8.35 (m, 2H), 8.23 (d, 1H, J=5.13 Hz), 8.05 (d, 1H, J=7.88 Hz), 7.81 (d, 1H, J=7.88 Hz), 7.73 (d, 1H, J=8.98 Hz), 7.61 (t, 1H, J=7.79 Hz), 7.37-7.49 (m, 3H), 7.21 (t, 2H, J=8.06 Hz), 6.94-6.99 (m, 1H), 6.65 (d, 1H, J=2.20 Hz), 6.44-6.50 (m, 2H), 4.06 (q, 2H, J=6.96 Hz), 3.24-3.27 (m, 2H), 3.11 (m, 4H), 2.93 (m, 2H), 2.60-2.69 (m, 6H), 2.17 (m, 1H), 1.91-1.98 (m, 2H), 1.74-1.81 (m, 2H), 1.35-1.45 (m, 2H), 1.24 (t, 3H, J=6.96 Hz). MS (ESI): 836 [M+H]⁺.

Example 93

N-(2,6-difluorophenyl)-3-[3-(2-{[2-(methyloxy)-4-(cis-4-{4-[2-(methylsulfonyl)-ethyl]-1-piperazinyl}cyclohexyl)phenyl]amino}-4-pyrimidinyl)imidazo[1,2-a]pyridin-2-yl]benzamide

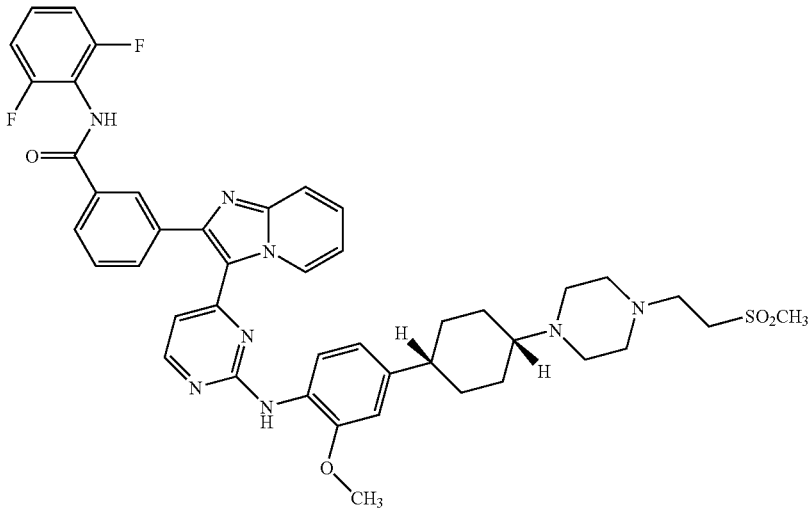

Step A: 1,4-dioxaspiro[4.5]dec-7-en-8-yl trifluoromethanesulfonate

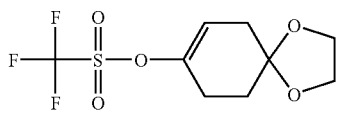

To a stirred solution of 1,4-dioxaspiro[4.5]decan-8-one (1.20 g, 7.69 mmol) and n-phenyltrifluoromethanesulfonimide (3.57 g, 10.0 mmol) in THF (77 mL) under N₂ at −78° C. was added 0.5 M potassium bis-trimethylsilylamide in toluene (20.0 mL, 10.0 mmol). The reaction was stirred 4 h, then quenched with H₂O, and extracted with ether. The combined ether extract layers were dried over MgSO₄, filtered and purified by silica gel chromatography to give the title compound of step A (2.21 g, 7.67 mmol, 100%) as a clear oil. ¹H NMR (400 MHz, DMSO-d₆) δ 5.64-5.68 (m, 1H), 3.98-4.00 (m, 4H), 2.51-2.57 (m, 2H), 2.39-2.42 (m, 2H), 1.90 (t, 2H, J=6.60 Hz).

Step B: 8-(4,4,5,5-tetramethyl-1,3,2-dioxaborolan-2-yl)-1,4-dioxaspiro[4.5]dec-7-ene

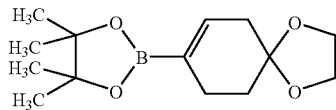

To a stirred solution of 1,4-dioxaspiro[4.5]dec-7-en-8-yl trifluoromethanesulfonate (2.20 g, 7.64 mmol) in dioxane (38 mL) was added bis(pinacolato)diboron (2.33 g, 9.17 mmol), [1,1'-bis(diphenylphosphino)ferrocene]dichloropalladium (II), complex with DCM (1:1) (0.187 g, 0.23 mmol), 1,1'-bis(diphenylphosphino)ferrocene (0.127 g, 0.23 mmol), and potassium acetate (2.25 g, 22.92 mmol). The mixture was degassed by purging the reaction flask with vacuum/then N₂ back-fill (3×). Under N₂, the reaction was then heated to 80° C. and stirred overnight (approx. 16 hrs). The reaction was cooled to rt and diluted with H₂O. The mixture was extracted with EtOAc (3×). The combined organic layers were washed with brine, dried over MgSO₄, filtered, then purified by silica gel chromatography to give the title compound of step B (1.65 g, 6.20 mmol, 81%) as a clear oil, that upon sitting in the fridge overnight changed to a white solid. MS (ESI): 267 [M+H]⁺.

Step C: 8-[3-(methyloxy)-4-nitrophenyl]-1,4-dioxaspiro[4.5]dec-7-ene

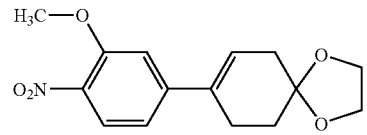

To a stirred solution of 8-(4,4,5,5-tetramethyl-1,3,2-dioxaborolan-2-yl)-1,4-dioxaspiro[4.5]dec-7-ene (1.09 g, 4.13 mmol) in dioxane (17 mL) was added 5-chloro-2-nitroanisole (0.64 g, 3.44 mmol), dichlorobis(triphenylphosphine)palladium(II) (0.12 g, 0.17 mmol) and 1.0 M Na₂CO₃ in H₂O (10.32 mL, 10.32 mmol). The mixture was degassed by purging the reaction flask with vacuum/then N₂ back-fill (5×). Under N₂ the reaction was then heated to 80° C. and stirred overnight (approximately 16 h). The reaction was cooled to rt and diluted with EtOAc, then filtered through Celite, washing with EtOAc. The filtrate was concentrated under vacuum. The residue was taken up in EtOAc and H₂O. The H₂O layer was separated and extracted with EtOAc. The combined organic layers were washed with brine, dried over MgSO₄, filtered, then concentrated and purified by silica gel chromatography to give the title compound of step C (911 mg, 3.13 mmol, 91%) as an amber oil. MS (ESI): 292 [M+H]⁺.

Step D:
4-[3-(methyloxy)-4-nitrophenyl]-3-cyclohexen-1-one

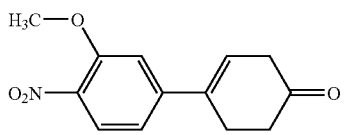

A solution of 20% TFA in DCM (25 mL) was added to 8-[3-(methyloxy)-4-nitrophenyl]-1,4-dioxaspiro[4.5]dec-7-ene (900 mg, 3.09 mmol) and the mixture was stirred at rt for approximately 14 h. The reaction was then concentrated under vacuum. The residue was dissolved in EtOAc and aqueous (saturated) NaHCO$_3$. The organic layer was separated, washed with H$_2$O, dried over MgSO$_4$, filtered, then concentrated and purified by silica gel chromatography to give the title compound of step D (520 mg, 2.10 mmol, 68%) as a tan solid. MS (ESI): 248 [M+H]$^+$.

Step E: 1,1-dimethylethyl 4-{4-[3-(methyloxy)-4-nitrophenyl]-3-cyclohexen-1-yl}-1-piperazinecarboxylate

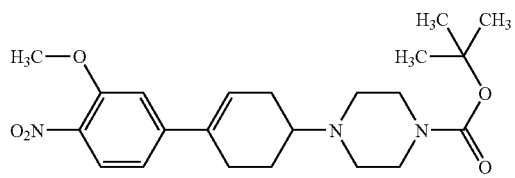

A solution of 4-[3-(methyloxy)-4-nitrophenyl]-3-cyclohexen-1-one (514 mg, 2.08 mmol) and 1-BOC-piperazine (430 mg, 2.28 mmol) were stirred in DCE (8 mL) at rt under N$_2$. To this mixture was added sodium triacetoxyborohydride (610 mg, 2.89 mmol) and HOAc (125 mg, 2.08 mmol). The reaction was stirred for approximately 24 h. The reaction was diluted with DCM and aqueous (saturated) NaHCO$_3$. The aqueous layer was extracted with DCM (3×). The combined organic layers were dried over MgSO$_4$, filtered, then concentrated and purified by silica gel chromatography to give the title compound of step E (669 mg, 1.60 mmol, 77%) as a tan solid. MS (ESI): 418 [M+H]$^+$.

Step F: 1-{4-[3-(methyloxy)-4-nitrophenyl]-3-cyclohexen-1-yl}piperazine

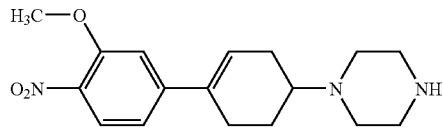

A solution of 1,1-dimethylethyl 4-{4-[3-(methyloxy)-4-nitrophenyl]-3-cyclohexen-1-yl}-1-piperazinecarboxylate (0.75 g, 1.80 mmol, combined batches) was stirred at rt under N$_2$ in 20% TFA in DCM (40 mL) for approximately 2 h. The solution was then concentrated under vacuum. The residue was dissolved in DCM and aqueous (saturated) NaHCO$_3$. The aqueous layer was separated and extracted with DCM (3×). The combined organic layers were dried over MgSO$_4$, filtered, then concentrated and purified by silica gel chromatography to give the title compound of step F (446 mg, 1.40 mmol, 78%) as a light tan solid. MS (ESI): 318 [M+H]$^+$.

Step G: 1-{4-[3-(methyloxy)-4-nitrophenyl]-3-cyclohexen-1-yl}-4-[2-(methylsulfonyl)-ethyl]piperazine

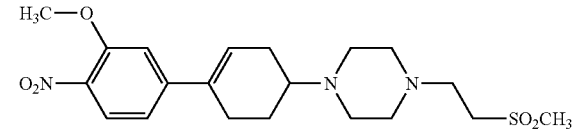

A solution of methyl vinyl sulfone (201 mg, 1.89 mmol) and 1-{4-[3-(methyloxy)-4-nitrophenyl]-3-cyclohexen-1-yl}piperazine (200 mg, 0.63 mmol) was stirred in dioxane (6 mL) under N$_2$. The reaction was then heated to 95° C. and stirred for approximately 3 h. The reaction was then cooled to rt and concentrated under vacuum. The residue was taken up in DCM and aqueous (saturated) NaHCO$_3$. The aqueous layer was extracted with DCM (2×). The combined organic layers were dried over MgSO$_4$, filtered, then concentrated and purified by silica gel chromatography to give the title compound of step G (222 mg, 0.52 mmol, 83%) as a light yellow solid. MS (ESI): 424 [M+H]$^+$.

Step H: [2-(methyloxy)-4-(trans-4-{4-[2-(methylsulfonyl)ethyl]-1-piperazinyl}-cyclohexyl)-phenyl]amine and [2-(methyloxy)-4-(cis-4-{4-[2-(methylsulfonyl)ethyl]-1-piperazinyl}-cyclohexyl)phenyl]amine

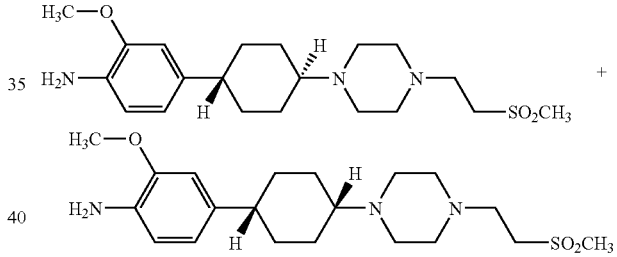

A solution of 1-{4-[3-(methyloxy)-4-nitrophenyl]-3-cyclohexen-1-yl}-4-[2-(methylsulfonyl)-ethyl]piperazine (212 mg, 0.50 mmol) and 10% Pd on carbon (100 mg, 0.09 mmol) was stirred in 8:2 EtOAc/MeOH (20 mL) under N$_2$ in a high-pressure hydrogenation flask. The flask was purged with N$_2$ and vacuum (3×), then purged with H$_2$ gas and vacuum (3×). The flask was then treated with H$_2$ gas at 50 psi for approximately 18 h. The reaction was de-gassed and then filtered through Celite, washing with DCM and MeOH. The filtrate was concentrated under vacuum. The residue was purified by silica gel chromatography to give the title compounds of step G.

Data for trans Isomer
(90 mg, 0.22 mmol, 45%) as a white solid. $^1$H NMR (400 MHz, CDCl$_3$) δ 6.61-6.68 (m, 3H), 3.82 (s, 3H), 3.64 (br s, 2H), 3.11 (t, 2H, J=6.32 Hz), 3.01 (s, 3H), 2.84 (t, 2H, J=6.32 Hz), 2.42-2.60 (m, 10H), 1.79-1.94 (m, 4H), 1.44-1.60 (m, 4H)

Data for cis Isomer
(94 mg, 0.23 mmol, 47%) as a white solid. $^1$H NMR (400 MHz, CDCl$_3$) δ 6.60-6.66 (m, 3H), 3.84 (s, 3H), 3.67 (br s, 2H), 3.14 (t, 2H, J=6.51 Hz), 3.04 (s, 3H), 2.88 (t, 2H, J=6.42 Hz), 2.50-2.65 (m, 8H), 2.28-2.41 (m, 2H), 1.93-2.03 (m, 4H), 1.32-1.50 (m, 4H).

Step I: N-(2,26-difluorophenyl)-3-[3-(2-{[2-(methyloxy)-4-(cis-4-{4-[2-(methylsulfonyl)-ethyl]-1-piperazinyl}cyclohexyl)phenyl]amino}-4-pyrimidinyl)imidazo[1,2-a]pyridin-2-yl]benzamide To 3-[3-(2-chloro-4-pyrimidinyl)imidazo[1,2-a]pyridin-2-yl]-N-(2,6-difluorophenyl)-benzamide (Intermediate Example 1) (50 mg, 0.11 mmol) and [2-(methyloxy)-4-(cis-4-{4-[2-(methylsulfonyl)ethyl]-1-piperazinyl}cyclohexyl)phenyl]amine (43 mg, 0.11 mmol) in 2,2,2-trifluoroethanol (1.0 mL) was added 4 M HCl in dioxane (54 µL, 0.22 mmol). The mixture was stirred and heated on a Biotage microwave at 175° C. for 40 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexanes was added until a precipitate was formed. The slurry was cooled at −10° C. for 30 min, then poured through a Teflon filter, washing the solids with cold hexanes. The solids were dried under vacuum to give the title compound (60 mg, 0.07 mmol, 67%) as a yellow solid. $^1$H NMR (400 MHz, DMSO-$d_6$) δ 10.24 (s, 1H), 9.41 (d, 1H, J=6.41 Hz), 8.50 (s, 1H), 8.34 (s, 1H), 8.26 (d, 1H, J=5.13 Hz), 8.06 (d, 1H, J=7.87 Hz), 7.82 (d, 1H, J=7.69 Hz), 7.74 (d, 1H, J=8.97 Hz), 7.61 (t, 2H, J=7.78 Hz), 7.34-7.51 (m, 2H), 7.21 (t, 2H, J=8.06 Hz), 7.00 (t, 1H, J=6.87 Hz), 6.95 (s, 1H), 6.77 (d, 1H, J=8.24 Hz), 6.55 (d, 1H, J=5.31 Hz), 3.82 (s, 3H), 3.24-3.29 (m, 2H), 3.02 (s, 3H), 2.67 (t, 2H, J=6.59 Hz), 2.38-2.55 (m, 9H), 2.28-2.36 (m, 1H), 1.84-1.93 (m, 4H), 1.45-1.55 (m, 2H), 1.29-1.40 (m, 2H). MS (ESI): 821 [M+H]$^+$.

Example 94

N-(2,6-difluorophenyl)-3-[3-(2-{[2-(methyloxy)-4-(trans-4-{4-[2-(methylsulfonyl)-ethyl]-1-piperazinyl}cyclohexyl)phenyl]amino}-4-pyrimidinyl)imidazo[1,2-a]pyridin-2-yl]benzamide

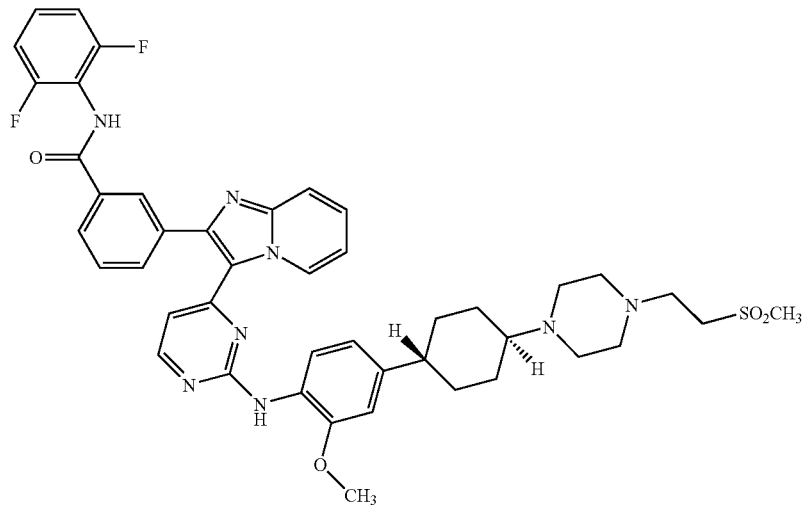

To 3-[3-(2-chloro-4-pyrimidinyl)imidazo[1,2-a]pyridin-2-yl]-N-(2,6-difluorophenyl)-benzamide (Intermediate Example 1) (50 mg, 0.11 mmol) and [2-(methyloxy)-4-(trans-4-{4-[2-(methylsulfonyl)ethyl]-1-piperazinyl}cyclohexyl)phenyl]amine (Example 93, step H) (43 mg, 0.11 mmol) in 2,2,2-trifluoroethanol (1.0 mL) was added 4 M HCl in dioxane (54 µL, 0.22 mmol). The mixture was stirred and heated on a Biotage microwave at 175° C. for 40 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (50 mg, 0.06 mmol, 56%) as a yellow solid. $^1$H NMR (400 MHz, DMSO-$d_6$) δ 10.24 (s, 1H), 9.42 (d, 1H, J=6.23 Hz), 8.54 (s, 1H), 8.34 (s, 1H), 8.26 (d, 1H, J=5.31 Hz), 8.06 (d, 1H, J=7.69 Hz), 7.82 (d, 1H, J=7.51 Hz), 7.74 (d, 1H, J=8.97 Hz), 7.59-7.66 (m, 2H), 7.34-7.51 (m, 2H), 7.21 (t, 2H, J=8.06 Hz), 6.98 (t, 1H, J=6.78 Hz), 6.94 (s, 1H), 6.80 (d, 1H, J=8.06 Hz), 6.54 (d, 1H, J=5.13 Hz), 3.82 (s, 3H), 3.24-3.29 (m, 2H), 3.02 (s, 3H), 2.67 (t, 2H, J=6.50 Hz), 2.34-2.60 (m, 12H), 2.18 (s, 1H), 1.91-1.99 (m, 2H), 1.77-1.89 (m, 2H), 1.44-1.60 (m, 4H). MS (ESI): 821 [M+H]$^+$.

Example 95

N-(2,6-difluorophenyl)-3-[3-(2-{[4-[1'-(2-fluoroethyl)-4,4'-bipiperidin-1-yl]-2-(methyloxy)phenyl]amino}-4-pyrimidinyl)imidazo[1,2-a]pyridin-2-yl]benzamide

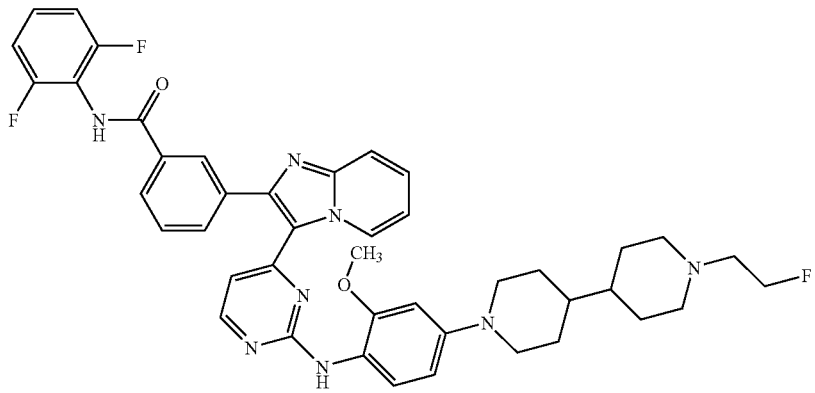

Step A: 1,1-dimethylethyl 4,4'-bipiperidine-1-carboxylate

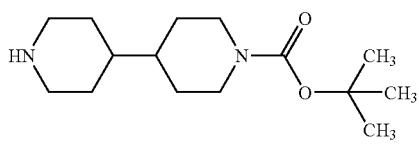

To 4,4'-bipiperidine (5.48 g, 32.6 mmol) in THF (160 mL) and CHCl₃ (160 mL) was added BOC-On (4.01 g) in THF (90 mL) dropwise over a 8 h period. The reaction was then concentrated and purified by flash chromatography. The residue was taken up in 1M KHSO₄ (250 mL) and washed with diethyl ether (three times). K₂CO₃ (38.0 g, 275 mmol) was added to the aqueous layer which was subsequently extracted with CHCl₃ (3×), dried (MgSO₄) and concentrated to provide the title compound of step A (1.98 g, 7.40 mmol, 45%). $^1$H NMR (400 MHz, CDCl₃) δ ppm 1.06-1.18 (m, 5H), 1.42 (s, 9H), 1.58-1.69 (m, 6H), 2.50-2.61 (m, 4H), 3.06 (d, J=12.1 Hz, 2H), 4.08 (br. s., 2H).

Step B: 1,1-dimethylethyl 1'-[3-(methyloxy)-4-nitrophenyl]-4,4'-bipiperidine-1-carboxylate

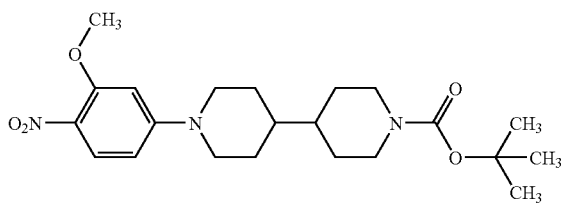

The title compound of step B (2.32 g, 5.50 mmol, 75%) was prepared in an analogous manner to that of Example 22, step B, with the following notable exception: 1,1-dimethylethyl 4,4'-bipiperidine-1-carboxylate was used instead of 1,4'-bipiperidine. $^1$H NMR (400 MHz, DMSO-d₆) δ ppm 0.92-1.03 (m, 2H), 1.10-1.21 (m, 3H), 1.27-1.39 (m, 10H), 1.60 (d, J=12.3 Hz, 2H), 1.70 (d, J=11.2 Hz, 2H), 2.58 (br. s., 2H), 2.83 (s, 2H), 3.85 (s, 3H), 3.91 (d, J=12.5 Hz, 2H), 4.03 (d, J=13.4 Hz, 2H), 6.43 (d, J=2.4 Hz, 1H), 6.53 (dd, J=9.4, 2.3 Hz, 1H), 7.82 (d, J=9.5 Hz, 1H).

Step C: 1-[3-(methyloxy)-4-nitrophenyl]-4,4'-bipiperidine

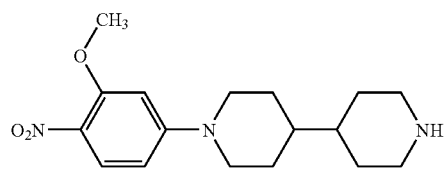

The title compound of step C (1.63 g, 5.10 mmol, 100%) was prepared from 1,1-dimethylethyl 1'-[3-(methyloxy)-4-nitro-phenyl]-4,4'-bipiperidine-1-carboxylate in an analogous manner to that described for Example 89, step B. $^1$H NMR (400 MHz, DMSO-d₆) δ ppm 0.92-1.03 (m, 2H), 1.10-1.21 (m, 3H), 1.27-1.39 (m, 10H), 1.60 (d, J=12.3 Hz, 2H), 1.70 (d, J=11.2 Hz, 2H), 2.58 (br. s., 2H), 2.83 (s, 2H), 3.85 (s, 3H), 3.91 (d, J=12.5 Hz, 2H), 4.03 (d, J=13.4 Hz, 2H), 6.43 (d, J=2.4 Hz, 1H), 6.53 (dd, J=9.4, 2.3 Hz, 1H), 7.82 (d, J=9.5 Hz, 1H).

Step D: 1-(2-fluoroethyl)-1'-[3-(methyloxy)-4-nitrophenyl]-4,4'-bipiperidine

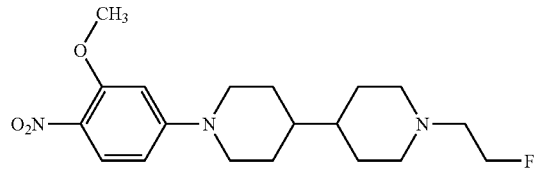

The title compound of step D (0.494 g, 1.35 mmol, 68%) was prepared from 1-[3-(methyloxy)-4-nitrophenyl]-4,4'-bipiperidine in an analogous manner to that described for Example 90, step A. $^1$H NMR (400 MHz, DMSO-d₆) δ ppm 0.96-1.07 (m, 1H), 1.11-1.22 (m, 4H), 1.27-1.38 (m, 1H), 1.61 (d, J=12.1 Hz, 2H), 1.74 (d, J=11.7 Hz, 2H), 1.89 (t, J=11.0 Hz, 2H), 2.54 (dt, J$_{HF}$=28.2 Hz, J=4.8 Hz 2H), 2.86 (t, J=11.6 Hz, 4H), 3.88 (s, 3H), 4.05 (d, J=13.6 Hz, 2H), 4.48 (dt, J$_{HF}$=48.0 Hz, J=4.8 Hz 2H), 6.46 (d, J=2.6 Hz, 1H), 6.55 (dd, J=9.5, 2.6 Hz, 1H), 7.85 (d, J=9.5 Hz, 1H).

Step E: 4-[1'-(2-fluoroethyl)-4,4'-bipiperidin-1-yl]-2-(methyloxy)aniline

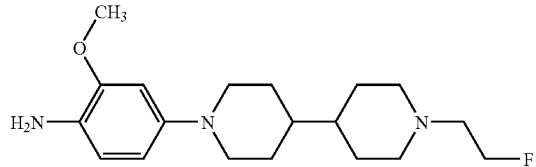

The title compound of step E (0.417 g, 1.24 mmol, 92%) was prepared from 1-(2-fluoroethyl)-1'-[3-(methyloxy)-4-nitrophenyl]-4,4'-bipiperidine in an analogous manner to that described for Example 87, step I. $^1$H NMR (400 MHz, DMSO-d$_6$) δ ppm 0.99-1.07 (m, 2H), 1.12-1.17 (m, 1H), 1.18-1.26 (m, 2H), 1.60 (d, J=11.9 Hz, 2H), 1.68 (d, J=12.8 Hz, 2H), 1.87 (t, J=11.0 Hz, 2H), 2.34-2.42 (m, 2H), 2.51 (dt, J$_{HF}$=28.2 Hz, J=4.9 Hz, 2H), 2.86 (d, J=11.5 Hz, 2H), 3.36 (d, J=11.7 Hz, 2H), 3.68 (s, 3H), 4.14 (br. s., 2H), 4.46 (dt, J$_{HF}$=47.8 Hz, J=4.9 Hz, 2H), 6.23 (dd, J=8.3, 2.3 Hz, 1H), 6.41-6.47 (m, 2H).

Step F: N-(2,6-difluorophenyl)-3-[3-(2-{[4-[1'-(2-fluoroethyl)-4,4'-bipiperidin-1-yl]-2-(methyloxy)phenyl]amino}-4-pyrimidinyl)imidazo[1,2-a]pyridin-2-yl]benzamide The title compound (0.078 g, 0.10 mmol, 41%) was prepared in an analogous manner to that described for Example 36, step E with the following notable exception: 4-[1'-(2-fluoroethyl)-4,4'-bipiperidin-1-yl]-2-(methyl-oxy)aniline was used instead of 2-(methyloxy)-4-[4-(1-piperidinyl-methyl)-1-piperidinyl]-aniline. $^1$H NMR (400 MHz, DMSO-d$_6$) δ ppm 0.76-0.84 (m, 1H), 0.97-1.07 (m, 1H), 1.13-1.25 (m, 4H), 1.62 (d, J=12.5 Hz, 2H), 1.72 (d, J=12.5 Hz, 2H), 1.88 (t, J=11.1 Hz, 2H), 2.48-2.59 (m, 4H), 2.87 (d, J=10.8 Hz, 2H), 3.69 (d, J=11.5 Hz, 2H), 3.75 (s, 3H), 4.47 (dt, J$_{HF}$=48.0 Hz, J=4.6 Hz, 2H), 6.39-6.46 (m, 2H), 6.63 (s, 1H), 6.94 (t, J=6.6 Hz, 1H), 7.17 (t, J=8.0 Hz, 2H), 7.32-7.39 (m, 2H), 7.40-7.45 (m, 1H), 7.57 (t, J=7.7 Hz, 1H), 7.69 (d, J=9.0 Hz, 1H), 7.78 (d, J=8.6 Hz, 1H), 8.02 (d, J=7.7 Hz, 1H), 8.16 (d, J=5.7 Hz, 1H), 8.30 (s, 1H), 8.42 (s, 1H), 9.36 (br. s., 1H), 10.21 (s, 1H). MS (M+H, ES+) 761.

Example 96

N-(2,6-difluorophenyl)-5-[3-(2-{[4-[1'-(2-fluoroethyl)-4,4'-bipiperidin-1-yl]-2-(methyloxy)phenyl]amino}-4-pyrimidinyl)imidazo[1,2-a]pyridin-2-yl]-2-(methyloxy)benzamide

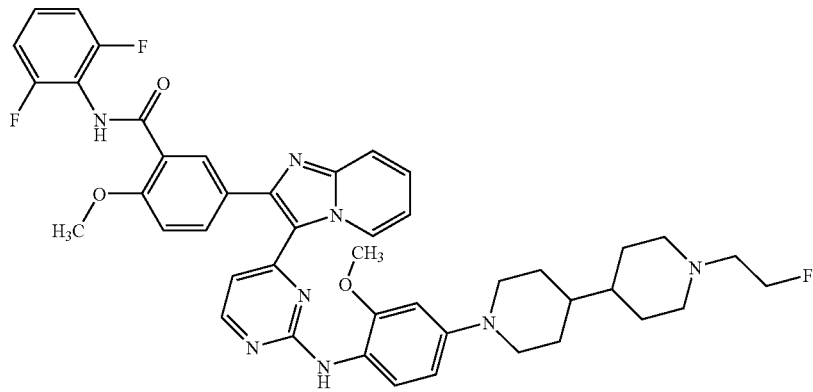

The title compound (0.057 g, 0.070 mmol, 29%) was prepared in an analogous manner to that described for Example 95, step F with the following notable exception: 5-[3-(2-chloro-4-pyrimidinyl)-imidazo[1,2-a]pyridin-2-yl]-N-(2,6-difluorophenyl)-2-(methyloxy)benzamide (Intermediate Example 2) was used instead of Intermediate Example 1. $^1$H NMR (400 MHz, DMSO-d$_6$) δ ppm 0.96-1.07 (m, 1H), 1.13-1.21 (m, 3H), 1.23-1.27 (m, 2H), 1.62 (d, J=12.6 Hz, 2H), 1.72 (d, J=12.6 Hz, 2H), 1.88 (t, J=9.5 Hz, 2H), 2.48-2.59 (m, 4H), 2.87 (d, J=10.8 Hz, 2H), 3.69 (d, J=12.1 Hz, 2H), 3.76 (s, 3H), 3.95 (s, 3H), 4.46 (dt, J$_{HF}$=47.6 Hz, J=5.5 Hz, 2H), 6.44 (d, J=9.7 Hz, 1H), 6.49 (d, J=4.9 Hz, 1H), 6.63 (s, 1H), 6.91 (t, J=6.2 Hz, 1H), 7.15 (t, J=8.1 Hz, 2H), 7.25 (d, J=8.4 Hz, 1H), 7.31-7.42 (m, 3H), 7.66 (d, J=9.3 Hz, 1H), 7.74 (d, J=8.2 Hz, 1H), 8.07 (s, 1H), 8.16 (d, J=5.3 Hz, 1H), 8.41 (s, 1H), 9.33 (br. s., 1H), 9.76 (s, 1H).

Example 97

N-(2,6-difluorophenyl)-3-(3-{2-[(2-(methyloxy)-4-{1'-[2-(methylsulfonyl)ethyl]-4,4'-bipiperidin-1-yl}phenyl)amino]-4-pyrimidinyl}imidazo[1,2-a]pyridin-2-yl)benzamide

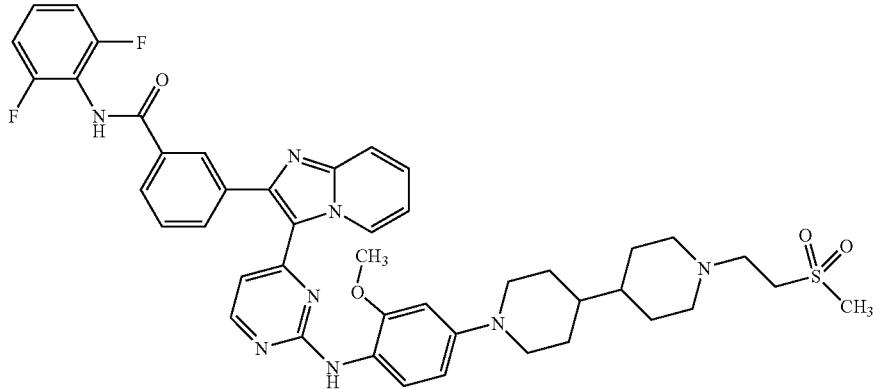

Step A: 1-[3-(methyloxy)-4-nitrophenyl]-1'-[2-(methylsulfonyl)ethyl]-4,4'-bipiperidine

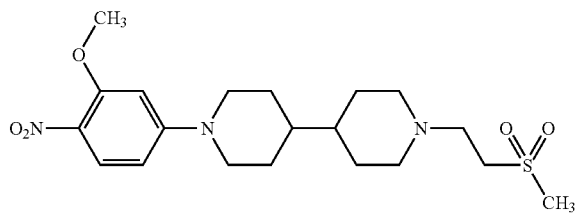

The title compound of step A (0.602 g, 1.41 mmol, 83%) was prepared from 1-[3-(methyloxy)-4-nitrophenyl]-4,4'-bipiperidine (Example 95, step C) in an analogous manner to that described for Example 8. $^1$H NMR (400 MHz, DMSO-$d_6$) δ ppm 0.95-1.04 (m, 1H), 1.08-1.19 (m, 4H), 1.25-1.35 (m, 1H), 1.60 (d, J=11.2 Hz, 2H), 1.71 (d, J=10.8 Hz, 2H), 1.82 (t, J=11.5 Hz, 2H), 2.60 (t, J=6.8 Hz, 2H), 2.79-2.89 (m, 4H), 2.96 (s, 3H), 3.21 (t, J=6.8 Hz, 2H), 3.85 (s, 3H), 4.02 (d, J=13.2 Hz, 2H), 6.43 (d, J=2.4 Hz, 1H), 6.52 (dd, J=9.5, 2.4 Hz, 1H), 7.82 (d, J=9.3 Hz, 1H).

Step B: 2-(methyloxy)-4-{1'-[2-(methylsulfonyl)ethyl]-4,4'-bipiperidin-1-yl}aniline

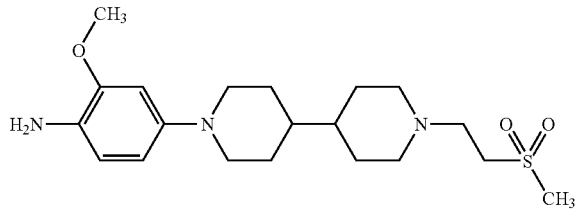

The title compound of step B (0.457 g, 1.16 mmol, 78%) was prepared from 1-[3-(methyloxy)-4-nitrophenyl]-1'-[2-(methylsulfonyl)ethyl]-4,4'-bipiperidine in a manner analogous to that described for Example 87, step I. $^1$H NMR (400 MHz, DMSO-$d_6$) δ ppm 1.00-1.04 (m, J=10.8 Hz, 1H), 1.06-1.13 (m, 2H), 1.15-1.25 (m, 3H), 1.65 (dd, J=19.0, 12.5 Hz, 4H), 1.83 (t, J=11.1 Hz, 2H), 2.33-2.42 (m, 2H), 2.61 (t, J=6.7 Hz, 2 H), 2.84-2.90 (m, 2H), 2.97 (s, 3H), 3.21 (t, J=6.8 Hz, 2H), 3.36 (d, J=11.4 Hz, 2H), 3.68 (s, 3H), 4.14 (br. s., 2H), 6.23 (dd, J=8.3, 2.3 Hz, 1H), 6.41-6.46 (m, 2H).

Step C: N-(2,6-difluorophenyl)-3-(3-{2-[(2-(methyloxy)-4-{1'-[2-(methylsulfonyl)ethyl]-4,4'-bipiperidin-1-yl}phenyl)amino]-4-pyrimidinyl}imidazo[1,2-a]pyridin-2-yl)benzamide The title compound (0.078 g, 0.10 mmol, 38%) was prepared in an analogous manner to that described for Example 36, step E) with the following notable exception: 2-(methyloxy)-4-{1'-[2-(methylsulfonyl)ethyl]-4,4'-bipiperidin-1-yl}aniline was used instead of 2-(methyloxy)-4-[4-(1-piperidinyl-methyl)-1-piperidinyl]-aniline. $^1$H NMR (400 MHz, DMSO-$d_6$) δ ppm 1.00-1.06 (m, 1H), 1.08-1.18 (m, 3H), 1.20-1.27 (m, 2H), 1.64 (d, J=11.7 Hz, 2H), 1.72 (d, J=10.8 Hz, 2H), 1.84 (t, J=11.1 Hz, 2H), 2.55 (t, J=12.5 Hz, 2H), 2.61 (t, J=6.8 Hz, 2H), 2.88 (d, J=10.8 Hz, 2H), 2.97 (s, 3H), 3.22 (t, J=6.7 Hz, 2H), 3.69 (d, J=12.1 Hz, 2H), 3.75 (s, 3H), 6.41-6.47 (m, 2H), 6.63 (s, 1H), 6.90-6.99 (m, 1H), 7.17 (t, J=8.2 Hz, 2H), 7.33-7.45 (m, 3H), 7.58 (t, J=7.8 Hz, 1H), 7.69 (d, J=8.8 Hz, 1H), 7.78 (d, J=7.5 Hz, 1H), 8.02 (d, J=8.1 Hz, 1H), 8.17 (d, J=5.3 Hz, 1H), 8.30 (s, 1H), 8.43 (s, 1H), 9.36 (br. s., 1H), 10.21 (s, 1H). MS (M−H, ES−) 819.

Example 98

N-(2,6-difluorophenyl)-2-(methyloxy)-5-(3-{2-[(2-(methyloxy)-4-{1'-[2-(methylsulfonyl)ethyl]-4,4'-bipiperidin-1-yl}phenyl)amino]-4-pyrimidinyl}imidazo[1,2-a]pyridin-2-yl)benzamide

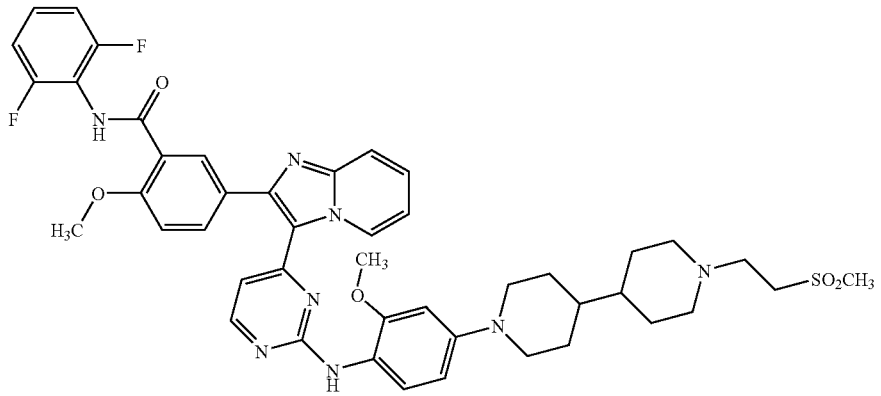

The title compound (0.077 g, 0.090 mmol, 36%) was prepared in an analogous manner to that described for Example 97, step C, with the following notable exception: 5-[3-(2-chloro-4-pyrimidinyl)-imidazo[1,2-a]pyridin-2-yl]-N-(2,6-difluorophenyl)-2-(methyloxy)benzamide (Intermediate Example 2) was used instead of Intermediate Example 1. $^1$H NMR (400 MHz, DMSO-$d_6$) δ ppm 1.00-1.06 (m, 1H), 1.08-1.18 (m, 3H), 1.20-1.27 (m, 2H), 1.64 (d, J=11.5 Hz, 2H), 1.72 (d, J=11.7 Hz, 2H), 1.80-1.88 (m, 2H), 2.55 (t, J=11.1 Hz, 2H), 2.62 (t, J=7.1 Hz, 2H), 2.88 (d, J=11.0 Hz, 2H), 2.97 (s, 3H), 3.22 (t, J=6.6 Hz, 2H), 3.69 (d, J=10.6 Hz, 2H), 3.75 (s, 3H), 3.95 (s, 3H), 6.41-6.51 (m, 2H), 6.62 (s, 1H), 6.91 (t, J=6.5 Hz, 1H), 7.15 (t, J=8.1 Hz, 2H), 7.25 (d, J=9.0 Hz, 1H), 7.31-7.42 (m, 3H), 7.66 (d, J=9.0 Hz, 1H), 7.74 (d, J=9.2 Hz, 1H), 8.07 (s, 1H), 8.16 (d, J=5.1 Hz, 1H), 8.41 (s, 1H), 9.33 (br. s., 1H), 9.75 (s, 1H). MS (M+H, ES+) 851.

Example 99

N-(2,6-difluorophenyl)-3-(3-{2-[(2-(methyloxy)-4-{1'-[2-(methylsulfonyl)ethyl]-1,4'-bipiperidin-4-yl}phenyl)amino]-4-pyrimidinyl}imidazo[1,2-a]pyridin-2-yl)benzamide

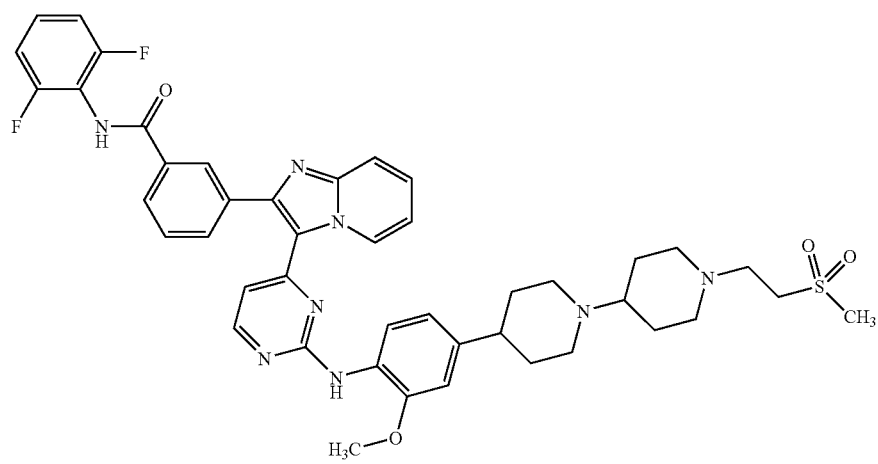

Step A: 1,1-dimethylethyl 4-[4-amino-3-(methyloxy)phenyl]-1-piperidine carboxylate

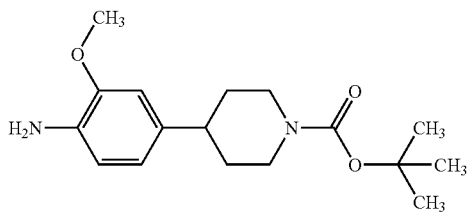

Step B: N-(2,6-difluorophenyl)-3-[3-(2-{[2-(methyloxy)-4-(4-piperidinyl)phenyl]amino}-4-pyrimidinyl)imidazo[1,2-a]pyridin-2-yl]benzamide

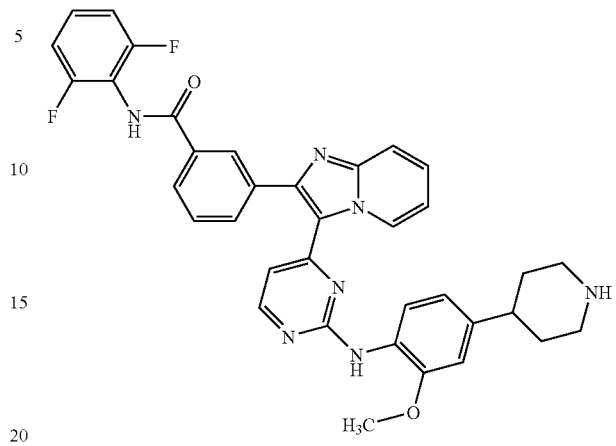

5-chloro-2-nitroanisole (0.094 g, 0.50 mmol), 1,1-dimethylethyl 4-(4,4,5,5-tetramethyl-1,3,2-dioxaborolan-2-yl)-3,6-dihydro-1(2H)-pyridinecarboxylate (0.19 g, 0.60 mmol), $Na_2CO_3$ (0.16 g, 1.5 mmol) and bis(triphenylphosphine)palladium(II) chloride (0.019 g, 0.030 mmol) in dioxane (3 mL) and $H_2O$ (1.5 mL) was degassed for 30 min. The mixture was heated at 120° C. for 20 min in the microwave. Upon completion by TLC, the reaction was placed under $H_2$ (1 atm.). The mixture was transferred to a separate flask and diluted with EtOH and subsequently stirred under $H_2$ (1 atm.) overnight. Upon completion by TLC, the reaction was filtered through Celite®, washed with EtOAc, dried ($MgSO_4$), concentrated and purified by flash chromatography to provide the title compound of step A (0.12 g, 0.40 mmol, 81%). $^1$H NMR (400 MHz, $CDCl_3$) δ ppm 1.48 (s, 9H), 1.52-1.64 (m, 2H), 1.79 (d, J=12.8 Hz, 2H), 2.54 (tt, J=12.1, 3.5 Hz, 1H), 2.77 (t, J=11.9 Hz, 2H), 3.65 (d, J=2.6 Hz, 1H), 3.70 (d, J=6.2 Hz, 1H), 3.83 (s, 3H), 4.22 (br. s., 2H), 6.60-6.66 (m, 3H).

The title compound of step B (1.68 g, 2.69 mmol, 76%, approximately 85% pure, used without further purification) was prepared in an analogous manner to that described for Example 36, step E, with the following notable exception: 1,1-dimethylethyl 4-[4-amino-3-(methyloxy)-phenyl]-1-piperidine carboxylate (different batch than described above) was used instead of 2-(methyloxy)-4-[4-(1-piperidinyl-methyl)-1-piperidinyl]-aniline. $^1$H NMR (400 MHz, DMSO-$d_6$) δ ppm 1.47-1.58 (m, 2H), 1.69 (d, J=11.4 Hz, 2H), 2.51-2.62 (m, 3H), 3.02 (d, J=11.9 Hz, 2H), 3.69 (s, 1H), 3.80 (s, 3H), 6.50 (d, J=5.3 Hz, 1H), 6.75 (dd, J=8.1, 1.6 Hz, 1H), 6.91 (s, 1H), 6.97 (t, J=6.4 Hz, 1H), 7.17 (t, J=8.1 Hz, 2H), 7.33-7.41 (m, 1H), 7.42-7.47 (m, 1H), 7.53-7.64 (m, 2H), 7.71 (d, J=9.0 Hz, 1H), 7.79 (d, J=7.7 Hz, 1H), 8.02 (d, J=7.9 Hz, 1H), 8.23 (d, J=5.3 Hz, 1H), 8.30 (s, 1H), 8.50 (s, 1H), 9.39 (d, J=6.2 Hz, 1H), 10.21 (s, 1H).

Step C: 1,1-dimethylethyl 4-[4-({4-[2-(3-{[(2,6-difluorophenyl)amino]carbonyl}-phenyl)imidazo[1,2-a]pyridin-3-yl]-2-pyrimidinyl}amino)-3-(methyloxy)phenyl]-1,4'-bipiperidine-1'-carboxylate

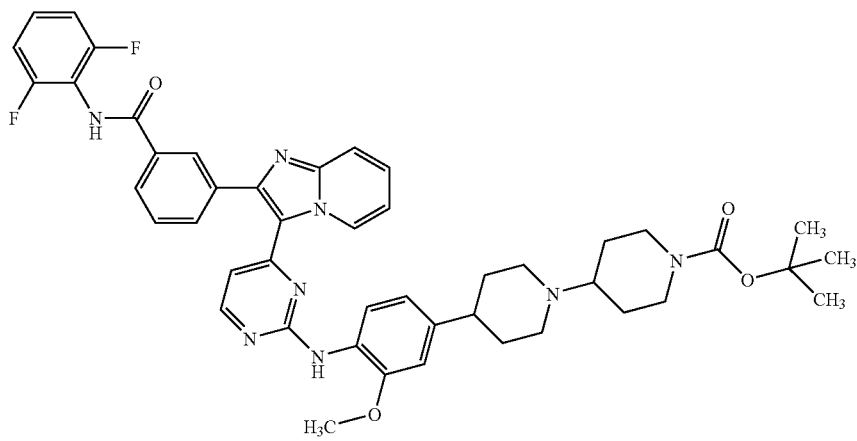

The title compound of step C (1.85 g, 2.26 mmol, 85%, approximately 85% pure, used without further purification) was prepared from N-(2,6-difluorophenyl)-3-[3-(2-{[2-(methyloxy)-4-(4-piperidinyl)phenyl]amino}-4-pyrimidinyl)imidazo[1,2-a]pyridin-2-yl]benzamide in an analogous manner to that described for Example 89, step C. $^1$H NMR (400 MHz, DMSO-$d_6$) δ ppm 1.19-1.31 (m, 2H), 1.33 (s, 9H), 1.62-1.72 (m, 5H), 2.14-2.24 (m, 2H), 2.32-2.43 (m, 2H), 2.56-2.70 (m, 3H), 2.83-2.94 (m, 2H), 3.79 (s, 3H), 3.93 (d, J=9.7 Hz, 2H), 6.50 (d, J=5.3 Hz, 1H), 6.75 (d, J=8.4 Hz, 1H), 6.93 (d, J=1.5 Hz, 1H), 6.97 (t, J=6.5 Hz, 1H), 7.17 (t, J=8.1 Hz, 2H), 7.33-7.41 (m, 1H), 7.41-7.47 (m, 1H), 7.58 (q, J=7.4 Hz, 2H), 7.70 (d, J=9.2 Hz, 1H), 7.78 (d, J=7.9 Hz, 1H), 8.02 (d, J=7.9 Hz, 1H), 8.22 (d, J=5.3 Hz, 1H), 8.31 (s, 1H), 8.49 (s, 1H), 9.39 (d, J=6.0 Hz, 1H), 10.20 (s, 1H).

Step D: 3-[3-(2-{[4-(1,4'-bipiperidin-4-yl)-2-(methyloxy)phenyl]amino}-4-pyrimidinyl)-imidazo[1,2-a]pyridin-2-yl]-N-(2,6-difluorophenyl)benzamide

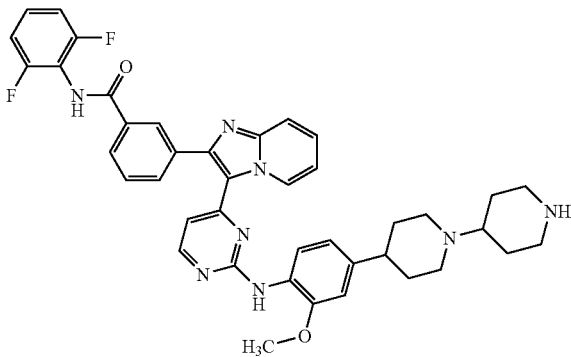

The title compound of step D (1.14 g, 1.59 mmol, 70%) was prepared from 1,1-dimethylethyl 4-[4-({4-[2-(3-{[(2,6-difluorophenyl)amino]carbonyl}phenyl)imidazo[1,2-a]pyridin-3-yl]-2-pyrimidinyl}amino)-3-(methyloxy)phenyl]-1,4'-bipiperidine-1'-carboxylate in an analogous manner to that described for Example 89, step B. $^1$H NMR (400 MHz, DMSO-$d_6$) δ ppm 1.21-1.32 (m, 2H), 1.56-1.67 (m, 5H), 1.68-1.77 (m, 2H), 2.17-2.29 (m, 3H), 2.33-2.43 (m, 3H), 2.88-2.98 (m, 4H), 3.80 (s, 3H), 6.50 (d, J=5.3 Hz, 1H), 6.76 (d, J=9.7 Hz, 1H), 6.94 (d, J=1.3 Hz, 1H), 6.97 (t, J=7.1 Hz, 1H), 7.17 (t, J=8.2 Hz, 2H), 7.33-7.41 (m, 1H), 7.42-7.47 (m, 1H), 7.55-7.63 (m, 2H), 7.71 (d, J=8.8 Hz, 1H), 7.79 (d, J=7.5 Hz, 1H), 8.02 (d, J=7.7 Hz, 1H), 8.22 (d, J=5.3 Hz, 1H), 8.30 (s, 1H), 8.49 (s, 1H), 9.39 (d, J=6.2 Hz, 1H), 10.20 (br. s., 1H).

Step E: N-(2,6-difluorophenyl)-3-(3-{2-[(2-(methyloxy)-4-{1'-[2-(methylsulfonyl)ethyl]-1,4'-bipiperidin-4-yl}phenyl)amino]-4-pyrimidinyl}imidazo[1,2-a]pyridin-2-yl)benzamide The title compound (0.21 g, 0.25 mmol, 73%) was prepared from 3-[3-(2-{[4-(1,4'-bipiperidin-4-yl)-2-(methyloxy)phenyl]amino}-4-pyrimidinyl)-imidazo[1,2-a]pyridin-2-yl]-N-(2,6-difluorophenyl)benzamide in an analogous manner to that described for Example 8. $^1$H NMR (400 MHz, DMSO-$d_6$) δ ppm 1.33-1.44 (m, 2H), 1.56-1.66 (m, 2H), 1.71 (t, J=11.6 Hz, 4H), 1.89 (t, J=11.0 Hz, 2H), 2.17 (t, J=10.4 Hz, 3H), 2.38-2.43 (m, 1H), 2.62 (t, J=6.8 Hz, 2H), 2.91 (t, J=12.0 Hz, 4H), 2.98 (s, 3H), 3.22 (t, J=6.7 Hz, 2H), 3.79 (s, 3H), 6.50 (d, J=5.3 Hz, 1H), 6.75 (d, J=8.2 Hz, 1H), 6.93 (d, J=1.5 Hz, 1H), 6.97 (t, J=6.8 Hz, 1H), 7.17 (t, J=8.1 Hz, 2H), 7.33-7.41 (m, 1H), 7.41-7.48 (m, 1H), 7.55-7.63 (m, 2H), 7.71 (d, J=9.0 Hz, 1H), 7.78 (d, J=7.7 Hz, 1H), 8.02 (d, J=7.9 Hz, 1H), 8.22 (d, J=5.1 Hz, 1H), 8.31 (s, 1H), 8.49 (s, 1H), 9.39 (d, J=7.3 Hz, 1H), 10.20 (s, 1H). MS (M+H, ES+) 821.

Example 100

N-(2,6-difluorophenyl)-3-[3-(2-{[4-[1'-(2-fluoroethyl)-1,4'-bipiperidin-4-yl]-2-(methyloxy)phenyl]amino}-4-pyrimidinyl)imidazo[1,2-a]pyridin-2-yl]benzamide

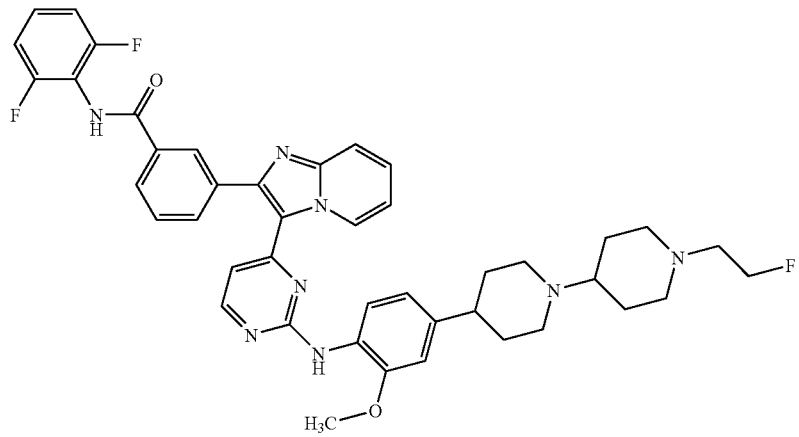

The title compound (0.15 g, 0.20 mmol, 58%) was prepared from 3-[3-(2-{[4-(1,4'-bipiperidin-4-yl)-2-(methyloxy)phenyl]amino}-4-pyrimidinyl)-imidazo[1,2-a]pyridin-2-yl]-N-(2,6-difluorophenyl)benzamide (Example 99, step D) in a manner analogous to that described for Example 90, step A. $^1$H NMR (400 MHz, DMSO-$d_6$) δ ppm 1.36-1.47 (m, 2H), 1.65-1.72 (m, 6H), 1.94 (t, J=11.0 Hz, 2H), 2.13-2.23 (m, 3H), 2.38-2.43 (m, 1H), 2.54 (dt, $J_{HF}$=28.4 Hz, J=4.8 Hz, 2H), 2.91 (dd, J=18.5, 12.1 Hz, 4H), 3.80 (s, 3H), 4.46 (dt, $J_{HF}$=47.8 Hz, J=5.1 Hz, 2H), 6.50 (d, J=5.1 Hz, 1H), 6.76 (d, J=8.8 Hz, 1H), 6.94 (s, 1H), 6.97 (t, J=6.4 Hz, 1H), 7.17 (t, J=8.2 Hz, 2H), 7.33-7.40 (m, 1H), 7.40-7.49 (m, 1H), 7.55-

7.63 (m, 2H), 7.71 (d, J=9.0 Hz, 1H), 7.78 (d, J=7.7 Hz, 1H), 8.02 (d, J=7.7 Hz, 1H), 8.23 (d, J=5.1 Hz, 1H), 8.30 (s, 1H), 8.49 (s, 1H), 9.39 (d, J=7.0 Hz, 1H), 10.20 (s, 1H). MS (M+H, ES+) 762.

Example 101

N-(2,6-difluorophenyl)-3-(3-{2-[(2-(methyloxy)-4-[4-[2-(methylsulfonyl)ethyl]-1,4'-bipiperidin-1'-yl]phenyl)amino}-4-pyrimidinyl]imidazo[1,2-a]pyridin-2-yl)benzamide

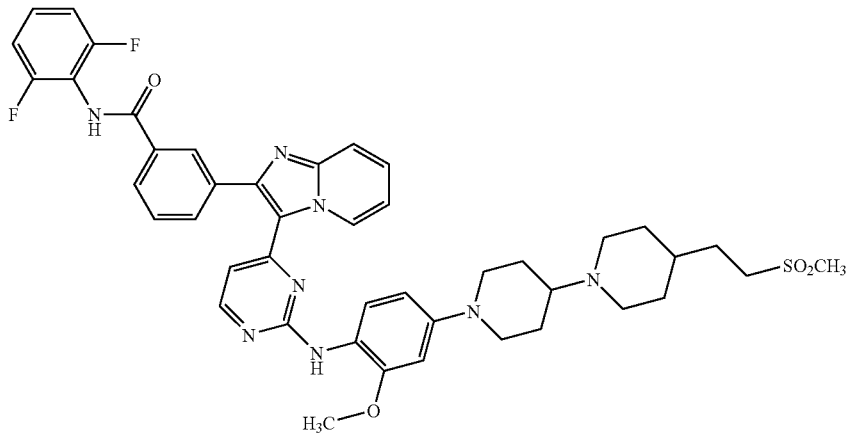

Step A: 1,1-dimethylethyl 4-(2-iodoethyl)-1-piperidinecarboxylate

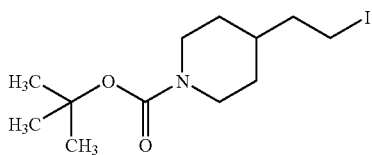

To N-Boc-4-piperidine-ethanol (5.00 g, 21.8 mmol) in THF (100 mL) was added triphenylphosphine (6.29 g, 24.0 mmol), imidazole (1.64 g, 24.1 mmol) and iodine (6.09 g, 24.0 mmol). The reaction was stirred at rt for 2 h. The mixture was filtered through Celite® purified by flash chromatography to provide the title compound of step A (6.31 g, 18.6 mmol, 85%). ¹H NMR (400 MHz, CDCl₃) δ ppm 1.07 (dq, J=12.2, 4.3 Hz, 2H), 1.42 (s, 9H), 1.49-1.58 (m, 1H), 1.62 (d, J=13.2 Hz, 2H), 1.75 (q, J=7.1 Hz, 2H), 2.67 (td, J=12.9, 2.5 Hz, 2H), 3.18 (t, J=7.1 Hz, 2H), 4.06 (d, J=13.0 Hz, 2H).

Step B: 1,1-dimethylethyl 4-[2-(methylthio)ethyl]-1-piperidinecarboxylate

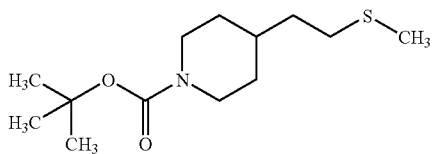

To 1,1-dimethylethyl 4-(2-iodoethyl)-1-piperidinecarboxylate (3.13 g, 9.23 mmol) in DMF (50 mL) was added sodium thiomethoxide (661 mg, 10.4 mmol) in one portion. The reaction was stirred for 3 days. Upon completion by TLC, the reaction was diluted with EtOAc (250 mL), washed with H₂O (4 times), dried (MgSO₄) and concentrated to provide the title compound of step B (2.37 g, 9.20 mmol, 99%, approximately 93% pure, used without further purification). ¹H NMR (400 MHz, CDCl₃) δ ppm 1.02-1.13 (m, 2H), 1.42 s, 9H), 1.48-1.55 (m, 3H), 1.63 (d, J=12.5 Hz, 2H), 2.07 (s, 3H), 2.45-2.53 (m, 2H), 2.65 (td, J=12.8, 2.6 Hz, 2H), 4.02-4.09 (m, 2H).

Step C: 1,1-dimethylethyl 4-[2-(methylsulfonyl)ethyl]-1-piperidinecarboxylate

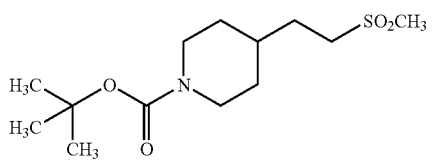

To 1,1-dimethylethyl 4-[2-(methylthio)ethyl]-1-piperidinecarboxylate (2.37 g, 9.20 mmol) in DCM (20 mL) at 0° C. was added meta-chloroperoxybenzoic acid (5.29 g, 77% by weight, 23.0 mmol) in portions. The reaction was stirred for 2 days. meta-Chloroperoxybenzoic acid (2.50 g, 77% by weight, 14.5 mmol) was added and the reaction was stirred overnight. The mixture was washed with saturated NaHCO₃, brine and H₂O. The organic layer was dried (MgSO₄) and concentrated. Purification by flash chromatography provided the title compound of step C (1.44 g, 4.90 mmol, 54%). ¹H NMR (400 MHz, CDCl₃) δ ppm 1.09-1.20 (m, 2H), 1.45 (s, 9H), 1.51-1.62 (m, 1H), 1.67 (dd, J=13.4, 2.0 Hz, 2H), 1.77-1.85 (m, 2H), 2.63-2.73 (m, 2H), 2.91 (s, 3H), 2.99-3.05 (m, 2H), 4.08-4.15 (m, 2H).

Step D: 4-[2-(methylsulfonyl)ethyl]piperidine

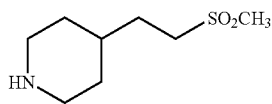

The title compound of step D (0.81 g, 4.3 mmol, 87%) was prepared from 1,1-dimethylethyl 4-[2-(methylsulfonyl)ethyl]-1-piperidinecarboxylate in an analogous manner to that of Example 89, step D. $^1$H NMR (400 MHz, CDCl$_3$) δ ppm 1.14-1.26 (m, 2H), 1.49-1.59 (m, 1H), 1.70 (d, J=13.6 Hz, 2H), 1.76-1.84 (m, 2H), 2.27 (br. s., 1H), 2.61 (td, J=12.3, 2.6 Hz, 2H), 2.90 (s, 3H), 2.99-3.05 (m, 2H), 3.11 (ddd, J=12.4, 3.3, 3.0 Hz, 2H).

Step E: 1'-[3-(methyloxy)-4-nitrophenyl]-4-[2-(methylsulfonyl)ethyl]-1,4'-bipiperidine

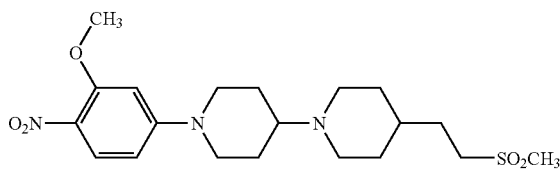

The title compound of step E (0.544 g, 1.28 mmol, 60%) was prepared in an analogous manner to that of Example 74, step A, with the following notable exception: 4-[2-(methylsulfonyl)ethyl]piperidine was used instead of 1,4'-bipiperidine. $^1$H NMR (400 MHz, DMSO-d$_6$) δ ppm 1.00-1.11 (m, 2H), 1.19-1.31 (m, 1H), 1.35-1.46 (m, 2H), 1.50-1.58 (m, 2H), 1.61 (d, J=11.4 Hz, 2H), 1.75 (d, J=11.4 Hz, 2H), 2.04 (t, J=11.4 Hz, 2H), 2.50 (s, 1H), 2.79 (d, J=12.6 Hz, 2H), 2.84-2.93 (m, 5H), 3.00-3.09 (m, 2H), 3.85 (s, 3H), 4.01 (d, J=14.1 Hz, 2H), 6.44 (d, J=2.2 Hz, 1H), 6.53 (dd, J=9.6, 2.3 Hz, 1H), 7.82 (d, J=9.5 Hz, 1H).

Step F: 2-(methyloxy)-4-{4-[2-(methylsulfonyl)ethyl]-1,4'-bipiperidin-1'-yl}aniline

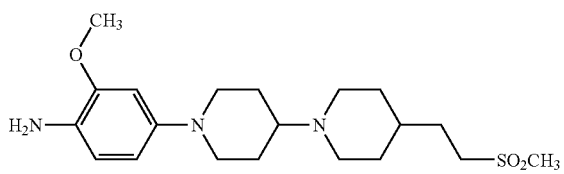

The title compound of step F (0.25 g, 0.64 mmol, 50%) was prepared from 1'-[3-(methyloxy)-4-nitrophenyl]-4-[2-(methylsulfonyl)ethyl]-1,4'-bipiperidine in a manner analogous to that described for Example 87, step I. $^1$H NMR (400 MHz, DMSO-d$_6$) δ ppm 1.01-1.12 (m, 2H), 1.20-1.31 (m, 1H), 1.42-1.67 (m, 6H), 1.72 (d, J=11.4 Hz, 2H), 2.05 (t, J=11.0 Hz, 2H), 2.21 (t, J=11.4 Hz, 1H), 2.39-2.44 (m, 2H), 2.82 (d, J=11.2 Hz, 2H), 2.90 (s, 3H), 3.02-3.11 (m, 2H), 3.38 (d, J=11.9 Hz, 2H), 3.68 (s, 3H), 4.14 (br. s., 2H), 6.24 (dd, J=8.3, 2.3 Hz, 1H), 6.41-6.49 (m, 2H).

Step G: N-(2,6-difluorophenyl)-3-(3-{2-[(2-(methyloxy)-4-{4-[2-(methylsulfonyl)ethyl]-1,4'-bipiperidin-1'-yl}phenyl)amino]-4-pyrimidinyl}imidazo[1,2-a]pyridin-2-yl)benzamide The title compound (0.12 g, 0.15 mmol, 60%) was prepared in an analogous manner to that described for Example 36, step E, with the following notable exception: 2-(methyloxy)-4-{4-[2-(methylsulfonyl)ethyl]-1,4'-bipiperidin-1'-yl}aniline was used instead of 2-(methyloxy)-4-[4-(1-piperidinyl-methyl)-1-piperidinyl]-aniline. $^1$H NMR (400 MHz, DMSO-d$_6$) δ ppm 1.02-1.13 (m, 2H), 1.19-1.31 (m, 1H), 1.41-1.69 (m, 6H), 1.76 (d, J=14.1 Hz, 2H), 2.06 (t, J=11.2 Hz, 2H), 2.32 (t, J=11.4 Hz, 1H), 2.61 (t, J=11.7 Hz, 2H), 2.83 (d, J=11.0 Hz, 2H), 2.90 (s, 3H), 3.02-3.11 (m, 2H), 3.70 (d, J=13.6 Hz, 2H), 3.76 (s, 3H), 6.40-6.47 (m, 2H), 6.63 (s, 1H), 6.94 (t, J=6.8 Hz, 1H), 7.17 (t, J=8.1 Hz, 2H), 7.33-7.45 (m, 3H), 7.57 (t, J=7.7 Hz, 1H), 7.69 (d, J=9.2 Hz, 1H), 7.78 (d, J=7.9 Hz, 1H), 8.02 (d, J=8.1 Hz, 1H), 8.17 (d, J=5.3 Hz, 1H), 8.30 (s, 1H), 8.41 (s, 1H), 9.31-9.42 (m, 1H), 10.20 (s, 1H). MS (M−H, ES−) 820.

Example 102

N-(2,6-difluorophenyl)-2-(methyloxy)-5-(3-{2-[(2-(methyloxy)-4-{4-[2-(methylsulfonyl)ethyl]-1,4'-bipiperidin-1'-yl}phenyl)amino]-4-pyrimidinyl}imidazo[1,2-a]pyridin-2-yl)benzamide

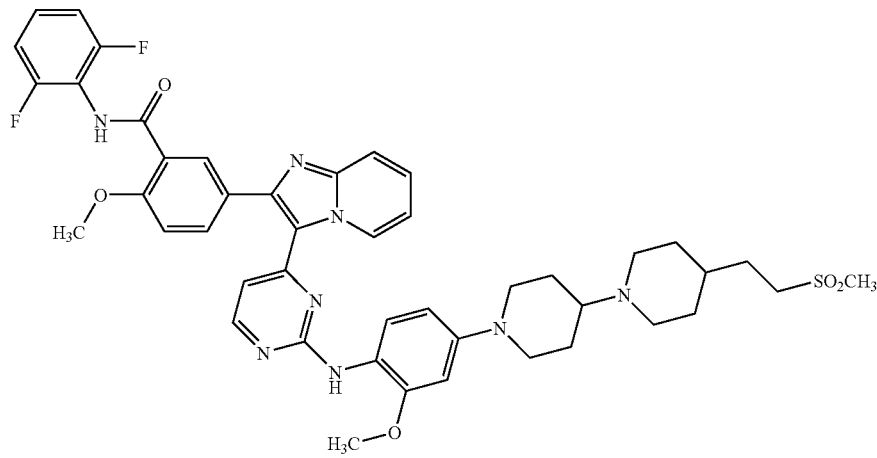

The title compound (0.12 g, 0.14 mmol, 56%) was prepared in an analogous manner to that described for Example 101, step G with the following notable exception: 5-[3-(2-chloro-4-pyrimidinyl)-imidazo[1,2-a]pyridin-2-yl]-N-(2,6-difluorophenyl)-2-(methyloxy)benzamide (Intermediate Example 2) was used instead of Intermediate Example 1. $^1$H NMR (400 MHz, DMSO-$d_6$) δ ppm 1.02-1.13 (m, 2H), 1.21-1.32 (m, 1H), 1.52-1.57 (m, 3H), 1.62 (d, J=11.9 Hz, 3H), 1.76 (d, J=10.8 Hz, 2H), 2.00-2.11 (m, 2H), 2.32 (t, J=14.8 Hz, 1H), 2.61 (t, J=11.9 Hz, 2H), 2.83 (d, J=12.6 Hz, 2H), 2.90 (s, 3H), 3.00-3.11 (m, 2H), 3.70 (d, J=10.1 Hz, 2H), 3.76 (s, 3H), 3.95 (s, 3H), 6.44 (d, J=7.5 Hz, 1H), 6.49 (d, J=4.9 Hz, 1H), 6.63 (s, 1H), 6.91 (t, J=6.3 Hz, 1H), 7.15 (t, J=8.2 Hz, 2H), 7.25 (d, J=8.4 Hz, 1H), 7.31-7.42 (m, 3H), 7.66 (d, J=9.3 Hz, 1H), 7.74 (d, J=9.2 Hz, 1H), 8.07 (br. s., 1H), 8.17 (d, J=4.9 Hz, 1H), 8.40 (s, 1H), 9.33 (br. s., 1H), 9.75 (s, 1H). MS (M+H, ES+) 851.

Example 103

N-(2,6-difluorophenyl)-2-(ethyloxy)-5-(3-{2-[(2-(methyloxy)-4-{4-[2-(methylsulfonyl)ethyl]-1,4'-bipiperidin-1'-yl}phenyl)amino]-4-pyrimidinyl}imidazo[1,2-a]pyridin-2-yl)benzamide

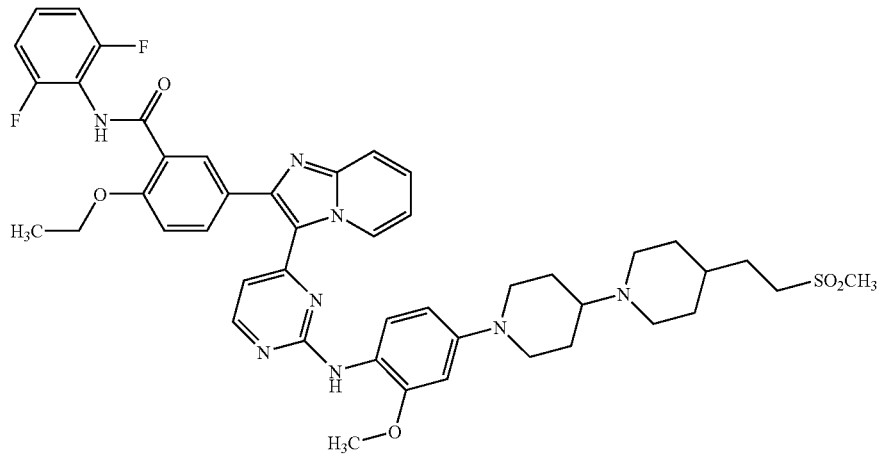

The title compound (0.07 g, 0.07 mmol, 53%) was prepared in an analogous manner to that described for Example 101, step G with the following notable exception: 5-[3-(2-chloro-4-pyrimidinyl)imidazo[1,2-a]pyridin-2-yl]-N-(2,6-difluorophenyl)-2-(ethyloxy)benzamide (Intermediate Example 6) was used instead of Intermediate Example 1. $^1$H NMR (400 MHz, DMSO-$d_6$) δ ppm 1.02-1.13 (m, 2H), 1.21-1.32 (m, 1H), 1.40 (t, J=6.7 Hz, 3H), 1.49-1.58 (m, 4H), 1.62 (d, J=10.4 Hz, 2H), 1.77 (d, J=13.6 Hz, 2H), 2.01-2.12 (m, 2H), 2.28-2.37 (m, 1H), 2.62 (t, J=11.5 Hz, 2H), 2.83 (d, J=10.4 Hz, 2H), 2.90 (s, 3H), 3.03-3.10 (m, 2H), 3.70 (d, J=12.5 Hz, 2H), 3.76 (s, 3H), 4.20-4.29 (m, 2H), 6.42-6.52 (m, 2H), 6.63 (s, 1H), 6.91 (t, J=7.0 Hz, 1H), 7.16 (t, J=7.8 Hz, 2H), 7.23 (d, J=9.5 Hz, 1H), 7.31-7.43 (m, 3H), 7.64-7.74 (m, 2H), 8.01 (s, 1H), 8.17 (d, J=5.5 Hz, 1H), 8.39 (s, 1H), 9.33 (br. s., 1H), 9.71 (s, 1H). MS (M−H, ES−) 864.

Example 104

3-[3-(2-{[4-(1,4'-bipiperidin-1'-yl)-5-chloro-2-(methyloxy)phenyl]amino}-4-pyrimidinyl)imidazo[1,2-a]pyridin-2-yl]-N-(2,6-difluorophenyl)benzamide

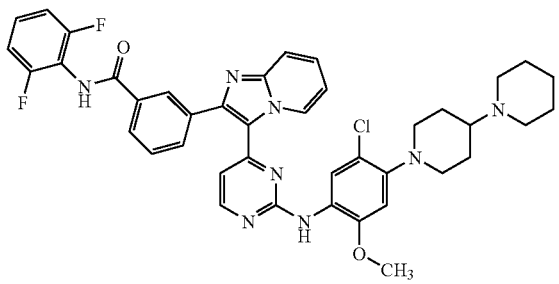

Step A: 4-chloro-5-fluoro-2-nitrophenol

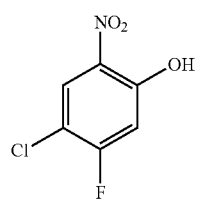

4-chloro-3-fluorophenol (2.38 g, 16.2 mmol) was dissolved in DCE (32 mL) and tetrabutylammonium bromide (0.524 g, 1.62 mmol) was added. HNO$_3$ 70% (2.1 mL, 32 mmol) was diluted with H$_2$O (18.9 mL) to make a 7% HNO$_3$ solution. This solution was added to the reaction mixture Step B: 4-chloro-5-fluoro-2-nitrophenyl methyl ether

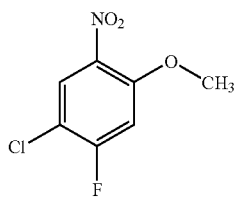

4-Chloro-5-fluoro-2-nitrophenol (2.29 g, 12.0 mmol) was dissolved in DMF (25 mL). K₂CO₃ (2.5 g, 18 mmol) and iodomethane (0.893 mL, 14.3 mmol) were added and the mixture was stirred at rt overnight. The mixture was then poured into H₂O and extracted with EtOAc (2×) and then the combined organics were extracted with H₂O (5×). The organic layer was dried with MgSO₄, filtered, and concentrated in vacuo to give the title compound of step B without further purification (2.19 g, 89%). $^1$H NMR (400 MHz, DMSO-$d_6$) δ ppm 8.22 (dd, J=7.8, 1.0 Hz, 1H), 7.54 (d, J=11.4 Hz, 1H), 3.90 (d, J=1.1 Hz, 3H).

Step C: 1'-[2-chloro-5-(methyloxy)-4-nitrophenyl]-1,4'-bipiperidine

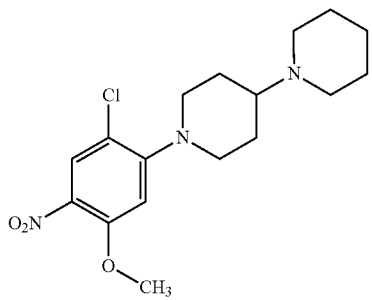

4-Chloro-5-fluoro-2-nitrophenyl methyl ether (2.19 g, 10.7 mmol) was dissolved in DMSO (10 mL). K₂CO₃ (2.2 g, 16 mmol) and 1,4'-bipiperidine (1.8 g, 11 mmol) were added and the reaction mixture was allowed to stir overnight at rt. The mixture was then poured into H₂O and extracted with EtOAc (2×) and then the combined organics were extracted with H₂O (5×). The organic layer was dried with MgSO₄, filtered, and concentrated in vacuo. The resulting residue was adsorbed onto silica gel and flash chromatographed to give the title compound of step C (2.69 g, 71%). MS (M+H, ES+) 354.

Step D: 4-(1,4'-bipiperidin-1'-yl)-5-chloro-2-(methyloxy)aniline

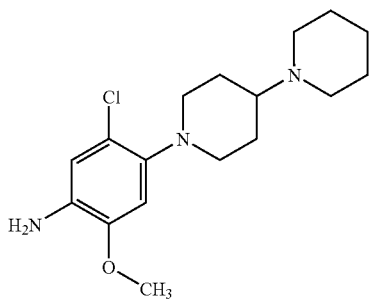

1'-[2-Chloro-5-(methyloxy)-4-nitrophenyl]-1,4'-bipiperidine was dissolved in EtOH and 5% sulfided platinum on carbon was added. The reaction was placed on a Fischer-Porter Hydrogenator under 50 psi of H₂ gas and was allowed to stir at rt overnight. TLC and MS showed the reaction was complete. The catalyst was filtered off and the filtrate was concentrated in vacuo to give the title compound of step D without further purification (2.36 g, 96%). $^1$H NMR (400 MHz, DMSO-$d_6$) δ ppm 6.56-6.62 (m, 2H), 4.57 (br. s, 2H), 3.70 (d, J=1.3 Hz, 3H), 3.06 (d, J=10.6 Hz, 2H), 2.52 (t, J=11.5 Hz, 2H), 2.39-2.44 (m, 4H), 2.24 (t, J=13.8 Hz, 1H), 1.70 (d, J=11.5 Hz, 2H), 1.54 (t, J=12.4 Hz, 2H), 1.41-1.48 (m, 4H), 1.30-1.38 (m, 2H).

Step E: 3-[3-(2-{[4-(1,4'-bipiperidin-1'-yl)-5-chloro-2-(methyloxy)phenyl]amino}-4-pyrimidinyl)imidazo[1,2-a]pyridin-2-yl]-N-(2,6-difluorophenyl)benzamide In a 10 mL vial with septum cap, 3-[3-(2-chloro-4-pyrimidinyl)imidazo[1,2-a]pyridin-2-yl]-N-(2,6-difluorophenyl)benzamide (Intermediate Example 1) (0.150 g, 0.325 mmol), 4-(1,4'-bipiperidin-1'-yl)-2-(methyloxy)aniline (0.158 g, 0.487 mmol) were taken up in iPrOH (3 mL) and pyridinium p-toluenesulfonate (0.196 g, 0.780 mmol) was added. The vial was sealed and heated to 80° C. overnight. When reaction was complete by MS, it was cooled rt, neutralized with 7N ammonia in MeOH, adsorbed onto silica gel and flash chromatographed to give the title compound (0.067 g, 27%). $^1$H NMR (400 MHz, DMSO-$d_6$) δ ppm 10.20 (s, 1H), 9.42 (br. s., 1H), 8.54 (br. s., 1H), 8.31 (br. s., 1H), 8.21-8.26 (m, 1H), 8.02 (d, J=7.7 Hz, 1H), 7.83 (s, 1H), 7.77 (d, J=7.5 Hz, 1H), 7.72 (d, J=9.7 Hz, 1H), 7.51-7.59 (m, 1H), 7.42-7.49 (m, 1H), 7.33 (br. s., 1H), 7.10-7.19 (m, 2H), 6.94-7.03 (m, 1H), 6.77-6.81 (m, 1H), 6.52 (t, J=4.7 Hz, 1H), 3.82 (s, 3H), 2.64 (t, J=11.0 Hz, 2H), 2.26-2.37 (m, 1H), 1.77 (d, J=13.2 Hz, 2H), 1.52-1.64 (m, 2H), 1.45 (s, 4H), 1.35 (br. s., 2H). MS (M+H, ES+) 749.

Example 105

5-[3-(2-{[4-(1,4'-bipiperidin-1'-yl)-5-chloro-2-(methyloxy)phenyl]amino}-4-pyrimidinyl)imidazo[1,2-a]pyridin-2-yl]-N-(2,6-difluorophenyl)-2-(methyloxy)benzamide

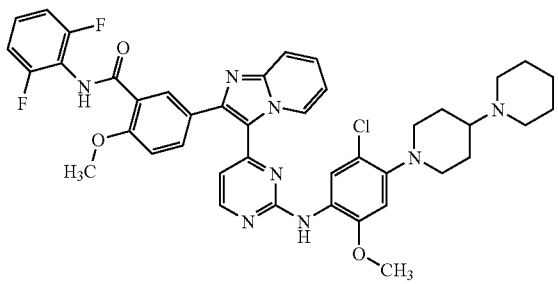

The title compound (0.032 g, 0.041 mmol, 40%) was prepared in an analogous manner to that described for Example 104, step E with the following notable exception: 5-[3-(2-chloro-4-pyrimidinyl)-imidazo[1,2-a]pyridin-2-yl]-N-(2,6-difluorophenyl)-2-(methyloxy)benzamide (Intermediate Example 2) was used instead of Intermediate Example 1 in the procedure described in Example 104, step E. $^1$H NMR (400 MHz, DMSO-d$_6$) δ ppm 9.78 (br. s., 1H), 9.41 (br. s., 1H), 8.55 (s, 1H), 8.28 (d, J=5.1 Hz, 1H), 8.10 (br. s., 1H), 7.87 (br. s., 1H), 7.78 (d, J=9.2 Hz, 1H), 7.71 (d, J=9.2 Hz, 1H), 7.41-7.51 (m, 1H), 7.33-7.41 (m, 1H), 7.28 (d, J=8.4 Hz, 1H), 7.18 (t, J=7.9 Hz, 2H), 7.00 (t, J=6.6 Hz, 1H), 6.83 (s, 1H), 6.62 (d, J=5.1 Hz, 1H), 3.98 (s, 3H), 3.84 (s, 3H), 3.31-3.37 (m, 4H), 2.61-2.71 (m, 2H), 2.29-2.41 (m, 3H), 1.80 (dd, J=14.3, 6.2 Hz, 2H), 1.55-1.67 (m, 2H), 1.49 (br. s., 4H), 1.38 (br. s., 2H). MS (M+H, ES+) 779.

Example 106

3-[3-(2-{[4-(1,4'-bipiperidin-1'-yl)-5-fluoro-2-(methyloxy)phenyl]amino}-4-pyrimidinyl)imidazo[1,2-a]pyridin-2-yl]-N-(2,6-difluorophenyl)benzamide

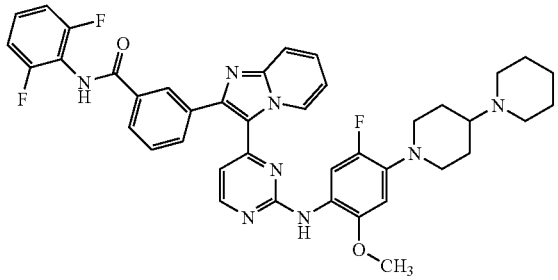

The title compound (0.0985 g, 0.134 mmol, 41% in final step) was prepared in an analogous manner to that described for Example 104 with the following notable exception: 3,4-difluorophenol was used instead of 4-chloro-3-fluorophenol in Example 104, step A. $^1$H NMR (400 MHz, DMSO-d$_6$) δ ppm 10.20 (s, 1H), 9.43 (s, 1H), 8.48 (s, 1H), 8.23-8.32 (m, 2H), 8.02 (d, J=7.7 Hz, 1H), 7.79 (d, J=7.7 Hz, 1H), 7.72 (d, J=9.2 Hz, 1H), 7.64 (d, J=13.9 Hz, 1H), 7.58 (t, J=7.5 Hz, 1H), 7.43-7.49 (m, 1H), 7.32-7.41 (m, 1H), 7.13-7.20 (m, 2H), 6.99 (t, J=6.4 Hz, 1H), 6.68 (d, J=7.9 Hz, 1H), 6.53 (d, J=5.1 Hz, 1H), 3.80 (s, 3H), 3.30-3.38 (m, 4H), 2.63 (t, J=11.9 Hz, 2H), 2.50-2.36 (m, 2H), 2.28 (t, J=12.6 Hz, 1H), 1.72-1.79 (m, 2H), 1.51-1.62 (m, 2H), 1.45 (br. s., 4H), 1.34 (br.s., 2H). MS (M+H, ES+) 733.

Example 107

5-[3-(2-{[4-(1,4'-bipiperidin-1'-yl)-5-fluoro-2-(methyloxy)phenyl]amino}-4-pyrimidinyl)imidazo[1,2-a]pyridin-2-yl]-N-(2,6-difluorophenyl)-2-(methyloxy)benzamide

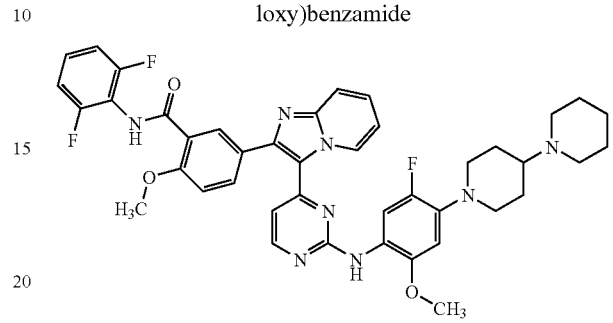

The title compound (0.0908 g, 0.119 mmol, 39% in final step) was prepared in an analogous manner to that described for Example 104 with the following notable exceptions:
a) 3,4-difluorophenol was used instead of 4-chloro-3-fluorophenol in Example 104, step A.
b) 5-[3-(2-chloro-4-pyrimidinyl)-imidazo[1,2-a]pyridin-2-yl]-N-(2,6-difluorophenyl)-2-(methyloxy)benzamide (Intermediate Example 2) was used instead of Intermediate Example 1 in the procedure described in Example 104, step E.

$^1$H NMR (400 MHz, DMSO-d$_6$) δ ppm 9.77 (s, 1H), 9.42 (d, J=6.6 Hz, 1H), 8.49 (s, 1H), 8.28 (d, J=5.1 Hz, 1H), 8.11 (d, J=2.2 Hz, 1H), 7.78 (d, J=8.8 Hz, 1H), 7.63-7.74 (m, 2H), 7.42-7.49 (m, 1H), 7.33-7.42 (m, 1H), 7.28 (d, J=8.8 Hz, 1H), 7.18 (t, J=8.1 Hz, 2H), 6.99 (t, J=7.0 Hz, 1H), 6.71 (d, J=8.4 Hz, 1H), 6.62 (d, J=5.1 Hz, 1H), 3.98 (s, 3H), 3.82 (s, 3H), 3.34-3.41 (m, 2H), 2.66 (t, J=11.0 Hz, 2H), 2.44-2.48 (m, 4H), 2.26-2.36 (m, 1H), 1.78 (d, J=10.3 Hz, 2H), 1.53-1.65 (m, 2H), 1.48 (s, 4H), 1.37 (br. s., 2H). MS (M+H, ES+) 763.

Example 108

3-[3-(2-{[4-(1,4'-bipiperidin-1'-yl)-5-methyl-2-(methyloxy)phenyl]amino}-4-pyrimidinyl)imidazo[1,2-a]pyridin-2-yl]-N-(2,6-difluorophenyl)benzamide

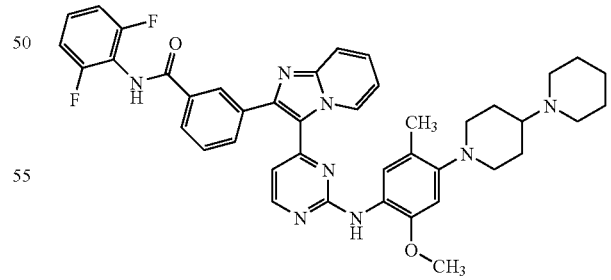

The title compound (0.0543 g, 0.075 mmol, 23% in final step) was prepared in an analogous manner to that described for Example 104 with the following notable exceptions: 3-fluoro-4-methylphenol was used instead of 4-chloro-3-fluorophenol in Example 104, step A. $^1$H NMR (400 MHz, DMSO-d$_6$) δ ppm 10.20 (br. s., 1H), 9.37 (br. s., 1H), 8.42 (br. s., 1H), 8.30 (br. s., 1H), 8.15-8.24 (m, 1H), 8.02 (d, J=7.9 Hz, 1H), 7.78 (d, J=6.6 Hz, 1H), 7.70 (d, J=7.9 Hz, 1H), 7.56 (t, J=7.0 Hz, 1H), 7.38-7.49 (m, 2H), 7.33 (s, 1H), 7.11-7.20 (m, 2H), 6.89-6.99 (m, 1H), 6.72 (s, 1H), 6.46 (d, J=5.1 Hz, 1H), 3.76 (s, 3H), 3.00-3.11 (m, 2H), 2.60 (t, J=12.2 Hz, 2H), 2.24-2.36 (m, 1H), 2.11 (s, 3H), 1.70-1.80 (m, 2H), 1.51-1.62 (m, 2H), 1.46 (br. s., 4H), 1.35 (br. s., 2H). MS (M+H, ES+) 729.

Example 109

5-[3-(2-{[4-(1,4'-bipiperidin-1'-yl)-5-methyl-2-(methyloxy)phenyl]amino}-4-pyrimidinyl)imidazo[1,2-a]pyridin-2-yl]-N-(2,6-difluorophenyl)-2-(methyloxy)benzamide

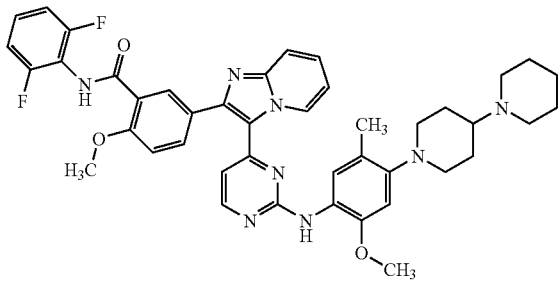

The title compound (0.0878 g, 0.116 mmol, 38% in final step) was prepared in an analogous manner to that described for Example 104 with the following notable exception:
a) 3-fluoro-4-methylphenol was used instead of 4-chloro-3-fluorophenol in Example 104, step A.
b) 5-[3-(2-chloro-4-pyrimidinyl)-imidazo[1,2-a]pyridin-2-yl]-N-(2,6-difluorophenyl)-2-(methyloxy)benzamide (Intermediate Example 2) was used instead of Intermediate Example 1 in the procedure described in Example 104, step E.
$^1$H NMR (400 MHz, DMSO-d$_6$) δ ppm 8.44 (s, 1H), 8.23 (d, J=5.1 Hz, 1H), 8.10 (br. s., 1H), 7.77 (d, J=9.9 Hz, 1H), 7.70 (d, J=9.2 Hz, 1H), 7.48 (s, 1H), 7.41-7.47 (m, 1H), 7.33-7.41 (m, 1H), 7.28 (d, J=8.8 Hz, 1H), 7.18 (t, J=8.1 Hz, 2H), 6.91-6.98 (m, 1H), 6.74 (s, 1H), 6.55 (d, J=5.5 Hz, 1H), 3.98 (s, 3H), 3.78 (s, 3H), 3.09 (d, J=11.4 Hz, 2H), 3.27-3.31 (m, 2H), 2.63 (t, J=11.9 Hz, 2H), 2.46-2.50 (m, 4H), 2.28-2.38 (m, 1H), 2.14 (s, 3H), 1.80 (d, J=10.6 Hz, 2H), 1.54-1.65 (m, 2H), 1.49 (dt, J=10.2, 5.0 Hz, 4H), 1.34-1.42 (m, 2H). MS (M+H, ES+) 759.

Example 110

3-[3-(2-{[4-(1,4'-bipiperidin-1'-yl)-2,5-bis(methyloxy)phenyl]amino}-4-pyrimidinyl)imidazo[1,2-a]pyridin-2-yl]-N-(2,6-difluorophenyl)benzamide

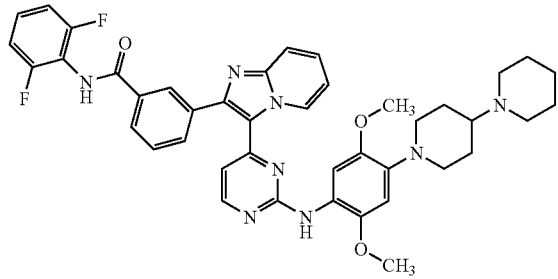

Step A: 1'-[2,5-bis(methyloxy)-4-nitrophenyl]-1,4'-bipiperidine

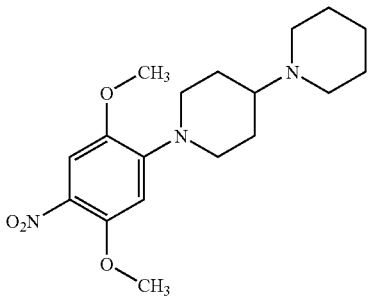

4-Chloro-2,5-dimethoxynitrobenzene (5.0 g, 23 mmol) was dissolved in DMSO (50 mL). K$_2$CO$_3$ (4.8 g, 34 mmol) and 4-piperidinopiperidine (3.9 g, 23 mmol) were added and the reaction mixture was heated to 80° C. and allowed to stir over the weekend. The mixture was then poured into H$_2$O and extracted with EtOAc (2×). The combined organics were dried with MgSO$_4$, filtered, and concentrated in vacuo. The resulting residue was adsorbed onto silica gel and flash chromatographed to give the title compound of step A (3.0 g, 37%). MS (M+H, ES+) 350.

Step B: 4-(1,4'-bipiperidin-1'-yl)-2,5-bis(methyloxy)aniline

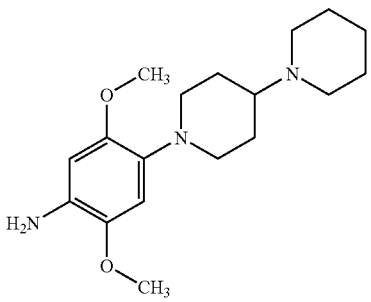

1'-[2,5-Bis(methyloxy)-4-nitrophenyl]-1,4'-bipiperidine (3.0 g, 8.6 mmol) was taken up in EtOH (50 mL) and EtOAc was added to help with solubility. The catalyst, 5% sulfided platinum on carbon (300 mg) was added. The reaction was placed on a Fischer-Porter Hydrogenator under 50 psi of H$_2$ gas and was allowed to stir at rt overnight. The catalyst was filtered off and the filtrate was concentrated in vacuo to give the title compound of step B without further purification (2.72 g, 99%). $^1$H NMR (400 MHz, DMSO-d$_6$) δ ppm 6.42 (s, 1H), 6.28 (s, 1H), 4.31 (s, 2H), 3.63 (s, 3H), 3.61 (s, 3H), 3.15 (d, J=11.4 Hz, 2H), 2.38-2.47 (m, 6H), 2.20 (t, J=11.5 Hz, 1H), 1.67 (d, J=11.7 Hz, 2H), 1.41-1.53 (m, 6H), 1.34 (d, J=4.8 Hz, 2H).

Step C: 3-[3-(2-{[4-(1,4'-bipiperidin-1'-yl)-2,5-bis(methyloxy)phenyl]amino}-4-pyrimidinyl)imidazo[1,2-a]pyridin-2-yl]-N-(2,6-difluorophenyl)benzamide In a 5 mL microwave vial with septum cap, 3-[3-(2-chloro-4-pyrimidinyl)imidazo[1,2-a]pyridin-2-yl]-N-(2,6-difluorophenyl)-benzamide (Intermediate Example 1) (0.200 g, 0.433 mmol), 4-(1,4'-bipiperidin-1'-yl)-2,5-bis(methyloxy) aniline (0.166 g, 0.520 mmol) were taken up in iPrOH (3 mL) and concentrated HCl (4 drops) was added. The vial was sealed and heated in the microwave at 180° C. for 40 min. Reaction was complete by MS, it was cooled rt, neutralized with 7N ammonia in MeOH, and concentrated in vacuo. The resulting residue was taken up in DCM and purified by column chromatography using basic alumina. The desired combined fractions were concentrated and the resulting solid was triturated with DCM and hexane, filtered and air dried to give the title compound (0.130 g, 40%). $^1$H NMR (400 MHz, DMSO-d$_6$) δ ppm 10.23 (s, 1H), 9.41 (br. s., 1H), 8.50 (s, 1H), 8.33 (s, 1H), 8.24 (d, J=5.1 Hz, 1H), 8.05 (d, J=7.7 Hz, 1H), 7.83 (d, J=8.1 Hz, 1H), 7.73 (d, J=9.2 Hz, 1H), 7.60 (t, J=7.9 Hz, 1H), 7.43-7.50 (m, 1H), 7.36-7.42 (m, 1H), 7.34 (s, 1H), 7.20 (t, J=8.1 Hz, 2H), 6.94-7.00 (m, 1H), 6.66 (s, 1H), 6.50 (d, J=5.1 Hz, 1H), 3.76 (s, 3H), 3.64 (s, 3H), 3.43 (d, J=11.7 Hz, 2H), 2.51-2.58 (m, 2H), 2.26-2.35 (m, 1H), 1.77 (d, J=13.6 Hz, 2H), 1.53-1.64 (m, 2H), 1.48 (s, 4H), 1.38 (s, 2H). MS (M+H, ES+) 745.

Example 111

N-(2,6-difluorophenyl)-3-[3-(2-{[4-{4-[4-(2-fluoroethyl)-1-piperazinyl]-1-piperidinyl}-2,5-bis(methyloxy)phenyl]amino}-4-pyrimidinyl)imidazo[1,2-a]pyridin-2-yl]benzamide DMSO-d$_6$) δ ppm 4.48 (dt, J$_{HF}$=47.8 Hz, J=4.9 Hz, 2H), 3.24-3.28 (m, 4H), 2.57 (dt, J$_{HF}$=28.7, J=4.9 Hz, 2H), 2.31-2.36 (m, 4H), 1.34 (s, 9H).

Step B: 1-(2-fluoroethyl)piperazine

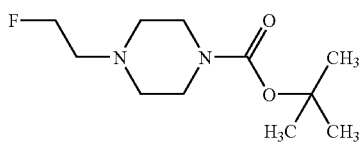

Crude 1,1-dimethylethyl 4-(2-fluoroethyl)-1-piperazinecarboxylate was dissolved in 40 mL of MeOH and 40 mL 37% HCl. Reaction was stirred for 1 h. Carefully neutralized with solid K$_2$CO$_3$ and concentrated in vacuo being careful not to heat the H$_2$O bath past 30° C. The resulting residue was taken up in diethyl ether and the solids were filtered and washed with diethyl ether and DCM several times. Filtrate was concentrated in vacuo, again being careful not to heat the H$_2$O bath past 30° C., to give desired product 1-(2-fluoroethyl)piperazine (5.2 g, 73% over 2 steps) which was used without further purification. $^1$H NMR (400 MHz, DMSO-d$_6$)

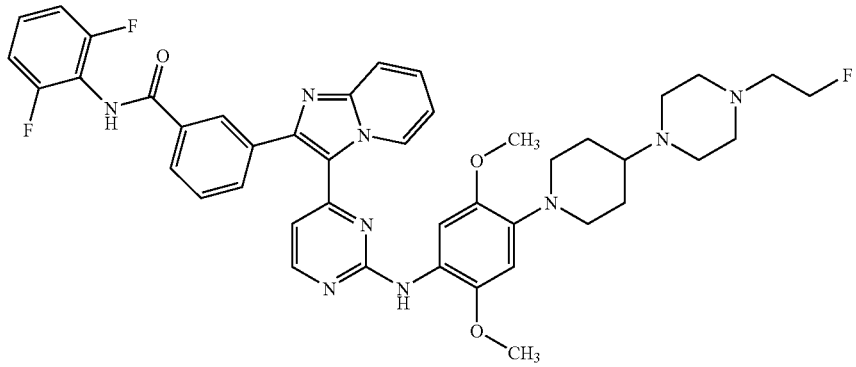

Step A: 1,1-dimethylethyl 4-(2-fluoroethyl)-1-piperazinecarboxylate

δ ppm 4.40-4.57 (m, 2H), 2.64-2.73 (m, 4H), 2.53-2.61 (m, 1H), 2.46-2.53 (m, 2H), 2.29-2.40 (m, 4H).

Step C: 1,1-dimethylethyl 4-[4-(2-fluoroethyl)-1-piperazinyl]-1-piperidinecarboxylate

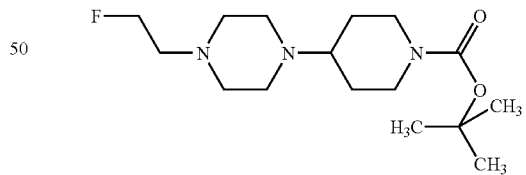

In a sealed tube, 1,1-dimethylethyl 1-piperazinecarboxylate (10.0 g, 54.0 mmol) was dissolved in 100 mL of THF. K$_2$CO$_3$ (11.2 g, 81.0 mmol) and 1-fluoro-2-iodoethane (11.3 g, 64.8 mmol) were added and the reaction was heated to 85° C. for 16 h. The reaction was cooled to rt and solids were filtered and washed with DCM. The filtrate was concentrated in vacuo being careful not to heat the H$_2$O bath past 30° C. The resulting crude product, 1,1-dimethylethyl 4-(2-fluoroethyl)-1-piperazinecarboxylate was carried on to the next step without further purification. $^1$H NMR (400 MHz, 1,1-Dimethylethyl 4-oxo-1-piperidinecarboxylate (15.7 g, 78.7 mmol) and 1-(2-fluoroethyl)piperazine (5.2 g, 39 mmol) were dissolved in 150 mL 1,2-DCE. HOAc (3.4 mL, 59 mmol) and TEA (5.5 mL, 39 mmol) were added followed by sodium triacetoxyborohydride (12.5 g, 59.0 mmol). The reaction was stirred for 3 h. TLC revealed the presence of starting material and so an additional 1.5 eq (12.5 g, 59.0 mmol) of sodium triacetoxyborohydride were added. Reaction was allowed to stir overnight. Saturated aqueous NaHCO$_3$ solution was added carefully until the reaction stopped bubbling. Aqueous layer was then extracted with EtOAc (3×). Combined organic layers were dried over MgSO₄, filtered and concentrated in vacuo. The resulting crude product was adsorbed onto silica gel and purified by flash chromatography to give title compound of step C (10.2 g, 82%). ¹H NMR (400 MHz, DMSO-d₆) δ ppm 4.39-4.57 (m, 2H), 3.90 (d, J=12.46 Hz, 2H), 2.61-2.73 (m, 2H), 2.47-2.61 (m, 2H), 2.36-2.47 (m, 8H), 2.24-2.35 (m, 1H), 1.69 (d, J=12.46 Hz, 2H), 1.37 (s, 9H), 1.14-1.26 (m, 2H).

Step D: 1-(2-fluoroethyl)-4-(4-piperidinyl)piperazine

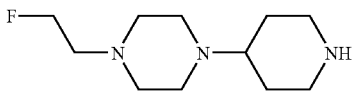

1,1-Dimethylethyl 4-[4-(2-fluoroethyl)-1-piperazinyl]-1-piperidinecarboxylate (10.2 g, 32.3 mmol) was dissolved in 40 mL of MeOH and 40 mL of 37% HCl. Reaction was stirred for 1 h, concentrated in vacuo and then a small amount of H₂O was added back to solubilize the HCl salt of the product. When everything was in solution, solid K₂CO₃ was added to neutralize. The mixture was then concentrated in vacuo to remove H₂O. Residue taken up in DCM and solids were filtered and washed with 20% MeOH/DCM. Filtrate was concentrated in vacuo and residue taken up in diethyl ether. Solids filtered and washed with diethyl ether several times. Combined filtrates were concentrated in vacuo to give desired product in two crops (2.42 g and 1.85 g) without further purification. Batches were combined together to give the title compound of step D (4.3 g, 68%). ¹H NMR (400 MHz, DMSO-d₆) δ ppm 4.40-4.58 (m, 2H), 3.15 (s, 1H), 2.91 (d, J=12.1 Hz, 2H), 2.35-2.59 (m, 12H), 2.15 (tt, J=11.36, 3.67 Hz, 1H), 1.63 (d, J=12.10 Hz, 2H), 1.19 (qd, J=11.85, 4.03 Hz, 2H).

Step E: 1-{1-[2,5-bis(methyloxy)-4-nitrophenyl]-4-piperidinyl}-4-(2-fluoroethyl)piperazine

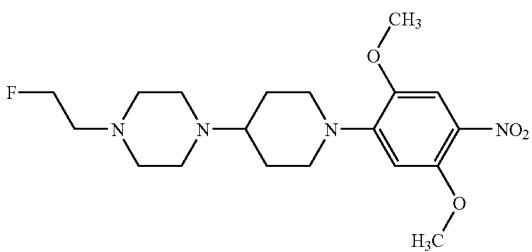

4-Chloro-2,5-dimethoxynitrobenzene (1.0 g, 4.6 mmol) was dissolved in DMSO (10 mL). K₂CO₃ (0.953 g, 6.9 mmol) and 1-(2-fluoroethyl)-4-(4-piperidinyl)piperazine (0.989 g, 4.6 mmol) were added and the reaction mixture was heated to 80° C. and allowed to stir for 60 h. The mixture was then poured into H₂O and extracted with EtOAc (2×). The combined organics were dried with MgSO₄, filtered, and concentrated in vacuo. The resulting residue was adsorbed onto silica gel and flash chromatographed to give the title compound of step E (1.36 g, 75%). MS (M+H, ES+) 397.

Step F: 4-{4-[4-(2-fluoroethyl)-1-piperazinyl]-1-piperidinyl}-2,5-bis(methyloxy)aniline

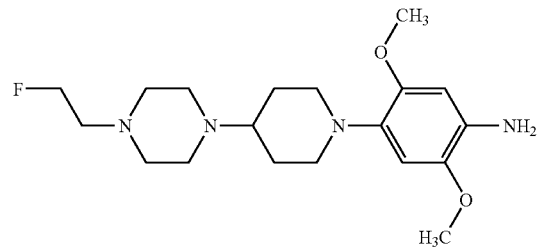

1-{1-[2,5-Bis(methyloxy)-4-nitrophenyl]-4-piperidinyl}-4-(2-fluoroethyl)piperazine (1.36 g, 3.43 mmol) was taken up in EtOH (50 mL) and EtOAc was added to help with solubility. The catalyst, 5% sulfided platinum on carbon (140 mg) was added. The reaction was placed on a Fischer-Porter Hydrogenator under 50 psi of H₂ gas and was allowed to stir at rt overnight. The catalyst was filtered off and the filtrate was concentrated in vacuo to give the title compound of step F without further purification (1.2 g, 95%). ¹H NMR (400 MHz, DMSO-d₆) δ ppm 6.42 (s, 1H), 6.28 (s, 1H), 4.53 (t, J=4.9 Hz, 1H), 4.41 (t, J=4.9 Hz, 1H), 4.31 (s, 2H), 3.63 (s, 3H), 3.61 (s, 3H), 3.15 (s, 2H), 2.57 (t, J=4.8 Hz, 1H), 2.49-2.51 (m, 1H), 2.45-2.48 (m, 6H), 2.42 (d, J=13.4 Hz, 4H), 2.17 (t, J=11.3 Hz, 1H), 1.73 (d, J=11.0 Hz, 2H), 1.46 (qd, J=11.7, 3.5 Hz, 2H).

Step G: N-(2,6-difluorophenyl)-3-[3-(2-{[4-{4-[4-(2-fluoroethyl)-1-piperazinyl]-1-piperidinyl}-2,5-bis(methyloxy)phenyl]amino}-4-pyrimidinyl)imidazo[1,2-a]pyridin-2-yl]benzamide In a 5 mL microwave vial with septum cap, 3-[3-(2-chloro-4-pyrimidinyl)imidazo[1,2-a]pyridin-2-yl]-N-(2,6-difluorophenyl)-benzamide (Intermediate Example 1) (0.200 g, 0.433 mmol), 4-{4-[4-(2-fluoroethyl)-1-piperazinyl]-1-piperidinyl}-2,5-bis(methyloxy)-aniline (0.190 g, 0.520 mmol) were taken up in iPrOH (3 mL) and concentrated HCl (4 drops) was added. The vial was sealed and heated in the microwave at 180° C. for 40 min. Reaction was complete by MS, it was cooled rt, neutralized with 7N ammonia in MeOH, and concentrated in vacuo. The resulting residue was taken up in DCM and purified by column chromatography using basic alumina followed by silica gel flash chromatography. The desired fractions were concentrated and the resulting solid was triturated with DCM and hexane, filtered and vacuum dried to give the title compound (0.110 g, 32%). ¹H NMR (400 MHz, DMSO-d₆) δ ppm 10.24 (s, 1H), 8.52 (s, 1H), 8.33 (s, 1H), 8.24 (d, J=5.1 Hz, 1H), 8.04 (d, J=7.9 Hz, 1H), 7.83 (d, J=7.9 Hz, 1H), 7.73 (d, J=9.0 Hz, 1H), 7.61 (t, J=7.8 Hz, 1H), 7.26-7.53 (m, 3H), 7.13-7.27 (m, 2H), 6.84-7.08 (m, 1H), 6.66 (s, 1H), 6.50 (d, J=5.1 Hz, 1H), 4.56 (t, J=4.9 Hz, 1H), 4.45 (t, J=4.9 Hz, 1H), 3.76 (s, 3H), 3.64 (s, 3H), 3.36-3.53 (m, 2H), 2.37-2.74 (m, 12H), 2.13-2.36 (m, 1H), 1.70-1.94 (m, 2H), 1.39-1.69 (m, 2H). MS (M+H, ES+) 792.

Example 112

3-[3-(2-{[5-chloro-4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]-N-(2,6-difluorophenyl)benzamide

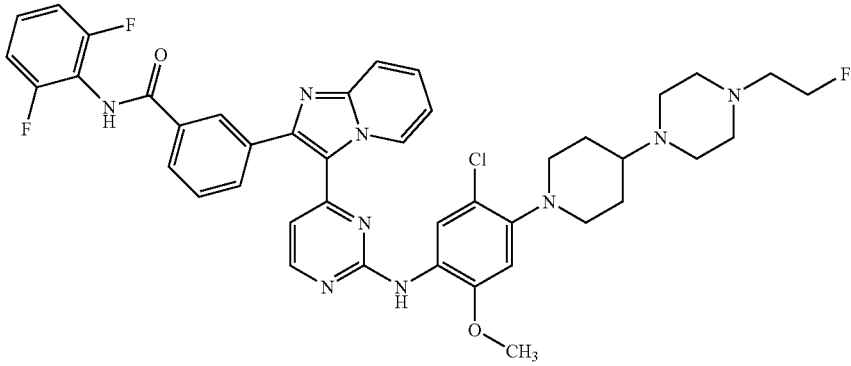

Step A: Phenylmethyl 4-(1-{[(1,1-dimethylethyl)oxy]carbonyl}-4-piperidinyl)-1-piperazinecarboxylate

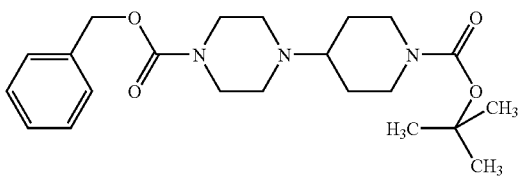

Combined 1-boc-4-piperidone (10.0 g, 50.2 mmol), benzyl 1-piperazine-carboxylate (19.3 mL, 100.4 mmol), HOAc (4.3 mL, 75.3 mmol) and TEA (7.0 mL, 50.2 mmol) in DCE (150 mL) were stirred at rt. Sodium triacetoxyborohydride was added (16.0 g, 75.3 mmol). The reaction was stirred for 3 h at which point TLC shows starting material is consumed. The reaction was quenched with NaHCO$_3$ and extracted with DCM (3×). Combined organics were dried over MgSO$_4$, filtered and concentrated in vacuo. Diluted crude material with DCM and adsorbed onto a prepacked silica gel solid loading cartridge and purified by column chromatography to give title compound of step A (yield not obtained). $^1$H NMR (400 MHz, DMSO-d$_6$) δ ppm 7.04-7.52 (m, 5H), 5.02 (s, 2H), 3.74-4.05 (m, 2H), 3.06-3.49 (m, 4H), 2.63 (br. s., 2H), 2.22-2.50 (m, 5H), 1.64 (d, J=12.1 Hz, 2H), 1.07-1.27 (m, 2H), 1.34 (s, 9H).

Step B: Phenylmethyl 4-(4-piperidinyl)-1-piperazinecarboxylate bis(trifluoroacetate) salt

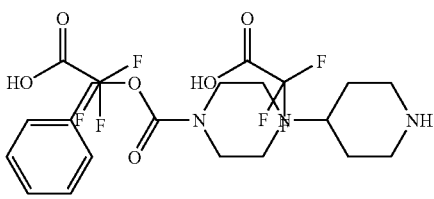

Phenylmethyl 4-(1-{[(1,1-dimethylethyl)oxy]carbonyl}-4-piperidinyl)-1-piperazinecarboxylate from previous step was dissolved in DCM (60 mL) and cooled to 0° C. TFA (20 mL) was added. Reaction was stirred for 1 h. TLC showed no starting material remaining. Removed DCM and TFA on rotovap to give title compound of step B (presumed to be the bis-TFA salt) (14.0 g, 53% over 2 steps) which was used in the next step without further purification. $^1$H NMR (400 MHz, DMSO-d$_6$) δ ppm 7.03-7.40 (m, 5H), 5.02 (s, 2H), 2.93-4.16 (m, 7H), 2.11-2.82 (m, 7H), 1.06-1.88 (m, 4H).

Step C: Phenylmethyl 4-{1-[2-chloro-5-(methyloxy)-4-nitrophenyl]-4-piperidinyl}-1-piperazinecarboxylate

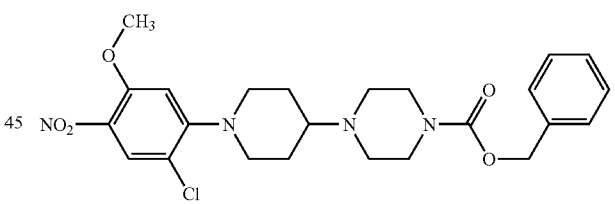

1-Chloro-2-fluoro-4-(methyloxy)-5-nitrobenzene (2.0 g, 9.7 mmol), from a different batch than previously described, was dissolved in DMSO (50 mL) and K$_2$CO$_3$ (6.7 g, 49 mmol), and phenylmethyl 4-(4-piperidinyl)-1-piperazinecarboxylate bis(trifluoroacetate) salt (5.1 g, 9.7 mmol) were added. Reaction was stirred overnight. Poured into H$_2$O and extracted (2×) with EtOAc. Combined organic layers were back-extracted (5×) with H$_2$O and then dried over MgSO$_4$, filtered, concentrated on to silica gel and flash chromatographed to give the title compound of step C (4.95 g, 100%). $^1$H NMR (400 MHz, DMSO-d$_6$) δ ppm 7.96 (s, 1H), 7.00-7.52 (m, 5H), 6.76 (s, 1H), 5.03 (s, 2H), 3.90 (s, 3H), 3.54 (d, J=12.1 Hz, 2H), 3.17-3.47 (m, 4H), 2.76 (t, J=11.4 Hz, 2H), 2.23-2.63 (m, 5H), 1.82 (d, J=11.5 Hz, 2H), 1.54 (qd, J=11.7, 3.0 Hz, 2H).

Step D: 1-{-[2-chloro-5-(methyloxy)-4-nitrophenyl]-4-piperidinyl}piperazine

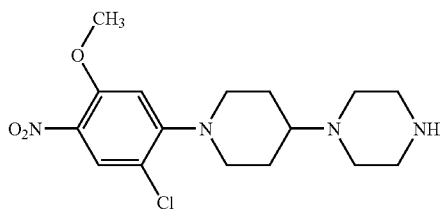

Phenyl methyl 4-{1-[2-chloro-5-(methyloxy)-4-nitrophenyl]-4-piperidinyl}-1-piperazine carboxylate (4.95 g, 12.9 mmol) was dissolved in 50 mL of TFA and heated to 50° C. over the weekend. The TFA was removed in vacuo. Diluted with EtOAc and neutralized with saturated NaHCO₃ solution. Aqueous layer extracted with EtOAc (3×). Combined organics were dried over MgSO₄, filtered and concentrated in vacuo. Crude product was triturated with EtOAc, filtered and dried to give the title compound of step D (2.86 g, 80%). MS (M+H, ES+) 355.

Step E: 1-{1-[2-chloro-5-(methyloxy)-4-nitrophenyl]-4-piperidinyl}-4-(2-fluoroethyl)piperazine

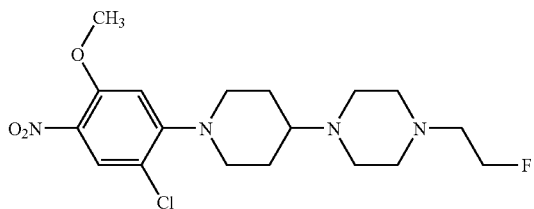

1-{1-[2-Chloro-5-(methyloxy)-4-nitrophenyl]-4-piperidinyl}piperazine (0.050 g, 1.41 mmol), 1-fluoroethyliodide (0.229 mL, 2.82 mmol), Na₂CO₃ (0.179 g, 1.69 mmol) were taken up in acetonitrile (10 mL), heated to 70° C. and stirred overnight. Reaction mixture was cooled and then poured onto prepackaged silica gel cartridge and dried by vacuum suction of air through cartridge and then flash chromatographed to give the title compound of step E (0.370 g, 65%). MS (M+H, ES+) 401.

Step F: 5-chloro-4-{4-[4-(2-fluoroethyl)-1-piperazinyl]-1-piperidinyl}-2-(methyloxy)aniline

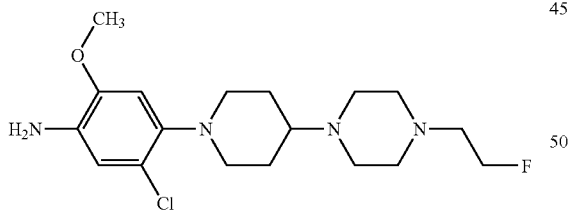

1-{1-[2-Chloro-5-(methyloxy)-4-nitrophenyl]-4-piperidinyl}-4-(2-fluoroethyl)piperazine (0.370 g, 0.923 mmol) was taken up in EtOH (50 mL) and EtOAc was added to help with solubility. The catalyst, 5% sulfided platinum on carbon (150 mg) was added. The reaction was placed on a Fischer-Porter Hydrogenator under 50 psi of H₂ gas and was allowed to stir at rt overnight. The catalyst was filtered off and the filtrate was concentrated in vacuo to give the title compound of step F without further purification (0.300 g, 88%). ¹H NMR (400 MHz, DMSO-d₆) δ ppm 6.62 (d, J=7.0 Hz, 2H), 4.51-4.79 (m, 3H), 4.37-4.51 (m, 1H), 3.73 (s, 3H), 2.95-3.21 (m, 2H), 2.20-2.80 (m, 13H), 1.72-1.85 (m, 2H), 1.37-1.61 (m, 2H).

Step G: 3-[3-(2-{[5-chloro-4-{4-[4-(2-fluoroethyl)-1-piperazinyl]-1-piperidinyl}-2-(methyl-oxy)phenyl]amino}-4-pyrimidinyl)imidazo[1,2-a]pyridin-2-yl]-N-(2,6-difluorophenyl)benzamide In a 10 mL vial with septum cap, 3-[3-(2-chloro-4-pyrimidinyl)imidazo[1,2-a]pyridin-2-yl]-N-(2,6-difluorophenyl)-benzamide (Intermediate Example 1) (0.200 g, 0.433 mmol), 5-chloro-4-{4-[4-(2-fluoroethyl)-1-piperazinyl]-1-piperidinyl}-2-(methyloxy)aniline (0.192 g, 0.520 mmol) were taken up in iPrOH (3 mL) and pyridinium p-toluenesulfonate (0.203 g, 1.04 mmol) was added. The vial was sealed and heated to 80° C. overnight. When reaction was complete by MS, it was cooled rt, neutralized with 7N ammonia in MeOH, adsorbed onto silica gel and flash chromatographed. Fractions containing the desired product were concentrated and the resulting solid was triturated with diethyl ether, filtered and air dried to give the title compound (0.040 g, 12%). ¹H NMR (400 MHz, DMSO-d₆) δ ppm 10.23 (s, 1H), 9.44 (br. s., 1H), 8.58 (s, 1H), 8.33 (s, 1H), 8.28 (d, J=5.3 Hz, 1H), 8.05 (d, J=8.1 Hz, 1H), 7.78-7.95 (m, 2H), 7.75 (d, J=9.0 Hz, 1H), 7.60 (t, J=7.8 Hz, 1H), 7.45-7.55 (m, 1H), 7.33-7.45 (m, 1H), 7.11-7.28 (m, 2H), 7.03 (t, J=7.0 Hz, 1H), 6.83 (s, 1H), 6.55 (d, J=5.3 Hz, 1H), 4.57 (t, J=4.9 Hz, 1H), 4.45 (t, J=4.9 Hz, 1H), 3.84 (s, 3H), 3.08-3.51 (m, 2H), 2.09-2.92 (m, 13H), 1.72-2.00 (m, 2H), 1.41-1.72 (m, 2H). MS (M+H, ES+) 796.

Example 113

N-(2,6-difluorophenyl)-3-[3-(2-{[4-{4-[4-(2-fluoroethyl)-1-piperazinyl]-1-piperidinyl}-5-methyl-2-(methyloxy)phenyl]amino}-4-pyrimidinyl)imidazo[1,2-a]pyridin-2-yl]benzamide

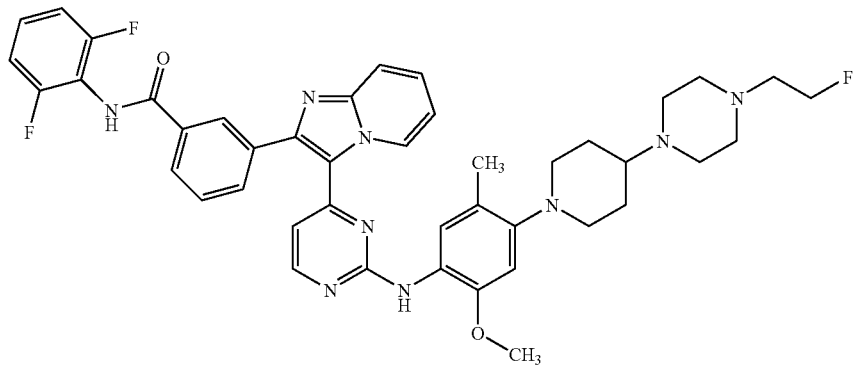

Step A: 5-fluoro-4-methyl-2-nitrophenol

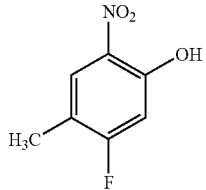

3-fluoro-4-methylphenol (3.66 g, 29.0 mmol) was dissolved in DCE (32 mL) and tetrabutylammonium bromide (0.935 g, 2.90 mmol) was added. HNO₃ 70% (3.7 mL, 58 mmol) was diluted with H₂O (33 mL) to make a 7% HNO₃ solution. This solution was added to the reaction mixture, which was then stirred at rt for 4 h at which time the reaction was judged complete by TLC. The reaction was poured into H₂O and extracted with DCM (3×). The combined organic layers were dried over MgSO₄, filtered and concentrated in vacuo. The resulting residue was adsorbed onto silica gel and flash chromatographed to give the title compound of step A (2.83 g, 57%). $^1$H NMR (400 MHz, DMSO-$d_6$) δ ppm 11.10 (s, 1H), 7.89 (d, J=8.1 Hz, 1H), 6.85 (d, J=11.0 Hz, 1H), 2.13 (s, 3H).

Step B: 5-fluoro-4-methyl-2-nitrophenyl methyl ether

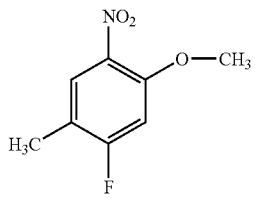

5-Fluoro-4-methyl-2-nitrophenol (2.83 g, 16.5 mmol) was dissolved in N,N-dimethylformamide (25 mL). K₂CO₃ (3.4 g, 25 mmol) and iodomethane (1.2 mL, 20 mmol) were added and the mixture was stirred at rt overnight. The mixture was then poured into H₂O and stirred until solids crashed out. The solids were filtered and air dried to give the title compound without further purification (2.76 g, 90%). $^1$H NMR (400 MHz, DMSO-$d_6$) δ ppm 7.92 (d, J=8.1 Hz, 1H), 7.25 (d, J=11.7 Hz, 1H), 3.89 (s, 3H), 2.19 (d, J=1.5 Hz, 3H).

Step C: Phenylmethyl 4-{1-[2-methyl-5-(methyloxy)-4-nitrophenyl]-4-piperidinyl}-1-piperazinecarboxylate

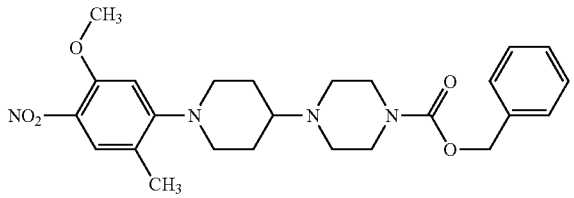

5-Fluoro-4-methyl-2-nitrophenyl methyl ether (2.76 g, 14.9 mmol) was dissolved in DMSO (50 mL), and K₂CO₃ (10.3 g, 74.5 mmol) and phenylmethyl 4-(4-piperidinyl)-1-piperazinecarboxylate bis(trifluoroacetate) salt (Example 112, step B) (8.0 g, 15 mmol) were added. Reaction was stirred overnight. Poured into H₂O and extracted (2×) with EtOAc. Combined organic layers were back-extracted (5×) with H₂O and then dried over MgSO₄, filtered, concentrated on to silica gel and flash chromatographed to give the title compound of step C (4.6 g, 66%). $^1$H NMR (400 MHz, DMSO-$d_6$) δ ppm 7.72 (s, 1H), 7.03-7.46 (m, 5H), 6.64 (s, 1H), 5.03 (s, 2H), 3.85 (s, 3H), 3.06-3.59 (m, 6H), 2.67 (t, J=11.5 Hz, 2H), 2.26-2.57 (m, 5H), 2.15 (s, 3H), 1.81 (d, J=11.5 Hz, 2H), 1.36-1.68 (m, 2H).

Step D: 4-{4-[4-(2-fluoroethyl)-1-piperazinyl]-1-piperidinyl}-5-methyl-2-(methyloxy)-aniline

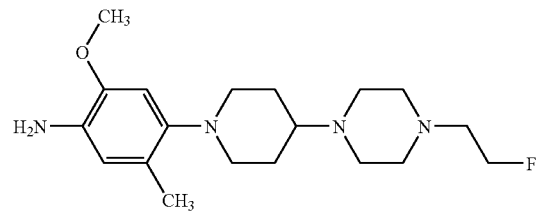

The title compound of step D (0.300 g, 0.856 mmol, 88% in final step) was prepared from phenyl methyl 4-{1-[2-methyl-5-(methyloxy)-4-nitrophenyl]-4-piperidinyl}-1-piperazinecarboxylate in three steps in a manner analogous to that described for Example 112, steps D-F. $^1$H NMR (400 MHz, DMSO-$d_6$) δ ppm 6.53 (s, 1H), 6.41 (s, 1H), 4.52-4.69 (m, 1H), 4.40-4.52 (m, 1H), 4.33 (t, J=5.1 Hz, 2H), 3.69 (s, 3H), 2.83-3.04 (m, 2H), 2.30-2.75 (m, 15H), 2.04 (s, 3H), 1.69-1.94 (m, 2H).

Step E: N-(2,6-difluorophenyl)-3-[3-(2-{[4-{4-[4-(2-fluoroethyl)-1-piperazinyl]-1-piperidinyl}-5-methyl-2-(methyloxy)phenyl]amino}-4-pyrimidinyl)imidazo[1,2-a]pyridin-2-yl]benzamide The title compound (0.110 g, 0.142 mmol, 33%) was prepared in an analogous manner to that described for Example 111, step G with the following notable exception: 4-{4-[4-(2-fluoroethyl)-1-piperazinyl]-1-piperidinyl}-5-methyl-2-(methyloxy)aniline was used instead of 4-{4-[4-(2-fluoroethyl)-1-piperazinyl]-1-piperidinyl}-2,5-bis(methyloxy)aniline. $^1$H NMR (400 MHz, DMSO-$d_6$) δ ppm 10.23 (s, 1H), 9.21-9.57 (m, 1H), 8.46 (s, 1H), 8.33 (s, 1H), 8.23 (d, J=5.1 Hz, 1H), 8.05 (d, J=7.7 Hz, 1H), 7.81 (d, J=7.7 Hz, 1H), 7.73 (d, J=9.0 Hz, 1H), 7.60 (t, J=7.7 Hz, 1H), 7.30-7.53 (m, 3H), 7.20 (t, J=8.1 Hz, 2H), 6.90-7.08 (m, 1H), 6.74 (s, 1H), 6.49 (d, J=5.1 Hz, 1H), 4.57 (t, J=4.8 Hz, 1H), 4.37-4.50 (m, 1H), 3.78 (s, 3H), 3.20-3.33 (m, 2H), 2.97-3.16 (m, 2H), 2.36-2.72 (m, 10H), 2.21-2.36 (m, 1H), 2.13 (s, 3H), 1.76-1.91 (m, 2H), 1.46-1.68 (m, 2H). MS (M+H, ES+) 776.

Example 114

3-[3-(2-{[5-chloro-2-(methyloxy)-4-(4-{4-[2-(methylsulfonyl)ethyl]-1-piperazinyl}-1-piperidinyl)phenyl]amino}-4-pyrimidinyl)imidazo[1,2-a]pyridin-2-yl]-N-(2,6-difluorophenyl)-benzamide

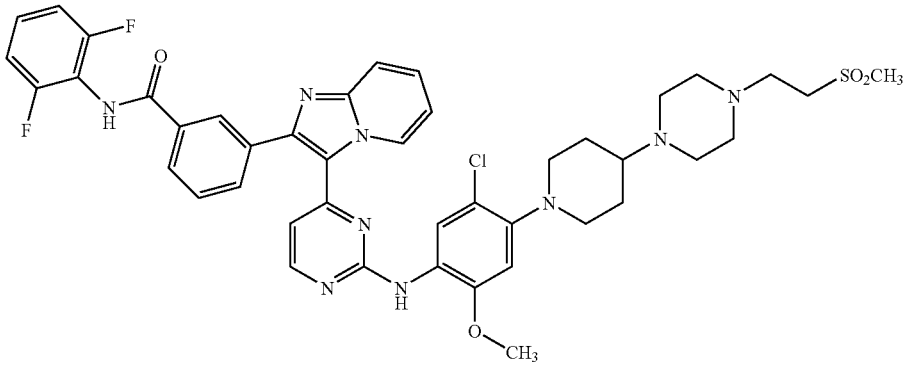

Step A: 1-{1-[2-chloro-5-(methyloxy)-4-nitrophenyl]-4-piperidinyl}-4-[2-(methylsulfonyl)-ethyl]piperazine

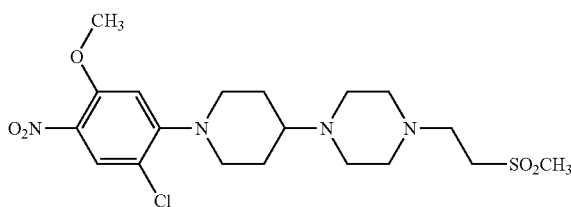

1-{1-[2-Chloro-5-(methyloxy)-4-nitrophenyl]-4-piperidinyl}piperazine (Example 112, step D) (0.050 g, 1.41 mmol) was taken up in THF (10 mL) and methylvinylsulfone (0.371 mL, 4.23 mmol) was added. DMSO was added to solubilize the starting material. Reaction was stirred overnight at rt. Reaction was not complete and over the next 3 days, 30 equivalents more methylvinylsulfone were added. Reaction was then stirred over the weekend. Poured reaction mixture onto prepackaged silica gel cartridge, dried by vacuum suction of air through cartridge and then flash chromatographed to give the title compound of step A (0.370 g, 57%). MS (M+H, ES+) 461.

Step B: 5-chloro-2-(methyloxy)-4-(4-{4-[2-(methylsulfonyl)ethyl]-1-piperazinyl}-1-piperidinyl)aniline

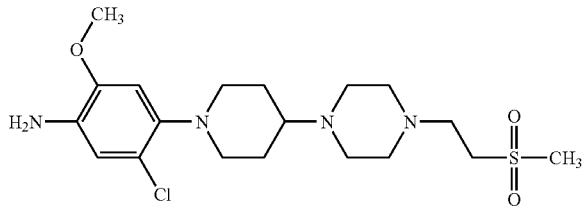

The title compound of step B (0.192 g, 0.445 mmol, 56%) was prepared from 1-{1-[2-chloro-5-(methyloxy)-4-nitrophenyl]-4-piperidinyl}-4-[2-(methylsulfonyl)ethyl]piperazine in a manner analogous to that described for Example 112, step F. $^1$H NMR (400 MHz, DMSO-$d_6$) δ ppm 6.60 (s, 1H), 6.58 (s, 1H), 4.58 (s, 2H), 3.70 (s, 3H), 3.16-3.28 (m, 4H), 3.01-3.11 (m, 2H), 2.98 (s, 3H), 2.63 (t, J=6.8 Hz, 2H), 2.29-2.57 (m, 10H), 2.13-2.25 (m, 1H), 1.75 (d, J=10.8 Hz, 2H), 1.37-1.61 (m, 2H).

Step C: 3-[3-(2-{[5-chloro-2-(methyloxy)-4-(4-{4-[2-(methylsulfonyl)ethyl]-1-piperazinyl}-1-piperidinyl)phenyl]amino}-4-pyrimidinyl)imidazo[1,2-a]pyridin-2-yl]-N-(2,6-difluorophenyl)benzamide The title compound (0.133 g, 0.155 mmol, 42%) was prepared in an analogous manner to that described for Example 112, step G with the following notable exception: 5-chloro-2-(methyloxy)-4-(4-{4-[2-(methylsulfonyl)ethyl]-1-piperazinyl}-1-piperidinyl)aniline was used instead of 5-chloro-4-{4-[4-(2-fluoroethyl)-1-piperazinyl]-1-piperidinyl}-2-(methyloxy)aniline. $^1$H NMR (400 MHz, DMSO-$d_6$) δ ppm 10.23 (s, 1H), 9.44 (br. s., 1H), 8.57 (s, 1H), 8.33 (s, 1H), 8.28 (d, J=5.3 Hz, 1H), 8.05 (d, J=7.9 Hz, 1H), 7.78-7.96 (m, 2H), 7.74 (d, J=9.0 Hz, 1H), 7.60 (t, J=7.8 Hz, 1H), 7.32-7.54 (m, 2H), 7.20 (t, J=8.1 Hz, 2H), 7.03 (s, 1H), 6.83 (s, 1H), 6.55 (d, J=5.3 Hz, 1H), 3.84 (s, 3H), 3.19-3.34 (m, 4H), 3.01 (s, 3H), 2.59-2.77 (m, 4H), 2.19-2.58 (m, 9H), 1.84 (dd, J=10.6, 0.9 Hz, 2H), 1.44-1.71 (m, 2H). MS (M+H, ES+) 856.

Example 115

N-(2,6-difluorophenyl)-3-[3-(2-{[5-methyl-2-(methyloxy)-4-(4-{4-[2-(methyl sulfonyl)ethyl]-1-piperazinyl}-1-piperidinyl)phenyl]amino}-4-pyrimidinyl)imidazo[1,2-a]pyridin-2-yl]benzamide

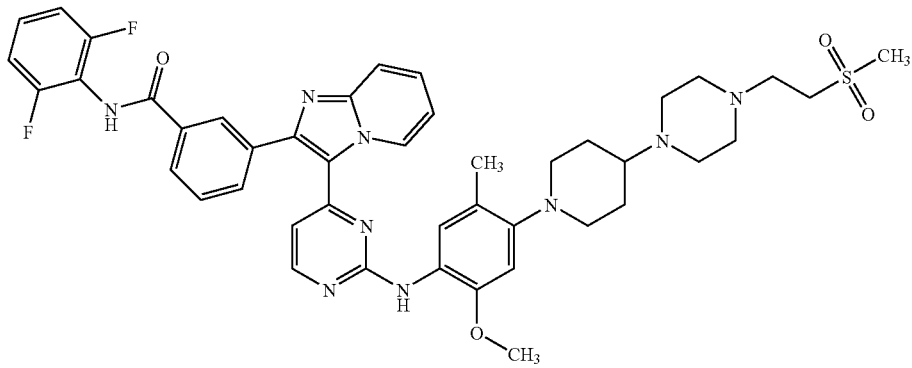

The title compound (0.257 g, 0.307 mmol, 71% in final step) was prepared in an analogous manner to that described for Example 114 with the following notable exception: 1-{1-[2-methyl-5-(methyloxy)-4-nitrophenyl]-4-piperidinyl}piperazine (intermediate described in Example 113, step D) was used instead of 1-{1-[2-Chloro-5-(methyloxy)-4-nitrophenyl]-4-piperidinyl}piperazine in the procedure described in Example 114, step A. $^1$H NMR (400 MHz, DMSO-$d_6$) δ ppm 10.20 (s, 1H), 9.37 (br. s., 1H), 8.43 (s, 1H), 8.30 (s, 1H), 8.20 (d, J=5.3 Hz, 1H), 8.02 (d, J=7.9 Hz, 1H), 7.79 (d, J=7.7 Hz, 1H), 7.70 (d, J=9.0 Hz, 1H), 7.57 (t, J=7.7 Hz, 3H), 7.27-7.51 (m, 2H), 7.17 (t, J=8.1 Hz, 2H), 6.95 (t, J=6.8 Hz, 1H), 6.71 (s, 1H), 6.46 (d, J=5.1 Hz, 1H), 3.75 (s, 4H), 3.24 (t, J=6.9 Hz, 2H), 3.06 (d, J=10.8 Hz, 2H), 2.99 (s, 3H), 2.54-2.79 (m, 4H), 2.32-2.54 (m, 6H), 2.20-2.32 (m, 1H), 2.10 (s, 3H), 1.81 (d, J=11.5 Hz, 2H), 1.34-1.69 (m, 2H). MS (M+H, ES+) 834.

Example 116

N-(2,6-difluorophenyl)-3-(3-{2-[(2-(ethyloxy)-4-{4-[4-(2-fluoroethyl)-1-piperazinyl]-1-piperidinyl}phenyl)amino]-4-pyrimidinyl}imidazo[1,2-a]pyridin-2-yl)benzamide

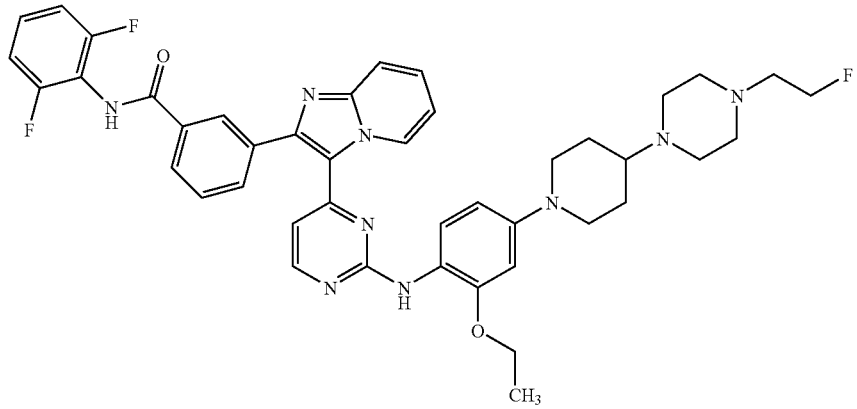

Step A: 2-(ethyloxy)-4-fluoro-1-nitrobenzene

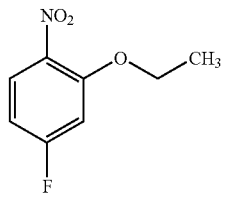

To 5-fluoro-2-nitrophenol (8.3 g, 52.83 mmol) in 50 mL of DMF was added $K_2CO_3$ (14.6 g, 105.7 mmol), and ethyl iodide (8.53 mL, 105.7 mmol). The mixture was stirred at 60° C. for 24 h in a sealed tube. The mixture was poured into 500 mL of $H_2O$ and extracted with diethyl ether, dried ($Na_2SO_4$), filtered, and rotovaped down to give the title compound of step A (9.69 g, 52.33 mmol, 99%). $^1$H NMR (400 MHz, CDCl$_3$) δ ppm 7.88-7.94 (m, 1H), 6.71-6.77 (m, 1H), 6.66-6.71 (m, 1H), 4.11-4.19 (m, 2H), 1.45-1.51 (m, 3H).

Step B: 2-(ethyloxy)-4-{4-[4-(2-fluoroethyl)-1-piperazinyl]-1-piperidinyl}aniline

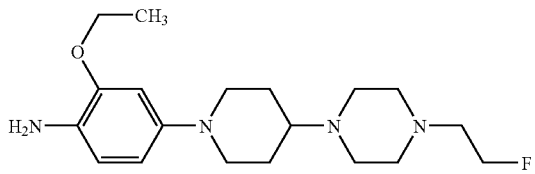

The title compound of step B (0.590 g, 1.68 mmol, 58% over final 2 steps) was prepared in an analogous manner to that described for Example 112, steps C-F with the following notable exception: 2-(ethyloxy)-4-fluoro-1-nitro-benzene was used instead of 1-chloro-2-fluoro-4-(methyloxy)-5-nitrobenzene in Example 112, step C. $^1$H NMR (400 MHz, DMSO-d$_6$) δ ppm 6.39-6.55 (m, 2H), 6.24 (dd, J=8.4, 2.2 Hz, 1H), 4.53 (t, J=4.9 Hz, 1H), 4.41 (t, J=4.9 Hz, 1H), 4.31 (t, J=4.9 Hz, 2H), 4.13 (br. s., 2H), 3.92 (q, J=7.0 Hz, 2H), 3.31-3.50 (m, 2H), 2.57 (t, J=4.9 Hz, 1H), 2.31-2.53 (m, 9H), 2.09-2.25 (m, 1H), 1.76 (d, J=12.1 Hz, 2H), 1.45 (qd, J=11.8, 3.3 Hz, 2H), 1.21-1.34 (m, 3H).

Step C: N-(2,6-difluorophenyl)-3-(3-{2-[(2-(ethyloxy)-4-{4-[4-(2-fluoroethyl)-1-piperazin-yl]-1-piperidinyl}phenyl)amino]-4-pyrimidinyl}imidazo[1,2-a]pyridin-2-yl)benzamide The title compound (0.042 g, 0.054 mmol, 13%) was prepared in an analogous manner to that described for Example 112, step G with the following notable exception: 2-(ethyloxy)-4-{4-[4-(2-fluoroethyl)-1-piperazinyl]-1-piperidinyl}aniline was used instead of 5-chloro-4-{4-[4-(2-fluoroethyl)-1-piperazinyl]-1-piperidinyl}-2-(methyloxy)aniline. $^1$H NMR (400 MHz, DMSO-d$_6$) δ ppm 10.20 (s, 1H), 9.34 (d, J=5.9 Hz, 1H), 8.32 (d, J=8.8 Hz, 2H), 8.19 (d, J=5.1 Hz, 1H), 8.01 (d, J=7.9 Hz, 1H), 7.78 (d, J=7.9 Hz, 1H), 7.70 (d, J=9.2 Hz, 1H), 7.57 (t, J=7.8 Hz, 1H), 7.29-7.50 (m, 3H), 7.17 (t, J=8.1 Hz, 2H), 6.93 (t, J=6.9 Hz, 1H), 6.62 (d, J=1.8 Hz, 1H), 6.36-6.55 (m, 2H), 4.53 (t, J=4.9 Hz, 1H), 4.41 (t, J=4.9 Hz, 1H), 4.02 (q, J=6.8 Hz, 2H), 3.67 (d, J=11.9 Hz, 2H), 3.27 (m, 2H), 2.54-2.76 (m, 2H), 2.31-2.50 (m, 8H), 2.17-2.31 (m, 1H), 1.67-1.91 (m, 2H), 1.36-1.66 (m, 2H), 1.20 (t, J=7.0 Hz, 3H). MS (M+H, ES+) 776.

Example 117

3-[3-(2-{[4-{4-[4-(2,2-difluoroethyl)-1-piperazinyl]-1-piperidinyl}-2-(ethyloxy)phenyl]-amino}-4-pyrimidinyl)imidazo[1,2-a]pyridin-2-yl]-N-(2,6-difluorophenyl)benzamide Step A: 4-{4-[4-(2,2-difluoroethyl)-1-piperazinyl]-1-piperidinyl}-2-(ethyloxy)aniline The title compound of step A (0.570 g, 1.43 mmol, 62% in final step) was prepared in an analogous manner to that described for Example 112, steps C-F with the following notable exceptions:
a) 2-(ethyloxy)-4-fluoro-1-nitro-benzene was used instead of 1-chloro-2-fluoro-4-(methyloxy)-5-nitrobenzene in Example 112, step C;
b) 1,1-difluoro-2-iodoethane was used instead of 1-fluoroethyliodide in the alkylation described in Example 112, step E.

$^1$H NMR (400 MHz, DMSO-$d_6$) δ ppm 7.81 (d, J=9.3 Hz, 1H), 6.52 (dd, J=9.5, 2.2 Hz, 1H), 6.44 (d, J=2.2 Hz, 1H), 5.81-6.32 (m, 1H), 4.13 (q, J=7.0 Hz, 2H), 3.97 (d, J=13.2 Hz, 2H), 2.89 (t, J=11.8 Hz, 2H), 2.64 (td, J=15.7, 4.3 Hz, 2H), 2.25-2.53 (m, 11H), 1.77 (d, J=11.9 Hz, 2H), 1.23-1.52 (m, 5H).

Step B: N-(2,6-difluorophenyl)-3-(3-{2-[(2-(ethyloxy)-4-{4-[4-(2-fluoroethyl)-1-piperazin-yl]-1-piperidinyl}phenyl)amino]-4-pyrimidinyl}imidazo[1,2-a]pyridin-2-yl)benzamide The title compound (0.285 g, 0.359 mmol, 83%) was prepared in an analogous manner to that described for Example 111, step G with the following notable exception: 4-{4-[4-(2,2-difluoroethyl)-1-piperazinyl]-1-piperidinyl}-2-(ethyloxy)aniline was used instead of 4-{4-[4-(2-fluoroethyl)-1-piperazinyl]-1-piperidinyl}-2,5-bis(methyloxy)aniline. $^1$H NMR (400 MHz, DMSO-$d_6$) δ ppm 10.23 (s, 1H), 9.36 (td, J=2.8, 1.7 Hz, 1H), 8.34 (d, J=10.6 Hz, 2H), 8.22 (d, J=5.3 Hz, 1H), 8.04 (d, J=7.7 Hz, 1H), 7.81 (d, J=7.7 Hz, 1H), 7.72 (d, J=9.0 Hz, 1H), 7.60 (t, J=7.8 Hz, 1H), 7.33-7.52 (m, 3H), 7.12-7.28 (m, 2H), 6.87-7.08 (m, 1H), 6.64 (d, J=2.2 Hz, 1H), 6.39-6.58 (m, 2H), 6.11 (tt, $J_{HF}$=56.0, J=4.4 Hz, 1H), 3.84-4.17 (m, 2H), 3.69 (d, J=12.6 Hz, 2H), 3.06-3.42 (m, 2H), 2.56-2.80 (m, 4H), 2.38-2.57 (m, 6H), 2.19-2.39 (m, 1H), 1.72-1.92 (m, 2H), 1.38-1.66 (m, 2H), 1.23 (t, J=7.0 Hz, 3H). MS (M+H, ES+) 794.

Example 118

N-(2,6-difluorophenyl)-3-(3-{2-[(2-(ethyloxy)-4-{4-[4-(3,3,3-trifluoropropyl)-1-piperazinyl]-1-piperidinyl}phenyl)amino]-4-pyrimidinyl}imidazo[1,2-a]pyridin-2-yl)benzamide

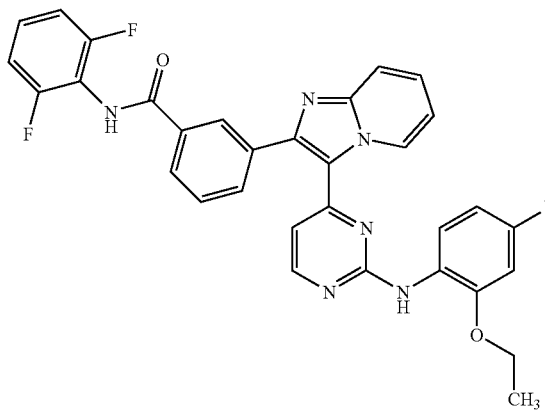

Step A: 2-(ethyloxy)-4-{4-[4-(3,3,3-trifluoropropyl)-1-piperazinyl]-1-piperidinyl}aniline

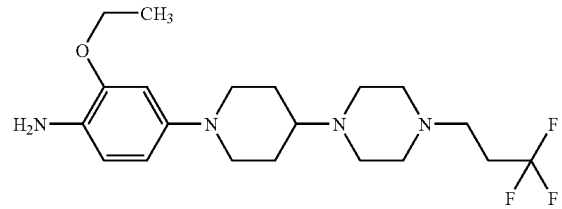

The title compound of step A (0.760 g, 1.90 mmol, 90% in final step) was prepared in an analogous manner to that described for Example 112, steps C-F with the following notable exceptions:
a) 2-(ethyloxy)-4-fluoro-1-nitro-benzene was used instead of 1-chloro-2-fluoro-4-(methyloxy)-5-nitrobenzene in Example 112, step C;
b) 1,1-difluoro-2-iodoethane at 50° C. was used instead of 1-fluoroethyliodide at 70° C. in the alkylation described in Example 112, step E;
c) 10% palladium on carbon was used instead of 5% sulfided platinum on carbon in the nitro reduction described in Example 112, step F.

$^1$H NMR (400 MHz, DMSO-$d_6$) δ ppm 6.46 (d, J=8.4 Hz, 1H), 6.42 (d, J=2.0 Hz, 1H), 6.24 (dd, J=8.4, 2.2 Hz, 1H), 4.13 (br. s., 2H), 3.92 (q, J=6.9 Hz, 2H), 3.36 (d, J=12.1 Hz, 2H), 2.25-2.59 (m, 14H), 2.09-2.24 (m, 1H), 1.76 (d, J=11.7 Hz, 2H), 1.45 (qd, J=11.8, 3.2 Hz, 2H), 1.27 (t, J=7.0 Hz, 3H).

Step B: N-(2,6-difluorophenyl)-3-(3-{2-[(2-(ethyloxy)-4-{4-[4-(3,3,3-trifluoropropyl)-1-piperazinyl]-1-piperidinyl}phenyl)amino]-4-pyrimidinyl}imidazo[1,2-a]pyridin-2-yl)benzamide The title compound (0.142 g, 0.172 mmol, 40%) was prepared in an analogous manner to that described for Example 112, step G with the following notable exception: 2-(ethyloxy)-4-{4-[4-(3,3,3-trifluoropropyl)-1-piperazinyl]-1-piperidinyl}aniline was used instead of 5-chloro-4-{4-[4-(2-fluoroethyl)-1-piperazinyl]-1-piperidinyl}-2-(methyloxy)aniline. $^1$H NMR (400 MHz, DMSO-$d_6$) δ ppm 10.23 (s, 1H), 9.24-9.51 (m, 1H), 8.34 (d, J=9.5 Hz, 2H), 8.22 (d, J=5.3 Hz, 1H), 8.04 (d, J=7.7 Hz, 1H), 7.81 (s, 1H), 7.73 (d, J=9.0 Hz, 1H), 7.60 (t, J=7.7 Hz, 1H), 7.30-7.53 (m, 3H), 7.20 (t, J=8.1 Hz, 2H), 6.87-7.04 (m, 1H), 6.65 (d, J=1.8 Hz, 1H), 6.39-6.54 (m, 2H), 4.05 (q, J=6.9 Hz, 2H), 3.57-3.84 (m, 2H), 3.15-3.44 (m, 2H), 2.56-2.71 (m, 2H), 2.34-2.57 (m, 10H), 2.19-2.34 (m, 1H), 1.75-1.94 (m, 2H), 1.41-1.59 (m, 2H), 1.23 (t, J=7.0 Hz, 3H). MS (M+H, ES+) 826.

Example 119

N-(2,6-difluorophenyl)-3-[3-(2-{[2-(ethyloxy)-4-(4-{4-[2-(methylsulfonyl)ethyl]-1-piperazin-yl}-1-piperidinyl)phenyl]amino}-4-pyrimidinyl)imidazo[1,2-a]pyridin-2-yl]benzamide

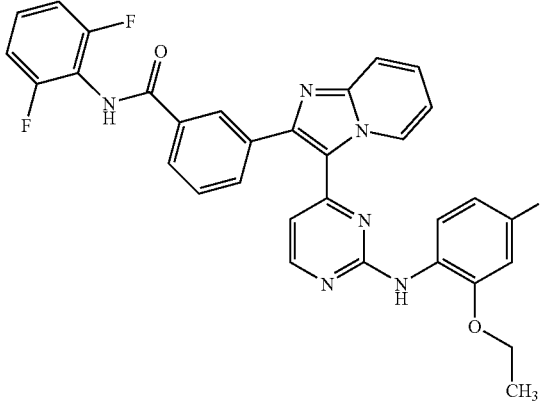

Step A: 2-(ethyloxy)-4-(4-{4-[2-(methylsulfonyl)ethyl]-1-piperazinyl}-1-piperidinyl)aniline

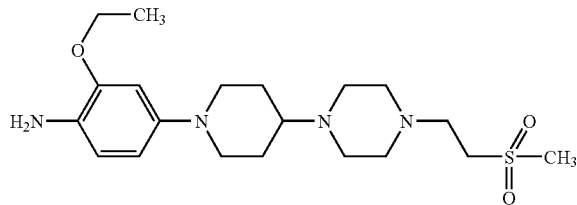

The title compound of step A (0.370 g, 0.901 mmol, 79% in final step) was prepared in an analogous manner to that described for Example 112, steps C-D and Example 114, steps A-B with the following notable exception: 2-(ethyloxy)-4-fluoro-1-nitro-benzene was used instead of 1-chloro-2-fluoro-4-(methyloxy)-5-nitrobenzene in the procedure described in Example 112, step C. $^1$H NMR (400 MHz, DMSO-d$_6$) δ ppm 6.39-6.55 (m, 2H), 6.27 (dd, J=8.4, 2.4 Hz, 1H), 4.15 (br. s., 2H), 3.94 (q, J=6.8 Hz, 2H), 3.34-3.44 (m, 2H), 3.22-3.29 (m, 2H), 3.00 (s, 3H), 2.65 (t, J=6.7 Hz, 2H), 2.33-2.57 (m, 10H), 2.11-2.25 (m, 1H), 1.78 (dd, J=11.6, 1.4 Hz, 2H), 1.39-1.58 (m, 2H), 1.29 (t, J=7.0 Hz, 3H).

Step B: N-(2,6-difluorophenyl)-3-[3-(2-{[2-(ethyloxy)-4-(4-{4-[2-(methylsulfonyl)ethyl]-1-piperazinyl}-1-piperidinyl)phenyl]amino}-4-pyrimidinyl)imidazo[1,2-a]pyridin-2-yl]benzamide The title compound (0.220 g, 0.263 mmol, 61%) was prepared in an analogous manner to that described for Example 111, step G with the following notable exception: 2-(ethyloxy)-4-(4-{4-[2-(methylsulfonyl)ethyl]-1-piperazinyl}-1-piperidinyl)aniline was used instead of 4-{4-[4-(2-fluoroethyl)-1-piperazinyl]-1-piperidinyl}-2,5-bis(methyloxy)aniline. $^1$H NMR (400 MHz, DMSO-d$_6$) δ ppm 10.23 (s, 1H), 9.36 (br. s., 1H), 8.34 (d, J=9.5 Hz, 2H), 8.22 (d, J=5.1 Hz, 1H), 8.04 (d, J=7.5 Hz, 1H), 7.81 (d, J=7.5 Hz, 1H), 7.72 (d, J=9.0 Hz, 1H), 7.60 (t, J=7.7 Hz, 1H), 7.33-7.53 (m, 3H), 7.20 (t, J=8.0 Hz, 2H), 6.81-7.07 (m, 1H), 6.64 (br. s., 1H), 6.37-6.55 (m, 2H), 4.05 (q, J=6.9 Hz, 2H), 3.69 (d, J=11.2 Hz, 2H), 3.25 (t, J=6.5 Hz, 2H), 3.01 (s, 3H), 2.56-2.79 (m, 4H), 2.34-2.47 (m, 8H), 2.21-2.34 (m, 1H), 1.82 (d, J=10.1 Hz, 2H), 1.38-1.59 (m, 2H), 1.23 (t, J=6.8 Hz, 3H). MS (M+H, ES+) 836.

Example 120

N-(2,6-difluorophenyl)-3-{3-[2-({4-(4-{4-[2-(methylsulfonyl)ethyl]-1-piperazinyl}-1-piperidinyl)-2-[(2,2,2-trifluoroethyl)oxy]phenyl}amino)-4-pyrimidinyl]imidazo[1,2-a]pyridin-2-yl}benzamide

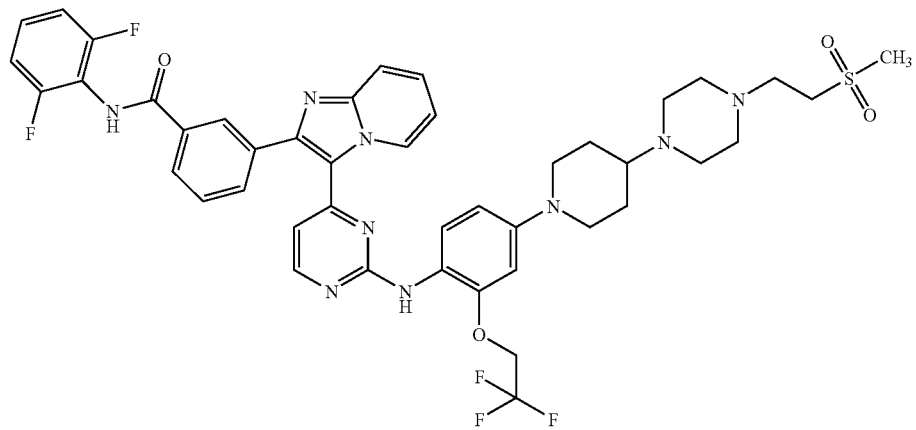

Step A: 5-fluoro-2-nitrophenyl 2,2,2-trifluoroethyl ether

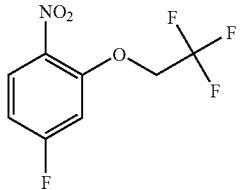

5-Fluoro-2-nitrophenol (3.07 g, 19.5 mmol) was dissolved in 50 mL of DMSO with cesium carbonate (7.62 g, 23.4 mmol) and stirred. 2,2,2-Trifluorethyl trifluoromethanesulfonate (5.00 g, 21.5 mmol) was added with 5 mL of DMSO. The reaction was stirred overnight and quenched with 50 mL of H$_2$O. The mixture was poured into 1:1 diethyl ether/hexanes and H$_2$O. The layers were separated, and the organic layer was washed with 10% K$_2$CO$_3$ (aqueous) (2×), H$_2$O, and brine. The organic layer was dried over MgSO$_4$, filtered, and concentrated in vacuo. The residue was purified by flash chromatography to afford 2.95 g (63%) of the title compound of step A. $^1$H NMR (400 MHz, DMSO-d$_6$) δ 8.06 (dd, J=9.0, 6.0 Hz, 1H), 7.45 (dd, J=10.7, 2.5 Hz, 1H), 7.08 (ddd, J=9.0, 7.9, 2.6 Hz, 1H), 4.97 (q, J=8.6 Hz, 2H).

Step B: 1-{4-nitro-3-[(2,2,2-trifluoroethyl)oxy]phenyl}-4-piperidinol

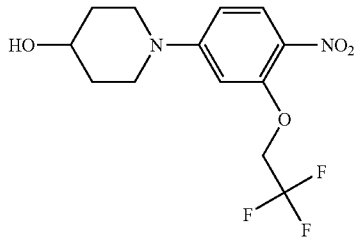

5-Fluoro-2-nitrophenyl 2,2,2-trifluoroethyl ether (1.48 g, 6.19 mmol) was dissolved in 30 mL of DMSO with K$_2$CO$_3$ (1.11 g, 8.03 mmol) and 4-hydroxypiperidine (0.657 g, 6.50 mmol). The reaction was stirred for 2.5 days and quenched with H$_2$O. The mixture was poured into EtOAc and H$_2$O. The layers were separated, and the organic layer was washed with H$_2$O (2×) and brine. The organic layer was dried over MgSO$_4$, filtered, and concentrated in vacuo. The residue was purified by flash chromatography to afford 1.83 g (92%) of the title compound of step B. $^1$H NMR (400 MHz, DMSO-d$_6$) δ 7.85 (d, J=9.5 Hz, 1H), 6.63 (dd, J=9.5, 2.4 Hz, 1H), 6.55 (d, J=2.4 Hz, 1H), 4.88 (q, J=8.8 Hz, 2H), 4.72 (d, J=4.2 Hz, 1H), 3.65-3.84 (m, 3H), 3.16 (ddd, J=13.3, 9.8, 2.9 Hz, 2H), 1.74 (br. s., 2H), 1.28-1.43 (m, 2H).

Step C: 1-{4-nitro-3-[(2,2,2-trifluoroethyl)oxy]phenyl}-4-piperidinone

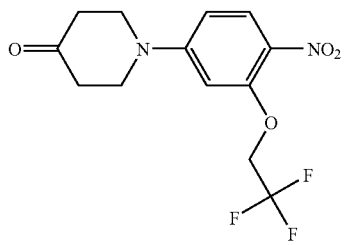

Oxalyl chloride (4.3 mL, 2.0M in DCM, 8.6 mmol) in 40 mL of DCM was cooled to −78° C. with stirring. DMSO (1.2 mL, 17 mmol) was added dropwise via addition funnel at such a rate so as to maintain the internal reaction temperature below −70° C. After ten min, 1-{4-nitro-3-[(2,2,2-trifluoroethyl)oxy]phenyl}-4-piperidinol (1.83 g, 5.71 mmol) in 8 mL of DMSO and 20 mL of DCM was added dropwise via addition funnel at such a rate so as to maintain the internal reaction temperature below −70° C. The addition funnel was rinsed with 10 mL of DCM, and the reaction was stirred for 1 h. TEA (4.0 mL, 29 mmol) was added dropwise via addition funnel, and the reaction was allowed to warm to rt. The reaction was poured into H$_2$O, and the layers were separated. The aqueous layer was poured into saturated NaHCO$_3$ (aqueous) and extracted with EtOAc. The DCM layer was washed with H$_2$O and brine. The combined organic layers was dried over MgSO$_4$, filtered, and concentrated in vacuo. The crude material was triturated with 2:1 diethyl ether/EtOAc, filtered, and washed with diethyl ether. The yellow solid was collected to afford 1.63 g (90%) of the title compound of step C. $^1$H NMR (400 MHz, DMSO-d$_6$) δ 7.94 (d, J=9.2 Hz, 1H), 6.70 (dd, J=9.5, 2.6 Hz, 1H), 6.63 (d, J=2.6 Hz, 1H), 4.94 (q, J=8.8 Hz, 2H), 3.82 (t, J=6.0 Hz, 4H), 3.02-3.13 (m, 2H), 1.16 (t, J=7.3 Hz, 2H).

Step D: 1,1-dimethylethyl 4-(1-{4-nitro-3-[(2,2,2-trifluoroethyl)oxy]phenyl}-4-piperidinyl)-1-piperazinecarboxylate

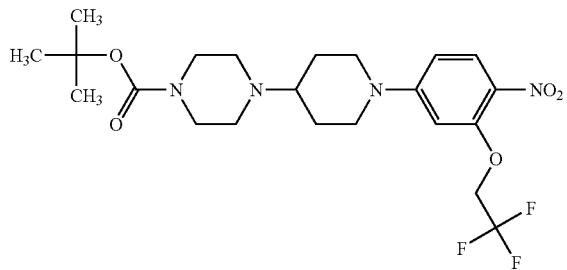

1-{4-Nitro-3-[(2,2,2-trifluoroethyl)oxy]phenyl}-4-piperidinone (1.63 g, 5.12 mmol) was dissolved in 20 mL of acetonitrile with stirring. HOAc (0.44 mL, 7.7 mmol) was added, and 20 mL of toluene was added. TEA (1.78 mL, 12.8 mmol) was added followed by 1-BOC-piperazine (1.91 g, 10.3 mmol). Sodium triacetoxyborohydride (2.71 g, 12.8 mmol) was added. After 1 h, 40 mL of acetonitrile and 20 mL of toluene were added, and the reaction was stirred overnight. The reaction was quenched with 1N NaOH and poured into H$_2$O and EtOAc. The layers were separated, and the organic layer was washed with brine. The combined aqueous layers were extracted with EtOAc. The combined organic layers was dried over MgSO$_4$, filtered, and concentrated in vacuo. Purification by flash chromatography afforded 1.35 g (54%) of the title compound of step D. $^1$H NMR (400 MHz, DMSO-d$_6$) δ ppm 7.85 (d, J=9.5 Hz, 1H), 6.63 (dd, J=9.6, 2.3 Hz, 1H), 6.56 (d, J=2.2 Hz, 1H), 4.88 (q, J=8.7 Hz, 2H), 3.98-4.10 (m, 2H), 3.27 (s, 4H), 2.84-2.97 (m, 2H), 2.33-2.55 (m, 5H), 1.76 (br. s., 2H), 1.29-1.45 (m, 11H).

Step E: 1-(1-{4-nitro-3-[(2,2,2-trifluoroethyl)oxy]phenyl}-4-piperidinyl)piperazine

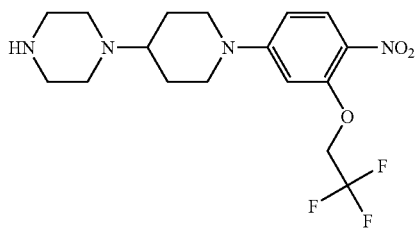

1,1-Dimethylethyl 4-(1-{4-nitro-3-[(2,2,2-trifluoroethyl)oxy]phenyl}-4-piperidinyl)-1-piperazinecarboxylate (1.35 g, 2.76 mmol) was dissolved in 40 mL of DCM with stirring. TFA (10.0 mL, 130 mmol) was added via syringe, and the reaction was stirred for 3 h and cooled to 0° C. The reaction was quenched with 20 mL of 6N NaOH (aqueous). Saturated NaHCO₃ (aqueous) was added until the pH was approximately 9. The mixture was poured into H₂O and DCM. The layers were separated, and the aqueous layer was washed with 4:1 DCM/iPrOH (2×) and 4:1 EtOAc/iPrOH. The combined organic layers was dried over MgSO₄, filtered, and concentrated in vacuo. Purification by flash chromatography afforded 0.879 g (82%) of the title compound of step E. $^1$H NMR (400 MHz, DMSO-d₆) δ 7.85 (d, J=9.5 Hz, 1H), 6.63 (dd, J=9.5, 2.4 Hz, 1H), 6.55 (d, J=2.4 Hz, 1H), 4.88 (q, J=8.7 Hz, 2H), 4.02 (d, J=13.6 Hz, 2H), 2.84-2.98 (m, 2H), 2.56-2.67 (m, 4H), 2.26-2.49 (m, 5H), 1.96 (br. s., 1H), 1.70-1.84 (m, 2H), 1.38 (d, J=8.2 Hz, 2H).

Step F: 2-(ethyloxy)-4-{4-[4-(2-fluoroethyl)-1-piperazinyl]-1-piperidinyl}aniline

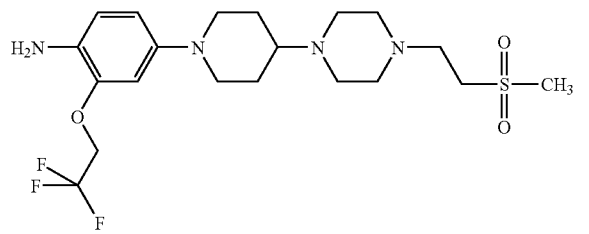

The title compound of step F (0.460 g, 0.990 mmol, 86% in final step) was prepared in an analogous manner to that described for Example 114, steps A-B. $^1$H NMR (400 MHz, DMSO-d₆) δ ppm 6.52-6.60 (m, 2H), 6.39 (dd, J=8.5, 2.3 Hz, 1H), 4.64 (q, J=9.0 Hz, 2H), 4.23 (s, 2H), 3.43 (d, J=12.1 Hz, 2H), 3.15-3.29 (m, 2H), 3.00 (s, 3H), 2.65 (t, J=6.8 Hz, 2H), 2.35-2.59 (m, 12H), 2.11-2.26 (m, 1H), 1.67-1.85 (m, 2H), 1.34-1.61 (m, 2H).

Step G: N-(2,6-difluorophenyl)-3-{3-[2-({4-(4-{4-[2-(methylsulfonyl)ethyl]-1-piperazinyl}-1-piperidinyl)-2-[(2,2,2-trifluoroethyl)oxy]phenyl}amino)-4-pyrimidinyl]imidazo[1,2-a]pyridin-2-yl}benzamide The title compound (0.188 g, 0.211 mmol, 49%) was prepared in an analogous manner to that described for Example 111, step G with the following notable exception: 2-(ethyloxy)-4-{4-[4-(2-fluoroethyl)-1-piperazinyl]-1-piperidinyl}aniline was used instead of 4-{4-[4-(2-fluoroethyl)-1-piperazinyl]-1-piperidinyl}-2,5-bis(methyloxy)aniline. $^1$H NMR (400 MHz, DMSO-d₆) δ ppm 10.24 (s, 1H), 9.32 (dd, J=3.5, 1.8 Hz, 1H), 8.53 (s, 1H), 8.34 (s, 1H), 8.20 (d, J=5.1 Hz, 1H), 8.05 (d, J=7.7 Hz, 1H), 7.79 (d, J=7.9 Hz, 1H), 7.72 (d, J=9.0 Hz, 1H), 7.59 (t, J=7.8 Hz, 1H), 7.35-7.53 (m, 2H), 7.32 (d, J=8.6 Hz, 1H), 7.20 (t, J=8.1 Hz, 2H), 6.94 (t, J=6.6 Hz, 1H), 6.79 (d, J=2.2 Hz, 1H), 6.59 (dd, J=8.8, 2.2 Hz, 1H), 6.47 (d, J=5.1 Hz, 1H), 4.72 (q, J=8.9 Hz, 2H), 3.75 (d, J=12.5 Hz, 2H), 3.26 (t, J=6.7 Hz, 2H), 3.01 (s, 3H), 2.57-2.80 (m, 4H), 2.42 (d, J=2.0 Hz, 8H), 2.18-2.35 (m, 1H), 1.82 (d, J=11.4 Hz, 2H), 1.33-1.63 (m, 2H). MS (M+H, ES+) 890.

Example 121

N-(2,6-difluorophenyl)-3-[3-(2-{[4-{4-[4-(2-fluoroethyl)-3-oxo-1-piperazinyl]-1-piperidinyl}-2-(methyloxy)phenyl]amino}-4-primidinyl)imidazo[1,2-a]pyridin-2-yl]benzamide

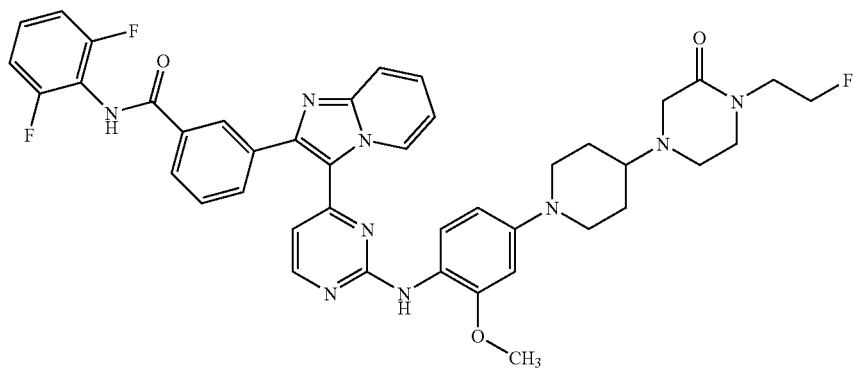

Step A: 4-{1-[3-(methyloxy)-4-nitrophenyl]-4-piperidinyl}-2-piperazinone

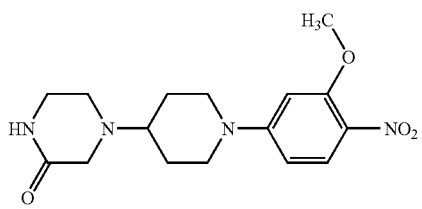

1-[3-(methyloxy)-4-nitrophenyl]-4-piperidinone (Example 57, step B) (1.00 g, 4.00 mmol) and 2-piperazinone (0.801 g, 8.00 mmol) were dissolved in 50 mL of toluene and 25 mL of acetonitrile with stirring. TEA (1.40 mL, 9.97 mmol) and HOAc (0.34 mL, 5.9 mmol) were added via syringe. Sodium triacetoxyborohydride (2.12 g, 10.0 mmol) was added in four equal portions over 1 h. The reaction was allowed to stir overnight and quenched by the addition of approximately 50 mL of 1N NaOH solution and 50 mL of MeOH. The mixture was stirred for 10 min and poured into $H_2O$ and EtOAc. The layers were separated, and the organic layer was washed with brine. The combined aqueous layers were extracted with DCM. The combined organic layers were dried over $MgSO_4$, filtered, and concentrated in vacuo. The residue was purified by flash chromatography to afford 0.970 g (73%) of the title compound of step A. $^1$H NMR (400 MHz, DMSO-$d_6$) δ 7.83 (d, J=9.5 Hz, 1H), 7.68 (br. s., 1H), 6.55 (dd, J=9.5, 2.4 Hz, 1H), 6.46 (d, J=2.56 Hz, 1H), 4.07-3.94 (m, 2H), 3.86 (s, 3H), 3.07 (br. s., 2H), 3.00 (s, 2H), 2.97-2.86 (m, 2H), 2.66-2.37 (m, 3H), 1.87-1.75 (m, 2H), 1.48-1.32 (m, 2H).

Step B: 1-(2-fluoroethyl)-4-{1-[3-(methyloxy)-4-nitrophenyl]-4-piperidinyl}-2-piperazinone

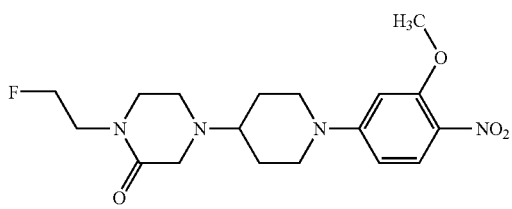

NaH (60% dispersion in mineral oil, 0.174 g, 4.35 mmol) was washed two times with hexanes. 10 mL of DMF and 5 mL of THF was added via syringe. 4-{1-[3-(Methyloxy)-4-nitrophenyl]-4-piperidinyl}-2-piperazinone (0.970 g, 2.90 mmol) in 20 mL of DMF and 10 mL of THF was added slowly via syringe. The reaction was stirred for 45 min, and 1-fluoro-2-iodoethane (0.28 mL, 3.4 mmol) was added via syringe. The reaction was stirred overnight and quenched by the addition of $H_2O$. The mixture was poured into EtOAc and $H_2O$, and the layers were separated. The organic layer was washed with brine, and the combined aqueous layers were extracted with EtOAc. The combined organic layers were dried over $MgSO_4$, filtered, and concentrated in vacuo. The residue was purified by flash chromatography to afford 0.834 g (76%) of the title compound of step B. $^1$H NMR (400 MHz, DMSO-$d_6$) δ 7.83 (d, J=9.0 Hz, 1H), 6.55 (dd, J=9.4, 2.5 Hz, 1H), 6.46 (d, J=2.4 Hz, 1H), 4.55 (t, J=4.9 Hz, 1H), 4.44 (t, J=4.9 Hz, 1H), 4.07-3.94 (m, 2H), 3.86 (s, 3H), 3.58 (t, J=4.9 Hz, 1H), 3.51 (t, J=5.1 Hz, 1H), 3.34-3.22 (m, 2H), 3.11 (s, 2H), 2.99-2.86 (m, 2H), 2.68 (t, J=5.2 Hz, 2H), 2.57-2.46 (m, 1H), 1.89-1.76 (m, 2H), 1.49-1.32 (m, 2H).

Step C: 4-{1-[4-amino-3-(methyloxy)phenyl]-4-piperidinyl}-1-(2-fluoroethyl)-2-piperazinone

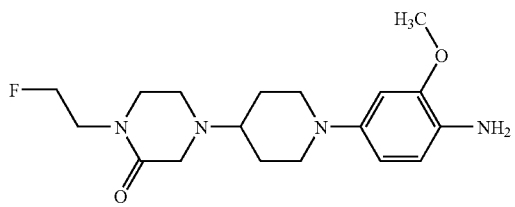

1-(2-Fluoroethyl)-4-{1-[3-(methyloxy)-4-nitrophenyl]-4-piperidinyl}-2-piperazinone (0.832 g, 2.19 mmol) was dissolved in 50 mL of dioxane with stirring and cooled to 0° C. Tin(II) chloride (1.66 g, 8.76 mmol) in concentrated HCl (37%, 15.0 mL, 167 mmol) was added dropwise via pipet. The reaction was warmed to rt and stirred overnight. The reaction was quenched by the slow addition of 6N NaOH solution until the pH was greater than 10. The mixture was extracted with EtOAc, and the organic layer was washed with brine. The combined aqueous layers were extracted with EtOAc. The combined organic layers were dried over $MgSO_4$, filtered, and concentrated in vacuo. The residue was purified by flash chromatography to afford 0.695 g (91%) of the title compound of step C. $^1$H NMR (400 MHz, DMSO-$d_6$) δ 6.50-6.40 (m, 2H), 6.25 (dd, J=8.4, 2.0 Hz, 1H), 4.56 (t, J=4.9 Hz, 1H), 4.44 (t, J=4.9 Hz, 1H), 4.15 (br. s., 2H), 3.69 (s, 3H), 3.58 (t, J=4.9 Hz, 1H), 3.52 (t, J=4.9 Hz, 1H), 3.44-3.33 (m, 2H), 3.32-3.23 (m, 2H), 3.10 (s, 2H), 2.69 (t, J=5.4 Hz, 2H), 2.52-2.39 (m, 2H), 2.32-2.20 (m, 1H), 1.74-1.86 (m, 2H), 1.39-1.55 (m, 2H).

Step D: N-(2,6-difluorophenyl)-3-[3-(2-{[4-{4-[4-(2-fluoroethyl)-3-oxo-1-piperazinyl]-1-piperidinyl}-2-(methyloxy)phenyl]amino}-4-pyrimidinyl)imidazo[1,2-a]pyridin-2-yl]benzamide The title compound (0.045 g, 0.058 mmol, 13%) was prepared in an analogous manner to that described for Example 112, step G, with the following notable exception: 4-{1-[4-amino-3-(methyloxy)phenyl]-4-piperidinyl}-1-(2-fluoroethyl)-2-piperazinone was used instead of 5-chloro-4-{4-[4-(2-fluoroethyl)-1-piperazinyl]-1-piperidinyl}-2-(methyloxy)aniline. $^1$H NMR (400 MHz, DMSO-$d_6$) δ ppm 10.23 (s, 1H), 8.46 (s, 1H), 8.32 (s, 1H), 8.20 (d, J=5.1 Hz, 1H), 8.04 (d, J=7.7 Hz, 1H), 7.81 (d, J=7.1 Hz, 1H), 7.72 (d, J=8.8 Hz, 1H), 7.60 (t, J=7.8 Hz, 1H), 7.30-7.53 (m, 3H), 7.11-7.28 (m, 2H), 6.89-7.05 (m, 1H), 6.68 (d, J=2.0 Hz, 1H), 6.37-6.56 (m, 2H), 4.60 (t, J=4.9 Hz, 1H), 4.48 (t, J=4.9 Hz, 1H), 3.79 (s, 3H), 3.66-3.77 (m, 2H), 3.62 (t, J=4.9 Hz, 1H), 3.49-3.58 (m, 1H), 3.23-3.33 (m, 2H), 2.59-2.82 (m, 4H), 2.34-2.59 (m, 3H), 1.79-1.96 (m, 2H), 1.39-1.65 (m, 2H). MS (M+H, ES+) 776.

Example 122

N-(2,6-difluorophenyl)-5-[3-(2-{[4-(4-hydroxy-1-piperidinyl)-2-(methyloxy)phenyl]amino}-4-pyrimidinyl)imidazo[1,2-a]pyridin-2-yl]-2-(methyloxy)benzamide

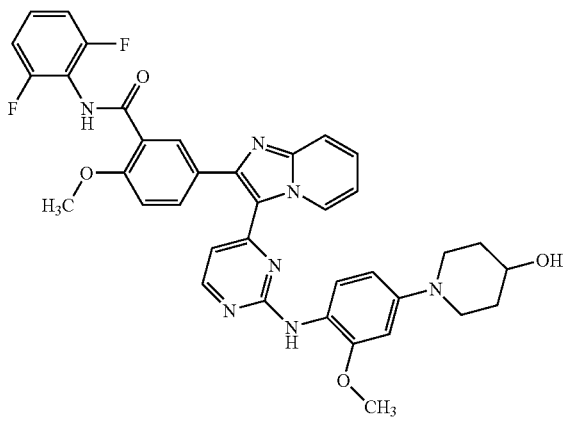

The title compound (0.098 g, 0.15 mmol, 54%) was prepared in an analogous manner to that described for Example 73, step B with the following notable exception: 5-[3-(2-chloro-4-pyrimidinyl)-imidazo[1,2-a]pyridin-2-yl]-N-(2,6-difluorophenyl)-2-(methyloxy)benzamide (Intermediate Example 2) was used instead of Intermediate Example 1. $^1$H NMR (400 MHz, DMSO-d$_6$) δ 9.77 (s, 1H), 9.35 (br s, 1H), 8.42 (s, 1H), 8.18 (d, J=5.6 Hz, 1H), 8.08 (d, J=1.6 Hz, 1H), 7.77-7.74 (m, 1H), 7.68 (d, J=9.2 Hz, 1H), 7.44-7.33 (m, 2H), 7.27 (d, J=8.4 Hz, 1H), 7.17 (t, J=8.0 Hz, 2H), 6.95-6.92 (m, 1H), 6.65 (d, J=2.4 Hz, 1H), 6.51-6.45 (m, 2H), 4.65 (d, J=4.0 Hz, 1H), 3.97 (s, 3H), 3.78 (s, 3H), 3.63-3.57 (m, 1H), 3.53-3.50 (m, 2H), 2.84-2.78 (m, 2H), 1.83-1.79 (m, 2H), 1.52-1.43 (m, 2H).

Example 123

N-(2,6-difluorophenyl)-3-[3-(2-{[4-[(9aS)-hexahydropyrazino[2,1-c][1,4]oxazin-8(1H)-yl]-2-(methyloxy)phenyl]amino}-4-pyrimidinyl)imidazo[1,2-a]pyridin-2-yl]benzamide

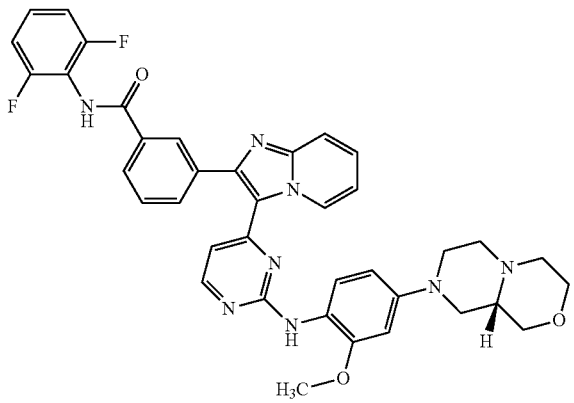

Step A: (9aS)-8-[3-(methyloxy)-4-nitrophenyl]octahydropyrazino[2,1-c][1,4]oxazine

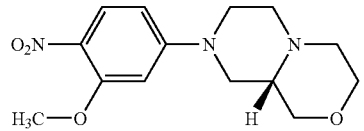

5-Fluoro-2-nitrophenyl methyl ether (Example 22, step A) (0.318 g, 1.86 mmol), (9aS)-octahydropyrazino[2,1-c][1,4]oxazine dihydrochloride (Example 87, step G) (0.190 g, 0.880 mmol) and K$_2$CO$_3$ (0.614 g, 4.44 mmol) were stirred in DMSO (4 mL) at rt overnight. The reaction was diluted with EtOAc, washed with H$_2$O (3×), dried (MgSO$_4$) and concentrated. Purification by flash chromatography provided the title compound of step A (0.196 g, 0.660 mmol, 76%). $^1$H NMR (400 MHz, DMSO-d$_6$) δ ppm 2.12-2.24 (m, 3H), 2.68 (d, J=11.4 Hz, 1H), 2.78-2.84 (m, 1H), 2.96 (td, J=12.3, 3.3 Hz, 1H), 3.10-3.18 (m, 1H), 3.52 (td, J=11.5, 2.4 Hz, 1H), 3.75 (dd, J=11.0, 2.9 Hz, 3H), 3.82-3.88 (m, 1H), 3.89 (s, 3H), 3.97 (d, J=13.9 Hz, 1H), 6.52 (d, J=2.6 Hz, 1H), 6.59 (dd, J=9.2, 2.6 Hz, 1H), 7.87 (d, J=9.5 Hz, 1H).

Step B: 4-[(9aS)-hexahydropyrazino[2,1-c][1,4]oxazin-8(1H)-yl]-2-(methyloxy)aniline

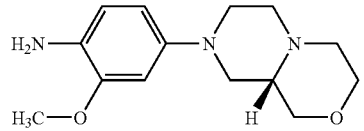

To (9aS)-8-[3-(methyloxy)-4-nitrophenyl]octahydropyrazino[2,1-c][1,4]oxazine (0.196 g, 0.660 mmol) in dioxane (8 mL) and THF (4 mL) cooled to 0° C. was added tin(II) chloride (0.544 g, 2.86 mmol) in HCl (2.20 mL, 37% in water, 24.6 mmol) dropwise. The reaction warmed to rt and stirred overnight. An additional amount of tin(II) chloride (1.00 g, 5.27 mmol) in HCl (4.40 mL, 37% in H$_2$O, 49.1 mmol) was added to the reaction. When complete by TLC, the reaction was cooled to 0° C. and quenched with 6N NaOH (50 mL). The mixture was poured into H$_2$O/EtOAc and separated. The organic layer was washed with brine and the resultant aqueous layer was back extracted with EtOAc. The combined organic layer was dried (MgSO$_4$) and concentrated to provide the title compound of step B (0.170 g, 0.640 mmol, 98%). $^1$H NMR (400 MHz, DMSO-d$_6$) b ppm 1.47 (dt, J=14.9, 6.5 Hz, 1H), 1.65-1.74 (m, 1H), 2.14-2.25 (m, 1H), 2.26-2.31 (m, 1H), 2.55-2.66 (m, 1H), 2.74 (d, J=10.8 Hz, 1H), 3.10 (t, J=10.4 Hz, 1H), 3.17 (d, J=11.5 Hz, 1H), 3.31 (d, J=11.7 Hz, 1H), 3.37 (q, J=6.2 Hz, 1H), 3.47 (td, J=11.3, 2.1 Hz, 1H), 3.60 (t, J=6.7 Hz, 1H), 3.63-3.74 (m, 4H), 4.41 (t, J=5.3 Hz, 1H), 4.46 (s, 1H), 6.23 (dd, J=8.3, 2.5 Hz, 1H), 6.42-6.50 (m, 2H).

Step C: N-(2,6-difluorophenyl)-3-[3-(2-{[4-[(9aS)-hexahydropyrazino[2,1-c][1,4]oxazin-8(1H)-yl]-2-(methyloxy)phenyl]amino}-4-pyrimidinyl)imidazo[1,2-a]pyridin-2-yl]benzamide The title compound (0.092 g, 0.13 mmol, 40%) was prepared in an analogous manner to that described for Example 36, step E with the following notable exception: 4-[(9aS)-hexahydropyrazino[2,1-c][1,4]oxazin-8(1H)-yl]-2-(methyloxy)aniline was used instead of 2-(methyloxy)-4-[4-(1-piperidinyl-methyl)-1-piperidinyl]aniline. $^1$H NMR (400 MHz, DMSO-d$_6$) δ ppm 2.21-2.31 (m, 4H), 2.67 (d, J=11.0 Hz, 1H), 2.75 (t, J=11.7 Hz, 1H), 2.81 (d, J=11.0 Hz, 1H), 3.11-3.21 (m, 1H), 3.46-3.57 (m, 2H), 3.64 (d, J=11.4 Hz, 1H), 3.71-3.78 (m, 2H), 3.79 (s, 3H), 6.42-6.51 (m, 2H), 6.67 (d, J=2.2 Hz, 1H), 6.94-7.02 (m, 1H), 7.20 (t, J=8.3 Hz, 2H), 7.38-7.49 (m, 3H), 7.60 (t, J=7.7 Hz, 1H), 7.72 (d, J=9.2 Hz, 1H), 7.81 (d, J=7.3 Hz, 1H), 8.05 (d, J=8.4 Hz, 1H), 8.20 (d, J=5.5 Hz, 1H), 8.33 (s, 1H), 8.45 (s, 1H), 9.39 (br. s., 1H), 10.23 (s, 1H). MS (M+H, ES+) 689.

Example 124

N-(2,6-difluorophenyl)-5-[3-(2-{[4-[(9aS)-hexahydropyrazino[2,1-c][1,4]oxazin-8(1H)-yl]-2-(methyloxy)phenyl]amino}-4-pyrimidinyl)imidazo[1,2-a]pyridin-2-yl]-2-(methyloxy)-benzamide

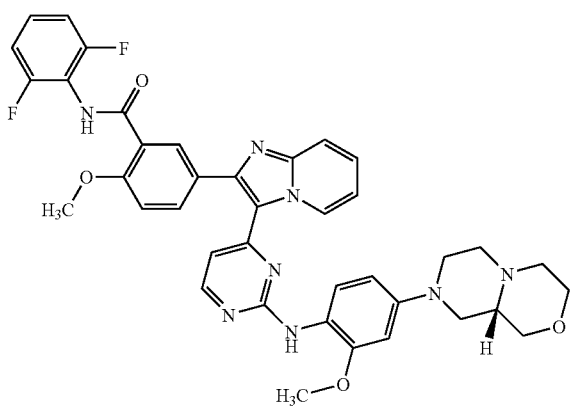

The title compound (0.11 g, 0.15 mmol, 46%) was prepared in an analogous manner to that described for Example 123, step C with the following notable exception: 5-[3-(2-chloro-4-pyrimidinyl)-imidazo[1,2-a]pyridin-2-yl]-N-(2,6-difluorophenyl)-2-(methyloxy)benzamide (Intermediate Example 2) was used instead of Intermediate Example 1. $^1$H NMR (400 MHz, DMSO-d$_6$) δ ppm 2.20-2.31 (m, 4H), 2.67 (d, J=10.6 Hz, 1H), 2.71-2.83 (m, 2H), 3.16 (t, J=10.5 Hz, 1H), 3.46-3.57 (m, 2H), 3.64 (d, J=10.3 Hz, 1H), 3.70-3.79 (m, 2H), 3.79 (s, 3H), 3.98 (s, 3H), 6.44-6.51 (m, 1H), 6.53 (d, J=5.5 Hz, 1H), 6.67 (d, J=2.6 Hz, 1H), 6.94 (t, J=7.5 Hz, 1H), 7.18 (t, J=8.1 Hz, 2H), 7.28 (d, J=8.8 Hz, 1H), 7.34-7.46 (m, 3H), 7.69 (d, J=9.2 Hz, 1H), 7.77 (dd, J=8.8, 2.2 Hz, 1H), 8.10 (d, J=1.8 Hz, 1H), 8.20 (d, J=5.1 Hz, 1H), 8.44 (s, 1H), 9.36 (br. s., 1H), 9.78 (s, 1H). MS (M+H, ES+) 719.

Example 125

N-(2,6-difluorophenyl)-3-{3-[2-({2-(methyloxy)-4-[4-(methyloxy)-1-piperidinyl]phenyl}-amino)-4-pyrimidinyl]imidazo[1,2-a]pyridin-2-yl}benzamide

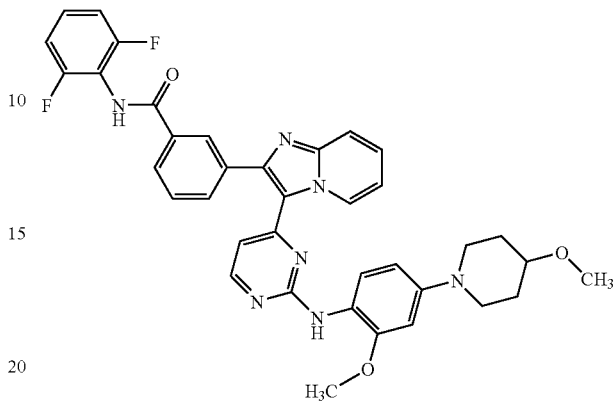

The title compound (0.041 g, 0.062 mmol, 29% in final step) was prepared in an analogous manner to that described for Example 22 with the following notable exceptions:
a) 4-(methyloxy)piperidine was used instead of 1,4'-bipiperidine in the procedure described in Example 22, step B;
b) p-toluenesulfonic acid in iPrOH under microwave conditions at 170° C. were used rather than concentrated HCl in trifluoroethanol at 85° C. in the procedure described in Example 22, step D.

$^1$H NMR (400 MHz, DMSO-d$_6$) δ 10.23 (s, 1H), 9.43-9.36 (m, 1H), 8.45 (s, 1H), 8.34-8.32 (m, 1H), 8.19 (d, J=5.5 Hz, 1H), 8.07-8.03 (m, 1H), 7.82-7.79 (m, 1H), 7.74-7.70 (m, 1H), 7.60 (at, J=7.7 Hz, 1H), 7.48-7.35 (m, 3H), 7.24-7.16 (m, 2H), 7.00-6.94 (m, 1H), 6.67 (d, J=2.6 Hz, 1H), 6.50-6.43 (m, 2H), 3.79 (s, 3H), 3.52-3.46 (m, 2H), 3.26 (s, 3H), 2.91-2.84 (m, 2H), 1.97-1.91 (m, 2H), 1.57-1.49 (m, 2H). MS (APCI+, m/z) 662 (M+1).

Example 126

N-(2,6-difluorophenyl)-2-(methyloxy)-5-{3-[2-({2-(methyloxy)-4-[4-(methyloxy)-1-piperidinyl]phenyl}amino)-4-pyrimidinyl]imidazo[1,2-a]pyridin-2-yl}benzamide

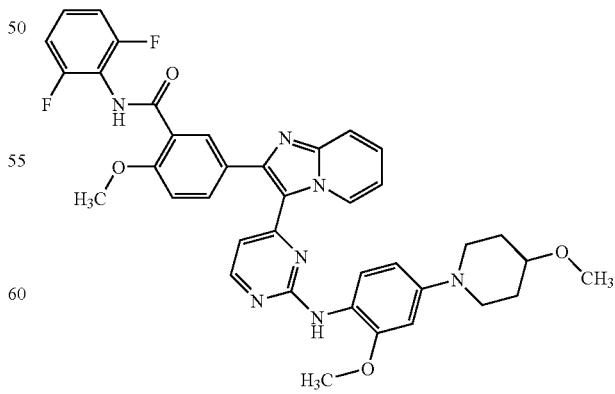

The title compound (0.045 g, 0.065 mmol, 32% in final step) was prepared in an analogous manner to that described for Example 125 with the following notable exceptions: 5-[3-(2-chloro-4-pyrimidinyl)-imidazo[1,2-a]pyridin-2-yl]-N-(2,6-difluorophenyl)-2-(methyloxy)benzamide (Intermediate Example 2) was used instead of Intermediate Example 1 in the final step. $^1$H NMR (400 MHz, DMSO-d$_6$) δ 9.78 (s, 1H), 9.39-9.32 (m, 1H), 8.43 (s, 1H), 8.19 (d, J=5.1 Hz, 1H), 8.11-8.08 (m, 1H), 7.80-7.75 (m, 1H), 7.71-7.67 (m, 1H), 7.46-7.35 (m, 3H), 7.30-7.25 (m, 1H), 7.21-7.15 (m, 2H), 6.97-6.90 (m, 1H), 6.69-6.66 (m, 1H), 6.55-6.46 (m, 2H), 3.98 (bs, 3H), 3.79 (s, 3H), 3.53-3.44 (m, 2H), 3.26 (s, 3H), 2.92-2.84 (m, 2H), 1.97-1.90 (m, 2H), 1.58-1.47 (m, 2H). MS (APCI+, m/z) 692 (M+1).

Example 127

N-(2,6-difluorophenyl)-5-{3-[2-({5-fluoro-2-(methyloxy)-4-[2-(1-piperidinyl)ethyl]phenyl}-amino)-4-pyrimidinyl]imidazo[1,2-a]pyridin-2-yl}-2-(methyloxy)benzamide

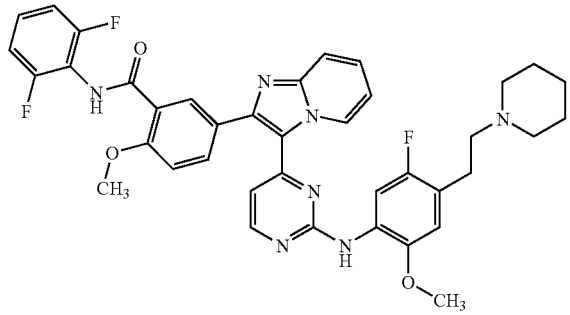

Step A: 5-bromo-4-fluoro-2-nitrophenyl methyl ether

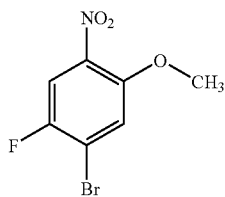

To 1-bromo-2,5-difluoro-4-nitrobenzene (5.0 g, 21 mmol) was added 0.5 N sodium methoxide (50 mL, 25 mmol). The mixture was stirred at 60° C. for 1 h. The MeOH was rotovaped down. The crude product was dissolved in DCM (100 mL), washed with H$_2$O, dried (Na$_2$SO$_4$), filtered, and rotovaped down to give the title compound of step A (5 g, 20 mmol, 95%) as a yellow solid. $^1$H NMR (400 MHz, CDCl$_3$) δ ppm 7.69 (s, 1H), 7.28 (s, 1H), 3.95 (s, 3H).

Step B: 5-ethenyl-4-fluoro-2-nitrophenyl methyl ether

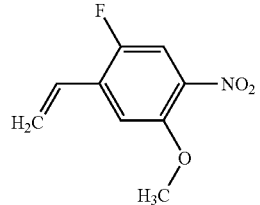

To 5-bromo-4-fluoro-2-nitrophenyl methyl ether (4.0 g, 16 mmol) in 40 mL of n-propanol was added, PdCl$_2$(dppf)*DCM (0.234 g, 0.31 mmol), potassium ethenyl(trifluoro)borate (2.57 g, 19.2 mmol), and TEA (1.62 g, 16 mmol). The mixture was heated to 100° C. for 3 h. The mixture was poured into 250 mL of H$_2$O and extracted with DCM, dried (Na$_2$SO$_4$), filtered, and rotovaped down to give the title compound of step B (2.73 g, 13.84 mmol, 86%). $^1$H NMR (400 MHz, CDCl$_3$) δ ppm 7.64 (d, J=9.52 Hz, 1H), 7.11 (d, J=6.04 Hz, 1H), 6.84 (dd, J=17.76, 11.17 Hz, 1H), 5.95 (d, J=17.76 Hz, 1H), 5.59 (d, J=11.17 Hz, 1H), 3.97 (s, 3H).

Step C: 1-{2-[2-fluoro-5-(methyloxy)-4-nitrophenyl]ethyl}piperidine

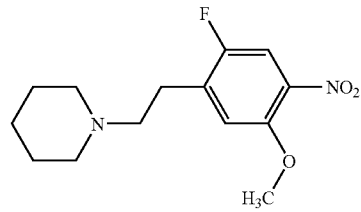

To 5-ethenyl-4-fluoro-2-nitrophenyl methyl ether (1.0 g, 5.1 mmol) in 10 mL of iPrOH was added, piperidine (1.3 g, 15.2 mmol). The mixture was heated to 180° C. 17 min in the microwave. The solvent was rotovaped down and the crude product was purified by flash chromatography to give the title compound of step C (0.81 g, 2.87 mmol, 57%). $^1$H NMR (400 MHz, CDCl$_3$) δ ppm 7.59 (d, J=8.97 Hz, 1H), 7.01 (d, J=5.86 Hz, 1H), 3.92 (s, 3H), 2.82-2.88 (m, 2H), 2.53-2.58 (m, 2H), 2.40-2.48 (m, 4H), 1.55-1.61 (m, J=5.49, 5.49, 5.49, 5.49 Hz, 4H), 1.40-1.47 (m, 2H).

Step D: 5-fluoro-2-(methyloxy)-4-[2-(1-piperidinyl)ethyl]aniline

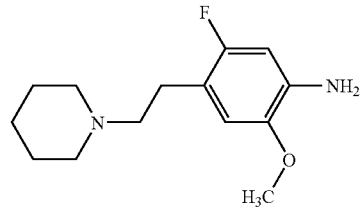

1-{2-[2-fluoro-5-(methyloxy)-4-nitrophenyl]ethyl}piperidine (0.81 g, 2.87 mmol) was placed in a 100 mL high pressure vessel and dissolved in 30 mL of EtOAc. 5 wt % Platinum(sulfided)/carbon (0.559 g, 0.143 mmol) was added followed quickly by a rubber septum. The flask was evacuated and filled with N$_2$ six times to remove oxygen. The vessel was then pressurized with H$_2$ (50 psi). The solution stirred overnight. The next morning the vessel was evacuated and filled with N₂ six times to remove H₂. The solution was filtered through celite and evaporated to afford the title compound of step D (0.586 g, 2.32 mmol, 81%). ¹H NMR (400 MHz, CD₃OD) δ ppm 6.72 (d, J=6.96 Hz, 1H), 6.46 (d, J=11.35 Hz, 1H), 3.81 (s, 3H), 3.21-3.27 (m, 2H), 3.13-3.21 (m, 4H), 2.93-2.99 (m, 2H), 1.82-1.89 (m, 4H), 1.62-1.71 (m, 2H).

Step E: N-(2,6-difluorophenyl)-5-{3-[2-({5-fluoro-2-(methyloxy)-4-[2-(1-piperidinyl)ethyl]-phenyl}amino)-4-pyrimidinyl]imidazo[1,2-a]pyridin-2-yl}-2-(methyloxy)benzamide 5-[3-(2-Chloro-4-pyrimidinyl)imidazo[1,2-a]pyridin-2-yl]-N-(2,6-difluorophenyl)-2-(methyloxy)benzamide (Intermediate Example 2) (100 mg, 0.2 mmol), 5-fluoro-2-(methyloxy)-4-[2-(1-piperidinyl)ethyl]aniline (46 mg, 0.18 mmol), and p-toluenesulfonic acid (92 mg, 0.49 mmol) were weighed into a 10 mL microwave vial. 5 mL of iPrOH was added and the mixture was heated in the microwave to 180° C. for 17 min. The mixture was transferred to a 50 mL round bottom and diluted with 10 mL of DCM. 1 g of silica gel was added. The solvent was rotovaped down and the pre-adsorbed solids were purified by flash chromatography, followed by MeOH re-crystallization to give the title compound (54 mg, 0.076 mmol, 37%). ¹H NMR (400 MHz, DMSO-d₆) δ ppm 9.76 (s, 1H), 9.42 (d, J=6.96 Hz, 1H), 8.50 (s, 1H), 8.30-8.34 (m, 1H), 8.11 (s, 1H), 7.80-7.86 (m, 1H), 7.77 (d, J=8.06 Hz, 1H), 7.71 (d, J=9.16 Hz, 1H), 7.43-7.48 (m, 1H), 7.32-7.40 (m, 1H), 7.26 (d, J=8.61 Hz, 1H), 7.16 (t, J=8.06 Hz, 2H), 7.00 (t, J=6.23 Hz, 2H), 6.67 (d, J=4.94 Hz, 1H), 3.97 (s, 3H), 3.82 (s, 3H), 3.26-3.27 (m, 2H), 2.70 (t, J=7.33 Hz, 2H), 2.34-2.42 (m, 4H), 1.43-1.50 (m, J=4.76 Hz, 4H), 1.32-1.39 (m, 2H). MS (ESI): 708 [M+H]⁺.

Example 128

N-(2,6-difluorophenyl)-3-{3-[2-({5-fluoro-2-(methyloxy)-4-[2-(1-piperidinyl)ethyl]phenyl}-amino)-4-pyrimidinyl]imidazo[1,2-a]pyridin-2-yl}benzamide

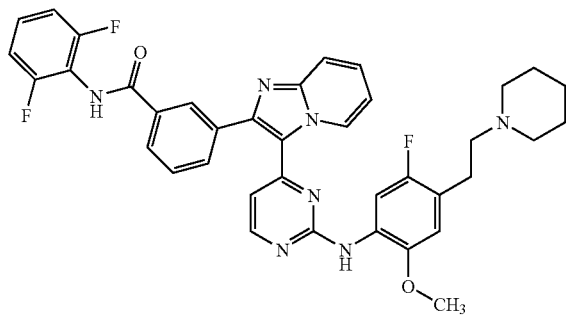

Step A: methyl 3-{3-[2-({5-fluoro-2-(methyloxy)-4-[2-(1-piperidinyl)ethyl]phenyl}amino)-4-pyrimidinyl]imidazo[1,2-a]pyridin-2-yl}benzoate

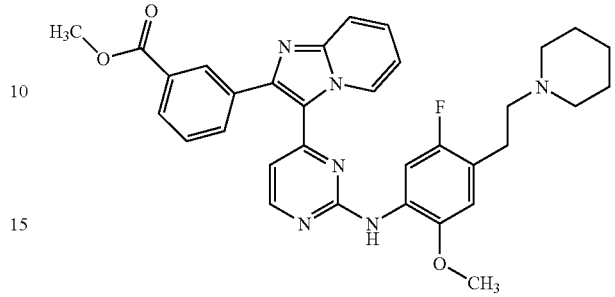

Methyl 3-[3-(2-chloro-4-pyrimidinyl)imidazo[1,2-a]pyridin-2-yl]benzoate (Intermediate Example 3) (300 mg, 0.82 mmol), 5-fluoro-2-(methyloxy)-4-[2-(1-piperidinyl)ethyl]aniline (Example 127, step D) (187 mg, 0.74 mmol), and p-toluenesulfonic acid (375 mg, 1.97 mmol) were weighed into a 10 mL microwave vial. 7 mL of iPrOH was added and the mixture was heated in the microwave to 180° C. for 17 min. The mixture was transferred to a 50 mL round bottom and diluted with 10 mL of DCM. 2 g of silica gel was added. The solvent was rotovaped down and the residue purified by flash chromatography to give the title compound of step A (220 mg, 0.38 mmol, 46%). ¹H NMR (400 MHz, CDCl₃) δ ppm 9.51 (d, J=6.97 Hz, 1H), 8.37-8.39 (m, 1H), 8.23-8.30 (m, 2H), 8.08-8.11 (m, 1H), 7.84-7.87 (m, 1H), 7.79 (s, 1H), 7.74 (d, J=8.80 Hz, 1H), 7.50 (t, J=7.70 Hz, 1H), 7.35-7.41 (m, 1H), 6.95 (t, J=6.97 Hz, 1H), 6.76 (d, J=6.97 Hz, 1H), 6.60 (d, J=5.50 Hz, 1H), 3.91 (s, 3H), 3.90 (s, 3H), 2.79-2.86 (m, 2H), 2.54-2.60 (m, 2H), 2.46-2.54 (m, 4H), 1.60-1.66 (m, J=5.68, 5.68, 5.68, 5.68 Hz, 4H), 1.43-1.50 (m, J=5.13 Hz, 2H).

Step B: N-(2,6-difluorophenyl)-3-{3-[2-({5-fluoro-2-(methyloxy)-4-[2-(1-piperidinyl)ethyl]phenyl}amino)-4-pyrimidinyl]imidazo[1,2-a]pyridin-2-yl}benzamide To 2,6-difluoroaniline (133 mg, 1 mmol) was added 1N NaHMDS in THF (1 mL, 1 mmol). The mixture stirred for 15 min at rt. Methyl 3-{3-[2-({5-fluoro-2-(methyloxy)-4-[2-(1-piperidinyl)ethyl]phenyl}amino)-4-pyrimidinyl]imidazo[1,2-a]pyridin-2-yl}benzoate (120 mg, 0.206 mmol) in 3 mL of dry THF was added. The mixture stirred at rt for 30 min. 1 mL of MeOH was added followed by 1 g of silica gel. The solvent was rotovaped down and the pre-adsorbed solids were purified by flash chromatography to give the title compound (52 mg, 0.0767 mmol, 37%). ¹H NMR (400 MHz, CDCl₃) δ ppm 9.46 (d, J=7.33 Hz, 1H), 8.21-8.29 (m, 3H), 8.11 (s, 1H), 8.02 (d, J=7.70 Hz, 1H), 7.74-7.83 (m, 2H), 7.66 (d, J=8.80 Hz, 1H), 7.47-7.56 (m, 1H), 7.32-7.40 (m, 1H), 7.22 (dd, J=8.43, 5.87 Hz, 1H), 6.91-7.01 (m, 3H), 6.76 (d, J=6.60 Hz, 1H), 6.63 (dd, J=5.32, 3.12 Hz, 1H), 3.92 (s, 3H), 2.79-2.87 (m, 2H), 2.54-2.61 (m, 2H), 2.45-2.54 (m, 4H), 1.59-1.68 (m, 4H), 1.42-1.52 (m, 2H). MS (ESI): 678 [M+H]⁺.

Example 129

3-{3-[2-({5-fluoro-2-(methyloxy)-4-[2-(1-piperidi-nyl)ethyl]phenyl}amino)-4-pyrimidinyl]imidazo[1,2-a]pyridin-2-yl}-N-(2,4,6-trifluorophenyl)benzamide

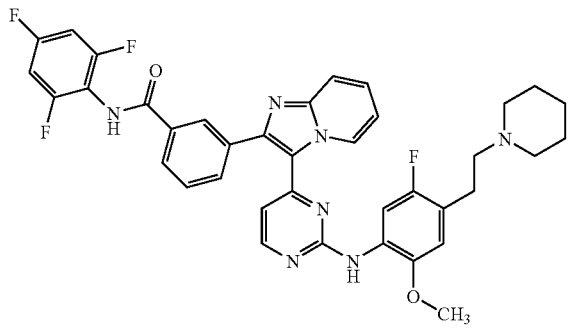

To 2,4,6-trifluoroaniline (127 mg, 1 mmol) was added 1N NaHMDS in THF (0.9 mL, 0.9 mmol). The mixture stirred for 15 min at rt. Methyl 3-{3-[2-({5-fluoro-2-(methyloxy)-4-[2-(1-piperidinyl)ethyl]phenyl}amino)-4-pyrimidinyl]imidazo[1,2-a]pyridin-2-yl}benzoate (Example 128, step A) (100 mg, 0.172 mmol) in 3 mL of dry THF was added. The mixture stirred at rt for 30 minutes. 1 mL of MeOH was added followed by 1 g of silica gel. The solvent was rotovaped down and the pre-adsorbed solids were purified by flash chromatography to give the title compound (74 mg, 0.11 mmol, 62%). $^1$H NMR (400 MHz, CDCl$_3$) δ ppm 9.44 (d, J=6.96 Hz, 1H), 8.20-8.26 (m, 4H), 7.99 (dt, J=7.83, 1.40 Hz, 1H), 7.74-7.78 (m, 2H), 7.62 (d, J=8.97 Hz, 1H), 7.48 (t, J=7.78 Hz, 1H), 7.31-7.36 (m, 1H), 6.91 (td, J=6.87, 1.28 Hz, 1H), 6.72-6.78 (m, 3H), 6.60 (d, J=5.13 Hz, 1H), 3.90 (s, 3H), 2.78-2.84 (m, 2H), 2.53-2.58 (m, 2H), 2.44-2.53 (m, 4H), 1.58-1.65 (m, J=5.59, 5.59, 5.59, 5.59 Hz, 4H), 1.46 (d, J=5.13 Hz, 2H). MS (ESI): 696 [M+H]$^+$.

Example 130

N-(2,6-difluorophenyl)-5-{3-[2-({5-fluoro-2-(methyloxy)-4-[2-(4-morpholinyl)ethyl]phenyl}-amino)-4-pyrimidinyl]imidazo[1,2-a]pyridin-2-yl}-2-(methyloxy)benzamide

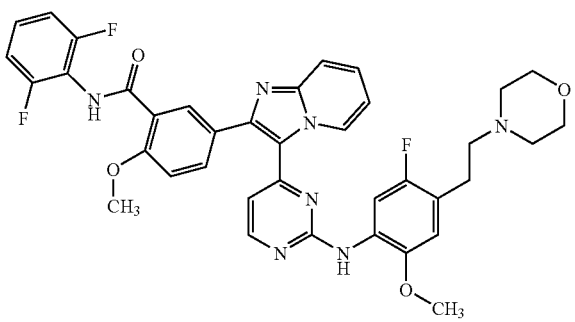

Step A: 4-{2-[2-fluoro-5-(methyloxy)-4-nitrophenyl]ethyl}morpholine

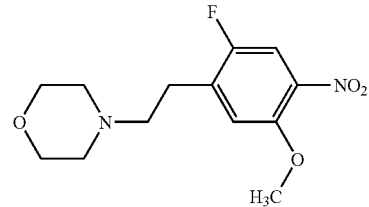

To 5-ethenyl-4-fluoro-2-nitrophenyl methyl ether (0.43 g, 2.2 mmol) in 10 mL of iPrOH was added, morpholine (0.56 g, 6.54 mmol). The mixture was heated to 180° C. 1.5 h in the microwave. The solvent was rotovaped down and the residue purified by flash chromatography to give the title compound of step A (0.4 g, 1.41 mmol, 64%). $^1$H NMR (400 MHz, CDCl$_3$) δ ppm 7.62 (d, J=8.80 Hz, 1H), 6.99 (d, J=6.23 Hz, 1H), 3.94 (s, 3H), 3.70-3.75 (m, 4H), 2.87 (t, J=7.33 Hz, 2H), 2.58-2.66 (m, 2H), 2.49-2.56 (m, 4H).

Step B: 5-fluoro-2-(methyloxy)-4-[2-(4-morpholinyl)ethyl]aniline

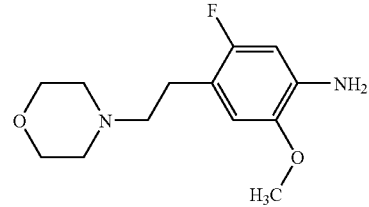

4-{2-[2-fluoro-5-(methyloxy)-4-nitrophenyl]ethyl}morpholine (0.4 g, 1.4 mmol) was placed in a 100 mL high pressure vessel and dissolved in 30 mL of EtOAc. 5 wt % Platinum(sulfided)/carbon (0.274 g, 0.07 mmol) was added followed quickly by a rubber septum. The flask was evacuated and filled with N$_2$ six times to remove any oxygen. The vessel was then pressurized with H$_2$ (50 psi). The solution stirred overnight. The next morning the vessel was evacuated and filled with N$_2$ six times to remove any hydrogen. The solution was filtered through celite and evaporated to give the title compound of step B (0.2 g, 0.79, 56%). $^1$H NMR (400 MHz, DMSO-d$_6$) δ ppm 6.69 (d, J=6.97 Hz, 1H), 6.40 (d, J=11.36 Hz, 1H), 4.97 (bs, 2H), 3.86-3.98 (m, 2H), 3.78-3.86 (m, 2H), 3.72 (s, 3H), 3.38-3.49 (m, 2H), 3.10-3.21 (m, 2H), 2.99-3.10 (m, 2H), 2.86-2.97 (m, 2H).

Step C: N-(2,6-difluorophenyl)-5-{3-[2-({5-fluoro-2-(methyloxy)-4-[2-(4-morpholinyl)ethyl]phenyl}amino)-4-pyrimidinyl]imidazo[1,2-a]pyridin-2-yl}-2-(methyloxy)benzamide 5-[3-(2-chloro-4-pyrimidinyl)imidazo[1,2-a]pyridin-2-yl]-N-(2,6-difluorophenyl)-2-(methyloxy)benzamide (Intermediate Example 2) (100 mg, 0.2 mmol), 5-fluoro-2-(methyloxy)-4-[2-(4-morpholinyl)ethyl]aniline (46 mg, 0.18 mmol), and p-toluenesulfonic acid (92 mg, 0.49 mmol) were weighed into a 10 mL microwave vial. 5 mL of iPrOH was added and the mixture was heated in the microwave to 180° C. for 17 min. The mixture was transferred to a 50 mL round bottom and neutralized with 1 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography, followed by MeOH re-crystallization to give the title compound (61 mg, 0.086 mmol, 47%). $^1$H NMR (400 MHz, CDCl$_3$) δ ppm 9.51 (d, J=6.97 Hz, 1H), 9.28 (s, 1H), 8.61 (d, J=2.20 Hz, 1H), 8.24-8.32 (m, 2H), 7.88 (dd, J=8.62, 2.38 Hz, 1H), 7.78 (s, 1H), 7.71 (d, J=8.80 Hz, 1H), 7.32-7.39 (m, 1H), 7.16-7.23 (m, 1H), 7.14 (d, J=8.80 Hz, 1H), 6.90-7.00 (m, 3H), 6.74 (d, J=6.60 Hz, 1H), 6.69 (d, J=5.13 Hz, 1H), 4.12 (s, 3H), 3.91 (s, 3H), 3.73-3.80 (m, 4H), 2.78-2.86 (m, 2H), 2.58-2.65 (m, 2H), 2.52-2.58 (m, 4H). MS (ESI): 710 [M+H]$^+$.

Example 131

N-(2,6-difluorophenyl)-2-(methyloxy)-5-{3-[2-({2-(methyloxy)-4-[2-(4-methyl-1-piperazinyl)ethyl]phenyl}amino)-4-pyrimidinyl]imidazo[1,2-a]pyridin-2-yl}benzamide

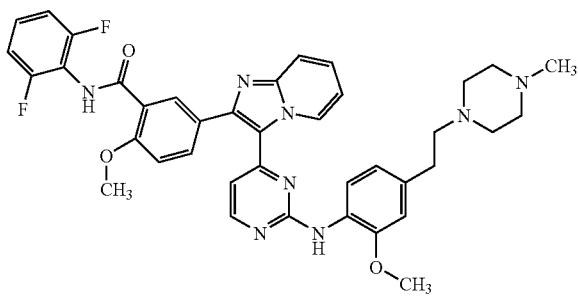

Step A: 5-bromo-2-nitrophenyl methyl ether

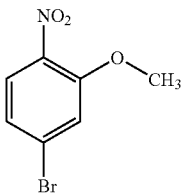

To 4-bromo-2-fluoro-1-nitrobenzene (8.0 g, 36.4 mmol) was added 0.5 N sodium methoxide (105 mL, 52.5 mmol). The mixture was stirred at 60° C. for 1 h. The MeOH was rotovaped down. The crude product was dissolved in DCM (100 mL), washed with H$_2$O, dried (Na$_2$SO$_4$), filtered, and rotovaped down to give the title compound of step A (8.1 g, 34.9 mmol, 96%) as a yellow solid. $^1$H NMR (400 MHz, CDCl$_3$) δ ppm 7.74 (d, J=8.61 Hz, 1H), 7.23 (d, J=2.01 Hz, 1H), 7.16 (dd, J=8.61, 1.83 Hz, 1H), 3.95 (s, 3H).

Step B: 5-ethenyl-2-nitrophenyl methyl ether

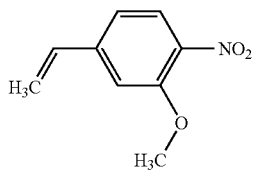

To 5-bromo-2-nitrophenyl methyl ether (8.0 g, 34.47 mmol) in 80 mL of n-propanol was added, PdCl$_2$(dppf)*DCM (0.5 g, 0.69 mmol), potassium ethenyl(trifluoro)borate (6.47 g, 48.3 mmol), and TEA (3.48 g, 34.47 mmol). The mixture was heated to 100° C. for 3 h. The mixture was poured into 250 mL of H$_2$O and extracted with DCM, dried (Na$_2$SO$_4$), filtered, and rotovaped down, and purified by flash chromatography to give the title compound of step B (3.58 g, 19.98 mmol, 58%). $^1$H NMR (400 MHz, CDCl$_3$) δ ppm 7.82-7.87 (m, 1H), 7.02-7.07 (m, 2H), 6.70 (dd, J=17.58, 10.80 Hz, 1H), 5.87 (d, J=17.58 Hz, 1H), 5.46 (d, J=10.99 Hz, 1H), 3.97 (s, 3H).

Step C: 1-methyl-4-{2-[3-(methyloxy)-4-nitrophenyl]ethyl}piperazine

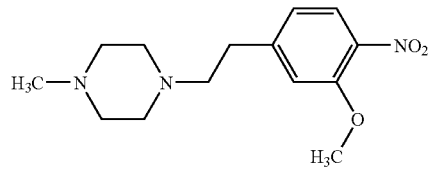

To 5-ethenyl-2-nitrophenyl methyl ether (0.55 g, 3.1 mmol) in 10 mL of iPrOH was added, 1-methylpiperazine (0.614 g, 6.13 mmol), and catalytic hydroquinone (0.033 g, 0.31 mmol). The mixture was heated to 90° C. for 18 h. The solvent was rotovaped down and the crude product was purified by flash chromatography to give the title compound of step C (0.6 g, 2.15 mmol, 70%). $^1$H NMR (400 MHz, CDCl$_3$) δ ppm 7.79 (d, J=8.24 Hz, 1H), 6.93 (s, 1H), 6.84 (dd, J=8.33, 1.19 Hz, 1H), 3.93 (s, 3H), 2.79-2.89 (m, 2H), 2.40-2.69 (m, 10H), 2.29 (s, 3H).

Step D: 2-(methyloxy)-4-[2-(4-methyl-1-piperazinyl)ethyl]aniline

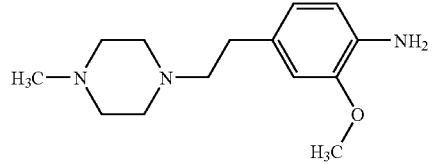

1-Methyl-4-{2-[3-(methyloxy)-4-nitrophenyl]ethyl}piperazine (0.6 g, 2.15 mmol) was placed in a 100 mL high pressure vessel and dissolved in 30 mL of 1 to 1 EtOAc/MeOH. 5 wt % Platinum(sulfided)/carbon (0.42 g, 0.107 mmol) was added followed quickly by a rubber septum. The flask was evacuated and filled with N$_2$ six times to remove any oxygen. The vessel was then pressurized with H$_2$ (50 psi). The solution stirred overnight. The next morning the vessel was evacuated and filled with N$_2$ six times to remove any H$_2$. The solution was filtered through celite and evaporated to afford the title compound of step D (0.460 g, 1.84 mmol, 86%). $^1$H NMR (400 MHz, CDCl$_3$) δ ppm 6.60-6.64 (m, 3H), 3.82 (s, 3H), 3.64 (bs, 2H), 2.64-2.73 (m, 2H), 2.38-2.63 (m, 10H), 2.29 (s, 3H).

Step E: N-(2,6-difluorophenyl)-2-(methyloxy)-5-{3-[2-({2-(methyloxy)-4-[2-(4-methyl-1-piperazinyl)ethyl]phenyl}amino)-4-pyrimidinyl]imidazo[1,2-a]pyridin-2-yl}benzamide 5-[3-(2-Chloro-4-pyrimidinyl)imidazo[1,2-a]pyridin-2-yl]-N-(2,6-difluorophenyl)-2-(methyloxy)benzamide (Intermediate Example 2) (100 mg, 0.2 mmol), 2-(methyloxy)-4-[2-(4-methyl-1-piperazinyl)ethyl]aniline (46 mg, 0.18 mmol), and p-toluenesulfonic acid (93 mg, 0.49 mmol) were weighed into a 10 mL microwave vial. 5 mL of iPrOH was added and the mixture was heated in the microwave to 180° C. for 17 min. The mixture was transferred to a 50 mL round bottom and neutralized with 1 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (97 mg, 0.138 mmol, 68%). $^1$H NMR (400 MHz, CDCl$_3$) δ ppm 9.52 (d, J=6.97 Hz, 1H), 9.29 (s, 1H), 8.63 (d, J=2.20 Hz, 1H), 8.30 (d, J=8.80 Hz, 1H), 8.23 (d, J=5.13 Hz, 1H), 7.87 (dd, J=8.43, 2.57 Hz, 1H), 7.66-7.75 (m, 2H), 7.30-7.38 (m, 1H), 7.15-7.23 (m, 1H), 7.13 (d, J=8.80 Hz, 1H), 6.94-7.01 (m, 2H), 6.84-6.90 (m, 1H), 6.78-6.82 (m, 2H), 6.64 (d, J=5.13 Hz, 1H), 4.11 (s, 3H), 3.92 (s, 3H), 2.75-2.86 (m, 2H), 2.43-2.74 (m, 10H), 2.32 (s, 3H). MS (ESI): 705 [M+H]$^+$.

Example 132

N-(2,6-difluorophenyl)-3-{3-[2-({2-(methyloxy)-4-[2-(4-methyl-1-piperazinyl)ethyl]phenyl}amino)-4-pyrimidinyl]imidazo[1,2-a]pyridin-2-yl}benzamide

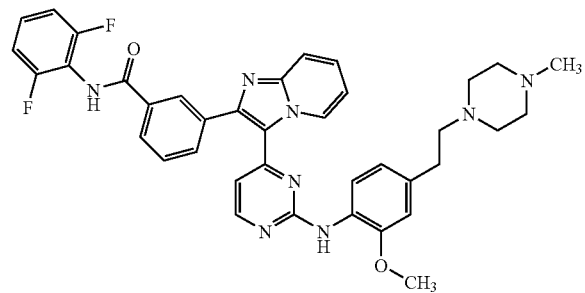

3-[3-(2-Chloro-4-pyrimidinyl)imidazo[1,2-a]pyridin-2-yl]-N-(2,6-difluorophenyl)-benzamide (Intermediate Example 1) (108 mg, 0.23 mmol), 2-(methyloxy)-4-[2-(4-methyl-1-piperazinyl)ethyl]aniline (Example 131, step D) (52 mg, 0.21 mmol), and p-toluenesulfonic acid (107 mg, 0.56 mmol) were weighed into a 10 mL microwave vial. 5 mL of iPrOH was added and the mixture was heated in the microwave to 180° C. for 17 min. The mixture was transferred to a 50 mL round bottom and neutralized with 1 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (61 mg, 0.09 mmol, 37%). $^1$H NMR (400 MHz, CDCl$_3$) δ ppm 9.47 (d, J=6.97 Hz, 1H), 8.27-8.31 (m, 2H), 8.26 (d, J=5.50 Hz, 1H), 7.98-8.06 (m, 2H), 7.81 (d, J=8.07 Hz, 1H), 7.71 (s, 1H), 7.67 (d, J=8.80 Hz, 1H), 7.51 (t, J=7.70 Hz, 1H), 7.32-7.40 (m, 1H), 7.18-7.26 (m, 1H), 6.98 (t, J=8.25 Hz, 2H), 6.89 (t, J=6.78 Hz, 1H), 6.78-6.84 (m, 2H), 6.60 (d, J=5.50 Hz, 1H), 3.93 (s, 3H), 2.76-2.85 (m, 2H), 2.43-2.75 (m, 10H), 2.32 (s, 3H). MS (ESI): 675 [M+H]$^+$.

Example 133

N-(2,6-difluorophenyl)-2-(ethyloxy)-5-{3-[2-({2-(methyloxy)-4-[2-(4-methyl-1-piperazinyl)ethyl]phenyl}amino)-4-pyrimidinyl]imidazo[1,2-a]pyridin-2-yl}benzamide

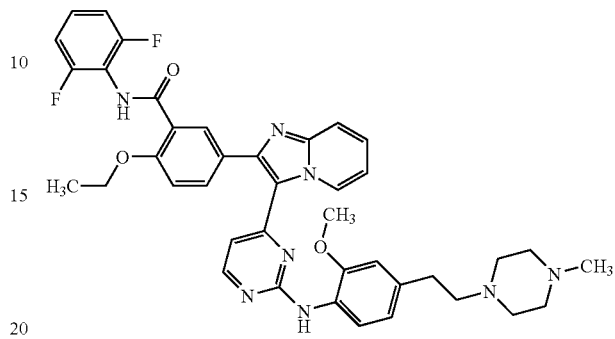

The title compound (0.12 g, 0.17 mmol, 67%) was prepared from 5-[3-(2-chloro-4-pyrimidinyl)imidazo[1,2-a]pyridin-2-yl]-N-(2,6-difluorophenyl)-2-(ethyloxy)benzamide (Intermediate Example 6) and 2-(methyloxy)-4-[2-(4-methyl-1-piperazinyl)ethyl]aniline (Example 131, step D) in an analogous manner to that described for Example 26, step E. $^1$H NMR (400 MHz, DMSO-d$_6$) δ ppm 1.40 (t, J=6.8 Hz, 3H), 2.10 (s, 3H), 2.28 (br. s., 4H), 2.40 (br. s., 3H), 2.49 (d, J=8.4 Hz, 3H), 2.63-2.72 (m, 2H), 3.79 (s, 3H), 4.23 (q, J=6.9 Hz, 2H), 6.57 (d, J=4.9 Hz, 1H), 6.71-6.79 (m, 1H), 6.91-6.99 (m, 2H), 7.16 (t, J=8.1 Hz, 2H), 7.23 (d, J=9.0 Hz, 1H), 7.30-7.37 (m, 1H), 7.37-7.46 (m, 1H), 7.62 (d, J=7.9 Hz, 1H), 7.64-7.74 (m, 2H), 8.02 (s, 1H), 8.23 (d, J=5.3 Hz, 1H), 8.47 (s, 1H), 9.35 (d, J=6.8 Hz, 1H), 9.71 (s, 1H). MS (M+H, ES+) 720.

Example 134

N-(2,6-difluorophenyl)-2-isopropoxy-5-{3-[2-({2-methoxy-4-[2-(4-methylpiperazin-1-yl)ethyl]phenyl}amino)pyrimidin-4-yl]imidazo[1,2-a]pyridin-2-yl}benzamide

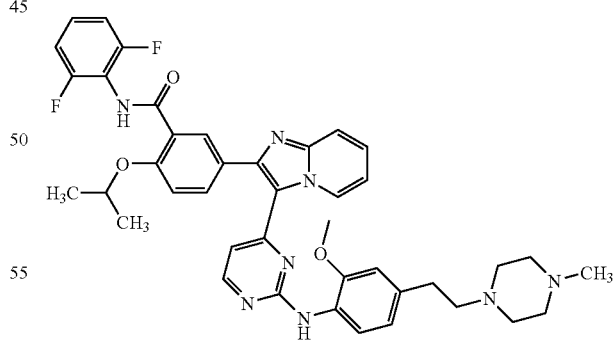

The title compound (0.092 g, 0.12 mmol, 51%) was prepared from 5-[3-(2-chloro-4-pyrimidinyl)imidazo[1,2-a]pyridin-2-yl]-N-(2,6-difluorophenyl)-2-[(1-methylethyl)oxy]benzamide (Intermediate Example 7) and 2-(methyloxy)-4-[2-(4-methyl-1-piperazinyl)ethyl]aniline (Example 131, step D) in an analogous manner to that described for Example 26, step E. $^1$H NMR (400 MHz, DMSO-d$_6$) δ ppm 1.39 (d, J=5.9 Hz, 6H), 2.13 (s, 3H), 2.26-2.35 (m, 3H), 2.38-2.45 (m, 3H), 2.52 (d, J=8.8 Hz, 4H), 2.66-2.75 (m, 2H), 3.82 (s, 3H), 4.82-4.91 (m, 1H), 6.63 (d, J=5.1 Hz, 1H), 6.76 (dd, J=8.3, 1.7 Hz, 1H), 6.92-7.03 (m, 2H), 7.19 (t, J=7.9 Hz, 2H), 7.30 (d, J=8.8 Hz, 1H), 7.34-7.40 (m, 1H), 7.44 (dd, J=8.4, 6.2 Hz, 1H), 7.64 (d, J=8.1 Hz, 1H), 7.67-7.77 (m, 2H), 8.07 (d, J=2.2 Hz, 1H), 8.27 (d, J=5.1 Hz, 1H), 8.49 (s, 1H), 9.36 (d, J=6.2 Hz, 1H), 9.70 (s, 1H). MS (M+H, ES+) 733.

Example 135

N-(2,6-difluorophenyl)-2-(methyloxy)-5-(3-{2-[(2-(methyloxy)-4-{4-[2-(methylsulfonyl)ethyl]-1-piperazinyl}phenyl)amino]-4-pyrimidinyl}imidazo[1,2-a]pyridin-2-yl)benzamide

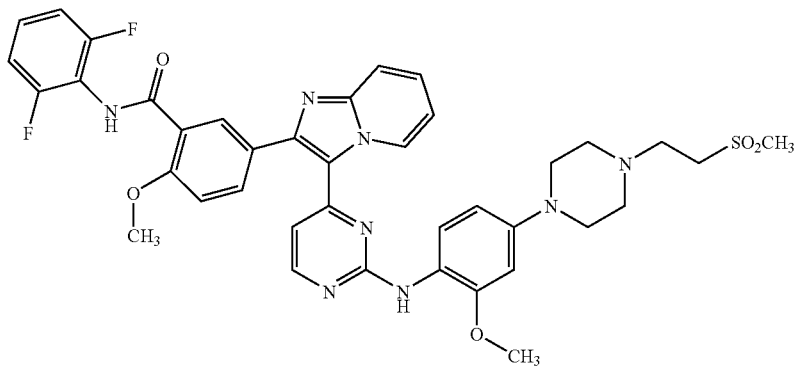

Step A: 1-[3-(methyloxy)-4-nitrophenyl]piperazine

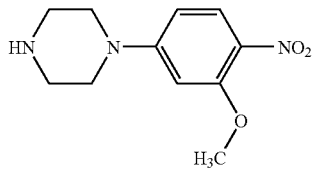

To 5-fluoro-2-nitrophenyl methyl ether (Example 22, step A) (0.8 g, 4.67 mmol) in 10 mL of dioxane was added, piperazine (1.2 g, 14 mmol). The mixture was heated to 120° C. for 2 h. The mixture was purified by flash chromatography to give the title compound of step A (1 g, 4.2 mmol, 90%). $^1$H NMR (400 MHz, DMSO-$d_6$) δ ppm 7.85 (d, J=9.34 Hz, 1H), 6.55 (d, J=2.56 Hz, 1H), 6.52 (s, 1H), 6.46 (d, J=2.56 Hz, 1H), 3.87 (s, 3H), 3.25-3.33 (m, 4H), 2.73-2.79 (m, 4H).

Step B: 1-[3-(methyloxy)-4-nitrophenyl]-4-[2-(methylsulfonyl)ethyl]piperazine

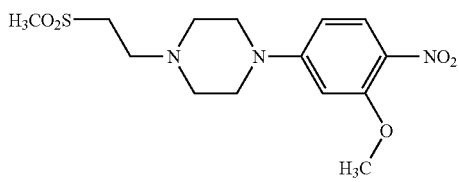

To 1-[3-(methyloxy)-4-nitrophenyl]piperazine (0.4 g, 1.74 mmol) in 10 mL of dioxane was added, methyl vinyl sulfone (0.46 g, 4.34 mmol). The mixture was heated to 120° C. for 1 h. The solvent was rotovaped down and the crude product was purified by flash chromatography to give the title compound of step B (0.55 g, 1.6 mmol, 92%). $^1$H NMR (400 MHz, CDCl$_3$) δ ppm 7.97 (d, J=9.34 Hz, 1H), 6.41 (dd, J=9.34, 2.56 Hz, 1H), 6.31 (d, J=2.38 Hz, 1H), 3.93 (s, 3H), 3.36-3.43 (m, 4H), 3.19 (t, J=6.41 Hz, 2H), 3.03 (s, 3H), 2.92-2.99 (m, 2H), 2.60-2.68 (m, 4H).

Step C: 2-(methyloxy)-4-{4-[2-(methylsulfonyl)ethyl]-1-piperazinyl}aniline

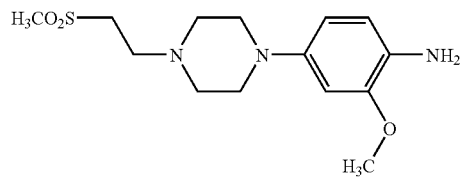

1-[3-(methyloxy)-4-nitrophenyl]-4-[2-(methylsulfonyl)ethyl]piperazine (0.55 g, 1.6 mmol) was placed in a 40 mL high vial and dissolved in 10 mL of 1 to 1 EtOAc/MeOH. 5 wt % Platinum(sulfided)/carbon (0.31 g, 0.08 mmol) was added followed quickly by a screw cap septum. The vial was evacuated and filled with N$_2$ six times to remove any oxygen. The vial was then pressurized with H$_2$ (balloon). The solution stirred overnight. The next morning the vessel was evacuated and filled with N$_2$ six times to remove any H$_2$. The solution was filtered through celite and evaporated to afford the title compound of step C (0.445 g, 1.42 mmol, 89%). $^1$H NMR (400 MHz, CDCl$_3$) δ ppm 6.62 (d, J=8.24 Hz, 1H), 6.47 (d, J=2.56 Hz, 1H), 6.37 (dd, J=8.42, 2.56 Hz, 1H), 3.81 (s, 3H), 3.15 (t, J=6.32 Hz, 2H), 2.98-3.08 (m, 7H), 2.91 (t, J=6.41 Hz, 2H), 2.62-2.70 (m, 4H).

Step D: N-(2,6-difluorophenyl)-2-(methyloxy)-5-(3-{2-[(2-(methyloxy)-4-{4-[2-(methylsulfonyl)ethyl]-1-piperazinyl]phenyl)amino}-4-pyrimidinyl}imidazo[1,2-a]pyridin-2-yl)benzamide 5-[3-(2-Chloro-4-pyrimidinyl)imidazo[1,2-a]pyridin-2-yl]-N-(2,6-difluorophenyl)-2-(methyloxy)benzamide (Intermediate Example 2) (100 mg, 0.2 mmol), 2-(methyloxy)-4-{4-[2-(methylsulfonyl)ethyl]-1-piperazinyl}aniline (57 mg, 0.18 mmol), and p-toluenesulfonic acid (93 mg, 0.49 mmol) were weighed into a 20 mL vial. 7 mL of iPrOH was added and the mixture was heated to 130° C. for 72 h. The mixture was transferred to a 50 mL round bottom and neutralized with 2 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (83 mg, 0.108 mmol, 59%). $^1$H NMR (400 MHz, DMSO-$d_6$) δ ppm 9.77 (s, 1H), 9.35 (s, 1H), 8.44 (s, 1H), 8.19 (d, J=5.31 Hz, 1H), 8.09 (d, J=2.20 Hz, 1H), 7.76 (dd, J=8.52, 2.11 Hz, 1H), 7.68 (d, J=8.97 Hz, 1H), 7.33-7.44 (m, 3H), 7.27 (d, J=8.61 Hz, 1H), 7.17 (t, J=8.06 Hz, 2H), 6.93 (t, J=6.87 Hz, 1H), 6.67 (d, J=2.38 Hz, 1H), 6.51 (d, J=5.31 Hz, 1H), 6.48 (dd, J=8.79, 2.56 Hz, 1H), 3.97 (s, 3H), 3.79 (s, 3H), 3.30-3.35 (m, 2H), 3.11-3.20 (m, 4H), 3.03 (s, 3H), 2.74 (t, J=6.78 Hz, 2H), 2.52-2.62 (m, 4H). MS (ESI): 769 [M+H]$^+$.

Example 136

N-(2,6-difluorophenyl)-3-(3-{2-[(2-(methyloxy)-4-{4-[2-(methylsulfonyl)ethyl]-1-piperazinyl}phenyl)amino]-4-pyrimidinyl}imidazo[1,2-a]pyridin-2-yl)benzamide

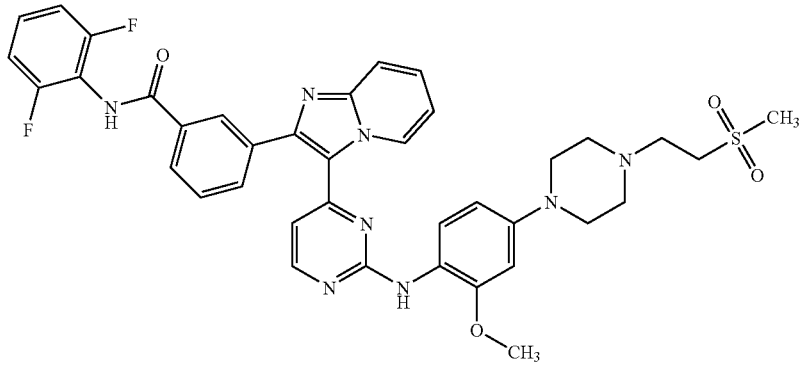

3-[3-(2-chloro-4-pyrimidinyl)imidazo[1,2-a]pyridin-2-yl]-N-(2,6-difluorophenyl)-benzamide (Intermediate Example 1) (100 mg, 0.21 mmol), 2-(methyloxy)-4-{4-[2-(methylsulfonyl)ethyl]-1-piperazinyl}aniline (60 mg, 0.19 mmol), and p-toluenesulfonic acid (98 mg, 0.51 mmol) were weighed into a 20 mL vial. 7 mL of iPrOH was added and the mixture was heated to 130° C. for 72 h. The mixture was transferred to a 50 mL round bottom and neutralized with 2 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (67 mg, 0.091 mmol, 46%). $^1$H NMR (400 MHz, DMSO-$d_6$) δ ppm 10.23 (s, 1H), 9.39 (d, J=2.01 Hz, 1H), 8.46 (s, 1H), 8.32 (s, 1H), 8.19 (s, 1H), 8.01-8.07 (m, 1H), 7.78-7.83 (m, 1H), 7.68-7.75 (m, 1H), 7.56-7.63 (m, 1H), 7.36-7.47 (m, 3H), 7.16-7.23 (m, 2H), 6.93-7.01 (m, 1H), 6.67 (s, 1H), 6.45 (d, J=4.40 Hz, 2H), 3.79 (s, 3H), 3.31-3.36 (m, 2H), 3.10-3.18 (m, 4H), 3.03 (s, 3H), 2.71-2.78 (m, 2H), 2.53-2.61 (m, 4H). MS (ESI): 739 [M+H]$^+$.

Example 137

N-(2,6-difluorophenyl)-2-(methyloxy)-5-[3-(2-{[2-(methyloxy)-4-(1-propyl-4-piperidinyl)phenyl]amino}-4-pyrimidinyl)imidazo[1,2-a]pyridin-2-yl]benzamide

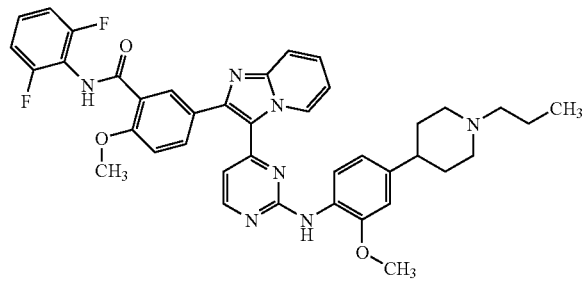

Step A: 4-[3-(methyloxy)-4-nitrophenyl]pyridine

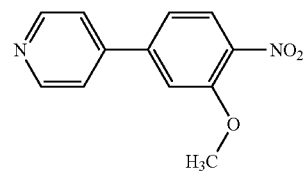

A solution of 4-chloro-2-(methyloxy)-1-nitrobenzene (34.7 g, 184.8 mmol), PdCl$_2$(PPh$_3$)$_2$ (6.5 g, 9.24 mmol) and 4-pyridylboronic acid (25.0 g, 203.2 mmol) in dioxane was deoxygenated by bubbling with N$_2$ (g) for ca 15 min. To this solution was added degassed 3.0 N Na$_2$CO$_3$ (aq) (203 mL, 3.0 equiv.) and the resulting slurry was warmed to 102° C. for 4 h. The dioxane was removed under reduced pressure and the solids were dissolved in EtOAc and washed twice with brine. The organic layer was dried over Na$_2$SO$_4$, taken to a residue under reduced pressure, and the residue purified by trituration with diethyl ether to afford 4-[3-(methyloxy)-4-nitrophenyl] pyridine as a brown solid (34.0 g, 147.68 mmol, 80%) of sufficient purity for use in subsequent transformations. $^1$H NMR (400 MHz, DMSO-d$_6$) δ ppm 8.64-8.73 (m, 2H), 8.00 (d, J=8.43 Hz, 1H), 7.78-7.85 (m, 2H), 7.67 (d, J=1.83 Hz, 1H), 7.51 (dd, J=8.43, 1.83 Hz, 1H), 4.03 (s, 3H).

Step B: 4-[3-(methyloxy)-4-nitrophenyl-]-1-propy-lpyridinium iodide

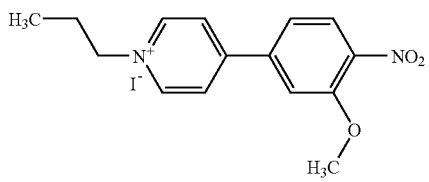

To 4-[3-(methyloxy)-4-nitrophenyl]pyridine (5 g, 21.72 mmol) in 50 mL of pinacolone was added, 1-iodopropane (14.77 g, 86.87 mmol). The mixture was heated to 102° C. for 24 h. The mixture was cooled and diluted with acetone. The resulting slurry was filtered and washed with acetone. The product was dried under vacuum to give the title compound of step B (5.7 g, 14.24 mmol, 65%). $^1$H NMR (400 MHz, DMSO-d$_6$) δ ppm 9.22 (d, J=6.78 Hz, 2H), 8.64 (d, J=6.78 Hz, 2H), 8.09 (d, J=8.42 Hz, 1H), 7.90 (d, J=1.65 Hz, 1H), 7.75 (dd, J=8.42, 1.65 Hz, 1H), 4.59 (t, J=7.33 Hz, 2H), 4.06 (s, 3H), 1.91-2.01 (m, 2H), 0.90 (t, J=7.33 Hz, 3H).

Step C: 4-[3-(methyloxy)-4-nitrophenyl]-1-propyl-1,2,3,6-tetrahydropyridine

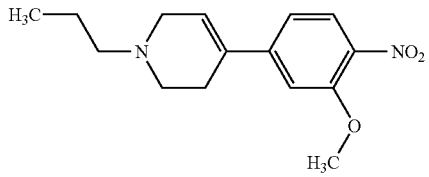

To 4-[3-(methyloxy)-4-nitrophenyl]-1-propylpyridinium iodide (5.7 g, 14.24 mmol) in 75 mL of MeOH at 0° C. was added, NaBH$_4$ (1.62 g, 42.73 mmol) over 1 h. The mixture was allowed to come to rt over 2 h. The solvent was reduced to approximately 20 mL and then diluted with EtOAc, washed with conc. NaHCO$_3$, dried (Na$_2$SO$_4$), filtered, rotovaped down, and purified by flash chromatography to give the title compound of step C (3.33 g, 12.05 mmol, 85%). $^1$H NMR (400 MHz, CDCl$_3$) δ ppm 7.84 (d, J=8.42 Hz, 1H), 7.02 (s, 1H), 6.99-7.02 (m, 1H), 6.19 (ddd, J=3.43, 1.92, 1.79 Hz, 1H), 3.95 (s, 3H), 3.20 (q, J=2.81 Hz, 2H), 2.72 (t, J=5.68 Hz, 2H), 2.54-2.60 (m, 2H), 2.41-2.48 (m, 2H), 1.54-1.64 (m, 2H), 0.94 (t, J=7.42 Hz, 3H).

Step D: 2-(methyloxy)-4-(1-propyl-4-piperidinyl)aniline

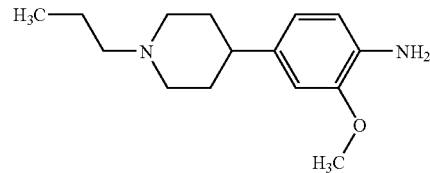

4-[3-(methyloxy)-4-nitrophenyl]-1-propyl-1,2,3,6-tetrahydropyridine (3.33 g, 12.05 mmol) was placed in a 250 mL high pressure vessel and dissolved in 60 mL of 1 to 1 EtOAc/MeOH. 5 wt % Platinum(sulfided)/C (4.7 g, 1.2 mmol) was added followed quickly by a rubber septum. The flask was evacuated and filled with N$_2$ six times to remove any oxygen. The vessel was then pressurized with H$_2$ (50 psi). The solution stirred overnight. The next morning the vessel was evacuated and filled with N$_2$ six times to remove any H$_2$. The solution was filtered through celite and evaporated to give the title compound of step D (2.4 g, 9.66 mmol, 80%). $^1$H NMR (400 MHz, CDCl$_3$) δ ppm 6.68 (s, 1H), 6.63 (s, 2H), 3.81 (s, 3H), 3.52 (bs, 2H), 3.07 (d, J=11.90 Hz, 2H), 2.40 (s, 1H), 2.32-2.38 (m, 2H), 1.98-2.07 (m, 2H), 1.80 (ddd, J=12.32, 6.00, 3.30 Hz, 4H), 1.51-1.61 (m, 2H), 0.91 (t, J=7.42 Hz, 3H).

Step E: N-(2,6-difluorophenyl)-2-(methyloxy)-5-[3-(2-{[2-(methyloxy)-4-(1-propyl-4-piperidinyl)phenyl]amino}-4-pyrimidinyl)imidazo[1,2-a]pyridin-2-yl]benzamide 5-[3-(2-Chloro-4-pyrimidinyl)imidazo[1,2-a]pyridin-2-yl]-N-(2,6-difluorophenyl)-2-(methyloxy)benzamide (Intermediate Example 2) (100 mg, 0.2 mmol), a different batch of 2-(methyloxy)-4-(1-propyl-4-piperidinyl)aniline (48 mg, 0.19 mmol), and p-toluenesulfonic acid (93 mg, 0.49 mmol) were weighed into a 20 mL vial. 7 mL of iPrOH was added and the mixture was heated to 120° C. for 24 h. The mixture was transferred to a 50 mL round bottom and neutralized with 2 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (92 mg, 0.13 mmol, 68%). $^1$H NMR (400 MHz, DMSO-d$_6$) δ ppm 9.77 (s, 1H), 9.37 (d, J=6.23 Hz, 1H), 8.50 (s, 1H), 8.24 (d, J=5.31 Hz, 1H), 8.10 (d, J=2.01 Hz, 1H), 7.76 (dd, J=8.61, 2.20 Hz, 1H), 7.66 (dd, J=18.77, 8.52 Hz, 2H), 7.34-7.45 (m, 2H), 7.27 (d, J=8.79 Hz, 1H), 7.17 (t, J=8.06 Hz, 2H), 6.92-6.99 (m, 2H), 6.78 (dd, J=8.06, 1.65 Hz, 1H), 6.58 (d, J=5.13 Hz, 1H), 3.97 (s, 3H), 3.81 (s, 3H), 2.87-2.97 (m, J=10.80 Hz, 2H), 2.39-2.46 (m, 1H), 2.17-2.27 (m, 2H), 1.86-1.97 (m, 2H), 1.64-1.75 (m, 4H), 1.38-1.48 (m, 2H), 0.84 (t, J=7.23 Hz, 3H). MS (ESI): 704 [M+H]$^+$.

Example 138

N-(2,6-difluorophenyl)-3-[3-(2-{[2-(methyloxy)-4-(1-propyl-4-piperidinyl)phenyl]amino}-4-pyrimidinyl)imidazo[1,2-a]pyridin-2-yl]benzamide

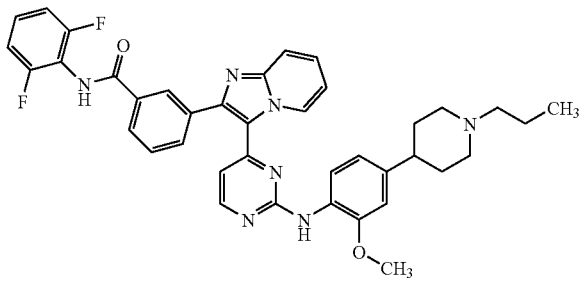

3-[3-(2-chloro-4-pyrimidinyl)imidazo[1,2-a]pyridin-2-yl]-N-(2,6-difluorophenyl)-benzamide (Intermediate Example 1) (100 mg, 0.2 mmol), a different batch of 2-(methyloxy)-4-(1-propyl-4-piperidinyl)aniline (Example 137, step D) (48 mg, 0.19 mmol), and p-toluenesulfonic acid (93 mg, 0.49 mmol) were weighed into a 20 mL vial. 7 mL of iPrOH was added and the mixture was heated to 120° C. for 24 hours. The mixture was transferred to a 50 mL round bottom and neutralized with 2 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (104 mg, 0.154 mmol, 80%). $^1$H NMR (400 MHz, DMSO-$d_6$) δ ppm 10.23 (s, 1H), 9.41 (d, J=6.59 Hz, 1H), 8.52 (s, 1H), 8.32 (s, 1H), 8.24 (d, J=5.31 Hz, 1H), 8.04 (d, J=7.87 Hz, 1H), 7.80 (d, J=7.87 Hz, 1H), 7.72 (d, J=8.97 Hz, 1H), 7.60 (q, J=7.63 Hz, 2H), 7.44-7.49 (m, 1H), 7.35-7.42 (m, 1H), 7.19 (t, J=8.15 Hz, 2H), 6.99 (t, J=6.96 Hz, 1H), 6.96 (d, J=1.47 Hz, 1H), 6.78 (dd, J=8.24, 1.65 Hz, 1H), 6.52 (d, J=5.31 Hz, 1H), 3.81 (s, 3H), 2.89-2.99 (m, J=8.79 Hz, 2H), 2.39-2.46 (m, 1H), 2.18-2.28 (m, 2H), 1.87-1.98 (m, 2H), 1.64-1.76 (m, 4H), 1.39-1.48 (m, 2H), 0.84 (t, J=7.33 Hz, 3H). MS (ESI): 674 [M+H]$^+$.

Example 139

N-(2,6-difluorophenyl)-3-{3-[2-({2-(methyloxy)-4-[3-(1-piperidinyl)propyl]phenyl}amino)-4-pyrimidinyl]imidazo[1,2-a]pyridin-2-yl}benzamide

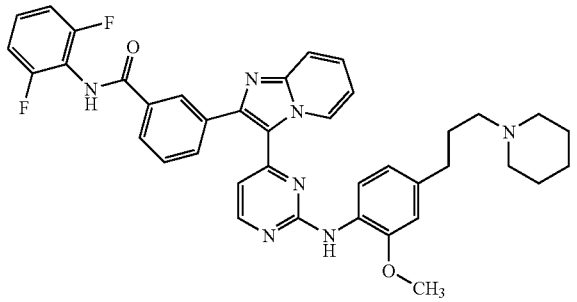

Step A: 3-[3-(methyloxy)-4-nitrophenyl]-2-propyn-1-ol

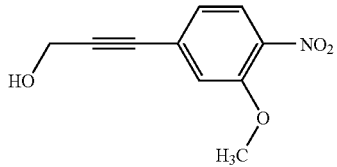

To 5-bromo-2-nitrophenyl methyl ether (4.0 g, 17.24 mmol) in 80 mL of acetonitrile was added, Bis(tri-t-butylphosphine)palladium(0) (0.253 g, 0.5 mmol), 2-propyn-1-ol (3.33 g, 59.4 mmol), and DABCO (4.44 g, 39.6 mmol). The mixture was heated to 60° C. for 1 h. The mixture was rotovaped down and then taken up in diethyl ether. The organic layer was washed with H$_2$O, dried (Na$_2$SO$_4$), filtered, and rotovaped. The crude product was purified by flash chromatography to give the title compound of step A (1.7 g, 8.2 mmol, 41%). $^1$H NMR (400 MHz, CDCl$_3$) δ ppm 7.80 (d, J=8.24 Hz, 1H), 7.12 (d, J=1.65 Hz, 1H), 7.06 (dd, J=8.33, 1.56 Hz, 1H), 4.52 (s, 2H), 3.94 (s, 3H).

Step B: 4-(3-chloro-1-propyn-1-yl)-2-(methyloxy)-1-nitrobenzene

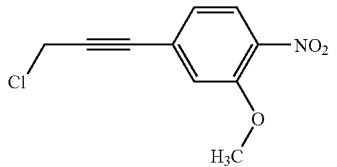

To 3-[3-(methyloxy)-4-nitrophenyl]-2-propyn-1-ol (1.6 g, 7.72 mmol) in 75 mL of DCM was added, triphenylphosphine (2.7 g, 10.27 mmol), and NCS (1.37 g, 10.27 mmol). The mixture stirred for 1 h. 10 g of silica gel was added. The solvent was rotovaped down and the pre-adsorbed solids were purified by flash chromatography to give the title compound of step B (1.7 g, 7.53 mmol, 97%). $^1$H NMR (400 MHz, CDCl$_3$) δ ppm 7.80 (d, J=8.42 Hz, 1H), 7.13 (d, J=1.47 Hz, 1H), 7.08 (dd, J=8.33, 1.56 Hz, 1H), 4.37 (s, 2 H), 3.95 (s, 3H).

Step C: 1-{3-[3-(methyloxy)-4-nitrophenyl]-2-propyn-1-yl}piperidine

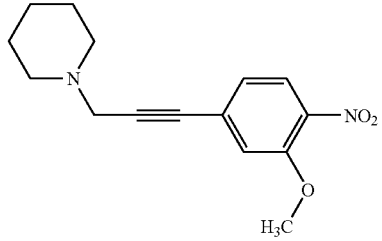

To 4-(3-chloro-1-propyn-1-yl)-2-(methyloxy)-1-nitrobenzene (0.250 g, 1.1 mmol) in 10 mL of dioxane was added, piperidine (0.26 g, 3.1 mmol). The mixture was heated to 110° C. for 3 h. The mixture was purified by flash chromatography to give the title compound of step C (0.29 g, 1.06 mmol, 95%). $^1$H NMR (400 MHz, CDCl$_3$) δ ppm 7.79 (d, J=8.42 Hz, 1H), 7.11 (d, J=1.47 Hz, 1H), 7.06 (dd, J=8.33, 1.56 Hz, 1H), 3.94 (s, 3H), 3.50 (s, 2H), 2.54-2.63 (m, 4H), 1.62-1.70 (m, 4H), 1.41-1.50 (m, 2H).

Step D:
2-(methyloxy)-4-[3-(1-piperidinyl)propyl]aniline

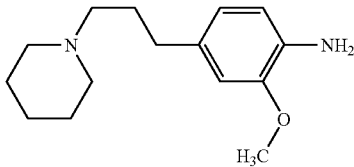

1-{3-[3-(methyloxy)-4-nitrophenyl]-2-propyn-1-yl}piperidine (0.29 g, 1.06 mmol) was placed in a 40 mL high vial and dissolved in 10 mL of 1 to 1 EtOAc/MeOH. 5 wt % Platinum(sulfided)/carbon (0.284 g, 0.07 mmol) was added followed quickly by a screw cap septum. The vial was evacuated and filled with $N_2$ six times to remove any oxygen. The vial was then pressurized with $H_2$ (balloon). The solution stirred overnight. The next morning the vessel was evacuated and filled with $N_2$ six times to remove any $H_2$. The solution was filtered through celite and evaporated to afford the title compound of step D (0.156 g, 0.63 mmol, 60%). $^1$H NMR (400 MHz, CDCl$_3$) δ ppm 6.56-6.64 (m, 3H), 3.83 (s, 3H), 3.40-3.75 (m, 2H), 2.50 (dt, J=19.14, 7.55 Hz, 4H), 2.37-2.45 (m, 2H), 1.86 (dt, J=15.29, 7.74 Hz, 1H), 1.63-1.70 (m, 2H), 1.59 (ddd, J=14.97, 7.55, 1.10 Hz, 2H), 1.45 (s, 1H), 0.92 (td, J=7.33, 1.10 Hz, 2H).

Step E: N-(2,6-difluorophenyl)-3-{3-[2-({2-(methyloxy)-4-[3-(1-piperidinyl)-propyl]phenyl}amino)-4-pyrimidinyl]imidazo[1,2-a]pyridin-2-yl}benzamide 3-[3-(2-chloro-4-pyrimidinyl)imidazo[1,2-a]pyridin-2-yl]-N-(2,6-difluorophenyl)-benzamide (Intermediate Example 1) (110 mg, 0.24 mmol), 2-(methyloxy)-4-[3-(1-piperidinyl)propyl]aniline (57 mg, 0.21 mol), and p-toluenesulfonic acid (109 mg, 0.57 mmol) were weighed into a 20 mL vial. 7 mL of iPrOH was added and the mixture was heated to 120° C. for 40 h. The mixture was transferred to a 50 mL round bottom and neutralized with 2 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (53 mg, 0.079 mmol, 37%). $^1$H NMR (400 MHz, DMSO-d$_6$) δ ppm 10.23 (s, 1H), 9.40 (d, J=6.23 Hz, 1H), 8.51 (s, 1H), 8.33 (s, 1H), 8.25 (d, J=5.13 Hz, 1H), 8.04 (d, J=7.87 Hz, 1H), 7.81 (d, J=7.69 Hz, 1H), 7.73 (dd, J=8.88, 0.82 Hz, 1H), 7.56-7.64 (m, 2H), 7.45 (dd, J=8.52, 7.23 Hz, 1H), 7.35-7.42 (m, 1H), 7.19 (t, J=8.15 Hz, 2H), 6.99 (t, J=6.87 Hz, 1H), 6.93 (s, 1H), 6.74 (d, J=8.06 Hz, 1H), 6.52 (d, J=5.13 Hz, 1H), 3.81 (s, 3H), 2.56 (t, J=7.51 Hz, 2H), 2.20-2.31 (m, 6H), 1.68-1.77 (m, 2H), 1.41-1.50 (m, 4H), 1.30-1.40 (m, 2H). MS (ESI): 674 [M+H]$^+$.

Example 140

N-(2,6-difluorophenyl)-2-(methyloxy)-5-{3-[2-({2-(methyloxy)-4-[3-(1-piperidinyl)propyl]phenyl}amino)-4-pyrimidinyl]imidazo[1,2-a]pyridin-2-yl}benzamide

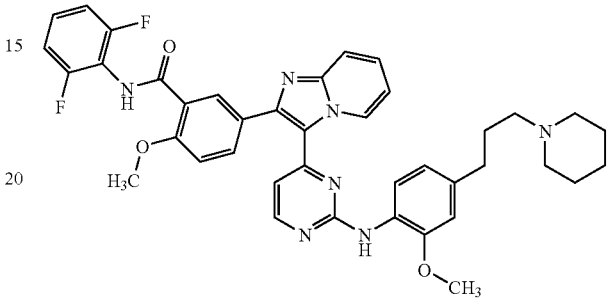

5-[3-(2-chloro-4-pyrimidinyl)imidazo[1,2-a]pyridin-2-yl]-N-(2,6-difluorophenyl)-2-(methyloxy)benzamide (Intermediate Example 2) (120 mg, 0.24 mmol), 2-(methyloxy)-4-[3-(1-piperidinyl)propyl]aniline (Example 139, step D) (55 mg, 0.22 mmol), and p-toluenesulfonic acid (111 mg, 0.59 mmol) were weighed into a 20 mL vial. 7 mL of iPrOH was added and the mixture was heated to 120° C. for 40 h. The mixture was transferred to a 50 mL round bottom and neutralized with 2 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (54 mg, 0.077 mmol, 35%). $^1$H NMR (400 MHz, DMSO-d$_6$) δ ppm 9.77 (s, 1H), 9.36 (s, 1H), 8.49 (s, 1H), 8.24 (s, 1H), 8.10 (s, 1H), 7.76 (s, 1H), 7.68 (s, 1H), 7.63 (s, 1H), 7.34-7.45 (m, J=17.58 Hz, 2H), 7.27 (s, 1H), 7.12-7.21 (m, 2H), 6.91-6.98 (m, 2H), 6.74 (s, 1H), 6.59 (s, 1H), 3.97 (s, 3H), 3.81 (s, 3H), 2.51-2.59 (m, 2H), 2.19-2.31 (m, 6H), 1.67-1.77 (m, 2H), 1.42-1.50 (m, 4H), 1.30-1.39 (m, 2H). MS (ESI): 704 [M+H]$^+$.

Example 141

N-(2,6-difluorophenyl)-3-{3-[2-({2-(methyloxy)-4-[3-(4-methyl-1-piperazinyl)propyl]phenyl}amino)-4-pyrimidinyl]imidazo[1,2-a]pyridin-2-yl}benzamide

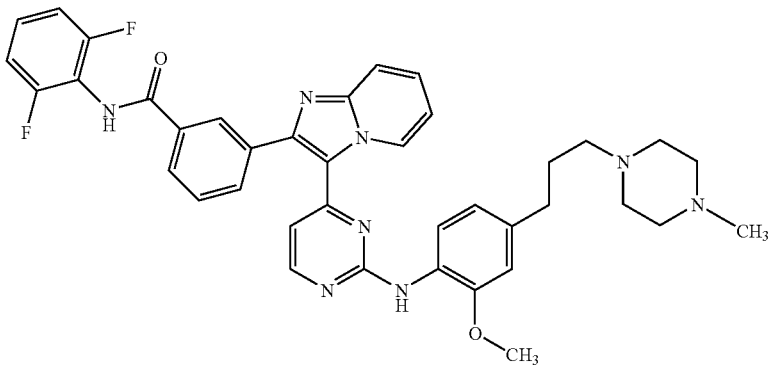

Step A: 1-methyl-4-{3-[3-(methyloxy)-4-nitrophenyl]-2-propyn-1-yl}piperazine

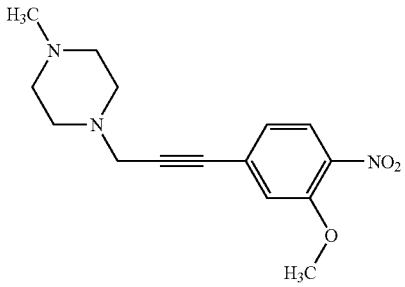

To 4-(3-chloro-1-propyn-1-yl)-2-(methyloxy)-1-nitrobenzene (Example 139, step B) (0.250 g, 1.1 mmol) in 10 mL of dioxane was added, 1-methylpiperazine (0.31 g, 3.1 mmol). The mixture was heated to 110° C. for 3 h. The mixture was purified by flash chromatography to give the title compound of step A (0.309 g, 1.07 mmol, 97%). $^1$H NMR (400 MHz, CDCl$_3$) δ ppm 7.78 (d, J=8.24 Hz, 1H), 7.11 (s, 1H), 7.04 (dd, J=8.33, 1.56 Hz, 1H), 3.94 (s, 3H), 3.55 (s, 2H), 2.64-2.78 (m, 4H), 2.47-2.62 (m, 4H), 2.33 (s, 3H).

Step B: 2-(methyloxy)-4-[3-(4-methyl-1-piperazinyl)propyl]aniline

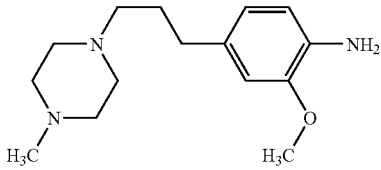

1-methyl-4-{3-[3-(methyloxy)-4-nitrophenyl]-2-propyn-1-yl}piperazine (0.309 g, 1.07 mmol) was placed in a 40 mL high vial and dissolved in 10 mL of 1 to 1 EtOAc/MeOH. 5 wt % Platinum(sulfided)/carbon (0.291 g, 0.075 mmol) was added followed quickly by a screw cap septum. The vial was evacuated and filled with N$_2$ six times to remove any oxygen. The vial was then pressurized with H$_2$ (balloon). The solution stirred overnight. The next morning the vessel was evacuated and filled with N$_2$ six times to remove any H$_2$. The solution was filtered through celite and evaporated to afford the title compound of step B (0.165 mg, 0.63 mmol, 60%). $^1$H NMR (400 MHz, CDCl$_3$) δ ppm 6.55-6.64 (m, 3H), 3.83 (s, 3H), 3.56 (bs, 2H), 2.47-2.56 (m, 8H), 2.36-2.41 (m, 2H), 2.31 (s, 3H), 1.75-1.83 (m, 1H), 1.53-1.64 (m, 1H), 0.92 (t, J=7.42 Hz, 2H).

Step C: N-(2,6-difluorophenyl)-3-{3-[2-({2-(methyloxy)-4-[3-(4-methyl-1-piperazinyl)propyl]phenyl}amino)-4-pyrimidinyl]imidazo[1,2-a]pyridin-2-yl}benzamide 3-[3-(2-Chloro-4-pyrimidinyl)imidazo[1,2-a]pyridin-2-yl]-N-(2,6-difluorophenyl)-benzamide (Intermediate Example 1) (110 mg, 0.24 mmol), 2-(methyloxy)-4-[3-(4-methyl-1-piperazinyl)propyl]aniline (56 mg, 0.21 mol), and p-toluenesulfonic acid (109 mg, 0.57 mmol) were weighed into a 20 mL vial. 7 mL of iPrOH was added and the mixture was heated to 120° C. for 40 hours. The mixture was transferred to a 50 mL round bottom and neutralized with 2 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (50 mg, 0.073 mmol, 34%). $^1$H NMR (400 MHz, DMSO-d$_6$) δ ppm 10.22 (s, 1H), 9.39 (d, J=6.59 Hz, 1H), 8.50 (s, 1H), 8.31-8.34 (m, 1H), 8.25 (d, J=5.31 Hz, 1H), 8.02-8.06 (m, 1H), 7.79-7.82 (m, 1H), 7.73 (d, J=8.97 Hz, 1H), 7.56-7.64 (m, 2H), 7.45 (ddd, J=8.88, 6.78, 1.19 Hz, 1H), 7.35-7.41 (m, 1H), 7.20 (td, J=8.06, 5.13 Hz, 2H), 6.98 (t, J=6.87 Hz, 1H), 6.93 (d, J=1.47 Hz, 1H), 6.74 (dd, J=8.15, 1.56 Hz, 1H), 6.52 (d, J=5.13 Hz, 1H), 3.80 (s, 3H), 2.56 (t, J=7.60 Hz, 2H), 2.32-2.42 (m, 2H), 2.21-2.32 (m, 8H), 2.11 (s, 3H), 1.67-1.76 (m, 2H). MS (ESI): 689 [M+H]$^+$.

Example 142

N-(2,6-difluorophenyl)-2-(methyloxy)-5-{3-[2-({2-(methyloxy)-4-[3-(4-methyl-1-piperazinyl)propyl]phenyl}amino)-4-pyrimidinyl]imidazo[1,2-a]pyridin-2-yl}benzamide

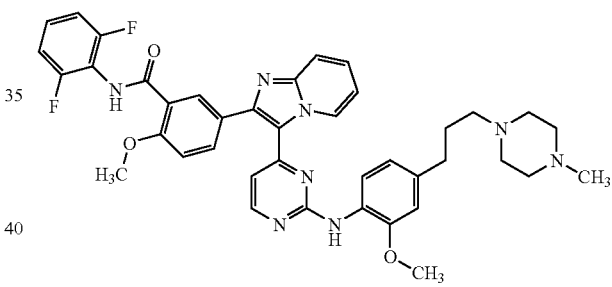

5-[3-(2-chloro-4-pyrimidinyl)imidazo[1,2-a]pyridin-2-yl]-N-(2,6-difluorophenyl)-2-(methyloxy)benzamide (Intermediate Example 2) (110 mg, 0.22 mmol), 22-(methyloxy)-4-[3-(4-methyl-1-piperazinyl) propyl]aniline (Example 141, step B) (53 mg, 0.20 mol), and p-toluenesulfonic acid (102 mg, 0.54 mmol) were weighed into a 20 mL vial. 7 mL of iPrOH was added and the mixture was heated to 120° C. for 40 h. The mixture was transferred to a 50 mL round bottom and neutralized with 2 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (50 mg, 0.07 mmol, 35%). $^1$H NMR (400 MHz, DMSO-d$_6$) δ ppm 9.77 (s, 1H), 9.36 (d, J=6.78 Hz, 1H), 8.49 (s, 1H), 8.25 (d, J=5.13 Hz, 1H), 8.10 (d, J=2.20 Hz, 1H), 7.76 (dd, J=8.61, 2.20 Hz, 1H), 7.67-7.73 (m, 1H), 7.63 (d, J=7.87 Hz, 1H), 7.40-7.45 (m, 1H), 7.33-7.40 (m, 1H), 7.27 (d, J=8.79 Hz, 1H), 7.13-7.21 (m, 2H), 6.94-6.98 (m, 1H), 6.93 (d, J=1.65 Hz, 1H), 6.74 (dd, J=8.06, 1.65 Hz, 1H), 6.58 (d, J=5.31 Hz, 1H), 3.97 (s, 3H), 3.80 (s, 3H), 2.56 (t, J=7.60 Hz, 2H), 2.32-2.42 (m, 2H), 2.20-2.32 (m, 8H), 2.09-2.13 (m, 3H), 1.67-1.76 (m, 2H). MS (ESI): 719 [M+H]$^+$.

Example 143

N-(2,6-difluorophenyl)-5-(3-{2-[(2-(ethyloxy)-4-{4-[2-(methylsulfonyl)ethyl]-1-piperazinyl}phenyl)amino]-4-pyrimidinyl}imidazo[1,2-a]pyridin-2-yl)-2-(methyloxy)benzamide

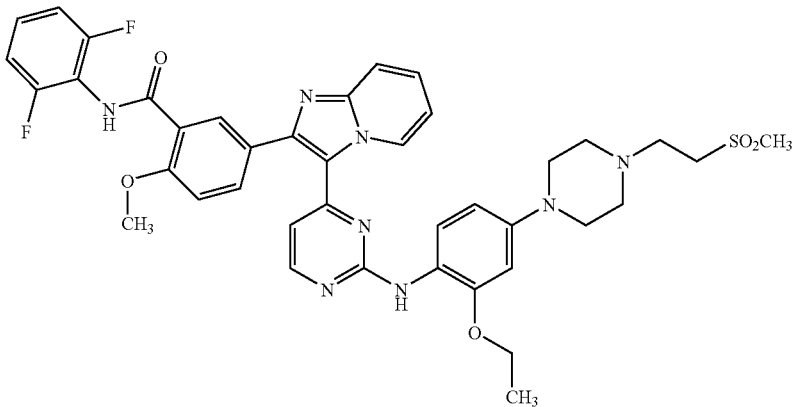

Step A: 1-[3-(ethyloxy)-4-nitrophenyl]piperazine

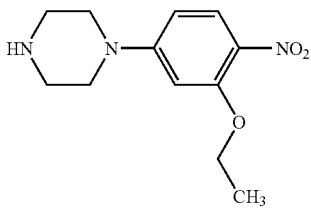

To 2-(ethyloxy)-4-fluoro-1-nitrobenzene (Example 116, step A) (3.0 g, 16.2 mmol) in 60 mL of dioxane was added, piperazine (4.19 g, 48.61 mmol). The mixture was heated to 120° C. 72 h. The mixture was purified by flash chromatography to give the title compound of step A (3.6 g, 14.33 mmol, 88%). $^1$H NMR (400 MHz, CDCl$_3$) δ ppm 7.95 (d, J=9.34 Hz, 1H), 6.40 (dd, J=9.34, 2.56 Hz, 1H), 6.30 (d, J=2.56 Hz, 1H), 4.13 (q, J=6.96 Hz, 2H), 3.30-3.33 (m, 4H), 2.95-3.02 (m, 4H), 1.48 (t, J=6.96 Hz, 3H).

Step B: 1-[3-(ethyloxy)-4-nitrophenyl]-4-[2-(methylsulfonyl)ethyl]piperazine

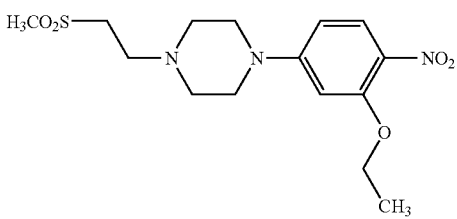

To 1-[3-(ethyloxy)-4-nitrophenyl]piperazine (0.5 g, 1.99 mmol) in 10 mL of dioxane was added, methyl vinyl sulfone (0.53 g, 4.97 mmol). The mixture was heated to 120° C. for 2 h. The solvent was rotovaped down and the crude product was purified by flash chromatography to give the title compound of step B (0.565 g, 1.58 mmol, 79%). $^1$H NMR (400 MHz, DMSO-d$_6$) δ ppm 7.83 (d, J=9.34 Hz, 1H), 6.57 (dd, J=9.43, 2.47 Hz, 1H), 6.51 (d, J=2.38 Hz, 1H), 4.16 (q, J=6.96 Hz, 2H), 3.36-3.41 (m, 4H), 3.30-3.34 (m, 2H), 3.01 (s, 3H), 2.73 (t, J=6.87 Hz, 2H), 2.49-2.55 (m, 4H), 1.32 (t, J=6.96 Hz, 3H).

Step C: 2-(ethyloxy)-4-{4-[2-(methylsulfonyl)ethyl]-1-piperazinyl}aniline

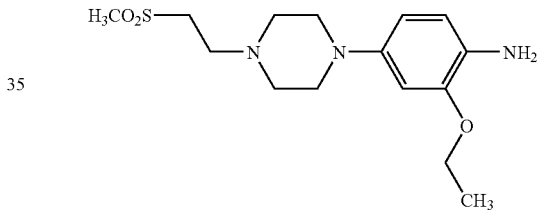

1-[3-(ethyloxy)-4-nitrophenyl]-4-[2-(methylsulfonyl)ethyl]piperazine (0.565 g, 1.58 mmol) was placed in a 40 mL high vial and dissolved in 10 mL of 1 to 1 EtOAc/MeOA. 5 wt % Platinum(sulfided)/carbon (0.308 g, 0.079 mmol) was added followed quickly by a screw cap septum. The vial was evacuated and filled with N$_2$ six times to remove any oxygen. The vial was then pressurized with H$_2$ (balloon). The solution stirred overnight. The next morning the vessel was evacuated and filled with N$_2$ six times to remove any H$_2$. The solution was filtered through celite and evaporated to afford the title compound (0.445 g, 1.36 mmol, 86%). $^1$H NMR (400 MHz, CDCl$_3$) δ ppm 6.63 (d, J=8.42 Hz, 1H), 6.51 (d, J=2.38 Hz, 1H), 6.40 (dd, J=8.33, 2.11 Hz, 1H), 4.03 (q, J=7.02 Hz, 2H), 3.19 (t, J=6.41 Hz, 2H), 3.04-3.07 (m, 4H), 3.03 (S, 3H), 2.95 (t, J=6.41 Hz, 2H), 2.64-2.72 (m, 4H), 1.41 (t, J=6.96 Hz, 3H).

Step D: N-(2,6-difluorophenyl)-5-(3-{2-[(2-(ethyloxy)-4-{4-[2-(methylsulfonyl)ethyl]-1-piperazinyl}phenyl)amino]-4-pyrimidinyl}imidazo[1,2-a]pyridin-2-yl)-2-(methyloxy)benzamide 5-[3-(2-Chloro-4-pyrimidinyl)imidazo[1,2-a]pyridin-2-yl]-N-(2,6-difluorophenyl)-2-(methyloxy)benzamide (Intermediate Example 2) (300 mg, 0.61 mmol), a different batch of 2-(ethyloxy)-4-{4-[2-(methylsulfonyl)ethyl]-1-piperazinyl}aniline (180 mg, 0.55 mmol), and p-toluenesulfonic acid (278 mg, 1.46 mmol) were weighed into a 40 mL vial. 25 mL of iPrOH was added and the mixture was heated to 130° C. for 48 h. The mixture was transferred to a 50 mL round bottom and neutralized with 5 mL of 0.5 N sodium methoxide. The solvent was rotovaped down. The residue was taken up in 30 mL of DCM. 3 g of silica gel was added. The solvent was rotovaped down and the pre-adsorbed solids were purified by flash chromatography to give the title compound (190 mg, 0.242 mmol, 44%). $^1$H NMR (400 MHz, DMSO-$d_6$) δ ppm 9.77 (s, 1H), 9.31 (s, 1H), 8.35 (s, 1H), 8.21 (d, J=5.31 Hz, 1H), 8.09 (d, J=2.20 Hz, 1H), 7.76 (dd, J=8.61, 2.20 Hz, 1H), 7.68 (d, J=8.97 Hz, 1H), 7.35-7.46 (m, 3H), 7.26 (d, J=8.79 Hz, 1H), 7.17 (t, J=8.06 Hz, 2H), 6.92 (t, J=6.68 Hz, 1H), 6.66 (d, J=2.38 Hz, 1H), 6.53 (d, J=5.13 Hz, 1H), 6.47 (dd, J=8.61, 2.38 Hz, 1H), 4.05 (q, J=7.08 Hz, 2H), 3.97 (s, 3H), 3.31-3.34 (m, 2H), 3.08-3.15 (m, 4H), 3.02 (s, 3H), 2.74 (t, J=6.78 Hz, 2H), 2.51-2.60 (m, 4H), 1.22 (t, J=6.96 Hz, 3H). MS (ESI): 783 [M+H]$^+$.

Example 144

N-(2,6-difluorophenyl)-2-(ethyloxy)-5-(3-{2-[(2-(ethyloxy)-4-{4-[2-(methylsulfonyl)ethyl]-1-piperazinyl}phenyl)amino]-4-pyrimidinyl}imidazo[1,2-a]pyridin-2-yl)benzamide 5-[3-(2-chloro-4-pyrimidinyl)imidazo[1,2-a]pyridin-2-yl]-N-(2,6-difluorophenyl)-2-(ethyloxy)benzamide (Intermediate Example 6) (150 mg, 0.3 mmol), 2-(ethyloxy)-4-{4-[2-(methylsulfonyl)ethyl]-1-piperazinyl}aniline (Example 143, step C) (87 mg, 0.27 mmol), and p-toluenesulfonic acid (135 mg, 0.71 mmol) were weighed into a 20 mL vial. 10 mL of iPrOH was added and the mixture was heated to 130° C. for 72 h. The mixture was transferred to a 50 mL round bottom and neutralized with 5 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (121 mg, 0.15 mmol, 57%). $^1$H NMR (400 MHz, DMSO-$d_6$) δ ppm 9.73 (s, 1H), 9.31 (s, 1H), 8.35 (s, 1H), 8.21 (d, J=5.31 Hz, 1H), 8.03 (d, J=2.01 Hz, 1H), 7.73 (dd, J=8.70, 2.11 Hz, 1H), 7.68 (d, J=8.97 Hz, 1H), 7.39-7.47 (m, 2H), 7.32-7.39 (m, 1H), 7.24 (d, J=8.79 Hz, 1H), 7.18 (t, J=8.06 Hz, 2H), 6.92 (t, J=7.05 Hz, 1H), 6.66 (d, J=2.38 Hz, 1H), 6.53 (d, J=5.31 Hz, 1H), 6.44-6.49 (m, 1H), 4.24 (q, J=6.90 Hz, 2H), 4.05 (q, J=6.96 Hz, 2H), 3.30-3.34 (m, 2H), 3.08-3.14 (m, 4H), 3.02 (s, 3H), 2.74 (t, J=6.87 Hz, 2H), 2.54-2.59 (m, 4H), 1.41 (t, J=6.87 Hz, 3H), 1.23 (t, J=6.96 Hz, 3H). MS (ESI): 797 [M+H]$^+$.

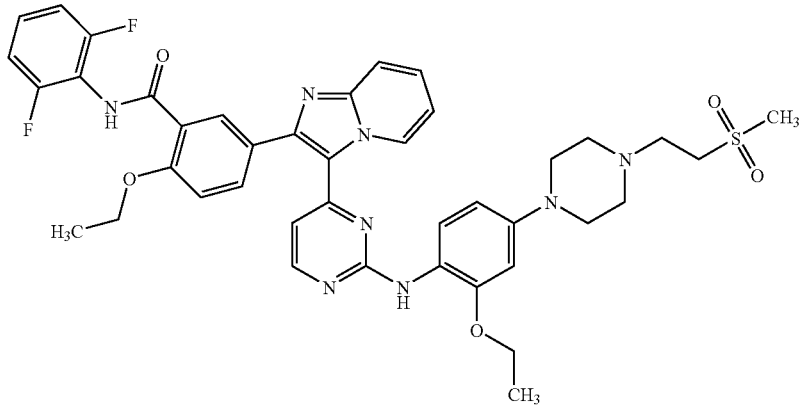

Example 145

N-(2,6-difluorophenyl)-3-(3-{2-[(2-(ethyloxy)-4-{4-[2-(methylsulfonyl)ethyl]-1-piperazinyl}phenyl)amino]-4-pyrimidinyl}imidazo[1,2-a]pyridin-2-yl)benzamide

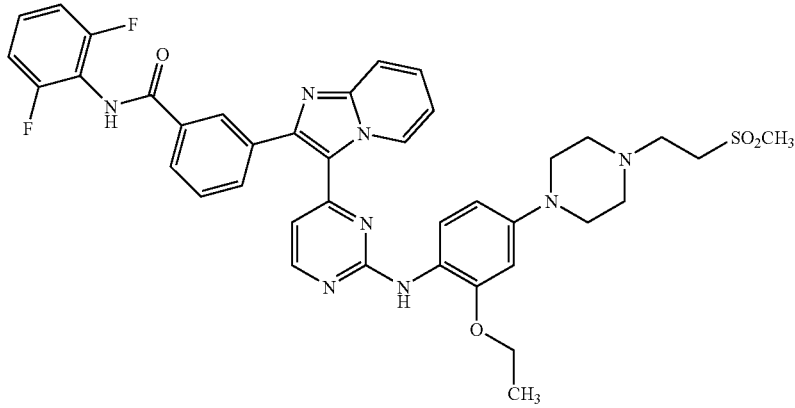

3-[3-(2-chloro-4-pyrimidinyl)imidazo[1,2-a]pyridin-2-yl]-N-(2,6-difluorophenyl)-benzamide (Intermediate Example 1) (100 mg, 0.22 mmol), 2-(ethyloxy)-4-{4-[2-(methylsulfonyl)-ethyl]-1-piperazinyl}aniline (Example 143, step C) (64 mg, 0.194 mmol), and p-toluenesulfonic acid (99 mg, 0.52 mmol) were weighed into a 20 mL vial. 10 mL of iPrOH was added and the mixture was heated to 130° C. for 72 h. The mixture was transferred to a 50 mL round bottom and neutralized with 2 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (98 mg, 0.13 mmol, 61%). $^1$H NMR (400 MHz, DMSO-d$_6$) δ ppm 10.22 (s, 1H), 9.36 (s, 1H), 8.34 (d, J=13.00 Hz, 2H), 8.21 (d, J=4.94 Hz, 1H), 8.02 (s, 1H), 7.79 (s, 1H), 7.72 (d, J=8.97 Hz, 1H), 7.59 (s, 1H), 7.36-7.48 (m, 3H), 7.19 (t, J=7.97 Hz, 2H), 6.96 (s, 1H), 6.66 (s, 1H), 6.41-6.52 (m, 2H), 4.05 (q, J=6.59 Hz, 2H), 3.30-3.37 (m, 2H), 3.07-3.14 (m, 4H), 3.02 (s, 3H), 2.74 (t, J=6.32 Hz, 2H), 2.54-2.61 (m, 4H), 1.22 (t, J=6.68 Hz, 3H). MS (ESI): 753 [M+H]$^+$.

Example 146

N-(2,6-difluorophenyl)-5-{3-[2-({2-(ethyloxy)-4-[2-(4-methyl-1-piperazinyl)ethyl]-phenyl}amino)-4-pyrimidinyl]imidazo[1,2-a]pyridin-2-yl}-2-(methyloxy)benzamide

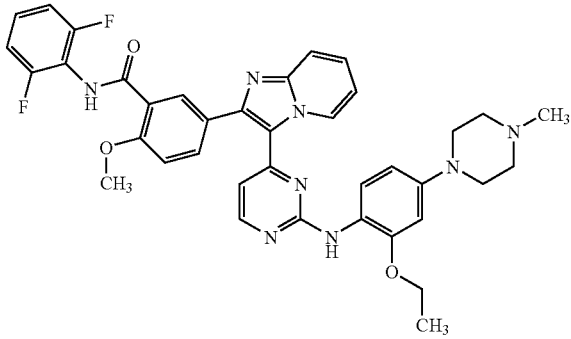

Step A: 5-bromo-2-nitrophenyl ethyl ether

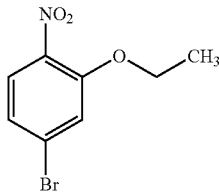

To 4-bromo-2-fluoro-1-nitrobenzene (8.3 g, 37.72 mmol) in 50 mL of EtOH was added 21% by weight sodium ethoxide (14.2 mL, 45.27 mmol). The mixture was stirred at 60° C. for 1 h. The ethanol was rotovaped down. The crude product was dissolved in DCM (100 mL), washed with H$_2$O, dried (Na$_2$SO$_4$), filtered, and rotovaped down to give the title compound of step A (8.82 g, 35.8 mmol, 95%) as a yellow solid. $^1$H NMR (400 MHz, CDCl$_3$) δ ppm 7.71 (d, J=8.61 Hz, 1H), 7.20 (d, J=1.83 Hz, 1H), 7.14 (dd, J=8.61, 1.83 Hz, 1H), 4.16 (q, J=7.02 Hz, 2H), 1.47 (t, J=6.96 Hz, 3H).

Step B: 5-ethenyl-2-nitrophenyl ethyl ether

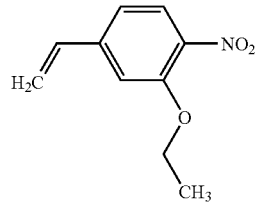

To 5-bromo-2-nitrophenyl ethyl ether (8.8 g, 35.76 mmol) in 80 mL of n-propanol was added, PdCl$_2$(dppf)*DCM (0.523 g, 0.72 mmol), potassium ethenyl(trifluoro)borate (6.71 g, 50 mmol), and TEA (3.61 g, 35.76 mmol). The mixture was heated to 100° C. for 3 h. The solvent was rotovaped down and the residue dissolved in DCM, and filtered to remove insoluble solids. 20 g of silica gel was added and the solvent rotovaped down, and purified by flash chromatography to give the title compound of step B (5.58 g, 28.89 mmol, 81%) as a white solid. $^1$H NMR (400 MHz, CDCl$_3$) δ ppm 7.81 (d, J=8.97 Hz, 1H), 7.01-7.03 (m, 1H), 6.68 (dd, J=17.67, 10.71 Hz, 1H), 5.84 (d, J=17.58 Hz, 1H), 5.44 (d, J=11.17 Hz, 1H), 4.19 (q, J=6.96 Hz, 2H), 1.47 (t, J=6.96 Hz, 3H).

Step C: 1-{2-[3-(ethyloxy)-4-nitrophenyl]ethyl}-4-methylpiperazine

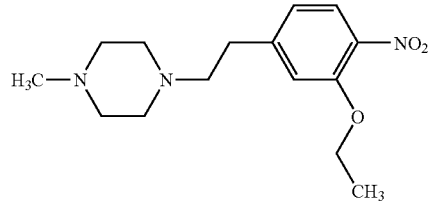

To 5-ethenyl-2-nitrophenyl ethyl ether (0.53 g, 2.74 mmol) in 10 mL of iPrOH was added, 1-methylpiperazine (0.41 g, 4.11 mmol). The mixture was heated to 120° C. for 2 h. The solvent was rotovaped down and the crude product was purified by flash chromatography to give the title compound of step C (0.708 g, 2.4 mmol, 88%). $^1$H NMR (400 MHz, CDCl$_3$) δ ppm 7.75 (d, J=8.42 Hz, 1H), 6.90 (d, J=1.47 Hz, 1H), 6.82 (dd, J=8.42, 1.47 Hz, 1H), 4.15 (q, J=6.96 Hz, 2H), 2.78-2.83 (m, 2H), 2.33-2.88 (m, 10H), 2.30 (s, 3H), 1.46 (t, J=6.96 Hz, 3H).

Step D: 2-(ethyloxy)-4-[2-(4-methyl-1-piperazinyl)ethyl]aniline

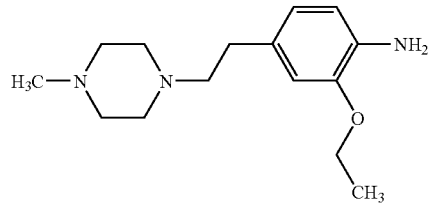

1-methyl-4-{2-[3-(ethyloxy)-4-nitrophenyl]ethyl}piperazine (0.373 g, 1.14 mmol) was placed in a 100 mL high pressure vessel and dissolved in 30 mL of 1 to 1 EtOAc/MeOH. 5 wt % Platinum(sulfided)/carbon (0.223 g, 0.057 mmol) was added followed quickly by a screw cap septum. The flask was evacuated and filled with $N_2$ six times to remove any oxygen. The vessel was then pressurized with $H_2$ (balloon). The solution stirred overnight. The next morning the vessel was evacuated and filled with $N_2$ six times to remove any $H_2$. The solution was filtered through celite and evaporated to afford the title compound of step D (0.308 g, 1.16 mmol, 100%). $^1$H NMR (400 MHz, CDCl$_3$) δ ppm 6.57-6.65 (m, 3H), 3.99-4.08 (m, 2H), 3.62-3.74 (m, 2H), 2.65-2.75 (m, 2H), 2.47-2.59 (m, 8H), 2.31 (s, 3H), 1.36-1.45 (m, 3H).

Step E: N-(2,6-difluorophenyl)-5-{3-[2-({2-(ethyloxy)-4-[2-(4-methyl-1-piperazinyl)ethyl]-phenyl}amino)-4-pyrimidinyl]imidazo[1,2-a]pyridin-2-yl}-2-(methyloxy)benzamide 5-[3-(2-chloro-4-pyrimidinyl)imidazo[1,2-a]pyridin-2-yl]-N-(2,6-difluorophenyl)-2-(methyloxy)benzamide (Intermediate Example 2) (100 mg, 0.2 mmol), 2-(ethyloxy)-4-[2-(4-methyl-1-piperazinyl)ethyl]aniline (44 mg, 0.17 mmol), and p-toluenesulfonic acid (93 mg, 0.49 mmol) were weighed into a 20 mL microwave vial. 7 mL of iPrOH was added and the mixture was heated to 130° C. for 72 h. The mixture was transferred to a 50 mL round bottom and neutralized with 2 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (85 mg, 0.118 mmol, 71%). $^1$H NMR (400 MHz, DMSO-d$_6$) δ ppm 9.77 (s, 1H), 9.32 (d, J=6.96 Hz, 1H), 8.39 (s, 1H), 8.27 (d, J=5.31 Hz, 1H), 8.11 (s, 1H), 7.76 (d, J=8.42 Hz, 1H), 7.68 (dd, J=11.81, 8.52 Hz, 2H), 7.33-7.45 (m, 2H), 7.26 (d, J=8.79 Hz, 1H), 7.17 (t, J=7.97 Hz, 2H), 6.88-6.99 (m, 2H), 6.74 (d, J=8.06 Hz, 1H), 6.61 (d, J=5.13 Hz, 1H), 4.06 (q, J=6.96 Hz, 2H), 3.97 (s, 3H), 2.62-2.72 (m, 2H), 2.19-2.57 (m, 10H), 2.11 (s, 3H), 1.27 (t, J=7.05 Hz, 3H). MS (ESI): 719 [M+H]$^+$.

Example 147

N-(2,6-difluorophenyl)-3-{3-[2-({2-(ethyloxy)-4-[2-(4-methyl-1-piperazinyl)ethyl]-phenyl}amino)-4-pyrimidinyl]imidazo[1,2-a]pyridin-2-yl}benzamide

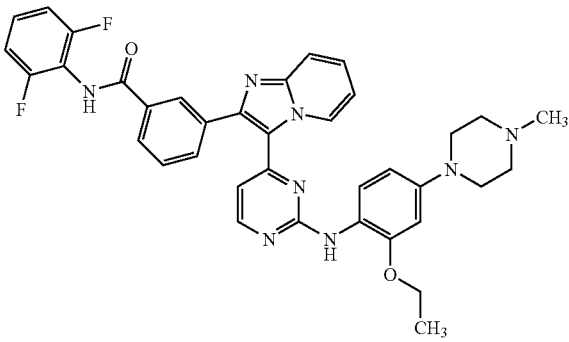

3-[3-(2-Chloro-4-pyrimidinyl)imidazo[1,2-a]pyridin-2-yl]-N-(2,6-difluorophenyl)-benzamide (Intermediate Example 1) (100 mg, 0.22 mmol), 2-(ethyloxy)-4-[2-(4-methyl-1-piperazinyl)ethyl]aniline (Example 146, step D) (46 mg, 0.17 mmol), and p-toluenesulfonic acid (99 mg, 0.52 mmol) were weighed into a 20 mL vial. 7 mL of iPrOH was added and the mixture was heated to 130° C. for 72 h. The mixture was transferred to a 50 mL round bottom and neutralized with 2 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (67 mg, 0.09 mmol, 56%); $^1$H NMR (400 MHz, DMSO-d$_6$) δ ppm 10.21 (s, 1H), 9.34 (s, 1H), 8.40 (s, 1H), 8.34 (s, 1H), 8.27 (s, 1H), 8.02 (s, 1H), 7.80 (s, 1H), 7.73 (s, 1H), 7.65 (s, 1H), 7.59 (s, 1H), 7.46 (s, 1H), 7.38 (s, 1H), 7.18 (s, 2H), 6.96 (s, 2H), 6.72 (s, 1H), 6.46 (s, 1H), 4.02-4.11 (m, 2H), 2.60-2.71 (m, 2H), 2.25-2.32 (m, 10H), 2.12 (s, 3H), 1.26 (s, 3H). MS (ESI): 689 [M+H]$^+$.

Example 148

N-(2,6-difluorophenyl)-3-(3-{2-[(5-methyl-2-(methyloxy)-4-{4-[2-(methylsulfonyl)ethyl]-1-piperazinyl}phenyl)amino]-4-pyrimidinyl}imidazo[1,2-a]pyridin-2-yl)benzamide

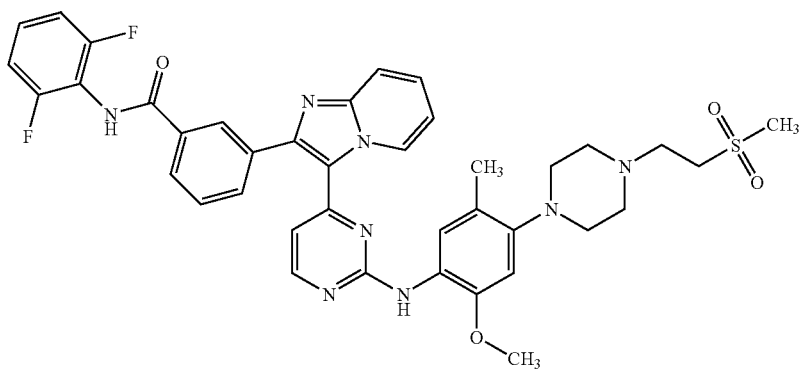

Step A: 1,1-dimethylethyl 4-[2-(methylsulfonyl)ethyl]-1-piperazinecarboxylate

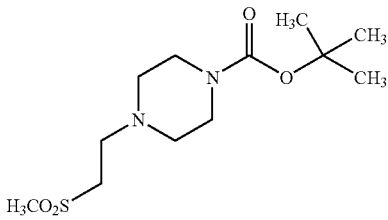

To a solution of 1,1-dimethylethyl 1-piperazinecarboxylate (72.8 g, 390 mmol) in acetonitrile (1.4 L) was added methyl vinyl sulfone (50 g, 470 mmol) and $Na_2CO_3$ (124 g, 1170 mmol) and the mixture was refluxed overnight. Then the mixture was cooled to rt, and poured into $H_2O$ and extracted with EtOAc. The organic layer was dried over $Na_2SO_4$ and the solvent was removed under reduced pressure to give the title compound (106 g, 93% yield). $^1$H NMR (400 MHz, $CDCl_3$) δ ppm 1.41-1.57 (m, 9H), 2.39-2.51 (m, 4H), 2.88 (t, J=8.4 Hz, 2H), 3.02 (s, 3H), 3.14 (t, J=8.4 Hz, 2H), 3.35-3.50 (m, 4H).

Step B: 1-[2-(methylsulfonyl)ethyl]piperazine hydrochloride

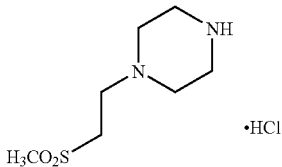

To the solution of 1,1-dimethylethyl 4-[2-(methylsulfonyl)ethyl]-1-piperazinecarboxylate (106 g, 360 mmol) in MeOH (500 mL) was added HCl/MeOH (5M, 1000 mL, 5000 mmol), and the mixture was heated at 50° C. for 1 h before evaporating most of the solvent. The residue was filtered and washed with MeOH to give the desired product as HCl salt (90.3 g, 95% yield). $^1$H NMR (400 MHz, $D_2O$) δ ppm 3.30-3.72 (m, 12H), 3.09 (s, 3H).

Step C: 1-[2-methyl-5-(methyloxy)-4-nitrophenyl]-4-[2-(methylsulfonyl)ethyl]piperazine

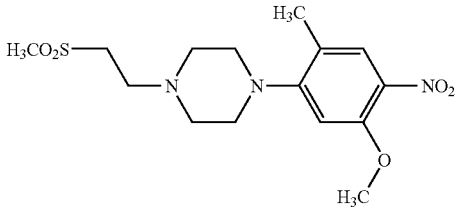

5-fluoro-4-methyl-2-nitrophenyl methyl ether (Example 113, step B) (5.0 g, 27 mmol), $K_2CO_3$ (11.2 g, 81 mmol), and 1-[2-(methylsulfonyl)ethyl]piperazine hydrochloride (8.0 g, 35 mmol) were weighed into a 150 mL sealed tube, taken up in 85 mL of DMSO and heated to 100° C. for 24 h. The mixture was poured into 500 mL of $H_2O$, filtered, washed with $H_2O$, air dried for 15 min, washed with hexanes (200 mL), washed with 20% Ether/Hexanes (200 mL), and air dried for 2 h to give the title compound of step C (6.6 g, 18.5 mmol, 68%). An additional (540 mg, 5.5%) of product was obtained by extraction of the $H_2O$ layer, followed by flash chromatography. $^1$H NMR (400 MHz, DMSO-$d_6$) δ ppm 7.75 (s, 1H), 6.70 (s, 1H), 3.90 (s, 3H), 3.31-3.35 (m, 2H), 3.04 (s, 3H), 2.99-3.03 (m, 4H), 2.77 (t, J=6.60 Hz, 2H), 2.56-2.63 (m, 4H), 2.19 (s, 3H).

Step D: 5-methyl-2-(methyloxy)-4-{4-[2-(methylsulfonyl)ethyl]-1-piperazinyl}aniline

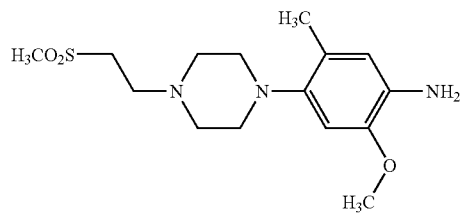

1-[2-methyl-5-(methyloxy)-4-nitrophenyl]-4-[2-(methylsulfonyl)ethyl]piperazine from a separate batch (0.257 g, 0.72 mmol) was placed in a 40 mL high vial and dissolved in 10 mL of 1 to 1 EtOAc/MeOH. 5 wt % Platinum(sulfided)/carbon (0.165 g, 0.043 mmol) was added followed quickly by a screw cap septum. The vial was evacuated and filled with $N_2$ six times to remove any oxygen. The vial was then pressurized with $H_2$ (balloon). The solution stirred overnight. The next morning the vessel was evacuated and filled with $N_2$ six times to remove any $H_2$. The solution was filtered through celite and evaporated to afford the title compound of step D (0.194 g, 0.59 mmol, 82%). $^1$H NMR (400 MHz, $CDCl_3$) δ ppm 6.54 (s, 2H), 3.80 (s, 3H), 3.30-3.37 (m, 2H), 3.07 (s, 3H), 2.91-2.98 (m, 6H), 2.82-2.90 (m, 4H), 2.15 (s, 3H).

Step E: N-(2,6-difluorophenyl)-3-(3-{2-[(5-methyl-2-(methyloxy)-4-{4-[2-(methylsulfonyl)-ethyl]-1-piperazinyl}phenyl)amino]-4-pyrimidinyl}imidazo[1,2-a]pyridin-2-yl)benzamide 3-[3-(2-chloro-4-pyrimidinyl)imidazo[1,2-a]pyridin-2-yl]-N-(2,6-difluorophenyl)-benzamide (Intermediate Example 1) (90 mg, 0.195 mmol), 5-methyl-2-(methyloxy)-4-{4-[2-(methylsulfonyl)ethyl]-1-piperazinyl}aniline (57 mg, 0.175 mmol), and p-toluenesulfonic acid (89 mg, 0.47 mmol) were weighed into a 20 mL vial. 10 mL of iPrOH was added and the mixture was heated to 120° C. for 48 h. The mixture was transferred to a 50 mL round bottom and neutralized with 2 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (65 mg, 0.086 mmol, 49%). $^1$H NMR (400 MHz, DMSO-$d_6$) δ ppm 10.22 (s, 1H), 9.39 (s, 1H), 8.46 (s, 1H), 8.32 (s, 1H), 8.22 (d, J=5.31 Hz, 1H), 8.04 (d, J=7.69 Hz, 1H), 7.80 (d, J=7.87 Hz, 1H), 7.72 (d, J=8.97 Hz, 1H), 7.59 (t, J=7.69 Hz, 1H), 7.42-7.51 (m, 2H), 7.34-7.42 (m, 1H), 7.13-7.23 (m, 2H), 6.97 (t, J=6.68 Hz, 1H), 6.75 (s, 1H), 6.48 (d, J=5.31 Hz, 1H), 3.79 (s, 3H), 3.30-3.35 (m, 2H), 3.05 (s, 3H), 2.82-2.90 (m, 4H), 2.76 (t, J=6.68 Hz, 2H), 2.53-2.64 (m, 4H), 2.13 (s, 3H). MS (ESI): 753 [M+H]$^+$.

Example 149

N-(2,6-difluorophenyl)-5-(3-{2-[(5-methyl-2-(methyloxy)-4-{4-[2-(methylsulfonyl)ethyl]-1-piperazinyl}phenyl)amino]-4-pyrimidinyl}imidazo[1,2-a]pyridin-2-yl)-2-(methyloxy)benzamide

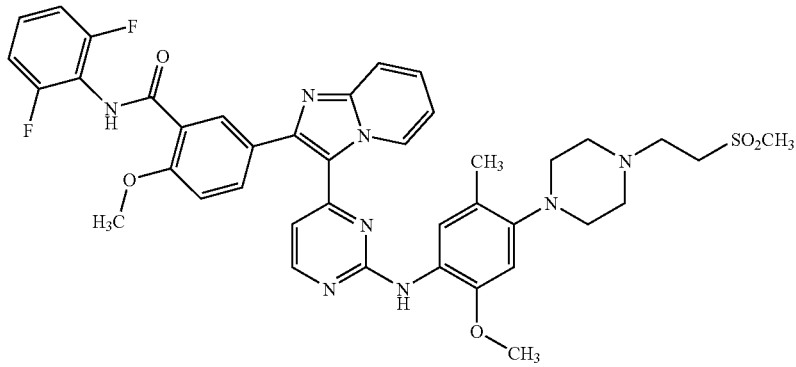

5-[3-(2-Chloro-4-pyrimidinyl)imidazo[1,2-a]pyridin-2-yl]-N-(2,6-difluorophenyl)-2-(methyloxy)benzamide (Intermediate Example 2) (100 mg, 0.203 mmol), 5-methyl-2-(methyloxy)-4-{4-[2-(methylsulfonyl)ethyl]-1-piperazinyl}aniline (Example 148, step D) (60 mg, 0.183 mmol), and p-toluenesulfonic acid (93 mg, 0.49 mmol) were weighed into a 20 mL vial. 10 mL of iPrOH was added and the mixture was heated to 120° C. for 48 h. The mixture was transferred to a 50 mL round bottom and neutralized with 2 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (65 mg, 0.086 mmol, 49%). $^1$H NMR (400 MHz, DMSO-d$_6$) δ ppm 9.77 (s, 1H), 9.35 (s, 1H), 8.45 (s, 1H), 8.22 (d, J=5.31 Hz, 1H), 8.09 (d, J=2.01 Hz, 1H), 7.76 (dd, J=8.61, 2.01 Hz, 1H), 7.68 (d, J=8.97 Hz, 1H), 7.49 (s, 1H), 7.40-7.45 (m, 1H), 7.33-7.40 (m, 1H), 7.27 (d, J=8.79 Hz, 1H), 7.17 (t, J=8.06 Hz, 2H), 6.94 (t, J=6.87 Hz, 1H), 6.75 (s, 1H), 6.55 (d, J=5.31 Hz, 1H), 3.97 (s, 3H), 3.79 (s, 3H), 3.31-3.35 (m, 2H), 3.05 (s, 3H), 2.82-2.90 (m, 4H), 2.76 (t, J=6.68 Hz, 2H), 2.53-2.65 (m, 4H), 2.13 (s, 3H). MS (ESI): 783 [M+H]$^+$.

Example 150

N-(2,6-difluorophenyl)-2-(ethyloxy)-5-(3-{2-[(5-methyl-2-(methyloxy)-4-{4-[2-(methylsulfonyl)ethyl]-1-piperazinyl}phenyl)amino]-4-pyrimidinyl}imidazo[1,2-a]pyridin-2-yl)benzamide

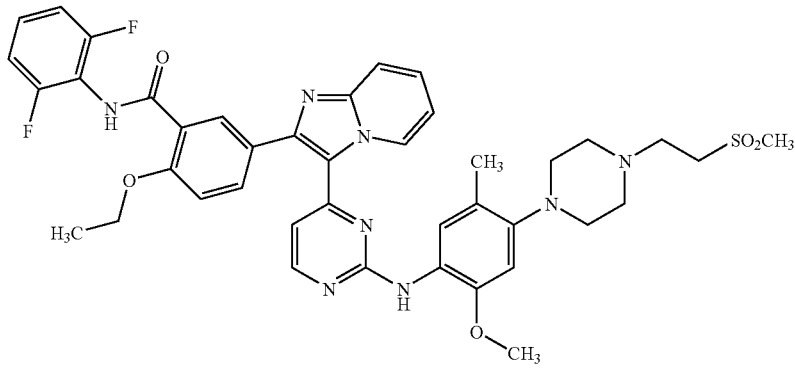

5-[3-(2-chloro-4-pyrimidinyl)imidazo[1,2-a]pyridin-2-yl]-N-(2,6-difluorophenyl)-2-(ethyloxy)benzamide (Intermediate Example 6) (115 mg, 0.227 mmol), 5-methyl-2-(methyloxy)-4-{4-[2-(methylsulfonyl)ethyl]-1-piperazinyl}aniline (Example 148, step D) (67 mg, 0.204 mmol), and p-toluenesulfonic acid (93 mg, 0.49 mmol) were weighed into a 20 mL vial. 10 mL of iPrOH was added and the mixture was heated to 120° C. for 48 h. The mixture was transferred to a 50 mL round bottom and neutralized with 2 mL of 0.5 N sodium methoxide. The solvent was rotovapeddown. The residue was taken up in 10 mL of DCM. 1 g of silica gel was added. The solvent was rotovaped down and the pre-adsorbed solids were purified by flash chromatography to give the title compound (82 mg, 0.103 mmol, 57%). ¹H NMR (400 MHz, DMSO-d₆) δ ppm 9.73 (s, 1H), 9.36 (s, 1H), 8.46 (s, 1H), 8.22 (d, J=5.31 Hz, 1H), 8.03 (d, J=2.01 Hz, 1H), 7.73 (dd, J=8.61, 2.01 Hz, 1H), 7.68 (d, J=8.97 Hz, 1H), 7.49 (s, 1H), 7.40-7.45 (m, 1H), 7.32-7.39 (m, 1H), 7.25 (d, J=8.61 Hz, 1H), 7.18 (t, J=8.15 Hz, 2H), 6.94 (t, J=6.87 Hz, 1H), 6.75 (s, 1H), 6.54 (d, J=5.31 Hz, 1H), 4.25 (q, J=6.78 Hz, 2H), 3.79 (s, 3H), 3.31-3.34 (m, 2H), 3.05 (s, 3H), 2.82-2.89 (m, 4H), 2.76 (t, J=6.68 Hz, 2H), 2.52-2.63 (m, 4H), 2.13 (s, 3H), 1.41 (t, J=6.87 Hz, 3H). MS (ESI): 797 [M+H]⁺.

Example 151

N-(2,6-difluorophenyl)-5-[3-(2-{[2-(ethyloxy)-4-(4-propyl-1-piperazinyl)phenyl]amino}-4-pyrimidinyl)imidazo[1,2-a]pyridin-2-yl]-2-(methyloxy)benzamide

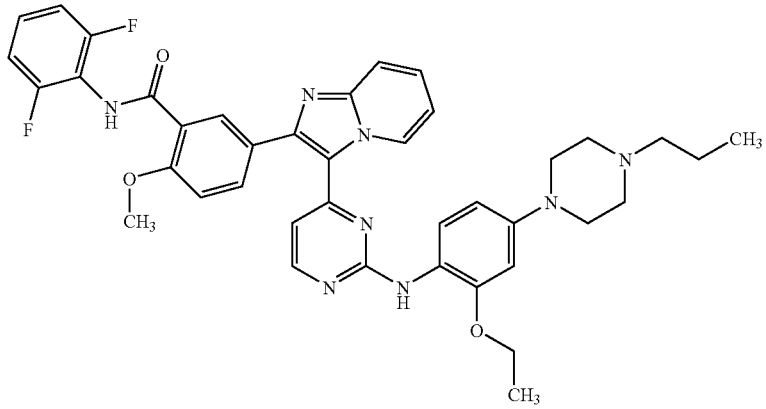

Step A:
1-[3-(ethyloxy)-4-nitrophenyl]-4-propylpiperazine

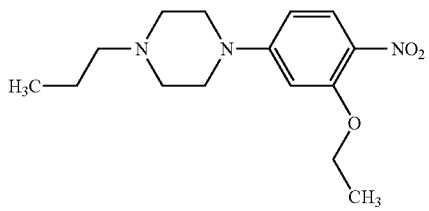

To 1-[3-(ethyloxy)-4-nitrophenyl]piperazine (Example 143, step A) (0.405 g, 1.61 mmol) in 10 mL of dioxane was added, 1-iodopropane (0.55 g, 3.22 mmol). The mixture was heated to 102° C. for 1 h. The solvent was rotovaped down and the crude product was purified by flash chromatography to give the title compound of step A (0.422 g, 1.44 mmol, 90%). ¹H NMR (400 MHz, CD₃OD) δ ppm 7.88 (d, J=9.34 Hz, 1H), 6.53 (dd, J=9.34, 2.56 Hz, 1H), 6.49 (d, J=2.56 Hz, 1H), 4.16 (q, J=7.02 Hz, 2H), 3.42-3.48 (m, 4H), 2.64-2.70 (m, 4H), 2.40-2.48 (m, 2H), 1.54-1.64 (m, 2H), 1.42 (t, J=6.96 Hz, 3H), 0.94 (t, J=7.42 Hz, 3H).

Step B:
2-(ethyloxy)-4-(4-propyl-1-piperazinyl)aniline

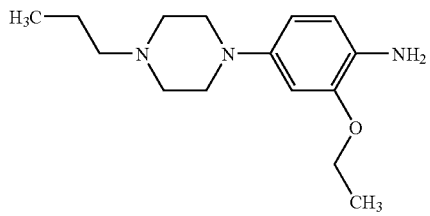

1-[3-(Ethyloxy)-4-nitrophenyl]-4-propylpiperazine (0.422 g, 1.44 mmol) was placed in a 40 mL high vial and dissolved in 10 mL of 1 to 1 EtOAc/MeOH. 5 wt % Platinum (sulfided)/carbon (0.28 g, 0.072 mmol) was added followed quickly by a screw cap septum. The vial was evacuated and filled with N₂ six times to remove any oxygen. The vial was then pressurized with H₂ (balloon). The solution stirred overnight. The next morning the vessel was evacuated and filled with N₂ six times to remove any H₂. The solution was filtered through celite and evaporated to afford the title compound of step B (0.295 g, 1.12 mmol, 78%). ¹H NMR (400 MHz, DMSO-d₆) δ ppm 6.45-6.53 (m, 2H), 6.28 (dd, J=8.33, 2.11 Hz, 1H), 3.95 (q, J=6.96 Hz, 2H), 2.96-3.07 (m, 4H), 2.84-2.95 (m, 4H), 2.63-2.74 (m, 2H), 1.50-1.60 (m, 2H), 1.27-1.32 (m, 3H), 0.87 (t, J=7.42 Hz, 3H).

Step C: N-(2,6-difluorophenyl)-5-[3-(2-{[2-(ethyloxy)-4-(4-propyl-1-piperazinyl)phenyl]-amino}-4-pyrimidinyl)imidazo[1,2-a]pyridin-2-yl]-2-(methyloxy)benzamide 5-[3-(2-Chloro-4-pyrimidinyl)imidazo[1,2-a]pyridin-2-yl]-N-(2,6-difluorophenyl)-2-(methyloxy)benzamide (Intermediate Example 2) (100 mg, 0.2 mmol), 2-(ethyloxy)-4-(4-propyl-1-piperazinyl)aniline (48 mg, 0.18 mmol), and p-toluenesulfonic acid (93 mg, 0.49 mmol) were weighed into a 20 mL vial. 7 mL of iPrOH was added and the mixture was heated to 130° C. for 48 h. The mixture was transferred to a 50 mL round bottom and neutralized with 3 mL of 0.5 N sodium methoxide 1 g of silica gel was added. The solvent was rotovaped down and the pre-adsorbed solids were purified by flash chromatography to give the title compound (52 mg, 0.072 mmol, 40%). ¹H NMR (400 MHz, DMSO-d₆) δ ppm 9.78 (s, 1H), 9.32 (s, 1H), 8.35 (s, 1H), 8.21 (d, J=5.31 Hz, 1H), 8.09 (d, J=2.01 Hz, 1H), 7.76 (dd, J=8.61, 2.01 Hz, 1H), 7.68 (d, J=8.97 Hz, 1H), 7.35-7.45 (m, 3H), 7.26 (d, J=8.79 Hz, 1H), 7.17 (t, J=8.06 Hz, 2H), 6.92 (t, J=6.87 Hz, 1H), 6.64 (d, J=2.20 Hz, 1H), 6.53 (d, J=5.31 Hz, 1H), 6.46 (dd, J=8.79, 2.38 Hz, 1H), 4.04 (q, J=6.96 Hz, 2H), 3.97 (s, 3H), 3.07-3.13 (m, 4H), 2.43-2.51 (m, 4H), 2.26 (t, J=7.23 Hz, 2H), 1.40-1.50 (m, J=7.36, 7.36, 7.36, 7.36, 7.36 Hz, 2H), 1.22 (t, J=6.96 Hz, 3H), 0.85 (t, J=7.42 Hz, 3H). MS (ESI): 719 [M+H]⁺.

Example 152

N-(2,6-difluorophenyl)-2-(ethyloxy)-5-[3-(2-{[2-(ethyloxy)-4-(4-propyl-1-piperazinyl)phenyl]amino}-4-pyrimidinyl)imidazo[1,2-a]pyridin-2-yl]benzamide

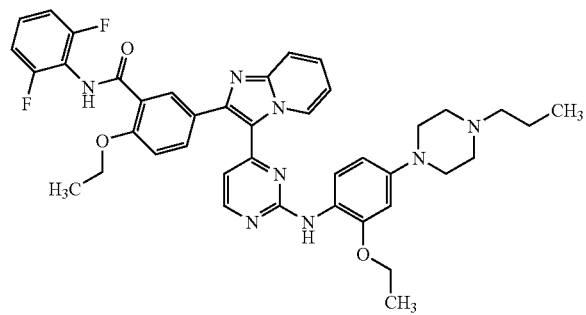

5-[3-(2-chloro-4-pyrimidinyl)imidazo[1,2-a]pyridin-2-yl]-N-(2,6-difluorophenyl)-2-(ethyloxy)benzamide (Intermediate Example 6) (100 mg, 0.2 mmol), 2-(ethyloxy)-4-(4-propyl-1-piperazinyl)aniline (Example 151, step B) (47 mg, 0.18 mmol), and p-toluenesulfonic acid (90 mg, 0.48 mmol) were weighed into a 20 mL vial. 7 mL of iPrOH was added and the mixture was heated to 130° C. for 72 h. The mixture was transferred to a 50 mL round bottom and neutralized with 3 mL of 0.5 N sodium methoxide 1 g of silica gel was added. The solvent was rotovaped down and the pre-adsorbed solids were purified by flash chromatography to give the title compound (67 mg, 0.091 mmol, 52%). ¹H NMR (400 MHz, DMSO-d₆) δ ppm 9.73 (s, 1H), 9.33 (s, 1H), 8.35 (s, 1H), 8.21 (d, J=5.13 Hz, 1H), 8.04 (d, J=2.01 Hz, 1H), 7.72 (dd, J=8.61, 2.01 Hz, 1H), 7.68 (d, J=8.97 Hz, 1H), 7.34-7.45 (m, 3H), 7.24 (d, J=8.61 Hz, 1H), 7.18 (t, J=8.06 Hz, 2H), 6.92 (t, J=6.59 Hz, 1H), 6.64 (d, J=2.20 Hz, 1H), 6.53 (d, J=5.13 Hz, 1H), 6.45 (dd, J=8.70, 2.47 Hz, 1H), 4.24 (q, J=6.78 Hz, 2H), 4.04 (q, J=6.96 Hz, 2H), 3.06-3.16 (m, 4H), 2.43-2.52 (m, 4H), 2.25 (t, J=6.96 Hz, 2H), 1.39-1.48 (m, 5H), 1.22 (t, J=6.96 Hz, 3H), 0.85 (t, J=7.33 Hz, 3H). MS (ESI): 733 [M+H]⁺.

Example 153

N-(2,6-difluorophenyl)-3-[3-(2-{[2-(ethyloxy)-4-(4-propyl-1-piperazinyl)phenyl]amino}-4-pyrimidinyl)imidazo[1,2-a]pyridin-2-yl]benzamide

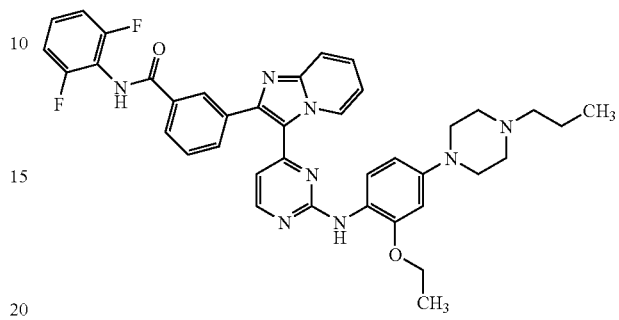

3-[3-(2-Chloro-4-pyrimidinyl)imidazo[1,2-a]pyridin-2-yl]-N-(2,6-difluorophenyl)-benzamide (Intermediate Example 1) (100 mg, 0.22 mmol), 2-(ethyloxy)-4-(4-propyl-1-piperazinyl)aniline (Example 151, step B) (51 mg, 0.19 mmol), and p-toluenesulfonic acid (98 mg, 0.52 mmol) were weighed into a 20 mL vial. 7 mL of iPrOH was added and the mixture was heated to 120° C. for 48 h. The mixture was transferred to a 50 mL round bottom and neutralized with 3 mL of 0.5 N sodium methoxide 1 g of silica gel was added. The solvent was rotovaped down and the pre-adsorbed solids were purified by flash chromatography to give the title compound (64 mg, 0.093 mmol, 47%). ¹H NMR (400 MHz, DMSO-d₆) δ ppm 10.23 (s, 1H), 9.35 (s, 1H), 8.34 (d, J=15.93 Hz, 2H), 8.21 (d, J=5.31 Hz, 1H), 8.03 (d, J=7.87 Hz, 1H), 7.80 (d, J=7.69 Hz, 1H), 7.71 (d, J=8.97 Hz, 1H), 7.59 (t, J=7.78 Hz, 1H), 7.35-7.46 (m, 3H), 7.16-7.22 (m, 2H), 6.95 (t, J=6.78 Hz, 1H), 6.64 (d, J=2.20 Hz, 1H), 6.43-6.48 (m, 2H), 4.04 (q, J=6.96 Hz, 2H), 3.07-3.13 (m, 4H), 2.42-2.51 (m, 4H), 2.25 (t, J=7.33 Hz, 2H), 1.40-1.48 (m, 2H), 1.22 (t, J=6.96 Hz, 3H), 0.85 (t, J=7.33 Hz, 3H). MS (ESI): 689 [M+H]⁺.

Example 154

N-(2,6-difluorophenyl)-5-[3-(2-{[2-(ethyloxy)-4-(1-propyl-4-piperidinyl)phenyl]amino}-4-pyrimidinyl)imidazo[1,2-a]pyridin-2-yl]-2-(methyloxy)benzamide

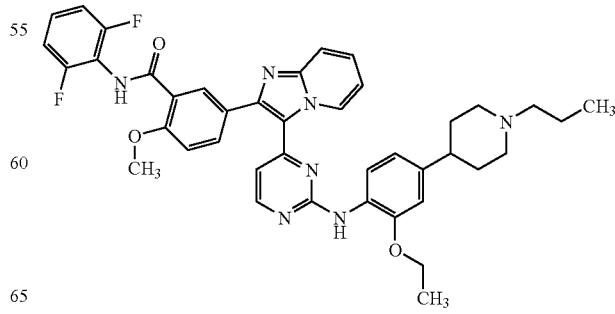

Step A: 4-[3-(ethyloxy)-4-nitrophenyl]pyridine

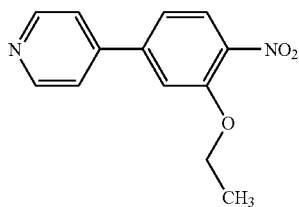

A solution of 5-bromo-2-nitrophenyl ethyl ether (Example 146, step A) (4.5 g, 18.3 mmol), PdCl₂(dppf)*DCM (1.34 g, 1.82 mmol) and 4-pyridylboronic acid (4.5 g, 36.6 mmol) in N,N-dimethylacetamide (110 mL) was deoxygenated by bubbling with $N_2$ (g) for ca 15 min. To this solution was added degassed 1.6 N $K_2CO_3$ (aq) (55 mL, 6.0 equiv.) and the resulting slurry was warmed to 80° C. for 24 h. The N,N-dimethylacetamide was removed under reduced pressure and the solids were taken up in EtOAc, filtered to remove insoluble solids, washed with $H_2O$, and dried ($Na_2SO_4$). The solvent was rotovaped down and the crude product was purified by flash chromatography to give the title compound of step A (2.46 g, 10.1 mmol, 55%). ¹H NMR (400 MHz, CDCl₃) δ ppm 8.72 (dd, J=4.67, 1.56 Hz, 2H), 7.93 (d, J=8.06 Hz, 1H), 7.45-7.51 (m, 2H), 7.21-7.26 (m, 2H), 4.26 (q, J=6.96 Hz, 2H), 1.51 (t, J=6.96 Hz, 3H).

Step B: 1-(2,4-dinitrophenyl)-4-[3-(ethyloxy)-4-nitrophenyl]pyridinium chloride

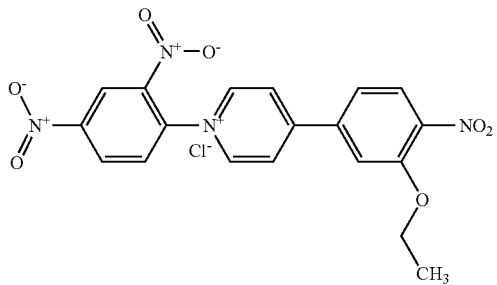

To 4-[3-(ethyloxy)-4-nitrophenyl]pyridine (2.2 g, 9.0 mmol) in 80 mL of EtOH was added, 1-chloro-2,4-dinitrobenzene (14.6 g, 72.06 mmol). The mixture was heated to 102° C. for 72 h. The mixture was cooled and rotovaped down. The product was taken up in acetone. The resulting slurry was filtered and washed with acetone. The product was dried under vacuum to give the title compound of step B (3.7 g, 7.93 mmol, 92%). MS (ESI): 411 [M+H]⁺.

Step C: 4-[3-(ethyloxy)-4-nitrophenyl]-1-propylpyridinium acetate

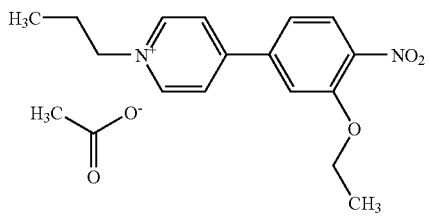

To 1-(2,4-dinitrophenyl)-4-[3-(ethyloxy)-4-nitrophenyl]pyridinium chloride (1.2 g, 2.57 mmol) in 10 mL of MeOH was added, propylamine (0.151 g, 2.57 mmol). The mixture was heated to 100° C. for 4 h. The mixture was cooled and rotovaped down. The product was taken up in acetone. This solution was loaded onto a short silica gel column and eluted with EtOAc (~500 mL) to remove the aniline by product. The product was then eluted with 300 mL of (10% HOAc/10% MeOH/80% DCM). The solvent was rotovaped down to give the title compound of step C (0.84 g, 2.42 mmol, 94%). ¹H NMR (400 MHz, DMSO-d₆) δ ppm 9.23 (d, J=6.96 Hz, 2H), 8.63 (d, J=6.96 Hz, 2H), 8.07 (d, J=8.42 Hz, 1H), 7.90 (d, J=1.65 Hz, 1H), 7.74 (dd, J=8.42, 1.83 Hz, 1H), 4.59 (t, J=7.23 Hz, 2H), 4.38 (q, J=7.08 Hz, 2H), 1.91-2.00 (m, 2H), 1.86 (s, 3H), 1.35 (t, J=6.96 Hz, 3H), 0.89 (t, J=7.33 Hz, 3H).

Step D: 4-[3-(ethyloxy)-4-nitrophenyl]-1-propyl-1,2,3,6-tetrahydropyridine

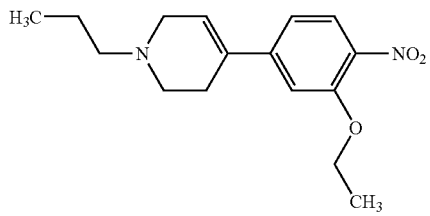

To 4-[3-(ethyloxy)-4-nitrophenyl]-1-propylpyridinium acetate (0.84 g, 2.42 mmol) in 25 mL of MeOH at 0° C. was added, NaBH₄ (0.275 g, 7.28 mmol) over 1 h. The mixture was allowed to come to rt over 2 h. The solvent was reduced to approximately 5 mL and then diluted with EtOAc, washed with conc. NaHCSO₃, dried (Na₂SO₄), filtered, rotovaped down, and purified by flash chromatography to give the title compound of step D (0.536 g, 1.85 mmol, 76%). ¹H NMR (400 MHz, DMSO-d₆) δ ppm 7.80 (d, J=8.61 Hz, 1H), 7.23 (d, J=1.46 Hz, 1H), 7.11 (dd, J=8.42, 1.65 Hz, 1H), 6.37 (t, J=3.57 Hz, 1H), 4.23 (q, J=6.96 Hz, 2H), 3.06 (d, J=3.11 Hz, 2H), 2.58 (t, J=5.59 Hz, 2H), 2.44-2.50 (m, 2H), 2.29-2.35 (m, 2H), 1.41-1.51 (m, J=7.36, 7.36, 7.36, 7.36, 7.36 Hz, 2H), 1.31 (t, J=6.96 Hz, 3H), 0.85 (t, J=7.33 Hz, 3H).

Step E: 2-(2-ethyloxy)-4-(1-propyl-4-piperidinyl)aniline

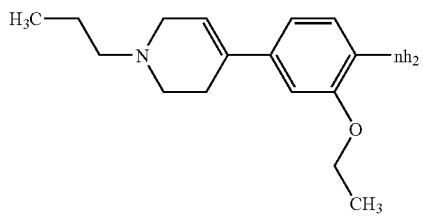

4-[3-(ethyloxy)-4-nitrophenyl]-1-propyl-1,2,3,6-tetrahydropyridine (0.536 g, 1.85 mmol) was place in a 40 mL high vial and dissolved in 10 mL of 1 to 1 EtOAc/MeOH. 5 wt % Platinum(sulfided)/carbon (0.196 g, 0.092 mmol) was added followed quickly by a screw cap septum. The vial was evacuated and filled with $N_2$ six times to remove any oxygen. The vial was then pressurized with $H_2$ (balloon). The solution stirred overnight. The next morning the vessel was evacuated and filled with $N_2$ six times to remove any $H_2$. The solution was filtered through celite and evaporated to afford the title compound of step E (0.491 g, 1.87 mmol, 99%). ¹H NMR (400 MHz, DMSO-d₆) δ ppm 6.61 (d, J=1.10 Hz, 1H), 6.47-6.53 (m, 2H), 4.41 (bs, 2H), 3.95 (q, J=6.96 Hz, 2H), 2.91 (d, J=10.07 Hz, 2H), 2.19-2.31 (m, 3H), 1.86-1.97 (m, 2H), 1.61-1.68 (m, 2H), 1.56 (td, J=12.18, 3.11 Hz, 2H), 1.37-1.47 (m, 2H), 1.29 (t, J=6.96 Hz, 3H), 0.83 (t, J=7.33 Hz, 3H).

Step F: N-(2,6-difluorophenyl)-5-[3-(2-{[2-(ethyloxy)-4-(1-propyl-4-piperidinyl)phenyl]-amino}-4-pyrimidinyl)imidazo[1,2-a]pyridin-2-yl]-2-(methyloxy)benzamide 5-[3-(2-chloro-4-pyrimidinyl)imidazo[1,2-a]pyridin-2-yl]-N-(2,6-difluorophenyl)-2-(methyloxy)benzamide (Intermediate Example 2) (100 mg, 0.2 mmol), 2-(2-ethyloxy)-4-(1-propyl-4-piperidinyl)aniline (48 mg, 0.18 mmol), and p-toluenesulfonic acid (93 mg, 0.49 mmol) were weighed into a 20 mL vial. 7 mL of iPrOH was added and the mixture was heated to 120° C. for 48 h. The mixture was transferred to a 50 mL round bottom and neutralized with 3 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (75 mg, 0.104 mmol, 57%). $^1$H NMR (400 MHz, DMSO-$d_6$) δ ppm 9.77 (s, 1H), 9.33 (d, J=6.78 Hz, 1H), 8.41 (s, 1H), 8.26 (d, J=5.13 Hz, 1H), 8.10 (d, J=1.83 Hz, 1H), 7.76 (dd, J=8.52, 1.92 Hz, 1H), 7.64-7.72 (m, 2H), 7.40-7.46 (m, 1H), 7.33-7.40 (m, 1H), 7.26 (d, J=8.61 Hz, 1H), 7.17 (t, J=8.06 Hz, 2H), 6.90-6.97 (m, 2H), 6.77 (d, J=8.24 Hz, 1H), 6.61 (d, J=5.31 Hz, 1H), 4.08 (q, J=6.96 Hz, 2H), 3.96 (s, 3H), 2.90-3.01 (m, 2H), 2.39-2.45 (m, 1H), 2.20-2.32 (m, 2H), 1.90-2.02 (m, 2H), 1.70-1.79 (m, 2H), 1.58-1.70 (m, 2H), 1.39-1.50 (m, 2H), 1.27 (t, J=6.96 Hz, 3H), 0.84 (t, J=7.33 Hz, 3H). MS (ESI): 718 [M+H]$^+$.

Example 155

N-(2,6-difluorophenyl)-3-[3-(2-{[2-(ethyloxy)-4-(1-propyl-4-piperidinyl)phenyl]amino}-4-pyrimidinyl)imidazo[1,2-a]pyridin-2-yl]benzamide

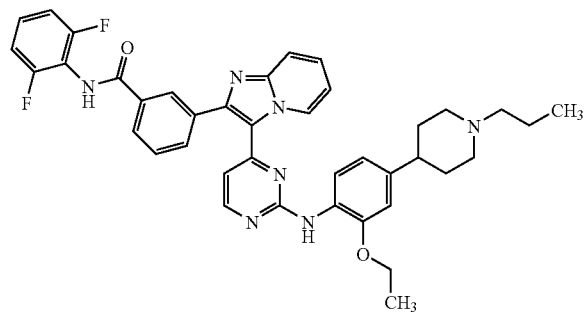

3-[3-(2-Chloro-4-pyrimidinyl)imidazo[1,2-a]pyridin-2-yl]-N-(2,6-difluorophenyl)-benzamide (Intermediate Example 1) (100 mg, 0.22 mmol), 2-(2-ethyloxy)-4-(1-propyl-4-piperidinyl)aniline (Example 154, step E) (51 mg, 0.19 mmol), and p-toluenesulfonic acid (98 mg, 0.51 mmol) were weighed into a 20 mL vial. 7 mL of iPrOH was added and the mixture was heated to 130° C. for 48 h. The mixture was transferred to a 50 mL round bottom and neutralized with 3 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (32 mg, 0.112 mmol, 24%). $^1$H NMR (400 MHz, DMSO-$d_6$) δ ppm 10.23 (s, 1H), 9.36 (d, J=6.78 Hz, 1H), 8.41 (s, 1H), 8.33 (s, 1H), 8.27 (d, J=5.31 Hz, 1H), 8.04 (d, J=7.87 Hz, 1H), 7.80 (d, J=7.87 Hz, 1H), 7.73 (d, J=8.97 Hz, 1H), 7.65 (d, J=8.06 Hz, 1H), 7.59 (t, J=7.78 Hz, 1H), 7.42-7.49 (m, 1H), 7.34-7.42 (m, 1H), 7.19 (t, J=8.06 Hz, 2H), 6.98 (t, J=6.78 Hz, 1H), 6.93 (s, 1H), 6.76 (d, J=8.42 Hz, 1H), 6.55 (d, J=5.13 Hz, 1H), 4.08 (q, J=6.90 Hz, 2H), 2.88-3.00 (m, 2H), 2.38-2.45 (m, 1H), 2.19-2.30 (m, 2H), 1.87-1.99 (m, 2H), 1.63-1.75 (m, 4H), 1.39-1.49 (m, 2H), 1.26 (t, J=6.96 Hz, 3H), 0.84 (t, J=7.23 Hz, 3H). MS (ESI): 688 [M+H]$^+$.

Example 156

N-(2,6-difluorophenyl)-2-(ethyloxy)-5-[3-(2-{[2-(ethyloxy)-4-(1-propyl-4-piperidinyl)phenyl]amino}-4-pyrimidinyl)imidazo[1,2-a]pyridin-2-yl]benzamide

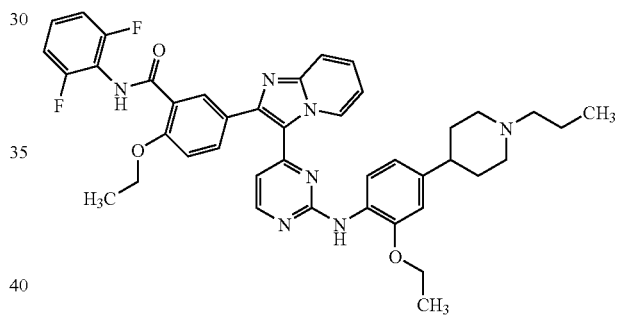

5-[3-(2-chloro-4-pyrimidinyl)imidazo[1,2-a]pyridin-2-yl]-N-(2,6-difluorophenyl)-2-(ethyloxy)benzamide (Intermediate Example 6) (100 mg, 0.2 mmol), 2-(2-ethyloxy)-4-(1-propyl-4-piperidinyl)aniline (Example 154, step E) (47 mg, 0.18 mmol), and p-toluenesulfonic acid (90 mg, 0.47 mmol) were weighed into a 20 mL vial. 7 mL of iPrOH was added and the mixture was heated to 130° C. for 48 h. The mixture was transferred to a 50 mL round bottom and neutralized with 3 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (82 mg, 0.112 mmol, 63%). $^1$H NMR (400 MHz, DMSO-$d_6$) δ ppm 9.73 (s, 1H), 9.32 (d, J=6.78 Hz, 1H), 8.40 (s, 1H), 8.26 (d, J=5.13 Hz, 1H), 8.05 (d, J=2.01 Hz, 1H), 7.72 (dd, J=8.70, 2.11 Hz, 1H), 7.64-7.71 (m, 2H), 7.40-7.45 (m, 1H), 7.32-7.40 (m, 1H), 7.24 (d, J=8.61 Hz, 1H), 7.17 (t, J=8.06 Hz, 2H), 6.91-6.97 (m, 2H), 6.76 (dd, J=8.24, 1.47 Hz, 1H), 6.61 (d, J=5.13 Hz, 1H), 4.24 (q, J=6.71 Hz, 2H), 4.08 (q, J=6.96 Hz, 2H), 2.93 (d, J=10.80 Hz, 2H), 2.38-2.45 (m, J=4.03 Hz, 1H), 2.16-2.27 (m, 2H), 1.91 (d, J=9.71 Hz, 2H), 1.67-1.75 (m, 2H), 1.64 (dd, J=12.00, 2.84 Hz, 2H), 1.38-1.46 (m, 5H), 1.26 (t, J=6.87 Hz, 3H), 0.84 (t, J=7.33 Hz, 3H). MS (ESI): 732 [M+H]$^+$.

Example 157

N-(2,6-difluorophenyl)-5-[3-(2-{[5-methyl-2-(methyloxy)-4-(1-propyl-4-piperidinyl)phenyl]-amino}-4-pyrimidinyl)imidazo[1,2-a]pyridin-2-yl]-2-(methyloxy)benzamide

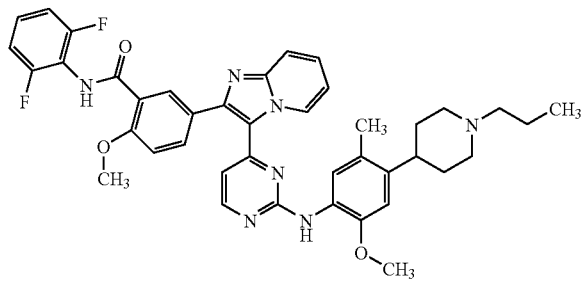

Step A:
4-[2-methyl-5-(methyloxy)-4-nitrophenyl]pyridine

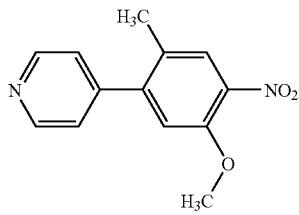

A solution of 5-bromo-4-methyl-2-nitrophenyl methyl ether (6.0 g, 24.38 mmol), PdCl$_2$(dppf)*DCM (1.43 g, 1.95 mmol) and 4-pyridylboronic acid (20.4 g, 165.8 mmol) in dioxane was deoxygenated by bubbling with N$_2$ (g) for ca 15 min. To this solution was added degassed 2.0 N Na$_2$CO$_3$ (aq) (170 mL, 14.0 equiv.) and the resulting slurry was warmed to 80° C. for 24 h. The dioxane was removed under reduced pressure and the solids were dissolved in EtOAc and washed with H$_2$O, dried (Na$_2$SO$_4$), and purified by flash chromatography to give the title compound of step A (2.81 g, 11.5 mmol, 57%). $^1$H NMR (400 MHz, CDCl$_3$) δ ppm 8.72 (d, J=4.77 Hz, 2H), 7.79 (s, 1H), 7.22-7.31 (m, 2H), 6.90 (s, 1H), 3.95 (s, 3H), 2.22 (s, 3H).

Step B: 4-[2-methyl-5-(methyloxy)-4-nitrophenyl]-1-propylpyridinium iodide

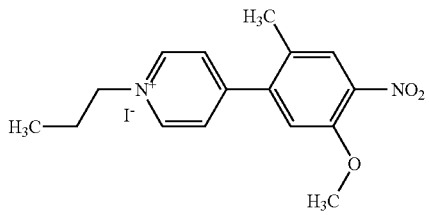

To 4-[2-methyl-5-(methyloxy)-4-nitrophenyl]pyridine (750 mg, 3.07 mmol) in 15 mL of pinacolone was added, 1-iodopropane (2.1 g, 2.66 mmol). The mixture was heated to 102° C. for 24 h. The mixture was cooled and diluted with acetone. The resulting slurry was filtered and washed with acetone. The product was dried under vacuum to give the title compound of step B (1.1 g, 14.24 mmol, 86%). $^1$H NMR (400 MHz, DMSO-d$_6$) δ ppm 9.19 (d, J=6.78 Hz, 2H), 8.30 (d, J=6.59 Hz, 2H), 7.94 (s, 1H), 7.37 (s, 1H), 4.61 (t, J=7.23 Hz, 2H), 3.93 (s, 3H), 2.26 (s, 3H), 1.92-2.02 (m, 2H), 0.92 (t, J=7.42 Hz, 3H).

Step C: 4-[2-methyl-5-(methyloxy)-4-nitrophenyl]-1-propyl-1,2,3,6-tetrahydropyridine

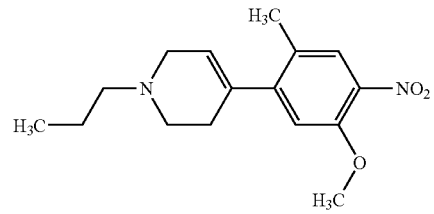

To 4-[2-methyl-5-(methyloxy)-4-nitrophenyl]-1-propylpyridinium iodide (1.04 g, 2.51 mmol) in 25 mL of MeOH at 0° C. was added, NaBH$_4$ (0.284 g, 7.53 mmol) over 1 h. The mixture was allowed to come to rt over 2 h. The solvent was reduced to approximately 5 mL and then diluted with EtOAc, washed with conc. NaHCO$_3$, dried (Na$_2$SO$_4$), filtered, rotovaped down, and purified by flash chromatography to give the title compound of step C (0.7 g, 2.41 mmol, 96%). $^1$H NMR (400 MHz, DMSO-d$_6$) δ ppm 7.71 (s, 1H), 7.00 (s, 1H), 5.61-5.67 (m, 1H), 3.87 (s, 3H), 2.98-3.07 (m, 2H), 2.60 (t, J=5.50 Hz, 2H), 2.28-2.37 (m, 4H), 2.20 (s, 3H), 1.43-1.53 (m, 2H), 0.87 (t, J=7.52 Hz, 3H).

Step D: 5-methyl-2-(methyloxy)-4-(1-propyl-4-piperidinyl)aniline

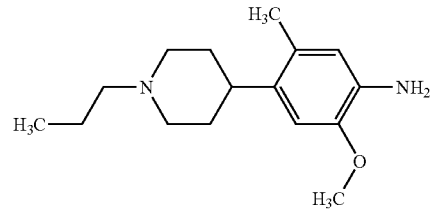

4-[2-Methyl-5-(methyloxy)-4-nitrophenyl]-1-propyl-1,2,3,6-tetrahydropyridine (0.7 g, 2.41 mmol) was place in a 250 mL high pressure vessel and dissolved in 60 mL of 1 to 1 EtOAc/MeOH. 5 wt % Platinum(sulfided)/carbon (0.256 g, 0.12 mmol) was added followed quickly by a rubber septum. The flask was evacuated and filled with N$_2$ six times to remove any oxygen. The vessel was then pressurized with H$_2$ (60 psi). The solution stirred overnight. The next morning the vessel was evacuated and filled with N$_2$ six times to remove any H$_2$. The solution was filtered through celite and evaporated to give the title compound of step D (0.577 g, 2.2 mmol, 91%). $^1$H NMR (400 MHz, DMSO-d$_6$) δ ppm 6.57 (s, 1H), 6.37 (s, 1H), 4.37 (bs, 2H), 3.69 (s, 3H), 2.88-2.98 (m, 2H), 2.43-2.52 (m, 1H), 2.19-2.29 (m, 2H), 2.06 (s, 3H), 1.91-2.01 (m, 2H), 1.53-1.64 (m, 4H), 1.38-1.48 (m, 2H), 0.84 (t, J=7.42 Hz, 3H).

Step E: N-(2,6-difluorophenyl)-5-[3-(2-{[5-methyl-2-(methyloxy)-4-(1-propyl-4-piperidinyl)phenyl]amino}-4-pyrimidinyl)imidazo[1,2-a]pyridin-2-yl]-2-(methyloxy)benzamide 5-[3-(2-chloro-4-pyrimidinyl)imidazo[1,2-a]pyridin-2-yl]-N-(2,6-difluorophenyl)-2-(methyloxy)benzamide (Intermediate Example 2) (100 mg, 0.2 mmol), 5-methyl-2-(methyloxy)-4-(1-propyl-4-piperidinyl)aniline (48 mg, 0.18 mmol), and p-toluenesulfonic acid (93 mg, 0.49 mmol) were weighed into a 20 mL vial. 7 mL of iPrOH was added and the mixture was heated to 120° C. for 48 h. The mixture was transferred to a 50 mL round bottom and neutralized with 3 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (90 mg, 0.125 mmol, 69%). $^1$H NMR (400 MHz, DMSO-$d_6$) δ ppm 9.77 (s, 1H), 9.38 (d, J=6.41 Hz, 1H), 8.46 (s, 1H), 8.24 (d, J=5.31 Hz, 1H), 8.09 (d, J=2.01 Hz, 1H), 7.76 (dd, J=8.61, 2.01 Hz, 1H), 7.69 (d, J=8.97 Hz, 1H), 7.52 (s, 1H), 7.41-7.46 (m, 1H), 7.33-7.40 (m, 1H), 7.27 (d, J=8.79 Hz, 1H), 7.17 (t, J=8.06 Hz, 2H), 6.95 (t, J=6.68 Hz, 1H), 6.89 (s, 1H), 6.57 (d, J=5.13 Hz, 1H), 3.97 (s, 3H), 3.80 (s, 3H), 2.91-3.01 (m, 2H), 2.58-2.67 (m, 1H), 2.20-2.30 (m, 2H), 2.18 (s, 3H), 1.92-2.03 (m, 2H), 1.62-1.73 (m, 4H), 1.40-1.49 (m, J=7.33, 7.33, 7.33, 7.33 Hz, 2H), 0.85 (t, J=7.33 Hz, 3H). MS (ESI): 718 [M+H]$^+$.

Example 158

N-(2,6-difluorophenyl)-2-(ethyloxy)-5-[3-(2-{[5-methyl-2-(methyloxy)-4-(1-propyl-4-piperidinyl)phenyl]amino}-4-pyrimidinyl)imidazo[1,2-a]pyridin-2-yl]benzamide

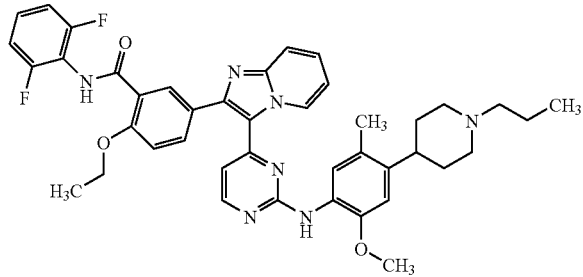

5-[3-(2-Chloro-4-pyrimidinyl)imidazo[1,2-a]pyridin-2-yl]-N-(2,6-difluorophenyl)-2-(ethyloxy)benzamide (Intermediate Example 6) (100 mg, 0.2 mmol), 5-methyl-2-(methyloxy)-4-(1-propyl-4-piperidinyl)aniline (Example 157, step D) (47 mg, 0.18 mmol), and p-toluenesulfonic acid (90 mg, 0.47 mmol) were weighed into a 20 mL vial. 7 mL of iPrOH was added and the mixture was heated to 120° C. for 48 h. The mixture was transferred to a 50 mL round bottom and neutralized with 3 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (65 mg, 0.089 mmol, 50%). $^1$H NMR (400 MHz, DMSO-$d_6$) δ ppm 9.73 (s, 1H), 9.38 (d, J=6.41 Hz, 1H), 8.46 (s, 1H), 8.24 (d, J=5.31 Hz, 1H), 8.03 (d, J=2.01 Hz, 1H), 7.66-7.76 (m, 2H), 7.53 (s, 1H), 7.41-7.46 (m, 1H), 7.32-7.41 (m, 1H), 7.25 (d, J=8.61 Hz, 1H), 7.17 (t, J=8.06 Hz, 2H), 6.95 (t, J=6.68 Hz, 1H), 6.89 (s, 1H), 6.57 (d, J=5.13 Hz, 1H), 4.25 (q, J=6.90 Hz, 2H), 3.80 (s, 3H), 2.90-3.02 (m, 2H), 2.57-2.68 (m, 1H), 2.21-2.32 (m, 2H), 2.17 (s, 3H), 1.91-2.02 (m, 2H), 1.62-1.74 (m, 4H), 1.38-1.49 (m, 5H), 0.85 (t, J=7.33 Hz, 3H). MS (ESI): 732 [M+H]$^+$.

Example 159

N-(2,6-difluorophenyl)-3-[3-(2-{[5-methyl-2-(methyloxy)-4-(1-propyl-4-piperidinyl)phenyl]amino}-4-pyrimidinyl)imidazo[1,2-a]pyridin-2-yl]benzamide

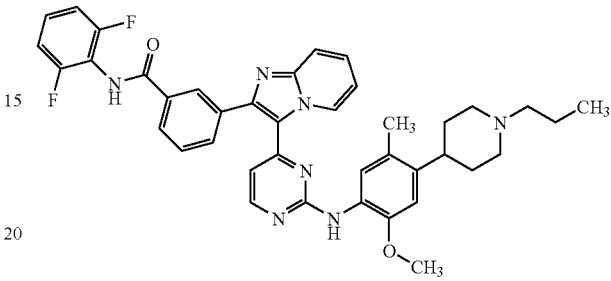

3-[3-(2-chloro-4-pyrimidinyl)imidazo[1,2-a]pyridin-2-yl]-N-(2,6-difluorophenyl)-benzamide (Intermediate Example 1) (100 mg, 0.22 mmol), 5-methyl-2-(methyloxy)-4-(1-propyl-4-piperidinyl)aniline (Example 157, step D) (51 mg, 0.19 mmol), and p-toluenesulfonic acid (99 mg, 0.52 mmol) were weighed into a 20 mL vial. 7 mL of iPrOH was added and the mixture was heated to 120° C. for 48 h. The mixture was transferred to a 50 mL round bottom and neutralized with 3 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (76 mg, 0.110 mmol, 57%). $^1$H NMR (400 MHz, DMSO-$d_6$) δ ppm 10.23 (s, 1H), 9.41 (d, J=6.41 Hz, 1H), 8.47 (s, 1H), 8.32 (s, 1H), 8.24 (d, J=5.31 Hz, 1H), 8.04 (d, J=7.87 Hz, 1H), 7.80 (d, J=7.87 Hz, 1H), 7.72 (d, J=8.97 Hz, 1H), 7.59 (t, J=7.78 Hz, 1H), 7.52 (s, 1H), 7.44-7.49 (m, 1H), 7.35-7.42 (m, 1H), 7.19 (t, J=8.15 Hz, 2H), 6.99 (t, J=6.68 Hz, 1H), 6.90 (s, 1H), 6.50 (d, J=5.31 Hz, 1H), 3.80 (s, 3H), 2.89-2.99 (m, 2H), 2.58-2.66 (m, 1H), 2.20-2.27 (m, 2H), 2.17 (s, 3H), 1.90-2.01 (m, 2H), 1.62-1.73 (m, 4H), 1.39-1.49 (m, 2H), 0.85 (t, J=7.33 Hz, 3H). MS (ESI): 688 [M+H]$^+$.

Example 160

N-(2,6-difluorophenyl)-2-(methyloxy)-5-{3-[2-({2-(methyloxy)-4-[1-(2-methylpropyl)-4-piperidinyl]phenyl}amino)-4-pyrimidinyl]imidazo[1,2-a]pyridin-2-yl}benzamide

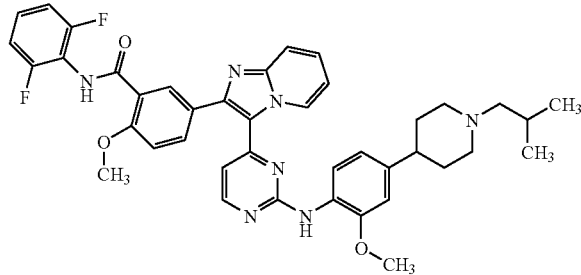

Step A: 4-[3-(methyloxy)-4-nitrophenyl]-1-(2-methylpropyl)pyridinium iodide

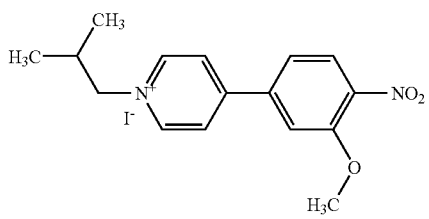

To a refluxing solution of 4-[3-(methyloxy)-4-nitrophenyl]pyridine (Example 137, step A) (1.0 g, 4.35 mmol) in anhydrous pinacolone (25 mL) was added 2-methyl-propyl iodide (2.4 mL, 22 mmol). The resulting solution was refluxed for 36 h at which time solids were collected via vacuum filtration and washed with diethyl ether to afford 3-(3-methyloxy-4-nitrophenyl)-1-isobutylpyridinium iodide as a solid (0.800 g, 1.9 mmol, 44%). Scaling of this reaction by a factor of five afforded an additional batch of 3-(3-methyloxy-4-nitrophenyl)-1-isobutylpyridinium iodide (2.55 g, 6.15 mmol, 28%) which was combined with the original batch. $^1$H NMR (400 MHz, DMSO-$d_6$) δ ppm 9.18 (d, J=7.33 Hz, 2H), 8.65 (d, J=6.97 Hz, 2H), 8.11 (d, J=8.43 Hz, 1H), 7.91 (d, J=1.83 Hz, 1H), 7.76 (dd, J=8.43, 1.83 Hz, 1H), 4.47 (d, J=7.70 Hz, 2H), 4.06 (s, 3H), 2.26 (dq, J=13.66, 6.93 Hz, 1H), 0.92 (d, J=6.60 Hz, 6H).

Step B: 4-[3-(methyloxy)-4-nitrophenyl]-1-(2-methylpropyl)-1,2,3,6-tetrahydropyridine

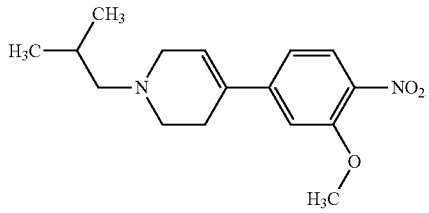

To a suspension of 3-(3-methyloxy-4-nitrophenyl)-1-isobutylpyridinium iodide (3.0 g, 7.25 mmol) in MeOH at 0° C. was added NaBH$_4$ portionwise over about 10 min (1.5 g, 36.2 mmol). The reaction was stirred for five h, concentrated under reduced pressure, diluted with saturated aqueous NaHCO$_3$ and the products extracted into EtOAc. Chromatography on SiO$_2$ (0 to 10% MeOH/DCM) affords 4-[3-(methyloxy)-4-nitrophenyl]-1-(2-methylpropyl)-1,2,3,6-tetrahydropyridine (1.9 g, 6.54 mmol, 90%) as a yellow oil. $^1$H NMR (400 MHz, CDCl$_3$) δ ppm 7.83 (d, J=8.42 Hz, 1H), 6.98-7.03 (m, 2H), 6.18 (t, J=3.39 Hz, 1H), 3.94 (s, 3H), 3.10-3.21 (m, 2H), 2.62-2.72 (m, 2H), 2.50-2.60 (m, 2H), 2.17-2.29 (m, 2H), 1.80-1.92 (m, 1H), 0.93 (d, J=6.59 Hz, 6H).

Step C: 2-(methyloxy)-4-[1-(2-methylpropyl)-4-piperidinyl]aniline

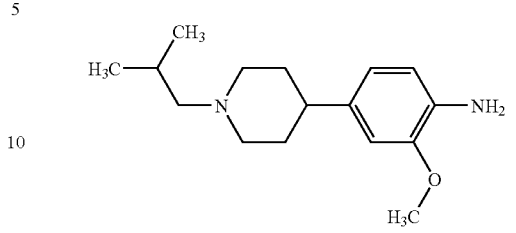

To a solution of 4-[3-(methyloxy)-4-nitrophenyl]-1-(2-methylpropyl)-1,2,3,6-tetrahydropyridine (1.90 g, 0.0655 mmol) in MeOH was added 10% Pd/carbon (0.800 g). The resulting suspension was stirred at rt under 60 psi H$_2$ overnight. Subsequent filtration through celite and concentration under reduced pressure afforded {2-(methyloxy)-4-[1-(2-methylpropyl)-4-piperidinyl]phenyl}amine (1.7 g, 89% yield) as a dark brown solid. $^1$H NMR (400 MHz, DMSO-$d_6$) δ ppm 6.63 (s, 1H), 6.51 (s, 2H), 4.44 (s, 2H), 3.72 (s, 3H), 2.87 (d, J=11.36 Hz, 2H), 2.22-2.33 (m, J=11.82, 7.79, 4.03, 3.85 Hz, 1H), 2.01 (d, J=7.33 Hz, 2H), 1.88 (td, J=11.55, 2.57 Hz, 2H), 1.75 (dt, J=13.66, 6.92 Hz, 1H), 1.60-1.67 (m, 2H), 1.56 (dd, J=12.28, 3.48 Hz, 2H), 0.84 (d, J=6.60 Hz, 6H).

Step D: N-(2,6-difluorophenyl)-5-[3-(2-{[5-methyl-2-(methyloxy)-4-(1-propyl-4-piperidinyl)phenyl]amino}-4-pyrimidinyl)imidazo[1,2-a]pyridin-2-yl]-2-(methyloxy)-benzamide 5-[3-(2-chloro-4-pyrimidinyl)imidazo[1,2-a]pyridin-2-yl]-N-(2,6-difluorophenyl)-2-(methyloxy)benzamide (Intermediate Example 2) (100 mg, 0.2 mmol), 2-(methyloxy)-4-[1-(2-methylpropyl)-4-piperidinyl]aniline (48 mg, 0.18 mmol), and p-toluenesulfonic acid (93 mg, 0.49 mmol) were weighed into a 20 mL vial. 7 mL of iPrOH was added and the mixture was heated to 120° C. for 48 h. The mixture was transferred to a 50 mL round bottom and neutralized with 3 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (52 mg, 0.072 mmol, 40%). $^1$H NMR (400 MHz, DMSO-$d_6$) δ ppm 9.78 (s, 1H), 9.37 (d, J=6.59 Hz, 1H), 8.50 (s, 1H), 8.24 (d, J=5.13 Hz, 1H), 8.10 (d, J=2.01 Hz, 1H), 7.76 (dd, J=8.61, 2.20 Hz, 1H), 7.69 (d, J=8.97 Hz, 1H), 7.65 (d, J=8.06 Hz, 1H), 7.40-7.46 (m, 1H), 7.32-7.40 (m, 1H), 7.27 (d, J=8.79 Hz, 1H), 7.17 (t, J=8.06 Hz, 2H), 6.93-6.98 (m, 2H), 6.78 (dd, J=8.24, 1.47 Hz, 1H), 6.58 (d, J=5.31 Hz, 1H), 3.97 (s, 3H), 3.82 (s, 3H), 2.90 (d, J=10.07 Hz, 2H), 2.38-2.46 (m, 1H), 1.98-2.08 (m, 2H), 1.87-1.98 (m, 2H), 1.65-1.76 (m, 5H), 0.84 (d, J=6.41 Hz, 6H). MS (ESI): 718 [M+H]$^+$.

Example 161

N-(2,6-difluorophenyl)-2-(ethyloxy)-5-{3-[2-({2-(methyloxy)-4-[1-(2-methylpropyl)-4-piperidinyl]phenyl}amino)-4-pyrimidinyl]imidazo[1,2-a]pyridin-2-yl}benzamide

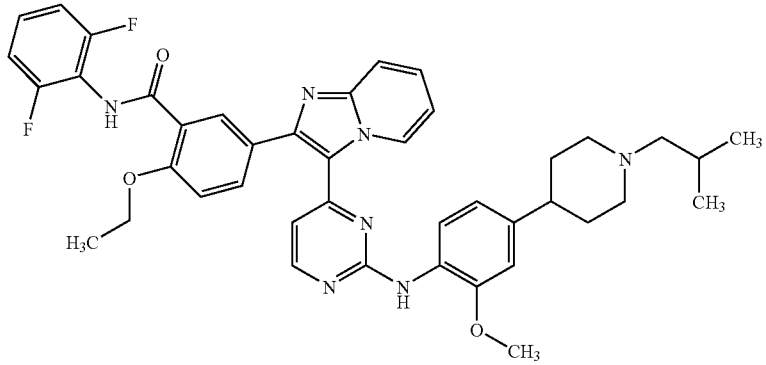

5-[3-(2-Chloro-4-pyrimidinyl)imidazo[1,2-a]pyridin-2-yl]-N-(2,6-difluorophenyl)-2-(ethyloxy)benzamide (Intermediate Example 6) (100 mg, 0.2 mmol), 2-(methyloxy)-4-[1-(2-methylpropyl)-4-piperidinyl]aniline (Example 160, step C) (47 mg, 0.18 mmol), and p-toluenesulfonic acid (90 mg, 0.47 mmol) were weighed into a 20 mL vial. 7 mL of iPrOH was added and the mixture was heated to 120° C. for 48 h. The mixture was transferred to a 50 mL round bottom and neutralized with 3 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (67 mg, 0.092 mmol, 52%). $^1$H NMR (400 MHz, DMSO-d$_6$) δ ppm 9.73 (s, 1H), 9.37 (d, J=6.78 Hz, 1H), 8.50 (s, 1H), 8.24 (d, J=5.31 Hz, 1H), 8.04 (d, J=2.01 Hz, 1H), 7.67-7.75 (m, 2H), 7.64 (d, J=8.06 Hz, 1H), 7.41-7.46 (m, 1H), 7.32-7.40 (m, 1H), 7.25 (d, J=8.79 Hz, 1H), 7.17 (t, J=8.15 Hz, 2H), 6.94-6.98 (m, 2H), 6.78 (dd, J=8.24, 1.46 Hz, 1H), 6.59 (d, J=5.31 Hz, 1H), 4.25 (q, J=6.84 Hz, 2H), 3.82 (s, 3H), 2.90 (d, J=10.44 Hz, 2H), 2.42-2.46 (m, 1H), 2.02 (d, J=7.14 Hz, 2H), 1.91 (t, J=10.44 Hz, 2H), 1.65-1.75 (m, 5H), 1.41 (t, J=6.87 Hz, 3H), 0.84 (d, J=6.41 Hz, 6H). MS (ESI): 732 [M+H]$^+$.

Example 162

N-(2,6-difluorophenyl)-3-{3-[2-({2-(methyloxy)-4-[1-(2-methylpropyl)-4-piperidinyl]phenyl}amino)-4-pyrimidinyl]imidazo[1,2-a]pyridin-2-yl}benzamide

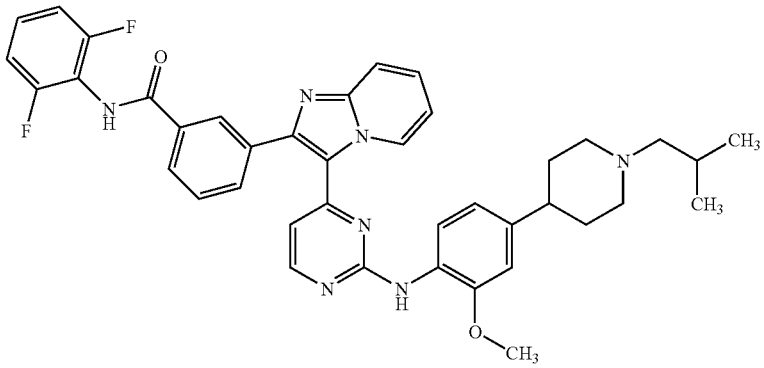

3-[3-(2-Chloro-4-pyrimidinyl)imidazo[1,2-a]pyridin-2-yl]-N-(2,6-difluorophenyl)-benzamide (Intermediate Example 1) (100 mg, 0.22 mmol), 2-(methyloxy)-4-[1-(2-methylpropyl)-4-piperidinyl]aniline (Example 160, step C) (51 mg, 0.19 mmol), and p-toluenesulfonic acid (98 mg, 0.52 mmol) were weighed into a 20 mL vial. 7 mL of iPrOH was added and the mixture was heated to 120° C. for 48 h. The mixture was transferred to a 50 mL round bottom and neutralized with 3 mL of 0.5 N sodium methoxide. The solvent was rotovaped down. The residue was taken up in 10 mL of DCM. 1 g of silica gel was added. The solvent was rotovaped down and the pre-adsorbed solids were purified by flash chromatography to give the title compound (72 mg, 0.105 mmol, 54%). $^1$H NMR (400 MHz, DMSO-d$_6$) δ ppm 10.23 (s, 1H), 9.41 (d, J=6.23 Hz, 1H), 8.52 (s, 1H), 8.33 (s, 1H), 8.24 (d, J=5.13 Hz, 1H), 8.04 (d, J=7.87 Hz, 1H), 7.80 (d, J=7.69 Hz, 1H), 7.72 (d, J=8.97 Hz, 1H), 7.57-7.65 (m, 2H), 7.43-7.49 (m, 1H), 7.35-7.43 (m, 1H), 7.16-7.22 (m, 2H), 6.99 (t, J=6.87 Hz, 1H), 6.95 (d, J=1.28 Hz, 1H), 6.78 (dd, J=8.24, 1.28 Hz, 1H), 6.48-6.54 (m, 1H), 3.82 (s, 3H), 2.90 (d, J=10.62 Hz, 2H), 2.40-2.46 (m, 1H), 1.97-2.05 (m, 2H), 1.91 (t, J=10.62 Hz, 2H), 1.65-1.76 (m, 5H), 0.84 (d, J=6.59 Hz, 6H). MS (ESI): 688 [M+H]$^+$.

Example 163

N-(2,6-difluorophenyl)-5-(3-{2-[(5-methyl-2-(methyloxy)-4-{1-[2-(methylsulfonyl)ethyl]-4-piperidinyl}phenyl)amino]-4-pyrimidinyl}imidazo[1,2-a]pyridin-2-yl)-2-(methyloxy)benzamide

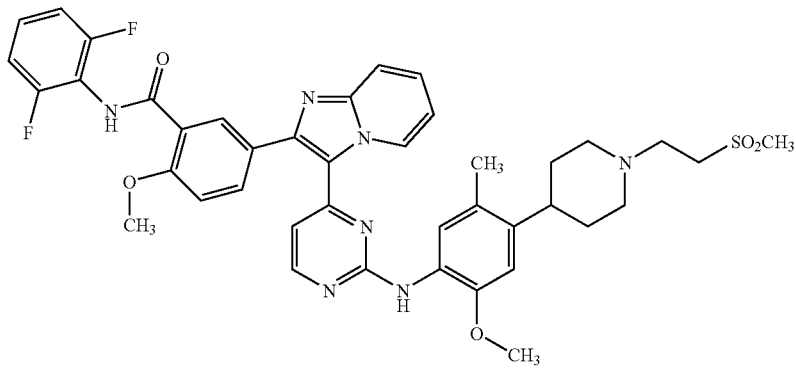

Step A:
5-methyl-2-(methyloxy)-4-(4-pyridinyl)aniline

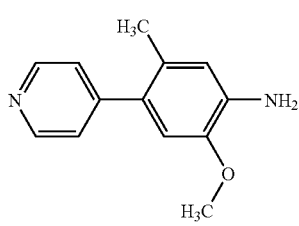

4-[2-methyl-5-(methyloxy)-4-nitrophenyl]pyridine (Example 157, step A) (2.44 g, 9.99 mmol) was placed in a 250 mL high pressure vessel and dissolved in 60 mL of 1 to 1 EtOAc/MeOH. 5 wt % Platinum(sulfided)/carbon (1.17 g, 0.3 mmol) was added followed quickly by a rubber septum. The flask was evacuated and filled with N$_2$ six times to remove any oxygen. The vessel was then pressurized with H$_2$ (60 psi). The solution stirred for 72 h. The vessel was evacuated and filled with N$_2$ six times to remove any H$_2$. The solution was filtered through celite and evaporated to give the title compound of step A (2.28 g, 10.6 mmol, 100%). $^1$H NMR (400 MHz, DMSO-d$_6$) δ ppm 8.50-8.53 (m, 2H), 7.30-7.33 (m, 2H), 6.68 (s, 1H), 6.54 (s, 1H), 4.88 (bs, 2H), 3.75 (s, 3H), 2.12 (s, 3H).

Step B: 2,2,2-trifluoro-N-[5-methyl-2-(methyloxy)-4-(4-pyridinyl)phenyl]acetamide

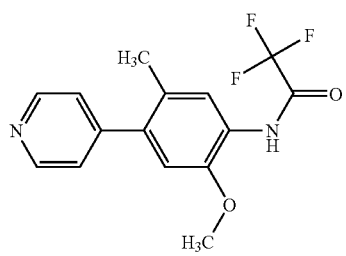

To 5-methyl-2-(methyloxy)-4-(4-pyridinyl)aniline (2.28 g, 10.6 mmol) in THF was added triethylamine (3.23 g, 32 mmol), and trifluoroacetic anhydride (4.5 g, 21.3 mmol). The mixture was heated to 40° C. overnight. The solvent was rotovaped down and the residue purified by flash chromatography to give the title compound of step B (2.37 g, 7.64 mmol, 71%). $^1$H NMR (400 MHz, DMSO-d$_6$) δ ppm 10.76 (s, 1H), 8.62-8.65 (m, 2H), 7.42-7.44 (m, 2H), 7.35 (s, 1H), 6.98 (s, 1H), 3.81 (s, 3H), 2.16 (s, 3H).

Step C: 2,2,2-trifluoro-N-[5-methyl-2-(methyloxy)-4-(4-piperidinyl)phenyl]acetamide acetate

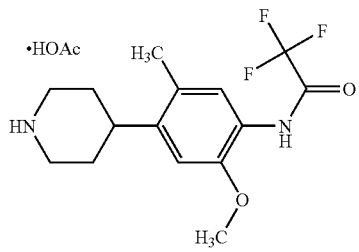

2,2,2-Trifluoro-N-[5-methyl-2-(methyloxy)-4-(4-pyridinyl)phenyl]acetamide (2.37 g, 7.64 mmol) was placed in a 250 mL high pressure vessel and dissolved in 70 mL of HOAc. Platinum oxide (0.173 g, 0.76 mmol) was added followed quickly by a rubber septum. The flask was evacuated en pressurized with H$_2$ (60 psi). The solution stirred for and filled with N₂ six times to remove any oxygen. The vessel w24 h. The vessel was evacuated and filled with N₂ six times to remove any H₂. The solution was filtered through celite and evaporated to give the title compound (2.83 g, 7.46 mmol, 98%). ¹H NMR (400 MHz, DMSO-d₆) δ ppm 7.11 (s, 1H), 6.86 (s, 1H), 3.76 (s, 3H), 3.14 (d, J=12.27 Hz, 2H), 2.82-2.91 (m, 1H), 2.72-2.81 (m, 2H), 2.20 (s, 3H), 1.81 (s, 3H), 1.64-1.75 (m, 4H).

Step D: 5-methyl-2-(methyloxy)-4-{1-[2-(methylsulfonyl)ethyl]-4-piperidinyl}aniline

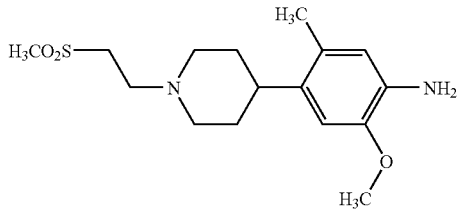

To 2,2,2-trifluoro-N-[5-methyl-2-(methyloxy)-4-(4-piperidinyl)phenyl]acetamide acetate (1.5 g, 4.0 mmol) in 30 mL of dioxane was added, TEA (2 g, 20 mmol), and methyl vinyl sulfone (1.06 g, 10 mmol). The mixture was heated to 90° C. for 72 h. The solvent was rotovaped down and the crude product was purified by flash chromatography to give 480 mg of 2,2,2-trifluoro-N-(5-methyl-2-(methyloxy)-4-{1-[2-(methylsulfonyl)ethyl]-4-piperidinyl}phenyl)acetamide and the title compound of step D (0.40 g, 1.2 mmol, 31%). ¹H NMR (400 MHz, CDCl₃) δ ppm 6.62 (s, 1H), 6.51 (s, 1H), 5.22 (s, 2H), 3.80 (bs, 3H), 3.29 (t, J=6.87 Hz, 2H), 3.13 (d, J=11.17 Hz, 2H), 3.04 (s, 3H), 2.98 (t, J=6.96 Hz, 2H), 2.61-2.70 (m, 1H), 2.24-2.31 (m, 2H), 2.17 (s, 3H), 1.73-1.81 (m, 4H).

Step E: N-(2,6-difluorophenyl)-5-(3-{2-[(5-methyl-2-(methyloxy)-4-{1-[2-(methylsulfonyl)ethyl]-4-piperidinyl}phenyl)amino]-4-pyrimidinyl}imidazo[1,2-a]pyridin-2-yl)-2-(methyloxy)benzamide 5-[3-(2-chloro-4-pyrimidinyl)imidazo[1,2-a]pyridin-2-yl]-N-(2,6-difluorophenyl)-2-(methyloxy)benzamide (Intermediate Example 2) (200 mg, 0.41 mmol), 5-methyl-2-(methyloxy)-4-{1-[2-(methylsulfonyl)ethyl]-4-piperidinyl}aniline (120 mg, 0.37 mmol), and p-toluenesulfonic acid (186 mg, 0.98 mmol) were weighed into a 20 mL microwave vial. 7 mL of trifluoroethanol was added and the mixture was heated in the microwave to 150° C. for 2 h. The mixture was transferred to a 50 mL round bottom and neutralized with 2.5 mL of 0.5 N sodium methoxide. The solvent was rotovaped down. The residue was taken up in 10 mL of DCM. 2 g of silica gel was added. The solvent was rotovaped down and the pre-adsorbed solids were purified by flash chromatography to give the title compound (115 mg, 0.147 mmol, 40%). ¹H NMR (400 MHz, DMSO-d₆) δ ppm 9.79 (s, 1H), 9.40 (d, J=6.97 Hz, 1H), 8.47 (s, 1H), 8.26 (d, J=5.13 Hz, 1H), 8.11 (d, J=2.57 Hz, 1H), 7.78 (dd, J=8.43, 2.20 Hz, 1H), 7.71 (d, J=8.80 Hz, 1H), 7.56 (s, 1H), 7.42-7.49 (m, 1H), 7.34-7.42 (m, 1H), 7.28 (d, J=8.80 Hz, 1H), 7.18 (t, J=8.07 Hz, 2H), 6.97 (t, J=6.97 Hz, 1H), 6.89 (s, 1H), 6.59 (d, J=5.13 Hz, 1H), 3.99 (s, 3H), 3.81 (s, 3H), 3.28-3.32 (m, 2H), 3.06 (s, 3H), 3.02 (d, J=11.36 Hz, 2H), 2.74 (t, J=6.97 Hz, 2H), 2.60-2.70 (m, 1H), 2.20 (s, 3H), 2.04-2.15 (m, 2H), 1.65-1.76 (m, 4H). MS (ESI): 782 [M+H]⁺.

Example 164

N-(2,6-difluorophenyl)-2-(ethyloxy)-5-(3-{2-[(5-methyl-2-(methyloxy)-4-{1-[2-(methylsulfonyl)ethyl]-4-piperidinyl}phenyl)amino]-4-pyrimidinyl}imidazo[1,2-a]pyridin-2-yl)benzamide

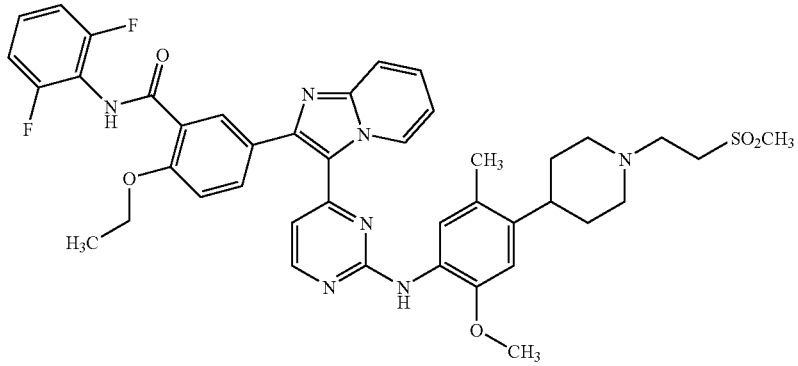

5-[3-(2-chloro-4-pyrimidinyl)imidazo[1,2-a]pyridin-2-yl]-N-(2,6-difluorophenyl)-2-(methyloxy)benzamide (Intermediate Example 2) (200 mg, 0.4 mmol), 5-methyl-2-(methyloxy)-4-{1-[2-(methylsulfonyl)ethyl]-4-piperidinyl}aniline (Example 163, step D) (117 mg, 0.36 mmol), and p-toluenesulfonic acid (180 mg, 0.95 mmol) were weighed into a 20 mL microwave vial. 7 mL of trifluoroethanol was added and the mixture was heated in the microwave to 150° C. for 2 h. The mixture was transferred to a 50 mL round bottom and neutralized with 2.5 mL of 0.5 N sodium methoxide. The solvent was rotovaped down. The residue was taken up in 10 mL of DCM. 2 g of silica gel was added. The solvent was rotovaped down and the pre-adsorbed solids were purified by flash chromatography to give the title compound (135 mg, 0.17 mmol, 43%). ¹H NMR (400 MHz, DMSO-d₆) δ ppm 9.74 (s, 1H), 9.39 (d, J=6.60 Hz, 1H), 8.46 (s, 1H), 8.26 (d, J=5.13 Hz, 1H), 8.05 (d, J=1.83 Hz, 1H), 7.74 (dd, J=8.62, 2.02 Hz, 1H), 7.70 (d, J=9.17 Hz, 1H), 7.56 (s, 1H), 7.41-7.49 (m, 1H), 7.37 (d, J=8.07 Hz, 1H), 7.26 (d, J=8.80 Hz, 1H), 7.19 (t, J=8.07 Hz, 2H), 6.96 (t, J=6.97 Hz, 1H), 6.89 (s, 1H), 6.58 (t, J=5.50 Hz, 1H), 4.26 (q, J=7.09 Hz, 2H), 3.79-3.82 (m, 3H), 3.26-3.36 (m, 2H), 3.06 (s, 3H), 3.02 (d, J=13.20 Hz, 4H), 2.68-2.76 (m, 2H), 2.59-2.68 (m, 1H), 2.20 (s, 3H), 2.02-2.14 (m, 2H), 1.65-1.76 (m, 2H), 1.43 (t, J=6.97 Hz, 3H). MS (ESI): 796 [M+H]⁺.

Example 165

N-(2,6-difluorophenyl)-3-(3-{2-[(5-methyl-2-(methyloxy)-4-{1-[2-(methylsulfonyl)ethyl]-4-piperidinyl}phenyl)amino]-4-pyrimidinyl}imidazo[1,2-a]pyridin-2-yl)benzamide

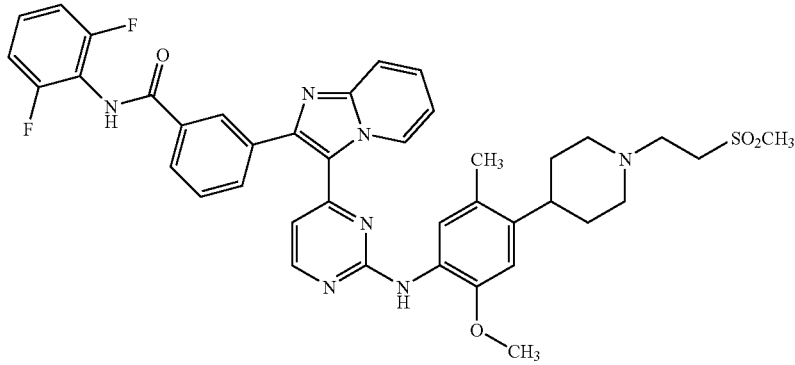

3-[3-(2-chloro-4-pyrimidinyl)imidazo[1,2-a]pyridin-2-yl]-N-(2,6-difluorophenyl)-benzamide (Intermediate Example 1) (200 mg, 0.43 mmol), 5-methyl-2-(methyloxy)-4-{1-[2-(methylsulfonyl)ethyl]-4-piperidinyl}aniline (Example 163, step D) (127 mg, 0.39 mmol), and p-toluenesulfonic acid (197 mg, 1 mmol) were weighed into a 20 mL microwave vial. 7 mL of trifluoroethanol was added and the mixture was heated in the microwave to 150° C. for 1 h. The mixture was transferred to a 50 mL round bottom and neutralized with 2.5 mL of 0.5 N sodium methoxide. The solvent was rotovaped down. The residue was taken up in 10 mL of DCM. 2 g of silica gel was added. The solvent was rotovaped down and the pre-adsorbed solids were purified by flash chromatography to give the title compound (135 mg, 0.17 mmol, 43%). $^1$H NMR (400 MHz, DMSO-d$_6$) δ ppm 10.22 (s, 1H), 9.41 (d, J=6.04 Hz, 1H), 8.47 (s, 1H), 8.32 (s, 1H), 8.24 (d, J=5.31 Hz, 1H), 8.04 (d, J=7.69 Hz, 1H), 7.80 (d, J=7.87 Hz, 1H), 7.72 (d, J=8.97 Hz, 1H), 7.59 (t, J=7.69 Hz, 1H), 7.53 (s, 1H), 7.43-7.49 (m, 1H), 7.39 (t, J=8.06 Hz, 1H), 7.19 (t, J=8.06 Hz, 2H), 6.98 (t, J=6.87 Hz, 1H), 6.88 (s, 1H), 6.51 (d, J=5.13 Hz, 1H), 3.80 (s, 3H), 3.27-3.30 (m, 2H), 3.05 (s, 3H), 2.98-3.03 (m, 2H), 2.73 (t, J=6.87 Hz, 2H), 2.59-2.68 (m, 1H), 2.18 (s, 3H), 2.03-2.14 (m, 2H), 1.64-1.74 (m, 4H). MS (ESI): 752 [M+H]$^+$.

Example 166

N-(2,6-difluorophenyl)-3-(3-{2-[(4-{1-[2-(methylsulfonyl)ethyl]-4-piperidinyl}-2-propylphenyl)amino]-4-pyrimidinyl}imidazo[1,2-a]pyridin-2-yl)benzamide

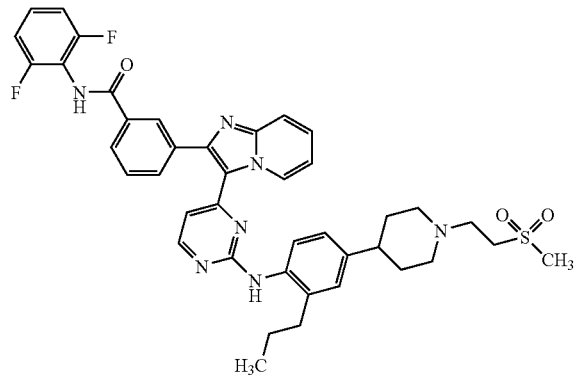

Step A: 1,1-dimethylethyl 4-(4-nitro-3-propylphenyl)-3,6-dihydro-1(2H)-pyridine-carboxylate

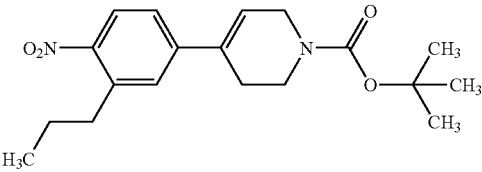

4-Chloro-1-nitro-2-propylbenzene (*J. Organometallic Chem.* 2001, 624(1-2), 167-171) (0.299 g, 1.50 mmol), 1,1-dimethylethyl 4-(4,4,5,5-tetramethyl-1,3,2-dioxaborolan-2-yl)-3,6-dihydro-1(2H)-pyridinecarboxylate (0.553 g, 1.79 mmol), Na$_2$CO$_3$ (0.509 g, 4.80 mmol) and bis(triphenylphosphine)palladium(II) chloride (0.0620 g, 0.0900 mmol) in dioxane (6 mL) and H$_2$O (3 mL) was degassed for 10 min. The mixture was heated at 80° C. overnight. The reaction was filtered through Celite®, washed with EtOAc and H$_2$O, dried (MgSO$_4$), concentrated and purified by flash chromatography to provide the title compound of step A (0.451 g, 1.30 mmol, 87%). $^1$H NMR (400 MHz, CDCl$_3$) δ ppm 0.97 (t, J=7.3 Hz, 3H), 1.46 (s, 9H), 1.65 (sextet, J=7.5 Hz, 2H), 2.50 (br. s., 2H), 2.83-2.88 (m, 2H), 3.62 (t, J=5.7 Hz, 2H), 4.08 (q, J=2.7 Hz, 2H), 6.14 (br. s., 1H), 7.25-7.29 (m, 2H), 7.87 (d, J=7.9 Hz, 1H).

Step B: 4-(4-nitro-3-propylphenyl)-1,2,3,6-tetrahydropyridine

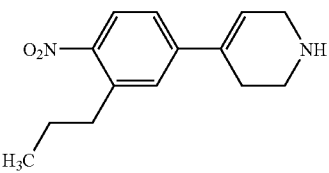

The title compound of step B (0.302 g, 1.23 mmol, 94%) was prepared from 1,1-dimethylethyl 4-(4-nitro-3-propyl phenyl)-3,6-dihydro-1(2H)-pyridine-carboxylate in an analogous manner to that described for Example 89, step D. ¹H NMR (400 MHz, CDCl₃) δ ppm 0.99 (t, J=7.3 Hz, 3H), 1.67 (dq, J=15.2, 7.5 Hz, 2H), 2.53 (dt, J=7.4, 2.9 Hz, 2H), 2.85-2.91 (m, 2H), 3.19 (t, J=5.7 Hz, 2H), 3.44 (br. s., 1H), 3.63 (q, J=2.7 Hz, 2H), 6.22-6.26 (m, 1H), 7.28-7.32 (m, 2H), 7.89 (d, J=9.2 Hz, 1H).

Step C: 1-[2-(methylsulfonyl)ethyl]-4-(4-nitro-3-propylphenyl)-1,2,3,6-tetrahydropyridine

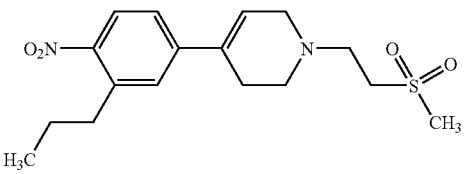

The title compound of step C (0.437 g, 1.23 mmol, 100%, approximately 85% pure, used without further purification) was prepared in an analogous manner to that described for N-(2,6-difluorophenyl)-3-[3-(2-{[2-methyl-4-({1-[2-(methylsulfonyl)ethyl]-4-piperidinyl}oxy)phenyl]amino}-4-pyrimidinyl)imidazo[1,2-a]pyridin-2-yl]benzamide (Example 8). ¹H NMR (400 MHz, DMSO-d₆) δ ppm 0.88 (t, J=7.3 Hz, 3H), 1.50-1.60 (m, 2H), 2.66 (t, J=5.6 Hz, 2H), 2.74-2.82 (m, 6H), 2.98 (s, 3H), 3.12-3.17 (m, 2H), 3.32 (t, J=6.9 Hz, 2H), 6.37 (t, J=3.3 Hz, 1H), 7.46 (dd, J=8.6, 1.8 Hz, 1H), 7.50 (d, J=1.8 Hz, 1H), 7.85 (d, J=8.6 Hz, 1H).

Step D: 4-{1-[2-(methylsulfonyl)ethyl]-4-piperidinyl}-2-propylaniline

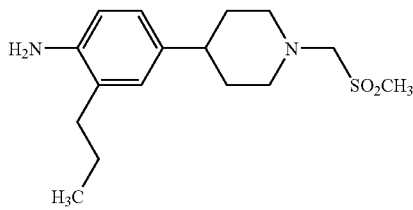

The title compound of step D (0.249 g, 0.770 mmol, 74%) was prepared from 1-[2-(methylsulfonyl)ethyl]-4-(4-nitro-3-propylphenyl)-1,2,3,6-tetrahydropyridine in an analogous manner to that of 4-{4-[(9aS)-hexahydropyrazino[2,1-c][1,4]oxazin-8(1H)-yl]-1-piperidinyl}-2-(methyloxy)aniline (Example 87, step I). ¹H NMR (400 MHz, CDCl₃) δ ppm 1.00 (t, J=7.3 Hz, 3H), 1.61-1.71 (m, 4H), 1.83 (d, J=14.3 Hz, 2H), 2.14 (td, J=11.7, 2.2 Hz, 2H), 2.38 (dt, J=12.0, 3.7 Hz, 1H), 2.41-2.47 (m, 2H), 2.89 (t, J=6.4 Hz, 2H), 3.01 (d, J=11.4 Hz, 2H), 3.06 (s, 3H), 3.17 (t, J=6.4 Hz, 2H), 3.54 (br. s., 2H), 6.60-6.64 (m, 1H), 6.85-6.89 (m, 2H).

Step E: N-(2,6-difluorophenyl)-3-(3-{2-[(4-{1-[2-(methylsulfonyl)ethyl]-4-piperidinyl}-2-propylphenyl)amino]-4-pyrimidinyl}imidazo[1,2-a]pyridin-2-yl)benzamide The title compound (0.10 g, 0.14 mmol, 56%) was prepared in an analogous manner to that described for Example 36, step E with the following notable exception: 4-{1-[2-(methylsulfonyl)ethyl]-4-piperidinyl}-2-propylaniline was used instead of 2-(methyloxy)-4-[4-(1-piperidinylmethyl)-1-piperidinyl]-aniline. ¹H NMR (400 MHz, DMSO-d₆) δ ppm 0.82 (t, J=7.3 Hz, 3H), 1.51 (td, J=14.8, 7.7 Hz, 2H), 1.59-1.70 (m, 2H), 1.73-1.82 (m, 2H), 2.07 (t, J=10.6 Hz, 2H), 2.44 (s, 1H), 2.50-2.60 (m, 4H), 2.72 (t, J=7.1 Hz, 2H), 2.98-3.03 (m, 2H), 3.03-3.07 (m, 3H), 6.46 (d, J=5.1 Hz, 1H), 6.83 (t, J=7.0 Hz, 1H), 7.10 (d, J=2.2 Hz, 1H), 7.14 (d, J=1.8 Hz, 1H), 7.20 (t, J=8.1 Hz, 2H), 7.28 (d, J=7.7 Hz, 1H), 7.36-7.47 (m, 2H), 7.62 (t, J=7.7 Hz, 1H), 7.71 (d, J=8.8 Hz, 1H), 7.81 (d, J=8.1 Hz, 1H), 8.06 (d, J=8.1 Hz, 1H), 8.18 (d, J=5.1 Hz, 1H), 8.31 (br. s., 1H), 8.95 (s, 1H), 9.31 (br. s., 1H), 10.24 (s, 1H). MS (M+H, ES+) 750.

Example 167

N-(2,6-difluorophenyl)-2-(methyloxy)-5-(3-{2-[(4-{1-[2-(methylsulfonyl)ethyl]-4-piperidinyl]-2-propylphenyl)amino}-4-pyrimidinyl}imidazo[1,2a]pyridin-2-yl)benzamide

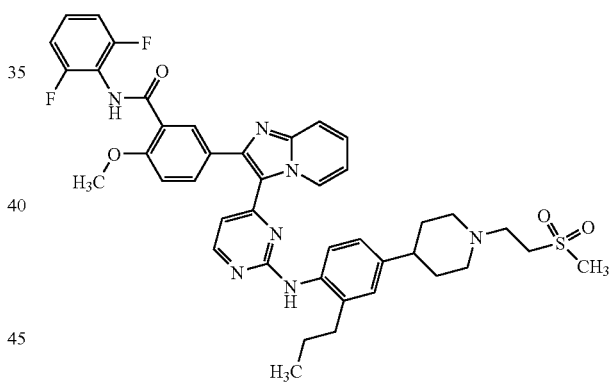

The title compound (0.063 g, 0.080 mmol, 32%) was prepared in an analogous manner to that described for Example 36, step E with the following notable exceptions:
a) 5-[3-(2-chloro-4-pyrimidinyl)-imidazo[1,2-a]pyridin-2-yl]-N-(2,6-difluorophenyl)-2-(methyloxy)benzamide (Intermediate Example 2) was used instead of Intermediate Example 1;
b) 4-{1-[2-(methylsulfonyl)ethyl]-4-piperidinyl}-2-propylaniline was used instead of 2-(methyloxy)-4-[4-(1-piperidinylmethyl)-1-piperidinyl]-aniline.

¹H NMR (400 MHz, DMSO-d₆) δ ppm 0.79 (t, J=7.1 Hz, 3H), 1.42-1.54 (m, 3H), 1.56-1.67 (m, 3H), 1.75 (d, J=9.9 Hz, 2H), 2.04 (t, J=11.9 Hz, 2H), 2.49-2.58 (m, 2H), 2.69 (t, J=6.6 Hz, 2H), 2.98 (d, J=9.9 Hz, 3H), 3.02 (s, 3H), 3.96 (s, 3H), 6.50 (d, J=5.3 Hz, 1H), 6.78 (t, J=7.1 Hz, 1H), 7.06 (d, J=1.3 Hz, 1H), 7.08-7.19 (m, 3H), 7.26 (d, J=8.1 Hz, 2H), 7.30-7.41 (m, 2H), 7.65 (d, J=9.0 Hz, 1H), 7.75 (d, J=8.6 Hz, 1H), 8.05 (s, 1H), 8.15 (d, J=4.9 Hz, 1H), 8.91 (s, 1H), 9.24 (br. s., 1H), 9.76 (s, 1H). MS (M−H, ES−) 779.

Example 168

N-(2,6-difluorophenyl)-2-(ethyloxy)-5-(3-{2-[(4-{1-[2-(methylsulfonyl)ethyl]-4-piperidinyl}-2-propylphenyl)amino]-4-pyrimidinyl}imidazo[1,2-a]pyridin-2-yl)benzamide

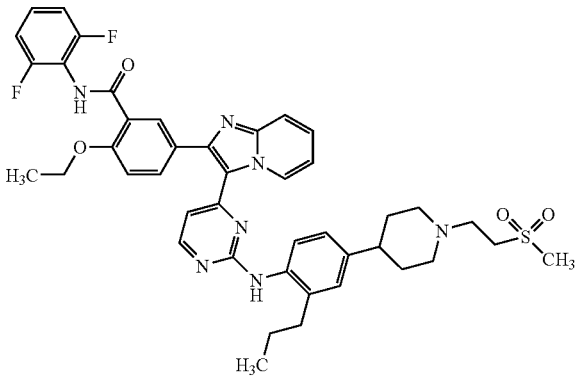

The title compound (0.12 g, 0.15 mmol, 58%) was prepared in an analogous manner to that described for Example 36, step E with the following notable exceptions:
a) 5-[3-(2-chloro-4-pyrimidinyl)imidazo[1,2-a]pyridin-2-yl]-N-(2,6-difluorophenyl)-2-(ethyloxy)benzamide (Intermediate Example 6) was used instead of Intermediate Example 1 in the procedure described in step;
b) 4-{1-[2-(methylsulfonyl)ethyl]-4-piperidinyl}-2-propylaniline was used instead of 2-(methyloxy)-4-[4-(1-piperidinylmethyl)-1-piperidinyl]-aniline.

$^1$H NMR (400 MHz, DMSO-d$_6$) δ ppm 0.82 (t, J=7.3 Hz, 3H), 1.39-1.47 (m, 3H), 1.47-1.56 (m, J=7.6, 7.6, 7.6, 7.6 Hz, 2H), 1.58-1.70 (m, 2H), 1.77 (d, J=12.1 Hz, 2H), 2.06 (t, J=10.6 Hz, 2H), 2.51-2.61 (m, 3H), 2.72 (t, J=6.6 Hz, 2H), 3.01 (d, J=11.0 Hz, 2H), 3.05 (s, 3H), 3.26-3.30 (m, 2H), 4.27 (q, J=6.8 Hz, 2H), 6.53 (d, J=5.1 Hz, 1H), 6.75-6.84 (m, 1H), 7.09 (dd, J=7.7, 1.8 Hz, 1H), 7.13 (s, 1H), 7.19 (t, J=7.9 Hz, 2H), 7.28 (t, J=7.9 Hz, 2H), 7.39 (td, J=15.0, 7.0 Hz, 2H), 7.67 (d, J=9.2 Hz, 1H), 7.74 (dd, J=8.4, 1.8 Hz, 1H), 8.02 (d, J=1.8 Hz, 1H), 8.18 (d, J=5.1 Hz, 1H), 8.95 (s, 1H), 9.26 (br. s., 1H), 9.75 (s, 1H). MS (M–H, ES–) 793.

Example 169

N-(2,6-difluorophenyl)-3-[3-(2-{[4-[(3S)-3-hydroxy-1-piperidinyl]-2-(methyloxy)phenyl]amino}-4-pyrimidinyl)imidazo[1,2-a]pyridin-2-yl]benzamide

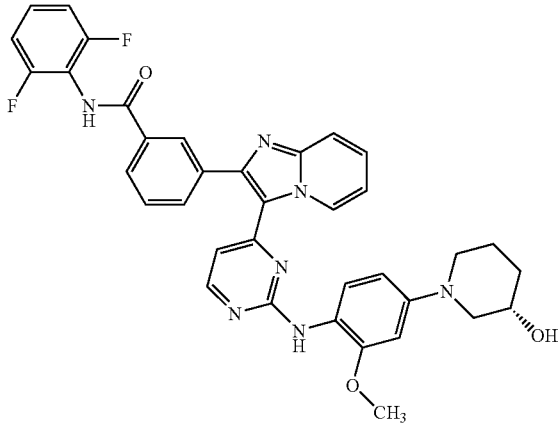

Step A: (3S)-1-[3-(methyloxy)-4-nitrophenyl]-3-piperidinol

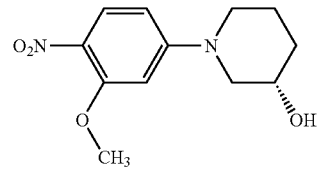

A solution of (3S)-3-piperidinol hydrochloride (3.00 g, 21.7 mmol), 5-fluoro-2-nitrophenyl methyl ether (Example 22, step A) (3.38 g, 19.76 mmol) and K$_2$CO$_3$ (9.00 g, 65.22 mmol) in DMSO (75 mL) was stirred overnight. The next morning, the reaction was diluted with diethyl ether and saturated aqueous sodium chloride. The ether layer was washed thrice with H$_2$O, and the combined aqueous layers were subsequently washed twice with diethyl ether. The combined organic layers were dried over Na$_2$SO$_4$, taken to a residue under reduced pressure, and purified by chromatography on SiO$_2$ to give the title compound as a pale yellow solid (3.90 g, 15.47 mmol, 78% yield). $^1$H NMR (400 MHz, CDCl$_3$) δ ppm 1.59-1.71 (m, 2H), 1.79 (s, 1H), 1.86-1.96 (m, J=12.96, 6.41, 6.27, 3.48 Hz, 1H), 1.96-2.04 (m, 1H), 3.13-3.24 (m, 2H), 3.47 (ddd, J=12.59, 6.36, 3.20 Hz, 1H), 3.66 (dd, J=12.82, 3.48 Hz, 1H), 3.86-3.92 (m, J=7.44, 3.94, 3.74, 3.74 Hz, 1H), 3.93 (s, 3H), 6.34 (d, J=2.56 Hz, 1H), 6.43 (dd, J=9.34, 2.38 Hz, 1H), 7.98 (d, J=9.34 Hz, 1H).

Step B: (3S)-1-[4-amino-3-(methyloxy)phenyl]-3-piperidinol

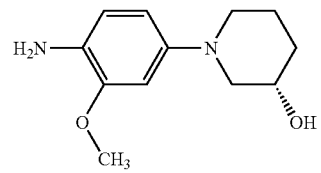

A solution of (3S)-1-[3-(methyloxy)-4-nitrophenyl]-3-piperidinol (3.90 g, 15.5 mmol), FeCl$_3$ (0.630 g, 3.9 mmol), activated carbon (4.0 g), and hydrazine hydrate (3.9 mL, 124 mmol) was heated in MeOH (100 mL) for 3 h. Once the starting material was judged consumed by TLC, the mixture was filtered over celite and concentrated to afford the title compound of step B as a dark purple solid (2.56 g, 11.53 mmol, 74% yield). $^1$H NMR (400 MHz, CDCl$_3$) δ ppm 1.62-1.72 (m, 2H), 1.75 (d, J=3.30 Hz, 1H), 1.93 (td, J=8.07, 4.40 Hz, 1H), 2.44 (s, 2H), 2.88 (s, 1H), 2.93 (d, J=9.53 Hz, 1H), 2.99 (dd, J=10.81, 6.05 Hz, 2H), 3.12 (d, J=10.63 Hz, 1H), 3.84 (s, 3H), 3.95 (s, 1H), 6.44 (d, J=8.07 Hz, 1H), 6.53 (s, 1H), 6.64 (d, J=8.07 Hz, 1H).

Step C: N-(2,6-difluorophenyl)-3-[3-(2-{[4-[(3S)-3-hydroxy-1-piperidinyl]-2-(methyloxy)phenyl]amino}-4-pyrimidinyl)imidazo[1,2-a]pyridin-2-yl]benzamide The title compound (0.104 g, 0.160 mmol, 59%) was prepared in an analogous manner to that described for Example 74, step C, with the following notable exception: (3S)-1-[4-amino-3-(methyloxy)phenyl]-3-piperidinol was used instead of 1-[4-amino-3-(methyloxy)phenyl]-N,N-dimethyl-4-piperidinamine. $^1$H NMR (400 MHz, DMSO-d$_6$) δ 10.23 (s, 1H), 9.41 (s, 1H), 8.45 (s, 1H), 8.32 (s, 1H), 8.19 (d, J=5.2 Hz, 1H), 8.05 (d, J=8.0 Hz, 1H), 7.82 (d, J=8.0 Hz, 1H), 7.72 (d, J=9.2

Hz, 1H), 7.61 (t, J=7.6 Hz, 1H), 7.48-7.38 (m, 3H), 7.20 (t, J=7.8 Hz, 2H), 6.97 (m, 1H), 6.64 (m, 1H), 6.48-6.44 (m, 2H), 4.80 (d, J=4.4 Hz, 1H), 3.79 (s, 3H), 3.59 (m, 2H), 3.48 (m, 1H), 2.67-2.62 (m, 1H), 1.90 (m, 1H), 1.75 (m, 1H), 1.54 (m, 1H), 1.26 (m, 1H). MS (ESI) m/z=648 [M+H]$^+$.

Example 170

N-(2,6-difluorophenyl)-3-[3-(2-{[4-[(3R)-3-hydroxy-1-piperidinyl]-2-(methyloxy)phenyl]amino}-4-pyrimidinyl)imidazo[1,2-a]pyridin-2-yl]benzamide

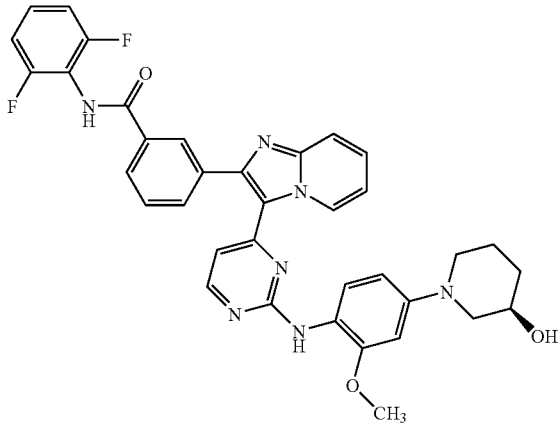

The title compound (0.101 g, 0.156 mmol, 58% in final step) was prepared in an analogous manner to that described for Example 169 with the following notable exception: (3R)-3-piperidinol hydrochloride was used instead of (3S)-3-piperidinol hydrochloride in the procedure described in Example 169, step A. $^1$H NMR (400 MHz, DMSO-d$_6$) δ 10.23 (s, 1H), 9.41 (s, 1H), 8.45 (s, 1H), 8.32 (s, 1H), 8.19 (d, J=5.2 Hz, 1H), 8.05 (d, J=8.0 Hz, 1H), 7.82 (d, J=8.0 Hz, 1H), 7.72 (d, J=9.2 Hz, 1H), 7.61 (t, J=7.6 Hz, 1H), 7.48-7.38 (m, 3H), 7.20 (t, J=7.8 Hz, 2H), 6.97 (m, 1H), 6.64 (m, 1H), 6.48-6.44 (m, 2H), 4.80 (d, J=4.4 Hz, 1H), 3.79 (s, 3H), 3.59 (m, 2H), 3.48 (m, 1H), 2.67-2.62 (m, 1H), 1.90 (m, 1H), 1.75 (m, 1H), 1.54 (m, 1H), 1.26 (m, 1H). MS (ESI) m/z=648 [M+H]$^+$.

Example 171

N-(2,6-difluorophenyl)-3-[3-[2-({2-(ethyloxy)-4-[4-(1-methylethyl)-1-piperazinyl]phenyl}amino)-4-pyrimidinyl]imidazo[1,2-a]pyridin-2-yl}benzamide

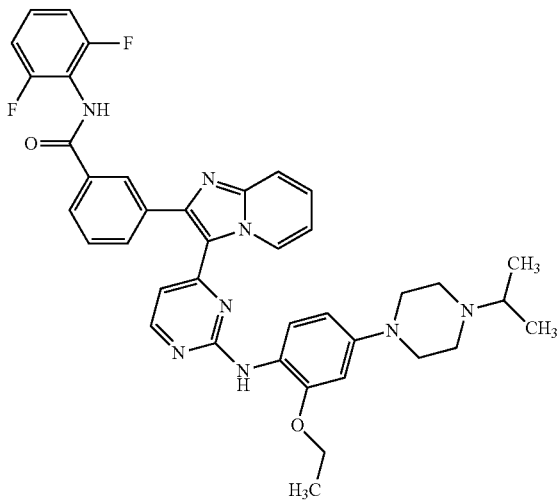

Step A: 1-[3-(ethyloxy)-4-nitrophenyl]-4-(1-methylethyl)piperazine

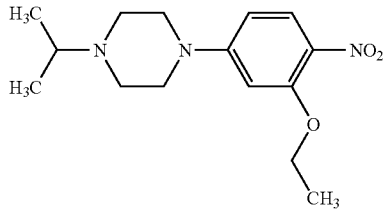

A mixture of 1-[3-(ethyloxy)-4-nitrophenyl]piperazine (Example 143, step A) (0.285 g, 1.13 mmol)) and acetone (0.13 g, 2.26 mmol) was stirred in DCE (5 mL) at rt under N$_2$. To this mixture was added sodium triacetoxyborohydride (0.60 g, 2.8 mmol) and HOAc (0.136 g, 2.26 mmol). The reaction was stirred for approximately 24 h. The reaction was diluted with DCM and aqueous (saturated) NaHCO$_3$. The aqueous layer was extracted with DCM (2×). The combined organic layers were dried over MgSO$_4$, filtered, concentrated, and chromatographed on silica gel to give the title compound of step A (291 mg, 0.99 mmol, 88%) as a yellow solid. MS (ESI): 294 [M+H]$^+$.

Step B: {2-(ethyloxy)-4-[4-(1-methylethyl)-1-piperazinyl]phenyl}amine

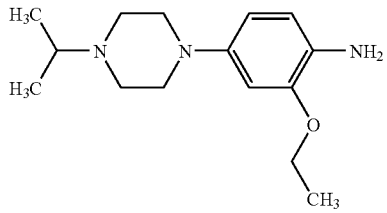

A mixture of 1-[3-(ethyloxy)-4-nitrophenyl]-4-(1-methylethyl)piperazine (0.285 g, 0.97 mmol) and nickel(II) chloride hexahydrate (0.116 g, 0.48 mmol) was stirred in 2:1 MeOH/THF (10 mL) under N$_2$ at rt. To this mixture was added NaBH$_4$ (0.129 g, 3.4 mmol) in 2 equal portions over 5 min. The reaction was stirred at rt for about 45 min, then concentrated under vacuum. The residue was dissolved in DCM and poured through Celite, washing with DCM and EtOAc. The filtrate was concentrated and chromatographed on silica gel to give the title compound of step B (238 mg, 0.90 mmol, 93%) as a grey oil. MS (ESI): 264 [M+H]$^+$.

Step C: N-(2,6-difluorophenyl)-3-{3-[2-({2-(ethyloxy)-4-[4-(1-methylethyl)-1-piperazinyl]phenyl}amino)-4-pyrimidinyl]imidazo[1,2-a]pyridin-2-yl}benzamide To 3-[3-(2-chloro-4-pyrimidinyl)imidazo[1,2-a]pyridin-2-yl]-N-(2,6-difluorophenyl)-benzamide (Intermediate Example 1) (100 mg, 0.22 mmol) and {2-(ethyloxy)-4-[4-(1-methylethyl)-1-piperazinyl]phenyl}amine (57 mg, 0.22 mmol) in 2,2,2-trifluoroethanol (1.1 mL) was added 4 M HCl in dioxane (108 μL, 0.43 mmol). The mixture was stirred and heated on a Biotage microwave at 175° C. for 30 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (98 mg, 0.14 mmol, 66%) as a yellow solid. $^1$H NMR (400 MHz, DMSO-d$_6$): δ 10.24 (s, 1H), 9.38 (brs, 1H), 8.36 (d, 2H, J=14.66 Hz), 8.23 (d, 1H, J=5.13 Hz), 8.05 (d, 1H, J=7.88 Hz), 7.81 (d, 1H, J=7.88 Hz), 7.73 (d, 1H, J=9.16 Hz), 7.61 (t, 1H, J=7.70 Hz), 7.36-7.49 (m, 3H), 7.21 (t, 2H, J=8.06 Hz), 6.97 (t, 1H, J=6.87 Hz), 6.65 (s, 1H), 6.45-6.50 (m, 2H), 4.06 (q, 2H, J=7.03 Hz), 3.08-3.14 (m, 4H), 2.64-2.69 (m, 1H), 2.54-2.61 (m, 4H), 1.24 (t, 3H, J=6.96 Hz), 1.00 (d, 6H, J=6.23 Hz). MS (ESI): 689 [M+H]$^+$.

Example 172

N-(2,6-difluorophenyl)-5-{3-[2-({2-(ethyloxy)-4-[4-(1-methylethyl)-1-piperazinyl]phenyl}-amino)-4-pyrimidinyl]imidazo[1,2-a]pyridin-2-yl}-2-(methyloxy)benzamide

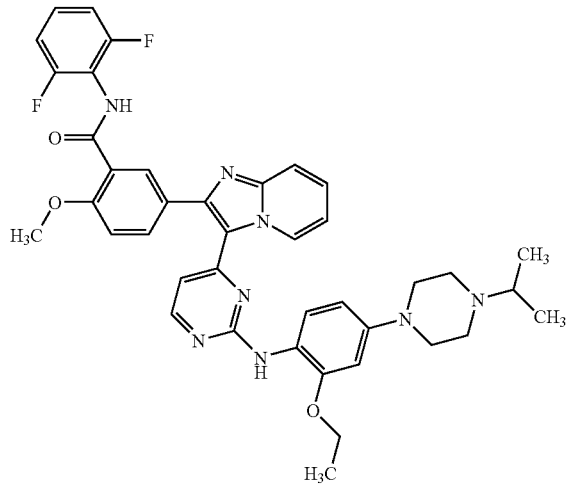

To 5-[3-(2-chloro-4-pyrimidinyl)imidazo[1,2-a]pyridin-2-yl]-N-(2,6-difluorophenyl)-2-(methyloxy)benzamide (Intermediate Example 2) (100 mg, 0.20 mmol) and {2-(ethyloxy)-4-[4-(1-methylethyl)-1-piperazinyl]phenyl}amine (Example 171, step B) (54 mg, 0.20 mmol) in 2,2,2-trifluoroethanol (1.0 mL) was added 4 M HCl in dioxane (102 µL, 0.41 mmol). The mixture was stirred and heated on a Biotage microwave at 175° C. for 30 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (86 mg, 0.12 mmol, 60%) as a yellow solid. $^1$H NMR (400 MHz, DMSO-d$_6$): δ 9.79 (s, 1H), 9.33 (br s, 1H), 8.37 (s, 1H), 8.23 (d, 1H, J=5.32 Hz), 8.11 (d, 1H, J=2.02 Hz), 7.77 (dd, 1H, J=2.02 and 8.61 Hz), 7.70 (d, 1H, J=8.98 Hz), 7.35-7.47 (m, 3H), 7.28 (d, 1H, J=8.61 Hz), 7.19 (t, 2H, J=8.06 Hz), 6.93 (t, 1H, J=6.96 Hz), 6.66 (d, 1H, J=2.20 Hz), 6.55 (d, 1H, J=5.13 Hz), 6.47 (dd, 1H, J=2.38 and 8.80 Hz), 4.06 (q, 2H, J=6.96 Hz), 3.99 (s, 3H), 3.08-3.16 (m, 4H), 2.55-2.75 (m, 5H), 1.24 (t, 3H, J=6.96 Hz), 1.02 (d, 6H, J=6.42 Hz). MS (ESI): 719 [M+H]$^+$.

Example 173

N-(2,6-difluorophenyl)-3-[3-(2-{[2-(methyloxy)-4-(4-propyl-1-piperazinyl)phenyl]amino}-4-pyrimidinyl)imidazo[1,2-a]pyridin-2-yl]benzamide

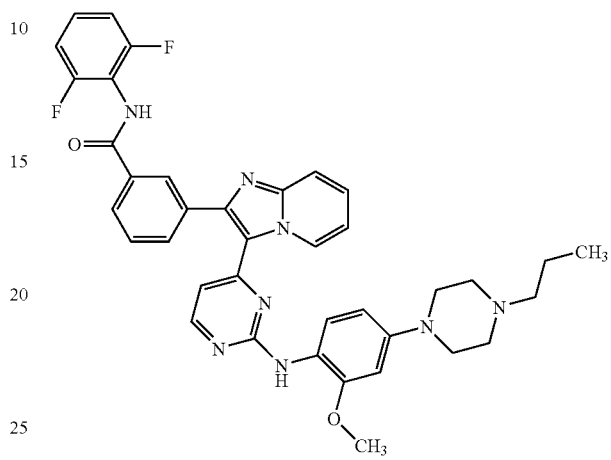

Step A:
1-[3-(methyloxy)-4-nitrophenyl]-4-propylpiperazine

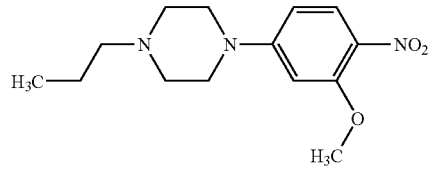

A mixture of 1-[3-(methyloxy)-4-nitrophenyl]piperazine (Example 135, step A) (0.50 g, 2.1 mmol) and 1-iodopropane (0.72 g, 4.22 mmol) was stirred in acetonitrile (42 mL) at rt under N$_2$. To this mixture was added NaHCO$_3$ (0.27 g, 2.5 mmol). The reaction was then heated to reflux and stirred for 24 h. The reaction was cooled to rt, concentrated under vacuum and the residue chromatographed on silica gel to give the title compound of step A (206 mg, 0.74 mmol, 35%) as a yellow oil. MS (ESI): 280 [M+H]$^+$.

Step B: [2-(methyloxy)-4-(4-propyl-1-piperazinyl)phenyl]amine

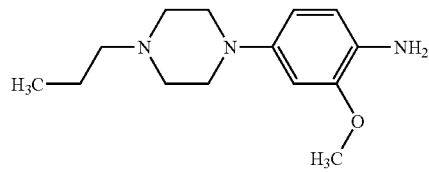

A mixture of 1-[3-(methyloxy)-4-nitrophenyl]-4-propylpiperazine (0.204 g, 0.73 mmol) and nickel(II) chloride hexahydrate (0.087 g, 0.37 mmol) was stirred in 2:1 MeOH/THF (7 mL) under N$_2$ at rt. To this mixture was added NaBH$_4$ (0.097 g, 2.6 mmol) in 2 equal portions over 5 min. The reaction was stirred at rt for about 45 min, then concentrated under vacuum. The residue was dissolved in DCM and poured through Celite, washing with DCM and EtOAc. The filtrate was concentrated and chromatographed on silica gel to give the title compound of step B (170 mg, 0.68 mmol, 93%) as a grey oil. ¹H NMR (400 MHz, DMSO-d₆): δ 6.50 (d, 1H, J=8.25), 6.47 (d, 1H, J=2.38 Hz), 6.26 (dd, 1H, J=2.47 and 8.34 Hz), 4.19 (br s, 2H), 3.72 (s, 3H), 2.90-2.94 (m, 4H), 2.43-2.47 (m, 4H), 2.25 (t, 2H, J=7.42 Hz), 1.44 (q, 2H, J=7.39 Hz), 0.86 (t, 3H, J=7.33 Hz).

N-(2,6-difluorophenyl)-3-[3-(2-{[2-(methyloxy)-4-(4-propyl-1-piperazinyl)phenyl]amino}-4-pyrimidinyl)imidazo[1,2-a]pyridin-2-yl]benzamide To 3-[3-(2-chloro-4-pyrimidinyl)imidazo[1,2-a]pyridin-2-yl]-N-(2,6-difluorophenyl)-benzamide (Intermediate Example 1) (100 mg, 0.22 mmol) and [2-(methyloxy)-4-(4-propyl-1-piperazinyl)phenyl]amine (54 mg, 0.22 mmol) in 2,2,2-trifluoroethanol (1.1 mL) was added 4 M HCl in dioxane (108 μL, 0.43 mmol). The mixture was stirred and heated on a Biotage microwave at 175° C. for 35 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (103 mg, 0.15 mmol, 70%) as a light yellow solid. ¹H NMR (400 MHz, DMSO-d₆): δ10.24 (s, 1H), 9.40 (brs, 1H), 8.46 (s, 1H), 8.33 (s, 1H), 8.20 (d, 1H, J=5.13 Hz), 8.05 (d, 1H, J=7.69 Hz), 7.82 (d, 1H, J=7.69 Hz), 7.73 (d, 1H, J=8.97 Hz), 7.61 (t, 1H, J=7.78 Hz), 7.36-7.49 (m, 3H), 7.21 (t, 2H, J=8.15 Hz), 6.98 (t, 1H, J=6.87 Hz), 6.68 (d, 1H, J=2.20 Hz), 6.45-6.50 (m, 2H), 3.80 (s, 3H), 3.12-3.17 (m, 4H), 2.45-2.55 (m, 4H), 2.28 (t, 2H, J=7.42 Hz), 1.47 (q, 2H, J=7.39 Hz), 0.87 (T, 3H, J=7.32 Hz). MS (ESI): 675 [M+H]⁺.

Example 174

N-(2,6-difluorophenyl)-2-(methyloxy)-5-[3-(2-{[2-(methyloxy)-4-(4-propyl-1-piperazinyl)phenyl]amino}-4-pyrimidinyl)imidazo[1,2-a]pyridin-2-yl]benzamide

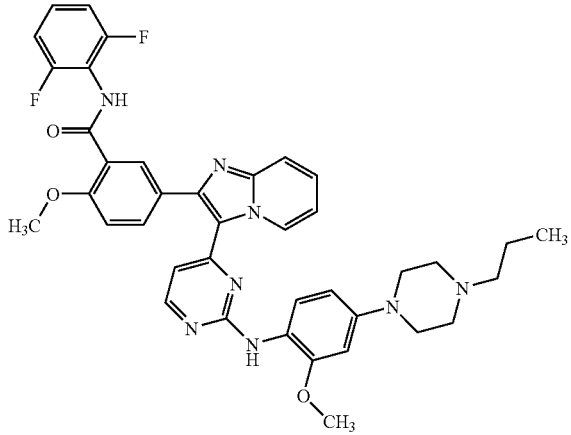

To 5-[3-(2-chloro-4-pyrimidinyl)imidazo[1,2-a]pyridin-2-yl]-N-(2,6-difluorophenyl)-2-(methyloxy)benzamide (Intermediate Example 2) (100 mg, 0.20 mmol) and [2-(methyloxy)-4-(4-propyl-1-piperazinyl)phenyl]amine (Example 173, step B) (51 mg, 0.20 mmol) in 2,2,2-trifluoroethanol (1.0 mL) was added 4 M HCl in dioxane (102 μL, 0.41 mmol). The mixture was stirred and heated on a Biotage microwave at 175° C. for 35 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (100 mg, 0.14 mmol, 70%) as a light yellow solid. ¹H NMR (400 MHz, DMSO-d₆): δ 9.77 (s, 1H), 9.35 (br s, 1H), 8.43 (s, 1H), 8.19 (d, 1H, J=5.13 Hz), 8.09 (m, 1H), 7.76 (m, 1H), 7.68 (d, 1H, J=8.97 Hz), 7.33-7.44 (m, 3H), 7.27 (d, 1H, J=8.61 Hz), 7.17 (t, 2H, J=8.06 Hz), 6.93 (t, 1H, J=6.87 Hz), 6.66 (d, 1H, J=2.20 Hz), 6.44-6.53 (m, 2H), 3.97 (s, 3H), 3.78 (s, 3H), 3.10-3.15 (m, 4H), 2.44-2.54 (m, 4H), 2.27 (t, 2H, J=7.42 Hz), 1.45 (q, 2H, J=7.45 Hz), 0.86 (t, 3H, J=7.32 Hz). MS (ESI): 705 [M+H]⁺.

Example 175

N-(2,6-difluorophenyl)-3-[3-(2-{[4-[4-(1-methylethyl)-1-piperazinyl]-2-(methyloxy)phenyl]amino}-4-pyrimidinyl)imidazo[1,2-a]pyridin-2-yl]benzamide

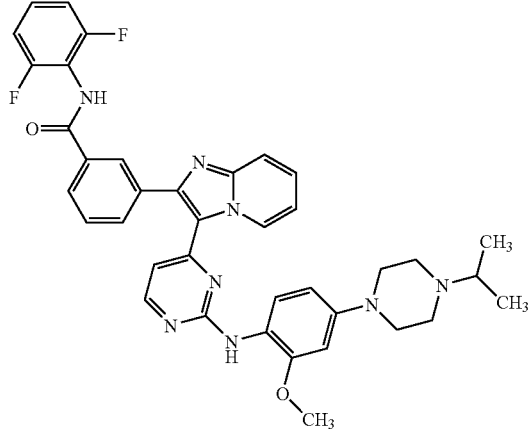

Step A: 1-(1-methylethyl)-4-[3-(methyloxy)-4-nitrophenyl]piperazine

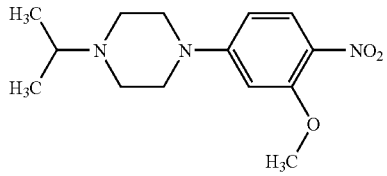

To 4-chloro-2-(methyloxy)-1-nitrobenzene (3.0 g, 16.0 mmol) in dioxane (75 mL) was added 1-(1-methylethyl)piperazine (4.1 g, 32.0 mmol), XANTPHOS (1.4 g, 2.4 mmol), and Cs₂CO₃ (10.4 g, 32.0 mmol). The mixture was bubbled with N₂ for 15 min prior to the addition of Pd₂(dba)₃ (1.5 g, 1.6 mmol). The reaction was stirred at 100° C. for 5 h. Following cooling to rt, the reaction mixture was diluted with EtOAc (150 mL) and H₂O (100 mL). The organic layer was dried over NaSO₄ taken to a residue under reduced pressure, and purified by silica gel chromatography to afford the title compound of step A (4.0 g, 90% yield). MS (ESI) (M+H)+=280.

Step B: 4-[4-(1-methylethyl)-1-piperazinyl]-2-(methyloxy)aniline

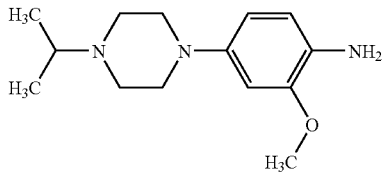

In a pressure vessel was placed a solution of 1-(1-methylethyl)-4-[3-(methyloxy)-4-nitrophenyl]piperazine (4.0 g, 14.3 mmol) in EtOH (100 mL). The solution was purged with $N_2$ for 15 min before the addition of 10% Pd/carbon (0.5 g). The reaction was stirred at rt for 5 h under 60 psi $H_2$. After releasing $H_2$ pressure, filtration removed the solid resin, and the filtrate was concentrated and purified with silica gel chromatography to furnish the title compound of step B (3.6 g, 99% yield). $^1$H NMR (400 MHz, CDCl$_3$) δ ppm 1.09 (d, J=6.6 Hz, 6H), 2.66-2.75 (m, 5H), 3.05-3.10 (m, 4H), 3.47 (s, 3H), 3.83 (s, 2H), 6.42 (dd, J=8.2, 2.4 Hz, 1H), 6.52 (d, J=2.2 Hz, 1H), 6.64 (d, J=8.4 Hz, 1H).

Step C: N-(2,6-difluorophenyl)-3-[3-(2-{[4-[4-(1-methylethyl)-1-piperazinyl]-2-(methyloxy)phenyl]amino}-4-pyrimidinyl)imidazo[1,2-a]pyridin-2-yl]benzamide The title compound (0.093 g, 0.14 mmol, 51%) was prepared in an analogous manner to that described for Example 38, step B) with the following notable exception: 4-[4-(1-methylethyl)-1-piperazinyl]-2-(methyloxy)aniline was used instead of 2-(methyloxy)-4-[4-(4-morpholinyl)-1-piperidinyl]aniline. $^1$H NMR (400 MHz, DMSO-d$_6$) δ 10.22 (s, 1H), 9.38 (brs, 1H), 8.44 (s, 1H), 8.31 (s, 1H), 8.18 (d, J=5.2 Hz, 1H), 8.03 (d, J=7.6 Hz, 1H), 7.80 (d, J=7.6 Hz, 1H), 7.70 (d, J=8.8 Hz, 1H), 7.59 (t, J=7.8 Hz, 1H), 7.45 (t, J=8.0 Hz, 1H), 7.40-7.36 (m, 2H), 7.18 (t, J=8.2 Hz, 1H), 6.95 (t, J=6.8 Hz, 1H), 6.64 (m, 1H), 6.46-6.44 (m, 2H), 3.77 (s, 3H), 3.29-3.10 (m, 4H), 2.68-2.62 (m, 1H), 2.57-2.55 (m, 4H), 0.98 (d, J=6.0 Hz, 6H). MS (ESI) m/z=675 [M+H]+.

Example 176

N-(2,6-difluorophenyl)-5-[3-(2-{[4-[4-(1-methylethyl)-1-piperazinyl]-2-(methyloxy)phenyl]-amino}-4-pyrimidinyl)imidazo[1,2-a]pyridin-2-yl]-2-(methyloxy)benzamide

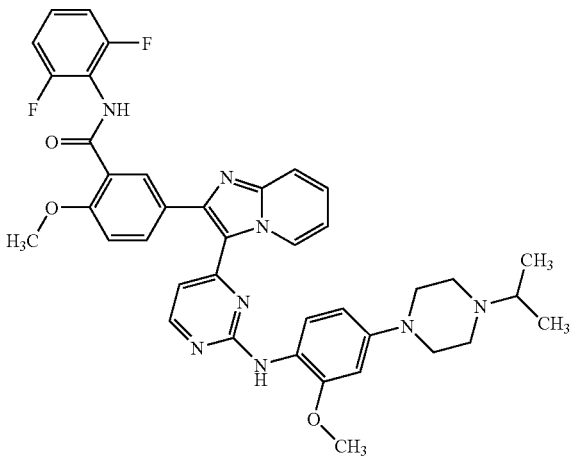

To 5-[3-(2-chloro-4-pyrimidinyl)imidazo[1,2-a]pyridin-2-yl]-N-(2,6-difluorophenyl)-2-(methyloxy)benzamide (Intermediate Example 2) (100 mg, 0.20 mmol) and 4-[4-(1-methylethyl)-1-piperazinyl]-2-(methyloxy)aniline (Example 175, step B) (51 mg, 0.20 mmol) in 2,2,2-trifluoroethanol (1.0 mL) was added 4 M HCl in dioxane (102 μL, 0.41 mmol). The mixture was stirred and heated on a Biotage microwave at 175° C. for 35 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (95 mg, 0.13 mmol, 66%) as a yellow solid. $^1$H NMR (400 MHz, DMSO-d$_6$): δ 9.79 (s, 1H), 9.37 (br s, 1H), 8.45 (s, 1H), 8.20 (d, 1H, J=5.32 Hz), 8.10 (d, 1H, J=1.83 Hz), 7.76-7.80 (m, 1H), 7.69 (d, 1H, J=8.98 Hz), 7.35-7.47 (m, 3H), 7.29 (d, 1H, J=8.61 Hz), 7.19 (t, 2H, J=8.06 Hz), 6.95 (t, 1H, J=6.87 Hz), 6.67 (d, 1H, J=2.38 Hz), 6.53 (d, 1H, J=5.13 Hz), 6.48 (dd, 1H, J=2.47 and 8.71 Hz), 3.99 (s, 3H), 3.80 (s, 2H), 3.11-3.16 (m, 4H), 2.64-2.72 (m, 1H), 2.56-2.61 (m, 4H), 1.01 (d, 6H, J=6.42 Hz). MS (ESI): 705 [M+H]+.

Example 177

N-(2,6-difluorophenyl)-2-(ethyloxy)-5-[3-(2-{[4-[4-(1-methylethyl)-1-piperazinyl]-2-(methyloxy)phenyl]amino}-4-pyrimidinyl)imidazo[1,2-a]pyridin-2-yl]benzamide

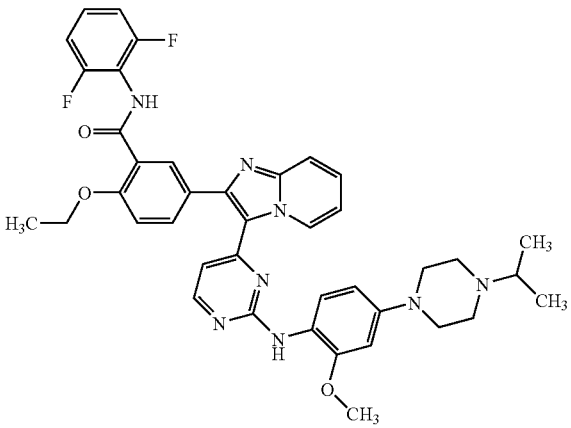

To 5-[3-(2-chloro-4-pyrimidinyl)imidazo[1,2-a]pyridin-2-yl]-N-(2,6-difluorophenyl)-2-(ethyloxy)benzamide (Intermediate Example 6) (100 mg, 0.20 mmol) and 4-[4-(1-methylethyl)-1-piperazinyl]-2-(methyloxy)aniline (49 mg, 0.20 mmol) (Example 175, step B) in 2,2,2-trifluoroethanol (1.0 mL) was added 4 M HCl in dioxane (99 μL, 0.40 mmol). The mixture was stirred and heated on a Biotage microwave at 175° C. for 35 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (110 mg, 0.15 mmol, 77%) as a yellow solid. $^1$H NMR (400 MHz, DMSO-d$_6$): δ 9.75 (s, 1H), 9.36 (br s, 1H), 8.45 (s, 1H), 8.20 (d, 1H, J=5.31 Hz), 8.05 (m, 1H), 7.74 (d, 1H, J=8.61 Hz), 7.69 (d, 1H, J=8.97 Hz), 7.35-7.47 (m, 3H), 7.27 (d, 1H, J=8.61 Hz), 7.19 (t, 2H, J=8.06 Hz), 6.95 (t, 1H, J=6.87 Hz), 6.67 (d, 1H, J=2.01 Hz), 6.53 (d, 1H, J=5.13 Hz), 6.47 (dd, 1H, J=2.11 and 8.70 Hz), 4.27 (q, 2H, J=6.78 Hz), 3.80 (s, 3H), 3.11-3.16 (m, 4H), 2.64-2.71 (m, 1H), 2.56-2.61 (m, 4H), 1.43 (t, 3H, J=6.78 Hz), 1.00 (d, 6H, J=6.41 Hz). MS (ESI): 719 [M+H]$^+$.

Example 178

N-(2,6-difluorophenyl)-2-(ethyloxy)-5-[3-(2-{[2-(methyloxy)-4-(4-propyl-1-piperazinyl)phenyl]amino}-4-pyrimidinyl)imidazo[1,2-a]pyridin-2-yl]benzamide

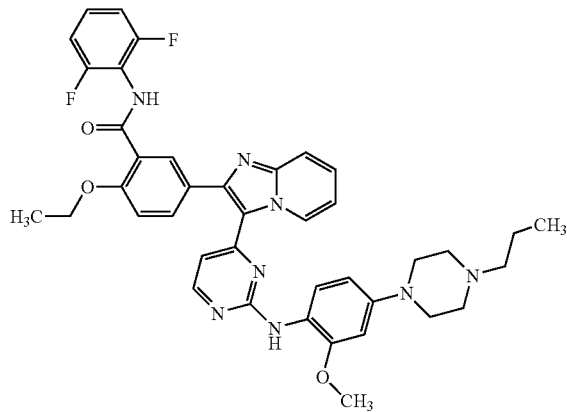

To 5-[3-(2-chloro-4-pyrimidinyl)imidazo[1,2-a]pyridin-2-yl]-N-(2,6-difluorophenyl)-2-(ethyloxy)benzamide (Intermediate Example 6) (100 mg, 0.20 mmol) and [2-(methyloxy)-4-(4-propyl-1-piperazinyl)phenyl]amine (Example 173, step B) (49 mg, 0.20 mmol) in 2,2,2-trifluoroethanol (1.0 mL) was added 4 M HCl in dioxane (99 µL, 0.40 mmol). The mixture was stirred and heated on a Biotage microwave at 175° C. for 35 minutes, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 minutes, then poured through a Teflon filter, washing the solids with cold hexanes. The solids were dried under vacuum to give the title compound (120 mg, 0.16 mmol, 85%) as a light yellow solid. $^1$H NMR (400 MHz, DMSO-d$_6$): δ 9.75 (s, 1H), 9.36 (br s, 1H), 8.45 (s, 1H), 8.20 (d, 1H, J=5.31 Hz), 8.05 (m, 1H), 7.74 (m, 1H), 7.69 (d, 1H, J=8.97 Hz), 7.34-7.46 (m, 3H), 7.27 (d, 1H, J=8.61 Hz), 7.19 (t, 2H, J=8.06 Hz), 6.95 (t, 1H, J=6.68 Hz), 6.68 (d, 1H, J=2.01 Hz), 6.53 (d, 1H, J=5.13 Hz), 6.48 (dd, 1H, J=2.20 and 8.61 Hz), 6.24-6.30 (m, 2H), 3.80 (s, 3H), 3.11-3.16 (m, 4H), 2.45-2.54 (m, 4H), 2.28 (t, 2H, J=7.42 Hz), 1.41-1.50 (m, 4H), 0.87 (t, 3H, J=7.42 Hz). MS (ESI): 719 [M+H]$^+$.

Example 179

N-(2,6-difluorophenyl)-5-[3-(2-{[4-[1-(2-fluoroethyl)-4-piperidinyl]-2-(methyloxy)phenyl]-amino}-4-pyrimidinyl)imidazo[1,2-a]pyridin-2-yl]-2-(methyloxy)benzamide

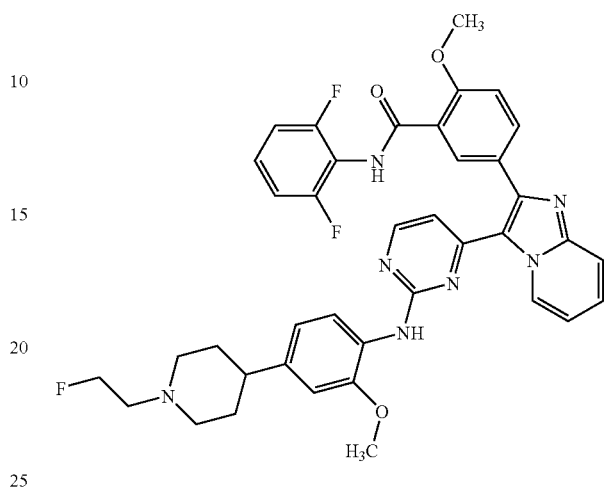

Step A: 1-(2-fluoroethyl)-4-[3-(methyloxy)-4-nitrophenyl]pyridinium bromide

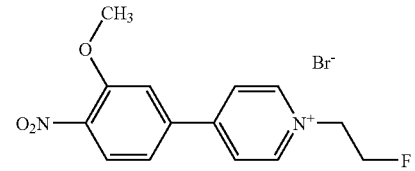

To 4-[3-(methyloxy)-4-nitrophenyl]pyridine (Example 137, step A) (2.3 g, 10 mmol) in pinacolone (25 mL) is added 1-bromo-2-fluoroethane (2.5 g, 20 mmol). The mixture was stirred at 110° C. in a sealed tube overnight. The solution was cooled to rt and the solid collected by vacuum filtration washing with acetone. The title compound of step A (2.0 g, 5.6 mmol, 56%) was obtained as a beige solid. $^1$H NMR (400 MHz, DMSO-d$_6$) δ9.21 (d, J=7.0 Hz, 2H), 8.68 (d, J=7.3 Hz, 2H), 8.12 (d, J=8.4 Hz, 1H), 7.92 (d, J=1.8 Hz, 1H), 7.77 (dd, J=8.4, 1.8 Hz, 1H), 5.05 (s, 2H), 5.00-4.90 (m, 2H), 4.07 (s, 3H). MS (ESI) m/z=277 [M].

Step B: 1-(2-fluoroethyl)-4-[3-(methyloxy)-4-nitrophenyl]-1,2,3,6-tetrahydropyridine

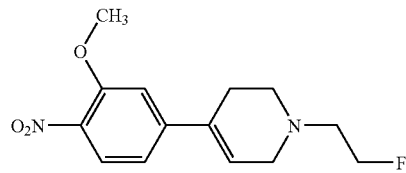

To 1-(2-fluoroethyl)-4-[3-(methyloxy)-4-nitrophenyl]pyridinium bromide (2.0 g, 5.6 mmol) in MeOH (10 mL) cooled in an ice bath was added NaBH$_4$ (1.1 g, 28 mmol) at such a rate to control the foaming which occurred. The mixture was stirred for 2 h then rotovaped down. EtOAc (200 mL) was added, and the solution was washed with saturated NaHCO$_3$ solution and H$_2$O. The solution was dried (MgSO$_4$), filtered, rotovaped and purified by silica gel chromatography. The desired fractions were combined and rotovaped to give the title compound of step B (0.90 g, 3.2 mmol, 57%) as an oil. ¹H NMR (400 MHz, CDCl₃) δ 7.86 (d, J=8.4 Hz, 1H), 7.05-7.00 (m, 2H), 6.22-6.18 (m, 1H), 4.73 (dd, J=5.1, 4.8 Hz, 1H), 4.61 (dd, J=5.1, 4.8 Hz, 1H), 3.97 (s, 3H), 3.36-3.31 (m, 2H), 2.94-2.82 (m, 4H), 2.65-2.57 (m, 2H).

Step C: 4-[1-(2-fluoroethyl)-4-piperidinyl]-2-(methyloxy)aniline

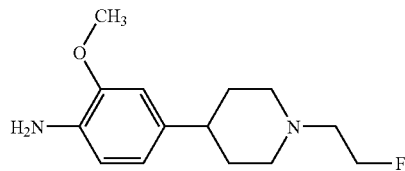

To 1-(2-fluoroethyl)-4-[3-(methyloxy)-4-nitrophenyl]-1,2,3,6-tetrahydropyridine (0.90 g, 3.2 mmol) in EtOAc (20 mL) was added Pd (10%) on carbon (100 mg). The reaction was evacuated then refilled with 10 psi H₂ gas. The reaction was stirred for 3 days. The reaction was evacuated and the atmosphere replaced with N₂. The solution was filtered to remove Pd/carbon and rotovaped down to give the title compound of step C as a red crystalline solid (800 mg, 3.2 mmol, 100% yield). ¹H NMR (400 MHz, CDCl₃) δ 6.69 (s, 1H), 6.66-6.64 (m, 2H), 4.70 (dd, J=5.1, 4.8 Hz, 1H), 4.58 (dd, J=5.1, 4.81 Hz, 1H), 3.83 (s, 3H), 3.69 (brs, 2H), 3.17-3.05 (m, 2H), 2.84-2.72 (m, 2H), 2.48-2.36 (m, 1H), 2.27-2.14 (m, 2H), 1.92-1.79 (m, 4H).

Step D: N-(2,6-difluorophenyl)-5-[3-(2-{[4-[1-(2-fluoroethyl)-4-piperidinyl]-2-(methyloxy)-phenyl]amino}-4-pyrimidinyl)imidazo[1,2-a]pyridin-2-yl]-2-(methyloxy)benzamide To 5-[3-(2-chloro-4-pyrimidinyl)imidazo[1,2-a]pyridin-2-yl]-N-(2,6-difluorophenyl)-2-(methyloxy)benzamide (Intermediate Example 2) (238 mg, 0.50 mmol) and 4-[1-(2-fluoroethyl)-4-piperidinyl]-2-(methyloxy)aniline (140 mg, 0.50 mmol) in iPrOH (1 mL) in a microwave vial was added p-toluenesulfonic acid monohydrate (190 mg, 1.0 mmol). The reaction was heated in a microwave at 175° C. for 1000 seconds. After cooling to rt the material was transferred to another flask, rinsing with a solution of DCM/MeOH. Silica gel was added and the solvent removed on the rotovap. The preabsorbed solids were purified by flash chromatography. The desired fractions were combined and the solvent removed on the rotovap to give product contaminated with an impurity. The material was placed under vacuum for 3 days then triturated with diethyl ether. The desired product was obtained as a white solid (23 mg, 0.033 mmol, 6.6% yield). ¹H NMR (400 MHz, DMSO-d₆) δ 9.75 (s, 1H), 9.35 (d, J=6.2 Hz, 1H), 8.47 (s, 1H), 8.22 (d, J=5.1 Hz, 1H), 8.08, (s, 1H), 7.75 (d, J=8.8 Hz, 1H), 7.71-7.60 (m, 2H), 7.42 (dd, J=8.4, 7.3 Hz, 1H), 7.35 (dd, J=7.1, 6.6 Hz, 1H), 7.25 (d, J=8.4 Hz, 1H), 7.15 (dd, J=8.1, 7.9 Hz, 2H), 6.97-6.90 (m, 2H), 6.77 (d, J=8.2 Hz, 1H), 6.56 (d, J=5.1 Hz, 1H), 4.51 (dt, J=48.0, 4.8 Hz, 2H), 3.95, (s, 3H), 3.80 (s, 3H), 2.97 (d, J=11.0 Hz, 2H), 2.60 (dt, J=28.2, 4.8 Hz, 2H), 2.08 (dd, J=11.5, 8.8 Hz, 2H), 1.77-1.59 (m, 4H). MS (ESI) m/z=708 [M+1].

Example 180

N-(2,6-difluorophenyl)-3-(3-{2-[(2-(methyloxy)-4-{1-[2-(methylsulfonyl)ethyl]-4-piperidinyl}phenyl)amino]-4-pyrimidinyl}imidazo[1,2-a]pyridin-2-yl)benzamide

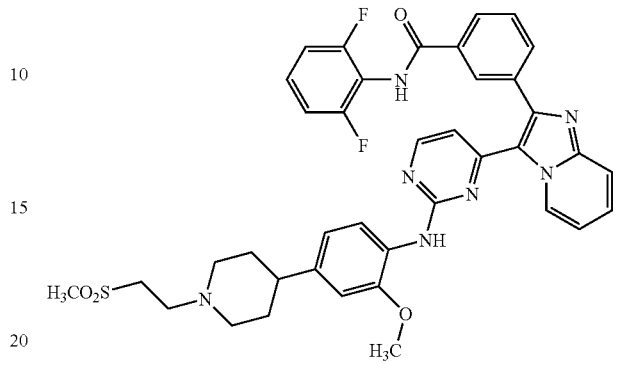

Step A: 2-(methyloxy)-4-(4-piperidinyl)aniline

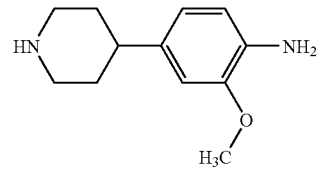

To 4-[3-(methyloxy)-4-nitrophenyl]pyridine (Example 137, step A) (4.6 g, 20 mmol) in HOAc (20 mL) is added platinum oxide (460 mg, 2 mmol). The reaction was evacuated then refilled with 60 psi H₂ gas. The reaction was stirred under a H₂ atmosphere for 3 days. The reaction was evacuated and the atmosphere replaced with N₂. The solvent was removed under vacuum, and the residue taken up in DCM/MeOH. Silica was added, and the solvent removed under vacuum. Silica gel chromatography provided material which contained product and other impurities. This material was dissolved in iPrOH and allowed to stand overnight. The crystals which formed were collected by decanting off the solvent and rinsing with iPrOH. Obtained the title compound of step A (500 mg, 2.4 mmol, 12%) slightly wet with iPrOH as colorless crystals. ¹H NMR (400 MHz, DMSO-d₆) δ 6.68-6.60 (m, 3H), 3.83 (s, 3H), 3.71 (br s, 2H), 3.38-3.31 (m, 2H), 2.85-2.75 (m, 2H), 2.59-2.49 (m, 1H), 1.91-1.75 (m, 5H).

Step B: 2-(methyloxy)-4-{1-[2-(methylsulfonyl)ethyl]-4-piperidinyl}aniline

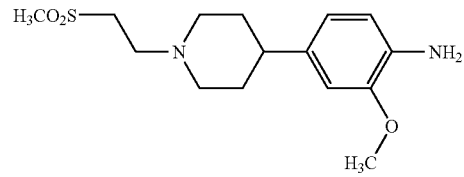

To 2-(methyloxy)-4-(4-piperidinyl)aniline (0.50 g, 2.4 mmol) in DCM (5 mL) was added methyl vinyl sulfone (0.25 g, 2.4 mmol). The mixture was stirred in a sealed tube overnight. Silica gel was added, the solvent was removed under vacuum, and the material was purified by silica gel chromatography. The desired fractions were combined and rotovaped to give the title compound of step B (0.45 g, 1.4 mmol, 58%) as an oil. ¹H NMR (400 MHz, CDCl₃) δ ¹H NMR (400 MHz, d6-DMSO) δ 6.63-6.57 (m, 3H), 3.79 (s, 3H), 3.71 (br s, 2H), 3.13 (t, J=6.6 Hz, 2H), 3.01 (s, 3H), 2.97 (d, J=11.4 Hz, 2H), 2.83 (t, J=6.6 Hz, 2H), 2.42-2.32 (m, 1H), 2.15-2.04 (m, 2H), 1.80 (d, J=12.1 Hz, 2H), 1.69-1.57 (m, 2H).

Step C: N-(2,6-difluorophenyl)-3-(3-{2-[(2-(methyloxy)-4-{1-[2-(methylsulfonyl)ethyl]-4-piperidinyl}phenyl)amino]-4-pyrimidinyl}imidazo[1,2-a]pyridin-2-yl)benzamide To 3-[3-(2-chloro-4-pyrimidinyl)imidazo[1,2-a]pyridin-2-yl]-N-(2,6-difluorophenyl)-benzamide (Intermediate Example 1) (230 mg, 0.50 mmol) and 2-(methyloxy)-4-{1-[2-(methylsulfonyl)ethyl]-4-piperidinyl}aniline (150 mg, 0.48 mmol) in trifluoroethanol (5 mL) was added p-toluenesulfonic acid monohydrate (230 mg, 1.2 mmol). The reaction was heated in a sealed-tube at 85° C. overnight. After cooling to rt, 0.5 N sodium methoxide in MeOH (5 mL) was added to the solution. The material was transferred to another flask, rinsing with a solution of DCM/MeOH. Silica gel was added and the solvent removed on the rotovap. The preabsorbed solids were purified by flash chromatography. The desired fractions were combined and the solvent removed on the rotovap to give product contaminated with an impurity. The material was dissolved in DCM and precipitated with diethyl ether. The title compound, as a white solid, was collected by vacuum filtration, rinsing with diethyl ether (170 mg, 0.23 mmol, 48% yield). ¹H NMR (400 MHz, CDCl₃) δ 9.46 (d, J=7.0 Hz, 1H), 8.33-8.26 (m, 3H), 8.07-8.02 (m, 1H), 7.85-7.81 (m, 1H), 7.74-7.69 (m, 3H), 7.54 (dd, J=7.7, 7.7 Hz, 1H), 7.41-7.35 (m, 1H), 7.26-7.20 (m, 1H), 7.00 (dd, J=8.1, 7.7 Hz, 2H), 6.93-6.88 (m, 1H), 6.83-6.78 (m, 2H), 6.65 (d, J=5.1 Hz, 1H), 3.93 (s, 3H), 3.19 (t, J=6.6 Hz, 2H), 3.09-3.02 (m, 5H), 2.92 (t, J=6.6 Hz, 2H), 2.58-2.48 (m, 1H), 2.23-2.15 (m, 2H), 1.94-1.88 (m, 2H), 1.78-1.68 (m, 2H). MS (ESI) m/z=738 [M+1].

Example 181

N-(2,6-difluorophenyl)-2-(methyloxy)-5-(3-{2-[(2-(methyloxy)-4-{1-[2-(methylsulfonyl)ethyl]-4-piperidinyl}phenyl)amino]-4-pyrimidinyl}imidazo[1,2-a]pyridin-2-yl)benzamide

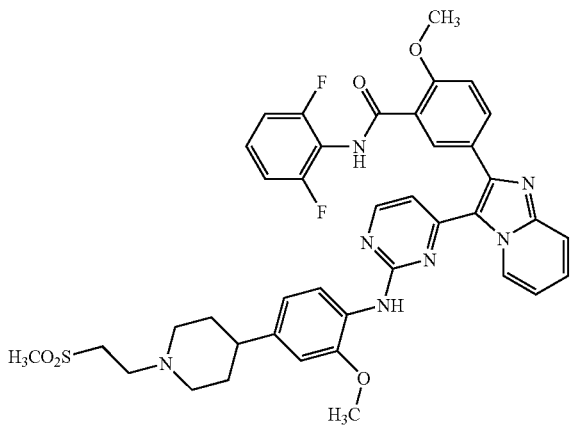

To 5-[3-(2-chloro-4-pyrimidinyl)imidazo[1,2-a]pyridin-2-yl]-N-(2,6-difluorophenyl)-2-(methyloxy)benzamide (Intermediate Example 2) (245 mg, 0.50 mmol) and 2-(methyloxy)-4-{1-[2-(methylsulfonyl)ethyl]-4-piperidinyl}aniline (Example 180, step B) (150 mg, 0.48 mmol) in trifluoroethanol (5 mL) was added p-toluenesulfonic acid monohydrate (230 mg, 1.2 mmol). The reaction was heated in a sealed-tube at 85° C. overnight. After cooling to rt, 0.5 N sodium methoxide in MeOH (5 mL) was added to the solution. The material was transferred to another flask, rinsing with a solution of DCM/MeOH. Silica gel was added and the solvent removed on the rotovap. The preabsorbed solids were purified by flash chromatography. The desired fractions were combined and the solvent removed on the rotovap to give product contaminated with an impurity. The material was triturated with diethyl ether. The title compound, as a white solid, was collected by vacuum filtration, rinsing with diethyl ether (212 mg, 0.28 mmol, 58% yield). ¹H NMR (400 MHz, DMSO-d₆) δ 9.78 (s, 1H), 9.38 (d, J=6.2 Hz, 1H), 8.52 (s, 1H), 8.25 (d, J=5.1 Hz, 1H), 8.10, (d, J=1.8 Hz, 1H), 7.79-7.63 (m, 3H), 7.47-7.35 (m, 2H), 7.28 (d, J=8.8 Hz, 1H), 7.18 (dd, J=8.4, 8.1 Hz, 2H), 6.99-6.93 (m, 2H), 6.82-6.77 (m, 1H), 6.59 (d, J=5.1 Hz, 1H), 3.98, (s, 3H), 3.83 (s, 3H), 3.32-3.27 (m, 5H), 3.04-2.98 (m, 2H), 2.72 (dd, J=7.0, 6.6 Hz, 2H), 2.06 (dd, J=11.4, 10.6 Hz, 2H), 1.82-1.61 (m, 5H). MS (ESI) m/z=384.5 [M+2]/2.

Example 182

N-(2,6-difluorophenyl)-2-(ethyloxy)-5-(3-{2-[(2-(methyloxy)-4-{1-[2-(methylsulfonyl)ethyl]-4-piperidinyl}phenyl)amino]-4-pyrimidinyl}imidazo[1,2-a]pyridin-2-yl)benzamide

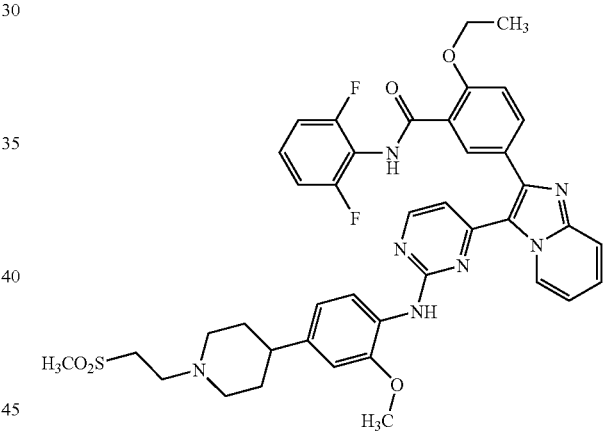

To 5-[3-(2-chloro-4-pyrimidinyl)imidazo[1,2-a]pyridin-2-yl]-N-(2,6-difluorophenyl)-2-(ethyloxy)benzamide (Intermediate Example 6) (250 mg, 0.50 mmol) and 2-(methyloxy)-4-{1-[2-(methylsulfonyl)ethyl]-4-piperidinyl}aniline (Example 180, step B) (150 mg, 0.48 mmol) in trifluoroethanol (5 mL) was added p-toluenesulfonic acid monohydrate (230 mg, 1.2 mmol). The reaction was heated in a sealed-tube at 85° C. overnight. After cooling to rt, 0.5 N sodium methoxide in MeOH (5 mL) was added to the solution. The material was transferred to another flask, rinsing with a solution of DCM/MeOH. Silica gel was added and the solvent removed on the rotovap. The preabsorbed solids were purified by flash chromatography. The desired fractions were combined and the solvent removed on the rotovap to give product contaminated with an impurity. The material was triturated with diethyl ether. The title compound, as a white solid, was collected by vacuum filtration, rinsing with diethyl ether (158 mg, 0.20 mmol, 42% yield). ¹H NMR (400 MHz, DMSO-d₆) δ 9.74 (s, 1H), 9.38 (d, J=6.2 Hz, 1H), 8.51 (s, 1H), 8.25 (d, J=5.1 Hz, 1H), 8.05, (d, J=2.0 Hz, 1H), 7.76-7.64 (m, 3H), 7.47-7.32 (m, 2H), 7.26 (d, J=8.8 Hz, 1H), 7.19 (dd, J=8.0, 8.0 Hz, 2H), 6.99-6.94 (m, 2H), 6.82-6.77 (m, 1H), 6.59 (d, J=5.1 Hz, 1H), 4.26 (q, J=7.0 Hz, 2H), 3.83 (s, 3H), 3.32-3.27 (m, 3H), 3.04-2.98 (m, 5H), 2.72 (dd, J=7.0, 6.6 Hz, 2H), 2.10-2.02 (m, 2H), 1.81-1.61 (m, 4H), 1.42 (t, J=7.0 Hz, 3H). MS (ESI) m/z=391.5 [M+2]/2.

Example 183

N-(2,6-difluorophenyl)-3-(3-{2-[(2-(ethyloxy)-4-{1-[2-(methylsulfonyl)ethyl]-4-piperidinyl}phenyl)amino]-4-pyrimidinyl}imidazo[1,2-a]pyridin-2-yl)benzamide

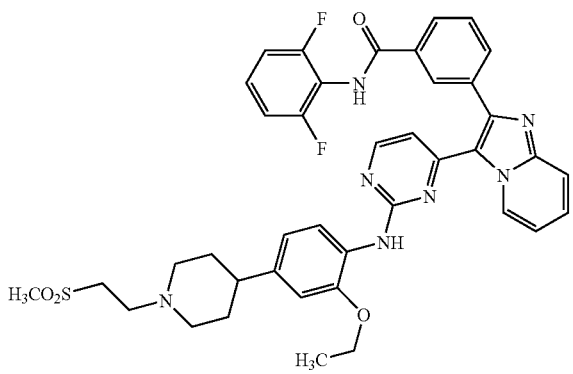

Step A: 5-bromo-2-nitrophenyl ethyl ether

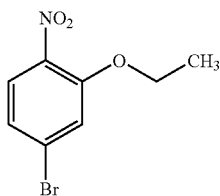

To 4-bromo-2-fluoro-1-nitrobenzene (8.2 g, 37.27 mmol) in 50 mL of ethanol was added 21% by weight sodium ethoxide (16.4 mL, 52.2 mmol). The mixture was stirred at 60° C. for 1 h. The EtOH was rotovaped down. The crude product was dissolved in DCM (100 mL), washed with H₂O, dried (MgSO₄), filtered, and rotovaped down to give the title compound of step A (9.14 g, 37.14 mmol, 99.7%) as a yellow solid. ¹H NMR (400 MHz, CDCl₃) δ ppm 7.71 (d, J=8.61 Hz, 1H), 7.20 (d, J=1.83 Hz, 1H), 7.14 (dd, J=8.61, 1.83 Hz, 1H), 4.16 (q, J=7.02 Hz, 2H), 1.47 (t, J=6.96 Hz, 3H).

Step B: 4-[3-(ethyloxy)-4-nitrophenyl]pyridine

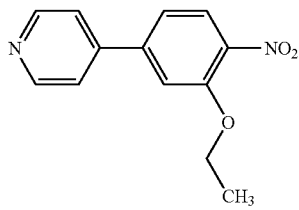

A solution of 5-bromo-2-nitrophenyl ethyl ether (4.64 g, 18.86 mmol), PdCl₂(dppf)*DCM (0.69 g, 0.94 mmol) and 4-pyridylboronic acid (4.03 g, 32.8 mmol) in N,N-dimethylacetamide (113 mL) was deoxygenated by bubbling with N₂ (g) for ca 15 min. To this solution was added degassed 1.6 N K₂CO₃ (aq) (56.6 mL, 6.0 equiv.) and the resulting slurry was warmed to 80° C. for 24 h. The mixture was poured into 300 mL of H₂O and neutralized with HOAc. The product was extracted with DCM, and dried (MgSO₄). The solvent was rotovaped down and the crude product was purified by flash chromatography to give the title compound of step B (3.57 g, 14.62 mmol, 77.5%). ¹H NMR (400 MHz, DMSO-d₆) δ ppm 8.66-8.70 (m, 2H), 7.97 (d, J=8.42 Hz, 1H), 7.77-7.81 (m, 2H), 7.64 (d, J=1.65 Hz, 1H), 7.47 (dd, J=8.42, 1.65 Hz, 1H), 4.33 (q, J=6.96 Hz, 2H), 1.34 (t, J=6.96 Hz, 3H).

Step C: 2-(ethyloxy)-4-(4-pyridinyl)aniline

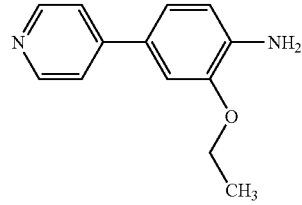

4-[3-(Ethyloxy)-4-nitrophenyl]pyridine (3.57 g, 14.62 mmol) was place in a 250 mL high pressure vessel and dissolved in 60 mL of 1 to 1 EtOAc/MeOH. 5 wt % Platinum (sulfided)/carbon (2.85 g, 0.73 mmol) was added followed quickly by a rubber septum. The flask was evacuated and filled with N₂ six times to remove any oxygen. The vessel was then pressurized with H₂ (60 psi). The solution stirred for 6 hours. The vessel was evacuated and filled with N₂ six times to remove any H₂. The solution was filtered through celite and evaporated to give the title compound of step C (2.62 g, 12.2 mmol, 83%). ¹H NMR (400 MHz, DMSO-d₆) δ ppm 8.44-8.48 (m, 2H), 7.57 (dd, J=4.58, 1.46 Hz, 2H), 7.16-7.21 (m, 2H), 6.70 (d, J=7.87 Hz, 1H), 5.09 (bs, 2H), 4.09 (q, J=6.96 Hz, 2H), 1.34 (t, J=6.96 Hz, 3H).

Step D: N-[2-(ethyloxy)-4-(4-pyridinyl)phenyl]-2,2,2-trifluoroacetamide

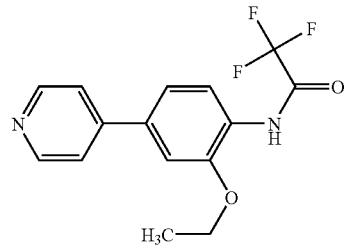

To 2-(ethyloxy)-4-(4-pyridinyl)aniline (2.62 g, 12.2 mmol) in THF was added TEA (3.71 g, 36.73 mmol), and trifluoroacetic anhydride (5.14 g, 24.5 mmol). The mixture was heated to 50° C. overnight. The solvent was rotovaped down and the residue purified by flash chromatography to give the title compound of step D with an equivalent of TEA present (4.6 g, 14.82 mmol, 120%). ¹H NMR (400 MHz, DMSO-d₆) δ ppm 10.71 (s, 1H), 8.62 (dd, J=4.67, 1.56 Hz, 2H), 7.74 (dd, J=4.58, 1.47 Hz, 2H), 7.53 (d, J=8.24 Hz, 1H), 7.47 (d, J=1.65 Hz, 1H), 7.39 (dd, J=8.06, 1.83 Hz, 1H), 4.20 (q, J=6.96 Hz, 2H), 1.32 (t, J=6.96 Hz, 3H).

Step E: N-[2-(ethyloxy)-4-(4-piperidinyl)phenyl]-2,2,2-trifluoroacetamide acetate

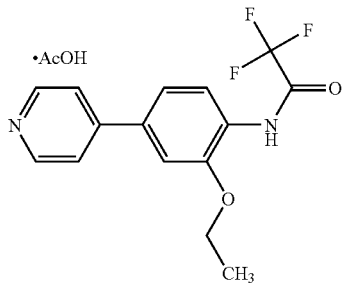

N-[2-(Ethyloxy)-4-(4-pyridinyl)phenyl]-2,2,2-trifluoroacetamide (4.6 g, 14.82 mmol) was place in a 250 mL high pressure vessel and dissolved in 70 mL of HOAc. Platinum oxide (0.373 g, 1.48 mmol) was added followed quickly by a rubber septum. The flask was evacuated and filled with $N_2$ six times to remove any oxygen. The vessel was then pressurized with $H_2$ (60 psi). The solution stirred for 24 h. The vessel was evacuated and filled with $N_2$ six times to remove any N $H_2$. The solution was filtered through celite and evaporated to give the title compound of step E (4.8 g, 7.46 mmol, 98%). $^1$H NMR (400 MHz, DMSO-$d_6$) δ ppm 7.27 (d, J=8.07 Hz, 1H), 6.94 (d, J=1.47 Hz, 1H), 6.81 (dd, J=8.07, 1.83 Hz, 1H), 4.05 (q, J=6.97 Hz, 2H), 3.20 (d, J=12.10 Hz, 2H), 2.79 (td, J=12.56, 2.38 Hz, 2H), 2.68-2.74 (m, 1H), 1.84 (s, 3H), 1.78-1.83 (m, 2H), 1.70 (td, J=12.56, 3.48 Hz, 2H), 1.28 (t, J=6.97 Hz, 3H).

Step F: N-(2-(ethyloxy)-4-{1-[2-(methylsulfonyl)ethyl]-4-piperidinyl}phenyl)-2,2,2-trifluoroacetamide

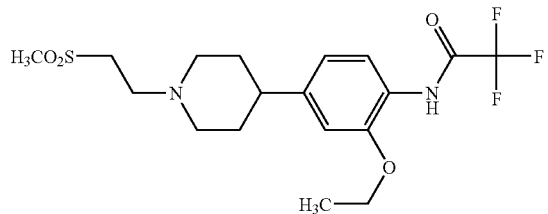

To N-[2-(ethyloxy)-4-(4-piperidinyl)phenyl]-2,2,2-trifluoroacetamide acetate (2.2 g, 5.9 mmol) and methyl vinyl sulfone (0.74 g, 7.0 mmol) in DCM (50 mL) was added $K_2CO_3$ (1.2 g, 8.8 mmol). A few drops of MeOH were added to help solubilize the reagents. The reaction was stirred in a sealed tube three h. The reaction was filtered then purified by silica gel chromatography. The desired fractions were combined, and the solvent was removed under vacuum to provide the title compound of step F as a white solid (1.4 g, 3.3 mmol, 58%). $^1$H NMR (400 MHz, DMSO-$d_6$) δ 8.52 (br s, 1H), 8.18 (d, J=8.2 Hz, 1H), 6.81 (dd, J=8.2, 1.6 Hz, 1H), 6.73 (d, J=1.6 Hz, 1H), 4.11 (q, J=7.0 Hz, 2H), 3.15 (t, J=6.6 Hz, 2H), 3.02 (s, 3H), 3.00 (d, J=11.7 Hz, 2H), 2.88 (t, J=6.6 Hz, 2H), 2.52-2.42 (m, 1H), 2.18-2.10 (m, 2H), 1.84 (d, J=12.8 Hz, 2H), 1.73-1.60 (m, 2H), 1.44 (t, J=7.0 Hz, 3H).

Step G: 2-(ethyloxy)-4-{1-[2-(methylsulfonyl)ethyl]-4-piperidinyl}aniline

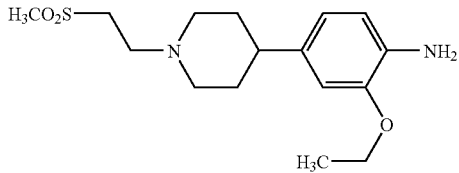

To N-(2-(ethyloxy)-4-{1-[2-(methylsulfonyl)ethyl]-4-piperidinyl}phenyl)-2,2,2-trifluoroacetamide (1.4 g, 3.3 mmol) in THF (25 mL) and $H_2O$ (25 mL) was added LiOH (0.21 g, 5.0 mmol). The mixture was stirred for two h and then more LiOH (0.21 g, 5.0 mmol) was added. After stirring for one h, the product was extracted with EtOAc. The organic layer was dried ($MgSO_4$), filtered and rotovaped to provided the title compound of step G as a colorless oil (1.0 g, 3.1 mmol, 94%). $^1$H NMR (400 MHz, DMSO-$d_6$) δ 6.66-6.56 (m, 3H), 4.02 (q, J=7.0 Hz, 2H), 3.15 (t, J=6.6 Hz, 2H), 3.03 (s, 3H), 2.99 (d, J=11.5 Hz, 2H), 2.88 (t, J=6.6 Hz, 2H), 2.42-2.32 (m, 1H), 2.13 (dd, J=11.9, 11.7 Hz, 2H), 1.82 (d, J=13.0 Hz, 2H), 1.70-1.58 (m, 2H), 1.39 (t, J=7.0 Hz, 3H).

Step H: N-(2,6-difluorophenyl)-3-(3-{2-[(2-(ethyloxy)-4-{1-[2-(methylsulfonyl)ethyl]-4-piperidinyl}phenyl)amino]-4-pyrimidinyl}imidazo[1,2-a]pyridin-2-yl)benzamide To 3-[3-(2-chloro-4-pyrimidinyl)imidazo[1,2-a]pyridin-2-yl]-N-(2,6-difluorophenyl)-benzamide (Intermediate Example 1) (230 mg, 0.50 mmol) and 2-(ethyloxy)-4-{1-[2-(methylsulfonyl)ethyl]-4-piperidinyl}aniline (250 mg, 0.76 mmol) in trifluoroethanol (5 mL) was added p-toluenesulfonic acid monohydrate (190 mg, 1.0 mmol). The reaction was heated in a sealed-tube at 80° C. overnight. After cooling to rt, 0.5 N sodium methoxide in MeOH (5 mL) was added to the solution. The material was transferred to another flask, rinsing with a solution of DCM/MeOH. Silica gel was added and the solvent removed on the rotovap. The preabsorbed solids were purified by flash chromatography. The desired fractions were combined and the solvent removed on the rotovap. The material was dissolved in DCM and precipitated with diethyl ether. The title compound, as a white solid, was collected by vacuum filtration, rinsing with diethyl ether (25 mg, 0.033 mmol, 6.6% yield). $^1$H NMR (400 MHz, $CDCl_3$) δ 9.43 (d, J=7.1 Hz, 1H), 8.31-8.25 (m, 3H), 8.01 (d, J=7.9 Hz, 1H), 7.81 (d, J=7.7 Hz, 1H), 7.74-7.68 (m, 2H), 7.60 (s, 1H), 7.51 (dd, J=7.9, 7.7 Hz, 1H), 7.38-7.34 (m, 1H), 7.26-7.18 (m, 1H), 6.97 (dd, J=8.1, 7.9 Hz, 2H), 6.87 (dd, J=6.8, 6.6 Hz, 1H), 6.79-6.74 (m, 2H), 6.61 (d, J=5.1 Hz, 1H), 4.12 (q, J=7.0 Hz, 2H), 3.16 (t, J=6.6 Hz, 2H), 3.06-2.99 (m, 5H), 2.89 (t, J=6.6 Hz, 2H), 2.53-2.42 (m, 1H), 2.20-2.12 (m, 2H), 1.93-1.84 (m, 2H), 1.77-1.64 (m, 2H), 1.47 (t, J=7.0 Hz, 3H). MS (ESI) m/z=752 [M+1].

Example 184

N-(2,6-difluorophenyl)-5-(3-{2-[(2-(ethyloxy)-4-{1-[2-(methylsulfonyl)ethyl]-4-piperidinyl}-phenyl)amino]-4-pyrimidinyl}imidazo[1,2-a]pyridin-2-yl)-2-(methyloxy)benzamide

Example 185

N-(2,6-difluorophenyl)-2-(ethyloxy)-5-(3-{2-[(2-(ethyloxy)-4-{1-[2-(methylsulfonyl)ethyl]-4-piperidinyl}phenyl)amino]-4-pyrimidinyl}imidazo[1,2-a]pyridin-2-yl)benzamide

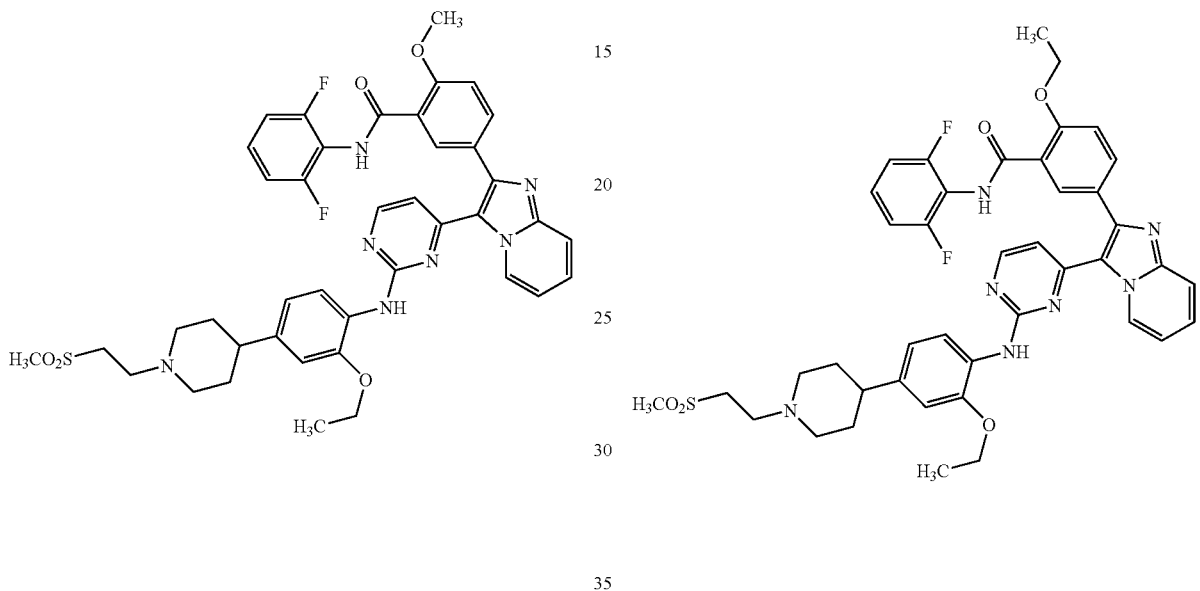

To 5-[3-(2-chloro-4-pyrimidinyl)imidazo[1,2-a]pyridin-2-yl]-N-(2,6-difluorophenyl)-2-(methyloxy)benzamide (Intermediate Example 2) (245 mg, 0.50 mmol) and 2-(ethyloxy)-4-{1-[2-(methylsulfonyl)ethyl]-4-piperidinyl}aniline (Example 183, step G) (250 mg, 0.76 mmol) in trifluoroethanol (5 mL) was added p-toluenesulfonic acid monohydrate (190 mg, 1. mmol). The reaction was heated in a sealed-tube at 80° C. overnight. After cooling to rt, 0.5 N sodium methoxide in MeOH (5 mL) was added to the solution. The material was transferred to another flask, rinsing with a solution of DCM/MeOH. Silica gel was added and the solvent removed on the rotovap. The preabsorbed solids were purified by flash chromatography. The desired fractions were combined and the solvent removed on the rotovap. The material was dissolved in DCM and precipitated with diethyl ether. The title compound, as a white solid, was collected by vacuum filtration, rinsing with diethyl ether (155 mg, 0.20 mmol, 40% yield). $^1$H NMR (400 MHz, CDCl$_3$) δ 9.49 (d, J=7.0 Hz, 1H), 9.25 (s, 1H), 8.60 (d, J=2.4 Hz, 1H), 8.30 (d, J=8.1 Hz, 1H), 8.22 (d, J=5.3 Hz, 1H), 7.85 (dd, J=8.4, 2.4 Hz, 1H), 7.71-7.66 (m, 2H), 7.35-7.29 (m, 1H), 7.22-7.09 (m, 2H), 6.99-6.91 (m, 2H), 6.85-6.74 (m, 3H), 6.63 (d, J=5.3 Hz, 1H), 4.12 (q, J=7.0 Hz, 2H), 4.09 (s, 3H), 3.16 (t, J=6.6 Hz, 2H), 3.06-2.98 (m, 5H), 2.89 (t, J=6.6 Hz, 2H), 2.53-2.43 (m, 1H), 2.20-2.12 (m, 2H), 1.92-1.85 (m, 2H), 1.77-1.64 (m, 2H), 1.46 (t, J=7.0 Hz, 3H). MS (ESI) m/z=391.5 [M+2]/2.

To 5-[3-(2-chloro-4-pyrimidinyl)imidazo[1,2-a]pyridin-2-yl]-N-(2,6-difluorophenyl)-2-(ethyloxy)benzamide (Intermediate Example 6) (250 mg, 0.50 mmol) and 2-(ethyloxy)-4-{1-[2-(methylsulfonyl)ethyl]-4-piperidinyl}aniline (Example 183, step G) (250 mg, 0.76 mmol) in trifluoroethanol (5 mL) was added p-toluenesulfonic acid monohydrate (190 mg, 1. mmol). The reaction was heated in a sealed-tube at 80° C. overnight. After cooling to rt, 0.5 N sodium methodixe in MeOH (5 mL) was added to the solution. The material was transferred to another flask, rinsing with a solution of DCM/MeOH. Silica gel was added and the solvent removed on the rotovap. The preabsorbed solids were purified by flash chromatography. The desired fractions were combined and the solvent removed on the rotovap. The material was dissolved in DCM and precipitated with diethyl ether. The title compound, as a white solid, was collected by vacuum filtration, rinsing with diethyl ether (70 mg, 0.088 mmol, 18% yield). $^1$H NMR (400 MHz, CDCl$_3$) δ 9.54 (s, 1H), 9.51 (d, J=7.0 Hz, 1H), 8.61 (d, J=2.4 Hz, 1H), 8.30 (d, J=8.2 Hz, 1H), 8.22 (d, J=5.1 Hz, 1H), 7.84 (dd, J=8.6, 2.4 Hz, 1H), 7.71-7.67 (m, 2H), 7.35-7.29 (m, 1H), 7.22-7.11 (m, 1H), 7.09 (d, J=8.8 Hz, 1H), 6.99-6.92 (m, 2H), 6.85-6.74 (m, 3H), 6.64 (d, J=5.5 Hz, 1H), 4.33 (q, J=7.1 Hz, 2H), 4.13 (q, J=7.0 Hz, 2H), 3.17 (t, J=6.6 Hz, 2H), 3.06-2.98 (m, 5H), 2.90 (t, J=6.6 Hz, 2H), 2.54-2.44 (m, 1H), 2.20-2.12 (m, 2H), 1.92-1.85 (m, 2H), 1.77-1.64 (m, 2H), 1.59 (t, J=7.1 Hz, 3H), 1.46 (t, J=7.0 Hz, 3H). MS (ESI) m/z=796 [M+1].

Example 186

N-(2,6-difluorophenyl)-5-(3-{2-[(2-(ethyloxy)-4-{1-[2-(methylsulfonyl)ethyl]-4-piperidinyl}phenyl)amino]-4-pyrimidinyl}imidazo[1,2-a]pyridin-2-yl)-2-[(1-methylethyl)oxy]benzamide

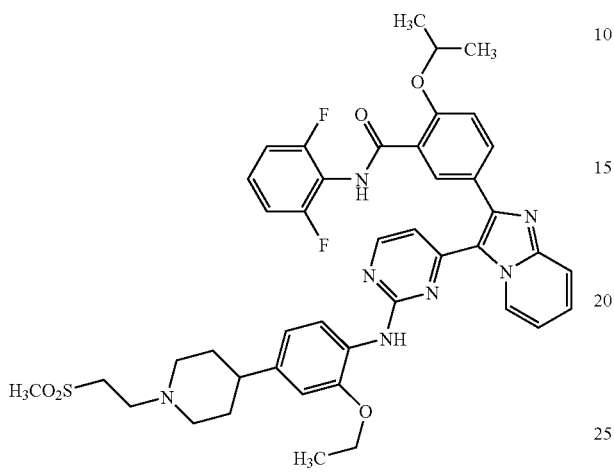

To 5-[3-(2-chloro-4-pyrimidinyl)imidazo[1,2-a]pyridin-2-yl]-N-(2,6-difluorophenyl)-2-[(1-methylethyl)oxy]benzamide (Intermediate Example 7) (260 mg, 0.50 mmol) and 2-(ethyloxy)-4-{1-[2-(methylsulfonyl)ethyl]-4-piperidinyl}aniline (Example 183, step G) (250 mg, 0.76 mmol) in trifluoroethanol (5 mL) was added p-toluenesulfonic acid monohydrate (190 mg, 1. mmol). The reaction was heated in a sealed-tube at 80° C. overnight. After cooling to rt, 0.5 N sodium methoxide in MeOH (5 mL) was added to the solution. The material was transferred to another flask, rinsing with a solution of DCM/MeOH. Silica gel was added and the solvent removed on the rotovap. The preabsorbed solids were purified by flash chromatography. The desired fractions were combined and the solvent removed on the rotovap. The material was dissolved in DCM and precipitated with diethyl ether. The title compound, as a white solid, was collected by vacuum filtration, rinsing with diethyl ether (98 mg, 0.12 mmol, 24% yield). $^1$H NMR (400 MHz, CDCl$_3$) δ 9.65 (s, 1H), 9.51 (d, J=7.3 Hz, 1H), 8.61 (d, J=2.4 Hz, 1H), 8.30 (d, J=8.2 Hz, 1H), 8.23 (d, J=5.3 Hz, 1H), 7.83 (dd, J=8.6, 2.4 Hz, 1H), 7.71-7.67 (m, 2H), 7.35-7.29 (m, 1H), 7.22-7.09 (m, 2H), 6.99-6.92 (m, 2H), 6.85-6.74 (m, 3H), 6.67 (d, J=5.3 Hz, 1H), 4.93-4.84 (m, 1H), 4.13 (q, J=7.0 Hz, 2H), 3.16 (t, J=6.6 Hz, 2H), 3.06-2.98 (m, 5H), 2.89 (t, J=6.6 Hz, 2H), 2.54-2.44 (m, 1H), 2.20-2.12 (m, 2H), 1.92-1.85 (m, 2H), 1.77-1.64 (m, 2H), 1.51 (d, J=6.0 Hz, 6H), 1.47 (t, J=7.0 Hz, 3H). MS (ESI) m/z=405.5 [M+2]/2.

Example 187

N-(2,6-difluorophenyl)-5-(3-{2-[(5-ethyl-2-(methyloxy)-4-{4-[2-(methylsulfonyl)ethyl]-1-piperazinyl}phenyl)amino]-4-pyrimidinyl}imidazo[1,2-a]pyridin-2-yl)-2-(methyloxy)benzamide

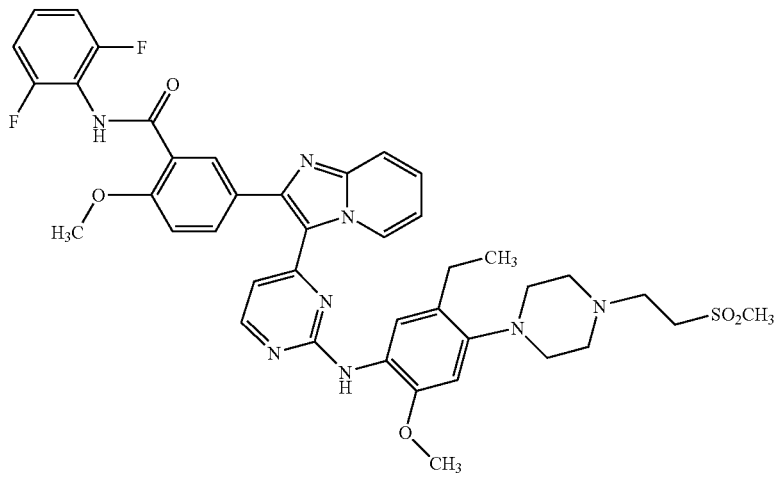

Step A: 4-ethyl-3-fluorophenol

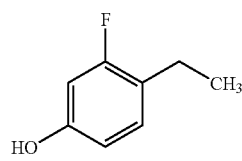

2-Fluoro-4-hydroxyacetophenone (15.14 g, 100 mmol) and zinc dust (19.61 g, 300 mmol) were suspended in 50 mL of H$_2$O with stirring. Concentrated HCl (37%, 50 mL, 610 mmol) were added and the mixture was heated to reflux for six h. The reaction was cooled to rt, and diethyl ether was added. The mixture was saturated with NaCl, and filtered through celite washing with diethyl ether. The filtrate was poured into brine, and the layers were separated. The aqueous layer was extracted with diethyl ether. The combined organic layers were dried over MgSO$_4$, filtered, and concentrated in vacuo. The residue was purified by flash chromatography to afford 7.24 g (52%) of the title compound of step A. $^1$H NMR (400 MHz, DMSO-$d_6$) δ 9.53 (s, 1H), 7.00 (t, J=8.8 Hz, 1H), 6.52-6.40 (m, 2H), 2.44 (q, J=7.5 Hz, 2H), 1.06 (t, J=7.5 Hz, 3H).

Step B: 4-ethyl-5-fluoro-2-nitrophenol

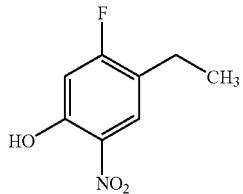

4-Ethyl-3-fluorophenol (7.24 g, 51.6 mmol) was dissolved in 100 mL of dichloroethane with stirring. Tetrabutylammonium bromide (1.66 g, 5.15 mmol) was added. A seven percent aqueous solution of HNO$_3$ (66 mL) was prepared and added to the reaction. The biphasic mixture was stirred vigorously overnight. The reaction was poured into DCM and H$_2$O, and the layers were separated. The aqueous layer was washed with DCM (2×). The combined organic layers were dried over MgSO$_4$, filtered, and concentrated in vacuo. The residue was purified by flash chromatography to afford 5.72 g (60%) of the title compound of step B. $^1$H NMR (400 MHz, DMSO-$d_6$) δ 11.17 (s, 1H), 7.89 (d, J=8.0 Hz, 1H), 6.89 (d, J=11.2 Hz, 1H), 2.56 (q, J=7.5 Hz, 2H), 1.13 (t, J=7.5 Hz, 3H).

Step C:
1-ethyl-2-fluoro-4-(methyloxy)-5-nitrobenzene

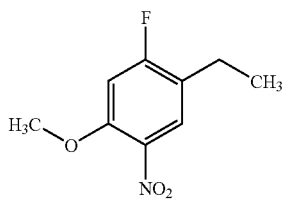

4-Ethyl-5-fluoro-2-nitrophenol (5.72 g, 30.9 mmol) was dissolved in 60 mL of DMSO with stirring. K$_2$CO$_3$ (6.41 g, 46.4 mmol) was added. Methyl iodide (2.5 mL, 40 mmol) was added via syringe. The reaction was stirred overnight and poured into H$_2$O and diethyl ether. The layers were separated, and the organic layer was washed with brine. The combined aqueous layers were extracted with EtOAc (2×). The combined organic layers were dried over MgSO$_4$, filtered, and concentrated in vacuo. The residue was purified by flash chromatography to afford 5.13 g (83%) of the title compound of step C. $^1$H NMR (400 MHz, DMSO-$d_6$) δ 7.88 (d, J=7.9 Hz, 1H), 7.23 (d, J=12.1 Hz, 1H), 3.86 (s, 3H), 2.56 (q, J=7.6 Hz, 2H), 1.11 (t, J=7.5 Hz, 3H).

Step D: 1-[2-ethyl-5-(methyloxy)-4-nitrophenyl]-4-[2-(methylsulfonyl)ethyl]piperazine

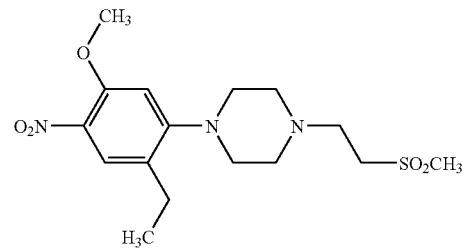

1-Ethyl-2-fluoro-4-(methyloxy)-5-nitrobenzene (1.0 g, 5.0 mmol) was dissolved in DMSO (8 mL). Potassium carbonate (2.1 g, 15 mmol) and 1-[2-(methylsulfonyl)ethyl]piperazine hydrochloride (Example 148, step B) (1.1 g, 5.0 mmol) were added and the reaction mixture was heated to 65° C. and allowed to stir over the weekend. The mixture was then poured into water and extracted with EtOAc (2×). The combined organics were dried with MgSO$_4$, filtered, and concentrated in vacuo to give the title compound without further purification (1.7 g, 4.7 mmol, 93%). MS (M+H, ES+) 372.

Step E: 5-ethyl-2-(methyloxy)-4-{4-[2-(methylsulfonyl)ethyl]-1-piperazinyl}aniline

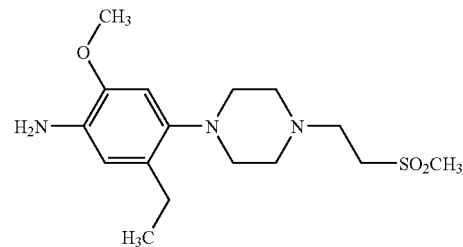

1-[2-Ethyl-5-(methyloxy)-4-nitrophenyl]-4-[2-(methylsulfonyl)ethyl]piperazine (1.7 g, 4.7 mmol) was taken up in EtOAc (30 mL) and EtOH (15 mL). The catalyst, 5% sulfided platinum on carbon (300 mg) was added. The reaction was placed under 1 atm of H$_2$ gas and was allowed to stir at room temperature for 5 days. The catalyst was filtered off and the filtrate was concentrated in vacuo to give the title compound without further purification (1.4 g, 4.1 mmol, 86%). MS (M+H, ES+) 342.

Step F: N-(2,6-difluorophenyl)-5-(3-{2-[(5-ethyl-2-(methyloxy)-4-{4-[2-(methylsulfonyl)ethyl]-1-piperazinyl]phenyl)amino}-4-pyrimidinyl}imidazo[1,2-a]pyridin-2-yl)-2-(methyloxy)benzamide In a microwave vial with septum cap, 5-[3-(2-chloro-4-pyrimidinyl)imidazo[1,2-a]pyridin-2-yl]-N-(2,6-difluorophenyl)-2-(methyloxy)benzamide (Intermediate Example 2) (0.246 g, 0.5 mmol) and 5-ethyl-2-(methyloxy)-4-{4-[2-(methylsulfonyl)ethyl]-1-piperazinyl}aniline (0.171 g, 0.5 mmol) were taken up in 1,1,1-trifluoroethanol (3 mL) and 4M HCl in dioxane (0.25 mL, 1.0 mmol) was added. The vial was sealed and heated in the microwave at 180° C. for 40 min. Reaction was complete by MS, it was cooled rt, neutralized with 7N NH$_3$ in MeOH, and concentrated in vacuo onto silica gel and flash chromatographed. The desired fractions were combined and concentrated and the resulting solid was triturated with diethyl ether, filtered and air dried to give the title compound (0.150 g, 0.19 mmol, 38%). 1H NMR (400 MHz, DMSO-d$_6$) δ ppm 9.78 (s, 1H), 9.34 (dd, J=3.1, 2.2 Hz, 1H), 8.49 (s, 1H), 8.24 (d, J=5.1 Hz, 1H), 8.11 (d, J=1.3 Hz, 1H), 7.78 (dd, J=8.9, 1.4 Hz, 1H), 7.70 (d, J=9.0 Hz, 1H), 7.54 (s, 1H), 7.33-7.50 (m, 2H), 7.28 (d, J=8.8 Hz, 1H), 7.18 (t, J=8.1 Hz, 2H), 6.94 (t, J=6.6 Hz, 1H), 6.83 (s, 1H), 6.57 (d, J=4.9 Hz, 1H), 3.98 (s, 3H), 3.80 (s, 3H), 3.28-3.40 (m, 2H), 3.06 (s, 3H), 2.82-2.92 (m, 4H), 2.77 (t, J=6.5 Hz, 2H), 2.50-2.69 (m, 6H), 1.08 (q, J=7.0 Hz, 3H). MS (M+H, ES+) 797.

Example 188

N-(2,6-difluorophenyl)-3-[8-fluoro-3-(2-{[4-{4-[4-(2-fluoroethyl)-1-piperazinyl]-1-piperidinyl}-2-(methyloxy)phenyl]amino}-4-primidinyl)imidazo[1,2-a]pyridin-2-yl]benzamide

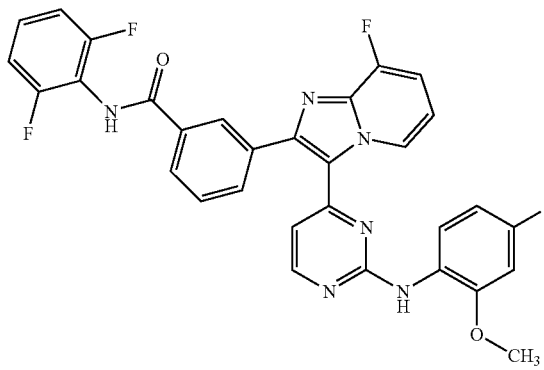

Step A: 3-[3-(2-chloro-4-pyrimidinyl)-8-fluoroimidazo[1,2-a]pyridin-2-yl]-N-(2,6-difluorophenyl)benzamide

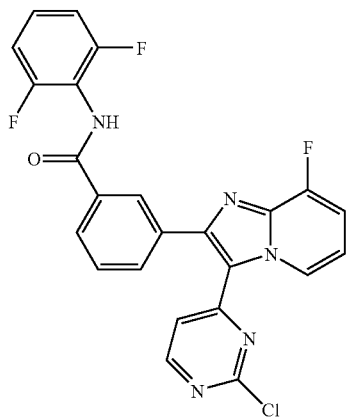

To a stirred solution of 3-[(2-chloro-4-pyrimidinyl)acetyl]-N-(2,6-difluorophenyl)-benzamide (Intermediate Example 1, step B) (4.0 g, 10.34 mmol) in DCM (103 mL) at rt under N$_2$ was added NBS (1.84 g, 10.34 mmol). The reaction was stirred approximately 30 min, then concentrated under vacuum to a foam like solid. The solid was dissolved in dioxane (103 mL) and 2-amino-3-fluoropyridine (3.47 g, 31.0 mmol) was added. The reaction was stirred under N$_2$, heated to 80° C., and stirred for approximately 40 h, then cooled to rt. The reaction was diluted with EtOAc (200 mL) and half-saturated aqueous NaHCO$_3$ (150 mL). The organic layer was separated and washed with brine. The combined aqueous layers were extracted with EtOAc (2×). The combined organic layers were dried over MgSO$_4$, filtered, and concentrated under vacuum. The residue was purified by silica gel chromatography to give a yellow solid. The solid was dissolved in minimal DCM and ether was added until a precipitate formed. The slurry was filtered, washing the solids with cold ether. The solids were dried under vacuum to give the title compound of step A (1.58 g, 3.29 mmol, 32%) as a white solid. MS (ESI): 480 [M+H]$^+$.

Step B: N-(2,6-difluorophenyl)-3-[8-fluoro-3-(2-{[4-{4-[4-(2-fluoroethyl)-1-piperazinyl]-1-piperidinyl}-2-(methyloxy)phenyl]amino}-4-pyrimidinyl)imidazo[, 2-a]pyridin-2-yl]benzamide To 3-[3-(2-chloro-4-pyrimidinyl)-8-fluoroimidazo[1,2-a]pyridin-2-yl]-N-(2,6-difluoro-phenyl)benzamide (100 mg, 0.21 mmol) and 4-{4-[4-(2-fluoroethyl)-1-piperazinyl]-1-piperidinyl}-2-(methyloxy)aniline (Example 57, step E) (63 mg, 0.19 mmol) in 2,2,2-trifluoroethanol (2 mL) was added p-toluenesulfonic acid monohydrate (135 mg, 0.71 mmol). The mixture was stirred and heated on a Biotage microwave at 150° C. for 30 min, then cooled to rt. The mixture was neutralized with 0.5M sodium methoxide in MeOH. The mixture was concentrated under vacuum and the residue purified by silica gel chromatography to give a yellow solid. The solid was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (71 mg, 0.09 mmol, 49%) as a yellow solid. $^1$H NMR (400 MHz, DMSO-d$_6$): δ 10.26 (s, 1H), 9.20 (m, 1H), 8.52 (s, 1H), 8.34 (s, 1H), 8.24 (d, 1H, J=5.13 Hz), 8.07 (d, 1H, J=7.88 Hz), 7.83 (d, 1H, J=7.70 Hz), 7.62 (t, 1H, J=7.79 Hz), 7.34-7.45 (m, 3H), 7.21 (t, 2H, J=8.06 Hz), 6.93-6.99 (m, 1H), 6.67 (d, 1H, J=2.20 Hz), 6.46-6.50 (m, 2H), 4.57 (t, 1H, J=4.86 Hz), 4.45 (t, 1H, J=4.86 Hz), 3.79 (s, 3H), 3.70-3.75 (m, 2H), 2.59-2.69 (m, 4H), 2.50-2.56 (m, 4H), 2.40-2.46 (m, 4H), 2.25-2.34 (m, 1H), 1.81-1.87 (m, 2H), 1.46-1.56 (m, 2H). MS (ESI): 780 [M+H]$^+$.

Example 189

N-(2,6-difluorophenyl)-3-[3-(2-{[4-{4-[4-(2-fluoro-ethyl)-1-piperazinyl]-1-piperidin}-2-(methyloxy)phenyl]amino}-4-pyrimidinyl)-7-(trifluoromethyl)imidazo[1,2-a]pyridin-2-yl]benzamide

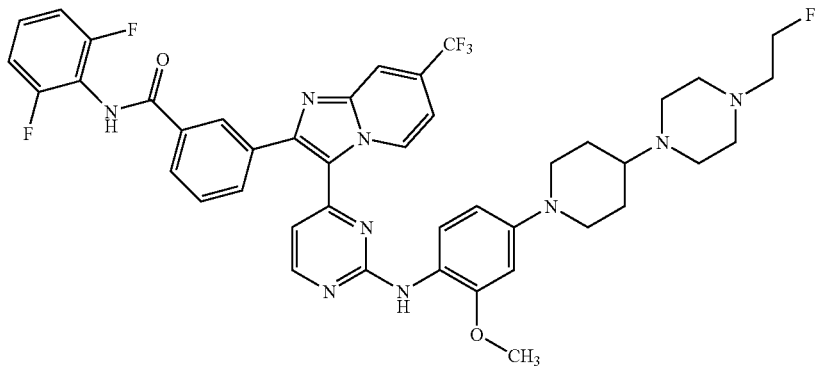

Step A: 3-[3-(2-chloro-4-pyrimidinyl)-7-(trifluoromethyl)imidazo[1,2-a]pyridin-2-yl]-N-(2,6-difluorophenyl)benzamide

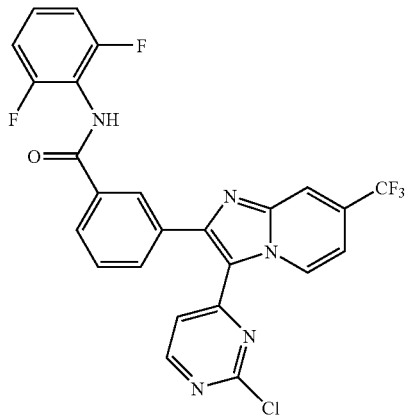

To a stirred solution of 3-[(2-chloro-4-pyrimidinyl)acetyl]-N-(2,6-difluorophenyl)-benzamide (Intermediate Example 1, step B) (0.4 g, 1.03 mmol) in DCM (10 mL) at rt under N₂ was added NBS (0.193 g, 1.09 mmol). The reaction was stirred approximately 30 min, then concentrated under vacuum to a foam like solid. The solid was dissolved in dioxane (10 mL) and 4-(trifluoromethyl)-2-pyridinamine (0.5 g, 3.10 mmol) was added. The reaction was stirred under nitrogen, heated to 80° C., and stirred for approximately 48 h, then cooled to rt. The reaction was diluted with EtOAc and half-saturated aqueous NaHCO₃. The organic layer was separated and washed brine. The combined aqueous layers were extracted with EtOAc (3×). The combined organic layers were dried over MgSO₄, filtered, and concentrated under vacuum. The residue was purified by silica gel chromatography to give a yellow solid. The solid was dissolved in minimal DCM and hexane was added until a precipitate formed. The slurry was filtered, washing the solids with cold hexane. The solids were dried under vacuum, however proton NMR indicates impurities so the solid was dissolved in minimal DCM and ether was added until a precipitate formed. The slurry was filtered, washing the solids with cold ether. The solids were dried under vacuum to give the title compound of step A (0.250 g, 0.47 mmol, 46%) as a white solid. MS (ESI): 530 [M+H]⁺.

Step B: N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)-7-(trifluoromethyl)imidazo[1,2-a]pyridin-2-yl]benzamide To 3-[3-(2-chloro-4-pyrimidinyl)-7-(trifluoromethyl)imidazo[1,2-a]pyridin-2-yl]-N-(2,6-difluorophenyl)benzamide (110 mg, 0.21 mmol) and 4-{4-[4-(2-fluoroethyl)-1-piperazinyl]-1-piperidinyl}-2-(methyloxy)aniline (Example 57, step E) (63 mg, 0.19 mmol) in 2,2,2-trifluoroethanol (2 mL) was added p-toluenesulfonic acid monohydrate (134 mg, 0.71 mmol). The mixture was stirred and heated on a microwave at 150° C. for 45 min, then cooled to rt. The mixture was neutralized with 0.5M sodium methoxide in MeOH. The mixture was concentrated under vacuum and the residue purified by silica gel chromatography to give a yellow solid. The solid was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (59 mg, 0.07 mmol, 38%) as a yellow solid. ¹H NMR (400 MHz, DMSO-d₆): δ 10.26 (s, 1H), 9.47 (br s, 1H), 8.56 (s, 1H), 8.34 (s, 1H), 8.27 (d, 1H, J=5.32 Hz), 8.24 (s, 1H), 8.08 (d, 1H, J=7.88 Hz), 7.84 (d, 1H, J=7.70 Hz), 7.64 (t, 1H, J=7.79 Hz), 7.31-7.45 (m, 2H), 7.21 (t, 3H, J=8.06 Hz), 6.70-6.72 (m, 1H), 6.47-6.53 (m, 2H), 4.56 (t, 1H, J=4.86 Hz), 4.44 (t, 1H, J=4.86 Hz), 3.80 (s, 3H), 3.71-3.77 (m, 2H), 2.59-2.70 (m, 4H), 2.40-2.55 (m, 8H), 2.25-2.34 (m, 1H), 1.81-1.87 (m, 2H), 1.46-1.56 (m, 2H). MS (ESI): 830 [M+H]⁺.

Example 190

3-[3-(2-{[4-(1,4'-bipiperidin-1'-yl)-2-(methyloxy)phenyl]amino}-4-pyrimidinyl)-8-fluoroimidazo[1,2-a]pyridin-2-yl]-N-(2,6-difluorophenyl)benzamide

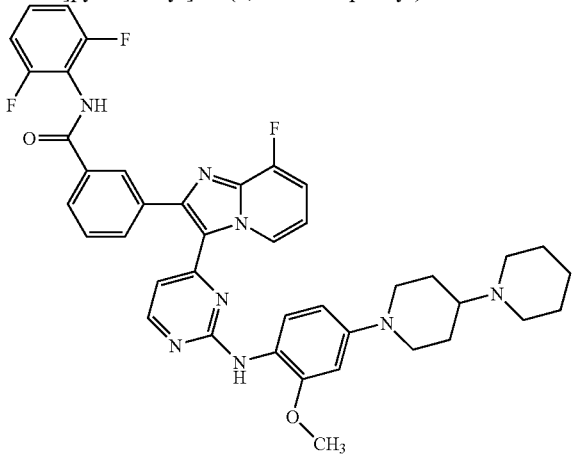

To 3-[3-(2-chloro-4-pyrimidinyl)-8-fluoroimidazo[1,2-a]pyridin-2-yl]-N-(2,6-difluoro-phenyl)benzamide (Example 188, step A) (100 mg, 0.21 mmol) and 4-(1,4'-bipiperidin-1'-yl)-2-(methyloxy)aniline (Example 22, step C) (54 mg, 0.19 mmol) in 2,2,2-trifluoroethanol (2 mL) was added p-toluenesulfonic acid monohydrate (95 mg, 0.50 mmol). The mixture was stirred and heated on a microwave at 145° C. for 30 min, then cooled to rt. The mixture was neutralized with 0.5M sodium methoxide in MeOH. The mixture was concentrated under vacuum and the residue purified by silica gel chromatography to give a yellow solid. The solid was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (90 mg, 0.12 mmol, 66%) as a yellow solid. $^1$H NMR (400 MHz, DMSO-$d_6$): δ 10.26 (s, 1H), 9.20 (br s, 1H), 8.52 (s, 1H), 8.34 (s, 1H), 8.24 (d, 1H, J=5.13 Hz), 8.07 (d, 1H, J=7.88 Hz), 7.83 (d, 1H, J=7.70 Hz), 7.62 (t, 1H, J=7.79 Hz), 7.34-7.45 (m, 3H), 7.21 (t, 2H, J=8.06 Hz), 6.93-6.99 (m, 1H), 6.66 (d, 1H, J=2.20 Hz), 6.45-6.50 (m, 2H), 3.79 (s, 3H), 3.70-3.77 (m, 2H), 2.59-2.68 (m, 2H), 2.42-2.48 (m, 4H), 2.28-2.37 (m, 1H), 1.76-1.83 (m, 2H), 1.35-1.60 (m, 8H). MS (ESI): 733 [M+H]$^+$.

Example 191

3-[3-(2-{[4-(1,4'-bipiperidin-1'-yl)-2-(methyloxy)phenyl]amino}-4-pyrimidinyl)-7-(trifluoromethyl)imidazo[1,2-a]pyridin-2-yl]-N-(2,6-difluorophenyl)benzamide

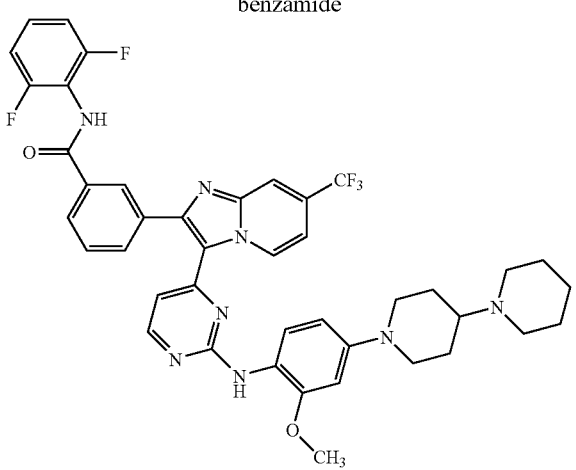

To 3-[3-(2-chloro-4-pyrimidinyl)-7-(trifluoromethyl)imidazo[1,2-a]pyridin-2-yl]-N-(2,6-difluorophenyl)benzamide (Example 189, step A) (110 mg, 0.21 mmol) and 4-(1,4'-bipiperidin-1'-yl)-2-(methyloxy)aniline (Example 22, step C) (54 mg, 0.19 mmol) in 2,2,2-trifluoroethanol (2 mL) was added p-toluenesulfonic acid monohydrate (95 mg, 0.50 mmol). The mixture was stirred and heated on a microwave at 145° C. for 40 min, then cooled to rt. The mixture was neutralized with 0.5M sodium methoxide in MeOH. The mixture was concentrated under vacuum and the residue purified by silica gel chromatography to give a yellow solid. The solid was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (95 mg, 0.12 mmol, 65%) as a yellow solid. $^1$H NMR (400 MHz, DMSO-$d_6$): δ 10.26 (s, 1H), 9.46 (br s, 1H), 8.56 (s, 1H), 8.34 (s, 1H), 8.23-8.28 (m, 2H), 8.08 (d, 1H, J=7.88 Hz), 7.84 (d, 1H, J=7.70 Hz), 7.64 (t, 1H, J=7.70 Hz), 7.18-7.45 (m, 5H), 6.70 (d, 1H, J=2.20 Hz), 6.47-6.53 (m, 2H), 3.74-3.81 (m, 5H), 2.61-2.68 (m, 2H), 2.42-2.48 (m, 4H), 2.28-2.37 (m, 1H), 1.75-1.82 (m, 2H), 1.34-1.59 (m, 8H). MS (ESI): 782 [M+H]$^+$.

Example 192

N-(2,6-difluorophenyl)-3-(8-fluoro-3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide

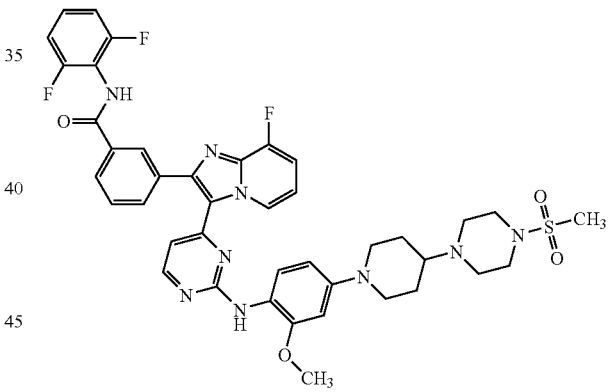

To 3-[3-(2-chloro-4-pyrimidinyl)-8-fluoroimidazo[1,2-a]pyridin-2-yl]-N-(2,6-difluoro-phenyl)benzamide (Example 188, step A) (80 mg, 0.17 mmol) and 2-(methyloxy)-4-{4-[4-(methylsulfonyl)-1-piperazinyl]-1-piperidinyl}aniline (Example 58, step B) (61 mg, 0.17 mmol) in 2,2,2-trifluoroethanol (0.80 mL) was added 4 M HCl in dioxane (84 μL, 0.33 mmol). The mixture was stirred and heated on a microwave at 175° C. for 35 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (111 mg, 0.13 mmol, 83%) as a yellow solid. $^1$H NMR (400 MHz, DMSO-$d_6$): δ 10.27 (s, 1H), 9.21 (br s, 1H), 8.52 (s, 1H), 8.34 (s, 1H), 8.24 (d, 1H, J=5.13 Hz), 8.07 (d, 1H, J=7.88 Hz), 7.83 (d, 1H, J=7.70 Hz), 7.62 (t, 1H, J=7.70 Hz), 7.34-7.45 (m, 3H), 7.21 (t, 2H, J=8.06 Hz), 6.92-6.99 (m, 1H), 6.66-6.69 (m, 1H), 6.46-6.50 (m, 2H), 3.79 (s, 3H), 3.71-3.76 (m, 2H), 3.06-3.11 (m, 4H), 2.86 (s, 3H), 2.57-2.71 (m, 5H), 2.38-2.46 (m, 1H), 1.80-1.87 (m, 2H), 1.48-1.60 (m, 2H). MS (ESI): 812 [M+H]+.

Example 193

N-(2,6-difluorophenyl)-3-[8-fluoro-3-(2-{[2-(methyloxy)-4-(4-{4-[2-(methylsulfonyl)ethyl]-1-piperazinyl}-1-piperidinyl)phenyl]amino}-4-pyrimidinyl)imidazo[1,2-a]pyridin-2-yl]benzamide

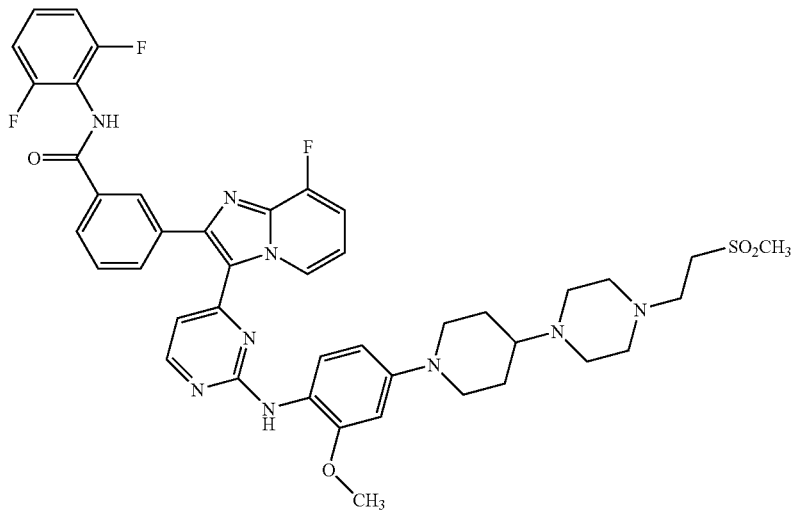

To 3-[3-(2-chloro-4-pyrimidinyl)-8-fluoroimidazo[1,2-a]pyridin-2-yl]-N-(2,6-difluoro-phenyl)benzamide (Example 188, step A) (90 mg, 0.19 mmol) and 2-(methyloxy)-4-(4-{4-[2-(methylsulfonyl)ethyl]-1-piperazinyl}-1-piperidinyl)aniline (Example 60, step B) (74 mg, 0.19 mmol) in 2,2,2-trifluoroethanol (0.90 mL) was added 4 M hydrochloric acid in dioxane (94 µL, 0.38 mmol). The mixture was stirred and heated on a microwave at 175° C. for 40 minutes, then cooled to room temperature. The mixture was neutralized with 0.5M sodium methoxide in methanol. The mixture was concentrated under vacuum and the residue purified by silica gel chromatography to give a yellow oil. The oil was dissolved in minimal dichloromethane, then hexane was added until a precipitate was formed. The slurry was cooled at −10° C. for 30 minutes, then poured through a Teflon filter, washing the solids with cold hexanes. The solids were dried under vacuum to give the title compound (110 mg, 0.13 mmol, 71%) as a yellow solid. $^1$H NMR (400 MHz, DMSO-$d_6$): δ10.27 (s, 1H), 9.20 (brs, 1H), 8.52 (s, 1H), 8.34 (s, 1H), 8.24 (d, 1H, J=5.13 Hz), 8.07 (d, 1H, J=7.70 Hz), 7.83 (d, 1H, J=7.88 Hz), 7.62 (t, 1H, J=7.70 Hz), 7.34-7.45 (m, 3H), 7.21 (t, 2H, J=8.06 Hz), 6.92-6.99 (m, 1H), 6.65-6.68 (m, 1H), 6.45-6.50 (m, 2H), 3.79 (s, 3H), 3.68-3.75 (m, 2H), 3.19-3.30 (m, 2H), 3.02 (s, 3H), 2.61-2.70 (m, 6H), 2.38-2.46 (m, 6H), 2.26-2.34 (m, 1H), 1.80-1.87 (m, 2H), 1.45-1.56 (m, 2H). MS (ESI): 840 [M+H]+.

Example 194

N-(2,6-difluorophenyl)-3-[7-fluoro-3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide

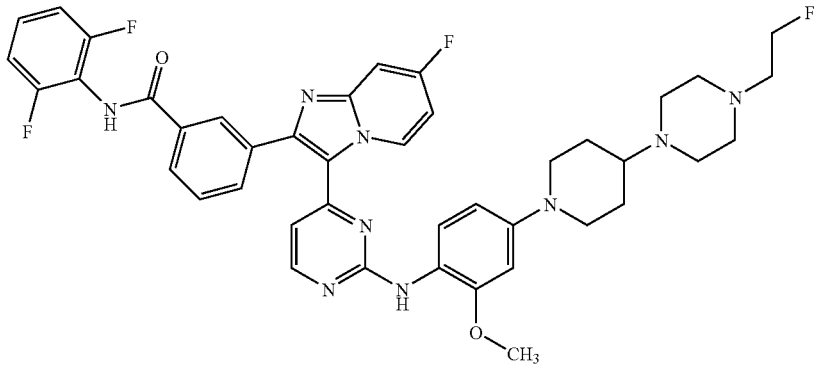

Step A: 4-fluoro-2-pyridinamine

To a mixture of 2-chloro-4-fluoropyridine (2.5 g, 19.1 mmol), benzophenone imine (4.14 g, 22.9 mmol), tris(dibenzylideneacetone)dipalladium(0) (349 mg, 0.4 mmol), XANTPHOS (662 mg, 1.1 mmol) and $Cs_2CO_3$ (8.68 g, 26.7 mmol) was added THF (76 mL). The mixture was stirred under $N_2$ and purged with vacuum/$N_2$ (3×), then stirred under $N_2$ and heated to 65° C. The reaction was stirred for 4 h then the temperature was reduced to 60° C. and the reaction was stirred overnight. The reaction was cooled to rt, diluted with ether (700 mL) and poured through Celite. The filtrate was concentrated under vacuum. The residue was dissolved in THF (75 mL) and treated with aqueous 2 N HCl (20 mL). The mixture was stirred for about 30 min, then the solution was diluted with aqueous 0.5 N HCl (about 300 mL) and hexane/EtOAc 2:1 (about 150 mL). The aqueous layer was separated. The aqueous layer was treated with $NaHCO_3$ until the solution's pH was basic, then the solution was extracted with DCM (3×). The combined DCM extracts were dried over $MgSO_4$, and concentrated under vacuum. The residue was chromatographed on silica gel to give the title compound of step A (645 mg, 30%) as white solid. $^1$H NMR (400 MHz, DMSO-$d_6$): δ 8.02 (dd, 1H, J=5.77 and 9.07 Hz), 6.39-6.44 (m, 1H), 6.17 (dd, 1H, J=2.20 and 10.81 Hz), 4.55 (brs, 2H); MS (ESI): 113 [M+H]$^+$.

Step B: 3-[3-(2-chloro-4-pyrimidinyl)-7-fluoroimidazo[1,2-a]pyridin-2-yl]-N-(2,6-difluorophenyl)benzamide

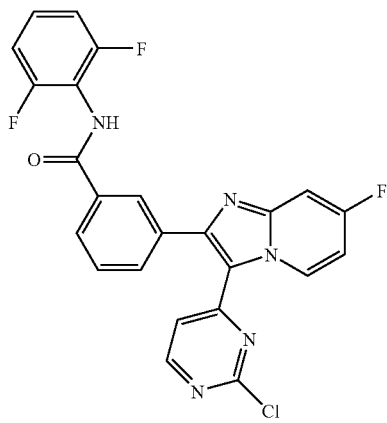

To a stirred solution of 3-[(2-chloro-4-pyrimidinyl)acetyl]-N-(2,6-difluorophenyl)-benzamide (Intermediate Example 1, step B) (0.6 g, 1.49 mmol) in DCM (15 mL) at rt under $N_2$ was added NBS (0.278 g, 1.56 mmol). The reaction was stirred approximately 60 min, then concentrated under vacuum to a foam like solid. The solid was dissolved in dioxane (15 mL) and 4-fluoro-2-pyridinamine (0.5 g, 4.46 mmol) was added. The reaction was stirred under $N_2$, heated to 75° C., and stirred for approximately 18 h, then cooled to rt. The reaction was diluted with EtOAc and half-saturated aqueous $NaHCO_3$. The organic layer was separated and washed with brine. The combined aqueous layers were extracted with EtOAc (3×). The combined organic layers were dried over $MgSO_4$, filtered, and concentrated under vacuum. The residue was purified by silica gel chromatography to give the title compound of step B (0.391 g, 0.81 mmol, 55%) as a light yellow solid. MS (ESI): 480 [M+H]$^+$.

Step C: N-(2,6-difluorophenyl)-3-[7-fluoro-3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide To 3-[3-(2-chloro-4-pyrimidinyl)-7-fluoroimidazo[1,2-a]pyridin-2-yl]-N-(2,6-difluoro-phenyl)benzamide (100 mg, 0.21 mmol) and 4-{4-[4-(2-fluoroethyl)-1-piperazinyl]-1-piperidinyl}-2-(methyloxy)aniline (Example 59, step E) (63 mg, 0.19 mmol) in 2,2,2-trifluoroethanol (2 mL) was added p-toluenesulfonic acid monohydrate (135 mg, 0.71 mmol). The mixture was stirred and heated on a microwave at 150° C. for 30 minutes, then cooled to room temperature. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (81 mg, 0.10 mmol, 55%) as a yellow solid. $^1$H NMR (400 MHz, DMSO-$d_6$): δ10.24 (s, 1H), 9.47 (brs, 1H), 8.51 (s, 1H), 8.32 (s, 1H), 8.20 (d, 1H, J=5.32 Hz), 8.06 (d, 1H, J=7.70 Hz), 7.81 (d, 1H, J=7.70 Hz), 7.59-7.64 (m, 2H), 7.34-7.44 (m, 2H), 7.21 (t, 2H, J=8.06 Hz), 7.02-7.08 (m, 1H), 6.69 (d, 1H, J=2.20 Hz), 6.43-6.51 (m, 2H), 4.57 (t, 1H, J=4.95 Hz), 4.45 (t, 1H, J=4.86 Hz), 3.80 (s, 3H), 3.71-3.77 (m, 2H), 2.59-2.70 (m, 4H), 2.40-2.46 (m, 8H), 2.26-2.34 (m, 1H), 1.81-1.87 (m, 2H), 1.46-1.56 (m, 2H). MS (ESI): 780 [M+H]$^+$.

Example 195

3-[3-(2-{[4-(1,4'-bipiperidin-1'-yl)-2-(methyloxy)phenyl]amino}-4-pyrimidinyl)-7-fluoroimidazo[1,2-a]pyridin-2-yl]-N-(2,6-difluorophenyl)benzamide

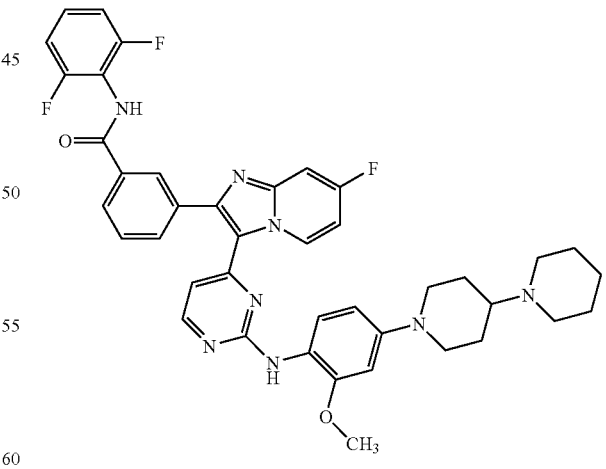

To 3-[3-(2-chloro-4-pyrimidinyl)-7-fluoroimidazo[1,2-a]pyridin-2-yl]-N-(2,6-difluoro-phenyl)benzamide (Example 194, step B) (100 mg, 0.21 mmol) and 4-(1,4'-bipiperidin-1'-yl)-2-(methyloxy)aniline (Example 22, step C) (54 mg, 0.19 mmol) in 2,2,2-trifluoroethanol (2 mL) was added p-toluenesulfonic acid monohydrate (95 mg, 0.50 mmol). The mixture was stirred and heated on a microwave at 150° C. for 30 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (84 mg, 0.11 mmol, 62%) as a yellow solid. $^1$H NMR (400 MHz, DMSO-d$_6$) δ 10.24 (s, 1H), 9.48 (br s, 1H), 8.51 (s, 1H), 8.32 (s, 1H), 8.20 (d, 1H, J=5.13 Hz), 8.06 (d, 1H, J=7.88 Hz), 7.82 (d, 1H, J=7.88 Hz), 7.59-7.64 (m, 2H), 7.35-7.45 (m, 2H), 7.21 (t, 2H, J=8.06 HZ), 7.01-7.09 (m, 1H), 6.67-6.69 (m, 1H), 6.43-6.51 (m, 2H), 3.70-3.81 (m, 5H), 2.65 (t, 2H, J=11.36 Hz), 2.42-2.48 (m, 4H), 2.29-2.37 (m, 1H), 1.75-1.83 (m, 2H), 1.44-1.59 (m, 6H), 1.34-1.41 (m, 2H). MS (ESI): 733 [M+H]$^+$.

Example 196

N-(2,6-difluorophenyl)-3-(7-fluoro-3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide

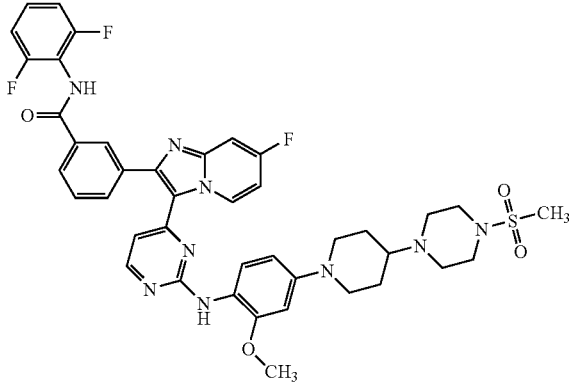

To 3-[3-(2-chloro-4-pyrimidinyl)-7-fluoroimidazo[1,2-a]pyridin-2-yl]-N-(2,6-difluoro-phenyl)benzamide (Example 194, step B) (80 mg, 0.17 mmol) and 2-(methyloxy)-4-{4-[4-(methylsulfonyl)-1-piperazinyl]-1-piperidinyl}aniline (Example 58, step B) (61 mg, 0.17 mmol) in 2,2,2-trifluoroethanol (0.80 mL) was added 4 M HCl in dioxane (84 μL, 0.33 mmol). The mixture was stirred and heated on a microwave at 175° C. for 35 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (95 mg, 0.11 mmol, 70%) as a yellow solid. $^1$H NMR (400 MHz, DMSO-d$_6$): δ 10.24 (s, 1H), 9.47 (br s, 1H), 8.50 (s, 1H), 8.32 (s, 1H), 8.20 (d, 1H, J=5.13 Hz), 8.06 (d, 1H, J=7.87 Hz), 7.82 (d, 1H, J=7.69 Hz), 7.59-7.64 (m, 2H), 7.34-7.45 (m, 2H), 7.21 (t, 2H, J=8.15 Hz), 7.02-7.08 (m, 1H), 6.68-6.71 (m, 1H), 6.50 (dd, 1H, J=2.11, 8.70 Hz), 6.45 (d, 1H, J=5.13 Hz), 3.73-3.81 (m, 5H), 3.06-3.11 (m, 4H), 2.85 (s, 3H), 2.68 (t, 2H, J=11.45 Hz), 2.58-2.62 (m, 4H), 2.38-2.46 (m, 1H), 1.80-1.87 (m, 2H), 1.48-1.60 (m, 2H). MS (ESI): 812 [M+H]$^+$.

Example 197

N-(2,6-difluorophenyl)-5-[7-fluoro-3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]-2-(methyloxy)benzamide

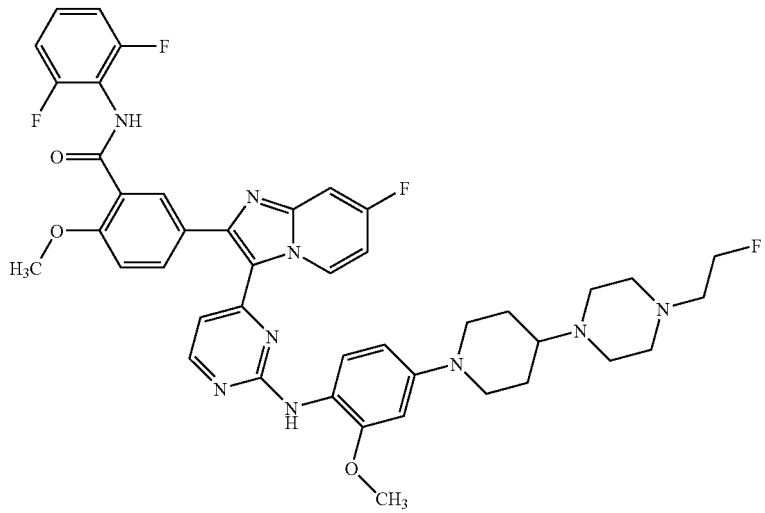

Step A: 5-[3-(2-chloro-4-pyrimidinyl)-7-fluoroimidazo[1,2-a]pyridin-2-yl]-N-(2,6-difluorophenyl)-2-(methyloxy)benzamide

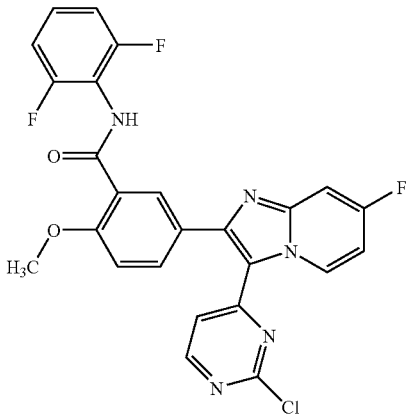

To a stirred solution of 3-[(2-chloro-4-pyrimidinyl)acetyl]-N-(2,6-difluorophenyl)-4-(methyloxy)benzamide (Intermediate Example 2, step E) (0.950 g, 2.28 mmol) in dichloromethane (23 mL) at rt under $N_2$ was added NBS (0.426 g, 2.39 mmol). The reaction was stirred approximately 30 min, then concentrated under vacuum to a foam like solid. The solid was dissolved in dioxane (23 mL) and 4-fluoro-2-pyridinamine (Example 194, step A) (0.765 g, 6.83 mmol) was added. The reaction was stirred under $N_2$, heated to 80° C., and stirred for approximately 16 h, then cooled to rt. The reaction was diluted with EtOAc and half-saturated aqueous $NaHCO_3$. The organic layer was separated and washed with brine. The combined aqueous layers were extracted with EtOAc (2×). The combined organic layers were dried over $MgSO_4$, filtered, and concentrated under vacuum. The residue was purified by silica gel chromatography to give the title compound of step A (0.700 g, 1.37 mmol, 61%) as a light tan solid. MS (ESI): 510 [M+H]⁺.

Step B: N-(2,6-difluorophenyl)-5-[7-fluoro-3-(2-{[4-{4-[4-(2-fluoroethyl)-1-piperazinyl]-1-piperidinyl}-2-(methyloxy)phenyl]amino}-4-pyrimidinyl)imidazo[, 2-a]pyridin-2-yl]-2-(methyloxy)benzamide To 5-[3-(2-chloro-4-pyrimidinyl)-7-fluoroimidazo[1,2-a]pyridin-2-yl]-N-(2,6-difluoro-phenyl)-2-(methyloxy)benzamide (114 mg, 0.22 mmol) and 4-{4-[4-(2-fluoroethyl)-1-piperazinyl]-1-piperidinyl}-2-(methyloxy)aniline (Example 57, step E) (75 mg, 0.22 mmol) in 2,2,2-trifluoroethanol (2 mL) was added 4 M HCl in dioxane (112 μL, 0.45 mmol). The mixture was stirred and heated on a microwave at 150° C. for 45 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 minutes, then poured through a Teflon filter, washing the solids with cold hexanes. The solids were dried under vacuum to give the title compound (112 mg, 0.14 mmol, 62%) as a light yellow solid. ¹H NMR (400 MHz, DMSO-$d_6$): δ 9.79 (s, 1H), 9.44 (br s, 1H), 8.49 (s, 1H), 8.20 (s, 1H), 8.09 (d, 1H, J=2.02 Hz), 7.75-7.79 (m, 1H), 7.58 (dd, 1H, J=2.57, 9.71 Hz), 7.35-7.41 (m, 2H), 7.29 (d, 1H, J=8.80 Hz), 7.19 (t, 2H, J=8.06 Hz), 6.98-7.04 (m, 1H), 6.69 (d, 1H, J=2.20 Hz), 6.48-6.53 (m, 2H), 4.57 (t, 1H, J=4.95 Hz), 4.45 (t, 1H, J=4.86 Hz), 3.99 (s, 3H), 3.80 (s, 3H), 3.71-3.77 (m, 2H), 2.59-2.70 (m, 4H), 2.50-2.56 (m, 4H), 2.39-2.46 (m, 4H), 2.26-2.34 (m, 1H), 1.81-1.87 (m, 2H), 1.46-1.56 (m, 2H). MS (ESI): 810 [M+H]⁺.

Example 198

5-[3-(2-{[4-(1,4'-bipiperidin-1'-yl)-2-(methyloxy)phenyl]amino}-4-pyrimidinyl)-7-fluoroimidazo[1,2-a]pyridin-2-yl]-N-(2,6-difluorophenyl)-2-(methyloxy)benzamide

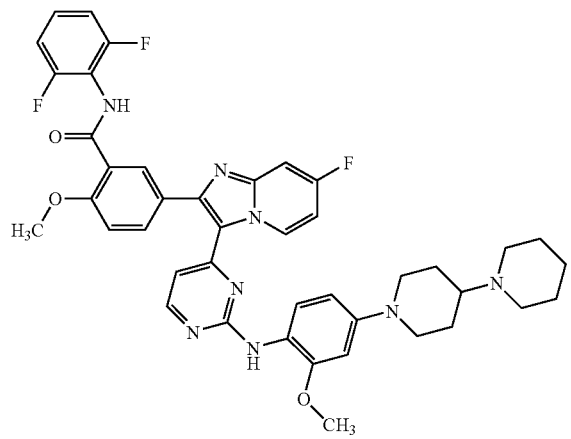

To 5-[3-(2-chloro-4-pyrimidinyl)-7-fluoroimidazo[1,2-a]pyridin-2-yl]-N-(2,6-difluoro-phenyl)-2-(methyloxy)benzamide (Example 197, step A) (114 mg, 0.22 mmol) and 4-(1,4'-bipiperidin-1'-yl)-2-(methyloxy)aniline (Example 22, step C) (65 mg, 0.22 mmol) in 2,2,2-trifluoroethanol (1.5 mL) was added 4 M HCl in dioxane (112 μL, 0.45 mmol). The mixture was stirred and heated on a microwave at 150° C. for 45 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (147 mg, 0.19 mmol, 86%) as a light yellow solid. ¹H NMR (400 MHz, DMSO-$d_6$): δ 9.79 (s, 1H), 9.44 (br s, 1H), 8.49 (s, 1H), 8.20 (d, 1H, J=5.32 Hz), 8.09 (d, 1H, J=2.02 Hz), 7.75-7.79 (m, 1H), 7.58 (dd, 1H, J=2.66, 9.62 Hz), 7.35-7.43 (m, 2H), 7.29 (d, 1H, J=8.80 Hz), 7.19 (t, 2H, J=8.06 Hz), 6.98-7.04 (m, 1H), 6.68 (d, 1H, J=2.20 Hz), 6.48-6.53 (m, 2H), 3.99 (s, 3H), 3.70-3.81 (m, 5H), 2.61-2.69 (m, 2H), 2.41-2.48 (m, 4H), 2.29-2.37 (m, 1H), 1.76-1.83 (m, 2H), 1.44-1.60 (m, 6H), 1.34-1.41 (m, 2H). MS (ESI): 763 [M+H]⁺.

Example 199

N-(2,6-difluorophenyl)-5-(7-fluoro-3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide

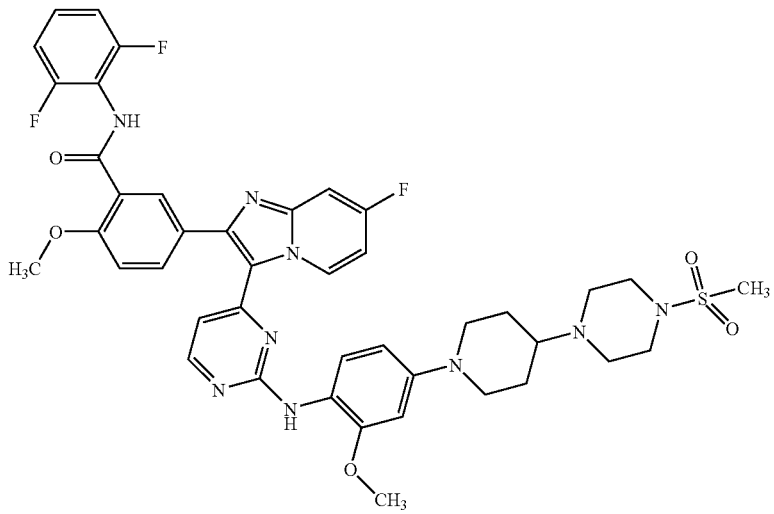

To 5-[3-(2-chloro-4-pyrimidinyl)-7-fluoroimidazo[1,2-a]pyridin-2-yl]-N-(2,6-difluoro-phenyl)-2-(methyloxy)benzamide (Example 197, step A) (85 mg, 0.17 mmol) and 2-(methyloxy)-4-{4-[4-(methylsulfonyl)-1-piperazinyl]-1-piperidinyl}aniline (Example 58, step B) (61 mg, 0.17 mmol) in 2,2,2-trifluoroethanol (0.80 mL) was added 4 M HCl in dioxane (83 µL, 0.33 mmol). The mixture was stirred and heated on a microwave at 175° C. for 35 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (85 mg, 0.10 mmol, 61%) as a yellow solid. $^1$H NMR (400 MHz, DMSO-$d_6$) δ 9.78 (s, 1H), 9.44 (br s, 1H), 8.49 (s, 1H), 8.20 (d, 1H, J=5.31 Hz), 8.07-8.11 (m, 1H), 7.75-7.80 (m, 1H), 7.58 (dd, 1H, J=2.56, 9.52 Hz), 7.35-7.42 (m, 2H), 7.29 (d, 1H, J=8.61 Hz), 7.18 (t, 2H, J=7.97 Hz), 6.97-7.04 (m, 1H), 6.68-6.70 (m, 1H), 6.48-6.53 (m, 2H), 3.99 (s, 3H), 3.73-3.81 (m, 5H), 3.06-3.11 (m, 4H), 2.85 (s, 3H), 2.68 (t, 2H, J=11.54 Hz), 2.58-2.62 (m, 4H), 2.38-2.46 (m, 1H), 1.80-1.87 (m, 2H), 1.48-1.60 (m, 2H). MS (ESI): 842 [M+H]$^+$.

Example 200

N-(2,6-difluorophenyl)-2-(ethyloxy)-5-(3-{2-[(2-(methyloxy)-4-{4-[2-(methylsulfonyl)ethyl]-1-piperidinyl}phenyl)amino]-4-pyrimidinyl}imidazo[1,2-a]pyridin-2-yl)benzamide

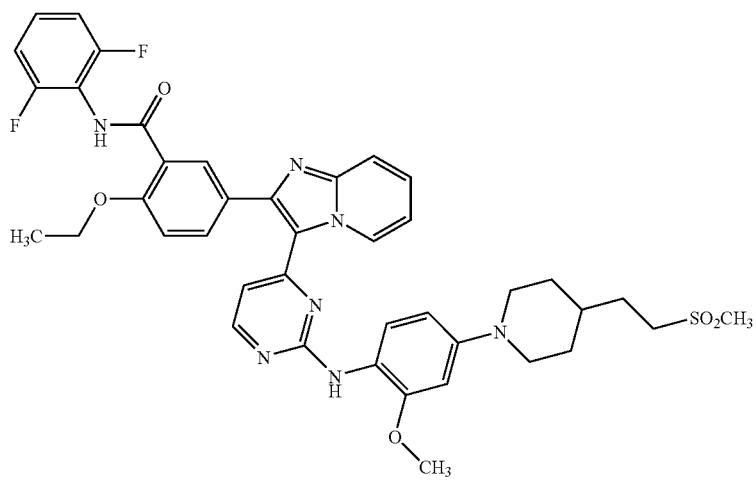

Step A: 1-[3-(methyloxy)-4-nitrophenyl]-4-[2-(methylsulfonyl)ethyl]piperidine

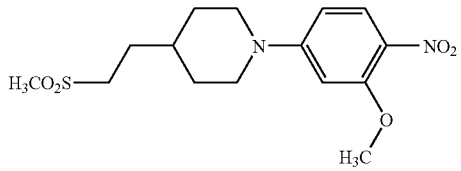

The title compound of step A (0.43 g, 1.3 mmol, 58%) was prepared in an analogous manner to that described for Example 22, steps A-B with the following notable exception: 4-[2-(methylsulfonyl)ethyl]piperidine (Example 101, step D) was used instead of 1,4'-bipiperidine in Example 22, step B. $^1$H NMR (400 MHz, CDCl$_3$) δ 1.38-1.57 (m, 3H), 1.72-1.80 (m, 1H), 1.83-1.89 (m, 4H), 2.90 (s, 3H), 2.93-2.98 (m, 1H), 3.00-3.07 (m, 2H), 3.87 (d, J=12.8 Hz, 2H), 3.93 (s, 3H), 6.48 (d, J=9.2 Hz, 1H), 6.55 (br. s., 1H), 7.97 (d, J=9.3 Hz, 1H).

Step B: 2-(methyloxy)-4-{4-[2-(methylsulfonyl)ethyl]-1-piperidinyl}aniline

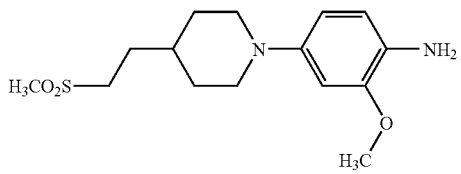

To 1-[3-(methyloxy)-4-nitrophenyl]-4-[2-(methylsulfonyl)ethyl]piperidine (0.42 g, 1.3 mmol) in THF (60 mL) cooled to 0° C. was added SnCl$_2$ (1.0 g, 5.4 mmol) dissolved in conc. HCl dropwise. The solution was stirred overnight at room temperature (TLC confirms consumption of starting material). The mixture was cooled to 0° C. and quenched with 6 N NaOH (25 mL). The solution was poured into EtOAc and H$_2$O was washed with brine, back extracted with EtOAc, dried (MgSO$_4$), filtered, and rotovaped down to give the title compound of step B (0.39 g, 1.3 mmol, 96%). $^1$H NMR (400 MHz, CDCl$_3$) δ 1.18-1.29 (m, 2H), 1.31-1.43 (m, 1H), 1.57-1.65 (m, 2H), 1.70 (d, J=12.5 Hz, 2H), 2.37-2.43 (m, 2H), 2.92 (s, 3H), 3.07-3.14 (m, 2H), 3.34 (d, J=11.5 Hz, 2H), 3.69 (s, 3H), 4.16 (br. s., 2H), 6.25 (d, J=7.7 Hz, 1H), 6.40-6.48 (m, 2H).

Step C: N-(2,6-difluorophenyl)-2-(ethyloxy)-5-(3-{2-[(2-(methyloxy)-4-{4-[2-(methylsulfonyl)ethyl]-1-piperidinyl}phenyl)amino]-4-pyrimidinyl}imidazo[1,2-a]pyridin-2-yl)benzamide To 5-[3-(2-chloro-4-pyrimidinyl)imidazo[1,2-a]pyridin-2-yl]-N-(2,6-difluorophenyl)-2-(ethyloxy)benzamide (Intermediate Example 6) (0.13 g, 0.25 mmol) and 2-(methyloxy)-4-{4-[2-(methylsulfonyl)ethyl]-1-piperidinyl}aniline (0.077 g, 0.25 mmol) in 2,2,2-trifluoroethanol (1.5 mL) was added HCl (0.13 mL, 4M in dioxane, 0.50 mmol). The reaction was heated at 180° C. for 40 min in the microwave. The reaction mixture was quenched with sodium methoxide (0.5M in MeOH) and concentrated. Purification by flash chromatography, and recrystallization with EtOH provided the title compound (0.082 g, 0.11 mmol, 43%). $^1$H NMR (400 MHz, DMSO-d$_6$) δ 1.19-1.30 (m, 2H), 1.39 (t, J=6.6 Hz, 3H), 1.43-1.53 (m, 1H), 1.57-1.68 (m, 2H), 1.74 (d, J=13.9 Hz, 2H), 2.53-2.64 (m, 2H), 2.92 (s, 3H), 3.07-3.18 (m, 2H), 3.66 (d, J=11.4 Hz, 2H), 3.76 (s, 3H), 4.23 (d, J=6.2 Hz, 2H), 6.43-6.53 (m, 2H), 6.63 (s, 1H), 6.86-6.97 (m, 1H), 7.15 (t, J=7.6 Hz, 2H), 7.23 (d, J=8.4 Hz, 1H), 7.32-7.43 (m, 3H), 7.66 (d, J=9.2 Hz, 1H), 7.71 (d, J=11.5 Hz, 1H), 8.01 (s, 1H), 8.16 (d, J=5.5 Hz, 1H), 8.39 (s, 1H), 9.33 (br. s., 1H), 9.71 (s, 1H). MS (ESI) m/z=782 [M+H]$^+$.

Example 201

N-(2,6-difluorophenyl)-2-(methyloxy)-5-(3-{2-[(2-(methyloxy)-4-{4-[2-(methylsulfonyl)ethyl]-1-piperidinyl}phenyl)amino]-4-pyrimidinyl}imidazo[1,2-a]pyridin-2-yl)benzamide

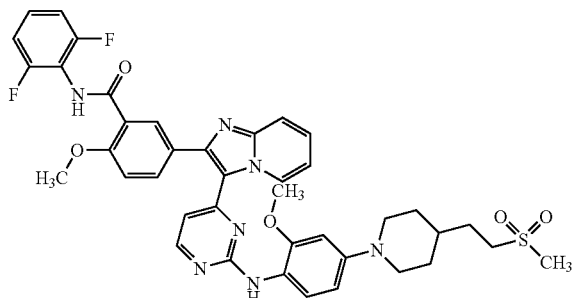

The title compound (0.088 g, 0.11 mmol, 46%) was prepared in an analogous manner to that described for Example 200, step C with the following notable exception: 5-[3-(2-chloro-4-pyrimidinyl)-imidazo[1,2-a]pyridin-2-yl]-N-(2,6-difluorophenyl)-2-(methyloxy)benzamide (Intermediate Example 2) was used instead of Intermediate Example 6. $^1$H NMR (400 MHz, DMSO-d$_6$) δ 1.19-1.31 (m, 2H), 1.41-1.52 (m, 1H), 1.58-1.69 (m, 2H), 1.75 (d, J=12.8 Hz, 2H), 2.54-2.64 (m, 2H), 2.92 (s, 3H), 3.08-3.17 (m, 2H), 3.66 (d, J=11.5 Hz, 2H), 3.76 (s, 3H), 3.95 (s, 3H), 6.46 (d, J=8.4 Hz, 1H), 6.49 (d, J=4.0 Hz, 1H), 6.63 (s, 1H), 6.85-6.97 (m, 1H), 7.15 (t, J=7.9 Hz, 2H), 7.25 (d, J=9.2 Hz, 1H), 7.31-7.43 (m, 3H), 7.65 (d, J=8.4 Hz, 1H), 7.74 (d, J=7.9 Hz, 1H), 8.06 (s, 1H), 8.16 (d, J=5.1 Hz, 1H), 8.39 (s, 1H), 9.33 (s, 1H), 9.74 (s, 1H). MS (ESI) m/z=768 [M+H]$^+$.

Example 202

N-(2,6-difluorophenyl)-3-(3-{2-[(2-(methyloxy)-4-{4-[2-(methylsulfonyl)ethyl]-1-piperidinyl}phenyl)amino]-4-pyrimidinyl}imidazo[1,2-a]pyridin-2-yl)benzamide

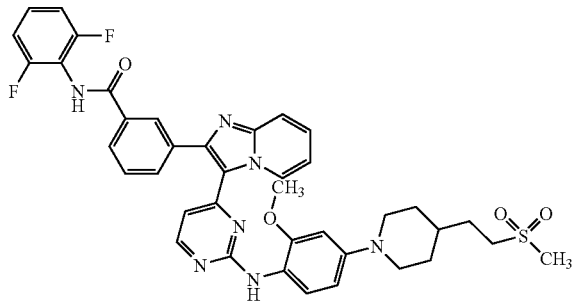

The title compound (0.055 g, 0.07 mmol, 30%) was prepared in an analogous manner to that described for Example 200, step C with the following notable exception: 3-[3-(2-chloro-4-pyrimidinyl)imidazo[1,2-a]pyridin-2-yl]-N-(2,6-difluorophenyl)-benzamide (Intermediate Example 1) was used instead of Intermediate Example 6. ¹H NMR (400 MHz, DMSO-d₆) δ 1.22-1.34 (m, 2H), 1.45-1.56 (m, 1H), 1.60-1.71 (m, 2H), 1.78 (d, J=13.9 Hz, 2H), 2.62 (t, J=12.8 Hz, 2H), 2.95 (s, 3H), 3.10-3.21 (m, 2H), 3.69 (d, J=12.1 Hz, 2H), 3.79 (s, 3H), 6.41-6.52 (m, 2H), 6.67 (s, 1H), 6.97 (s, 1H), 7.20 (t, J=8.1 Hz, 2H), 7.33-7.42 (m, 2H), 7.42-7.50 (m, 1H), 7.60 (t, J=7.3 Hz, 1H), 7.72 (d, J=8.4 Hz, 1H), 7.81 (d, J=7.3 Hz, 1H), 8.04 (d, J=7.7 Hz, 1H), 8.19 (d, J=5.5 Hz, 1H), 8.32 (s, 1H), 8.45 (s, 1H), 9.40 (br. s., 1H), 10.23 (s, 1H). MS (ESI) m/z=738 [M+H]⁺.

Example 203

N-(2,6-difluorophenyl)-2-(ethyloxy)-5-(3-{2-[(5-methyl-2-(methyloxy)-4-{4-[2-(methylsulfonyl)ethyl]hexahydro-1H-1,4-diazepin-1-yl}phenyl)amino]-4-pyrimidinyl}imidazo[1,2-a]pyridin-2-yl)benzamide

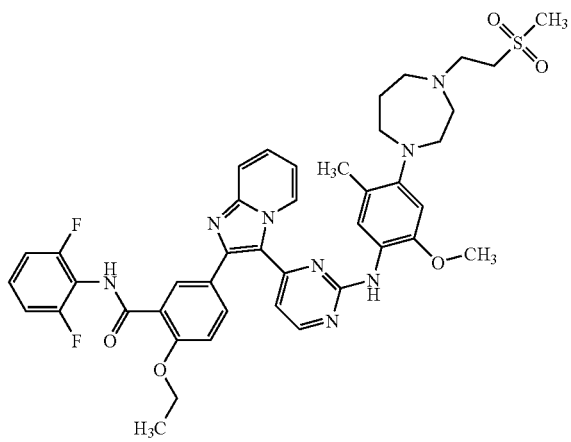

Step A: 1,1-dimethylethyl 4-[2-methyl-5-(methyloxy)-4-nitrophenyl]hexahydro-1H-1,4-diazepine-1-carboxylate

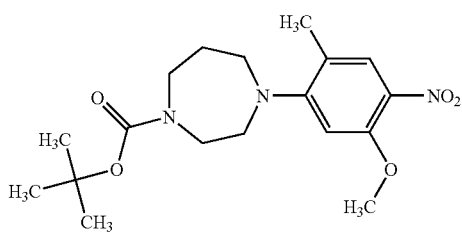

To 1-fluoro-2-methyl-5-(methyloxy)-4-nitrobenzene (1.6 g, 8.64 mmol) (Example 113, Step B) in 25 mL of DMSO was added, 1,1-dimethylethyl hexahydro-1H-1,4-diazepine-1-carboxylate (2.6 g, 13 mmol), and K₂CO₃ (3.6 g, 26 mmol). The mixture was heated to 130° C. for 24 h. The mixture was then poured into 400 mL of H₂O and extracted with EtOAc. The product was isolated by flash chromatography to give the title compound of step A (0.7 g, 1.96 mmol, 22%). ¹H NMR (400 MHz, DMSO-d₆) δ 7.73 (s, 1H), 6.66 (d, J=4.58 Hz, 1H), 3.87 (s, 3H), 3.40-3.52 (m, 4H), 3.33 (d, J=9.34 Hz, 2H), 3.24 (d, J=4.58 Hz, 2H), 2.19 (s, 3H), 1.80-1.90 (m, 2H), 1.36 (s, 5H), 1.30 (s, 4H).

Step B: 1-[2-methyl-5-(methyloxy)-4-nitrophenyl]-4-[2-(methylsulfonyl)ethyl]hexahydro-1H-1,4-diazepine

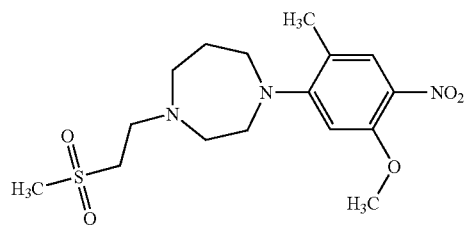

1,1-Dimethylethyl 4-[2-methyl-5-(methyloxy)-4-nitrophenyl]hexahydro-1H-1,4-diazepine-1-carboxylate (0.7 g, 2.0 mmol) was taken up in 20 mL of DCM and treated with 7 mL of TFA. The mixture stirred for 1 h and was then reduced in vacuo. The solids were transferred to a 50 mL sealed tube and taken up in 20 mL of dioxane. TEA (0.58 g, 5.75 mmol) was added followed by ethenyl methyl sulfone (0.51 g, 4.79 mmol). The mixture was heated to 30° C. for 24 h. The solvent was rotovaped down and the crude product was purified by flash chromatography to give the title compound of step B (0.7 g, 1.88 mmol, 98%). ¹H NMR (400 MHz, DMSO-d₆) δ 7.73 (s, 1H), 6.56 (s, 1H), 3.86 (s, 3H), 3.33-3.42 (m, 4H), 3.26 (t, J=6.68 Hz, 2H), 2.99 (s, 3H), 2.87 (t, J=6.59 Hz, 2H), 2.74-2.81 (m, 2H), 2.67-2.74 (m, 2H), 2.20 (s, 3H), 1.81-1.89 (m, 2H).

Step C: 5-methyl-2-(methyloxy)-4-{4-[2-(methylsulfonyl)ethyl]hexahydro-1H-1,4-diazepin-1-yl}aniline

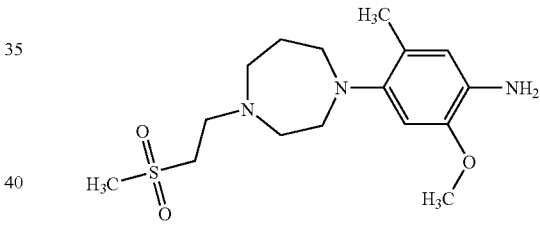

1-[2-Methyl-5-(methyloxy)-4-nitrophenyl]-4-[2-(methylsulfonyl)ethyl]hexahydro-1H-1,4-diazepine (0.70 g, 1.9 mmol) was placed in a 200 mL high pressure vessel and dissolved in 40 mL of 1 to 1 EtOAc/MeOH. 5 wt % Platinum (sulfided)/C (0.51 g, 0.132 mmol) was added followed quickly by a rubber septum. The vial was evacuated and filled with N₂ six times to remove any oxygen. The vial was then pressurized with H₂ (60 psi). The solution stirred for 2 h. The vessel was evacuated and filled with N₂ six times to remove any H₂. The solution was filtered through celite and evaporated to afford the title compound of step C (0.585 g, 1.71 mmol, 91%). ¹H NMR (400 MHz, DMSO-d₆) δ 6.54 (s, 1H), 6.38 (s, 1H), 4.27 (br. s., 2H), 3.67 (s, 3H), 3.24 (t, J=6.59 Hz, 2H), 3.02 (s, 3H), 2.86-2.97 (m, 6H), 2.75 (t, J=5.49 Hz, 2H), 2.68-2.73 (m, 2H), 2.05 (s, 3H), 1.74-1.81 (m, 2H).

Step D: N-(2,6-difluorophenyl)-2-(ethyloxy)-5-(3-{2-[(5-methyl-2-(methyloxy)-4-{4-[2-(methylsulfonyl)ethyl]hexahydro-1H-1,4-diazepin-1-yl}phenyl)amino]-4-pyrimidinyl}imidazo[1,2-a]pyridin-2-yl)benzamide 5-[3-(2-Chloro-4-pyrimidinyl)imidazo[1,2-a]pyridin-2-yl]-N-(2,6-difluorophenyl)-2-(ethyloxy)benzamide (Intermediate Example 6) (100 mg, 0.2 mmol), 5-methyl-2-(methyloxy)-4-{4-[2-(methylsulfonyl)ethyl]hexahydro-1H-1,4-diazepin-1-yl}aniline (67 mg, 0.2 mmol), and p-toluenesulfonicacid (90 mg, 0.47 mmol) were weighed into a 20 mL vial. 1 mL of trifluoroethanol was added and the mixture was heated to 100° C. for 24 h. 2 mL of 2 N ammonia in MeOH was added. The solvent was rotovaped down. The residue was taken up in 3 mL of DCM. 1 g of silica gel was added. The solvent was rotovaped down and the pre-absorbed solids were purified by flash chromatography to give the title compound (94 mg, 0.12 mmol, 59%). $^1$H NMR (400 MHz, DMSO-d$_6$) δ 9.74 (s, 1H), 9.36 (s, 1H), 8.44 (s, 1H), 8.22 (d, J=5.13 Hz, 1H), 8.04 (d, J=2.20 Hz, 1H), 7.74 (dd, J=8.62, 2.02 Hz, 1H), 7.69 (d, J=8.80 Hz, 1H), 7.41-7.48 (m, 2H), 7.32-7.41 (m, 1H), 7.26 (d, J=8.80 Hz, 1H), 7.18 (t, J=8.07 Hz, 2H), 6.94 (t, J=6.78 Hz, 1H), 6.79 (s, 1H), 6.55 (d, J=5.13 Hz, 1H), 4.26 (q, J=6.97 Hz, 2H), 3.78 (s, 3H), 3.28 (t, J=7.15 Hz, 2H), 3.06-3.14 (m, 4H), 3.04 (s, 3H), 2.92 (t, J=6.78 Hz, 2H), 2.80 (t, J=5.68 Hz, 4H), 2.15 (s, 3H), 1.85 (qd, J=5.74, 5.50 Hz, 2H), 1.42 (t, J=6.78 Hz, 3H); MS (ESI): 811 [M+H]$^+$.

Example 204

N-(2,6-difluorophenyl)-5-(3-{2-[(5-ethyl-2-(ethyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide

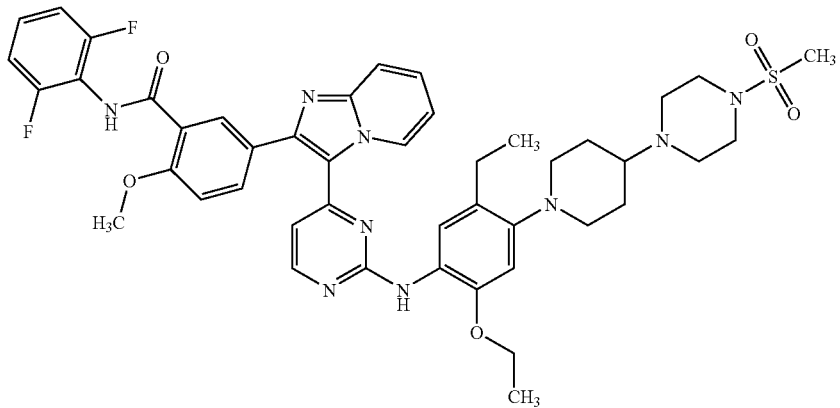

Step A: 1,1-dimethylethyl 4-(methylsulfonyl)-1-piperazinecarboxylate

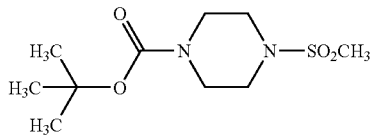

To 1,1-dimethylethyl 1-piperazinecarboxylate (568 g, 3.05 mol) in DCM (4 L) was added TEA (617 g, 6.10 mol). After stirring for 10 min at 0° C., methanesulfonyl chloride (384 g, 3.35 mol) was added via addition funnel. The mixture was stirred at rt overnight. The mixture was poured into H$_2$O (1 L) and extracted with DCM (1 L). The organic layer was separated, washed with H$_2$O (1 L), dried (Na$_2$SO$_4$), and rotovapped down to provide the title compound of step A (720 g, 2.72 mol, 90%) which was used without further purification. $^1$H NMR (400 MHz, CDCl$_3$) δ 1.44 (s, 9H), 2.76 (s, 3H), 3.11-3.17 (m, 4H), 3.50-3.53 (m, 4H).

Step B: 1-(methylsulfonyl)piperazine hydrochloride

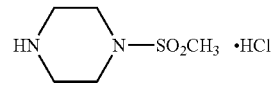

To 1,1-dimethylethyl 4-(methylsulfonyl)-1-piperazinecarboxylate (360 g, 1.36 mol) in MeOH (1 L) was added HCl (6 M in MeOH, 2 L) dropwise. The mixture was stirred at rt for 1 h. About 1 L of MeOH was rotovapped off. The resultant precipitate was filtered, washed with MeOH, and dried on high vacuum to provide the title compound of Step B (A combination of 2 batches, 570 g) which was used without further purification. $^1$H NMR (400 MHz, D$_2$O) δ 2.95 (s, 3H), 3.27-3.29 (m, 4H), 3.42-3.46 (m, 4H).

Step C: 1-(methylsulfonyl)-4-(4-piperidinyl)piperazine dihydrochloride

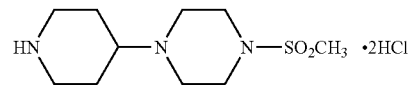

To 1-(methylsulfonyl)piperazine hydrochloride (150 g, 632 mmol) in DCE (3.5 L) was added TEA (192 g, 1.90 mol). The mixture was stirred at rt for 1 h and then acetic acid (94.8 g, 1.58 mol) and 1,1-dimethylethyl 4-oxo-1-piperidinecarboxylate (251 g, 1.26 mol) was added. After stirring another h, the reaction was cooled with an ice water bath and NaBH(OAc)$_3$ (294 g, 1.39 mol) was added in four portions. The mixture was stirred overnight at rt. The reaction mixture was neutralized with saturated Na$_2$CO$_3$ to pH 8-9. The organic phase was washed with brine and H$_2$O, dried (Na$_2$SO$_4$), and rotovapped down to provide the crude Boc-protected amine (A combination of 3 batches, 720 g). This amount was split into 2 batches and used without further purification. To 1,1-dimethylethyl 4-[4-(methylsulfonyl)-1-piperazinyl]-1-piperidinecarboxylate (360 g, 1.04 mol) in MeOH (1 L) was added HCl (6 M in MeOH, 2 L). The mixture was stirred at rt for 30 min. About 1 L of MeOH was rotovapped off. The resultant precipitate was filtered, washed with MeOH, and dried on high vacuum to provide the title compound of Step C (A combination of 2 batches, 600 g, 1.87 mol, 89% over 2 steps). ¹H NMR (400 MHz, D₂O) δ 1.87-1.91 (m, 2H), 2.33-2.36 (m, 2H), 2.97 (s, 3H), 2.99-3.05 (m, 2H), 3.45-3.59 (m, 11H).

Step D: 1-{1-[2-ethyl-5-(ethyloxy)-4-nitrophenyl]-4-piperidinyl}-4-(methylsulfonyl)-piperazine

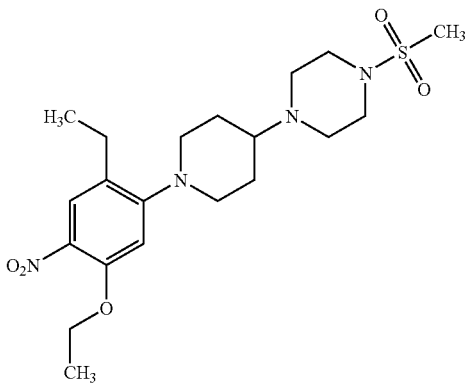

A mixture of 1-ethyl-4-(ethyloxy)-2-fluoro-5-nitrobenzene (Example 208, step A) (0.80 g, 3.75 mmol), 1-(methylsulfonyl)-4-(4-piperidinyl)piperazine (0.928 g, 3.75 mmol) and K₂CO₃ (0.622 g, 4.50 mmol) in DMSO (20 mL) was heated at 90° C. for 48 h. The reaction had not progressed sufficiently so the reaction was then heated at 120° C. for an additional 4 h. The reaction was cooled to rt, poured into H₂O and extracted exhaustively with DCM. The combined organics were washed with H₂O then dried over MgSO₄. The resultant solution was concentrated onto silica and purified by flash chromatography to afford 1-{1-[2-ethyl-5-(ethyloxy)-4-nitrophenyl]-4-piperidinyl}-4-(methylsulfonyl)piperazine (0.551 g, 33%) as a yellow solid. ¹H NMR (400 MHz, DMSO-d₆) δ ppm 7.75 (s, 1H), 6.74 (s, 1H), 4.19 (q, J=6.93 Hz, 2H), 3.19-3.28 (m, 2H), 3.06-3.14 (m, 4H), 2.87 (s, 3H), 2.52-2.79 (m, 9H), 1.80-1.92 (m, 2H), 1.46-1.67 (m, 2H), 1.33 (t, J=6.97 Hz, 3H), 1.19 (t, J=7.47 Hz, 3H).

Step E: 5-ethyl-2-(ethyloxy)-4-{4-[4-(methylsulfonyl)-1-piperazinyl]-1-piperidinyl}aniline

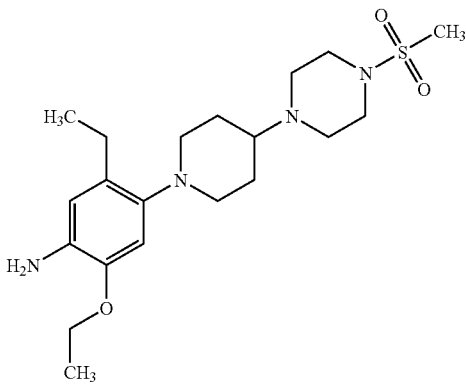

A mixture of 1-{1-[2-ethyl-5-(ethyloxy)-4-nitrophenyl]-4-piperidinyl}-4-(methylsulfonyl)piperazine (0.511 g, 1.160 mmol) and sulfided platinum on carbon (0.181 g, 0.046 mmol) in EtOAc (30 mL) was sealed in a round bottom flask with a rubber septum. The reaction mixture was purged with N₂ gas and then a balloon of H₂ gas was connected and the vessel was flushed with the H₂ gas. The reaction was stirred at rt for 48 h. TLC analysis showed the complete consumption of the starting nitro compound so the reaction vessel was purged with N₂ and the reaction mixture was filtered through celite to remove the catalyst. The filtrate was concentrated onto silica gel and purified by flash chromatography to afford 5-ethyl-2-(ethyloxy)-4-{4-[4-(methylsulfonyl)-1-piperazinyl]-1-piperidinyl}aniline (0.452 g, 95%). ¹H NMR (400 MHz, DMSO-d₆) δ ppm 6.58 (s, 1H), 6.47 (s, 1H), 4.33 (br. s., 2H), 3.94 (q, J=6.93 Hz, 2H), 3.04-3.15 (m, 4H), 2.79-2.93 (m, 5H), 2.54-2.66 (m, 6H), 2.28-2.40 (m, 1H), 1.72-1.85 (m, 2H), 1.45-1.61 (m, 2H), 1.30 (t, J=6.92 Hz, 3H), 1.09 (t, J=7.51 Hz, 3H).

Step F: N-(2,6-difluorophenyl)-5-(3-{2-[(5-ethyl-2-(ethyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide A mixture of 5-[3-(2-chloro-4-pyrimidinyl)imidazo[1,2-a]pyridin-2-yl]-N-(2,6-difluorophenyl)-2-(methyloxy)benzamide (Intermediate Example 2) (0.1 g, 0.203 mmol), (5-ethyl-2-(ethyloxy)-4-{4-[4-(methylsulfonyl)-1-piperazinyl]-1-piperidinyl}phenyl)amine (0.083 g, 0.203 mmol) and HCl (4N,1,4-Dioxane, 0.102 mL, 0.407 mmol) in Trifluoroethanol (8 mL) was heated at 170° C. for 40 min in the microwave. LCMS analysis indicated that the starting materials had been consumed. The reaction was quenched with 7N NH₃ in MeOH and then concentrated to dryness. The residue was then dissolved in DCM and concentrated onto silica gel. Purification by flash column chromatography followed by recrystallization from DCM and EtOH afforded the title compound N-(2,6-difluorophenyl)-5-(3-{2-[(5-ethyl-2-(ethyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide (0.119 g, 64%). ¹H NMR (400 MHz, DMSO-d₆) δ ppm 9.79 (s, 1H), 9.27-9.38 (m, 1H), 8.40 (s, 1H), 8.28 (d, J=5.22 Hz, 1H), 8.13 (d, J=1.92 Hz, 1H), 7.80 (dd, J=8.39, 1.88 Hz, 1H), 7.72 (d, J=8.98 Hz, 1H), 7.58 (s, 1H), 7.35-7.51 (m, 2H), 7.29 (d, J=8.71 Hz, 1H), 7.14-7.25 (m, 2H), 6.88-6.98 (m, 1H), 6.81 (s, 1H), 6.60 (d, J=5.13 Hz, 1H), 4.06 (q, J=6.97 Hz, 2H), 4.00 (s, 3H), 3.07-3.15 (m, 4H), 2.98-3.06 (m, 2H), 2.87 (s, 3H), 2.60-2.74 (m, 6H), 2.52-2.59 (m, 2H), 2.36-2.46 (m, 1H), 1.80-1.87 (m, 2H), 1.50-1.67 (m, 2H), 1.26 (t, J=6.97 Hz, 3H), 1.09 (t, J=7.51 Hz, 3H). MS (M+H, ES+) 866.

Example 205

N-(2,6-difluorophenyl)-5-(3-{2-[(5-ethyl-2-(ethyloxy)-4-{4-[4-(methylsulfonyl)-1-piperazinyl]-1-piperidinyl}phenyl)amino]-4-pyrimidinyl}imidazo[1,2-a]pyridin-2-yl)-2-(ethyloxy)benzamide

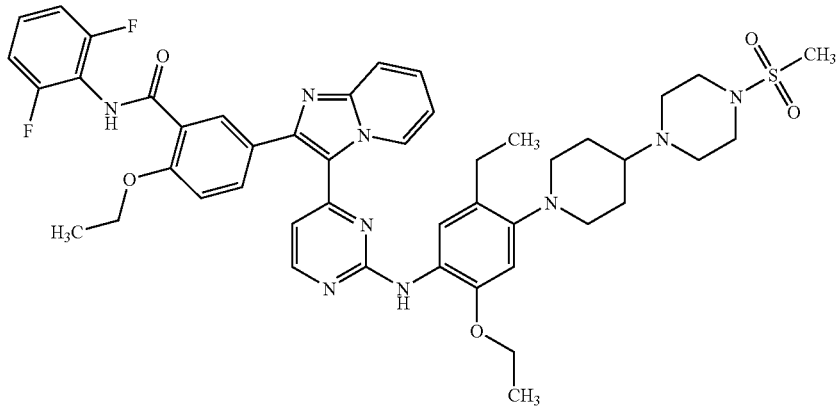

A mixture of 5-[3-(2-chloro-4-pyrimidinyl)imidazo[1,2-a]pyridin-2-yl]-N-(2,6-difluorophenyl)-2-(ethyloxy)benzamide (Intermediate Example 6) (0.10 g, 0.198 mmol), 5-ethyl-2-(ethyloxy)-4-{4-[4-(methylsulfonyl)-1-piperazinyl]-1-piperidinyl}aniline (Example 204, Step E) (0.081 g, 0.198 mmol) and HCl (4N,1,4-Dioxane, 0.099 mL, 0.395 mmol) in Trifluoroethanol (8 mL) was heated at 170° C. for 40 min in the microwave. The reaction was quenched with 7N NH₃ in MeOH and then concentrated to dryness. The residue was then dissolved in DCM and concentrated onto silica gel. Purification by flash column chromatography followed by recrystallization from DCM and EtOH afforded the title compound N-(2,6-difluorophenyl)-5-(3-{2-[(5-ethyl-2-(ethyloxy)-4-{4-[4-(methylsulfonyl)-1-piperazinyl]-1-piperidinyl}phenyl)amino]-4-pyrimidinyl}imidazo[1,2-a]pyridin-2-yl)-2-(ethyloxy)benzamide (0.112 g, 61%) as a yellow solid. ¹H NMR (400 MHz, DMSO-d₆) δ ppm 9.75 (s, 1H), 9.26-9.40 (m, 1H), 8.40 (s, 1H), 8.27 (d, J=5.22 Hz, 1H), 8.07 (d, J=2.02 Hz, 1H), 7.77 (dd, J=8.57, 2.25 Hz, 1H), 7.71 (d, J=8.98 Hz, 1H), 7.59 (s, 1H), 7.33-7.51 (m, 2H), 7.27 (d, J=8.61 Hz, 1H), 7.15-7.24 (m, 2H), 6.88-6.98 (m, 1H), 6.81 (s, 1H), 6.60 (d, J=5.22 Hz, 1H), 4.21-4.34 (m, 2H), 4.07 (q, J=6.93 Hz, 2H), 3.07-3.17 (m, 4H), 2.97-3.06 (m, 2H), 2.87 (s, 3H), 2.59-2.77 (m, 6H), 2.55 (q, J=7.45 Hz, 2H), 2.37-2.46 (m, 1H), 1.79-1.90 (m, 2H), 1.53-1.68 (m, 2H), 1.44 (t, J=6.92 Hz, 3H), 1.26 (t, J=6.97 Hz, 3H), 1.10 (t, J=7.51 Hz, 3H). MS (M-2H, ES–) 878.

Example 206

N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(ethyloxy)benzamide

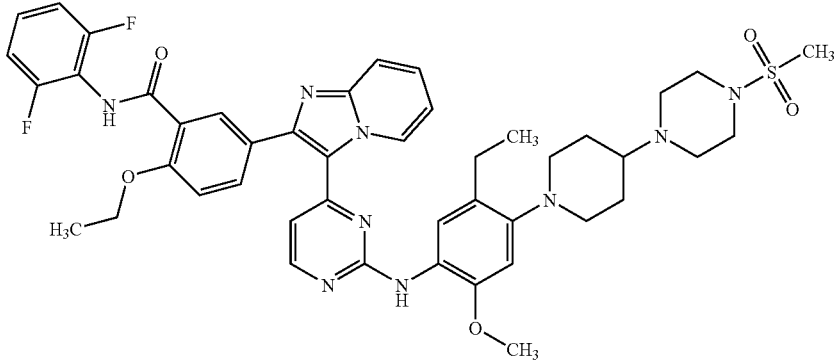

Step A: 1-{1-[2-ethyl-5-(methyloxy)-4-nitrophenyl]-4-piperidinyl}-4-(methylsulfonyl)piperazine

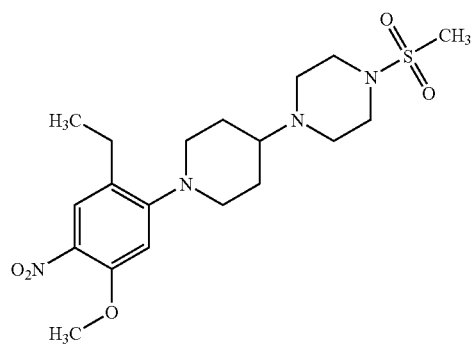

A mixture of 1-ethyl-2-fluoro-4-(methyloxy)-5-nitrobenzene (Example 187, step C) (0.93 g, 4.67 mmol), 1-(methyl sulfonyl)-4-(4-piperidinyl)piperazine (Example 204, step C) (1.16 g, 4.67 mmol) and K$_2$CO$_3$ (0.774 g, 5.60 mmol) in DMSO (20 mL) was heated at 90° C. for 48 h. The reaction had not progressed sufficiently so the reaction was then heated at 120° C. for an additional 4 h. The reaction was cooled to rt, poured into H$_2$O and extracted with DCM. Some saturated brine solution was added and the resultant was exhaustively extracted with DCM. The combined organics were washed with H$_2$O then dried over MgSO$_4$. The resultant solution was concentrated onto silica and purified by flash chromatography to afford 1-{1-[2-ethyl-5-(methyloxy)-4-nitrophenyl]-4-piperidinyl}-4-(methylsulfonyl)piperazine (1.12 g, 56%). $^1$H NMR (400 MHz, DMSO-d$_6$) δ ppm 7.73-7.80 (m, 1H), 6.75 (s, 1H), 3.91 (s, 3H), 3.23-3.30 (m, 1H), 3.05-3.19 (m, 3H), 2.87 (s, 2H), 2.70-2.84 (m, 2H), 2.53-2.67 (m, 5H), 1.77-1.94 (m, 2H), 1.48-1.67 (m, 2H), 1.19 (t, J=7.42 Hz, 3H).

Step B: 5-ethyl-2-(methyloxy)-4-{4-[4-(methylsulfonyl)-1-piperazinyl]-1-piperidinyl}aniline

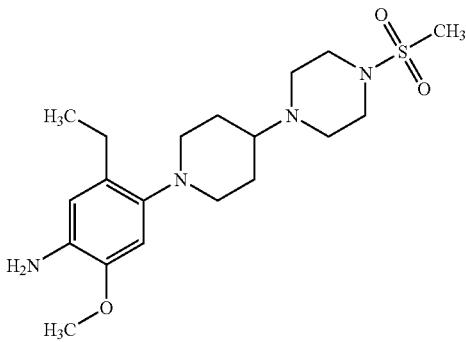

A mixture of 1-{1-[2-ethyl-5-(methyloxy)-4-nitrophenyl]-4-piperidinyl}-4-(methylsulfonyl)piperazine (1.12 g, 2.63 mmol) and sulfided platinum on carbon (0.410 g, 0.105 mmol) in EtOAc (40 mL) was sealed in a round bottom flask with a rubber septum. The reaction mixture was purged with N$_2$ gas and then a balloon of H$_2$ gas was connected and the vessel was flushed with the H$_2$ gas. The reaction was stirred at rt for 2 d. TLC analysis showed the complete consumption of the starting nitro compound so the reaction mixture was filtered through celite to remove the catalyst. The filtrate was concentrated onto silica gel and purified by flash chromatography to afford 5-ethyl-2-(methyloxy)-4-{4-[4-(methylsulfonyl)-1-piperazinyl]-1-piperidinyl}aniline (0.479 g, 46%). $^1$H NMR (400 MHz, DMSO-d$_6$) δ ppm 6.60 (s, 1H), 6.46 (s, 1H), 4.35 (br. s., 2H), 3.71 (s, 3H), 3.03-3.16 (m, 4H), 2.81-2.93 (m, 5H), 2.56-2.68 (m, 6H), 2.29-2.42 (m, 1H), 1.72-1.89 (m, 2H), 1.44-1.62 (m, 2H), 1.09 (t, J=7.51 Hz, 3H).

Step C: N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(ethyloxy)benzamide A mixture of 5-[3-(2-chloro-4-pyrimidinyl)imidazo[1,2-a]pyridin-2-yl]-N-(2,6-difluorophenyl)-2-(ethyloxy)benzamide (Intermediate Example 6) (0.125 g, 0.247 mmol), 5-ethyl-2-(methyloxy)-4-{4-[4-(methylsulfonyl)-1-piperazinyl]-1-piperidinyl}aniline (0.098 g, 0.247 mmol) and HCl (4N,1,4-Dioxane, 0.12 mL, 0.494 mmol) in trifluoroethanol (8 mL) was heated at 170° C. for 40 min in the microwave. The reaction was quenched with 7 N NH$_3$ in MeOH and then concentrated to dryness. The residue was then dissolved in DCM and concentrated onto silica gel. Purification by flash column chromatography followed by recrystallization from DCM and EtOH afforded the title compound N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(ethyloxy)benzamide (0.150 g, 67%) as a yellow solid. $^1$H NMR (400 MHz, DMSO-d$_6$) δ ppm 9.76 (s, 1H), 9.30-9.43 (m, 1H), 8.50 (s, 1H), 8.25 (d, J=5.22 Hz, 1H), 8.06 (d, J=2.02 Hz, 1H), 7.74-7.80 (m, 1H), 7.71 (d, J=8.89 Hz, 1H), 7.53 (s, 1H), 7.34-7.49 (m, 2H), 7.28 (d, J=8.43 Hz, 1H), 7.16-7.25 (m, 2H), 6.91-7.00 (m, 1H), 6.83 (s, 1H), 6.58 (d, J=5.04 Hz, 1H), 4.20-4.33 (m, 2H), 3.81 (s, 3H), 3.08-3.16 (m, 4H), 3.00-3.08 (m, 2H), 2.88 (s, 3H), 2.67-2.78 (m, 2H), 2.61-2.66 (m, 4H), 2.56 (q, J=7.51 Hz, 2H), 2.38-2.47 (m, 1H), 1.79-1.92 (m, 2H), 1.52-1.68 (m, 2H), 1.44 (t, J=6.92 Hz, 3H), 1.11 (t, J=7.51 Hz, 3H). MS (M+H, ES+) 866.

Example 207

N-(2,6-difluorophenyl)-5-(3-{2-[(5-ethyl-2-(methyloxy)-4-{4-[2-(methylsulfonyl)ethyl]-1-piperidinyl}phenyl)amino]-4-pyrimidinyl}imidazo[1,2-a]pyridin-2-yl)-2-(methyloxy)benzamide

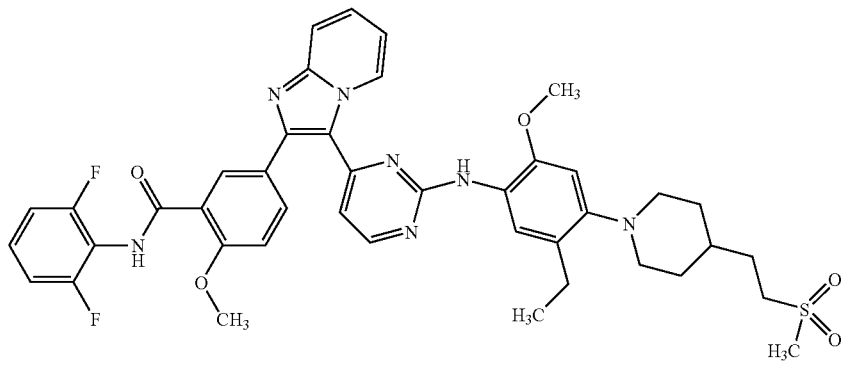

Step A: 1-[2-ethyl-5-(methyloxy)-4-nitrophenyl]-4-[2-(methylsulfonyl)ethyl]piperidine

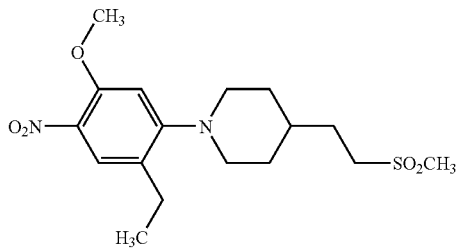

To 1-ethyl-2-fluoro-4-(methyloxy)-5-nitrobenzene (Example 187, Step C) (0.20 g, 1.0 mmol), 4-[2-(methylsulfonyl)ethyl]piperidine (Example 101, Step D) (0.23 g, 1.2 mmol), and $K_2CO_3$ (0.49 g, 3.5 mmol) was added DMSO (10 mL). The reaction was heated to 100° C. for two days. The reaction was determined to be complete by TLC. The reaction mixture was diluted with $H_2O$ and extracted with DCM and EtOAc sequentially for two iterations. The organic was dried ($MgSO_4$), filtered, and rotovapped down. Purification by flash chromatography provided the title compound of Step A (0.25 g, 0.68 mmol, 68%). $^1$H NMR (400 MHz, $CDCl_3$) δ 7.84 (s, 1H), 6.56 (s, 1H), 3.92 (s, 3H), 3.22 (d, J=11.5 Hz, 2H), 3.00-3.14 (m, 2H), 2.92 (s, 3H), 2.69 (t, J=11.7 Hz, 2H), 2.57 (q, J=7.4 Hz, 2H), 1.76-1.97 (m, 4H), 1.35-1.70 (m, 3H), 1.24 (t, 3H).

Step B: 5-ethyl-2-(methyloxy)-4-{4-[2-(methylsulfonyl)ethyl]-1-piperidinyl}aniline

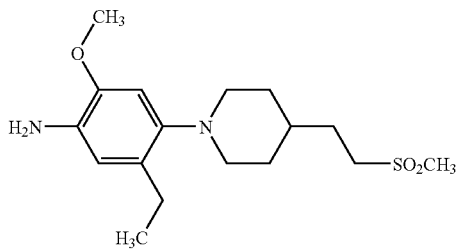

To 1-[2-ethyl-5-(methyloxy)-4-nitrophenyl]-4-[2-(methylsulfonyl)ethyl]piperidine (0.25 g, 0.68 mmol) in EtOAc (30 mL) was added platinum on carbon (sulfided) (0.13 g, 0.034 mmol). The mixture was stirred under $H_2$ (1 atm.) overnight. Filtering the mixture through Celite® and concentrating provided the title compound of Step B (0.18 g, 0.54 mmol, 79%). $^1$H NMR (400 MHz, DMSO-$d_6$) δ 6.55 (s, 1H), 6.42 (s, 1H), 4.30 (br. s., 2H), 3.67 (s, 3H), 3.04-3.16 (m, 2H), 2.92 (s, 3H), 2.77 (d, J=11.5 Hz, 2H), 2.52 (t, J=10.9 Hz, 2H), 2.38-2.44 (m, 2H), 1.56-1.75 (m, 4H), 1.39 (ddd, J=10.7, 7.1, 3.5 Hz, 1H), 1.24 (qd, J=11.7, 3.2 Hz, 2H), 1.04 (t, J=7.6 Hz, 3H).

Step C: N-(2,6-difluorophenyl)-5-(3-{2-[(5-ethyl-2-(methyloxy)-4-{4-[2-(methylsulfonyl)ethyl]-1-piperidinyl}phenyl)amino]-4-pyrimidinyl}imidazo[1,2-a]pyridin-2-yl)-2-(methyloxy)benzamide In a microwave vial with septum cap, 5-[3-(2-chloro-4-pyrimidinyl)imidazo[1,2-a]pyridin-2-yl]-N-(2,6-difluorophenyl)-2-(methyloxy)benzamide (Intermediate Example 2) (0.131 g, 0.267 mmol) and 5-ethyl-2-(methyloxy)-4-{4-[2-(methylsulfonyl)ethyl]-1-piperidinyl}aniline (0.091 g, 0.27 mmol) were taken up in 1,1,1-trifluoroethanol (1.5 mL) and 4M HCl in dioxane (0.134 mL, 0.535 mmol) was added. The vial was sealed and heated in the microwave at 180° C. for 40 min. Reaction was complete by MS, it was cooled to rt, neutralized with 7N ammonia in MeOH, and concentrated in vacuo onto silica gel and flash chromatographed. The desired fractions were combined and concentrated and the resulting solid was triturated with diethyl ether, filtered and air dried to give the title compound (0.12 g, 0.15 mmol, 56%). $^1$H NMR (400 MHz, DMSO-$d_6$) δ ppm 9.75 (s, 1H), 9.23-9.40 (m, 1H), 8.44 (s, 1H), 8.21 (d, J=5.2 Hz, 1H), 8.08 (s, 1H), 7.75 (dd, J=8.4, 1.6 Hz, 1H), 7.67 (d, J=9.0 Hz, 1H), 7.49 (s, 1H), 7.29-7.45 (m, 2H), 7.21-7.29 (m, 1H), 7.07-7.21 (m, 2H), 6.91 (t, J=6.8 Hz, 1H), 6.78 (s, 1H), 6.54 (d, J=5.1 Hz, 1H), 3.95 (s, 3H), 3.76 (s, 3H), 3.06-3.20 (m, 2H), 2.86-3.01 (m, 5H), 2.57-2.72 (m, 2H), 2.51 (q, J=7.5 Hz, 2H), 1.75 (dd, J=11.6, 0.6 Hz, 2H), 1.60-1.71 (m, 2H), 1.40-1.55 (m, 1H), 1.20-1.39 (m, 2H), 1.06 (t, J=7.5 Hz, 3H). MS (M+H, ES+) 796.

Example 208

N-(2,6-difluorophenyl)-5-(3-{2-[(5-ethyl-2-(ethyloxy)-4-{4-[2-(methylsulfonyl)ethyl]-1-piperidinyl}phenyl)amino]-4-pyrimidinyl}imidazo[1,2-a]pyridin-2-yl)-2-(ethyloxy)benzamide

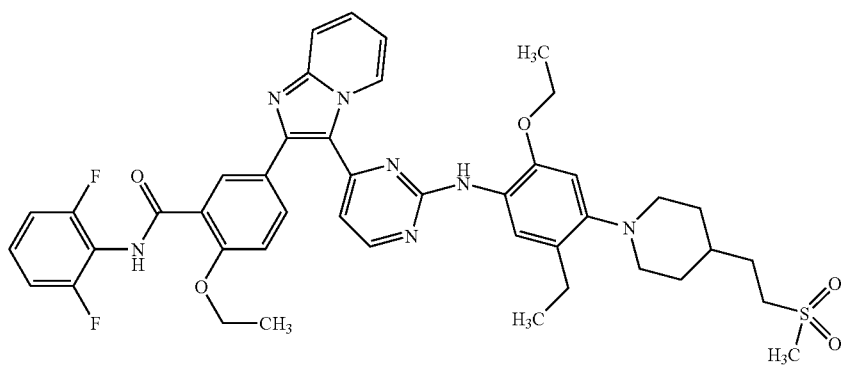

Step A: 1-ethyl-4-(ethyloxy)-2-fluoro-5-nitrobenzene

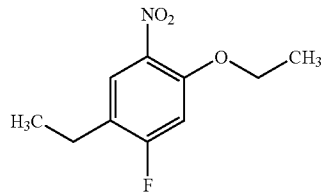

The title compound of Step A (1.6 g, 6.8 mmol, 90%) was prepared in an analogous manner to that described for the preparation of Example 187, Step C, with the following exception: ethyl iodide was used instead of methyl iodide. $^1$H NMR (400 MHz, CDCl$_3$) δ 7.81 (d, J=7.9 Hz, 1H), 6.73 (d, J=11.3 Hz, 1H), 4.14 (q, J=7.0 Hz, 2H), 2.65 (q, J=7.6 Hz, 2H), 1.43-1.54 (m, 3H), 1.24 (t, J=7.6 Hz, 3H).

Step B: 1-[2-ethyl-5-(ethyloxy)-4-nitrophenyl]-4-[2-(methylsulfonyl)ethyl]piperidine

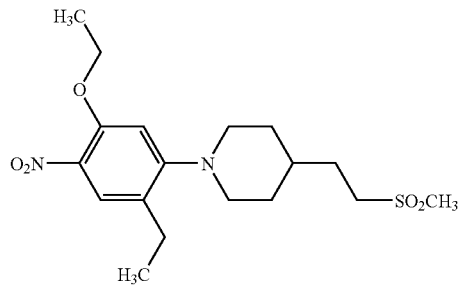

To 1-ethyl-4-(ethyloxy)-2-fluoro-5-nitrobenzene (0.19 g, 0.89 mmol), 4-[2-(methylsulfonyl)ethyl]piperidine (Example 101, Step D) (0.20 g, 1.1 mmol), and K$_2$CO$_3$ (0.43 g, 3.1 mmol) was added DMSO (12 mL). The reaction was heated to 100° C. for two days. Reaction was determined to be complete by TLC. The reaction mixture was diluted with H$_2$O and extracted with DCM and EtOAc sequentially for two iterations. The organic was dried (MgSO$_4$), filtered, and rotovapped down. Purification by flash chromatography provided the title compound of Step B (0.22 g, 0.57 mmol, 65% yield). $^1$H NMR (400 MHz, CDCl$_3$) δ 7.80 (s, 1H), 6.57 (s, 1H), 4.13 (q, J=6.9 Hz, 2H), 3.20 (d, J=11.6 Hz, 2H), 3.00-3.13 (m, 2H), 2.92 (s, 3H), 2.67 (t, J=11.7 Hz, 2H), 2.57 (q, J=7.4 Hz, 2H), 1.77-1.97 (m, 4H), 1.36-1.68 (m, 6H), 1.24 (t, 3H).

Step C: 5-ethyl-2-(ethyloxy)-4-{4-[2-(methylsulfonyl)ethyl]-1-piperidinyl}aniline

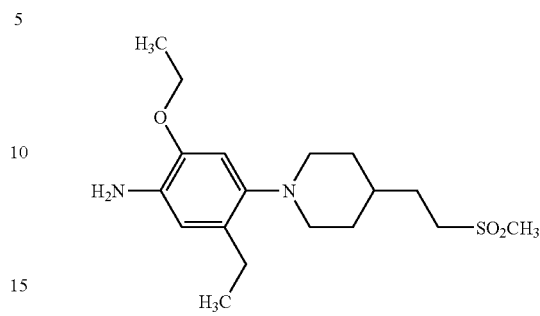

To 1-[2-ethyl-5-(ethyloxy)-4-nitrophenyl]-4-[2-(methylsulfonyl)ethyl]piperidine (0.22 g, 0.57 mmol) in EtOAC (30 mL) was added platinum on carbon (sulfided) (0.11 g, 0.029 mmol). The mixture was stirred under H$_2$ (1 atm) overnight. Filtering the mixture through Celite® and concentrating provided the title compound of Step C (0.21 g, 0.56 mmol, 98%). $^1$H NMR (400 MHz, DMSO-d$_6$) δ 6.55 (s, 1H), 6.44 (s, 1H), 4.29 (br. s., 2H), 3.91 (q, J=7.1 Hz, 2H), 3.02-3.21 (m, 2H), 2.94 (s, 3H), 2.78 (d, J=11.2 Hz, 2H), 2.37-2.59 (m, 6H), 1.57-1.77 (m, 3H), 1.34-1.49 (m, 1H), 1.18-1.34 (m, 4H), 1.05 (t, J=7.5 Hz, 3H).

Step D: N-(2,6-difluorophenyl)-5-(3-{2-[(5-ethyl-2-(ethyloxy)-4-{4-[2-(methylsulfonyl)ethyl]-1-piperidinyl}phenyl)amino]-4-pyrimidinyl}imidazo[1,2-a]pyridin-2-yl)-2-(ethyloxy)benzamide In a microwave vial with septum cap, 5-[3-(2-chloro-4-pyrimidinyl)imidazo[1,2-a]pyridin-2-yl]-N-(2,6-difluorophenyl)-2-(ethyloxy)benzamide (Intermediate Example 6) (0.148 g, 0.293 mmol) and 5-ethyl-2-(ethyloxy)-4-{4-[2-(methylsulfonyl)ethyl]-1-piperidinyl}aniline (0.104 g, 0.293 mmol) were taken up in 1,1,1-trifluoroethanol (1.5 mL) and 4M HCl in dioxane (0.147 mL, 0.587 mmol) was added. The vial was sealed and heated in the microwave at 180° C. for 40 min. Reaction was complete by MS, it was cooled to rt, neutralized with 7N ammonia in MeOH, and concentrated in vacuo onto silica gel and flash chromatographed. The desired fractions were combined and concentrated and the resulting solid was triturated with diethyl ether, filtered and air dried to give the title compound (0.14 g, 0.17 mmol, 58%). $^1$H NMR (400 MHz, DMSO-d$_6$) δ ppm 9.70 (s, 1H), 9.29 (d, J=6.8 Hz, 1H), 8.34 (s, 1H), 8.23 (d, J=5.2 Hz, 1H), 8.03 (s, 1H), 7.61-7.79 (m, 2H), 7.55 (s, 1H), 7.29-7.48 (m, 2H), 7.08-7.28 (m, 3H), 6.89 (t, J=6.8 Hz, 1H), 6.76 (s, 1H), 6.56 (d, J=5.1 Hz, 1H), 4.23 (q, J=6.7 Hz, 2H), 4.03 (q, J=6.9 Hz, 2H), 3.07-3.20 (m, 2H), 2.84-3.04 (m, 5H), 2.60 (t, J=10.9 Hz, 2H), 2.51 (q, J=7.5 Hz, 2H), 1.75 (d, J=11.2 Hz, 2H), 1.60-1.70 (m, 4H), 1.35-1.55 (m, 4H), 1.15-1.36 (m, 5H), 1.05 (td, J=7.2, 1.9 Hz, 3H). MS (M+H, ES+) 824.

Example 209

N-(2,6-difluorophenyl)-5-(3-{2-[(5-ethyl-2-(methyloxy)-4-{4-[2-(methylsulfonyl)ethyl]-1-piperidinyl}phenyl)amino]-4-pyrimidinyl}imidazo[1,2-a]pyridin-2-yl)-2-(ethyloxy)benzamide

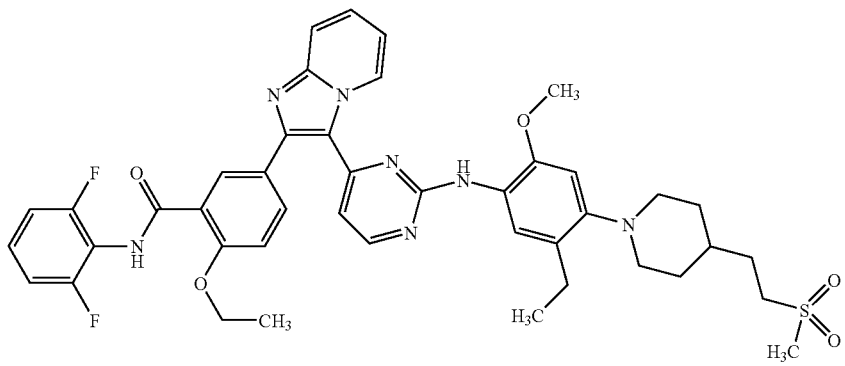

The title compound (0.14 g, 0.17 mmol, 65%) was prepared in an analogous manner to that described for Example 207, with the following notable exception in step C: 5-[3-(2-chloro-4-pyrimidinyl)imidazo[1,2-a]pyridin-2-yl]-N-(2,6-difluorophenyl)-2-(ethyloxy)benzamide (Intermediate Example 6) was used instead of 5-[3-(2-chloro-4-pyrimidinyl)imidazo[1,2-a]pyridin-2-yl]-N-(2,6-difluorophenyl)-2-(methyloxy)benzamide (Intermediate Example 2). $^1$H NMR (400 MHz, DMSO-d$_6$) δ ppm 9.71 (s, 1H), 9.31 (td, J=2.7, 1.0 Hz, 1H), 8.44 (s, 1H), 8.21 (d, J=5.2 Hz, 1H), 8.02 (s, 1H), 7.61-7.80 (m, 2H), 7.49 (s, 1H), 7.28-7.46 (m, 2H), 7.23 (d, J=8.6 Hz, 1H), 7.16 (t, J=8.1 Hz, 2H), 6.91 (t, J=6.7 Hz, 1H), 6.78 (s, 1H), 6.54 (d, J=5.1 Hz, 1H), 4.16-4.30 (m, 2H), 3.76 (s, 3H), 3.08-3.19 (m, 2H), 2.88-3.01 (m, 5H), 2.63 (t, J=10.9 Hz, 2H), 2.51 (q, J=7.6 Hz, 2H), 1.75 (d, J=11.0 Hz, 2H), 1.60-1.71 (m, 2H), 1.20-1.53 (m, 6H), 1.06 (t, J=7.4 Hz, 3H). MS (M+H, ES+) 810.

Example 210

N-(2,6-difluorophenyl)-5-(3-{2-[(5-ethyl-2-(ethyloxy)-4-{4-[2-(methylsulfonyl)ethyl]-1-piperidinyl}phenyl)amino]-4-pyrimidinyl}imidazo[1,2-a]pyridin-2-yl)-2-(methyloxy)benzamide

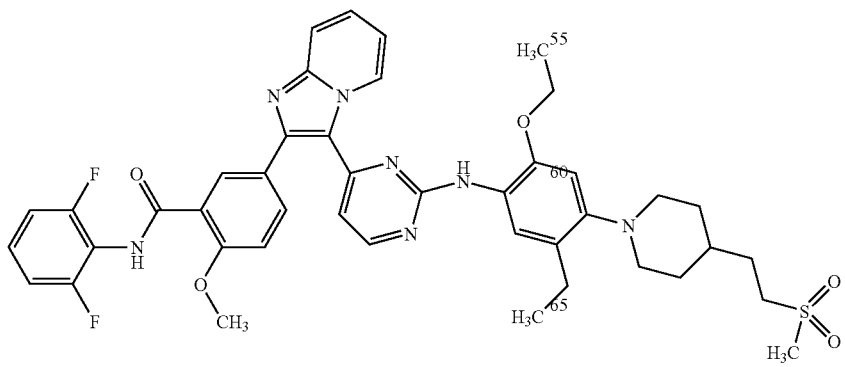

The title compound (0.12 g, 0.15 mmol, 50%) was prepared in an analogous manner to that described for Example 208, with the following notable exception in step D: 5-[3-(2-chloro-4-pyrimidinyl)imidazo[1,2-a]pyridin-2-yl]-N-(2,6-difluorophenyl)-2-(methyloxy)benzamide (Intermediate Example 2) was used instead of 5-[3-(2-chloro-4-pyrimidinyl)imidazo[1,2-a]pyridin-2-yl]-N-(2,6-difluorophenyl)-2-(ethyloxy)benzamide (Intermediate Example 6). $^1$H NMR (400 MHz, DMSO-d$_6$) δ ppm 9.74 (s, 1H), 9.29 (d, J=6.5 Hz, 1H), 8.34 (s, 1H), 8.23 (d, J=5.2 Hz, 1H), 8.09 (d, J=1.5 Hz, 1H), 7.71-7.82 (m, 1H), 7.67 (d, J=9.0 Hz, 1H), 7.54 (s, 1H), 7.29-7.47 (m, 2H), 7.25 (d, J=8.6 Hz, 1H), 7.15 (t, J=8.0 Hz, 2H), 6.89 (t, J=6.8 Hz, 1H), 6.76 (s, 1H), 6.56 (d, J=5.2 Hz, 1H), 4.02 (q, J=6.9 Hz, 2H), 3.95 (s, 3H), 3.06-3.19 (m, 2H), 2.86-3.01 (m, 5H), 2.56-2.66 (m, 2H), 2.47-2.55 (m, 2H), 1.70-1.81 (m, 2H), 1.60-1.71 (m, 2H), 1.38-1.54 (m, 1H), 1.15-1.36 (m, 5H), 1.05 (t, J=7.5 Hz, 3H). MS (M+H, ES+) 810.

Example 211

N-(2,6-difluorophenyl)-5-(3-{2-[(5-ethyl-2-(ethyloxy)-4-{4-[2-(methylsulfonyl)ethyl]-1-piperazinyl}phenyl)amino]-4-pyrimidinyl}imidazo[1,2-a]pyridin-2-yl)-2-(ethyloxy)benzamide

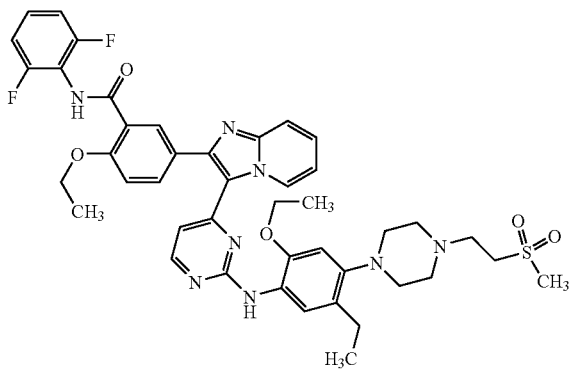

Step A: 1-[2-ethyl-5-(ethyloxy)-4-nitrophenyl]-4-[2-(methylsulfonyl)ethyl]piperazine

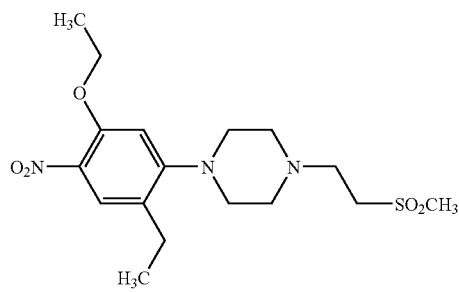

1-Ethyl-2-fluoro-4-(ethyloxy)-5-nitrobenzene (Example 208, step A) (0.50 g, 2.3 mmol) was dissolved in DMSO (15 mL). K$_2$CO$_3$ (0.97 g, 7.0 mmol) and 1-[2-(methylsulfonyl)ethyl]piperazine hydrochloride (Example 148, step B) (1.0 g, 4.7 mmol) were added and the reaction mixture was heated to 80° C. and allowed to stir over the weekend. The mixture was then heated to 120° C. for 4 h. The mixture was cooled to rt then poured into H$_2$O and extracted with DCM. The combined organics were dried with MgSO$_4$, filtered, and concentrated in vacuo. The crude product was purified on a 40 g ISCO column (EtOAc to 10% MeOH in EtOAc). The desired fractions were combined and the solvent removed in vacuo to give the title compound of Step A (0.63 g, 1.6 mmol, 66%) as a yellow solid. $^1$H NMR (400 MHz, CDCl$_3$) δ 7.78 (s, 1H), 6.56 (s, 1H), 4.12 (q, J=7.0 Hz, 2H), 3.23-3.12 (m, 2H), 3.03 (s, 3H), 3.00-2.91 (m, 6H), 2.72-2.62 (m, 4H), 2.57 (q, J=7.5 Hz, 2H), 2.22 (s, 3H), 1.44 (t, J=7.0 Hz, 3H), 1.22 (t, J=7.5 Hz, 3H). MS (M+H, ES+) 386.

Step B: 5-ethyl-2-(methyloxy)-4-{4-[2-(methylsulfonyl)ethyl]-1-piperazinyl}aniline

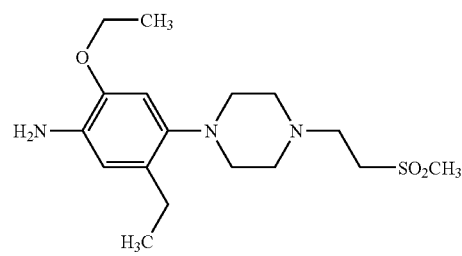

1-[2-Ethyl-5-(ethyloxy)-4-nitrophenyl]-4-[2-(methylsulfonyl)ethyl]piperazine (0.63 g, 1.6 mmol) was taken up in EtOAc (30 mL) and MeOH (5 mL). The catalyst, 5% sulfided platinum on carbon (0.25 g) was added. The reaction was placed under 1 atm of H$_2$ gas and was allowed to stir at rt overnight. The catalyst was filtered off and the filtrate was concentrated in vacuo to give the title compound without further purification (0.55 g, 1.5 mmol, 91%). MS (ESI) m/z=356 [M+H]$^+$.

Step C: N-(2,6-difluorophenyl)-5-(3-{2-[(5-ethyl-2-(ethyloxy)-4-{4-[2-(methylsulfonyl)ethyl]-1-piperazinyl}phenyl)amino]-4-pyrimidinyl}imidazo[1,2-a]pyridin-2-yl)-2-(ethyloxy)benzamide To 5-[3-(2-chloro-4-pyrimidinyl)imidazo[1,2-a]pyridin-2-yl]-N-(2,6-difluorophenyl)-2-(ethyloxy)benzamide (Intermediate Example 6) (0.43 g, 0.84 mmol) and (5-ethyl-2-(ethyloxy)-4-{4-[2-(methylsulfonyl)ethyl]-1-piperazinyl}phenyl)amine (0.30 g, 0.84 mmol) in trifluoroethanol (5 mL) was added p-toluene sulfonic acid (0.32 g, 1.7 mmol), and the vial was sealed and heated to 85° C. overnight. The reaction was then cooled to rt and excess NH$_3$ in MeOH (10% in DCM) was added. The solution was transferred to a roundbottom flask and silica was added. The solvent was removed on a rotovap and the product purified on a 40 g ISCO column. Desired fractions were combined and rotovaped down. The resulting foam was dissolved in DCM and ether was added to provide the title compound (0.23 g, 0.26 mmol, 30% yield) as a yellow solid. $^1$H NMR (400 MHz, DMSO-d$_6$) δ ppm 9.71 (s, 1H), 9.29 (d, J=6.2 Hz, 1H), 8.36 (s, 1H), 8.24 (d, J=5.3 Hz, 1H), 8.03 (s, 1H), 7.73-7.70 (m, 1H), 7.67 (d, J=9.0 Hz, 1H), 7.56 (s, 1H), 7.42-7.31 (m, 2H), 7.23 (d, J=8.4 Hz, 1H), 7.16 (t, J=8.2 Hz, 2H), 6.90 (t, J=6.6 Hz, 1H), 6.78 (s, 1H), 6.57 (d, J=5.3 Hz, 1H), 4.23 (q, J=7.3 Hz, 2H), 4.04 (q, J=7.1 Hz, 2H), 3.31-3.26 (m, 2H), 3.03 (s, 3H), 2.84-2.78 (m, 2H), 2.74 (t, J=6.5 Hz, 2H), 2.63-2.46 (m, 6H), 1.40 (t, J=6.8 Hz, 3H), 1.22 (t, J=6.9 Hz, 3H), 1.05 (t, J=7.5 Hz, 3H). MS (ESI) m/z=824 [M+H]$^+$.

Example 212

5-(3-{2-[(5-chloro-2-(methyloxy)-4-{4-[2-(methylsulfonyl)ethyl]-1-piperazinyl}phenyl)amino]-4-pyrimidinyl}imidazo[1,2-a]pyridin-2-yl)-N-(2,6-difluorophenyl)-2-(ethyloxy)benzamide

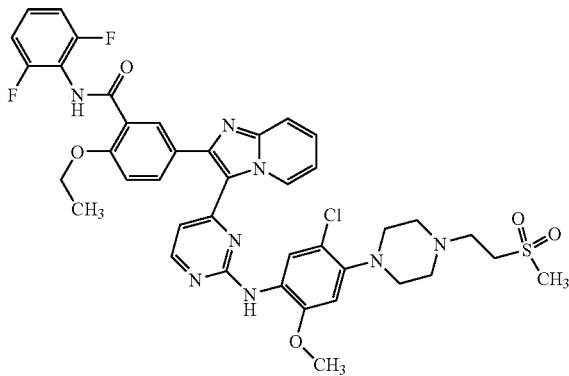

Step A: 1-[2-chloro-5-(methyloxy)-4-nitrophenyl]-4-[2-(methylsulfonyl)ethyl]piperazine

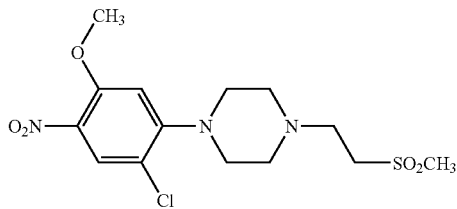

To 1-chloro-2-fluoro-4-(methyloxy)-5-nitrobenzene (Example 104, Step B) (0.822 g, 4.0 mmol), 4-[2-(methylsulfonyl)ethyl]piperazine hydrochloride (Example 148, Step B) (0.915 g, 4.0 mmol), and $K_2CO_3$ (1.7 g, 12 mmol) was added DMSO (8 mL). The reaction was heated to 100° C. for two days. The reaction was determined to be complete by TLC. The reaction mixture was diluted with $H_2O$ and extracted with DCM and EtOAc sequentially for two iterations. The organic was dried ($MgSO_4$), filtered, and rotovapped down. Purification by flash chromatography provided the title compound of Step A (1.38 g, 91%). MS (M+H, ES+) 378.

Step B: 5-chloro-2-(methyloxy)-4-{4-[2-(methylsulfonyl)ethyl]-1-piperazinyl}aniline

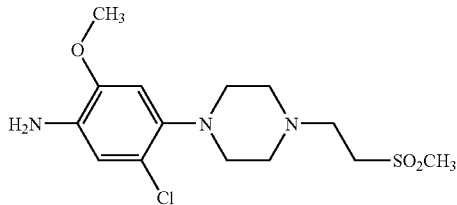

To 1-[2-chloro-5-(methyloxy)-4-nitrophenyl]-4-[2-(methylsulfonyl)ethyl]piperazine (1.38 g, 3.65 mmol) in EtOH (30 mL) was added EtOAc to help with solubility. The catalyst, 5% sulfided platinum on carbon (0.138 g, 0.035 mmol) was added. The reaction was placed on a Fischer-Porter Hydrogenator under 50 psi of $H_2$ gas and was allowed to stir at rt overnight. The catalyst was filtered off and the filtrate was concentrated in vacuo, adsorbed onto silica gel and flash chromatographed. The desired fractions were combined and concentrated to give the title compound of step B (0.880 g, 69%). 1H NMR (400 MHz, DMSO-$d_6$) δ ppm 6.58-6.70 (m, 2H), 4.64 (s, 2H), 3.74 (s, 3H), 3.22-3.37 (m, 2H), 3.04 (s, 3H), 2.84 (t, J=4.4 Hz, 4H), 2.74 (t, J=6.7 Hz, 2H), 2.50-2.63 (m, 4H).

Step C: 5-(3-{2-[(5-chloro-2-(methyloxy)-4-{4-[2-(methylsulfonyl)ethyl]-1-piperazinyl}phenyl)amino]-4-pyrimidinyl}imidazo[1,2-a]pyridin-2-yl)-N-(2,6-difluorophenyl)-2-(ethyloxy)benzamide In a 10 mL vial with septum cap, 5-[3-(2-chloro-4-pyrimidinyl)imidazo[1,2-a]pyridin-2-yl]-N-(2,6-difluorophenyl)-2-(ethyloxy)benzamide (Intermediate Example 6) (0.200 g, 0.395 mmol), 5-chloro-2-(methyloxy)-4-{4-[2-(methylsulfonyl)ethyl]-1-piperazinyl}aniline (0.165 g, 0.474 mmol) were taken up in iPrOH (3 mL) and pyridinium p-toluenesulfonate (0.238 g, 0.949 mmol) was added. The vial was sealed and heated to 80° C. overnight. When reaction was complete by MS, it was cooled to rt, neutralized with 7N ammonia in MeOH, absorbed onto silica gel and flash chromatographed. Fractions containing the desired product were concentrated and the resulting solid was triturated with diethyl ether, filtered and air dried to give the title compound (0.12 g, 0.15 mmol, 37%). $^1$H NMR (400 MHz, DMSO-$d_6$) δ ppm 9.71 (s, 1H), 9.38 (dd, J=4.4, 1.1 Hz, 1H), 8.53 (s, 1H), 8.25 (d, J=5.3 Hz, 1H), 8.02 (d, J=0.4 Hz, 1H), 7.87 (s, 1H), 7.63-7.79 (m, 2H), 7.28-7.50 (m, 2H), 7.10-7.28 (m, 3H), 6.97 (t, J=6.9 Hz, 1H), 6.82 (s, 1H), 6.60 (d, J=5.2 Hz, 1H), 4.23 (q, J=6.7 Hz, 2H), 3.83 (s, 3H), 3.27-3.34 (m, 2H), 3.03 (s, 3H), 2.93-3.01 (m, 4H), 2.75 (t, J=6.6 Hz, 2H), 2.51-2.64 (m, 4H), 1.40 (t, J=6.8 Hz, 3H). MS (M+H, ES+) 817.

Example 213

5-(3-{2-[(5-chloro-2-(methyloxy)-4-{4-[2-(methylsulfonyl)ethyl]-1-piperazinyl}phenyl)amino]-4-pyrimidinyl}imidazo[1,2-a]pyridin-2-yl)-N-(2,6-difluorophenyl)-2-(methyloxy)benzamide

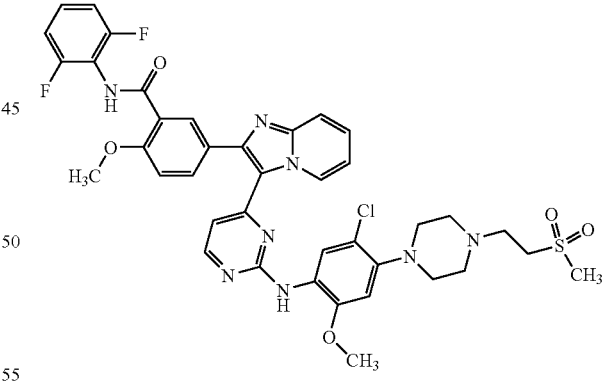

The title compound (0.16 g, 0.20 mmol, 49%) was prepared in an analogous manner to that described for Example 212, with the following notable exception in step C: 5-[3-(2-chloro-4-pyrimidinyl)imidazo[1,2-a]pyridin-2-yl]-N-(2,6-difluorophenyl)-2-(methyloxy)benzamide (Intermediate Example 2) was used instead of 5-[3-(2-chloro-4-pyrimidinyl)imidazo[1,2-a]pyridin-2-yl]-N-(2,6-difluorophenyl)-2-(ethyloxy)benzamide (Intermediate Example 6). $^1$H NMR (400 MHz, DMSO-$d_6$) δ ppm 9.75 (s, 1H), 9.38 (d, J=4.9 Hz, 1H), 8.53 (s, 1H), 8.26 (d, J=5.2 Hz, 1H), 8.08 (d, J=0.9 Hz, 1H), 7.87 (s, 1H), 7.71-7.82 (m, 1H), 7.68 (d, J=9.0 Hz, 1H), 7.29-7.48 (m, 2H), 7.25 (d, J=8.7 Hz, 1H), 7.15 (t, J=8.1 Hz, 2H), 6.97 (t, J=6.8 Hz, 1H), 6.82 (s, 1H), 6.60 (d, J=5.1 Hz, 1H), 3.95 (s, 3H), 3.83 (s, 3H), 3.23-3.32 (m, 2H), 2.90-3.10 (m, 7H), 2.75 (t, J=6.6 Hz, 2H), 2.50-2.65 (m, 4H). MS (M+H, ES+) 803.

Example 214

N-(2,6-difluorophenyl)-2-[(1-methylethyl)oxy]-5-(3-{2-[(5-methyl-2-(methyloxy)-4-{4-[2-(methylsulfonyl)ethyl]-1-piperidinyl}phenyl)amino]-4-pyrimidinyl}imidazo[1,2-a]pyridin-2-yl)benzamide

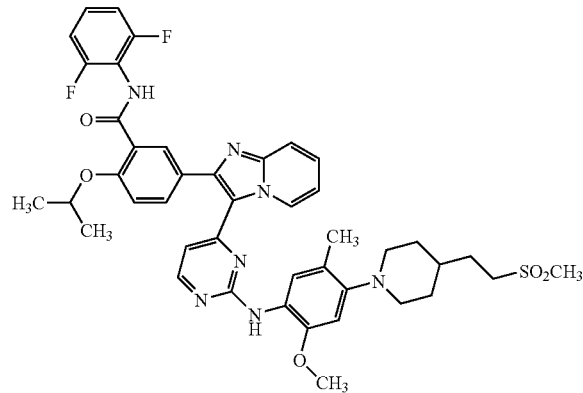

Step A: 1,1-dimethylethyl 4-[2-(methylthio)ethyl]-1-piperidinecarboxylate

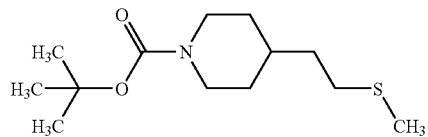

To 1,1-dimethylethyl 4-(2-iodoethyl)-1-piperidinecarboxylate (Example 101, Step A) (23.6 g, 69.5 mmol) in DMF (100 mL) was added sodium thiomethoxide (5.37 g, 76.4 mmol). The mixture was stirred at 50° C. overnight. The mixture was diluted with EtOAc, washed with H₂O (6×), dried (MgSO₄), and rotovapped down to provide the title compound of Step A (17.9 g, 68.8 mmol, 99%). $^1$H NMR (400 MHz, CDCl₃) δ 1.09 (dd, 2H), 1.44 (s, 9H), 1.53 (t, J=5.6 Hz, 3H), 1.65 (d, J=12.6 Hz, 2H), 2.08 (s, 3H), 2.51 (t, J=6.9 Hz, 2H), 2.67 (t, J=12.6 Hz, 2H), 4.06 (d, J=13.2 Hz, 2H).

Step B: 1,1-dimethylethyl 4-[2-(methylsulfonyl)ethyl]-1-piperidinecarboxylate

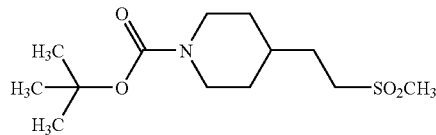

To a combined batch of (two separate reactions) 1,1-dimethylethyl 4-[2-(methylthio)ethyl]-1-piperidinecarboxylate (20.2 g, 77.9 mmol) in CH₃CN (700 mL) was added KMnO₄ (77.5 g, 491 mmol) over an hours time. The mixture was stirred at rt for approximately 4 h. The mixture was filtered through Celite® and washed with CH₃CN. Hydrazine monohydrate (12 mL) was added slowly, the solid was filtered, and the solution was rotovapped down to provide the title compound of Step B (22.2 g, 76.3 mmol, 98%). $^1$H NMR (400 MHz, CDCl₃) δ 1.11 (qd, J=12.3, 4.0 Hz, 2H), 1.42 (s, 9H), 1.47-1.60 (m, 1H), 1.64 (d, J=13.0 Hz, 2H), 1.72-1.83 (m, 2H), 2.53-2.77 (m, 2H), 2.88 (s, 3H), 2.96-3.04 (m, 2H), 3.95-4.22 (m, 2H).

Step C: 4-[2-(methylsulfonyl)ethyl]piperidine

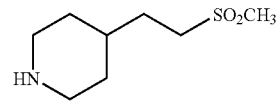

The title compound of step C (9.85 g, 51.5 mmol, 67%) was prepared from 1,1-dimethylethyl 4-[2-(methylsulfonyl)ethyl]-1-piperidinecarboxylate in an analogous manner to that of Example 89, step D. $^1$H NMR (400 MHz, CDCl₃) δ 1.18 (q, 2H), 1.45-1.60 (m, 1H), 1.68 (d, J=12.6 Hz, 2H), 1.72-1.82 (m, 2H), 2.59 (t, J=12.1 Hz, 2H), 2.88 (s, 4H), 2.99 (d, J=8.2 Hz, 1H), 3.09 (d, J=12.5 Hz, 2H).

Step D: 1-[2-methyl-5-(methyloxy)-4-nitrophenyl]-4-[2-(methylsulfonyl)ethyl]piperidine

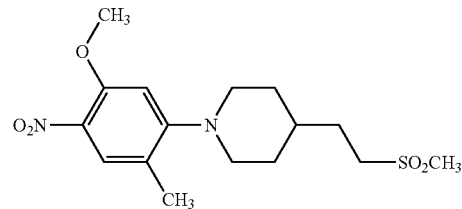

To 1-fluoro-2-methyl-5-(methyloxy)-4-nitrobenzene (Example 113, Step B) (2.02 g, 10.9 mmol) and 4-[2-(methylsulfonyl)ethyl]piperidine (2.48 g, 13.0 mmol) in DMSO (75 mL) was added K₂CO₃ (5.26 g, 38.1 mmol). The mixture was stirred at 100° C. for 2 days. The mixture was diluted with EtOAc, washed with H₂O (4×), and rotovapped down. The crude residue was taken up in DCM and dried (MgSO₄), filtered, and concentrated. Purification by flash chromatography provided the title compound of Step D (3.26 g, 9.14 mmol, 84%). $^1$H NMR (400 MHz, DMSO-d₆) δ 1.30 (q, J=11.0 Hz, 2H), 1.52 (br. s., 1H), 1.60-1.72 (m, 2H), 1.78 (d, J=12.1 Hz, 2H), 2.17 (s, 3H), 2.67 (t, J=11.6 Hz, 2H), 2.95 (s, 3H), 3.07-3.21 (m, 2H), 3.21-3.35 (m, 2H), 3.88 (s, 3H), 6.66 (s, 1H), 7.74 (s, 1H).

Step E: 5-methyl-2-(methyloxy)-4-{4-[2-(methylsulfonyl)ethyl]-1-piperidinyl}aniline

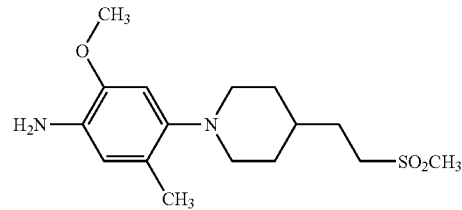

To 1-[2-methyl-5-(methyloxy)-4-nitrophenyl]-4-[2-(methylsulfonyl)ethyl]piperidine (3.26 g, 9.14 mmol) in EtOAc (100 mL) was added platinum on carbon (sulfided) (1.77 g, 0.460 mmol). The mixture was stirred under H₂ (1 atm.)

overnight. Filtering the mixture through Celite® and concentrating provided the title compound of Step E (1.77 g, 5.42 mmol, 59%). $^1$H NMR (400 MHz, DMSO-$d_6$) δ 6.55 (s, 1H), 6.43 (s, 1H), 4.29 (s, 2H), 3.71 (s, 3H), 3.10-3.19 (m, 2H), 2.97 (s, 3H), 2.88 (d, 2H), 2.51-2.58 (m, 2H), 2.06 (s, 3H), 1.61-1.79 (m, 4H), 1.19-1.52 (m, 3H).

Alternative Method for Making Aniline Described in Steps A-E.

Step F: 2-{1-[2-methyl-5-(methyloxy)-4-nitrophenyl]-4-piperidinyl}ethanol

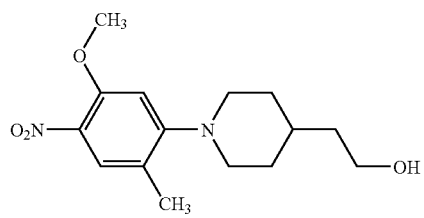

To 1-fluoro-2-methyl-5-(methyloxy)-4-nitrobenzene (Example 113, Step B) (21.5 g, 116 mmol) in DMSO (100 mL) was added 2-(4-piperidinyl)ethanol (15 g, 116 mmol) and $K_2CO_3$ (48.1 g, 348 mmol). The reaction was heated in a sealed tube at 80° C. overnight. The reaction mixture was cooled to rt and poured into $H_2O$. The resultant solid was filtered, air dried, dissolved in DCM, dried ($Na_2SO_4$), filtered, and rotovapped down to give the title compound of Step F (32.6 g, 111 mmol, 95%). $^1$H NMR (400 MHz, DMSO-$d_6$) δ 7.71 (s, 1H), 6.63 (s, 1H), 4.33 (t, J=5.0 Hz, 1H), 3.85 (s, 3H), 3.39-3.49 (m, 2H), 3.23 (d, J=12.2 Hz, 2H), 2.65 (t, J=11.3 Hz, 2H), 2.14 (s, 3H), 1.72 (d, J=11.4 Hz, 2H), 1.46-1.61 (m, 1H), 1.39 (q, J=6.6 Hz, 2H), 1.25 (qd, J=12.0, 3.4 Hz, 2H).

Step G: 4-(2-iodoethyl)-1-[2-methyl-5-(methyloxy)-4-nitrophenyl]piperidine

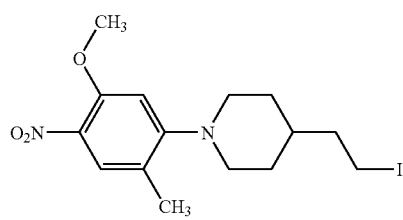

To 2-{1-[2-methyl-5-(methyloxy)-4-nitrophenyl]-4-piperidinyl}ethanol (32.6 g, 111 mmol), triphenylphosphine (32.0 g, 122 mmol), and imidazole (8.29 g, 122 mmol) in THF (554 mL) was added iodine (30.9 g, 122 mmol) in one portion, slowly due to observable exotherm. The reaction mixture was filtered through Celite® and washed with DCM. Purification by flash chromatography provided the crude title compound which was washed with saturated $Na_2SO_3$ to remove any residual iodine. The aqueous layer was back extracted with DCM. The combined organic layers were dried (MgSO$_4$), filtered, and rotovapped down to give the title compound of step G (40.6 g, 100 mmol, 91% yield). $^1$H NMR (400 MHz, DMSO-$d_6$) δ 7.74 (d, J=0.5 Hz, 1H), 6.68 (s, 1H), 3.89 (s, 3H), 3.33 (t, J=7.5 Hz, 2H), 3.26 (d, J=12.4 Hz, 2H), 2.63- 2.74 (m, 2H), 2.17 (s, 3H), 1.78 (q, J=7.1 Hz, 4H), 1.46-1.61 (m, J=7.2, 7.2, 7.1, 3.8 Hz, 1H), 1.30 (qd, J=12.0, 3.6 Hz, 2H).

Step H: 1-[2-methyl-5-(methyloxy)-4-nitrophenyl]-4-[2-(methylthio)ethyl]piperidine

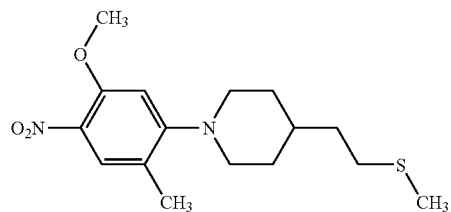

To 4-(2-iodoethyl)-1-[2-methyl-5-(methyloxy)-4-nitrophenyl]piperidine (40.6 g, 100 mmol) was added sodium thiomethoxide (7.75 g, 111 mmol) and diluted with DMF (201 mL). The reaction was stirred at 50° C. overnight. The solution was diluted with EtOAc and washed with $H_2O$. The organic layer was dried (MgSO$_4$), filtered, and rotovapped down to provide the title compound of step H (33.5 g) which was used without further purification. $^1$H NMR (400 MHz, DMSO-$d_6$) δ 7.72 (s, 1H), 6.64 (s, 1H), 3.86 (s, 3H), 3.23 (d, J=12.1 Hz, 2H), 2.60-2.72 (m, 2H), 2.46-2.52 (m, 2H), 2.14 (s, 3H), 2.01 (s, 3H), 1.75 (d, J=12.1 Hz, 2H), 1.50 (t, J=5.7 Hz, 3H), 1.16-1.35 (m, 2H).

Step I: 1-[2-methyl-5-(methyloxy)-4-nitrophenyl]-4-[2-(methylsulfonyl)ethyl]piperidine

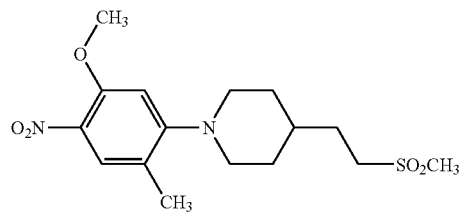

To OXONE® (155 g, 253 mmol) in $H_2O$ (425 mL) and EtOH (250 mL) at 0° C. was added 1-[2-methyl-5-(methyloxy)-4-nitrophenyl]-4-[2-(methylthio)ethyl]piperidine (32.8 g, 101 mmol) in EtOAc (250 mL) via addition funnel over the period of an hour. The reaction was warmed to rt and allowed to stir for 30 min at which time it was determined to be complete by LCMS. The reaction was diluted with $H_2O$ and EtOAc. The resultant precipitate was filtered and washed with EtOAc. The layers of the filtrate were separated and the aqueous layer was washed with EtOAc (3×). The filtered solids were dissolved with DCM and $H_2O$ and the layers were separated. The organic layer was washed with DCM (2×). The combined organic layer was dried (MgSO$_4$), filtered, and rotovapped down. The resultant solid was triturated with diethyl ether, filtered, and dried under vacuum to provide the title compound of Step I (26.1 g, 73.2 mmol, 73%). $^1$H NMR (400 MHz, DMSO-$d_6$) δ 7.74 (s, 1H), 6.67 (s, 1H), 3.88 (s, 3H), 3.27 (d, J=12.3 Hz, 2H), 3.10-3.20 (m, 2H), 2.96 (s, 3H), 2.68 (t, J=11.3 Hz, 2H), 2.17 (s, 3H), 1.79 (d, J=11.2 Hz, 2H), 1.62-1.73 (m, 2H), 1.46-1.60 (m, J=10.7, 7.0, 3.5, 3.5 Hz, 1H), 1.31 (qd, J=11.9, 3.5 Hz, 2H).

Step J: 5-methyl-2-(methyloxy)-4-{4-[2-(methylsulfonyl)ethyl]-1-piperidinyl}aniline

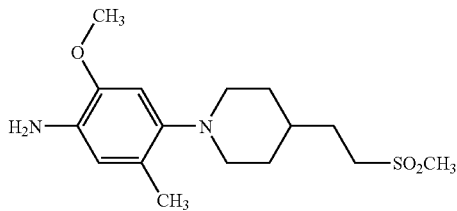

To 1-[2-methyl-5-(methyloxy)-4-nitrophenyl]-4-[2-(methylsulfonyl)ethyl]piperidine (26 g, 73 mmol) in EtOAc (1 L) and MeOH (200 mL) was added platinum on carbon (sulfided) (14 g, 73 mmol) as a slurry in EtOAc (100 mL). The mixture was stirred under $H_2$ (1 atm.) for 2 days. The catalyst was filtered off and rinsed with EtOAc, MeOH, and DCM and the filtrate was rotovapped down. The resultant solid was triturated with diethyl ether to provide the title compound of Step J (20 g, 61 mmol, 82%). $^1$H NMR (400 MHz, DMSO-$d_6$) δ 6.50 (s, 1H), 6.39 (s, 1H), 4.24 (s, 2H), 3.66 (s, 3H), 3.05-3.16 (m, 2H), 2.92 (s, 3H), 2.83 (d, 2H), 2.39-2.54 (m, 2H), 2.01 (s, 3H), 1.55-1.76 (m, 4H), 1.32-1.46 (m, J=10.6, 7.0, 3.5, 3.5 Hz, 1H), 1.24 (qd, J=11.7, 3.4 Hz, 2H).

Step K: N-(2,6-difluorophenyl)-2-[(6-methylethyl)oxy]-5-(3-{2-[(5-methyl-2-(methyloxy)-4-{4-[2-(methylsulfonyl)ethyl]-1-piperidinyl}phenyl)amino]-4-pyrimidinyl}imidazo[1,2-a]pyridin-2-yl)benzamide To 5-[3-(2-chloro-4-pyrimidinyl)imidazo[1,2-a]pyridin-2-yl]-N-(2,6-difluorophenyl)-2-[(1-methylethyl)oxy]benzamide (Intermediate Example 7) (1.72 g, 3.31 mmol) and 5-methyl-2-(methyloxy)-4-{4-[2-(methylsulfonyl)ethyl]-1-piperidinyl}aniline (1.08 g, 3.31 mmol) in 2,2,2-trifluoroethanol (20 mL) was added HCl (4M in dioxane) (1.654 mL, 6.62 mmol). The reaction was heated to 180° C. for 40 min in a microwave. The reaction was determined to be complete by HPLC. The HPLC analysis revealed that approximately 10% of the product had been converted to the phenol. The mixture was quenched with 0.5 N NaOMe (20 mL) and extracted with DCM and EtOAc. The organic was dried (MgSO$_4$), filtered, and rotovapped down. The residue was taken up in DCM (80 mL) and treated with imidazole (0.495 g, 7.28 mmol) followed by t-butyldimethylsilyl chloride (0.499 g, 3.31 mmol). The reaction was determined to be complete by HPLC analysis. Purification by flash chromatography provided the title compound 94% clean. The impure compound was taken up in DCM and treated with polystyrene bound p-toluene sulfonic acid (1.20 g, 3.31 mmol) and TEA (0.461 mL, 3.31 mmol). The reaction was determined to be complete by HPLC. The mixture was filtered and rotovapped down. The residue was taken up in EtOAc and washed with half saturated NaHCO$_3$. The organic layer was dried (MgSO$_4$), filtered, and rotovapped down. The residue was triturated with diethyl ether, filtered, and washed with diethyl ether to provide the title compound of Step K (1.61 g, 1.99 mmol, 60% yield). $^1$H NMR (400 MHz, DMSO-$d_6$) δ 9.72 (s, 1H), 9.26-9.44 (m, 1H), 8.47 (s, 1H), 8.26 (d, J=5.1 Hz, 1H), 8.08 (br. s., 1H), 7.65-7.82 (m, 2H), 7.26-7.53 (m, 4H), 7.21 (t, J=8.0 Hz, 2H), 6.97 (t, J=6.7 Hz, 1H), 6.77 (s, 1H), 6.60 (d, J=4.9 Hz, 1H), 4.89 (dt, J=11.3, 5.5 Hz, 1H), 3.81 (s, 3H), 3.12-3.24 (m, 2H), 3.07 (d, J=11.0 Hz, 2H), 2.98 (s, 3H), 2.63 (t, 2H), 2.15 (s, 3H), 1.80 (d, J=12.0 Hz, 2H), 1.65-1.76 (m, 2H), 1.51 (br. s., 1H), 1.26-1.46 (m, 8H). MS (M+H, ES+) 810.

Example 215

N-(2,6-difluorophenyl)-5-(3-{2-[(2-(ethyloxy)-5-methyl-4-{4-[2-(methylsulfonyl)ethyl]-1-piperidinyl}phenyl)amino]-4-pyrimidinyl}imidazo[1,2-a]pyridin-2-yl)-2-[(1-methylethyl)oxy]benzamide

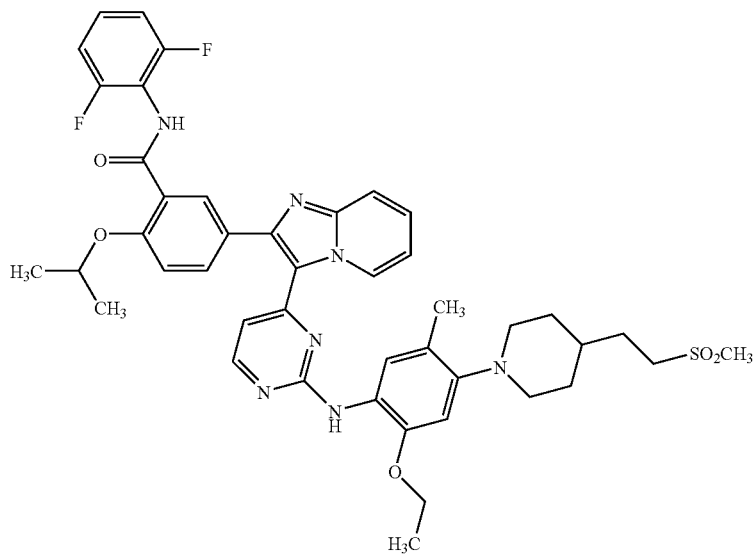

Step A:
1-methyl-2-fluoro-4-(ethyloxy)-5-nitrobenzene

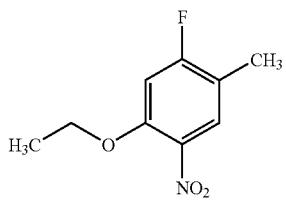

4-Methyl-5-fluoro-2-nitrophenol (11.1 g, 65.0 mmol) and iodoethane (12.2 g, 78.0 mmol) were dissolved in 100 mL of DMSO with stirring. $K_2CO_3$ (13.5 g, 97.5 mmol) was added. The reaction was stirred for 3 h and then diluted with DCM and filtered. The filtrate was poured into $H_2O$ and extracted with DCM. The combined organic layers were dried over $MgSO_4$, filtered, and concentrated in vacuo to provide the title compound of step A (8.0 g, 39.4 mmol) as a pale yellow crystalline solid. $^1$H NMR (400 MHz, CDCl$_3$) δ 7.76 (d, J=8.1 Hz, 1H), 6.70 (d, J=11.0 Hz, 1H), 4.10 (q, J=7.0 Hz, 2H), 2.22 (s, 3H), 1.45 (t, J=7.0 Hz, 3H).

Step B: 1-[5-(ethyloxy)-2-methyl-4-nitrophenyl]-4-[2-(methylsulfonyl)ethyl]piperidine

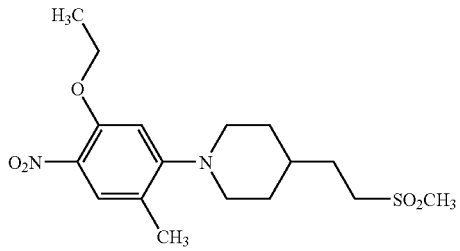

The title compound of Step B (3.0 g, 8.0 mmol, 79%) was prepared in an analogous manner to that described for the preparation of Example 214, Step D, with the following notable exception: 1-(ethyloxy)-5-fluoro-4-methyl-2-nitrobenzene (Example 215, step A) was used instead of 1-fluoro-2-methyl-5-(methyloxy)-4-nitrobenzene (Example 113, Step B). $^1$H NMR (400 MHz, DMSO-d$_6$) δ 1.22-1.39 (m, 5H), 1.52 (br. s., 1H), 1.61-1.73 (m, 2H), 1.78 (d, J=12.1 Hz, 2H), 2.16 (s, 3H), 2.65 (t, J=11.6 Hz, 2H), 2.94 (s, 3H), 3.10-3.19 (m, 2H), 3.24 (d, J=11.7 Hz, 2H), 4.16 (q, J=6.8 Hz, 2H), 6.65 (s, 1H), 7.71 (s, 1H).

Step C: 2-(ethyloxy)-5-methyl-4-{4-[2-(methylsulfonyl)ethyl]-1-piperidinyl}aniline

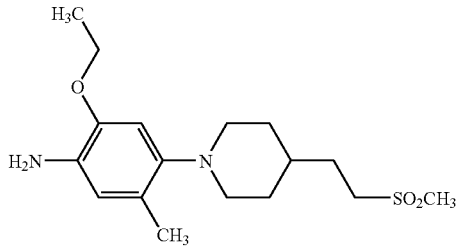

The title compound of Step C (2.59 g, 7.62 mmol, 95%) was prepared in an analogous manner to that described for the preparation of Example 214, Step E, with the following exception: 1-[5-(ethyloxy)-2-methyl-4-nitrophenyl]-4-[2-(methylsulfonyl)ethyl]piperidine was used instead of 1-[2-methyl-5-(methyloxy)-4-nitrophenyl]-4-[2-(methylsulfonyl)ethyl]piperidine (Example 214, Step E). $^1$H NMR (400 MHz, DMSO-d$_6$) δ 1.18-1.25 (m, 2H), 1.27 (t, J=6.9 Hz, 4H), 1.33-1.48 (m, 1H), 1.57-1.67 (m, 2H), 1.70 (d, J=11.9 Hz, 2H), 2.02 (s, 3H), 2.44 (br. s., 1H), 2.49 (br. s., 1H), 2.84 (d, J=11.4 Hz, 2H), 2.94 (s, 3H), 3.07-3.18 (m, 2H), 3.91 (q, J=6.9 Hz, 2H), 4.24 (s, 2H), 6.41 (s, 1H), 6.50 (s, 1H).

Step D: N-(2,6-difluorophenyl)-5-(3-{2-[(2-(ethyloxy)-5-methyl-4-{4-[2-(methylsulfonyl)ethyl]-1-piperidinyl}phenyl)amino]-4-pyrimidinyl}imidazo[1,2-a]pyridin-2-yl)-2-[(1-methylethyl)oxy]benzamide To 5-[3-(2-chloro-4-pyrimidinyl)imidazo[1,2-a]pyridin-2-yl]-N-(2,6-difluorophenyl)-2-[(1-methylethyl)oxy]benzamide (Intermediate Example 7) (0.13 g, 0.25 mmol) and 2-(ethyloxy)-5-methyl-4-{4-[2-(methylsulfonyl)ethyl]-1-piperidinyl}aniline (0.087 g, 0.25 mmol) in 2,2,2-trifluoroethanol (1.5 mL) was added HCl (4M in dioxane) (0.13 mL, 0.50 mmol). The reaction was heated to 180° C. for 40 min in a microwave. The reaction was determined to be complete by HPLC. The reaction mixture was quenched with saturated NaHCO$_3$ and sequentially extracted with DCM and EtOAc. The organic layer was dried (MgSO$_4$), filtered, and rotovapped down. Purification by flash chromatography provided the title compound (0.05 g, 0.06 mmol, 24%). $^1$H NMR (400 MHz, DMSO-d$_6$) δ 9.72 (s, 1H), 9.36 (d, J=5.9 Hz, 1H), 8.37 (s, 1H), 8.28 (d, J=4.9 Hz, 1H), 8.09 (br. s., 1H), 7.74 (dd, J=14.1, 8.9 Hz, 2H), 7.56 (s, 1H), 7.27-7.52 (m, 3H), 7.21 (t, J=7.9 Hz, 2H), 6.96 (t, J=6.6 Hz, 1H), 6.75 (s, 1H), 6.63 (d, J=4.8 Hz, 1H), 4.79-4.97 (m, 1H), 4.07 (q, J=6.7 Hz, 2H), 3.12-3.24 (m, 2H), 3.05 (d, J=11.1 Hz, 2H), 2.98 (s, 3H), 2.61 (t, 2H), 2.14 (s, 3H), 1.62-1.87 (m, 4H), 1.17-1.59 (m, 12H). MS (M+H, ES+) 824.

Example 216

N-(2,6-difluorophenyl)-5-(7-fluoro-3-{2-[(2-(methyloxy)-4-{4-[2-(methylsulfonyl)ethyl]-1-piperidinyl}phenyl)amino]-4-pyrimidinyl}imidazo[1,2-a]pyridin-2-yl)-2-(methyloxy)benzamide

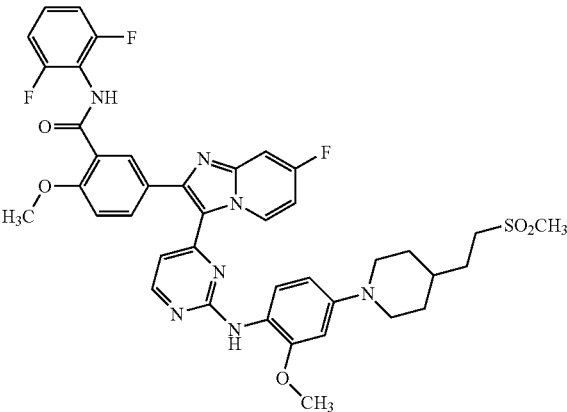

To 5-[3-(2-chloro-4-pyrimidinyl)-7-fluoroimidazo[1,2-a]pyridin-2-yl]-N-(2,6-difluoro-phenyl)-2-(methyloxy)benzamide (Example 197, step A) (126 mg, 0.25 mmol) and 2-(methyloxy)-4-{4-[2-(methylsulfonyl)ethyl]-1-piperidinyl}aniline (Example 200, step B) (70 mg, 0.22 mmol) in 2,2,2-trifluoroethanol (1.0 mL) was added 4 M HCl in dioxane (112 μL, 0.45 mmol). The mixture was stirred and heated on a microwave at 170° C. for 45 min, then cooled to rt. The mixture was neutralized with 0.5M sodium methoxide in MeOH. The mixture was concentrated under vacuum and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (135 mg, 0.17 mmol, 77%) as a yellow solid. ¹H NMR (400 MHz, DMSO-d₆): 6 ppm 9.80 (s, 1H), 9.40-9.53 (m, 1H), 8.50 (s, 1H), 8.21 (d, J=5.1 Hz, 1H), 8.11 (d, J=1.3 Hz, 1H), 7.79 (d, J=8.4 Hz, 1H), 7.59 (dd, J=9.5, 2.4 Hz, 1H), 7.33-7.46 (m, 2H), 7.30 (d, J=8.6 Hz, 1H), 7.20 (t, J=8.1 Hz, 2H), 6.97-7.07 (m, 1H), 6.70 (d, J=1.6 Hz, 1H), 6.45-6.58 (m, 2H), 4.00 (s, 3H), 3.81 (s, 3H), 3.70-3.75 (m, 2H), 3.14-3.22 (m, 2H), 2.97 (s, 3H), 2.64 (t, J=11.4 Hz, 2H), 1.74-1.85 (m, 2H), 1.62-1.72 (m, 2H), 1.46-1.58 (m, 1H), 1.21-1.37 (m, 2H). MS (ESI): 785 [M+H]⁺.

Example 217

N-(2,6-difluorophenyl)-2-(ethyloxy)-5-(3-{2-[(2-(ethyloxy)-5-methyl-4-{4-[2-(methylsulfonyl)ethyl]-1-piperidinyl}phenyl)amino]-4-pyrimidinyl}imidazo[1,2-a]pyridin-2-yl)benzamide

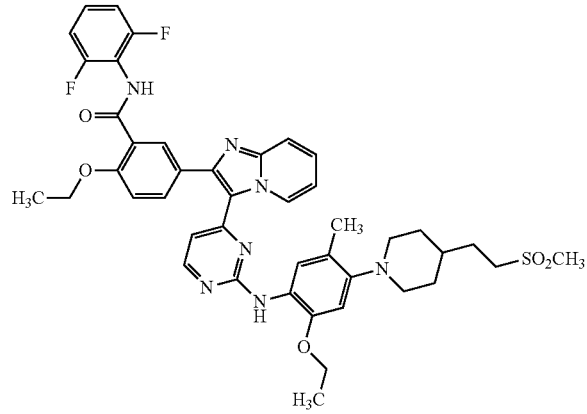

The title compound (0.08 g, 0.1 mmol, 39%) was prepared in an analogous manner to that described for the preparation of Example 215, with the following notable exception: 5-[3-(2-chloro-4-pyrimidinyl)imidazo[1,2-a]pyridin-2-yl]-N-(2,6-difluorophenyl)-2-(ethyloxy)benzamide (Intermediate Example 6) was used instead of 5-[3-(2-chloro-4-pyrimidinyl)imidazo[1,2-a]pyridin-2-yl]-N-(2,6-difluorophenyl)-2-[(1-methylethyl)oxy]benzamide (Intermediate Example 7) in step D. ¹H NMR (400 MHz, DMSO-d₆) δ 9.76 (s, 1H), 9.37 (d, J=5.8 Hz, 1H), 8.37 (s, 1H), 8.27 (d, J=5.0 Hz, 1H), 8.07 (br. s., 1H), 7.74 (dd, J=16.4, 8.7 Hz, 2H), 7.56 (s, 1H), 7.33-7.53 (m, 2H), 7.11-7.33 (m, 3H), 6.96 (t, J=6.6 Hz, 1H), 6.75 (s, 1H), 6.59 (d, J=4.9 Hz, 1H), 4.28 (d, J=6.6 Hz, 2H), 4.07 (q, J=6.7 Hz, 2H), 3.12-3.25 (m, 2H), 2.94-3.12 (m, 5H), 2.61 (t, 2H), 2.15 (s, 3H), 1.63-1.87 (m, 4H), 1.19-1.58 (m, 9H). MS (M+H, ES+) 810.

Example 218

N-(2,6-difluorophenyl)-5-(3-{2-[(2-(ethyloxy)-5-methyl-4-{4-[2-(methylsulfonyl)ethyl]-1-piperidinyl}phenyl)amino]-4-pyrimidinyl}-7-fluoroimidazo[1,2-a]pyridin-2-yl)-2-(methyloxy)benzamide

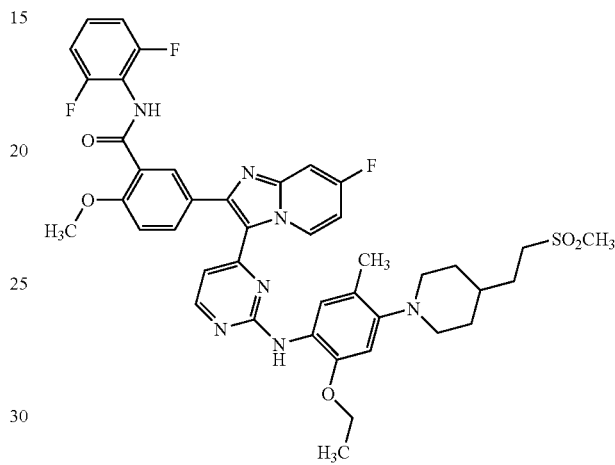

To 5-[3-(2-chloro-4-pyrimidinyl)-7-fluoroimidazo[1,2-a]pyridin-2-yl]-N-(2,6-difluoro-phenyl)-2-(methyloxy)benzamide (Example 197, step A) (132 mg, 0.26 mmol) and 2-(ethyloxy)-5-methyl-4-{4-[2-(methylsulfonyl)ethyl]-1-piperidinyl}aniline (Example 215, step C) (80 mg, 0.24 mmol) in 2,2,2-trifluoroethanol (1.0 mL) was added 4 M HCl in dioxane (120 μL, 0.47 mmol). The mixture was stirred and heated on a microwave at 170° C. for 45 min, then cooled to rt. The mixture was neutralized with 0.5M sodium methoxide in MeOH. The mixture was concentrated under vacuum, and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (139 mg, 0.17 mmol, 73%) as a yellow solid. ¹H NMR (400 MHz, DMSO-d₆): 6 ppm 9.79 (s, 1H), 9.39-9.48 (m, 1H), 8.41 (s, 1H), 8.27 (d, J=5.1 Hz, 1H), 8.12 (d, J=1.8 Hz, 1H), 7.79 (dd, J=8.5, 1.7 Hz, 1H), 7.61 (dd, J=9.6, 2.5 Hz, 1H), 7.53 (s, 1H), 7.35-7.44 (m, 1H), 7.29 (d, J=8.6 Hz, 1H), 7.17-7.23 (m, 2H), 6.99-7.04 (m, 1H), 6.76 (s, 1H), 6.59 (d, J=5.1 Hz, 1H), 4.07 (q, J=7.0 Hz, 2H), 4.00 (s, 3H), 3.14-3.22 (m, 2H), 3.03-3.10 (m, 2H), 2.98 (s, 3H), 2.61 (t, J=10.9 Hz, 2H), 2.15 (s, 3H), 1.77-1.84 (m, 2H), 1.67-1.73 (m, 2H), 1.45-1.54 (m, 1H), 1.30-1.41 (m, 2H), 1.23-1.28 (m, 3H). MS (ESI): 813 [M+H]⁺.

Example 219

N-(2,6-difluorophenyl)-5-(3-{2-[(2-(ethyloxy)-5-methyl-4-{4-[2-(methylsulfonyl)ethyl]-1-piperidinyl}phenyl)amino]-4-pyrimidinyl}imidazo[1,2-a]pyridin-2-yl)-2-(methyloxy)benzamide

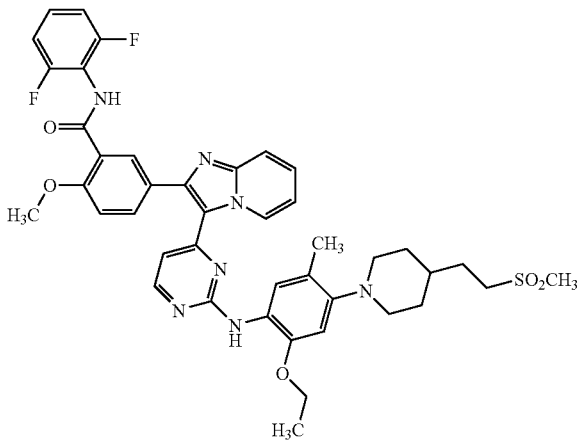

Step A: 1,1-dimethylethyl 4-(2-hydroxyethyl)-1-piperidinecarboxylate

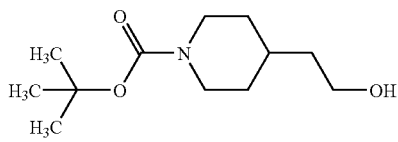

The reaction was prepared in 2 batches, with both batches purified together. The amounts of reactants and product reflect the sum of both batches. To 2-(4-piperidinyl)ethanol (175 g, 1.35 mol) in THF and NaOH (1N, 1.6 L) at 0° C. was added di-t-butyl dicarbonate (310 g, 1.42 mol) dropwise. The solution was stirred at rt overnight. The reaction was diluted with EtOAc, the aqueous layer was separated. The organic layer was dried ($Na_2SO_4$) and rotovapped down to provide the title compound of Step A (344 g). The compound was used without further purification. $^1$H NMR (400 MHz, $CDCl_3$) δ 0.95-1.12 (m, 2H), 1.38 (s, 9H), 1.40-1.55 (m, 4H), 2.10-2.16 (m, 1H), 2.55-2.70 (m, 2H), 3.55-3.68 (m, 2H), 3.92-4.08 (m, 2H).

Step B: 1,1-dimethylethyl 4-{2-[(methylsulfonyl)oxy]ethyl}-1-piperidinecarboxylate

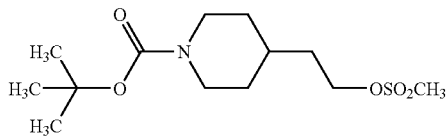

The reaction was prepared in 2 batches, with both batches purified together. The amounts of reactants and product reflect the sum of both batches. To 1,1-dimethylethyl 4-(2-hydroxyethyl)-1-piperidinecarboxylate (172 g, 750 mmol) in DCM (4 L) was added TEA (304 g, 1.50 mol). The mixture was cooled 0° C. and methanesulfonyl chloride (190 g, 827 mmol) was added dropwise. The reaction mixture was stirred at rt for 2 h. The reaction was determined to be complete by TLC. The reaction was diluted with DCM and washed with saturated $Na_2CO_3$ and the aqueous layer was separated. The organic layer was dried ($Na_2SO_4$), and rotovapped down to provide the title compound of Step B (280 g, 911 mmol, 61%). $^1$H NMR (400 MHz, $CDCl_3$) δ 0.95-1.15 (m, 2H), 1.38 (s, 9H), 1.47-1.68 (m, 5H), 2.53-2.70 (m, 2H), 2.94 (s, 3H), 3.95-4.10 (m, 2H), 4.21 (t, J=8.8 Hz, 2H).

Step C: 1,1-dimethylethyl 4-[2-(methylthio)ethyl]-1-piperidinecarboxylate

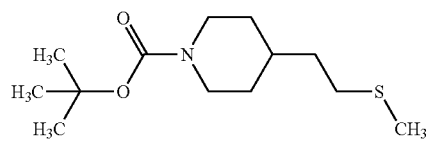

The title compound of Step C (280 g, crude used without further purification) was prepared in an analogous manner to that described for the preparation of Example 214, Step A, with the following exception: 1,1-dimethylethyl 4-{2-[(methylsulfonyl)oxy]ethyl}-1-piperidinecarboxylate (Example 219, Step B) was used instead of 1,1-dimethylethyl 4-(2-iodoethyl)-1-piperidinecarboxylate (Example 101, Step A). $^1$H NMR (400 MHz, $CDCl_3$) δ 0.95-1.10 (m, 2H), 1.38 (s, 9H), 1.41-1.52 (m, 3H), 1.57-1.67 (m, 2H), 2.00 (s, 3H), 2.39-2.54 (m, 2H), 3.95-4.09 (m, 2H).

Step D: 1,1-dimethylethyl 4-[2-(methylsulfonyl)ethyl]-1-piperidinecarboxylate

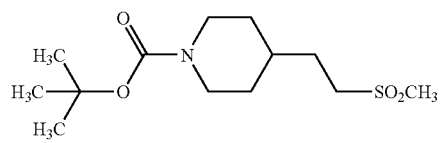

The title compound of Step D (240 g, 824 mmol, 83%) was prepared in an analogous manner to that described for the preparation of Example 214, Step B. $^1$H NMR (400 MHz, $CDCl_3$) δ 1.05-1.18 (m, 2H), 1.40 (s, 9H), 1.50-1.70 (m, 3H), 1.72-1.85 (m, 2H), 2.60-2.71 (m, 2H), 3.85 (s, 3H), 3.00-3.10 (m, 2H), 4.01-4.19 (m, 2H).

Step E: 4-[2-(methylsulfonyl)ethyl]piperidine hydrochloride

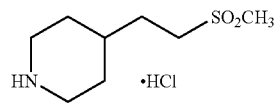

To 1,1-dimethylethyl 4-[2-(methylsulfonyl)ethyl]-1-piperidinecarboxylate (240 g, 824 mmol) in MeOH at 0° C. was added saturated HCl in MeOH slowly. The suspension was stirred at rt overnight. The mixture was washed with MeOH then dried by vacuum to provide the title compound of Step E (135 g, 593 mmol, 72%). $^1$H NMR (400 MHz, DMSO-$d_6$) δ 1.25-1.40 (m, 2H), 1.52-1.65 (m, 3H), 1.70-1.80 (m, 2H), 2.68-2.83 (m, 2H), 2.79 (s, 3H), 3.07-3.20 (m, 4H).

Step F: 1-[5-(ethyloxy)-2-methyl-4-nitrophenyl]-4-[2-(methylsulfonyl)ethyl]piperidine

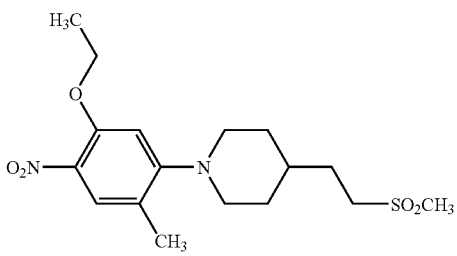

To 1-(ethyloxy)-5-fluoro-4-methyl-2-nitrobenzene (Example 215, step A) (13.1 g, 65.9 mmol), 4-[2-(methylsulfonyl)ethyl]piperidine hydrochloride (15.0 g, 65.9 mmol) and K$_2$CO$_3$ (31.9 g, 231 mmol) was added DMSO (300 mL). The reaction mixture was heated at 100° C. overnight. The reaction was cooled to rt and diluted with EtOAc and DCM. The organic layer was washed with H$_2$O and the aqueous layer was backextracted with DCM. The combined organic layers were dried (MgSO$_4$), filtered and rotovapped down. Purification by flash chromatography provided the title compound of Step F (16.2 g, 43.6 mmol, 66% yield). This reaction was carried out in duplicate to provide an overall amount of 33.2 g, 89.4 mmol of the title compound of Step F. $^1$H NMR (400 MHz, DMSO-d$_6$) δ 7.79 (s, 1H), 6.56-6.73 (m, 1H), 4.16 (q, J=7.0 Hz, 2H), 3.30 (d, J=12.2 Hz, 2H), 3.04-3.15 (m, 2H), 2.95 (s, 3H), 2.74 (t, J=11.5 Hz, 2H), 2.26 (s, 3H), 1.81-1.97 (m, 4H), 1.42-1.74 (m, 6H).

Step G: 2-(ethyloxy)-5-methyl-4-{4-[2-(methylsulfonyl)ethyl]-1-piperidinyl}aniline

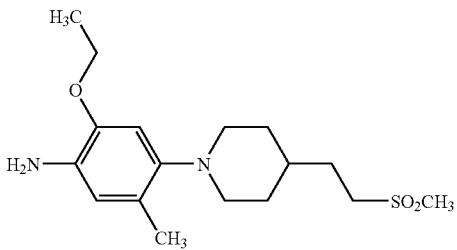

To 1-[5-(ethyloxy)-2-methyl-4-nitrophenyl]-4-[2-(methylsulfonyl)ethyl]piperidine (33.1 g, 89.0 mmol) in EtOAc (800 mL) and MeOH (200 mL) was added platinum on carbon (sulfided) (17.5 g, 4.47 mmol). The mixture was stirred under H$_2$ (1 atm.) over the weekend. The mixture was filtered through Celite®, washed with DCM, and rotovapped down. The resultant solid was triturated with diethyl ether to provide the title compound of Step G (27.3 g, 80 mmol, 90% yield). $^1$H NMR (400 MHz, DMSO-d$_6$) δ 6.54 (s, 1H), 6.44 (s, 1H), 4.28 (s, 2H), 3.94 (q, J=6.9 Hz, 2H), 3.11-3.22 (m, 2H), 2.97 (s, 3H), 2.87 (d, J=11.5 Hz, 2H), 2.44-2.56 (m, 2H), 2.06 (s, 3H), 1.59-1.80 (m, 4H), 1.43 (ddd, J=14.2, 7.0, 3.5 Hz, 1H), 1.21-1.36 (m, 5H).

Step H: N-(2,6-difluorophenyl)-5-(3-{2-[(2-(ethyloxy)-5-methyl-4-{4-[2-(methylsulfonyl)ethyl]-1-piperidinyl}phenyl)amino]-4-pyrimidinyl}imidazo[1,2-a]pyridin-2-yl)-2-(methyloxy)benzamide To 5-[3-(2-chloro-4-pyrimidinyl)imidazo[1,2-a]pyridin-2-yl]-N-(2,6-difluorophenyl)-2-(methyloxy)benzamide (Intermediate Example 2) (19.7 g, 39.9 mmol) and 2-(ethyloxy)-5-methyl-4-{4-[2-(methylsulfonyl)ethyl]-1-piperidinyl}aniline (13.6 g, 39.9 mmol) in 2,2,2-trifluoroethanol (200 mL) was added HCl (4M in dioxane) (19.97 mL, 80 mmol). The reaction mixture was heated at 85° C. for 2 days. The reaction was determined to be complete by LCMS. The reaction was cooled and quenched with solid NaOMe. The suspension was concentrated. Purification by flash chromatography, followed by trituration with EtOH provided the title compound of Step H (18.1 g, 22.7 mmol, 57% yield). Alternatively, this reaction can be effected using microwave irradiation. Additionally, further purification of the title compound can be effected by recrystallization from equal parts DCM and EtOH. $^1$H NMR (400 MHz, DMSO-d$_6$) δ 9.80 (s, 1H), 9.37 (d, J=6.0 Hz, 1H), 8.38 (s, 1H), 8.27 (d, J=5.1 Hz, 1H), 8.12 (s, 1H), 7.64-7.83 (m, 2H), 7.55 (s, 1H), 7.35-7.52 (m, 2H), 7.29 (d, J=8.6 Hz, 1H), 7.20 (t, J=8.0 Hz, 2H), 6.96 (t, J=6.6 Hz, 1H), 6.75 (s, 1H), 6.59 (d, J=5.0 Hz, 1H), 3.92-4.15 (m, 5H), 3.11-3.27 (m, 2H), 2.91-3.11 (m, 5H), 2.61 (t, 2H), 2.15 (s, 3H), 1.62-1.87 (m, 4H), 1.42-1.57 (m, 1H), 1.21-1.42 (m, 5H). MS (M+H, ES+) 796.

Example 220

N-(2,6-difluorophenyl)-5-(7-fluoro-3-{2-[(5-methyl-2-(methyloxy)-4-{4-[2-(methylsulfonyl)ethyl]-1-piperidinyl}phenyl)amino]-4-pyrimidinyl}imidazo[1,2-a]pyridin-2-yl)-2-(methyloxy)benzamide

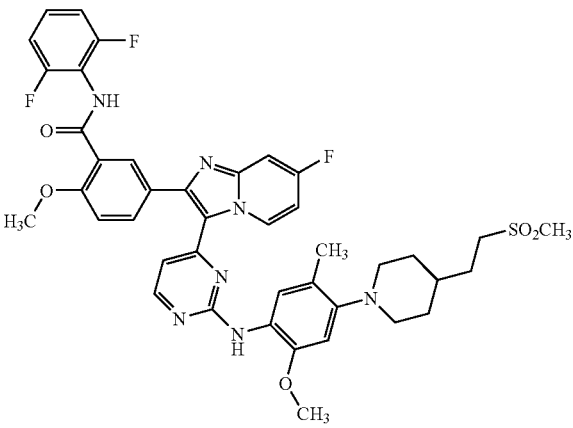

To 5-[3-(2-chloro-4-pyrimidinyl)-7-fluoroimidazo[1,2-a]pyridin-2-yl]-N-(2,6-difluoro-phenyl)-2-(methyloxy)benzamide (Example 197, step A) (137 mg, 0.27 mmol) and 5-methyl-2-(methyloxy)-4-{4-[2-(methylsulfonyl)ethyl]-1-piperidinyl}aniline (Example 214, step E) (80 mg, 0.25 mmol) in 2,2,2-trifluoroethanol (1.0 mL) was added 4 M HCl in dioxane (120 μL, 0.47 mmol). The mixture was stirred and heated on a microwave at 175° C. for 40 min, then cooled to rt. The mixture was neutralized with 0.5M sodium methoxide in MeOH. The mixture was concentrated under vacuum, and the residue purified by silica gel chromatography to give a yellow oil. The oil was dissolved in minimal DCM, then hexane was added until a precipitate was formed. The slurry was cooled at −10° C. for 30 min, then poured through a Teflon filter, washing the solids with cold hexanes. The solids were dried under vacuum to give the title compound (83 mg, 0.10 mmol, 42%) as a yellow solid. $^1$H NMR (400 MHz, DMSO-d$_6$): δ ppm 9.80 (s, 1H), 9.41-9.51 (m, 1H), 8.51 (s, 1H), 8.25 (d, J=5.3 Hz, 1H), 8.11 (d, J=1.6 Hz, 1H), 7.79 (dd, J=8.6, 1.8 Hz, 1H), 7.61 (dd, J=9.5, 2.6 Hz, 1H), 7.48 (s, 1H), 7.36-7.46 (m, 1H), 7.30 (d, J=8.8 Hz, 1H), 7.16-7.25 (m, 2H), 6.98-7.06 (m, 1H), 6.78 (s, 1H), 6.56 (d, J=5.1 Hz, 1H), 4.00 (s, 3H), 3.81 (s, 3H), 3.14-3.22 (m, 2H), 3.03-3.12 (m, 2H), 2.98 (s, 3H), 2.58-2.69 (m, 2H), 2.15 (s, 3H), 1.77-1.85 (m, 2H), 1.66-1.77 (m, 2H), 1.45-1.56 (m, 1H), 1.28-1.42 (m, 2H). MS (ESI): 799 [M+H]+.

Example 221

N-(2,6-difluorophenyl)-3-(3-{2-[(2-(ethyloxy)-5-methyl-4-{4-[2-(methylsulfonyl)ethyl]-1-piperidinyl}phenyl)amino]-4-pyrimidinyl}imidazo[1,2-a]pyridin-2-yl)benzamide

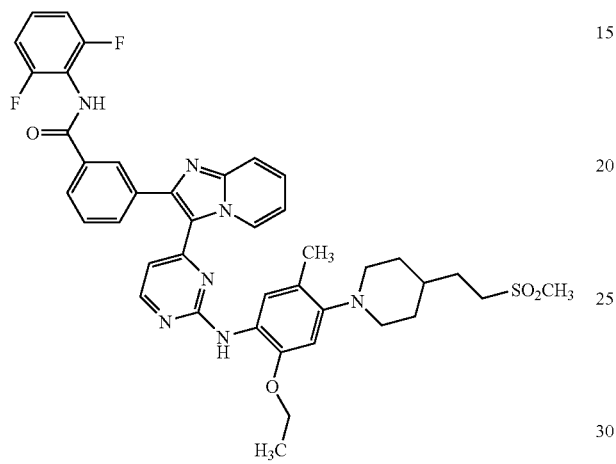

The title compound (0.10 g, 0.13 mmol, 51%) was prepared in an analogous manner to that described for the preparation of Example 215, with the following notable exception: 3-[3-(2-chloro-4-pyrimidinyl)imidazo[1,2-a]pyridin-2-yl]-N-(2,6-difluorophenyl)benzamide (Intermediate Example 1) was used instead of 5-[3-(2-chloro-4-pyrimidinyl)-imidazo[1,2-a]pyridin-2-yl]-N-(2,6-difluorophenyl)-2-[(1-methylethyl)oxy]benzamide (Intermediate Example 7) in step D. $^1$H NMR (400 MHz, DMSO-$d_6$) δ 10.25 (s, 1H), 9.41 (d, J=6.4 Hz, 1H), 8.19-8.50 (m, 3H), 8.06 (d, J=7.7 Hz, 1H), 7.69-7.93 (m, 2H), 7.33-7.69 (m, 4H), 7.22 (t, J=8.1 Hz, 2H), 7.00 (t, J=6.7 Hz, 1H), 6.75 (s, 1H), 6.53 (d, J=5.1 Hz, 1H), 4.07 (q, J=6.8 Hz, 2H), 3.12-3.26 (m, 2H), 2.93-3.12 (m, 5H), 2.61 (t, 2H), 2.14 (s, 3H), 1.61-1.91 (m, 4H), 1.18-1.61 (m, 6H). MS (M+H, ES+) 766.

Example 222

N-(2,6-difluorophenyl)-2-(ethyloxy)-5-(3-{2-[(2-(ethyloxy)-4-{4-[4-(methylsulfonyl)-1-piperazinyl]-1-piperidinyl}phenyl)amino]-4-pyrimidinyl}imidazo[1,2-a]pyridin-2-yl)benzamide

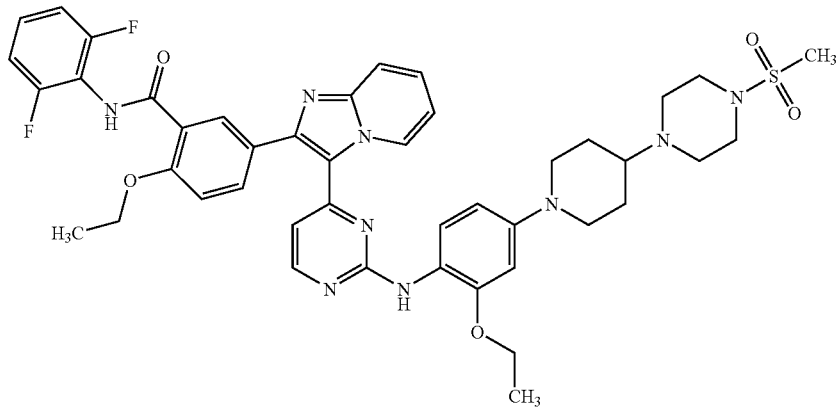

Step A: 1-[3-(ethyloxy)-4-nitrophenyl]-4-piperidinol

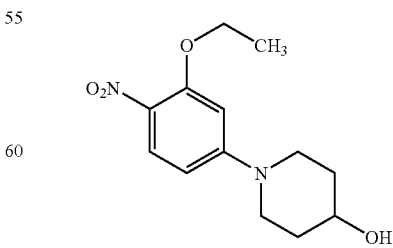

The title compound of Step A was prepared in an analogous manner to that described for Example 22, step B, with the following notable exceptions:

a) 2-(ethyloxy)-4-fluoro-1-nitrobenzene (Example 116, Step A) was used instead of 4-fluoro-2-(methyloxy)-1-nitrobenzene;
b) 4-piperidinol was used instead of 1,4'-bipiperidine.

$^1$H NMR (400 MHz, DMSO-d$_6$) δ1.49 (t, J=7.53 Hz, 3H), 1.60-1.71 (m, 2H), 1.95-2.05 (m, 2H), 3.13-3.23 (m, 2H), 3.67-3.77 (m, 2H), 3.90-4.02 (m, 1H), 4.15 (q, 2H), 6.32 (d, J=2.26, 1H), 6.43 (dd, J=8.87 Hz, J=2.26 Hz, 1H), 7.95 (d, J=2.26 Hz, 1H).

Step B:
1-[3-(ethyloxy)-4-nitrophenyl]-4-piperidinone

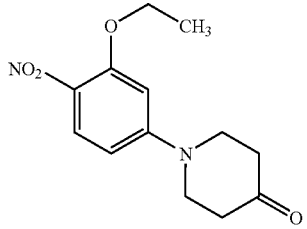

To a stirring solution of 1-[3-(ethyloxy)-4-nitrophenyl]-4-piperidinol (4.00 g, 15.0 mmol) in DCM (150 mL) was sequentially added solid NaHCO$_3$ (6.31 g, 75.1 mmol), Dess-Martin Periodane (7.65 g, 18.0 mmol) and H$_2$O (0.27 mL, 15.0 mmol). The reaction was then vigorously stirred at rt for 1 h. The reaction was quenched with equal volumes of saturated sodium thiosulfate (aq) and saturated NaHCO$_3$ (aq) and allowed to stir for an additional 0.5 h. The layers were separated and the aqueous layer was extracted with DCM. The combined organic layers were then dried, filtered and concentrated in vacuo. The residue was purified by flash chromatography to afford 1-[3-(ethyloxy)-4-nitrophenyl]-4-piperidinone (2.15 g, 54%) as a yellow solid. $^1$H NMR (400 MHz, DMSO-d$_6$) δ ppm 7.91 (d, J=9.3 Hz, 1H), 6.61 (dd, J=9.4, 2.6 Hz, 1H), 6.53 (d, J=2.5 Hz, 1H), 4.21 (q, J=7.0 Hz, 2H), 3.81 (t, J=6.1 Hz, 4H), 2.46-2.53 (m, 4H), 1.36 (t, J=7.0 Hz, 3H).

Step C: 1-{1-[3-(ethyloxy)-4-nitrophenyl]-4-piperidinyl}-4-(methylsulfonyl)piperazine

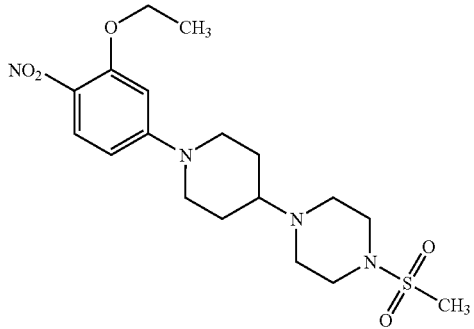

Sodiumtriacetoxyborohydride (2.59 g, 12.2 mmol) was added to a stirring suspension of 1-[3-(ethyloxy)-4-nitrophenyl]-4-piperidinone (2.15 g, 8.14 mmol), 1-(methylsulfonyl)piperazine (2.67 g, 16.3 mmol), acetic acid (0.70 mL, 12.2 mmol), and TEA (1.13 mL, 8.14 mmol) in 1,2-DCE (100 mL). The reaction was stirred at rt overnight then poured into saturated NaHCO$_3$ (aq). The layers were separated and the aqueous layer was extracted with DCM. The combined organic layers were then dried, filtered and concentrated in vacuo. The residue was purified by flash chromatography to afford 1-{1-[3-(ethyloxy)-4-nitrophenyl]-4-piperidinyl}-4-(methylsulfonyl)piperazine (1.50 g, 45%). $^1$H NMR (400 MHz, DMSO-d$_6$) δ ppm 7.86 (d, J=9.4 Hz, 1H), 6.58 (dd, J=9.5, 2.4 Hz, 1H), 6.50 (d, J=2.5 Hz, 1H), 4.18 (q, J=7.0 Hz, 2H), 3.99-4.08 (m, 2H), 3.04-3.12 (m, 4H), 2.90-2.99 (m, 2H), 2.86 (s, 3H), 2.55-2.61 (m, 4H), 1.77-1.88 (m, 2H), 1.39-1.50 (m, 2H), 1.35 (t, J=6.9 Hz, 3H).

Step D: 2-(ethyloxy)-4-{4-[4-(methylsulfonyl)-1-piperazinyl]-1-piperidinyl}aniline

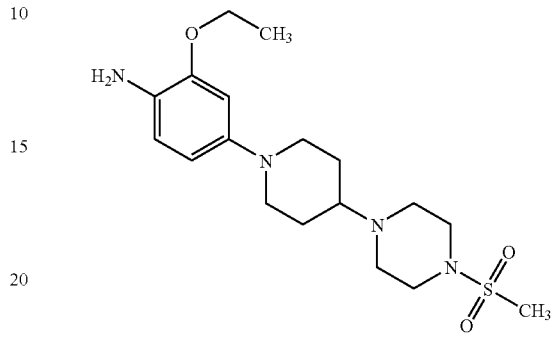

Sodium borohydride (0.41 g, 10.9 mmol) was added in portions to a stirring suspension of 1-{1-[3-(ethyloxy)-4-nitrophenyl]-4-piperidinyl}-4-(methylsulfonyl)piperazine (1.50 g, 3.64 mmol) and NiCl$_2$.6H$_2$O (0.26 g, 1.1 mmol) in THF (15 mL) and MeOH (30 mL) at rt. The reaction mixture was allowed to stir at rt overnight and then it was concentrated in vacuo. The residue was taken up in DCM and passed through a bed of celite. The resultant filtrate was then concentrated onto silica gel and purified by flash chromatography to afford 2-(ethyloxy)-4-{4-[4-(methylsulfonyl)-1-piperazinyl]-1-piperidinyl}aniline (0.40 g, 30%). $^1$H NMR (400 MHz, DMSO-d$_6$) δ ppm 6.42-6.56 (m, 2H), 6.29 (dd, J=8.4, 2.3 Hz, 1H), 4.21 (br. s., 2H), 3.96 (q, J=6.9 Hz, 2H), 3.37-3.48 (m, 2H), 3.05-3.12 (m, 4H), 2.86 (s, 3H), 2.56-2.63 (m, 4H), 2.26-2.37 (m, 1H), 1.75-1.85 (m, 2H), 1.42-1.61 (m, 2H), 1.31 (t, J=7.0 Hz, 3H).

Step E: N-(2,6-difluorophenyl)-2-(ethyloxy)-5-(3-{2-[(2-(ethyloxy)-4-{4-[4-(methylsulfonyl)-1-piperazinyl]-1-piperidinyl}phenyl)amino]-4-pyrimidinyl}imidazo[1,2-a]pyridin-2-yl)benzamide A mixture of 5-[3-(2-chloro-4-pyrimidinyl)imidazo[1,2-a]pyridin-2-yl]-N-(2,6-difluorophenyl)-2-(ethyloxy)benzamide (Intermediate Example 6) (0.10 g, 0.20 mmol), 2-(ethyloxy)-4-{4-[4-(methylsulfonyl)-1-piperazinyl]-1-piperidinyl}aniline (0.076 g, 0.20 mmol) and para-toluenesulfonic acid (0.090 g, 0.47 mmol) in i-PrOH (5 mL) was heated in a microwave at 175° C. for 25 min. The reaction mixture was concentrated onto silica gel and purified by flash chromatography. Recrystallization from DCM and diethyl ether afforded N-(2,6-difluorophenyl)-2-(ethyloxy)-5-(3-{2-[(2-(ethyloxy)-4-{4-[4-(methylsulfonyl)-1-piperazinyl]-1-piperidinyl}phenyl)amino]-4-pyrimidinyl}imidazo[1,2-a]pyridin-2-yl)benzamide (0.072 g, 43%) as a yellow solid. $^1$H NMR (400 MHz, DMSO-d$_6$) δ ppm 9.76 (s, 1H), 9.35 (br. s., 1H), 8.36 (s, 1H), 8.24 (d, J=5.2 Hz, 1H), 8.06 (d, J=1.7 Hz, 1H), 7.66-7.81 (m, 2H), 7.35-7.48 (m, 3H), 7.15-7.32 (m, 3H), 6.89-7.01 (m, 1H), 6.67 (d, J=2.3 Hz, 1H), 6.54-6.60 (m, 1H), 6.44-6.53 (m, 1H), 4.23-4.33 (m, 2H), 4.07 (q, J=6.9 Hz, 2H), 3.66-3.80 (m, 2H), 3.05-3.13 (m, 4H), 2.87 (s, 3H), 2.56-2.73 (m, 5H), 2.36-2.46 (m, 2H), 1.78-1.89 (m, 2H), 1.49-1.61 (m, 2H), 1.44 (t, J=6.9 Hz, 3H), 1.25 (t, J=7.0 Hz, 3H). MS (M−H, ES−) 850.

Example 223

N-(2,6-difluorophenyl)-5-(3-{2-[(2-(ethyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide

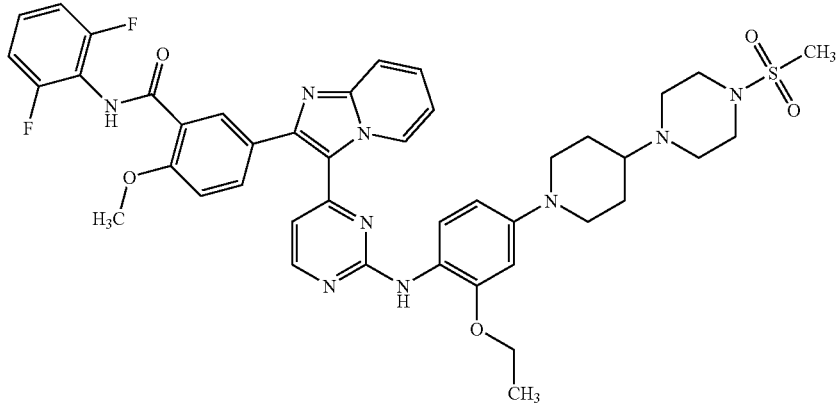

A mixture of 5-[3-(2-chloro-4-pyrimidinyl)imidazo[1,2-a]pyridin-2-yl]-N-(2,6-difluorophenyl)-2-(methyloxy)benzamide (Intermediate Example 2) (0.10 g, 0.20 mmol), 2-(ethyloxy)-4-{4-[4-(methylsulfonyl)-1-piperazinyl]-1-piperidinyl}aniline (Example 222, Step D) (0.078 g, 0.20 mmol) and para-toluenesulfonic acid (0.093 g, 0.49 mmol) in i-PrOH (5 mL) was heated in a microwave at 175° C. for 25 min. The reaction mixture was concentrated onto silica gel and purified by flash chromatography. Recrystallization from DCM and diethyl ether afforded N-(2,6-difluorophenyl)-5-(3-{2-[(2-(ethyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide (0.090 g, 53%) as a yellow solid. $^1$H NMR (400 MHz, DMSO-$d_6$) δ ppm 9.80 (s, 1H), 9.35 (br. s., 1H), 8.36 (s, 1H), 8.24 (d, J=5.3 Hz, 1H), 8.12 (d, J=1.7 Hz, 1H), 7.75-7.83 (m, 1H), 7.71 (d, J=9.0 Hz, 1H), 7.36-7.49 (m, 3H), 7.29 (d, J=8.7 Hz, 1H), 7.15-7.25 (m, 2H), 6.88-7.01 (m, 1H), 6.67 (d, J=2.3 Hz, 1H), 6.56 (d, J=5.1 Hz, 1H), 6.49 (dd, J=8.7, 2.4 Hz, 1H), 4.07 (q, J=6.9 Hz, 2H), 4.00 (s, 3H), 3.68-3.80 (m, 2H), 3.04-3.17 (m, 4H), 2.87 (s, 3H), 2.57-2.73 (m, 6H), 2.38-2.46 (m, 1H), 1.79-1.89 (m, 2H), 1.47-1.61 (m, 2H), 1.25 (t, J=6.9 Hz, 3H). MS (M–H, ES–) 836.

Example 224

N-(2,6-difluorophenyl)-3-(3-{2-[(2-(ethyloxy)-4-{4-[4-(methylsulfonyl)-1-piperazinyl]-1-piperidinyl}phenyl)amino]-4-pyrimidinyl}imidazo[1,2-a]pyridin-2-yl)benzamide

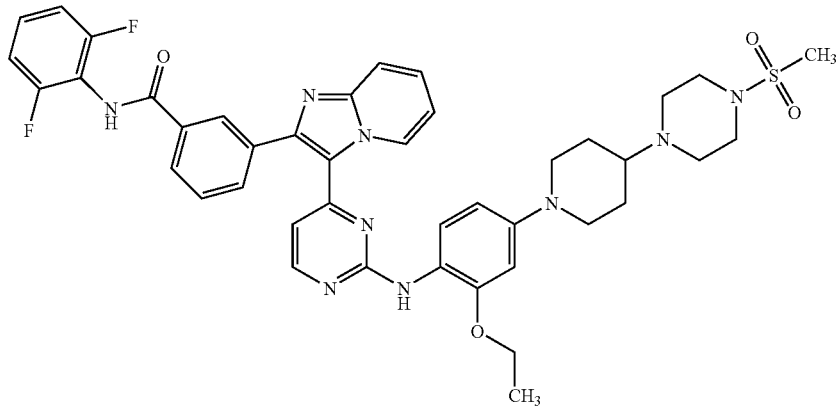

A mixture of 3-[3-(2-chloro-4-pyrimidinyl)imidazo[1,2-a]pyridin-2-yl]-N-(2,6-difluorophenyl)benzamide (Intermediate Example 1) (0.10 g, 0.22 mmol), 2-(ethyloxy)-4-{4-[4-(methylsulfonyl)-1-piperazinyl]-1-piperidinyl}aniline (Example 222, Step D) (0.083 g, 0.22 mmol) and para-toluenesulfonic acid (0.099 g, 0.52 mmol) in i-PrOH (5 mL) was heated in a microwave at 175° C. for 25 min. The reaction mixture was concentrated onto silica gel and purified by flash chromatography. Recrystallization from DCM and diethyl ether afforded N-(2,6-difluorophenyl)-3-(3-{2-[(2-(ethyloxy)-4-{4-[4-(methylsulfonyl)-1-piperazinyl]-1-piperidinyl}phenyl)amino]-4-pyrimidinyl}imidazo[1,2-a]pyridin-2-yl)benzamide (0.110 g, 63%) as a yellow solid. $^1$H NMR (400 MHz, DMSO-$d_6$) δ ppm 10.25 (s, 1H), 9.39 (br. s., 1H), 8.38 (s, 1H), 8.35 (s, 1H), 8.24 (d, J=5.2 Hz, 1H), 8.06 (d, J=7.9 Hz, 1H), 7.82 (d, J=7.8 Hz, 1H), 7.74 (d, J=9.0 Hz, 1H), 7.62 (t, J=7.7 Hz, 1H), 7.36-7.52 (m, 3H), 7.16-7.26 (m, 2H), 6.94-7.02 (m, 1H), 6.67 (d, J=2.2 Hz, 1H), 6.45-6.54 (m, 2H), 4.07 (q, J=6.9 Hz, 2H), 3.66-3.79 (m, 2H), 3.04-3.15 (m, 4H), 2.87 (s, 3H), 2.57-2.72 (m, 6H), 2.36-2.47 (m, 1H), 1.78-1.91 (m, 2H), 1.45-1.62 (m, 2H), 1.25 (t, J=7.0 Hz, 3H). MS (M−H, ES−) 806.

Example 225

N-(2,6-difluorophenyl)-5-{3-[2-({5-methyl-2-(methyloxy)-4-[4-(methylsulfonyl)-1-piperazinyl]phenyl}amino)-4-pyrimidinyl]imidazo[1,2-a]pyridin-2-yl}-2-(methyloxy)benzamide

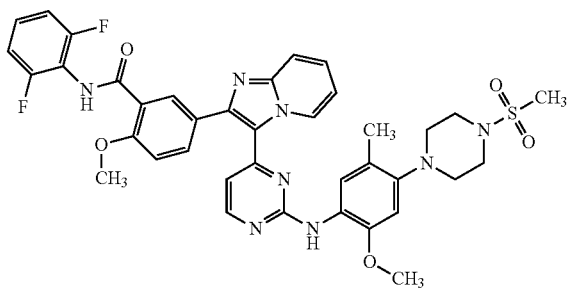

Step A: 1-[3-(methyloxy)-4-nitrophenyl]piperazine

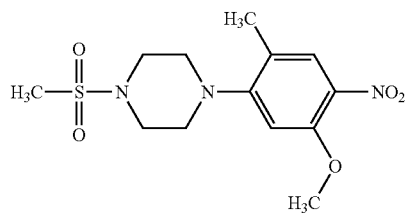

To 1-fluoro-2-methyl-5-(methyloxy)-4-nitrobenzene (Example 113, step B) (0.5 g, 2.7 mmol) in 25 mL of DMSO was added, 1-(methylsulfonyl)piperazine (0.53 g, 3.24 mmol), and $K_2CO_3$ (1.12 g, 8.1 mmol). The mixture was heated to 130° C. for 24 h. The mixture was poured into 500 mL of $H_2O$, filter, washed with $H_2O$, air dried for 15 min, dissolved in DCM, dried ($MgSO_4$), filtered, and rotovaped down to give the title compound of step A (0.87 g, 2.64 mmol, 98%). $^1$H NMR (400 MHz, DMSO-$d_6$) δ ppm 7.77 (s, 1H), 6.76 (s, 1H), 3.89 (s, 3H), 3.23-3.28 (m, 4H), 3.06-3.11 (m, 4H), 2.93 (s, 3H), 2.20 (s, 3H).

Step B: 5-methyl-2-(methyloxy)-4-[4-(methylsulfonyl)-1-piperazinyl]aniline

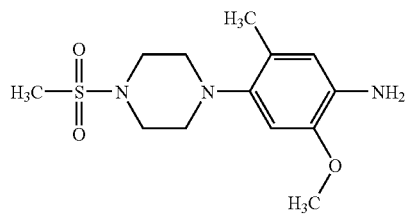

1-[2-methyl-5-(methyloxy)-4-nitrophenyl]-4-(methylsulfonyl)piperazine (0.87 g, 2.64 mmol) was placed in a 100 mL high pressure vessel and dissolved in 60 mL of 1 to 1 to 1 EtOAc/MeOH/DCM. 5 wt % Platinum(sulfided)/C (1.03 g, 0.26 mmol) was added followed quickly by a rubber septum. The vessel was evacuated and filled with $N_2$ six times to remove any oxygen. The vessel was then pressurized with $H_2$ (60 psi). The solution stirred overnight. The next morning the vessel was evacuated and filled with $N_2$ six times to remove any $H_2$. The solution was filtered through celite and evaporated to afford the title compound of step B (0.602 g, 2.01 mmol, 76%). $^1$H NMR (400 MHz, DMSO-$d_6$) δ ppm 6.58 (s, 1H), 6.43 (s, 1H), 4.44 (s, 2H), 3.69 (s, 3H), 3.15-3.23 (m, 4H), 2.90 (s, 3H), 2.77-2.83 (m, 4H), 2.06 (s, 3H).

Step C: N-(2,6-difluorophenyl)-5-{3-[2-({5-methyl-2-(methyloxy)-4-[4-(methylsulfonyl)-1-piperazinyl]phenyl}amino)-4-pyrimidinyl]imidazo[1,2-a]pyridin-2-yl}-2-(methyloxy)benzamide 5-[3-(2-Chloro-4-pyrimidinyl)imidazo[1,2-a]pyridin-2-yl]-N-(2,6-difluorophenyl)-2-(methyloxy)benzamide (Intermediate Example 2) (100 mg, 0.2 mmol), 5-methyl-2-(methyloxy)-4-[4-(methylsulfonyl)-1-piperazinyl]aniline (53 mg, 0.18 mmol), and p-toluenesulfonicacid (93 mg, 0.49 mmol) were weighed into a 20 mL vial. 1 mL of trifluoroethanol was added and the mixture was heated to 100° C. for 72 h. 2 mL of 2 N ammonia in MeOH was added. The solvent was rotovaped down. The residue was taken up in 3 mL of DCM. 1 g of silica gel was added. The solvent was rotovaped down and the pre-absorbed solids were purified by flash chromatography to give the title compound (50 mg, 0.066 mmol, 37%). $^1$H NMR (400 MHz, DMSO-$d_6$) d ppm 9.78 (s, 1H), 9.38 (d, J=6.97 Hz, 1H), 8.49 (s, 1H), 8.24 (d, J=5.13 Hz, 1H), 8.10 (d, J=2.20 Hz, 1H), 7.78 (dd, J=8.80, 2.20 Hz, 1H), 7.70 (d, J=8.80 Hz, 1H), 7.54 (s, 1H), 7.42-7.48 (m, 1H), 7.34-7.42 (m, 1H), 7.28 (d, J=8.80 Hz, 1H), 7.18 (t, J=8.07 Hz, 2H), 6.92-7.01 (m, 1H), 6.83 (s, 1H), 6.57 (d, J=5.13 Hz, 1H), 3.98 (s, 3H), 3.81 (s, 3H), 3.24-3.30 (m, 4H), 2.95-2.99 (m, 4H), 2.94 (s, 3H), 2.17 (s, 3H); MS (ESI): 755 [M+H]$^+$.

Example 226

N-(2,6-difluorophenyl)-3-{3-[2-({5-methyl-2-(methyloxy)-4-[4-(methylsulfonyl)-1-piperazinyl]phenyl}amino)-4-pyrimidinyl]imidazo[1,2-a]pyridin-2-yl}benzamide

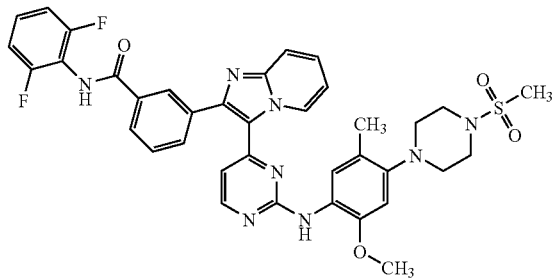

3-[3-(2-Chloro-4-pyrimidinyl)imidazo[1,2-a]pyridin-2-yl]-N-(2,6-difluorophenyl)benzamide (Intermediate Example 1) (100 mg, 0.22 mmol), 5-methyl-2-(methyloxy)-4-[4-(methylsulfonyl)-1-piperazinyl]aniline (Example 225, step B) (53 mg, 0.18 mmol), and p-toluenesulfonicacid (99 mg, 0.52 mmol) were weighed into a 20 mL vial. 1 mL of trifluoroethanol was added and the mixture was heated to 100° C. for 72 h. 2 mL of 2 N ammonia in MeOH was added. The solvent was rotovaped down. The residue was taken up in 3 mL of DCM. 1 g of silica gel was added. The solvent was rotovaped down and the pre-absorbed solids were purified by flash chromatography to give the title compound (67 mg, 0.092 mmol, 52%). $^1$H NMR (400 MHz, DMSO-$d_6$) d ppm 10.23 (s, 1H), 9.40 (s, 1H), 8.50 (s, 1H), 8.33 (s, 1H), 8.24 (d, J=5.50 Hz, 1H), 8.05 (d, J=7.70 Hz, 1H), 7.82 (d, J=8.07 Hz, 1H), 7.73 (d, J=9.17 Hz, 1H), 7.61 (t, J=7.70 Hz, 1H), 7.53 (s, 1H), 7.45-7.51 (m, 1H), 7.36-7.44 (m, 1H), 7.20 (t, J=8.07 Hz, 2H), 7.00 (t, J=6.97 Hz, 1H), 6.83 (s, 1H), 6.51 (d, J=5.13 Hz, 1H), 3.81 (s, 3H), 3.23-3.30 (m, 4H), 2.95-2.99 (m, 4H), 2.94 (s, 3H), 2.17 (s, 3H); MS (ESI): 725 [M+H]$^+$.

Example 227

N-(2,6-difluorophenyl)-2-[(1-methylethyl)oxy]-5-(3-{2-[(2-(methyloxy)-4-[4-(4-(methylsulfonyl)-1-piperazinyl]-1-piperidinyl}phenyl)amino]-4-pyrimidinyl]imidazo[1,2-a]pyridin-2-yl)benzamide

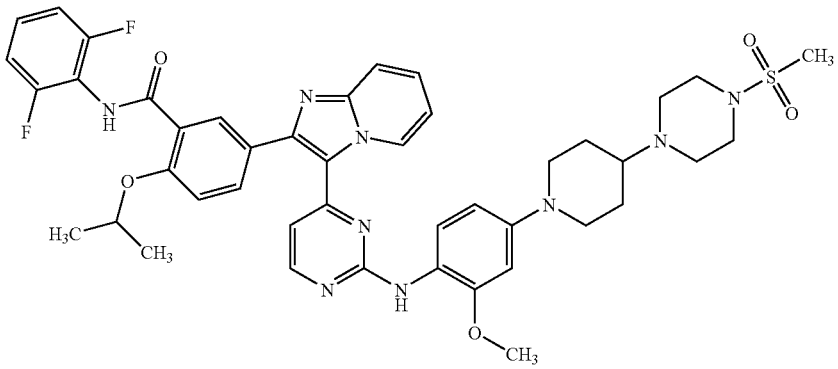

A mixture of 5-[3-(2-chloro-4-pyrimidinyl)imidazo[1,2-a]pyridin-2-yl]-N-(2,6-difluorophenyl)-2-[(1-methylethyl)oxy]benzamide (Intermediate Example 7) (0.10 g, 0.19 mmol), 2-(methyloxy)-4-{4-[4-(methylsulfonyl)-1-piperazinyl]-1-piperidinyl}aniline (Example 58, Step B) (0.071 g, 0.19 mmol) and para-toluenesulfonic acid (0.088 g, 0.46 mmol) in i-PrOH (5 mL) was heated in a microwave at 175° C. for 25 min. The reaction mixture was concentrated onto silica gel and purified by flash chromatography. Recrystallization from DCM and diethyl ether afforded N-(2,6-difluorophenyl)-2-[(1-methylethyl)oxy]-5-(3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide (0.057 g, 35%) as a yellow solid. $^1$H NMR (400 MHz, DMSO-$d_6$) δ ppm 9.72 (s, 1H), 9.36 (br. s., 1H), 8.45 (s, 1H), 8.23 (d, J=5.2 Hz, 1H), 8.08 (d, J=1.9 Hz, 1H), 7.66-7.80 (m, 2H), 7.35-7.49 (m, 3H), 7.31 (d, J=8.8 Hz, 1H), 7.15-7.26 (m, 2H), 6.96 (t, J=6.6 Hz, 1H), 6.68 (d, J=2.4 Hz, 1H), 6.57 (d, J=5.1 Hz, 1H), 6.49 (dd, J=8.8, 2.3 Hz, 1H), 4.83-4.95 (m, 1H), 3.81 (s, 3H), 3.71-3.78 (m, 2H), 3.04-3.14 (m, 4H), 2.87 (s, 3H), 2.64-2.72 (m, 2H), 2.58-2.63 (m, 4H), 2.38-2.47 (m, 1H), 1.77-1.90 (m, 2H), 1.47-1.63 (m, 2H), 1.41 (d, J=6.0 Hz, 6H). MS (M–H, ES–) 850.

Example 228

N-(2,6-difluorophenyl)-2-(ethyloxy)-5-(3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide

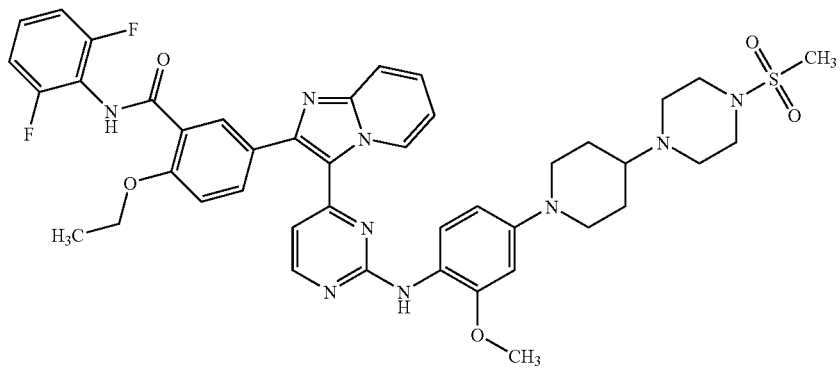

A mixture of 5-[3-(2-chloro-4-pyrimidinyl)imidazo[1,2-a]pyridin-2-yl]-N-(2,6-difluorophenyl)-2-(ethyloxy)benzamide (Intermediate Example 6) (0.10 g, 0.20 mmol), 2-(methyloxy)-4-{4-[4-(methylsulfonyl)-1-piperazinyl]-1-piperidinyl}aniline (Example 58, Step B) (0.073 g, 0.20 mmol) and para-toluenesulfonic acid (0.090 g, 0.47 mmol) in i-PrOH (5 mL) was heated in a microwave at 175° C. for 25 min. The reaction mixture was concentrated onto silica gel and purified by flash chromatography. Recrystallization from DCM and diethyl ether afforded N-(2,6-difluorophenyl)-2-(ethyloxy)-5-(3-{2-[(2-(methyloxy)-4-{4-[4-(methylsulfonyl)-1-piperazinyl]-1-piperidinyl}phenyl)amino]-4-pyrimidinyl}-imidazo[1,2-a]pyridin-2-yl)benzamide (0.066 g, 40%) as a brown solid. $^1$H NMR (400 MHz, DMSO-$d_6$) δ ppm 9.76 (s, 1H), 9.37 (br. s., 1H), 8.45 (s, 1H), 8.21 (d, J=5.2 Hz, 1H), 8.06 (d, J=1.5 Hz, 1H), 7.65-7.81 (m, 2H), 7.35-7.50 (m, 3H), 7.28 (d, J=8.6 Hz, 1H), 7.16-7.25 (m, 2H), 6.88-7.02 (m, 1H), 6.69 (d, J=2.3 Hz, 1H), 6.46-6.61 (m, 2H), 4.22-4.33 (m, 2H), 3.81 (s, 3H), 3.71-3.79 (m, 2H), 3.03-3.15 (m, 4H), 2.87 (s, 3H), 2.64-2.73 (m, 2H), 2.58-2.64 (m, 4H), 2.38-2.46 (m, 1H), 1.80-1.89 (m, 2H), 1.50-1.62 (m, 2H), 1.44 (t, J=6.9 Hz, 3H). MS (M+H, ES+) 838.

Example 229

N-(2,6-difluorophenyl)-2-(ethyloxy)-5-(3-{2-[(5-methyl-2-(methyloxy)-4-{4-[2-(methylsulfonyl)ethyl]-1-piperidinyl}phenyl)amino]-4-pyrimidinyl}imidazo[1,2-a]pyridin-2-yl)benzamide

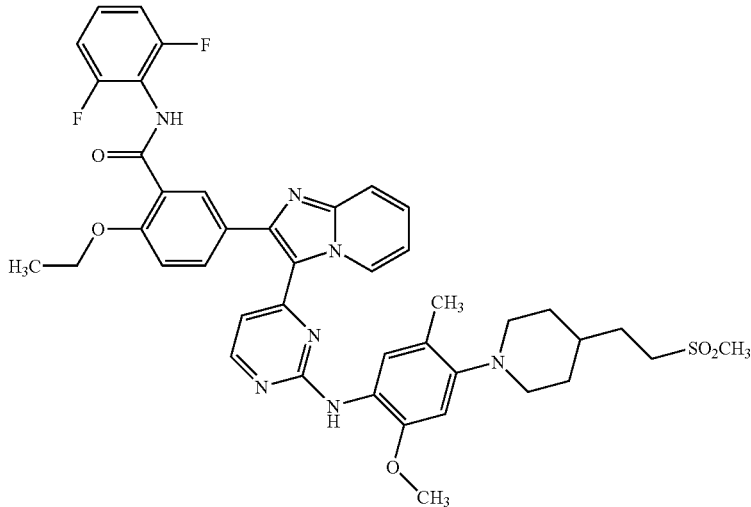

The title compound (0.11 g, 0.13 mmol, 53%) was prepared in an analogous manner to that described for the preparation Example 215, step D, with the following notable exceptions:
(a) 5-methyl-2-(methyloxy)-4-{4-[2-(methylsulfonyl)ethyl]-1-piperidinyl}aniline (Example 214, step E) was used instead of 2-(ethyloxy)-5-methyl-4-{4-[2-(methylsulfonyl)ethyl]-1-piperidinyl}aniline;
(b) [3-(2-chloro-4-pyrimidinyl)imidazo[1,2-a]pyridin-2-yl]-N-(2,6-difluorophenyl)-2-(ethyloxy)benzamide (Intermediate Example 6) was used instead of 5-[3-(2-chloro-4-pyrimidinyl)imidazo[1,2-a]pyridin-2-yl]-N-(2,6-difluorophenyl)-2-[(1-methylethyl)oxy]benzamide (Intermediate Example 7).

$^1$H NMR (400 MHz, DMSO-$d_6$) δ 9.76 (br. s., 1H), 9.26-9.53 (m, 1H), 8.47 (br. s., 1H), 8.25 (d, J=4.7 Hz, 1H), 8.06 (br. s., 1H), 7.74 (dd, J=18.8, 8.1 Hz, 2H), 7.34-7.62 (m, 3H), 7.11-7.34 (m, 3H), 6.84-7.10 (m, 1H), 6.77 (br. s., 1H), 6.57 (d, J=4.0 Hz, 1H), 4.28 (d, J=6.2 Hz, 2H), 3.81 (s, 3H), 2.84-3.28 (m, 7H), 2.63 (t, 2H), 2.15 (br. s., 3H), 1.60-1.93 (m, 4H), 1.24-1.60 (m, 6H). MS (M+H, ES+) 796.

Example 230

N-(2,6-difluorophenyl)-5-(3-{2-[(5-methyl-2-(methyloxy)-4-{4-[2-(methylsulfonyl)ethyl]-1-piperidinyl}phenyl)amino]-4-pyrimidinyl}imidazo[1,2-a]pyridin-2-yl)-2-(methyloxy)benzamide

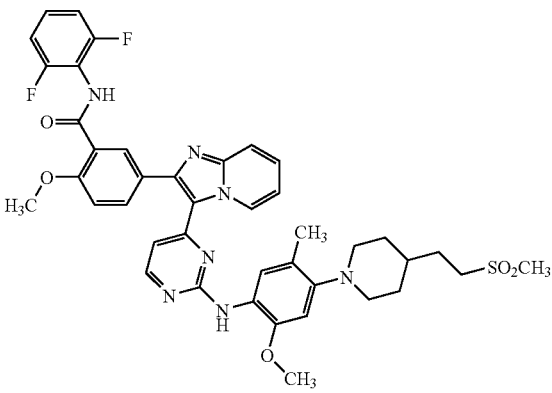

The title compound (0.08 g, 0.1 mmol, 42%) was prepared in an analogous manner to that described for the preparation Example 215, step D with the following notable exceptions:

a) 5-[3-(2-chloro-4-pyrimidinyl)imidazo[1,2-a]pyridin-2-yl]-N-(2,6-difluorophenyl)-2-(methyloxy)benzamide (Intermediate Example 2) was used instead of 5-[3-(2-chloro-4-pyrimidinyl)imidazo[1,2-a]pyridin-2-yl]-N-(2,6-difluorophenyl)-2-[(1-methylethyl)oxy]benzamide (Intermediate Example 7);
b) 5-methyl-2-(methyloxy)-4-{4-[2-(methylsulfonyl)ethyl]-1-piperidinyl}aniline (Example 214, step E) was used instead of 2-(ethyloxy)-5-methyl-4-{4-[2-(methylsulfonyl)ethyl]-1-piperidinyl}aniline.

$^1$H NMR (400 MHz, DMSO-$d_6$) δ 9.80 (br. s., 1H), 9.39 (ddd, J=2.7, 1.6, 1.4 Hz, 1H), 8.47 (br. s., 1H), 8.25 (d, J=4.6 Hz, 1H), 8.12 (br. s., 1H), 7.61-7.87 (m, 2H), 7.35-7.61 (m, 3H), 7.12-7.36 (m, 3H), 6.87-7.08 (m, 1H), 6.77 (br. s., 1H), 6.48-6.66 (m, 1H), 4.00 (br. s., 3H), 3.81 (s, 3H), 2.90-3.25 (m, 7H), 2.57-2.76 (m, 2H), 2.15 (br. s., 3H), 1.62-1.90 (m, 4H), 1.23-1.60 (m, 3H). MS (M+H, ES+) 782.

Example 231

N-(2,6-difluorophenyl)-3-(3-{2-[(5-methyl-2-(methyloxy)-4-{4-[2-(methylsulfonyl)ethyl]-1-piperidinyl}phenyl)amino]-4-pyrimidinyl}imidazo[1,2-a]pyridin-2-yl)benzamide

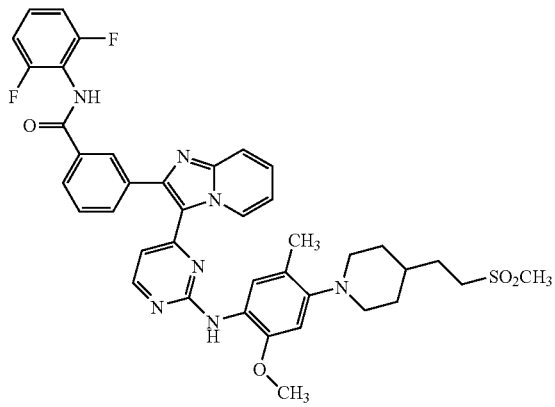

The title compound (0.08 g, 0.1 mmol, 45%) was prepared in an analogous manner to that described for the preparation Example 215, with the following notable exceptions:

a) 3-[3-(2-chloro-4-pyrimidinyl)imidazo[1,2-a]pyridin-2-yl]-N-(2,6-difluorophenyl)benzamide (Intermediate Example 1) was used instead of 5-[3-(2-chloro-4-pyrimidinyl)imidazo[1,2-a]pyridin-2-yl]-N-(2,6-difluorophenyl)-2-[(1-methylethyl)oxy]benzamide (Intermediate Example 7);

b) 5-methyl-2-(methyloxy)-4-{4-[2-(methylsulfonyl)ethyl]-1-piperidinyl}aniline (Example 214, step E) was used instead of 2-(ethyloxy)-5-methyl-4-{4-[2-(methylsulfonyl)ethyl]-1-piperidinyl}aniline, describe in Example 214, Step B.

$^1$H NMR (400 MHz, DMSO-d$_6$) δ 10.25 (s, 1H), 9.33-9.54 (m, 1H), 8.48 (s, 1H), 8.35 (s, 1H), 8.25 (d, J=5.1 Hz, 1H), 8.07 (d, J=7.6 Hz, 1H), 7.70-7.91 (m, 2H), 7.62 (t, J=7.7 Hz, 1H), 7.33-7.57 (m, 3H), 7.22 (t, J=8.0 Hz, 2H), 6.93-7.10 (m, 1H), 6.77 (s, 1H), 6.51 (d, J=4.9 Hz, 1H), 3.81 (s, 3H), 2.93-3.26 (m, 7H), 2.56-2.72 (m, 2H), 2.15 (s, 3H), 1.63-1.87 (m, 4H), 1.25-1.62 (m, 3H). MS (M+H, ES+) 752.

Example 232

N-(2,6-difluorophenyl)-2-(ethyloxy)-5-{3-[2-({2-(methyloxy)-4-[4-(methylsulfonyl)-1-piperazinyl]phenyl}amino)-4-pyrimidinyl]imidazo[1,2-a]pyridin-2-yl}benzamide

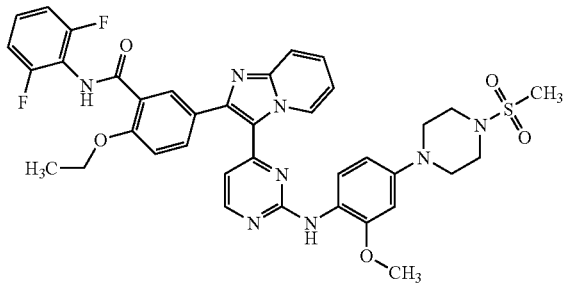

Step A: 1-[3-(methyloxy)-4-nitrophenyl]-4-(methylsulfonyl)piperazine

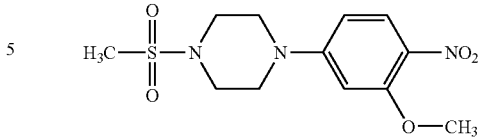

To 4-fluoro-2-(methyloxy)-1-nitrobenzene (Example 22, step A) (1 g, 5.8 mmol) in 10 mL of DMSO was added, 1-(methylsulfonyl)piperazine (1.15 g, 7.02 mmol), and K$_2$CO$_3$ (2.42 g, 17.5 mmol). The mixture was heated to 80° C. overnight. In the morning, the mixture was poured into 100 mL of H$_2$O, Solid precipitated and was filtered off, washed with H$_2$O and let air dried for a few hours. After drying under high vacuum overnight, the title compound of step A was isolated as a yellow solid. (1.09 g, 3.46 mmol, 60%). MS (ESI): 316 [M+H]$^+$.

Step B: 2-(methyloxy)-4-[4-(methylsulfonyl)-1-piperazinyl]aniline

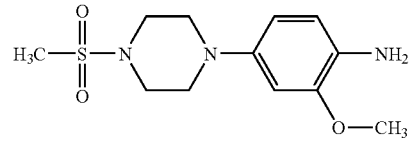

1-[3-(Methyloxy)-4-nitrophenyl]-4-(methylsulfonyl)piperazine (1.09 g, 3.46 mmol) was suspended in 5 mL THF and 10 mL MeOH in a 100 mL round bottom flask. Nickle(II) chloride hexahydrate (0.247 g, 1.04 mmol) was added followed by slow addition of NaBH$_4$ (0.392 g, 10.38 mmol). TLC analysis indicated reaction complete after addition of NaBH$_4$. Reaction mixture was adsorbed on SiO$_2$ and purified via column chromatography using a gradient of 0-10% MeOH in DCM. Fractions were combined and rotovapped to give the title compound of step B. (0.925 g, 3.24 mmol, 93%); MS (ESI): 285 [M+H]$^+$.

Step C: N-(2,6-difluorophenyl)-2-(ethyloxy)-5-{3-[2-({2-(methyloxy)-4-[4-(methylsulfonyl)-1-piperazinyl]phenyl}amino)-4-pyrimidinyl]imidazo[1,2-a]pyridin-2-yl}benzamide

[3-(2-Chloro-4-pyrimidinyl)imidazo[1,2-a]pyridin-2-yl]-N-(2,6-difluorophenyl)-2-(ethyloxy)benzamide (Intermediate Example 6) (100 mg, 0.2 mmol), 2-(methyloxy)-4-[4-(methylsulfonyl)-1-piperazinyl]aniline (51 mg, 0.18 mmol), and p-toluenesulfonicacid (90 mg, 0.47 mmol) were weighed into a 20 mL vial. 1 mL of trifluoroethanol was added and the mixture was heated to 100° C. for 72 h. 2 mL of 2 N ammonia in MeOH was added. The solvent was rotovaped down. The residue was taken up in 3 mL of DCM. 1 g of silica gel was added. The solvent was rotovaped down and the pre-absorbed solids were purified by flash chromatography to give the title compound (75 mg, 0.099 mmol, 56%). $^1$H NMR (400 MHz, DMSO-d$_6$) δ ppm 9.74 (s, 1H), 9.37 (s, 1H), 8.48 (s, 1H), 8.21 (d, J=5.13 Hz, 1H), 8.04 (d, J=1.83 Hz, 1H), 7.74 (dd, J=8.61, 2.38 Hz, 1H), 7.69 (d, J=8.80 Hz, 1H), 7.42-7.49 (m, 2H), 7.34-7.40 (m, 1H), 7.26 (d, J=8.80 Hz, 1H), 7.19 (t, J=8.07 Hz, 2H), 6.96 (t, J=7.15 Hz, 1H), 6.73 (d, J=2.57 Hz, 1H), 6.50-6.56 (m, 2H), 4.26 (q, J=6.97 Hz, 2H), 3.81 (s, 3H), 3.25 (br. s., 8H), 2.92 (s, 3H), 1.43 (t, J=6.97 Hz, 3H); MS (ESI): 755 [M+H]$^+$.

Example 233

N-(2,6-difluorophenyl)-2-(methyloxy)-5-{3-[2-({2-(methyloxy)-4-[4-(methylsulfonyl)-1-piperazinyl]phenyl}amino)-4-pyrimidinyl]imidazo[1,2-a]pyridin-2-yl}benzamide

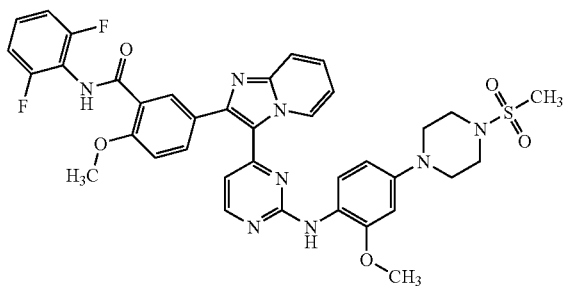

5-[3-(2-Chloro-4-pyrimidinyl)imidazo[1,2-a]pyridin-2-yl]-N-(2,6-difluorophenyl)-2-(methyloxy)benzamide (Intermediate Example 2) (100 mg, 0.2 mmol), 2-(methyloxy)-4-[4-(methylsulfonyl)-1-piperazinyl]aniline (Example 232, step B) (51 mg, 0.18 mmol), and p-toluenesulfonicacid (93 mg, 0.49 mmol) were weighed into a 20 mL vial. 1 mL of trifluoroethanol was added and the mixture was heated to 100° C. for 72 h. 2 mL of 2 N ammonia in MeOH was added. The solvent was rotovaped down. The residue was taken up in 3 mL of DCM. 1 g of silica gel was added. The solvent was rotovaped down and the pre-absorbed solids were purified by flash chromatography to give the title compound (96 mg, 0.12 mmol, 69%). $^1$H NMR (400 MHz, DMSO-$d_6$) δ ppm 9.78 (s, 1H), 9.37 (s, 1H), 8.48 (s, 1H), 8.21 (d, J=5.13 Hz, 1H), 8.10 (d, J=1.83 Hz, 1H), 7.77 (dd, J=8.61, 2.02 Hz, 1H), 7.69 (d, J=8.80 Hz, 1H), 7.36-7.48 (m, 3H), 7.28 (d, J=8.43 Hz, 1H), 7.18 (t, J=8.07 Hz, 2H), 6.96 (t, J=6.78 Hz, 1H), 6.73 (d, J=2.20 Hz, 1H), 6.49-6.57 (m, 2H), 3.98 (s, 3H), 3.81 (s, 3H), 3.25 (br. s., 8H), 2.92 (s, 3H); MS (ESI): 741 [M+H]$^+$.

Example 234

N-(2,6-difluorophenyl)-3-{3-[2-({2-(methyloxy)-4-[4-(methylsulfonyl)-1-piperazinyl]phenyl}amino)-4-pyrimidinyl]imidazo[1,2-a]pyridin-2-yl}benzamide

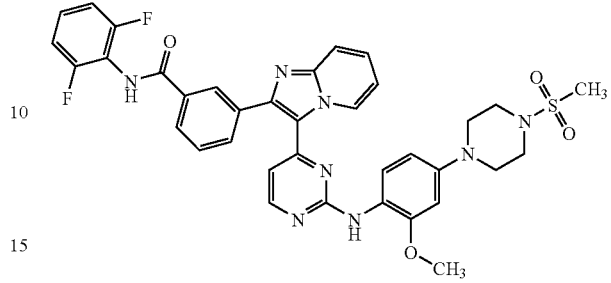

3-[3-(2-Chloro-4-pyrimidinyl)imidazo[1,2-a]pyridin-2-yl]-N-(2,6-difluorophenyl)benzamide (Intermediate Example 1) (100 mg, 0.22 mmol), 2-(methyloxy)-4-[4-(methylsulfonyl)-1-piperazinyl]aniline (Example 232, step B) (51 mg, 0.18 mmol), and p-toluenesulfonicacid (99 mg, 0.52 mmol) were weighed into a 20 mL vial. 1 mL of trifluoroethanol was added and the mixture was heated to 100° C. for 72 h. 2 mL of 2 N ammonia in MeOH was added. The solvent was rotovaped down. The residue was taken up in 3 mL of DCM. 1 g of silica gel was added. The solvent was rotovaped down and the pre-absorbed solids were purified by flash chromatography to give the title compound (92 mg, 0.13 mmol, 73%). $^1$H NMR (400 MHz, DMSO-$d_6$) δ ppm 10.24 (s, 1H), 9.40 (s, 1H), 8.49 (s, 1H), 8.33 (s, 1H), 8.21 (d, J=5.13 Hz, 1H), 8.05 (d, J=7.70 Hz, 1H), 7.82 (d, J=7.70 Hz, 1H), 7.73 (d, J=8.80 Hz, 1H), 7.61 (t, J=7.70 Hz, 1H), 7.43-7.49 (m, 2H), 7.35-7.43 (m, 1H), 7.16-7.24 (m, 2H), 6.99 (t, J=6.78 Hz, 1H), 6.73 (d, J=2.20 Hz, 1H), 6.52 (dd, J=8.62, 2.38 Hz, 1H), 6.48 (d, J=5.13 Hz, 1H), 3.81 (s, 3H), 3.25 (br. s., 8H), 2.92 (s, 3H); MS (ESI): 711 [M+H]$^+$.

Example 235

N-(2,6-difluorophenyl)-5-(3-{2-[(5-ethyl-2-(methyloxy)-4-{4-[2-(methylsulfonyl)ethyl]-1-piperazinyl}phenyl)amino]-4-pyrimidinyl}imidazo[1,2-a]pyridin-2-yl)-2-(ethyloxy)benzamide

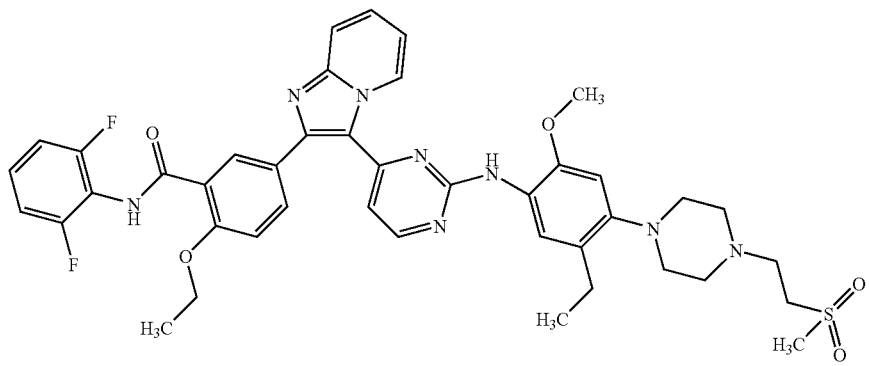

The title compound (0.09 g, 0.10 mmol, 22%) was prepared in an analogous manner to that described for Example 187, with the following notable exception: 5-[3-(2-chloro-4-pyrimidinyl)imidazo[1,2-a]pyridin-2-yl]-N-(2,6-difluorophenyl)-2-(ethyloxy)benzamide (Intermediate Example 6) was used instead of 5-[3-(2-chloro-4-pyrimidinyl)imidazo[1,2-a]pyridin-2-yl]-N-(2,6-difluorophenyl)-2-(methyloxy)benzamide (Intermediate Example 2) in step F. $^1$H NMR (400

MHz, DMSO-d$_6$) δ ppm 9.71 (s, 1H), 9.24-9.40 (m, 1H), 8.46 (s, 1H), 8.21 (d, J=5.2 Hz, 1H), 8.02 (s, 1H), 7.61-7.78 (m, 2H), 7.51 (s, 1H), 7.29-7.47 (m, 2H), 7.10-7.28 (m, 3H), 6.86-6.98 (m, 1H), 6.80 (s, 1H), 6.54 (d, J=5.1 Hz, 1H), 4.17-4.30 (m, 2H), 3.77 (s, 3H), 3.23-3.34 (m, 2H), 3.03 (s, 3H), 2.79-2.90 (m, 4H), 2.74 (t, J=6.3 Hz, 2H), 2.47-2.65 (m, 6H), 1.40 (t, J=6.8 Hz, 3H), 1.06 (t, J=7.4 Hz, 3H). MS (M+H, ES+) 811.

Example 236

N-(2,6-difluorophenyl)-5-(3-{2-[(5-methyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide

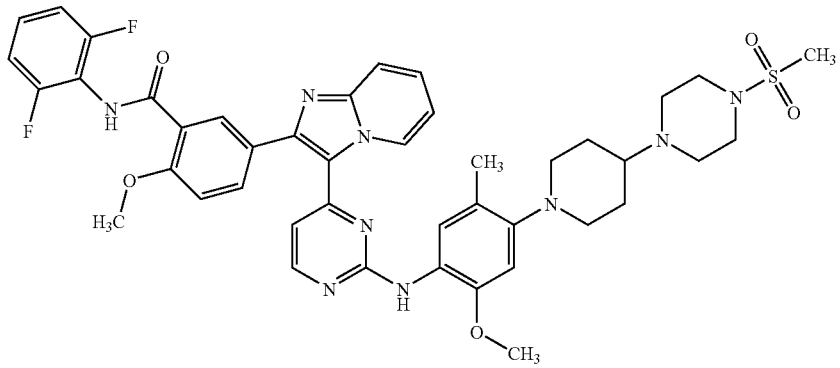

Step A: 1-{1-[2-methyl-5-(methyloxy)-4-nitrophenyl]-4-piperidinyl}-4-(methylsulfonyl)-piperazine

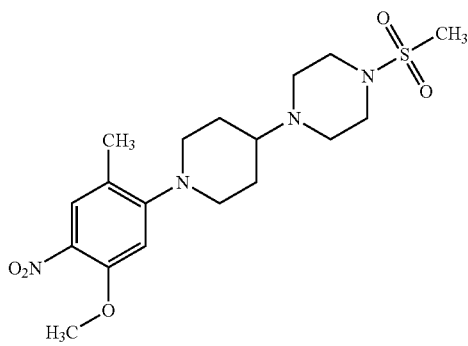

A mixture of 1-fluoro-2-methyl-5-(methyloxy)-4-nitrobenzene (Example 113, Step B) (0.90 g, 4.9 mmol), 1-(methylsulfonyl)-4-(4-piperidinyl)piperazine (Example 204, step C) (1.20 g, 4.9 mmol) and K$_2$CO$_3$ (0.81 g, 5.8 mmol) in DMSO (15 mL) was heated at 100° C. for 48 h. The reaction was cooled to rt, poured into H$_2$O and extracted exhaustively with DCM. The combined organics were washed with H$_2$O then dried over MgSO$_4$. The resultant solution was concentrated onto silica and purified by flash chromatography to afford 1-{1-[2-methyl-5-(methyloxy)-4-nitrophenyl]-4-piperidinyl}-4-(methylsulfonyl)piperazine (1.09 g, 55%). $^1$H NMR (400 MHz, DMSO-d$_6$) δ ppm 7.77 (s, 1H), 6.69 (s, 1H), 3.90 (s, 3H), 3.29-3.38 (m, 2H), 3.06-3.15 (m, 4H), 2.87 (s, 3H), 2.68-2.79 (m, 2H), 2.59-2.66 (m, 4H), 2.40-2.48 (m, 1H), 2.20 (s, 3H), 1.80-1.92 (m, 2H), 1.49-1.67 (m, 2H).

Step B: 5-methyl-2-(methyloxy)-4-{4-[4-(methylsulfonyl)-1-piperazinyl]-1-piperidinyl}-aniline

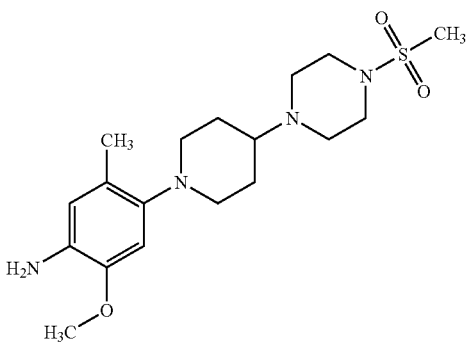

Sodium borohydride (0.30 g, 7.93 mmol) was added in portions to a stirring suspension of 1-{1-[2-methyl-5-(methyloxy)-4-nitrophenyl]-4-piperidinyl}-4-(methylsulfonyl)piperazine (1.09 g, 2.64 mmol) and Nickel(II)chloride hexahydrate (0.19 g, 0.8 mmol) in THF (10 mL) and MeOH (20 mL) at rt. The reaction mixture was allowed to stir at rt for 2 h and then it was concentrated in vacuo. The residue was taken up in DCM and passed through a bed of celite. The resultant filtrate was then concentrated onto silica gel and purified by flash chromatography to afford 5-methyl-2-(methyloxy)-4-{4-[4-(methylsulfonyl)-1-piperazinyl]-1-piperidinyl}aniline (0.58 g, 57%). $^1$H NMR (400 MHz, DMSO-d$_6$) δ ppm 6.55 (s, 1H), 6.43 (s, 1H), 4.30 (s, 2H), 3.70 (s, 3H), 3.05-3.15 (m, 4H), 2.89-2.96 (m, 2H), 2.86 (s, 3H), 2.52-2.65 (m, 6H), 2.26-2.41 (m, 1H), 2.06 (s, 3H), 1.74-1.85 (m, 2H), 1.43-1.63 (m, 2H).

403

Step C: N-(2,6-difluorophenyl)-5-(3-{2-[(5-methyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide A mixture of 5-[3-(2-chloro-4-pyrimidinyl)imidazo[1,2-a]pyridin-2-yl]-N-(2,6-difluorophenyl)-2-(methyloxy)benzamide (Intermediate Example 2) (0.075 g, 0.15 mmol), 5-methyl-2-(methyloxy)-4-{4-[4-(methylsulfonyl)-1-piperazinyl]-1-piperidinyl}aniline (0.058 g, 0.15 mmol) and para-toluenesulfonic acid (0.070 g, 0.37 mmol) in i-PrOH (5 mL) was heated in a microwave at 175° C. for 25 min. The reaction mixture was concentrated onto silica gel and purified by flash chromatography. Recrystallization from DCM and diethyl ether afforded N-(2,6-difluorophenyl)-5-(3-{2-[(5-methyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide (0.038 g, 30%). $^1$H NMR (400 MHz, DMSO-$d_6$) δ ppm 9.80 (s, 1H), 9.33-9.43 (m, 1H), 8.47 (s, 1H), 8.25 (d, J=5.2 Hz, 1H), 8.08-8.14 (m, 1H), 7.76-7.84 (m, 1H), 7.71 (d, J=9.0 Hz, 1H), 7.34-7.55 (m, 3H), 7.30 (d, J=8.7 Hz, 1H), 7.15-7.25 (m, 2H), 6.97 (t, J=6.8 Hz, 1H), 6.76 (s, 1H), 6.57 (d, J=5.1 Hz, 1H), 4.00 (s, 3H), 3.80 (s, 3H), 3.06-3.19 (m, 6H), 2.88 (s, 3H), 2.59-2.72 (m, 6H), 2.38-2.44 (m, 1H), 2.16 (s, 3H), 1.80-1.91 (m, 2H), 1.50-1.71 (m, 2H). MS (M+2H, ES+) 839.

Example 237

N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide

404

A mixture of 5-[3-(2-chloro-4-pyrimidinyl)imidazo[1,2-a]pyridin-2-yl]-N-(2,6-difluorophenyl)-2-(methyloxy)benzamide (Intermediate Example 2) (0.60 g, 1.22 mmol), 5-ethyl-2-(methyloxy)-4-{4-[4-(methylsulfonyl)-1-piperazinyl]-1-piperidinyl}aniline (Example 206, Step B) (0.48 g, 1.22 mmol) and HCl (4N,1,4-Dioxane, 0.61 mL, 2.44 mmol) in trifluoroethanol (15 mL) was heated at 170° C. for 40 min in the microwave. The reaction mixture was concentrated onto silica gel and purified by flash column chromatography. Recrystallization from DCM and EtOH afforded the title compound N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide (0.61 g, 56%).
$^1$H NMR (400 MHz, DMSO-$d_6$) δ ppm 9.80 (s, 1H), 9.36 (br. s., 1H), 8.50 (s, 1H), 8.26 (d, J=5.22 Hz, 1H), 8.12 (d, J=2.11 Hz, 1H), 7.80 (dd, J=8.80, 2.02 Hz, 1H), 7.71 (d, J=9.07 Hz, 1H), 7.53 (s, 1H), 7.36-7.50 (m, 2H), 7.30 (d, J=8.80 Hz, 1H), 7.14-7.25 (m, 2H), 6.91-7.00 (m, 1H), 6.83 (s, 1H), 6.58 (d, J=5.22 Hz, 1H), 4.00 (s, 3H), 3.80 (s, 3H), 3.08-3.15 (m, 4H), 3.00-3.07 (m, 2H), 2.88 (s, 3H), 2.67-2.76 (m, 2H), 2.61-2.66 (m, 4H), 2.56 (q, J=7.51 Hz, 2H), 2.38-2.46 (m, 1H), 1.80-1.91 (m, 2H), 1.50-1.68 (m, 2H), 1.11 (t, J=7.51 Hz, 3H). MS (M+H, ES+) 852.

Separately, the Title Compound was Prepared in the Following Manner:

A mixture of 5-[3-(2-chloro-4-pyrimidinyl)imidazo[1,2-a]pyridin-2-yl]-N-(2,6-difluorophenyl)-2-(methyloxy)benzamide (Intermediate Example 2) (23.0 g, 46.8 mmol), 5-ethyl-2-(methyloxy)-4-{4-[4-(methylsulfonyl)-1-piperazinyl]-1-piperidinyl}aniline (Example 206, Step B) (18.6 g, 46.8 mmol) and HCl (4N,1,4-Dioxane, 23.4 mL, 93.6 mmol) in trifluoroethanol (200 mL) was heated in a sealed vessel at 85° C. for 48 h. After cooling to rt, the reaction mixture was treated with an excess of 7N NH$_3$ in MeOH and then subjected to filtration. The filtrate was concentrated onto silica gel and purified by flash chromatography. The chromatographed product was dissolved in DCM and treated with an excess of diethyl ether. The resultant bright yellow precipitate was collected by filtration and then recrystallized from DCM and EtOH to afford the title compound N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide (28.2 g, 67%).

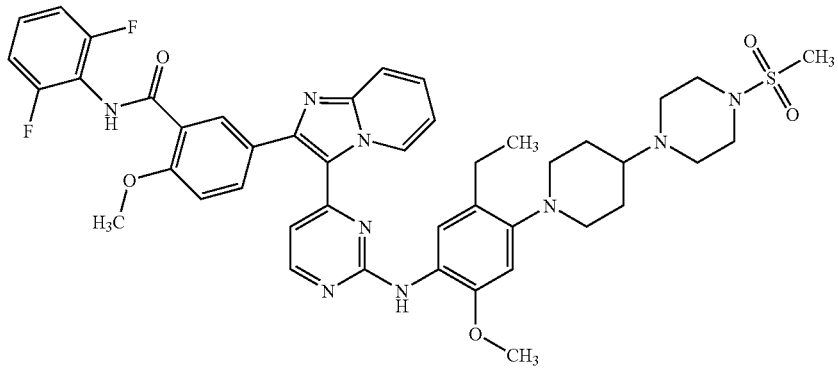

Example 238

N-(2,6-difluorophenyl)-2-(ethyloxy)-5-(3-{2-[(2-(methyloxy)-4-{4-[2-(methyloxy)ethyl]-1-piperazinyl}phenyl)amino]-4-pyrimidinyl}imidazo[1,2-a]pyridin-2-yl)benzamide

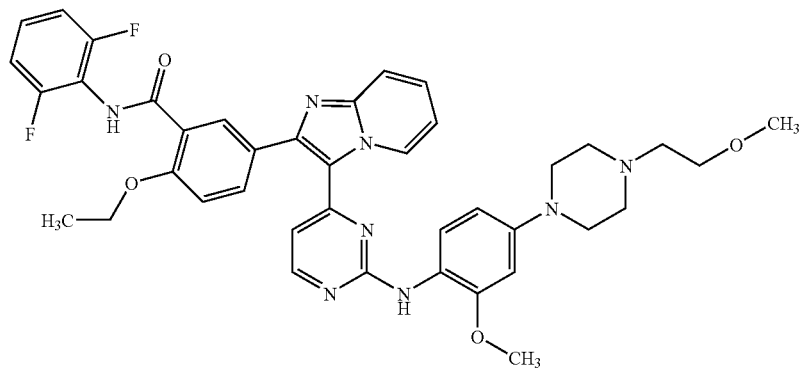

Step A: 2-(methyloxy)-4-{4-[2-(methyloxy)ethyl]-1-piperazinyl}aniline

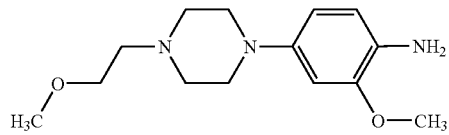

To 4-fluoro-2-(methyloxy)-1-nitrobenzene (which may be prepared according to Example 22, step A) (1 g, 5.8 mmol) in 15 mL of DMSO was added, 1-[2-(methyloxy)ethyl]piperazine (0.92 g, 6.4 mmol), and $K_2CO_3$ (2.4 g, 17.4 mmol). The mixture was heated to 80° C. overnight. The mixture was then poured into 100 mL of $H_2O$ and extracted with EtOAc, washed with a saturated NaCl solution, dried over $Na_2SO_4$, filtered and rotovapped to dryness to give 1.8 g of crude 1-[2-(methyloxy)ethyl]-4-[3-(methyloxy)-4-nitrophenyl]piperazine. MS (ESI): 296 [M+H]$^+$. This material was dissolved in 15 mL EtOH and 1 mL DMF in a 100 mL round bottom flask. Platinum on Carbon (5% by weight) (0.2 g) was added and the flask was flushed with $N_2$. After about 15 min, a balloon containing $H_2$ was added and the $N_2$ was removed. $H_2$ was bubbled through the solution for a few minutes. The reaction mixture was let stir overnight under balloon pressure. In the morning the balloon was removed and the flask flushed with $N_2$ to remove all $H_2$. The solution was filtered through celite and evaporated to afford the title compound of step A (1.49 g, 5.62 mmol, 92%); MS (ESI): 266 [M+H]$^+$.

Step B: N-(2,6-difluorophenyl)-2-(ethyloxy)-5-(3-{2-[(2-(methyloxy)-4-{4-[2-(methyloxy)ethyl]-1-piperazinyl}phenyl)amino]-4-pyrimidinyl}imidazo[1,2-a]pyridin-2-yl)benzamide 5-[3-(2-Chloro-4-pyrimidinyl)imidazo[1,2-a]pyridin-2-yl]-N-(2,6-difluorophenyl)-2-(ethyloxy)benzamide (Intermediate Example 6) (100 mg, 0.2 mmol), 2-(methyloxy)-4-{4-[2-(methyloxy)ethyl]-1-piperazinyl}aniline (47 mg, 0.18 mmol), and p-toluenesulfonicacid (90 mg, 0.47 mmol) were weighed into a 20 mL vial. 1 mL of trifluoroethanol was added and the mixture was heated to 100° C. for 72 h. 2 mL of 2 N ammonia in MeOH was added. The solvent was rotovaped down. The residue was taken up in 3 mL of DCM. 1 g of silica gel was added. The solvent was rotovaped down and the pre-absorbed solids were purified by flash chromatography to give the title compound (90 mg, 0.122 mmol, 69%). $^1$H NMR (400 MHz, DMSO-$d_6$) δ ppm 9.75 (s, 1H), 9.36 (s, 1H), 8.46 (s, 1H), 8.19 (d, J=5.13 Hz, 1H), 8.04 (d, J=1.83 Hz, 1H), 7.74 (dd, J=8.80, 2.20 Hz, 1H), 7.69 (d, J=9.17 Hz, 1H), 7.34-7.46 (m, 3H), 7.26 (d, J=8.43 Hz, 1H), 7.19 (t, J=8.07 Hz, 2H), 6.94 (t, J=6.78 Hz, 1H), 6.67 (d, J=2.20 Hz, 1H), 6.52 (d, J=5.13 Hz, 1H), 6.43-6.50 (m, 1H), 4.26 (q, J=6.97 Hz, 2H), 3.79 (s, 3H), 3.42-3.48 (m, 2H), 3.24 (s, 3H), 3.08-3.17 (m, 4H), 2.53-2.58 (m, 4H), 2.49-2.53 (m, 2H), 1.43 (t, J=6.97 Hz, 3H); MS (ESI): 735 [M+H]$^+$.

Example 239

N-(2,6-difluorophenyl)-2-(methyloxy)-5-(3-{2-[(2-(methyloxy)-4-{4-[2-(methyloxy)ethyl]-1-piperazinyl}phenyl)amino]-4-pyrimidinyl}imidazo[1,2-a]pyridin-2-yl)benzamide

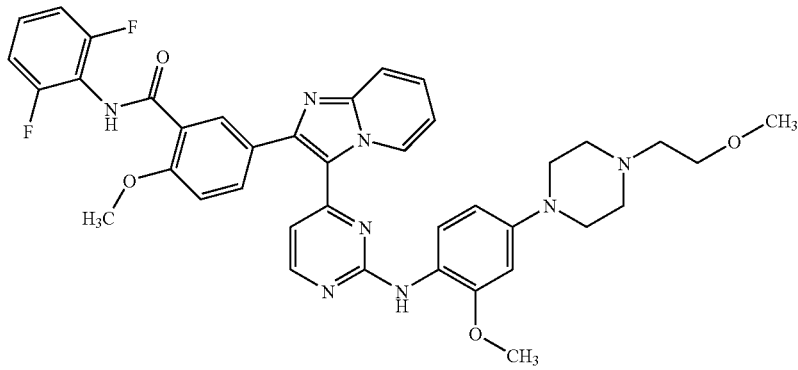

5-[3-(2-Chloro-4-pyrimidinyl)imidazo[1,2-a]pyridin-2-yl]-N-(2,6-difluorophenyl)-2-(methyloxy)benzamide (Intermediate Example 2) (100 mg, 0.2 mmol), 2-(methyloxy)-4-{4-[2-(methyloxy)ethyl]-1-piperazinyl}aniline (Example 238, step A) (48 mg, 0.18 mmol), and p-toluenesulfonicacid (93 mg, 0.49 mmol) were weighed into a 20 mL vial. 1 mL of trifluoroethanol was added and the mixture was heated to 100° C. for 72 h. 2 mL of 2 N ammonia in MeOH was added. The solvent was rotovaped down. The residue was taken up in 3 mL of DCM. 1 g of silica gel was added. The solvent was rotovaped down and the pre-absorbed solids were purified by flash chromatography to give the title compound (85 mg, 0.12 mmol, 64%). $^1$H NMR (400 MHz, DMSO-$d_6$) δ ppm 9.78 (s, 1H), 9.36 (s, 1H), 8.45 (s, 1H), 8.20 (d, J=5.50 Hz, 1H), 8.10 (d, J=2.20 Hz, 1H), 7.77 (dd, J=8.80, 2.20 Hz, 1H), 7.69 (d, J=9.17 Hz, 1H), 7.34-7.46 (m, 3H), 7.28 (d, J=8.80 Hz, 1H), 7.18 (t, J=8.07 Hz, 2H), 6.90-6.98 (m, 1H), 6.67 (d, J=2.57 Hz, 1H), 6.52 (d, J=5.13 Hz, 1H), 6.45-6.51 (m, 1H), 3.98 (s, 3H), 3.79 (s, 3H), 3.46 (t, J=5.87 Hz, 2H), 3.24 (s, 3H), 3.10-3.17 (m, 4H), 2.53-2.58 (m, 4H), 2.51 (t, J=5.87 Hz, 2H); MS (ESI): 721 [M+H]$^+$.

Example 240

N-(2,6-difluorophenyl)-3-(3-{2-[(2-(methyloxy)-4-{4-[2-(methyloxy)ethyl]-1-piperazinyl}phenyl)amino]-4-pyrimidinyl}imidazo[1,2-a]pyridin-2-yl)benzamide

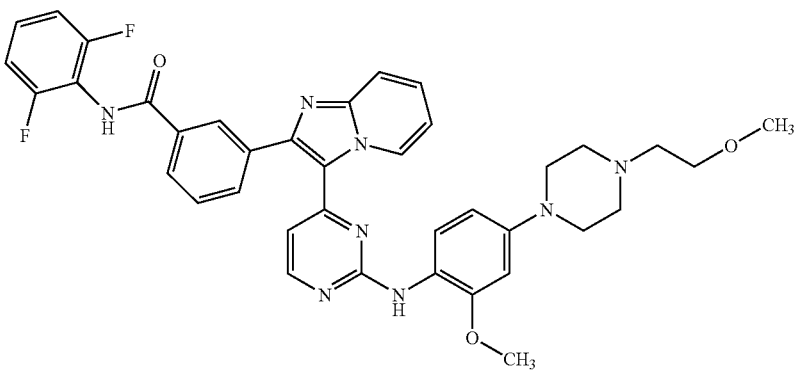

3-[3-(2-Chloro-4-pyrimidinyl)imidazo[1,2-a]pyridin-2-yl]-N-(2,6-difluorophenyl)benzamide (Intermediate Example 1) (100 mg, 0.22 mmol), 2-(methyloxy)-4-{4-[2-(methyloxy)ethyl]-1-piperazinyl}aniline (Example 238, step A) (51 mg, 0.194 mmol), and p-toluenesulfonicacid (99 mg, 0.52 mmol) were weighed into a 20 mL vial. 1 mL of trifluoroethanol was added and the mixture was heated to 100° C. for 72 h. 2 mL of 2 N ammonia in MeOH was added. The solvent was rotovaped down. The residue was taken up in 3 mL of DCM. 1 g of silica gel was added. The solvent was rotovaped down and the pre-absorbed solids were purified by flash chromatography to give the title compound (72 mg, 0.104 mmol, 53%). ¹H NMR (400 MHz, DMSO-d₆) δ ppm 10.24 (s, 1H), 9.40 (s, 1H), 8.47 (s, 1H), 8.33 (s, 1H), 8.20 (d, J=5.50 Hz, 1H), 8.05 (d, J=7.70 Hz, 1H), 7.81 (d, J=8.07 Hz, 1H), 7.72 (d, J=8.80 Hz, 1H), 7.61 (t, J=7.88 Hz, 1H), 7.43-7.49 (m, 1H), 7.35-7.43 (m, 2H), 7.17-7.24 (m, 2H), 6.97 (t, J=6.97 Hz, 1H), 6.67 (d, J=2.20 Hz, 1H), 6.46 (d, J=5.50 Hz, 2H), 3.79 (s, 3H), 3.46 (t, J=5.68 Hz, 2H), 3.24 (s, 3H), 3.09-3.16 (m, 4H), 2.53-2.58 (m, 4H), 2.51 (t, J=5.87 Hz, 2H); MS (ESI): 691 [M+H]⁺.

Example 241

N-(2,6-difluorophenyl)-2-(ethyloxy)-5-(3-{2-[(5-methyl-2-(methyloxy)-4-{4-[2-(methyloxy)ethyl]-1-piperazinyl}phenyl)amino]-4-pyrimidinyl}imidazo[1,2-a]pyridin-2-yl)benzamide 1-[2-methyl-5-(methyloxy)-4-nitrophenyl]-4-[2-(methyloxy)ethyl]piperazine (1.44 g, 4.66 mmol) was placed in a 100 mL high pressure vessel and dissolved in 60 mL of 1 to 1 EtOAc/MeOH. 5 wt % Platinum(sulfided)/C (1.09 g, 0.28 mmol) was added followed quickly by a rubber septum. The vial was evacuated and filled with N₂ six times to remove any oxygen. The vial was then pressurized with H₂ (60 psi). The solution stirred overnight. The next morning the vessel was evacuated and filled with N₂ six times to remove any H₂. The solution was filtered through celite and evaporated to afford the title compound of step B (1.15 g, 17.07 mmol, 88%). ¹H NMR (400 MHz, DMSO-d₆) δ ppm 6.56 (s, 1H), 6.42 (s, 1H), 4.30 (s, 2H), 3.70 (s, 3H), 3.43 (t, J=5.87 Hz, 2H), 3.23 (s, 3H), 2.71 (t, J=4.58 Hz, 4H), 2.45-2.56 (m, 6H), 2.04 (s, 3H)

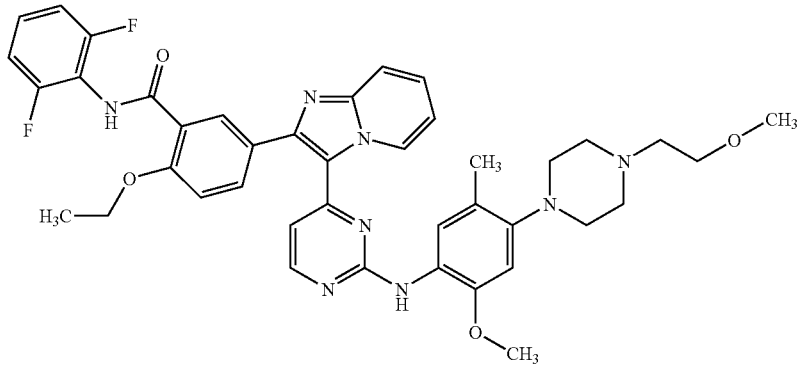

Step A: 1-[2-methyl-5-(methyloxy)-4-nitrophenyl]-4-[2-(methyloxy)ethyl]piperazine

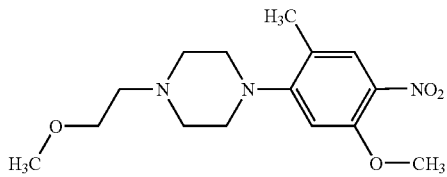

To 1-fluoro-2-methyl-5-(methyloxy)-4-nitrobenzene (prepared according to Example 113, Step B) (1 g, 5.4 mmol) in 10 mL of DMSO was added, 1-[2-(methyloxy)ethyl]piperazine (1 g, 7 mmol), and K₂CO₃ (1.27 g, 4.2 mmol). The mixture was heated to 130° C. for 24 h. The mixture was then poured into 100 mL of H₂O and extracted with EtOAc. The product was isolated by flash chromatography to give the title compound of step A (1.44 g, 4.65 mmol, 86%). ¹H NMR (400 MHz, DMSO-d₆) δ ppm 7.74 (s, 1H), 6.68 (s, 1H), 3.88 (s, 3H), 3.44 (t, J=5.68 Hz, 2H), 3.22 (s, 3H), 2.95-3.01 (m, 4H), 2.50-2.58 (m, 6H), 2.17 (s, 3H).

Step B: 5-methyl-2-(methyloxy)-4-{4-[2-(methyloxy)ethyl]-1-piperazinyl}aniline

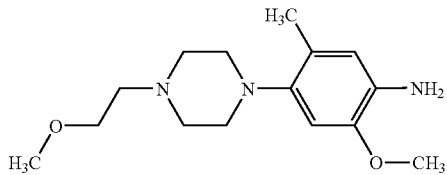

Step C: N-(2,6-difluorophenyl)-2-(ethyloxy)-5-(3-{2-[(5-methyl-2-(methyloxy)-4-{4-[2-(methyloxy)ethyl]-1-piperazinyl}phenyl)amino]-4-pyrimidinyl}imidazo[1,2-a]pyridin-2-yl)benzamide 5-[3-(2-Chloro-4-pyrimidinyl)imidazo[1,2-a]pyridin-2-yl]-N-(2,6-difluorophenyl)-2-(ethyloxy)benzamide (Intermediate Example 6) (200 mg, 0.4 mmol), 5-methyl-2-(methyloxy)-4-{4-[2-(methyloxy)ethyl]-1-piperazinyl}aniline (99 mg, 0.36 mmol) and p-toluenesulfonic acid (180 mg, 0.95 mmol) were weighed into a 20 mL vial. 2 mL of trifluoroethanol was added and the mixture was heated to 100° C. for 72 h. 2 mL of 2 N ammonia in MeOH was added. The solvent was rotovaped down. The residue was taken up in 3 mL of DCM. 1 g of silica gel was added. The solvent was rotovaped down and the pre-absorbed solids were purified by flash chromatography to give the title compound (150 mg, 0.2 mmol, 56%). ¹H NMR (400 MHz, DMSO-d₆) δ ppm 9.74 (s, 1H), 9.36 (s, 1H), 8.46 (s, 1H), 8.23 (d, J=5.13 Hz, 1H), 8.04 (d, J=1.83 Hz, 1H), 7.74 (dd, J=8.43, 2.20 Hz, 1H), 7.69 (d, J=9.17 Hz, 1H), 7.49 (s, 1H), 7.41-7.47 (m, 1H), 7.34-7.41 (m, 1H), 7.26 (d, J=8.43 Hz, 1H), 7.19 (t, J=8.07 Hz, 2H), 6.95 (t, J=6.97 Hz, 1H), 6.77 (s, 1H), 6.55 (d, J=5.13 Hz, 1H), 4.26 (q, J=6.84 Hz, 2H), 3.80 (s, 3H), 3.42-3.48 (m, 2H), 3.24 (s, 3H), 2.86 (t, J=4.40 Hz, 4H), 2.50-2.61 (m, 6H), 2.14 (s, 3H), 1.43 (t, J=6.97 Hz, 3H); MS (ESI): 749 [M+H]⁺.

Example 242

N-(2,6-difluorophenyl)-5-(3-{2-[(5-methyl-2-(methyloxy)-4-{4-[2-(methyloxy)ethyl]-1-piperazinyl}phenyl)amino]-4-pyrimidinyl}imidazo[1,2-a]pyridin-2-yl)-2-(methyloxy)benzamide

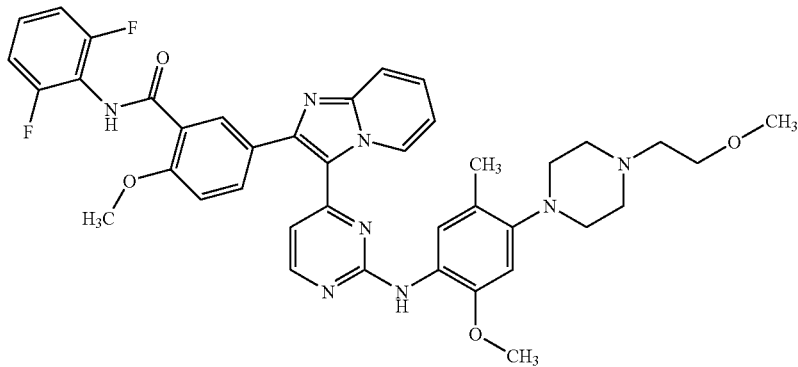

5-[3-(2-Chloro-4-pyrimidinyl)imidazo[1,2-a]pyridin-2-yl]-N-(2,6-difluorophenyl)-2-(methyloxy)benzamide (Intermediate Example 2) (200 mg, 0.4 mmol), 5-methyl-2-(methyloxy)-4-{4-[2-(methyloxy)ethyl]-1-piperazinyl}aniline (Example 241, step B) (102 mg, 0.37 mmol) and p-toluenesulfonicacid (185 mg, 0.98 mmol) were weighed into a 20 mL vial. 2 mL of trifluoroethanol was added and the mixture was heated to 100° C. for 72 h. 2 mL of 2 N ammonia in MeOH was added. The solvent was rotovaped down. The residue was taken up in 3 mL of DCM. 1 g of silica gel was added. The solvent was rotovaped down and the pre-absorbed solids were purified by flash chromatography to give the title compound (125 mg, 0.17 mmol, 47%). $^1$H NMR (400 MHz, DMSO-$d_6$) δ ppm 9.75 (s, 1H), 9.33 (s, 1H), 8.43 (s, 1H), 8.20 (d, J=5.31 Hz, 1H), 8.07 (d, J=1.83 Hz, 1H), 7.74 (dd, J=8.70, 1.74 Hz, 1H), 7.66 (d, J=8.97 Hz, 1H), 7.45 (s, 1H), 7.33-7.45 (m, 2H), 7.25 (d, J=8.79 Hz, 1H), 7.15 (t, J=8.06 Hz, 2H), 6.89-6.95 (m, 1H), 6.74 (s, 1H), 6.53 (d, J=5.13 Hz, 1H), 3.95 (s, 3H), 3.76 (s, 3H), 3.43 (t, J=5.77 Hz, 2H), 3.21 (s, 3H), 2.83 (t, J=4.40 Hz, 4H), 2.47-2.58 (m, 6H), 2.11 (s, 3H); MS (ESI): 735 [M+H]$^+$.

Example 243

N-(2,6-difluorophenyl)-3-(3-{2-[(5-methyl-2-(methyloxy)-4-{4-[2-(methyloxy)ethyl]-1-piperazinyl}phenyl)amino]-4-pyrimidinyl}imidazo[1,2-a]pyridin-2-yl)benzamide

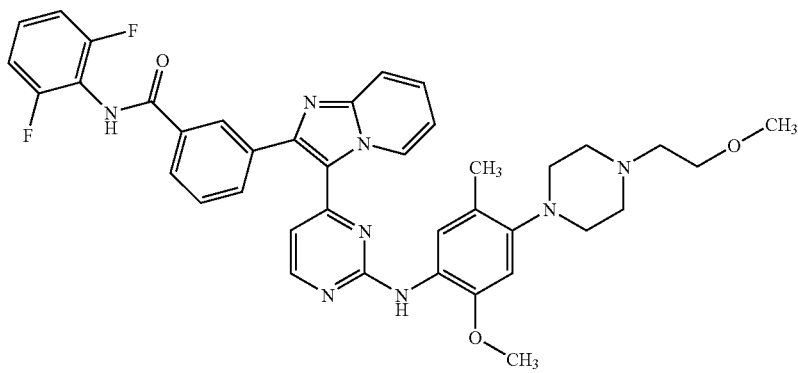

3-[3-(2-Chloro-4-pyrimidinyl)imidazo[1,2-a]pyridin-2-yl]-N-(2,6-difluorophenyl)benzamide (Intermediate Example 1) (200 mg, 0.43 mmol), 5-methyl-2-(methyloxy)-4-{4-[2-(methyloxy)ethyl]-1-piperazinyl}aniline (Example 241, step B) (108 mg, 0.39 mmol) and p-toluenesulfonicacid (197 mg, 0.95 mmol) were weighed into a 20 mL vial. 2 mL of trifluoroethanol was added and the mixture was heated to 100° C. for 24 h. 2 mL of 2 N ammonia in MeOH was added. The solvent was rotovaped down. The residue was taken up in 3 mL of DCM. 1 g of silica gel was added. The solvent was rotovaped down and the pre-absorbed solids were purified by flash chromatography to give the title compound (125 mg, 0.18 mmol, 46%). $^1$H NMR (400 MHz, DMSO-d$_6$) δ ppm 10.23 (s, 1H), 9.40 (s, 1H), 8.48 (s, 1H), 8.33 (s, 1H), 8.23 (d, J=5.13 Hz, 1H), 8.05 (d, J=7.70 Hz, 1H), 7.82 (d, J=8.07 Hz, 1H), 7.73 (d, J=9.16 Hz, 1H), 7.60 (t, J=7.70 Hz, 1H), 7.45-7.50 (m, 2H), 7.40 (tt, J=8.43, 6.23 Hz, 1H), 7.14-7.24 (m, 2H), 6.98 (t, J=6.97 Hz, 1H), 6.78 (s, 1H), 6.49 (d, J=5.13 Hz, 1H), 3.79 (s, 3H), 3.46 (t, J=5.87 Hz, 2H), 3.24 (s, 3H), 2.86 (t, J=4.58 Hz, 4H), 2.50-2.62 (m, 6H), 2.14 (s, 3H); MS (ESI): 705 [M+H]$^+$. 1H), 3.79 (s, 3H), 3.46 (t, J=5.87 Hz, 2H), 3.24 (s, 3H), 2.86 (t, J=4.58 Hz, 4H), 2.50-2.62 (m, 6H), 2.14 (s, 3H); MS (ESI): 705 [M+H]$^+$.

Example 244

N-(2,6-difluorophenyl)-3-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide A mixture of 3-[3-(2-chloro-4-pyrimidinyl)imidazo[1,2-a]pyridin-2-yl]-N-(2,6-difluorophenyl)benzamide (Intermediate Example 1) (0.050 g, 0.11 mmol), 5-ethyl-2-(methyloxy)-4-{4-[4-(methylsulfonyl)-1-piperazinyl]-1-piperidinyl}aniline (Example 206, Step B) (0.043 g, 0.11 mmol) and para-toluenesulfonic acid (0.049 g, 0.26 mmol) in i-PrOH (5 mL) was heated in a microwave at 175° C. for 20 min. The reaction mixture was concentrated onto silica gel and purified by flash chromatography to afford the title compound (0.031 g, 35%). $^1$H NMR (400 MHz, DMSO-d$_6$) δ ppm 9.80 (s, 1H), 9.36 (br. s., 1H), 8.50 (s, 1H), 8.26 (d, J=5.22 Hz, 1H), 8.12 (d, J=2.11 Hz, 1H), 7.80 (dd, J=8.80, 2.02 Hz, 1H), 7.71 (d, J=9.07 Hz, 1H), 7.53 (s, 1H), 7.36-7.50 (m, 2H), 7.30 (d, J=8.80 Hz, 1H), 7.14-7.25 (m, 2H), 6.91-7.00 (m, 1H), 6.83 (s, 1H), 6.58 (d, J=5.22 Hz, 1H), 4.00 (s, 3H), 3.80 (s, 3H), 3.08-3.15 (m, 4H), 3.00-3.07 (m, 2H), 2.88 (s, 3H), 2.67-2.76 (m, 2H), 2.61-2.66 (m, 4H), 2.56 (q, J=7.51 Hz, 2H), 2.38-2.46 (m, 1H), 1.80-1.91 (m, 2H), 1.50-1.68 (m, 2H), 1.11 (t, J=7.51 Hz, 3H). MS (M–H, ES–) 820.

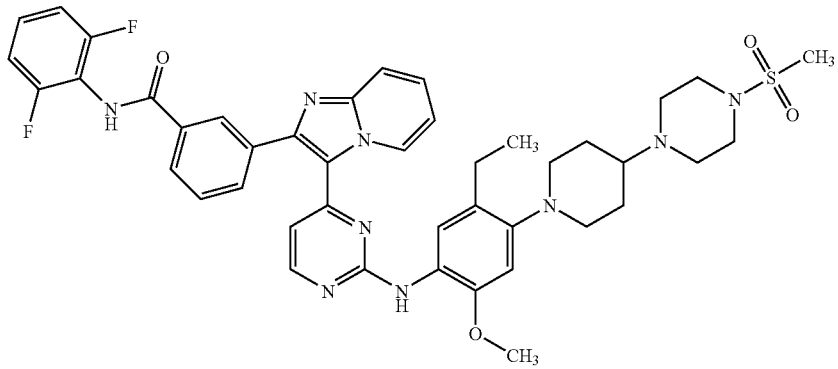

Example 245

N-(2,6-difluorophenyl)-3-(3-{2-[(5-methyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide

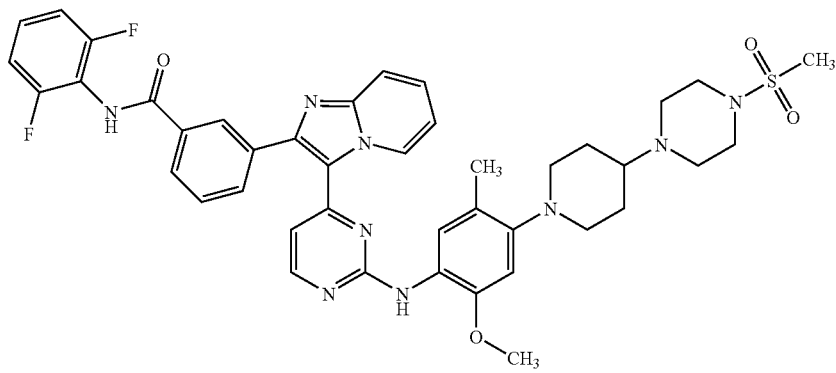

A mixture of 3-[3-(2-chloro-4-pyrimidinyl)imidazo[1,2-a]pyridin-2-yl]-N-(2,6-difluorophenyl)benzamide (Intermediate Example 1) (0.050 g, 0.11 mmol), 5-methyl-2-(methyloxy)-4-{4-[4-(methylsulfonyl)-1-piperazinyl]-1-piperidinyl}aniline (Example 236, Step B) (0.041 g, 0.11 mmol) and para-toluenesulfonic acid (0.049 g, 0.26 mmol) in i-PrOH (5 mL) was heated in a microwave at 175° C. for 20 min. The reaction mixture was concentrated onto silica gel and purified by flash chromatography to afford the title compound (0.031 g, 35%). $^1$H NMR (400 MHz, DMSO-$d_6$) δ ppm 10.24 (s, 1H), 9.42 (br. s., 1H), 8.48 (s, 1H), 8.34 (s, 1H), 8.25 (d, J=5.1 Hz, 1H), 8.06 (d, J=8.1 Hz, 1H), 7.83 (d, J=7.8 Hz, 1H), 7.75 (d, J=8.9 Hz, 1H), 7.62 (t, J=7.7 Hz, 1H), 7.34-7.55 (m, 3H), 7.17-7.29 (m, 2H), 6.95-7.06 (m, 1H), 6.77 (s, 1H), 6.51 (d, J=5.2 Hz, 1H), 3.80 (s, 3H), 3.05-3.17 (m, 6H), 2.88 (s, 3H), 2.59-2.73 (m, 6H), 2.38-2.46 (m, 1H), 2.16 (s, 3H), 1.81-1.90 (m, 2H), 1.53-1.68 (m, 2H). MS (M−H, ES−) 806.

Example 246

N-(2,6-difluorophenyl)-3-(3-{2-[(2-(ethyloxy)-5-methyl-4-{4-[2-(methylsulfonyl)ethyl]-1-piperazinyl}phenyl)amino]-4-pyrimidinyl}imidazo[1,2-a]pyridin-2-yl)benzamide

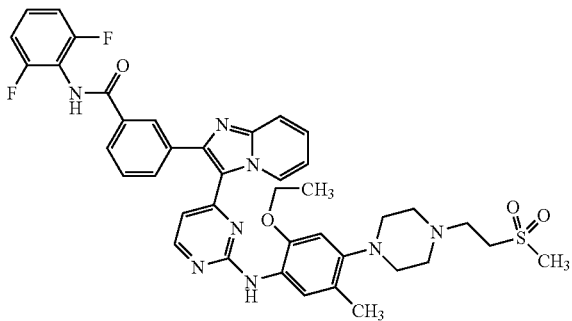

To 3-[3-(2-chloro-4-pyrimidinyl)imidazo[1,2-a]pyridin-2-yl]-N-(2,6-difluorophenyl)benzamide (Intermediate Example 1) (100 mg, 0.217 mmol) and (5-methyl-2-(ethyloxy)-4-{4-[2-(methylsulfonyl)ethyl]-1-piperazinyl}phenyl)amine (Example 248, Step B) (100 mg, 0.293 mmol) in trifluoroethanol (5 mL) was added p-toluene sulfonic acid (100 mg, 0.526 mmol), and the vial was sealed and heated to 80° C. overnight. The reaction was then cooled to rt and silica was added. The solvent was removed on a rotovap and the product purified on a 12 g ISCO column. Desired fractions were combined and rotovaped down. The resulting foam was dissolved in DCM and ether was added to provide the title compound (25 mg, 0.032 mmol, 15%) as a yellow solid. $^1$H NMR (400 MHz, DMSO-$d_6$) δ ppm 10.19 (s, 1H), 9.36 (d, J=7.5 Hz, 1H), 8.33 (s, 1H), 8.31 (s, 1H), 8.23 (d, J=5.1 Hz, 1H), 8.01 (d, J=7.8 Hz, 1H), 7.78 (d, J=7.9 Hz, 1H), 7.71 (d, J=9.0 Hz, 1H), 7.60-7.51 (m, 2H), 7.48-7.32 (m, 2H), 7.17 (t, J=8.1 Hz, 2H), 6.95 (t, J=6.3 Hz, 1H), 6.71 (s, 1H), 6.50 (d, J=5.1 Hz, 1H), 4.03 (q, J=7.2 Hz, 2H), 3.36-3.24 (m, 2H), 3.03 (s, 3H), 2.86-2.79 (m, 4H), 2.74 (t, J=7.0 Hz, 2H), 2.64-2.50 (m, 4H), 2.10 (s, 3H), 1.22 (t, J=7.0 Hz, 3H). MS (ESI) m/z=384 [M+2H]$^{+2}$.

Example 247

N-(2,6-difluorophenyl)-5-(3-{2-[(2-(ethyloxy)-5-methyl-4-{4-[2-(methylsulfonyl)ethyl]-1-piperazinyl}phenyl)amino]-4-pyrimidinyl}imidazo[1,2-a]pyridin-2-yl)-2-(methyloxy)benzamide

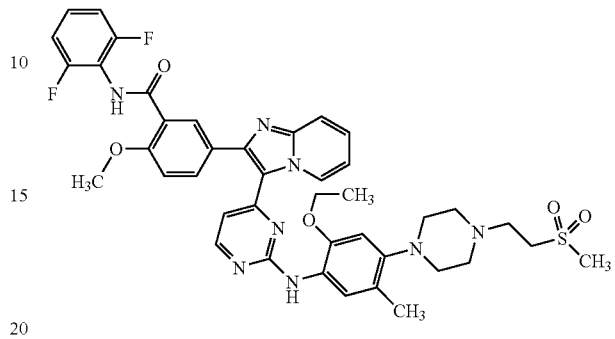

To 5-[3-(2-Chloro-4-pyrimidinyl)imidazo[1,2-a]pyridin-2-yl]-N-(2,6-difluorophenyl)-2-(methyloxy)benzamide (Intermediate Example 2) (200 mg, 0.407 mmol) and (5-methyl-2-(ethyloxy)-4-{4-[2-(methylsulfonyl)ethyl]-1-piperazinyl}phenyl)amine (200 mg, 0.586 mmol) (Example 248, Step B) in trifluoroethanol (10 mL) was added p-toluene sulfonic acid (200 mg, 1.05 mmol), and the vial was sealed and heated to 80° C. overnight. The reaction was then cooled to rt and silica was added. The solvent was removed on a rotovap and the product purified on a 12 g ISCO column. Desired fractions were combined and rotovaped down. The resulting foam was dissolved in DCM and ether was added to provide the title compound (100 mg, 0.125 mmol, 31%) as a yellow solid. 1H NMR (400 MHz, DMSO-$d_6$) δ ppm 9.74 (s, 1H), 9.33 (d, J=7.1 Hz, 1H), 8.32 (s, 1H), 8.23 (d, J=5.3 Hz, 1H), 8.08 (s, 1H), 7.75 (d, J=8.4 Hz, 1H), 7.67 (d, J=8.6 Hz, 1H), 7.53 (s, 1H), 7.43-7.33 (m, 2H), 7.25 (d, J=8.4 Hz, 1H), 7.15 (t, J=8.0 Hz, 2H), 6.92 (t, J=6.9 Hz, 1H), 6.71 (s, 1H), 6.56 (d, J=5.3 Hz, 1H), 4.03 (q, J=6.8 Hz, 2H), 3.95 (s, 3H), 3.36-3.25 (m, 2H), 3.03 (s, 3H), 2.86-2.78 (m, 4H), 2.74 (t, J=6.7 Hz, 2H), 2.63-2.50 (m, 4H), 2.11 (s, 3H), 1.22 (t, J=7.0 Hz, 3H). MS (ESI) m/z=398 [M+2H]$^{+2}$.

Example 248

N-(2,6-difluorophenyl)-2-(ethyloxy)-5-(3-{2-[(2-(ethyloxy)-5-methyl-4-{4-[2-(methylsulfonyl)ethyl]-1-piperazinyl}phenyl)amino]-4-pyrimidinyl}imidazo[1,2-a]pyridin-2-yl)benzamide

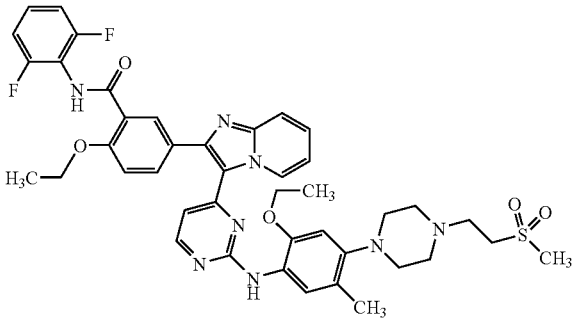

Step A: 1-[2-methyl-5-(ethyloxy)-4-nitrophenyl]-4-[2-(methylsulfonyl)ethyl]piperazine

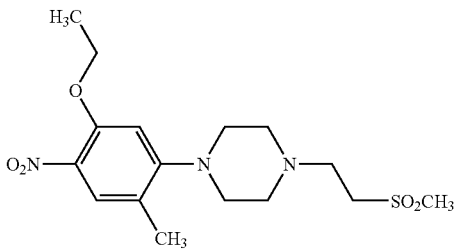

1-Methyl-2-fluoro-4-(ethyloxy)-5-nitrobenzene (Example 215, step A) (5.74 g, 28.8 mmol) was dissolved in DMSO (60 mL). $K_2CO_3$ (11.9 g, 86.4 mmol) and 1-[2-(methylsulfonyl)ethyl]piperazine hydrochloride (Example 148, step B) (9.85 g, 43.2 mmol) were added and the reaction mixture was heated to 100° C. and allowed to stir overnight. The mixture was cooled to rt then diluted with DCM and filtered. The filtrate was poured into $H_2O$ and extracted with DCM. The combined organics were dried with $MgSO_4$, filtered, and concentrated in vacuo to give the title compound of Step A (9.70 g, 26.1 mmol, 90%) as an orange solid. $^1$H NMR (400 MHz, $CDCl_3$) δ 7.75 (s, 1H), 6.51 (s, 1H), 4.11 (q, J=7.0 Hz, 2H), 3.16 (t, J=6.5 Hz, 2H), 3.03 (s, 3H), 3.00-2.91 (m, 6H), 2.72-2.62 (m, 4H), 2.21 (s, 3H), 1.44 (t, J=7.0 Hz, 3H).

Step B: 5-Methyl-2-(ethyloxy)-4-{4-[2-(methylsulfonyl)ethyl]-1-piperazinyl}aniline

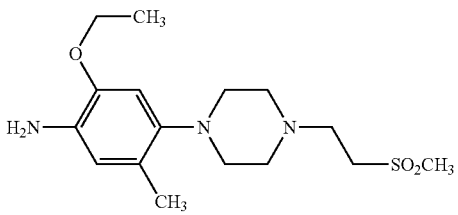

1-[2-Methyl-5-(ethyloxy)-4-nitrophenyl]-4-[2-(methylsulfonyl)ethyl]piperazine (9.7 g, 26 mmol) was taken up in EtOH (100 mL). The catalyst, 5% sulfided platinum on carbon (1.0 g) was added. The reaction was placed under 1 atm of $H_2$ gas and was allowed to stir at rt overnight. The catalyst was filtered off and the filtrate was concentrated onto silica in vacuo. The product was purified on a 120 g ISCO column (DCM to 2% (2N $NH_3$ in MeOH) to give the title compound of Step B (1.9 g, 5.7 mmol, 22%) as a pale orange oil. The mixed fractions (product and starting material) were resubmitted to the above conditions to provide additional product (5.2 g, 15 mmol, 58%). $^1$H NMR (400 MHz, $CDCl_3$) δ 6.53 (s, 1H), 6.52 (s, 1H), 3.99 (q, J=7.0 Hz, 2H), 3.56 (s, 2H), 3.15 (t, J=6.3 Hz, 2H), 3.05 (s, 3H), 2.91 (t, J=6.4 Hz, 2H), 2.84-2.78 (m, 4H), 2.67-2.54 (m, 4H), 2.13 (s, 3H), 1.38 (t, J=7.0 Hz, 3H).

Step C: N-(2,6-difluorophenyl)-2-(ethyloxy)-5-(3-{2-[(2-(ethyloxy)-5-methyl-4-{4-[2-(methylsulfonyl)ethyl]-1-piperazinyl}phenyl)amino]-4-pyrimidinyl}imidazo[1,2-a]pyridin-2-yl)benzamide To 5-[3-(2-chloro-4-pyrimidinyl)imidazo[1,2-a]pyridin-2-yl]-N-(2,6-difluorophenyl)-2-(ethyloxy)benzamide (Intermediate Example 6) (2.9 g, 5.7 mmol) and (5-methyl-2-(ethyloxy)-4-{4-[2-(methylsulfonyl)ethyl]-1-piperazinyl}phenyl)amine (2.0 g, 5.7 mmol) in trifluoroethanol (100 mL) was added p-toluene sulfonic acid (2.2 g, 11 mmol), and the vial was sealed and heated to 80° C. overnight. The reaction was then cooled to rt and excess 0.5 M NaOMe in MeOH was added. The solution was transferred to a roundbottom flask and silica was added. The solvent was removed on a rotovap and the product purified on a 120 g ISCO column. Desired fractions were combined and rotovaped down. The resulting foam was dissolved in DCM and ether was added to provide the title compound 2.5 g, 3.1 mmol, 54% yield) as a yellow solid. $^1$H NMR (400 MHz, DMSO-$d_6$) δ ppm 9.71 (s, 1H), 9.33 (d, J=6.7 Hz, 1H), 8.32 (s, 1H), 8.23 (d, J=5.4 Hz, 1H), 8.02 (s, 1H), 7.73-7.70 (m, 1H), 7.67 (d, J=9.0 Hz, 1H), 7.53 (s, 1H), 7.43-7.31 (m, 2H), 7.23 (d, J=8.6 Hz, 1H), 7.16 (t, J=8.0 Hz, 2H), 6.92 (t, J=6.6 Hz, 1H), 6.71 (s, 1H), 6.56 (d, J=5.1 Hz, 1H), 4.23 (q, J=7.2 Hz, 2H), 4.04 (q, J=7.0 Hz, 2H), 3.33-3.25 (m, 2H), 3.03 (s, 3H), 2.84-2.78 (m, 4H), 2.74 (t, J=6.6 Hz, 2H), 2.63-2.46 (m, 4H), 2.11 (s, 3H), 1.40 (t, J=6.8 Hz, 3H), 1.23 (t, J=7.0 Hz, 3H). MS (ESI) m/z=811 [M+H]$^+$.

Example 249

N-(2,6-difluorophenyl)-5-(3-{2-[(2-(ethyloxy)-5-methyl-4-{4-[2-(methylsulfonyl)ethyl]-1-piperazinyl}phenyl)amino]-4-pyrimidinyl}imidazo[1,2-a]pyridin-2-yl)-2-[(1-methylethyl)oxy]benzamide

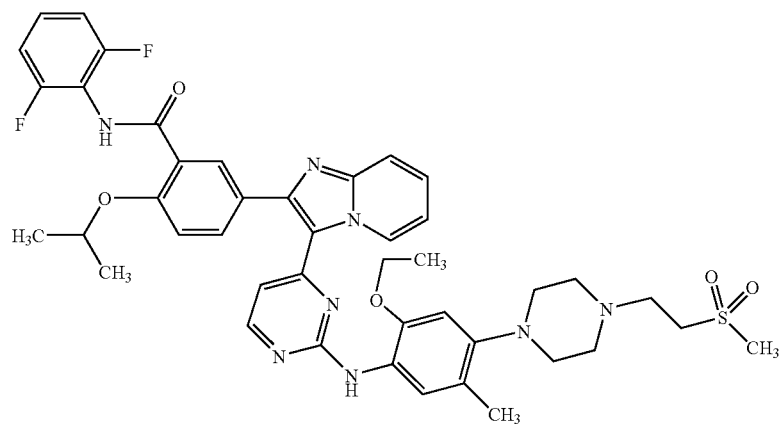

To 5-[3-(2-chloro-4-pyrimidinyl)imidazo[1,2-a]pyridin-2-yl]-N-(2,6-difluorophenyl)-2-[(1-methylethyl)oxy]benzamide (Intermediate Example 7) (200 mg, 0.385 mmol) and (5-methyl-2-(ethyloxy)-4-{4-[2-(methylsulfonyl)ethyl]-1-piperazinyl}phenyl)amine (Example 248, Step B) (200 mg, 0.586 mmol) in trifluoroethanol (10 mL) was added p-toluene sulfonic acid (200 mg, 1.05 mmol), and the vial was sealed and heated to 80° C. overnight. The reaction was then cooled to rt and silica was added. The solvent was removed on a rotovap and the product purified on a 12 g ISCO column. Desired fractions were combined and rotovaped down. The resulting foam was dissolved in DCM and ether was added to provide the title compound (110 mg, 0.133 mmol, 35%) as a yellow solid. $^1$H NMR (400 MHz, DMSO-d$_6$) δ 9.70 (s, 1H), 9.34 (d, J=7.0 Hz, 1H), 8.35 (s, 1H), 8.27 (d, J=5.2 Hz, 1H), 8.07 (s, 1H), 7.75-7.73 (m, 1H), 7.70 (d, J=8.8 Hz, 1H), 7.56 (s, 1H), 7.46-7.34 (m, 2H), 7.29 (d, J=8.8 Hz, 1H), 7.19 (t, J=8.0 Hz, 2H), 6.95 (t, J=7.1 Hz, 1H), 6.74 (s, 1H), 6.61 (d, J=5.2 Hz, 1H), 4.91-4.81 (m, 1H), 4.08 (q, J=7.0 Hz, 2H), 3.39-3.28 (m, 2H), 3.06 (s, 3H), 2.88-2.81 (m, 4H), 2.77 (t, J=6.8 Hz, 2H), 2.67-2.53 (m, 4H), 2.13 (s, 3H), 1.39 (d, J=5.8 Hz, 6H), 1.25 (t, J=7.0 Hz, 3H). MS (ESI) m/z=412 [M+ 2H]$^{+2}$.

Example 250

N-(2,6-difluorophenyl)-5-[3-(2-{[4-{(3S)-3-(1-methylethyl)-4-[2-(methylsulfonyl)ethyl]-1-piperazinyl}-2-(methyloxy)phenyl]amino}-4-pyrimidinyl)imidazo[1,2-a]pyridin-2-yl]-2-(methyloxy)benzamide

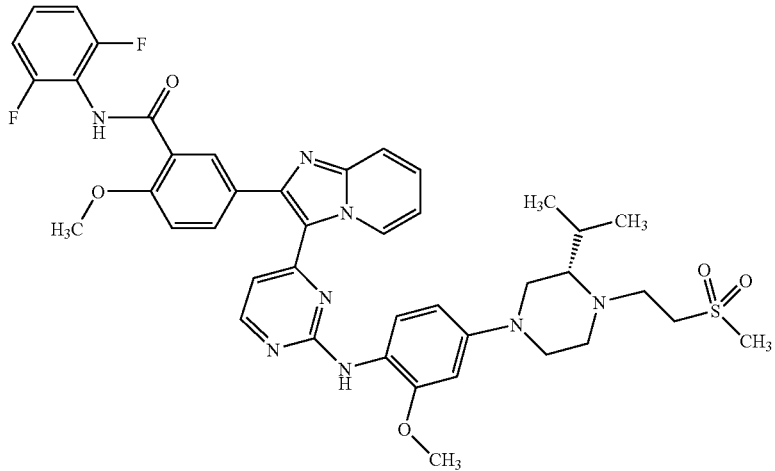

Step A: (5S)-5-(1-methylethyl)-1-(phenylmethyl)-2,3-piperazinedione

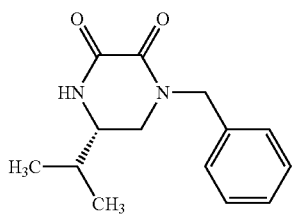

[(2S)-2-Amino-3-methylbutyl](phenylmethyl)amine (Katritzky, A. R. *Tetrahedron: Asymmetry* 2002, 13, 933-938) (2.57 g, 13.4 mmol) was dissolved in 100 mL of EtOH with stirring. Diethyl oxalate (1.82 mL, 13.4 mmol) was added via syringe. The mixture was heated to reflux for 3.5 days and subsequently cooled to rt. The mixture was concentrated in vacuo. Purification by flash chromatography afforded the title compound of step A (2.43 g, 9.87 mmol, 74%). $^1$H NMR (400 MHz, DMSO-d$_6$) δ 8.74 (br. s, 1H), 7.38-7.24 (m, 5H), 4.54 (AB, Δν$_{AB}$=88.7 Hz, J$_{AB}$=14.7 Hz, 2H), 3.48 (dd, J=13.2, 4.2 Hz, 1H), 3.31 (dd, J=13.2, 6.2 Hz, 1H), 3.17 (m, 1H), 1.61 (m, 1H), 0.82 (d, J=6.8 Hz, 3H), 0.63 (d, J=6.8 Hz, 3H).

Step B: (3S)-3-(1-methylethyl)-1-(phenylmethyl)piperazine

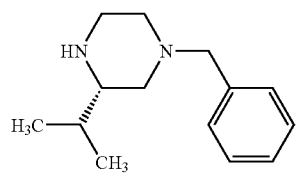

LAH (1.87 g, 49.3 mmol) was suspended in 60 mL of THF with stirring and cooled to 0° C. under an inert atmosphere. (5S)-5-(1-methylethyl)-1-(phenylmethyl)-2,3-piperazinedione (2.43 g, 9.87 mmol) was dissolved in 50 mL of THF and added dropwise via addition funnel over 20 min. The funnel was rinsed with an additional 10 mL of THF. The reaction was warmed to rt and stirred for 2 days. The reaction was quenched by the careful sequential addition of 1.9 mL of H$_2$O, 1.9 mL of 1N NaOH (aq.), and 5.7 mL of H$_2$O. The slurry was stirred for 30 min and filtered. The solids were washed with DCM. The filtrate was concentrated in vacuo. Purification by flash chromatography afforded the title compound of step B (1.68 g, 7.69 mmol, 78%). $^1$H NMR (400 MHz, DMSO-d$_6$) δ 7.33-7.18 (m, 5H), 3.40 (AB, Δν$_{AB}$=34.5 Hz, J$_{AB}$=13.2 Hz, 2H), 2.78 (m, 1H), 2.71-2.51 (m, 3H), 2.28 (m, 1H), 1.88-1.72 (m, 2H), 1.63 (t, J=10.3 Hz, 1H), 1.45 (m, 1H), 0.83 (d, J=6.8 Hz, 3H), 0.79 (d, J=6.8 Hz, 3H).

Step C: 1,1-dimethylethyl (2S)-2-(1-methylethyl)-1-piperazinecarboxylate

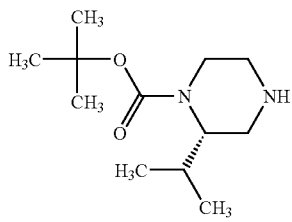

(3S)-3-(1-Methylethyl)-1-(phenylmethyl)piperazine (1.68 g, 7.69 mmol) was dissolved in 75 mL of DCM with stirring. Di-t-butyl dicarbonate (2.01 g, 9.21 mmol) was added, and the reaction was stirred for 24 h. The mixture was concentrated in vacuo. Purification by flash chromatography afforded the desired compound, which was carried on to the next step. The compound was dissolved in 70 mL of EtOH with stirring. Approximately 10 drops of acetic acid was added. 10% Palladium on carbon (0.409 g, 0.384 mmol) was added, and the mixture was placed under 1 atm of $H_2$ using a balloon. The reaction was stirred overnight, and subsequently filtered through celite, washing with MeOH. The filtrate was concentrated in vacuo. Purification by flash chromatography afforded the title compound of step C (1.58 g, 6.92 mmol, 90%). $^1$H NMR (400 MHz, DMSO-$d_6$) δ 3.65 (m, 1H), 3.38 (m, 1H), 2.88 (d, J=12.6 Hz, 1H), 2.72 (d, J=11.5 Hz, 1H), 2.67 (m, 1H), 2.48-2.33 (m, 3H), 2.25 (m, 1H), 1.33 (s, 9H), 0.83 (d, J=6.6 Hz, 3H), 0.72 (d, J=6.8 Hz, 3H).

Step D: 1,1-dimethylethyl (2S)-2-(1-methylethyl)-4-[3-(methyloxy)-4-nitrophenyl]-1-piperazinecarboxylate

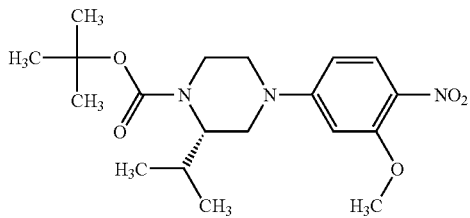

4-Fluoro-2-(methyloxy)-1-nitrobenzene (Example 22, step A) (0.429 g, 2.51 mmol), and $K_2CO_3$ (0.410 g, 2.97 mmol) were placed in a flask with 14 mL of DMSO and stirred with a stir bar. 1,1-Dimethylethyl (2S)-2-(1-methylethyl)-1-piperazinecarboxylate (0.521 g, 2.28 mmol) was dissolved in 6.6 mL of THF and added via syringe. The mixture was stirred for 8 days and poured into $H_2O$ and EtOAc. The layers were separated, and the organic layer was washed with brine. The combined aqueous layers were extracted with EtOAc. The combined organic layers were dried over $MgSO_4$, filtered, and concentrated in vacuo. Purification by flash chromatography afforded the title compound of step D (0.515 g, 1.36 mmol, 60%). $^1$H NMR (400 MHz, DMSO-$d_6$) δ 7.84 (d, J=9.3 Hz, 1H), 6.54 (dd, J=9.4, 2.3 Hz, 1H), 6.43 (d, J=2.4 Hz, 1H), 4.01 (d, J=13.5 Hz, 1H), 3.86 (s, 5H), 3.60-3.75 (m, 1H), 3.22-3.28 (m, 1H), 3.06 (dd, J=13.6, 3.7 Hz, 1H), 2.90-3.02 (m, 1H), 1.79-1.92 (m, 1H), 1.37 (s, 9H), 0.92 (d, J=6.6 Hz, 3H), 0.75 (d, J=6.8 Hz, 3H).

Step E: (3S)-3-(1-methylethyl)-1-[3-(methyloxy)-4-nitrophenyl]piperazine

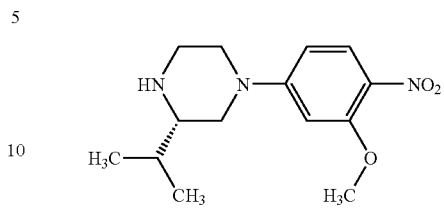

1,1-Dimethylethyl (2S)-2-(1-methylethyl)-4-[3-(methyloxy)-4-nitrophenyl]-1-piperazinecarboxylate (0.482 g, 1.27 mmol) was dissolved in 20 mL of DCM with stirring. TFA (4.0 mL, 52 mmol) was added, and the reaction was stirred for 4 h. The reaction was cooled to 0° C. and slowly quenched with 40 mL of 3N NaOH (aq.). The mixture was poured into $H_2O$ and DCM, and the layers were separated. The aqueous layer was washed with DCM. The combined organic layers were dried over $MgSO_4$, filtered, and concentrated in vacuo to afford the title compound of step E (0.356 g, 1.27 mmol, 100%). $^1$H NMR (400 MHz, DMSO-$d_6$) δ 7.86 (d, J=9.5 Hz, 1H), 6.57 (dd, J=9.5, 2.6 Hz, 1H), 6.46 (d, J=2.6 Hz, 1H), 3.88 (s, 3H), 3.77-3.86 (m, 2H), 2.93-3.02 (m, 1H), 2.82 (td, J=11.9, 3.3 Hz, 1H), 2.54-2.71 (m, 2H), 2.29-2.39 (m, 1H), 2.22 (br. s., 1H), 1.55-1.67 (m, 1H), 0.94 (d, J=6.8 Hz, 3H), 0.92 (d, J=6.8 Hz, 3H).

Step F: (2S)-2-(1-methylethyl)-4-[3-(methyloxy)-4-nitrophenyl]-1-[2-(methylsulfonyl)-ethyl]piperazine

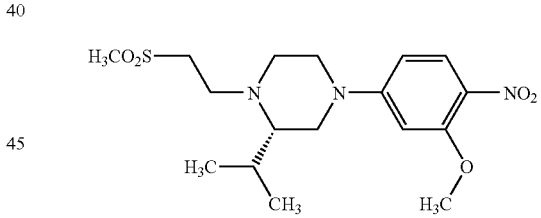

(3S)-3-(1-Methylethyl)-1-[3-(methyloxy)-4-nitrophenyl] piperazine (0.355 g, 1.27 mmol) was dissolved in 15 mL of dioxane with stirring. Methyl vinyl sulfone (0.34 mL, 3.88 mmol) was added via syringe. The reaction was heated to 60° C. for 2.5 days. Additional methyl vinyl sulfone (0.68 mL, 7.76 mmol) was added, and the heat was increased to 90° C. The reaction was maintained at that temperature for one week. The reaction was cooled to rt and concentrated onto silica gel. Purification by flash chromatography afforded the title compound of step G (0.383 g, 0.994 mmol, 78%). $^1$H NMR (400 MHz, DMSO-$d_6$) δ 7.84 (d, J=9.5 Hz, 1H), 6.53 (dd, J=9.5, 2.4 Hz, 1H), 6.40 (d, J=2.4 Hz, 1H), 3.86 (s, 3H), 3.77 (d, J=12.5 Hz, 1H), 3.66 (br. s., J=12.5 Hz, 1H), 3.28-3.39 (m, 1H), 3.13-3.24 (m, 1H), 3.00-3.13 (m, 2H), 2.88-3.00 (m, 5H), 2.77-2.88 (m, 1H), 2.39-2.51 (m, 1H), 2.17-2.26 (m, 1H), 1.93-2.07 (m, 1H), 0.96 (d, J=6.8 Hz, 3H), 0.85 (d, J=6.8 Hz, 3H).

Step G: 4-{(3S)-3-(1-methylethyl)-4-[2-(methylsulfonyl)ethyl]-1-piperazinyl}-2-(methyloxy)aniline

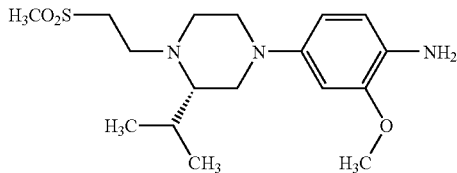

(2S)-2-(1-Methylethyl)-4-[3-(methyloxy)-4-nitrophenyl]-1-[2-(methylsulfonyl)-ethyl]piperazine (0.382 g, 0.991 mmol) was dissolved in 15 mL of EtOH with stirring. 10% Palladium on carbon (0.105 g, 0.0987 mmol) was added, and the reaction was placed under 1 atm of $H_2$ using a balloon. The reaction was stirred for 8 h and filtered through celite washing with EtOAc. The filtrate was concentrated in vacuo to provide the title compound of step G (0.349 g, 0.982 mmol, 99%). $^1$H NMR (400 MHz, DMSO-$d_6$) δ 6.47 (d, J=8.4 Hz, 1H), 6.41 (d, J=2.4 Hz, 1H), 6.25 (dd, J=8.4, 2.4 Hz, 1H), 4.17 (br. s., 2H), 3.69 (s, 3H), 3.28-3.39 (m, 1H), 3.04-3.23 (m, 4H), 2.98 (s, 3H), 2.90 (d, J=11.0 Hz, 1H), 2.70-2.81 (m, 1H), 2.48-2.58 (m, 1H), 2.30-2.44 (m, 2H), 2.16-2.25 (m, 1H), 2.02-2.15 (m, 1H), 0.91 (d, J=7.0 Hz, 3H), 0.83 (d, J=6.8 Hz, 3H).

Step H: N-(2,6-difluorophenyl)-5-[3-(2-{[4-{(3S)-3-(1-methylethyl)-4-[2-(methylsulfonyl)-ethyl]-1-piperazinyl}-2-(methyloxy)phenyl]amino}-4-pyrimidinyl)imidazo[1,2-a]pyridin-2-yl]-2-(methyloxy)benzamide To 5-[3-(2-Chloro-4-pyrimidinyl)imidazo[1,2-a]pyridin-2-yl]-N-(2,6-difluorophenyl)-2-(methyloxy)benzamide (Intermediate Example 2) (0.241 g, 0.490 mmol) and 4-{(3S)-3-(1-methylethyl)-4-[2-(methylsulfonyl)ethyl]-1-piperazinyl}-2-(methyloxy)aniline (0.174 g, 0.489 mmol) were dissolved in 5 mL of trifluoroethanol with stirring in a pressure vessel. Hydrogen chloride (0.49 mL, 4N in dioxane, 2.0 mmol) was added, and the vessel was sealed. The reaction was heated to 80° C. for 3 days and subsequently cooled to rt. The reaction was poured into 10 mL of 7N $NH_3$ in MeOH and concentrated onto silica gel. The compound was purified by flash chromatography, and the fractions containing the desired compound were concentrated in vacuo. The material was triturated with diethyl ether, filtered, and washed with diethyl ether. The solid was collected to afford the title compound (0.191 g, 0.236 mmol, 48%). $^1$H NMR (400 MHz, DMSO-$d_6$) δ ppm 9.75 (s, 1H), 9.33 (br. s., 1H), 8.42 (s, 1H), 8.17 (d, J=5.1 Hz, 1H), 8.03-8.09 (m, 1H), 7.70-7.78 (m, 1H), 7.66 (d, J=9.0 Hz, 1H), 7.29-7.43 (m, 3H), 7.25 (d, J=8.8 Hz, 1H), 7.10-7.19 (m, 2H), 6.87-6.95 (m, 1H), 6.61 (s, 1H), 6.43-6.52 (m, 2H), 3.95 (s, 3H), 3.77 (s, 3H), 3.43-3.51 (m, 1H), 3.30-3.41 (m, 2H), 3.27 (s, 3H), 2.99 (s, 3H), 2.91-2.98 (m, 1H), 2.68-2.85 (m, 2H), 2.51-2.60 (m, 1H), 2.22-2.30 (m, 1H), 2.05-2.16 (m, 1H), 0.96 (d, J=6.8 Hz, 3H), 0.87 (d, J=7.0 Hz, 3H). MS (M+H, ES+) 811.

Biological Examples

A. IR and IGF1R Time Resolved Fluorescence Resonance Energy Transfer (TR-FRET) Assay Using Peptide as the Phosphoacceptor
Substrate Phosphorylation Assays are Carried Out as Follows:
The Source of Substrate Peptide
The biotinylated substrate peptide, (sequence—Biotin-aminohexyl-AEEEEY*MMMMAKKKK-$NH_2$) SEQ. ID. 1 is purchased from QCB, Inc. (Hopkinton, Mass.). Purity is determined by HPLC. The calculated molecular mass of the peptide is 2216 dalton. Tyrosine phosphorylation by human IGF1R (hIGF1R) or human IR (hIR) occurs as indicated (Y*) in the peptide sequence described. Solid peptide sample is dissolved to approximately 1 mM in DMSO, aliquoted, and stored at −20° C. until use. True peptide concentration is determined by amino acid analysis.
The Source of Enzyme:
hIGF1R: GST-rTEV-IGF-1R(957-1367) containing amino acid residues 957-1367 of human IGF1R (as annotated by National Center for Biotechnology Information (NCBI) accession number NP_000866) is purified from a baculovirus expression system in Sf9 cells using Glutathione Sepharose 4FF column chromatography followed by Sephadex-200 size exclusion column chromatography. Enzyme purity of approximately 95% is achieved. Samples, in 25 mM Tris-HCl, 250 mM NaCl, 5% glycerol, 1 mM DTT, pH 7.5, are stored at −80° C. until use.
hIR: GST-rTEV-IR(979-1382) containing amino acid residues 979-1382 of human IR (as annotated by NCBI accession number NP_000199) is expressed and purified by the same process as hIGF1R Enzyme purity of approximately 92% is achieved. Samples, in 25 mM Tris-HCl, 250 mM NaCl, 5% glycerol, 1 mM DTT, pH 7.5, are stored at −80° C. until use.
Activation of hIGF1R and hIR by Autophosphorylation:
hIGF1R: Activation of GST-rTEV-IGF-1R(957-1367) is achieved by a 4 minute incubation of hIGF1R (2.7 µM final) with 2 mM ATP in 50 mM HEPES, 20 mM $MgCl_2$, 0.1 mg/mL BSA, at room temperature. Autophosphorylation is stopped by addition of EDTA (to 100 mM final). Aliquoted samples are flash frozen in liquid nitrogen and stored at −80° C. until use.
hIR: Activation of GST-rTEV-IGF-1R(957-1367) is achieved by a 5 minute incubation of hIR (2.7 µM final) with 2 mM ATP in 100 mM HEPES, 10 mM $MgCl_2$, 0.1 mg/mL BSA, at room temperature. Autophosphorylation is stopped by addition of EDTA (to 100 mM final). Aliquoted samples are flash frozen in liquid nitrogen and stored at −80° C. until use.
Kinase Assay of Purified hIGF1R or hIR:
Assays are performed in 384-well (Greiner, Catalog No. 784076) microtiter plates. Reaction buffer (50 mM HEPES buffer, pH 7.5; 10 mM $MgCl_2$; 3 mM DTT; 1 mM CHAPS; 0.1 mg/mL BSA) for peptide phosphorylation (10 µl volume) contained, in final concentrations, 500 nM biotinylated peptide substrate; 10 µM ATP; and purified, activated hIGF1R or hIR (0.5 nM). Some compounds were initially assayed against IGF1R in buffer without DTT or CHAPS. Results obtained under these conditions are comparable to results obtained in the presence of DTT and CHAPS. Compounds, titrated in DMSO, are evaluated at eleven concentrations ranging from 50 µM to 0.2 nM. Final assay concentrations of DMSO do not exceed 10%. No effect on activity relative to controls without DMSO is observed for hIGF1R or IR at these DMSO amounts. Reactions are incubated for 1 hour at room temperature and are stopped by a 5 µl addition of EDTA (to 33 mM). A further addition of 5 µl detection reagents (for final 7 nM Streptavidin-APC (PerkinElmer #CR130-150), 1 nM Europium-labeled anti-phosphotyrosine monoclonal antibody (PerkinElmer#AD0067), added in reaction buffer (without DTT), is required for signal generation. After 30 minutes, signal is read on PerkinElmer Viewlux microplate imager or Wallac Victor fluorometer.

The data for compound concentration responses were plotted as % Inhibition, calculated with the data reduction formula $100*(1-[(U1-C2)/(C1-C2)])$, versus concentration of compound, where U is the unknown value,
C1 is the average control value obtained for DMSO only, and
C2 is the average control value obtained for reactions stopped with EDTA at t=0.

Data were fitted to the curve described by:

$$y=((Vmax*x)/(K+x))\text{ where}$$

Vmax is the upper asymptote and
K is the $IC_{50}$.

The results for each tested compound were recorded as $pIC_{50}$ calculated as follows:

$$pIC_{50}=-\text{Log }10(K).$$

The results are reported in Table 1, below. In Table 1:
"+" indicates no average $pIC_{50}$ measurement greater than 6 against the kinase tested
"++" indicates at least one average $pIC_{50}$ measurement greater than 6 against the kinase tested but no average measurement greater than $pIC_{50}$ of 7; and
"+++" indicates at least one average $pIC_{50}$ measurement of greater than 7 against the kinase tested.

TABLE 1

IGF-1R and IR Enzyme Activity Results

| Example | IGF-1R $pIC_{50}$ | IR $pIC_{50}$ |
|---------|------|------|
| 1 | +++ | +++ |
| 2 | +++ | +++ |
| 3 | +++ | +++ |
| 4 | +++ | +++ |
| 5 | +++ | +++ |
| 6 | +++ | +++ |
| 7 | +++ | +++ |
| 8 | +++ | +++ |
| 9 | +++ | +++ |
| 10 | +++ | +++ |
| 11 | +++ | +++ |
| 12 | +++ | +++ |
| 13 | +++ | +++ |
| 14 | +++ | +++ |
| 15 | +++ | +++ |
| 16 | +++ | +++ |
| 17 | +++ | +++ |
| 18 | +++ | +++ |
| 19 | +++ | +++ |
| 20 | +++ | +++ |
| 21 | +++ | +++ |
| 22 | +++ | +++ |
| 23 | +++ | +++ |
| 24 | +++ | +++ |
| 25 | +++ | +++ |
| 26 | +++ | +++ |
| 27 | +++ | +++ |
| 28 | +++ | +++ |
| 29 | +++ | +++ |
| 30 | +++ | +++ |
| 31 | +++ | +++ |
| 32 | +++ | +++ |
| 33 | +++ | +++ |
| 34 | +++ | +++ |
| 35 | +++ | +++ |
| 36 | +++ | +++ |
| 37 | +++ | +++ |
| 38 | +++ | +++ |
| 39 | +++ | +++ |
| 40 | +++ | +++ |
| 41 | +++ | +++ |
| 42 | +++ | +++ |
| 43 | +++ | +++ |
| 44 | +++ | +++ |
| 45 | +++ | +++ |
| 46 | +++ | +++ |
| 47 | +++ | +++ |
| 48 | +++ | +++ |
| 49 | +++ | +++ |
| 50 | +++ | +++ |
| 51 | +++ | +++ |
| 52 | +++ | +++ |
| 53 | +++ | +++ |
| 54 | +++ | +++ |
| 55 | +++ | +++ |
| 56 | +++ | +++ |
| 57 | +++ | +++ |
| 58 | +++ | +++ |
| 59 | +++ | +++ |
| 60 | +++ | +++ |
| 61 | +++ | +++ |
| 62 | +++ | +++ |
| 63 | +++ | +++ |
| 64 | +++ | +++ |
| 65 | +++ | +++ |
| 66 | +++ | +++ |
| 67 | +++ | +++ |
| 68 | +++ | +++ |
| 69 | +++ | +++ |
| 70 | +++ | +++ |
| 71 | +++ | +++ |
| 72 | +++ | +++ |
| 73 | +++ | +++ |
| 74 | +++ | +++ |
| 75 | +++ | +++ |
| 76 | +++ | +++ |
| 77 | +++ | +++ |
| 78 | +++ | +++ |
| 79 | +++ | +++ |
| 80 | +++ | +++ |
| 81 | +++ | +++ |
| 82 | +++ | +++ |
| 83 | +++ | +++ |
| 84 | +++ | +++ |
| 85 | +++ | +++ |
| 86 | +++ | +++ |
| 87 | +++ | +++ |
| 88 | +++ | +++ |
| 89 | +++ | +++ |
| 90 | +++ | +++ |
| 91 | +++ | +++ |
| 92 | +++ | +++ |
| 93 | +++ | +++ |
| 94 | +++ | +++ |
| 95 | +++ | +++ |
| 96 | +++ | +++ |
| 97 | +++ | +++ |
| 98 | +++ | +++ |
| 99 | +++ | +++ |
| 100 | +++ | +++ |
| 101 | +++ | +++ |
| 102 | +++ | +++ |
| 103 | +++ | +++ |
| 104 | +++ | +++ |
| 105 | +++ | +++ |
| 106 | +++ | +++ |
| 107 | +++ | +++ |
| 108 | +++ | +++ |
| 109 | +++ | +++ |
| 110 | +++ | +++ |
| 111 | +++ | +++ |
| 12 | +++ | +++ |
| 113 | +++ | +++ |
| 114 | +++ | +++ |
| 115 | +++ | +++ |
| 116 | +++ | +++ |
| 117 | +++ | +++ |

TABLE 1-continued

IGF-1R and IR Enzyme Activity Results

| Example | IGF-1R pIC$_{50}$ | IR pIC$_{50}$ |
|---|---|---|
| 118 | +++ | +++ |
| 119 | +++ | +++ |
| 120 | +++ | +++ |
| 121 | +++ | +++ |
| 122 | +++ | +++ |
| 123 | +++ | +++ |
| 124 | +++ | +++ |
| 125 | +++ | +++ |
| 126 | +++ | +++ |
| 127 | +++ | +++ |
| 128 | +++ | +++ |
| 129 | +++ | +++ |
| 130 | +++ | +++ |
| 131 | +++ | +++ |
| 132 | +++ | +++ |
| 133 | +++ | +++ |
| 134 | +++ | +++ |
| 135 | +++ | +++ |
| 136 | +++ | +++ |
| 137 | +++ | +++ |
| 138 | +++ | +++ |
| 139 | +++ | +++ |
| 140 | +++ | +++ |
| 141 | +++ | +++ |
| 142 | +++ | +++ |
| 143 | +++ | +++ |
| 144 | +++ | +++ |
| 145 | +++ | +++ |
| 146 | +++ | +++ |
| 147 | +++ | +++ |
| 148 | +++ | +++ |
| 149 | +++ | +++ |
| 150 | +++ | +++ |
| 151 | +++ | +++ |
| 152 | +++ | +++ |
| 153 | +++ | +++ |
| 154 | +++ | +++ |
| 155 | +++ | +++ |
| 156 | +++ | +++ |
| 157 | +++ | +++ |
| 158 | +++ | +++ |
| 159 | +++ | +++ |
| 160 | +++ | +++ |
| 161 | +++ | +++ |
| 162 | +++ | +++ |
| 163 | +++ | +++ |
| 164 | +++ | +++ |
| 165 | +++ | +++ |
| 166 | +++ | +++ |
| 167 | +++ | +++ |
| 168 | +++ | +++ |
| 169 | +++ | +++ |
| 170 | +++ | +++ |
| 171 | +++ | +++ |
| 172 | +++ | +++ |
| 173 | +++ | +++ |
| 174 | +++ | +++ |
| 175 | +++ | +++ |
| 176 | +++ | +++ |
| 177 | +++ | +++ |
| 178 | +++ | +++ |
| 179 | +++ | +++ |
| 180 | +++ | +++ |
| 181 | +++ | +++ |
| 182 | +++ | +++ |
| 183 | +++ | +++ |
| 184 | +++ | +++ |
| 185 | +++ | +++ |
| 186 | ++ | ++ |
| 187 | +++ | +++ |
| 188 | +++ | +++ |
| 189 | +++ | +++ |
| 190 | +++ | +++ |
| 191 | +++ | +++ |
| 192 | +++ | +++ |
| 193 | +++ | +++ |
| 194 | +++ | +++ |
| 195 | +++ | +++ |
| 196 | +++ | +++ |
| 197 | +++ | +++ |
| 198 | +++ | +++ |
| 199 | +++ | +++ |
| 200 | +++ | +++ |
| 201 | +++ | +++ |
| 202 | +++ | +++ |
| 203 | +++ | +++ |
| 204 | +++ | +++ |
| 205 | ++ | ++ |
| 206 | ++ | ++ |
| 207 | +++ | +++ |
| 208 | ++ | ++ |
| 209 | ++ | +++ |
| 210 | +++ | +++ |
| 211 | +++ | +++ |
| 212 | +++ | +++ |
| 213 | +++ | +++ |
| 214 | ++ | +++ |
| 215 | ++ | ++ |
| 216 | +++ | +++ |
| 217 | ++ | +++ |
| 218 | +++ | +++ |
| 219 | +++ | +++ |
| 220 | +++ | +++ |
| 221 | +++ | +++ |
| 222 | +++ | +++ |
| 223 | +++ | +++ |
| 224 | +++ | +++ |
| 225 | +++ | +++ |
| 226 | +++ | +++ |
| 227 | +++ | +++ |
| 228 | +++ | +++ |
| 229 | +++ | +++ |
| 230 | +++ | +++ |
| 231 | +++ | +++ |
| 232 | +++ | +++ |
| 233 | +++ | +++ |
| 234 | +++ | +++ |
| 235 | +++ | +++ |
| 236 | +++ | +++ |
| 237 | +++ | +++ |
| 238 | +++ | +++ |
| 239 | +++ | +++ |
| 240 | +++ | +++ |
| 241 | +++ | +++ |
| 242 | +++ | +++ |
| 243 | +++ | +++ |
| 244 | +++ | +++ |
| 245 | +++ | +++ |
| 246 | +++ | +++ |
| 247 | +++ | +++ |
| 248 | +++ | +++ |
| 249 | ++ | +++ |
| 250 | +++ | +++ |

B. EGRF and ErbB2 Enzyme Assay:

Compounds of the invention were tested for EGFR and ErbB-2 protein tyrosine kinase inhibitory activity in substrate phosphorylation assays using enzymes purified from a baculovirus expression system. Reagent production was conducted essentially as described in Brignola, P. S., et al, (2002) *J. Biol. Chem.* 277(2):1576-1585. The method measures the ability of the isolated enzyme to catalyze the transfer of the gamma-phosphate from ATP onto the tyrosine residue of a biotinylated synthetic peptide referenced "Peptide C" in Brignola, P. S., et al, (2002) *J. Biol. Chem.* 277(2):1576-1585. The extent of tyrosine phosphorylation was measured using an anti-phosphotyrosine antibody, and quantified by homogenous time-resolved fluorescence (HTRF).

Reactions were performed in black 384-well polystyrene flat-bottom plates in a final volume of 10 μl. Assays were performed by adding 5 μl of each of the following solutions, substrate Mix and enzyme mix: The Substrate mix, final concentration in plate, contained 50 mM 3-[N-morpholino] propanesulfonic acid (MOPS) (pH 7.5), 2 mM $MnCl_2$, 20 μM ATP, 0.01% Tween-20, 0.1 mg/mL (BSA), 0.8 uM peptide substrate, and 1 mM dithiothreitol. The enzyme mix contained 50 mM MOPS (pH7.5); 0.01% Tween-20; 0.1 mg/mL BSA, and either 0.5 nM EGFR or 3 nM ErbB2.

To quantify compound potencies, the enzyme mix was added to the compound plates and the plates were incubated at 20° C. for 1 hour. The reactions were then started by adding the substrate mix. The reactions were allowed to proceed for 90 minutes at 20° C. The reactions were then terminated by the addition of 5 μl 150 mM EDTA to each well. 5 μl/well of HTRF detection mix were added to the assay plates. The final concentrations of the detection reagents were: 100 mM HEPES (pH7.5), 0.1 mg/mL BSA, 15 nM streptavidin-labeled allophycocyanin (PerkinElmer), and 1 nM europium-labeled anti-phosphotyrosine antibody (PerkinElmer). Assay plates were left unsealed and were counted in a Viewlux Counter (PerkinElmer).

Compounds under analysis were dissolved in $Me_2SO$ to 1.0 mM and serially diluted 1 to 3 with $Me_2SO$ through eleven dilutions. 0.1 μl of each concentration was transferred to the corresponding well of an assay plate. This creates a final compound concentration range from 0.00017 to 10 μM.

The data for dose responses were plotted as % Inhibition calculated with the data reduction formula 100*(1−(U1−C2)/(C1−C2)) versus concentration of compound where U is the unknown value, C1 is the average control value obtained for 1% DMSO, and C2 is the average control value obtained for 0.035 M EDTA. Data were fitted with a curve described by:

$$y = A + \frac{B - A}{1 + [10x/10c]D}$$

where A is the minimum y, B is the maximum y concentration [M], D is the slope factor, and x is the $\log_{10}$ of the compound. The results for each compound were recorded as pIC50s, calculated as follows:

$pIC_{50} = -\text{Log } 10(K)$

Many of the exemplified compounds Examples 1-250 were run in the recited assay and the results are reported in the following Table 2. In the following table:

"+" indicates no $pIC_{50}$ measurement greater than 6 against either ErbB2 or EGFR;

"++" indicates at least one $pIC_{50}$ measurement greater than 6 against either ErbB2 or EGFR but no measurement greater than $pIC_{50}$ of 7 and "+++" indicates at least one $pIC_{50}$ measurement of greater than 7 against either ErbB2 or EGFR.

TABLE 2

EGFR and ErbB2 Enzyme Activity Results

| Example | pIC50 |
| --- | --- |
| 1 | + |
| 2 | + |
| 3 | + |
| 4 | + |
| 5 | ++ |
| 6 | +++ |

TABLE 2-continued

EGFR and ErbB2 Enzyme Activity Results

| Example | pIC50 |
| --- | --- |
| 7 | +++ |
| 8 | ++ |
| 9 | +++ |
| 10 | ++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | ++ |
| 22 | +++ |
| 23 | + |
| 24 | +++ |
| 25 | + |
| 26 | + |
| 27 | +++ |
| 28 | + |
| 29 | +++ |
| 30 | ++ |
| 31 | + |
| 32 | +++ |
| 33 | +++ |
| 34 | +++ |
| 35 | +++ |
| 36 | +++ |
| 37 | +++ |
| 38 | +++ |
| 39 | +++ |
| 40 | +++ |
| 41 | +++ |
| 42 | +++ |
| 43 | +++ |
| 44 | ++ |
| 45 | ++ |
| 46 | +++ |
| 47 | +++ |
| 48 | +++ |
| 49 | +++ |
| 50 | +++ |
| 51 | +++ |
| 52 | +++ |
| 53 | +++ |
| 54 | +++ |
| 55 | + |
| 56 | + |
| 57 | +++ |
| 58 | +++ |
| 59 | +++ |
| 60 | +++ |
| 61 | ++ |
| 62 | +++ |
| 63 | + |
| 64 | +++ |
| 65 | + |
| 66 | + |
| 67 | +++ |
| 68 | +++ |
| 69 | + |
| 70 | +++ |
| 71 | +++ |
| 72 | ++ |
| 73 | ++ |
| 74 | +++ |
| 75 | +++ |
| 76 | +++ |
| 77 | +++ |
| 78 | +++ |
| 79 | +++ |
| 80 | +++ |
| 81 | + |
| 82 | +++ |

TABLE 2-continued

EGFR and ErbB2 Enzyme Activity Results

| Example | pIC50 |
|---|---|
| 83 | +++ |
| 84 | + |
| 85 | +++ |
| 86 | +++ |
| 87 | +++ |
| 88 | + |
| 89 | +++ |
| 90 | +++ |
| 91 | +++ |
| 92 | +++ |
| 93 | +++ |
| 94 | +++ |
| 95 | +++ |
| 96 | + |
| 97 | +++ |
| 98 | + |
| 99 | +++ |
| 100 | +++ |
| 101 | +++ |
| 102 | + |
| 103 | + |
| 104 | +++ |
| 105 | + |
| 106 | +++ |
| 107 | + |
| 108 | +++ |
| 109 | + |
| 110 | +++ |
| 111 | +++ |
| 112 | +++ |
| 113 | +++ |
| 114 | +++ |
| 115 | +++ |
| 116 | +++ |
| 117 | +++ |
| 118 | +++ |
| 119 | +++ |
| 120 | +++ |
| 121 | +++ |
| 122 | + |
| 123 | +++ |
| 124 | + |
| 125 | +++ |
| 126 | + |
| 127 | + |
| 128 | +++ |
| 129 | +++ |
| 130 | + |
| 131 | + |
| 132 | +++ |
| 133 | + |
| 134 | + |
| 135 | + |
| 136 | +++ |
| 137 | + |
| 138 | +++ |
| 139 | +++ |
| 140 | + |
| 141 | +++ |
| 142 | + |
| 143 | + |
| 144 | + |
| 145 | +++ |
| 146 | +++ |
| 147 | + |
| 148 | +++ |
| 149 | + |
| 150 | + |
| 151 | + |
| 152 | + |
| 153 | +++ |
| 154 | + |
| 155 | +++ |
| 156 | + |
| 157 | ++ |
| 158 | + |
| 159 | +++ |
| 160 | + |
| 161 | + |
| 162 | +++ |
| 163 | + |
| 164 | + |
| 165 | +++ |
| 166 | +++ |
| 167 | + |
| 168 | + |
| 169 | +++ |
| 170 | +++ |
| 171 | +++ |
| 172 | ++ |
| 173 | +++ |
| 174 | ++ |
| 175 | +++ |
| 176 | ++ |
| 177 | + |
| 178 | + |
| 179 | + |
| 180 | +++ |
| 181 | + |
| 182 | + |
| 183 | +++ |
| 184 | + |
| 185 | + |
| 186 | + |
| 187 | + |
| 188 | +++ |
| 189 | +++ |
| 190 | +++ |
| 191 | +++ |
| 192 | +++ |
| 193 | +++ |
| 194 | +++ |
| 195 | +++ |
| 196 | +++ |
| 197 | + |
| 198 | + |
| 199 | + |
| 200 | + |
| 201 | + |
| 202 | +++ |
| 203 | + |
| 204 | + |
| 205 | + |
| 206 | + |
| 207 | + |
| 208 | + |
| 209 | + |
| 210 | + |
| 211 | + |
| 212 | + |
| 213 | + |
| 214 | + |
| 215 | + |
| 216 | + |
| 217 | + |
| 218 | + |
| 219 | + |
| 220 | + |
| 221 | ++ |
| 222 | + |
| 223 | + |
| 224 | ++ |
| 225 | + |
| 226 | + |
| 227 | + |
| 228 | + |
| 229 | + |
| 230 | + |
| 231 | ++ |
| 232 | + |
| 233 | + |
| 234 | ++ |

TABLE 2-continued

EGFR and ErbB2 Enzyme Activity Results

| Example | pIC50 |
|---|---|
| 235 | + |
| 236 | + |
| 237 | + |
| 238 | + |
| 239 | + |
| 240 | + |
| 241 | + |
| 242 | + |
| 243 | +++ |
| 244 | +++ |
| 245 | +++ |
| 246 | +++ |
| 247 | + |
| 248 | + |
| 249 | + |
| 250 | + |

C. Inhibition of Cell Proliferation

Cell proliferation was measured by either CellTiter-Glo (measures cellular ATP level as a surrogate for total cell number) or by InCell analyzer (counts number of nuclei as a measure of cell number). For CellTiter-Glo assay, exponentially growing cell lines of different tumor origins, cultured in appropriate media containing 10% fetal bovine serum at 37° C. in a 5% $CO_2$ incubator, were plated at low density (less than 2000 cells/well) in 96-well plates. Twenty four hours post-plating, cells were treated with different concentrations of test compounds ranging from 30 uM to 1.5 nM. Several wells were left untreated as a control. Seventy two hours post-treatment, cell numbers were determined using 50-100 ul per well of CellTiter-Glo (Promega #G7573). Plates were incubated at 37° C. for 30 minutes and the chemiluminescent signal was read on the Victor V or Envison 2100 reader. Percent inhibition of cell growth was expressed as percent proliferation relative to 100% proliferation (control). Concentration of test compound that inhibited 50% of cell growth ($IC_{50}$) was determined by 4 parameter fit of data using XLfit, (value of no cell control was subtracted from all samples for background). Results are reported in Table 3A. In Table 3A:
+ indicates an $IC_{50}$ measurement of greater than 1000 nM;
++ indicates an $IC_{50}$ measurement of 250-1000 nM; and
+++ indicates an $IC_{50}$ measurement of less than 250 nM.

TABLE 3A

Cell Titre Glo Assay Results

| Example | COLO205 (colon) $IC_{50}$ (nM) | NCI-H929 (multiple myeloma) $IC_{50}$ (nM) |
|---|---|---|
| 1 | +++ | |
| 2 | ++ | |
| 3 | ++ | |
| 4 | ++ | |
| 5 | + | |
| 11 | ++ | |
| 15 | +++ | |
| 16 | ++ | |
| 17 | ++ | |
| 18 | ++ | |
| 20 | +++ | |
| 22 | ++ | +++ |
| 23 | +++ | |
| 24 | ++ | |
| 25 | ++ | |
| 26 | ++ | |
| 27 | + | |
| 30 | ++ | |
| 31 | ++ | |
| 32 | ++ | |
| 33 | ++ | |
| 34 | ++ | |
| 35 | ++ | |
| 36 | ++ | |
| 37 | ++ | |
| 38 | ++ | |
| 39 | + | |
| 40 | ++ | |
| 41 | ++ | ++ |
| 42 | + | + |
| 43 | ++ | |
| 44 | ++ | |
| 45 | ++ | |
| 46 | + | |
| 47 | ++ | |
| 48 | ++ | ++ |
| 49 | ++ | ++ |
| 50 | ++ | |
| 51 | ++ | ++ |
| 52 | ++ | ++ |
| 53 | ++ | |
| 54 | + | + |
| 55 | + | + |
| 56 | + | ++ |
| 57 | ++ | +++ |
| 58 | ++ | +++ |
| 59 | ++ | +++ |
| 60 | ++ | ++ |
| 61 | ++ | +++ |
| 62 | ++ | |
| 63 | ++ | +++ |
| 64 | ++ | +++ |
| 65 | ++ | +++ |
| 66 | ++ | +++ |
| 67 | ++ | ++ |
| 68 | ++ | ++ |
| 69 | ++ | |
| 70 | ++ | +++ |
| 71 | ++ | |
| 72 | ++ | |
| 73 | ++ | |
| 74 | +++ | |
| 75 | ++ | |
| 76 | ++ | |
| 77 | ++ | |
| 78 | +++ | |
| 79 | +++ | |
| 80 | +++ | |
| 81 | +++ | |
| 82 | +++ | |
| 83 | ++ | |
| 84 | +++ | |
| 85 | ++ | |
| 86 | ++ | |
| 87 | ++ | +++ |
| 88 | + | +++ |
| 89 | +++ | |
| 90 | ++ | |
| 91 | ++ | |
| 92 | +++ | |
| 93 | ++ | |
| 94 | + | |
| 95 | + | ++ |
| 96 | + | ++ |
| 97 | ++ | ++ |
| 98 | ++ | ++ |
| 99 | +++ | +++ |
| 100 | ++ | ++ |
| 101 | ++ | +++ |

TABLE 3A-continued

Cell Titre Glo Assay Results

| Example | COLO205 (colon) IC$_{50}$ (nM) | NCI-H929 (multiple myeloma) IC$_{50}$ (nM) |
|---|---|---|
| 102 | ++ | +++ |
| 103 | ++ | +++ |
| 104 | ++ | |
| 105 | +++ | |
| 106 | ++ | |
| 107 | ++ | |
| 109 | +++ | |
| 110 | ++ | +++ |
| 111 | ++ | +++ |
| 12 | ++ | +++ |
| 113 | + | ++ |
| 114 | ++ | +++ |
| 115 | ++ | +++ |
| 116 | ++ | ++ |
| 117 | + | ++ |
| 118 | ++ | ++ |
| 119 | ++ | +++ |
| 120 | ++ | +++ |
| 121 | ++ | +++ |
| 122 | +++ | |
| 123 | ++ | ++ |
| 124 | + | +++ |
| 125 | ++ | |
| 126 | ++ | |
| 127 | ++ | |
| 128 | ++ | |
| 129 | ++ | |
| 130 | ++ | |
| 131 | +++ | |
| 132 | ++ | |
| 133 | ++ | |
| 134 | ++ | |
| 135 | ++ | |
| 136 | ++ | |
| 137 | ++ | +++ |
| 138 | ++ | +++ |
| 139 | ++ | |
| 140 | ++ | |
| 141 | ++ | |
| 142 | ++ | |
| 143 | ++ | +++ |
| 144 | +++ | +++ |
| 145 | ++ | |
| 146 | ++ | |
| 147 | + | |
| 148 | +++ | +++ |
| 149 | +++ | +++ |
| 150 | +++ | +++ |
| 151 | ++ | +++ |
| 152 | ++ | +++ |
| 153 | ++ | ++ |
| 154 | ++ | +++ |
| 155 | ++ | +++ |
| 156 | ++ | +++ |
| 157 | +++ | +++ |
| 158 | +++ | +++ |
| 159 | ++ | +++ |
| 160 | ++ | +++ |
| 161 | ++ | +++ |
| 162 | ++ | +++ |
| 163 | ++ | +++ |
| 164 | +++ | +++ |
| 165 | ++ | +++ |
| 166 | ++ | ++ |
| 167 | + | + |
| 168 | ++ | +++ |
| 169 | ++ | |
| 170 | ++ | |
| 171 | ++ | ++ |
| 172 | ++ | +++ |
| 173 | ++ | ++ |
| 174 | ++ | +++ |
| 175 | ++ | |
| 176 | ++ | +++ |
| 177 | ++ | +++ |
| 178 | ++ | +++ |
| 179 | ++ | |
| 180 | ++ | +++ |
| 181 | ++ | +++ |
| 182 | +++ | +++ |
| 183 | ++ | |
| 184 | +++ | +++ |
| 185 | +++ | +++ |
| 186 | +++ | +++ |
| 188 | + | ++ |
| 189 | + | ++ |
| 190 | ++ | ++ |
| 191 | + | + |
| 192 | ++ | ++ |
| 193 | + | +++ |
| 194 | ++ | ++ |
| 195 | ++ | ++ |
| 196 | ++ | +++ |
| 197 | ++ | +++ |
| 198 | ++ | +++ |
| 199 | ++ | +++ |
| 200 | +++ | +++ |
| 201 | ++ | +++ |
| 202 | ++ | +++ |
| 203 | +++ | +++ |
| 204 | +++ | +++ |
| 205 | +++ | +++ |
| 206 | +++ | +++ |
| 207 | +++ | +++ |
| 208 | +++ | +++ |
| 209 | +++ | +++ |
| 210 | +++ | +++ |
| 211 | +++ | +++ |
| 212 | +++ | +++ |
| 213 | +++ | +++ |
| 214 | +++ | +++ |
| 215 | +++ | +++ |
| 216 | ++ | +++ |
| 217 | +++ | +++ |
| 218 | ++ | +++ |
| 219 | +++ | +++ |
| 220 | ++ | +++ |
| 221 | ++ | +++ |
| 222 | +++ | +++ |
| 223 | +++ | +++ |
| 224 | ++ | +++ |
| 225 | +++ | +++ |
| 226 | +++ | +++ |
| 227 | +++ | +++ |
| 228 | +++ | +++ |
| 229 | +++ | +++ |
| 230 | +++ | +++ |
| 231 | | +++ |
| 232 | +++ | +++ |
| 233 | ++ | +++ |
| 234 | ++ | +++ |
| 235 | +++ | +++ |
| 236 | +++ | +++ |
| 237 | +++ | +++ |
| 238 | ++ | +++ |
| 239 | ++ | +++ |
| 240 | ++ | ++ |
| 241 | ++ | +++ |
| 242 | ++ | +++ |
| 243 | ++ | +++ |
| 244 | ++ | ++ |
| 245 | ++ | +++ |
| 246 | +++ | +++ |
| 247 | +++ | +++ |
| 248 | +++ | +++ |
| 249 | +++ | +++ |

TABLE 3A-continued

Cell Titre Glo Assay Results

| Example | COLO205 (colon) IC$_{50}$ (nM) | NCI-H929 (multiple myeloma) IC$_{50}$ (nM) |
|---|---|---|
| 250 | ++ | +++ |

For InCell Analyser assay, various cell lines of different tumor origins were grown to 70-80% confluency in appropriate culture media containing 10% fetal bovine serum at 37° C. in a 5% CO$_2$ incubator. On day −1, cells were seeded at 2 densities in 384-well plates and incubated at 37° C. overnight. Stock compound plates were prepared in advance which contained dimethyl sulfoxide (DMSO) alone and a 9-point half-log decreasing dose range of the compound of Example 22 in DMSO. The compound plates were stored at −80° C. and each plate was only thawed once and used. On day 0, the main assay plates received compound or DMSO via a sonic delivery system (ECHO). The highest final concentration of compound of the dose range in the culture plates was 10 uM. These plates were cultured at 37° C. for 3 days. A parallel set of cell line plates, which did not receive compound, were processed and read on day 0 to provide a T=0 (time zero). On day 3, the compound treated plates were stained and fixed to measure proliferation, apoptosis, and mitotic index using an InCell1000 analyser. A nuclear stain was used to identify cells in the wells. By counting the number of nuclei, the proliferation index of compound treated groups were calculated as a percentage relative to the DMSO control, which was set to 100%. The IC$_{50}$ values were calculated using model 205 in ExcelFit. Results are reported in Table 3B. In table 3B:
+indicates an IC$_{50}$ measurement of greater than 5 μM;
++ indicates an IC$_{50}$ measurement of 1-5 μM; and
+++ indicates an IC$_{50}$ measurement of less than 1 μM.

TABLE 3B

InCell Analyzer Assay Results for Compound of Example No. 22

| Cell Line | Tumor Type | IC$_{50}$ Mean (μM) | Cell Line | Tumor Type | IC$_{50}$ Mean (μM) |
|---|---|---|---|---|---|
| RWPE-1 | Prostate | +++ | A2780 | Ovary | +++ |
| SW48 | Colon | +++ | NCI-H716 | Colon | +++ |
| HT-29 | Colon | +++ | HOS | Sarcoma | +++ |
| GDM-1 | AML | +++ | Capan-1 | Pancreas | +++ |
| NCI-H630 | Rectum | +++ | A-431 | Skin | +++ |
| BE(2)C | Brain | +++ | MC-IXC | neuroblastoma | +++ |
| LS1034 | Colon | +++ | JEG-3 | Placenta | +++ |
| SJRH30 | Sarcoma - rhabdomyosarcoma | +++ | MT-3 | Breast | +++ |
|  |  |  | SW1417 | Colon | +++ |
| SW1463 | Rectum | +++ | SCC-25 | H&N | +++ |
| MCF7 | Breast | +++ | HT-1080 | Sarcoma - fibrosarcoma | +++ |
| MiaPaCa | Pancreas | +++ |  |  |  |
| HPAC | Pancreas | +++ | NCI-H322 | Lung | +++ |
| RPMI8226 | Myeloma | +++ | NCI-N87 | Stomach | +++ |
| SK-N-FI | neuroblastoma | +++ | SW962 | Vulva | +++ |
| AsPC-1 | Pancreas | +++ | MCF10a | Breast (Normal) | +++ |
| NCI-H358 | Lung | +++ | TO175.T | Skin | ++ |
| SW403 | Colon | +++ | G-401 | kidney | ++ |
| SaOS-2 | Sarcoma | +++ | J.RT3-T3.5 | acute lymphoblastic leukaemia | ++ |
| TE381.T | Sarcoma - rhabdomyosarcoma | +++ |  |  |  |
|  |  |  | BC-3 | lymphoma - B cell unspecified | ++ |
| A673 | Sarcoma | +++ |  |  |  |
| BFTC-905 | Bladder | +++ | BC-2 | lymphoma - B cell unspecified | ++ |
| RD-ES | Sarcoma | +++ |  |  |  |
| NCI-H526 | Lung | +++ | HCC38 | Breast | ++ |
| CHP-212 | neuroblastoma | +++ | NCI-H460 | Lung | ++ |
| SW954 | Vulva | +++ | NCI-H209 | Lung | ++ |
| IGROV1 | Ovary | +++ | SR | lymphoma - large cell immunoblastic | ++ |
| CML-T1 | CML blast phase | +++ |  |  |  |
| OVCAR-5 | Ovary | +++ | OVCAR-8 | Ovary | ++ |
| RPMI2650 | H&N | ++ | SK-BR-3 | Breast | ++ |
| MOLT-16 | acute lymphoblastic leukaemia | ++ | 786-0 | Kidney | ++ |
|  |  |  | NCI-H522 | Lung | ++ |
| G-402 | Kidney | ++ | Caki-2 | Kidney | ++ |
| T-47D | Breast | ++ | NCI-H292 | Lung | ++ |
| CHL-1 | Skin | ++ | A427 | Lung | ++ |
| SK-N-DZ | neuroblastoma | ++ | SW872 | Sarcoma | ++ |
| NCI-H82 | Lung | ++ | JAR | Placenta | ++ |
| RL | lymphoma - non-Hodgkin | ++ | ES-2 | Ovary | ++ |
|  |  |  | SK-N-AS | neuroblastoma | ++ |
| CGTH-W-1 | Thyroid | ++ | SF-268 | glioma | ++ |
| Raji | lymphoma - Burkitt | ++ | 639-V | Bladder | ++ |
| Hut78 | lymphoma - cutaneous T cell | ++ | 769-P | Kidney | ++ |
|  |  |  | SH-4 | Skin | ++ |
| NCI-H727 | Lung | ++ | U-2OS | Sarcoma | ++ |
| SW579 | Thyroid | ++ | C-4II | Cervix | ++ |
| BeWo | Placenta | ++ | C-33A | Cervix | ++ |
| GCT | Sarcoma | ++ | BC-1 | lymphoma - B cell unspecified | ++ |
| MDA-MB-435 | Breast (Melanoma) | ++ |  |  |  |
|  |  |  | HMCB | Skin | ++ |

TABLE 3B-continued

InCell Analyzer Assay Results for Compound of Example No. 22

| Cell Line | Tumor Type | IC$_{50}$ Mean (µM) | Cell Line | Tumor Type | IC$_{50}$ Mean (µM) |
|---|---|---|---|---|---|
| NCI-H69 | Lung | ++ | RPMI6666 | lymphoma - Hodgkin | ++ |
| HCC-2998 | Colon | ++ | | | |
| SHP-77 | Lung | ++ | MDA-MB-453 | Breast | ++ |
| HCC1395 | Breast | ++ | | | |
| TK-10 | Kidney | ++ | CCF-STTG1 | glioma | ++ |
| MC-CAR | #N/A | ++ | | | |
| NCI-H520 | Lung | ++ | C3A | Liver | ++ |
| EKVX | Lung | ++ | NCI-H661 | Lung | ++ |
| HCC1954 | Breast | ++ | DB | lymphoma - diffuse large B cell | ++ |
| Hep3B | Liver | ++ | | | |
| BT474 | Breast | ++ | SCaBER | Bladder | ++ |
| CAL-54 | Kidney | ++ | M14 | Skin | ++ |
| BPH1 | Prostate | ++ | SNU-475 | Liver | ++ |
| SK-LMS-1 | Sarcoma | ++ | LS174T | Colon | ++ |
| MX-1 | Breast | ++ | HN5 | H&N | ++ |
| Capan-2 | Pancreas | ++ | NCI-H747 | Colon | ++ |
| HepG2 | Liver | ++ | OVCAR-4 | Ovary | ++ |
| A375 | Skin | ++ | RL95-2 | Uterus | ++ |
| SCC-4 | H&N | ++ | C-4I | Cervix | ++ |
| BV-173 | CML blast phase | ++ | A204 | Sarcoma - rhabdomyosarcoma | ++ |
| KLE | Uterus | ++ | | | |
| MDA-MB-231 | Breast | ++ | NCI/ADR-RES | Breast | ++ |
| CAOV-3 | Ovary | ++ | SNU-387 | Liver | ++ |
| CRO-AP2 | lymphoma - B cell unspecified | ++ | HCC1143 | Breast | ++ |
| | | | SNU-182 | Liver | ++ |
| THP-1 | AML | ++ | SK-UT-1 | Sarcoma | ++ |
| NALM-1 | CML blast phase | ++ | SiHa | Cervix | ++ |
| KPL-1 | Breast | ++ | SW756 | Cervix | ++ |
| SW480 | Colon | ++ | HCC70 | Breast | ++ |
| FaDu | H&N | ++ | SN12C | Kidney | ++ |
| SNU-423 | Liver | ++ | C32TG | Skin | ++ |
| U266B1 | Myeloma | ++ | EFM-19 | Breast | ++ |
| D283Med | medulloblastoma | ++ | MDA-MB-175-VII | Breast | ++ |
| CAL-62 | Thyroid | ++ | | | |
| ACHN | Kidney | ++ | BT-20 | Breast | ++ |
| 647-V | Bladder | ++ | A101D | Skin | ++ |
| SW1990 | Pancreas | ++ | Detroit562 | H&N | ++ |
| SW1088 | glioma | ++ | AN3CA | Uterus | ++ |
| KHOS-240S | Sarcoma | ++ | HEC-1-B | Uterus | ++ |
| | | | MDA-MB-468 | Breast | ++ |
| U251 | glioma | ++ | | | |
| UO-31 | Kidney | ++ | SCC-9 | H&N | + |
| A172 | glioma | ++ | SNU-449 | Liver | + |
| SW620 | Colon | ++ | NCI-H146 | Lung | + |
| UACC-62 | Skin | ++ | SCC-13 | H&N | + |
| ST486 | lymphoma - Burkitt | ++ | K-562 | CML | + |
| UACC-257 | Skin | ++ | MALME-3M | Skin | + |
| SCLC-3 | Lung | ++ | | | |
| Detroit562 | H&N | ++ | SW982 | Sarcoma | + |
| J82 | Bladder | ++ | NCI-H660 | Prostate | + |
| DK-MG | glioma | ++ | H4 | glioma | + |
| A-498 | Kidney | ++ | SNB-19 | glioma | + |
| SKO-007 | Myeloma | ++ | LOX IMVI | Skin | + |
| RXF393 | Kidney | ++ | UM-UC-3 | Bladder | + |
| MV-4-11 | acute leukaemia of ambiguous lineage | ++ | SW684 | Sarcoma | + |
| | | | CRO-AP5 | lymphoma - B cell unspecified | + |
| SK-MEL-28 | Skin | ++ | | | |
| SNU-398 | Liver | ++ | SW1353 | Sarcoma | + |
| MJ | lymphoma - cutaneous T cell | ++ | SW948 | Colon | + |
| | | | SF-539 | glioma | + |
| AGS | Stomach | ++ | HCC2157 | Breast | + |
| A7 | Skin | ++ | SNB-75 | glioma | + |
| HOP-92 | Lung | ++ | KM12 | Colon | + |
| ARH-77 | Myeloma - plasma cell | ++ | MES-SA | Sarcoma | + |
| | | | SK-MEL-3 | Skin | + |
| DU4475 | Breast | ++ | 5637 | Bladder | + |
| SW780 | Bladder | + | CESS | AML | + |
| SNU-16 | Stomach | + | HT-3 | Cervix | + |
| U-138MG | glioma | + | SCC-12 | H&N | + |
| BHT-101 | Thyroid | + | HS746T | Stomach | + |
| DoTc2-4510 | Cervix | + | Caki-1 | Kidney | + |
| | | | COLO-704 | Ovary | + |
| HPAFII | Pancreas | + | EM-2 | CML blast phase | + |

TABLE 3B-continued

InCell Analyzer Assay Results for Compound of Example No. 22

| Cell Line | Tumor Type | IC$_{50}$ Mean (μM) | Cell Line | Tumor Type | IC$_{50}$ Mean (μM) |
|---|---|---|---|---|---|
| Colo-829 | Skin | + | SW837 | Colon | + |
| HEC-1-A | Uterus | + | SW1116 | Colon | + |
| HT1197 | Bladder | + | YAPC | Pancreas | + |
| NCI-H596 | Lung | + | ML-2 | AML | + |
| HOP-62 | Lung | + | SK-OV-3 | Ovary | + |
| T24 | Bladder | + | HT1376 | Bladder | + |
| Cal27 | H&N | + | HCC1937 | Breast | + |
| KATOIII | Stomach | + | HCC2218 | Breast | + |
| SNU-1 | Stomach | + | UACC-812 | Breast | + |
| HuP-T4 | Pancreas | + | ZR-75-1 | Breast | + |
| DBTRG-05MG | glioma | + | HeLa | Cervix | + |
|  |  |  | SK-NEP-1 | Kidney | + |
| SW1783 | glioma | + | NCI-H1395 | Lung | + |
| OVCAR-3 | Ovary | + | NCI-H2087 | Lung | + |
| HEL-92.1.7 | erythroleukemia | + | BxPC-3 | Pancreas | + |
| SF-295 | glioma | + | Y79 | Eye | + |
| SCC-15 | H&N | + | SNU-5 | Stomach | + |
| SK-MEL-1 | Skin | + | OV-90 | Ovary | + |
| CEM/C1 | acute lymphoblastic leukaemia | + | NCI-H295R | Cervix | + |
|  |  |  | RD | Sarcoma - rhabdomyosarcoma | + |
| WM115 | Skin | + |  |  |  |
| U-87MG | glioma | + |  |  |  |

D. IGF-1R and IR Cellular Autophosphorylation (DELFIA)

NIH-3T3 cells over expressing human IGF-1R or IR were plated in 96-well plates (10,000 cells/well) in culture media containing 10% fetal bovine serum and incubated at 37° C. in a 5% CO$_2$ incubator. Twenty four hours post-plating, cells were treated with different concentrations of test compounds ranging from 30 uM to 1.5 nM. Two hours after compound addition, cells were stimulated with either human IGF-1 (30 ng/mL) or insulin (3 ug/mL) for 15 minutes. Cell lysates are analyzed for phosphorylated receptors using dissociation enhanced lanthanide fluor-immuno assay (DELFIA) with anti-IGF-1R (MAB391, R&D Systems, Minneapolis, Minn.) or anti-IR☐ (sc-711, Santa Cruz Biotechnology, Santa Cruz, Calif.) capture antibody and europium-labeled anti-pTyr antibody (Eu—N1 PT66, Perkin Elmer, Waltham, Mass.) for detection. The fluorescence signal for cells treated with compounds was expressed as percent relative to 100% stimulation (IGF-1 or insulin stimulated signal). Concentration of test compound that inhibited 50% of ligand-induced receptor phosphorylation (IC$_{50}$) was determined by 4 parameter fit of data using XLfit, (value of no cell control was subtracted from all samples for background). Results are reported in Table 4. In table 4:

+ indicates IC$_{50}$ measurement greater than 500 nM;
++ indicates an IC$_{50}$ measurement of 100-500 nM;
+++ indicates an IC$_{50}$ measurement of less than 100.

TABLE 4

IGF-1R and IR Cellular AutoPhosphorylation Assay Results

| Example | IGF-1R IC50 (nM) | IR IC50 (nM) |
|---|---|---|
| 1 | +++ | ++ |
| 2 | + | + |
| 3 | ++ |  |
| 4 | +++ | +++ |
| 5 | +++ | +++ |
| 6 | ++ | + |
| 7 | +++ | + |
| 8 | +++ | ++ |
| 9 | ++ |  |
| 10 | ++ |  |
| 11 | ++ | ++ |
| 12 | ++ |  |
| 13 | +++ |  |
| 14 | + |  |
| 15 | ++ | + |
| 16 | +++ | +++ |
| 17 | ++ | + |
| 18 | +++ | ++ |
| 20 | ++ |  |
| 22 | +++ | +++ |
| 23 | +++ | +++ |
| 24 | +++ |  |
| 25 | ++ |  |
| 26 | +++ | + |
| 27 |  | + |
| 28 | ++ |  |
| 29 | ++ |  |
| 30 | ++ |  |
| 31 | +++ |  |
| 32 | + | + |
| 33 | +++ | ++ |
| 34 | +++ | ++ |
| 35 | ++ | ++ |
| 36 | +++ | +++ |
| 37 | +++ | +++ |
| 38 | +++ |  |
| 39 | +++ | ++ |
| 40 | +++ | ++ |
| 41 | +++ | ++ |
| 42 | +++ | + |
| 43 | +++ | ++ |
| 44 | +++ | ++ |
| 45 | +++ | ++ |
| 46 | ++ | ++ |
| 47 | +++ | ++ |
| 48 | +++ | ++ |

TABLE 4-continued

IGF-1R and IR Cellular AutoPhosphorylation Assay Results

| Example | IGF-1R IC50 (nM) | IR IC50 (nM) |
|---|---|---|
| 49 | ++ | +++ |
| 50 | +++ | +++ |
| 51 | +++ | ++ |
| 52 | +++ | ++ |
| 53 | +++ | ++ |
| 54 | + | + |
| 55 | ++ | + |
| 56 | ++ | ++ |
| 57 | +++ | +++ |
| 58 | +++ | +++ |
| 59 | +++ | +++ |
| 60 | +++ | +++ |
| 61 | +++ | +++ |
| 62 | +++ | +++ |
| 63 | +++ | +++ |
| 64 | ++ | +++ |
| 65 | +++ | +++ |
| 66 | +++ | +++ |
| 67 | +++ | ++ |
| 68 | ++ | ++ |
| 69 | +++ | +++ |
| 70 | +++ | +++ |
| 71 | +++ | |
| 72 | +++ | +++ |
| 73 | +++ | ++ |
| 74 | +++ | |
| 75 | +++ | |
| 76 | +++ | |
| 77 | +++ | |
| 78 | +++ | +++ |
| 79 | +++ | +++ |
| 80 | +++ | +++ |
| 81 | +++ | +++ |
| 82 | +++ | ++ |
| 83 | +++ | ++ |
| 84 | +++ | |
| 85 | ++ | ++ |
| 86 | +++ | +++ |
| 87 | +++ | +++ |
| 88 | +++ | +++ |
| 89 | +++ | +++ |
| 90 | +++ | +++ |
| 91 | +++ | +++ |
| 92 | +++ | +++ |
| 93 | +++ | +++ |
| 94 | +++ | ++ |
| 95 | +++ | ++ |
| 96 | +++ | +++ |
| 97 | +++ | +++ |
| 98 | +++ | +++ |
| 99 | +++ | +++ |
| 100 | +++ | +++ |
| 101 | +++ | +++ |
| 102 | +++ | +++ |
| 103 | +++ | +++ |
| 104 | +++ | +++ |
| 105 | +++ | +++ |
| 106 | +++ | +++ |
| 107 | +++ | +++ |
| 108 | +++ | +++ |
| 109 | +++ | +++ |
| 110 | +++ | +++ |
| 111 | +++ | +++ |
| 112 | +++ | +++ |
| 113 | +++ | +++ |
| 114 | +++ | +++ |
| 115 | +++ | +++ |
| 116 | +++ | +++ |
| 117 | +++ | +++ |
| 118 | ++ | ++ |
| 119 | +++ | +++ |
| 120 | +++ | +++ |
| 121 | +++ | +++ |
| 122 | +++ | +++ |
| 123 | ++ | +++ |
| 124 | +++ | +++ |
| 125 | +++ | |
| 126 | +++ | |
| 127 | +++ | |
| 128 | ++ | |
| 129 | ++ | |
| 130 | ++ | |
| 131 | +++ | |
| 132 | +++ | |
| 133 | +++ | +++ |
| 134 | +++ | +++ |
| 135 | +++ | +++ |
| 136 | +++ | +++ |
| 137 | +++ | +++ |
| 138 | +++ | +++ |
| 139 | +++ | ++ |
| 140 | +++ | +++ |
| 141 | ++ | ++ |
| 142 | +++ | +++ |
| 143 | +++ | +++ |
| 144 | +++ | +++ |
| 145 | ++ | +++ |
| 146 | + | + |
| 147 | +++ | +++ |
| 148 | +++ | +++ |
| 149 | +++ | +++ |
| 150 | +++ | +++ |
| 151 | +++ | +++ |
| 152 | +++ | +++ |
| 153 | ++ | +++ |
| 154 | +++ | +++ |
| 155 | +++ | +++ |
| 156 | +++ | +++ |
| 157 | +++ | +++ |
| 158 | +++ | +++ |
| 159 | +++ | +++ |
| 160 | +++ | +++ |
| 161 | +++ | +++ |
| 162 | +++ | +++ |
| 163 | +++ | +++ |
| 164 | +++ | +++ |
| 165 | +++ | +++ |
| 166 | +++ | ++ |
| 167 | +++ | +++ |
| 168 | +++ | +++ |
| 169 | ++ | ++ |
| 170 | +++ | ++ |
| 171 | +++ | +++ |
| 172 | +++ | +++ |
| 173 | +++ | +++ |
| 174 | +++ | +++ |
| 175 | +++ | |
| 176 | +++ | +++ |
| 177 | +++ | +++ |
| 178 | +++ | +++ |
| 179 | +++ | +++ |
| 180 | +++ | +++ |
| 181 | +++ | +++ |
| 182 | +++ | +++ |
| 183 | +++ | +++ |
| 184 | +++ | +++ |
| 185 | +++ | +++ |
| 186 | +++ | +++ |
| 187 | +++ | +++ |
| 188 | +++ | ++ |
| 189 | ++ | + |
| 190 | +++ | ++ |
| 191 | ++ | + |
| 192 | +++ | ++ |
| 193 | +++ | ++ |
| 194 | +++ | ++ |
| 195 | +++ | +++ |
| 196 | +++ | +++ |

TABLE 4-continued

IGF-1R and IR Cellular AutoPhosphorylation Assay Results

| Example | IGF-1R IC50 (nM) | IR IC50 (nM) |
|---|---|---|
| 197 | +++ | +++ |
| 198 | +++ | +++ |
| 199 | +++ | +++ |
| 200 | +++ | +++ |
| 201 | +++ | +++ |
| 202 | ++ | ++ |
| 203 | +++ | +++ |
| 204 | +++ | +++ |
| 205 | +++ | +++ |
| 206 | +++ | +++ |
| 207 | +++ | +++ |
| 208 | +++ | +++ |
| 209 | +++ | +++ |
| 210 | +++ | +++ |
| 211 | +++ | +++ |
| 212 | +++ | +++ |
| 213 | +++ | +++ |
| 214 | +++ | +++ |
| 215 | +++ | +++ |
| 216 | +++ | +++ |
| 217 | +++ | +++ |
| 218 | +++ | +++ |
| 219 | +++ | +++ |
| 220 | +++ | +++ |
| 221 | +++ | +++ |
| 222 | +++ | +++ |
| 223 | +++ | +++ |
| 224 | +++ | +++ |
| 225 | +++ | +++ |
| 226 | +++ | +++ |
| 227 | +++ | +++ |
| 228 | +++ | +++ |
| 229 | +++ | +++ |
| 230 | +++ | +++ |
| 231 | +++ | +++ |
| 232 | +++ | +++ |
| 233 | +++ | +++ |
| 234 | +++ | +++ |
| 235 | +++ | +++ |
| 236 | +++ | +++ |
| 237 | +++ | +++ |
| 238 | +++ | +++ |
| 239 | +++ | +++ |
| 240 | +++ | +++ |
| 241 | +++ | +++ |
| 242 | +++ | +++ |
| 243 | +++ | +++ |
| 244 | +++ | +++ |
| 245 | +++ | +++ |
| 246 | +++ | +++ |
| 247 | +++ | +++ |
| 248 | +++ | +++ |
| 249 | +++ | +++ |
| 250 | +++ | +++ |

E. In Vivo Efficacy—Mouse Models

The efficacy of the compounds of Examples 57 and 58 were assessed together in an in vivo efficacy experiment performed on mice bearing LISN cell (mouse 3T3 fibroblasts transduced with human IGF-1R) tumors. Fifty six female nude mice bearing subcutaneous LISN cell tumors were measured for tumor size and body weight and block randomized into seven groups of eight mice with an equal average tumor volume of approximately 200 mm3. Mice were dosed with either vehicle (20% SBE pH3.5), Example 57 or Example 58. The dosing schedules for each compound were based on previous experiments with the compounds and doses chosen to give the highest tumor growth inhibition and a dose response. Example 58 was dosed at 30, 100 and 300 mg/kg QD for 21 days while Example 57 was dosed at 30 mg/kg QD for 21 days, 15 mg/kg BID for 21 days and 30 mg/kg QD×3 days/week for 3 weeks.

The tumors on mice being treated with vehicle grew with the expected exponential growth throughout the 21 day study. Mice dosed with Example 58 at the higher concentrations of 100 and 300 mg/kg showed a tumor growth inhibition of 46% and 45%, respectively. The lower dose of 30 mg/kg of Example 58 achieved 28% tumor growth inhibition. Throughout the study no effect of Example 58 on body weight loss in mice was observed; in general the mice appeared healthy and active. Mice administered Example 57 at 30 mg/kg QD for 21 days, 15 mg/kg BID for 21 days and 30 mg/kg QD×3 days/week for 3 weeks showed a tumor growth inhibition of 34%, 50% and 69%, respectively. There was no body weight loss in the 30 mg/kg QD and 15 mg/kg BID treated groups and the compound appeared to be well tolerated at these doses. The 30 mg/kg QD×3 days/week for 3 weeks dose caused significant body weight loss over the three consecutive days of dosing, but the animals were able to recover that body weight loss with the four days recovery time in between doses.

In addition to the LISN xenograft efficacy studies, Example 57 has also been assessed in vivo in two other mouse models of cancer, including: Colo-205 tumor bearing mice (colon carcinoma cell line) and BT474 tumor bearing mice (breast carcinoma cell line). Forty female nude mice bearing Colo-205 tumors (average tumor size of 200 mm3) were randomized into five groups of eight mice and dosed with either vehicle (20% SBE pH3.5) or Example 57 at 100, 30, 10 mg/kg QD or 30 mg/kg BID for 21 days. The groups of mice dosed with the higher doses of Example 57 (100 mg/kg QD and 30 mg/kg BID) lost greater than 20% body weight within 10 days of dosing so were taken off the study and allowed to recover. Mice dosed with Example 57 at 30 and 10 mg/kg QD×21 showed 40 and 17% tumor growth inhibition, respectively with no body weight loss. The higher doses of 100 mg/kg QD×10 and 30 mg/kg BID×10 achieved 72 and 49% tumor growth inhibition respectively.

Due to the body weight loss seen with the higher doses in the Colo-205 xenograft efficacy study, the dosing regime was altered for the follow up BT474 study. Forty female nude mice bearing subcutaneous BT474 cell tumors (average tumor size of 200 mm3) were randomized into five groups each containing eight mice and dosed with either vehicle (20% SBE pH3.5) or Example 57 at 60, 30 or 15 mg/kg QD or 15 mg/kg BID for 21 days. Note the maximal QD dose was reduced from 100 mg/kg to 60 mg/kg and the BID dose reduced from 30 mg/kg to 15 mg/kg. In addition to these changes the mice in this study were given weekend holidays from dosing. Mice dosed with 60, 30, mg·kg QD×21 of Example 57 showed 37, 37 and 16% tumor growth inhibition respectively, while the 15 mg/kg BID×21 group showed 54% tumor growth inhibition. For all groups the mice displayed no body weight loss and appeared healthy and active throughout the study.

The efficacy of the compounds of Examples 237 and 219 were assessed together in an in vivo efficacy experiment performed on mice bearing LISN cell (mouse 3T3 fibroblasts transduced with human IGF-1R) tumors. Sixty four female nude mice bearing subcutaneous LISN cell tumors were measured for tumor size and body weight and block randomized into eight groups of eight mice with an equal average tumor volume of approximately 362 mm³. Mice were dosed with either vehicle (20% SBE pH3.5), Example 237 or Example 219. The dosing schedules for each compound were based on previous experiments with the compounds and doses chosen to give the highest tumor growth inhibition and a dose response. Example 237 was administered at 30 and 60 mg/kg QD for 21 days and 30 mg/kg BID for 21 days while Example 219 was administered at 50 and 100 mg/kg QD for 21 days, 25 and 50 mg/kg BID for 21 days.

The tumors on mice being treated with vehicle grew with the expected exponential growth throughout the 21 day study. Mice dosed with Example 237 at the higher concentrations of 30 mg/kg BID and 60 mg/kg QD showed a tumor growth inhibition of 84% and 41% at day 21, respectively. The lower dose of 30 mg/kg QD of Example 237 achieved 15% tumor growth inhibition at day 21 (note: 2 animals were euthanized prior to the last measurement). An initial body weight loss of 6% was observed with Example 237 at 30 mg/kg BID. This recovered to 3% by the end of dosing and fully recovered after dosing was concluded. In other groups dosed with Example 237 there was no effect on body weight loss and in general the mice appeared healthy and active. Mice administered Example 219 at the higher concentrations of 50 mg/kg BID and 100 mg/kg QD for 21 days showed a tumor growth inhibition of 76% and 44% at day 21, respectively. The lower concentrations of 50 mg/kg QD and 25 mg/kg BID for 21 days showed a tumor growth inhibition of 29% and 16% at day 21, respectively. There was no body weight loss in the mice that were administered Example 219 at 100 mg/kg and 50 mg/kg QD and the compound appeared to be well tolerated at both doses. Mice administered Example 219 at 25 mg/kg BID and 50 mg/kg BID for 21 days showed a body weight loss of 4% and 6% respectively. This recovered fully within 4 days after the completion of dosing.

F. In Vitro Combination of Lapatinib and the Compound of Example No. 57

The combination of lapatinib (TYKERB®) and Example 57, was investigated in cell growth inhibition assays. Lapatinib is commercially available and may be prepared using methods known in the art such as those described in PCT Publication No. WO99/35146, published 15 Jul. 1999. Three human breast tumor cell lines, MDA-MB-453, MDA-MB-468 and MCF-7 and a human lung tumor cell line, A549 were tested for their response to the combination of lapatinib and Example 57. Inhibition of cell growth was determined by staining cells with methylene blue after three days of treatment with compounds or vehicle (DMSO). Combination index (CI) values were generated using a modification of the method of Chou and Talalay. The data are provided below.

Methods:

Human tumor cell lines from breast (MDA-MB-468, MCF-7 and MDA-MB-453) and lung (A549) were cultured in a humidified incubator at 37° C. in 95% air, 5% $CO_2$ in media RPMI containing 10% fetal bovine serum (FBS). Cells were assayed in a 96-well tissue culture plate (Falcon 3075) with the following plating densities of 10,000 cells/well. Approximately 24 hours after plating cells were exposed to compounds, cells were treated with ten, three-fold serial dilutions of Example 57 or lapatinib or the combination of the two agents at concentrations resulting in complete dose response curves of each compound. Cells were incubated in the presence of compounds for 3 days. Media were then removed by aspiration. Cell biomass was estimated by staining cells at rt for at least 30 min with 100 µL per well methylene blue (Sigma M9140, 0.5% in 1:1 ethanol:water). Stain was removed, and the plates rinsed by immersion in deionized water and air-dried. To release stain from the cells, 100 µL of solubilization solution was added (1% N-lauroyl sarcosine, Sodium salt, Sigma L5125, in PBS), and plates were shaken gently for about 30 min. Optical density at 620 nM was measured on a microplate reader. Cell growth was calculated relative to vehicle treated control wells. Concentration of compound that inhibits 50% of control cell growth ($IC_{50}$) was interpolated using nonlinear regression and the equation, $y=V_{max}*(1-(x/(K+x)))+Y2$. Combination Index values were generated by inserting the interpolated $IC_{50}$ values in to the mutually non-exclusive equation derived by Chou and Talalay (*Adv. Enzyme Regul.* 22:27-55, 1984) Briefly, if the two compounds fit the mutually non-exclusive model of Chou, one calculates the combination index (CI) using the formula:

$$CI=D_a/IC_{50(a)}+D_b/IC_{50(b)}+(D_a*D_b)/(IC_{50(a)}*IC_{50(b)})$$

where $IC_{50(a)}$ is the $IC_{50}$ of lapatinib, $IC_{50(b)}$ is the $IC_{50}$ for the compound of Example 57, $D_a$ is the concentration of lapatinib in combination with the Example 57 that inhibited 50% of cell growth and $D_b$ is the concentration of the compound of Example 57 in combination with lapatinib that inhibited 50% of cell growth.

CI values between 0.9 and 1.10 are interpreted as additive; CI values less than 0.9 are interpreted as indicative of synergy. Combination Index values >1.10 are interpreted to indicate antagonism.

Results:

TABLE 5

CI values from multiple experiments combining lapatinib and Example 57.

| Cell Line | Tissue Type | CI lapatinib + Example 57 |
| --- | --- | --- |
| MDA-MB-453 | Breast | 0.31 ± 0.07 (n = 3)* |
| MDA-MB-468 | Breast | 0.78, 1.25 (n = 2) |
| MCF-7 | Breast | 1.00 ± 0.2 (n = 3)* |
| A549 | Lung | <1 (n = 2) |

*Averages ± SD

Pharmaceutical Formulation Examples

A. Preparation of Capsules Containing a Compound of the Invention (as the freebase, hydrate or solvate version):
  Contents in each capsule:
    =60 mg Active Pharmaceutical ingredient (API)+60 mg Avicel+13 mg SSG.
  133 mg total powder in a size 0 hard gelatin capsule. The Avicel/SSG weight may be reasonably approximate. Most critical weight is API.
  Procedure:
1. Separate the halves of hard-gelatin capsule and mark/identify each as appropriate/needed.
2. Place the bottom capsule half in capsule filler with the filling funnel on top.
3. Weigh the components (Avicel, Sodium Starch Glycolate (SSG), API) onto a single weigh paper (tared on an analytical balance between each weighing).
4. Record weights of each component.
5. Carefully and thoroughly mix the dry powders on the weigh paper with a small spatula.
6. Carefully transfer the mixed powders into the capsule through the funnel.
7. Place the top half onto the capsule and close until secure (should feel a snap), shake capsule to mix/distribute contents.
8. IF powder begins to near top of capsule, gently tap capsule and powder should settle.
9. Place the capsule into a small appropriately labeled bottle (but large enough to easily remove it).

B. Preparation of Tablets Containing a Compound of the Invention:

| Component | Quantity (mg/tablet) | % w/w |
|---|---|---|
| Core Tablet | | |
| API | 405.0 | 71.6 |
| Lactose monohydrate | 59.0 | 10.4 |
| Polysorbate 80 | 1.0 | 0.2 |
| Povidone | 40.0 | 7.1 |
| Colloidal Silicon Dioxide | 5.5 | 1.0 |
| Crospovidone | 51.0 | 9.0 |
| Magnesium Stearate | 4.5 | 0.8 |
| Purified Water | qs | |
| Film Coating | | |
| Opadry ® Orange, | 17.0 | 3.0 |
| Purified water | qs | |

Procedure:

1. Sieve Lactose, Silicon dioxide, Crospovidone and half Povidone.
2. Add API.
3. Granulate in High Shear Granulator with granulating solution containing dissolved Polysorbate 80 and other half of Povidone in Purified water.
4. Mill
5. Dry using Fluid Bed Dryer
6. Mill
7. Add Crospovidone, magnesium stereate.
8. Blend 5 minute
9. Compress tablet
10. Aqueous film coat tablet

What is claimed is:

1. A compound of formula (I):

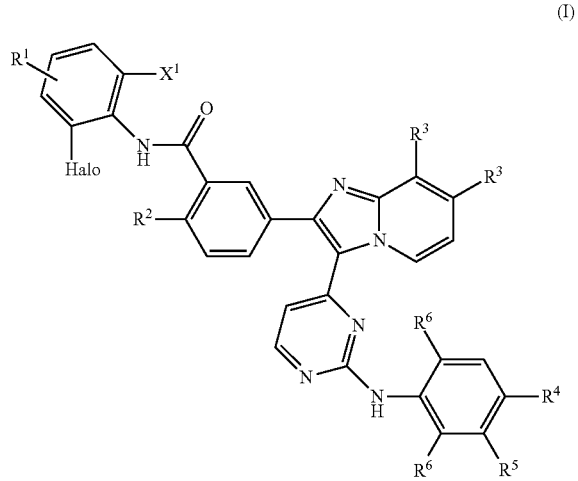

wherein:
$X^1$ is H or halo;
$R^1$ is H, halo or haloalkyl;
$R^2$ is H or O-alkyl;
each $R^3$ is the same or different and is independently selected from H, halo, alkyl, haloalkyl and O-alkyl;
one of $R^4$ and $R^5$ is selected from H, halo, alkyl and O-alkyl, and the other is a moiety selected from:

$$—O—(CHR^7)_a—R^8 \quad (i)$$

$$—(CHR^9)_b—\text{A}—(R^{10})_n \quad \text{and} \quad (ii)$$

$$\text{B}(R^{11})_q—(CHR^{12})_c—\text{C}—(R^{13})_p \quad (iii)$$

SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Substrate Peptide

<400> SEQUENCE: 1

Ala Glu Glu Glu Glu Tyr Met Met Met Met Ala Lys Lys Lys Lys Asn
1               5                   10                  15 wherein:
(i) each $R^7$ is the same or different and is independently selected from H, alkyl and OH;
a is 0, 1, 2 or 3;
$R^8$ is selected from $NH_2$, N(H)alkyl, $N(alkyl)_2$ and a group of formula (iv):

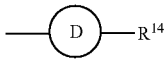

(iv)

wherein:
Ring D is a 5-6 membered N-heterocycle optionally including 1 or 2 additional heteroatoms selected from N, O and S and
$R^{14}$ is selected from H, halo, alkyl, OH, O-alkyl, oxo, $SO_2$alkyl, alkylene-O-alkyl and alkylene-$SO_2$alkyl;
(ii) b is 0, 1, 2 or 3;
each $R^9$ is the same or different and is independently selected from H, alkyl and OH;
Ring A is selected from 5-10 membered heterocycles including 1, 2 or 3 heteroatoms selected from N, O and S and 5-6 membered heteroaryls including 1, 2 or 3 heteroatoms selected from N, O and S;
n is 0, 1 or 2;
each $R^{10}$ is the same or different and is independently selected from halo, alkyl, haloalkyl, OH, O-alkyl, oxo, $NH_2$, N(H)alkyl, $N(alkyl)_2$, $N(alkylene-O-alkyl)_2$, C(O)alkyl, $SO_2$alkyl, alkylene-O-alkyl, alkylene-$NH_2$, alkylene-N(H)alkyl, alkylene-$N(alkyl)_2$, alkylene-C(O)alkyl, and alkylene-$SO_2$alkyl;
(iii) c is 0, 1 or 2;
each $R^{12}$ is the same or different and is independently H or alkyl;
Ring B is selected from cyclohexylene, 5-6 membered heterocycle including 1, 2 or 3 heteroatoms selected from N, O and S and 5-6 membered heteroaryl including 1, 2 or 3 heteroatoms selected from N, O and S;
q is 0 or 1;
$R^{11}$ is halo, alkyl or haloalkyl;
Ring C is a 5-10 membered heterocycle including 1, 2 or 3 heteroatoms selected from N, O and S;
p is 0, 1 or 2;
each $R^{13}$ is the same or different and is independently selected from halo, alkyl, haloalkyl, OH, O-alkyl, oxo, $NH_2$, N(H)alkyl, $N(alkyl)_2$, $N(alkylene-O-alkyl)_2$, C(O)alkyl, $SO_2$alkyl, alkylene-O-alkyl, alkylene-$NH_2$, alkylene-N(H)alkyl, alkylene-$N(alkyl)_2$, alkylene-C(O)alkyl, and alkylene-$SO_2$alkyl; and
each $R^6$ is the same or different and is independently selected from H, halo, alkyl, haloalkyl, O-alkyl and O-haloalkyl;
or a pharmaceutically acceptable salt thereof.

2. The compound according to claim 1, wherein $X^1$ is halo and $R^1$ is H.

3. The compound according to claim 1 wherein $R^2$ is H or O—$C_{1-3}$alkyl.

4. The compound according to claim 1 wherein at least one $R^3$ is H and the other is selected from H, halo, $C_{1-3}$alkyl, halo$C_{1-3}$alkyl and O—$C_{1-3}$alkyl.

5. The compound according to claim 1 wherein one of $R^4$ and $R^5$ is selected from H, halo, alkyl and O-alkyl, and the other is a moiety:

(i).

6. The compound according to claim 1, wherein $R^4$ is H and $R^5$ is a moiety:

(i).

7. The compound according to claim 1, wherein a is 2 or 3 and each $R^7$ is the same or different and is independently H or OH.

8. The compound according to claim 1, wherein $R^8$ is selected from $N(alkyl)_2$ and a group of formula (iv):

(iv)

9. The compound according to claim 1, wherein one of $R^4$ and $R^5$ is selected from H, halo, alkyl and O-alkyl, and the other is a moiety:

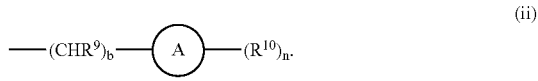

(ii)

10. The compound according to claim 1, wherein $R^5$ is H and $R^4$ is a moiety:

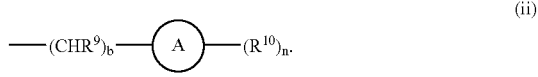

(ii)

11. The compound according to claim 1, wherein b is 0, 1 or 2 and each $R^9$ is H.

12. The compound according to claim 1, wherein Ring A is selected from 5-6 membered heterocycle or heteroaryl including 1 or 2 heteroatoms selected from N, O and S.

13. The compound according to claim 1, wherein n is 0 or 1 and $R^{10}$ is selected from halo, alkyl, haloalkyl, O-alkyl, oxo, $NH_2$, N(H)alkyl, $N(alkyl)_2$, $SO_2$alkyl, alkylene-$N(alkyl)_2$ and alkylene-$SO_2$alkyl.

14. The compound according to claim 1 wherein one of $R^4$ and $R^5$ is selected from H, halo, alkyl and O-alkyl, and the other is a moiety:

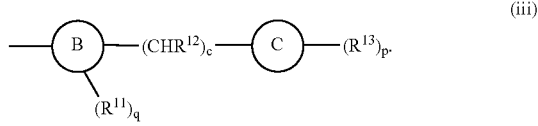

(iii)

15. The compound according to claim 1, wherein $R^5$ is H, F, Cl or methyl and $R^4$ is a moiety (iii-a):

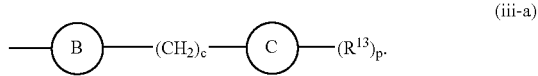

(iii-a)

16. The compound according to claim 1, wherein $R^5$ is H and $R^4$ is a moiety (iii-b):

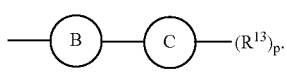

(iii-b)

17. The compound according to claim 1, wherein Ring B is selected from 5-6 membered N-heterocycle or N-heteroaryl optionally including 1 or 2 additional heteroatoms selected from N, O and S.

18. The compound according to claim 1, wherein Ring C is selected from 5-6 membered and 9-10 membered N-heterocycles optionally including 1 or 2 additional heteroatoms selected from N, O and S.

19. The compound according to claim 1, wherein p is 0 or 1.

20. The compound according to claim 1, wherein each $R^{13}$ is the same or different and is independently selected from alkyl, haloalkyl, OH, O-alkyl, oxo, $NH_2$, N(H)alkyl, $N(alkyl)_2$, $SO_2$alkyl, alkylene-$NH_2$, alkylene-N(H)alkyl, alkylene-$N(alkyl)_2$ and alkylene-$SO_2$alkyl.

21. The compound according to claim 1, wherein at least one $R^6$ is H.

22. A compound selected from:
3-[3-(2-{[4-(1,4'-bipiperidin-1'-yl)-2-(methyloxy)phenyl]amino}-4-pyrimidinyl)imidazo[1,2-a]pyridin-2-yl]-N-(2,6-difluorophenyl)benzamide;
N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide;
N-(2,6-difluorophenyl)-3-(3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)benzamide;
N-(2,6-difluorophenyl)-3-(3-{2-[(5-methyl-2-(methyloxy)-4-{4-[2-(methylsulfonyl)ethyl]-1-piperazinyl}phenyl)amino]-4-pyrimidinyl}imidazo[1,2-a]pyridin-2-yl)benzamide;
N-(2,6-difluorophenyl)-2-(ethyloxy)-5-(3-{2-[(5-methyl-2-(methyloxy)-4-{-4-[2-(methylsulfonyl)ethyl]-1-piperazinyl}phenyl)amino]-4-pyrimidinyl}imidazo[1,2-a]pyridin-2-yl)benzamide;
N-(2,6-difluorophenyl)-2-(ethyloxy)-5-(3-{2-[(5-methyl-2-(methyloxy)-4-{1-[2-(methylsulfonyl)ethyl]-4-piperidinyl}phenyl)amino]-4-pyrimidinyl}imidazo[1,2-a]pyridin-2-yl)benzamide; and
N-(2,6-difluorophenyl)-5-(7-fluoro-3-{2-[(2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide;
N-(2,6-difluorophenyl)-5-(3-{2-[(2-(ethyloxy)-5-methyl-4-{4-[2-(methylsulfonyl)ethyl]-1-piperidinyl}phenyl)amino]-4-pyrimidinyl}imidazo[1,2-a]pyridin-2-yl)-2-(methyloxy)benzamide;
N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide;

and pharmaceutically acceptable salts thereof.

23. N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide or a pharmaceutically acceptable salt thereof.

24. N-(2,6-difluorophenyl)-3-[3-(2-{[4-{4-[4-(2-fluoroethyl)-1-piperazinyl]-1-piperidinyl}-2-(methyloxy)phenyl]amino}-4-pyrimidinyl)imidazo[1,2-a]pyridin-2-yl]benzamide

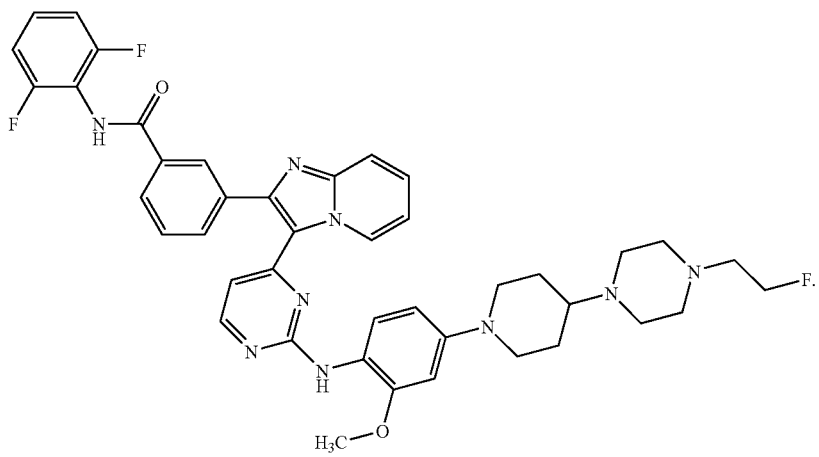

25. N-(2,6-difluorophenyl)-5-(3-{2-[(2-(ethyloxy)-5-methyl-4-{4-[2-(methylsulfonyl)ethyl]-1-piperidinyl}phenyl)amino]-4-pyrimidinyl}imidazo[1,2-a]pyridin-2-yl)-2-(methyloxy)benzamide

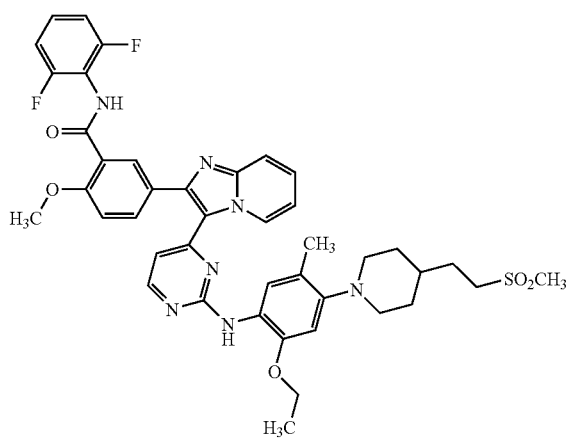

or a pharmaceutically acceptable salt thereof.

26. N-(2,6-difluorophenyl)-5-(3-{2-[(2-(ethyloxy)-5-methyl-4-{4-[2-(methylsulfonyl)ethyl]-1-piperidinyl}phenyl)amino]-4-pyrimidinyl}imidazo[1,2-a]pyridin-2-yl)-2-(methyloxy)benzamide

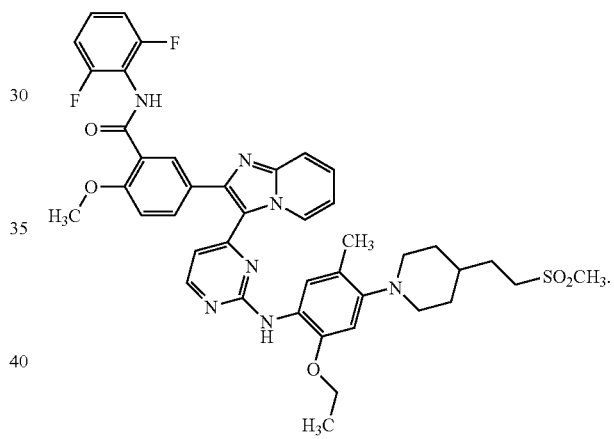

27. N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide

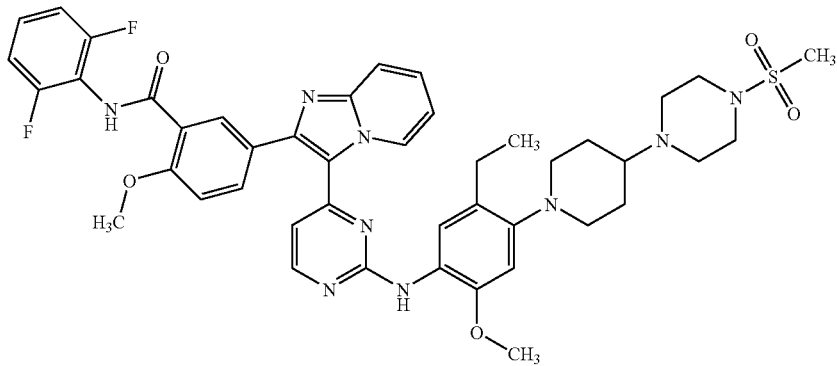

or a pharmaceutically acceptable salt thereof.

28. N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide

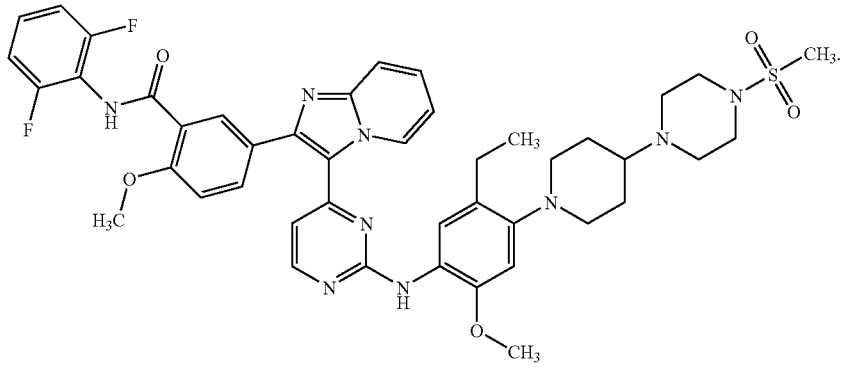

29. N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide monocitric acid salt.

30. A pharmaceutical composition comprising a compound according to claim 1 and a pharmaceutically acceptable carrier, diluent or excipient.

31. The pharmaceutical composition according to claim 30 further comprising a chemotherapeutic agent.

32. The pharmaceutical composition according to claim 30, wherein the compound is N-(2,6-difluorophenyl)-5-(3-{2-[(2-(ethyloxy)-5-methyl-4-{4-[2-(methylsulfonyl)ethyl]-1-piperidinyl}phenyl)amino]-4-pyrimidinyl}imidazo[1,2-a]pyridin-2-yl)-2-(methyloxy)benzamide or a pharmaceutically acceptable salt thereof.

33. The pharmaceutical composition according to claim 30, wherein the compound is N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide or a pharmaceutically acceptable salt thereof.

34. The pharmaceutical composition according to claim 30, wherein the compound is N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide.

35. The pharmaceutical composition according to claim 30, wherein the compound is N-(2,6-difluorophenyl)-5-(3-{2-[(5-ethyl-2-(methyloxy)-4-{4-[4-(methylsulfonyl)-1-piperazinyl]-1-piperidinyl}phenyl)amino]-4-pyrimidinyl}imidazo[1,2-a]pyridin-2-yl)-2-(methyloxy)benzamide monocitric acid salt.

36. A process for preparing a compound according to claim 1 comprising reacting a compound of formula (V):

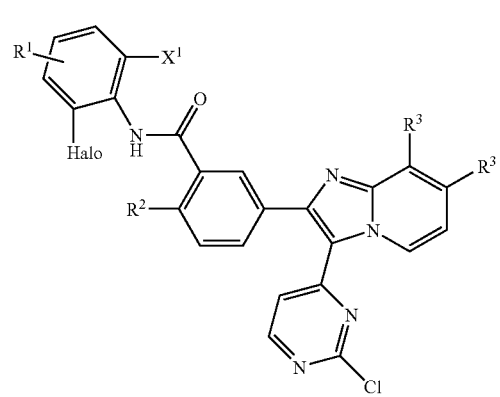

with an aniline of formula (VI):

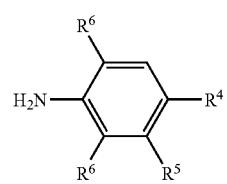

wherein all variables are as defined in claim 1, to prepare a compound of formula (I).

37. A process for preparing a compound according to claim 1 comprising reacting a compound of formula (XV):
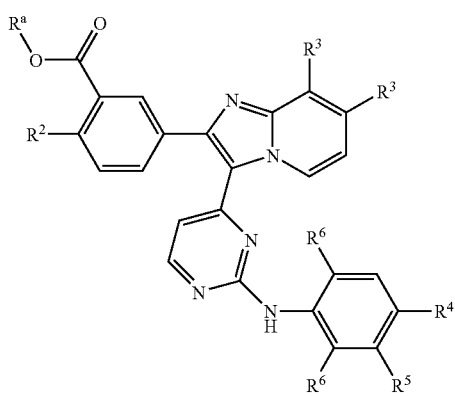
wherein $R^a$ is alkyl or cycloalkyl, and
with an aniline of formula (IX):
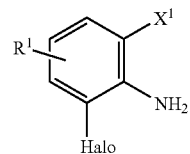
wherein all variables are as defined in claim 1, to prepare a compound of formula (I).
* * * * *